US007846722B2

(12) United States Patent
Williams et al.

(10) Patent No.: US 7,846,722 B2
(45) Date of Patent: Dec. 7, 2010

(54) LUMINESCENCE RESONANCE ENERGY TRANSFER (LRET) ASSAYS FOR CLOSTRIDIAL TOXIN ACTIVITY

(75) Inventors: Dudley J. Williams, Laguna Niguel, CA (US); Marcella A. Gilmore, Santa Ana, CA (US); Lance E. Steward, Irvine, CA (US); Marc Verhagen, Irvine, CA (US); Kei Roger Aoki, Coto de Caza, CA (US); Ester Fernandez-Salas, Fullerton, CA (US)

(73) Assignee: Allergan, Inc., Irvine, CA (US)

( * ) Notice: Subject to any disclaimer, the term of this patent is extended or adjusted under 35 U.S.C. 154(b) by 503 days.

(21) Appl. No.: 11/754,046

(22) Filed: May 25, 2007

(65) Prior Publication Data

US 2008/0220456 A1 Sep. 11, 2008

Related U.S. Application Data

(63) Continuation of application No. 11/752,596, filed on May 23, 2007, and a continuation-in-part of application No. 09/942,098, filed on Aug. 28, 2001, now Pat. No. 7,332,567, and a continuation-in-part of application No. 10/947,071, filed on Sep. 21, 2004, now abandoned.

(51) Int. Cl.
*C12N 5/00* (2006.01)
*C12N 5/02* (2006.01)
*C12N 5/071* (2006.01)

(52) U.S. Cl. .................. 435/325; 435/368; 435/369; 435/370; 435/372

(58) Field of Classification Search .................. None
See application file for complete search history.

(56) References Cited

U.S. PATENT DOCUMENTS

| 5,693,476 | A | 12/1997 | Scheller | |
|---|---|---|---|---|
| 5,804,604 | A | 9/1998 | Frankel et al. | |
| 5,962,637 | A | 10/1999 | Shone et al. | |
| 5,965,699 | A | 10/1999 | Schmidt et al. | |
| 5,981,200 | A | 11/1999 | Tsien et al. | |
| 5,989,545 | A | 11/1999 | Foster et al. | |
| 6,043,042 | A | 3/2000 | Shone et al. | |
| 6,169,074 | B1 | 1/2001 | Montal et al. | |
| 6,197,534 | B1 | 3/2001 | Lakowicz et al. | |
| 6,197,928 | B1 | 3/2001 | Tsien et al. | |
| 6,221,355 | B1 | 4/2001 | Dowdy | |
| 6,469,154 | B1 | 10/2002 | Tsien et al. | |
| 6,504,006 | B1 | 1/2003 | Shine et al. | |
| 6,762,280 | B2 | 7/2004 | Schmidt et al. | |
| 7,183,066 | B2* | 2/2007 | Fernandez-Salas et al. | 435/7.32 |
| 7,208,285 | B2* | 4/2007 | Steward et al. | 435/7.32 |
| 7,332,567 | B2* | 2/2008 | Steward et al. | 530/300 |
| 7,374,896 | B2* | 5/2008 | Steward et al. | 435/7.32 |
| 7,399,607 | B2* | 7/2008 | Williams et al. | 435/23 |
| 7,419,676 | B2* | 9/2008 | Dolly et al. | 424/239.1 |
| 7,422,877 | B2* | 9/2008 | Dolly et al. | 435/69.1 |
| 7,495,069 | B2* | 2/2009 | Steward et al. | 530/300 |
| 7,514,088 | B2* | 4/2009 | Steward et al. | 424/239.1 |
| 7,556,817 | B2* | 7/2009 | Steward et al. | 424/239.1 |
| 7,632,655 | B2* | 12/2009 | Williams et al. | 435/23 |
| 7,635,574 | B2* | 12/2009 | Williams et al. | 435/23 |
| 7,638,294 | B2* | 12/2009 | Williams et al. | 435/23 |
| 7,645,570 | B2* | 1/2010 | Fernandez-Salas et al. | 435/4 |
| 7,674,601 | B2* | 3/2010 | Williams et al. | 435/23 |
| 7,678,550 | B1* | 3/2010 | Steward et al. | 435/7.32 |
| 7,709,608 | B2* | 5/2010 | Steward et al. | 530/350 |
| 7,718,766 | B2* | 5/2010 | Steward et al. | 530/300 |
| 7,749,759 | B2* | 7/2010 | Fernandez-Salas et al. | 435/325 |
| 2003/0027752 | A1 | 2/2003 | Steward et al. | |
| 2003/0077685 | A1 | 4/2003 | Schmidt et al. | |
| 2003/0143650 | A1 | 7/2003 | Steward et al. | |
| 2003/0143651 | A1 | 7/2003 | Steward et al. | |
| 2003/0219462 | A1 | 11/2003 | Steward et al. | |
| 2004/0072270 | A1 | 4/2004 | Fernandez-Salas et al. | |
| 2004/0115727 | A1 | 6/2004 | Steward et al. | |
| 2004/0146963 | A1 | 7/2004 | Schmidt et al. | |
| 2006/0063221 | A1* | 3/2006 | Williams et al. | 435/23 |
| 2007/0122858 | A1* | 5/2007 | Fernandez-Salas et al. | 435/7.32 |
| 2007/0243565 | A1* | 10/2007 | Williams et al. | 435/7.32 |
| 2008/0032318 | A1* | 2/2008 | Steward et al. | 435/7.32 |
| 2008/0038756 | A1* | 2/2008 | Steward et al. | 435/7.32 |
| 2008/0064054 | A1* | 3/2008 | Fernandez-Salas et al. | 435/29 |

(Continued)

FOREIGN PATENT DOCUMENTS

CA 2082770 8/1993

(Continued)

OTHER PUBLICATIONS

Bark et al, Gene, 1994, 139:291-292.*
Becker et al, Bioconjugate Chemistry, 2004, 15/5:1118-1124.*
Anne et al., "High-Throughput Fluorogenic Assay for Determination of Botulinum Type B Neurotoxin Protease Activity," *Analytical Biochemistry* 291:253-261 (2001).
Adams et al., "New biarsenical ligands and tetracysteine motifs for protein labeling in vitro and in vivo: Synthesis and biological applications," *J. Am. Chem. Soc.* 124(21):6063-6076 (2002).
Ausubel et al. *Current Protocols in Molecular Biology*, John Wiley & Sons, Inc.: New York (2000) 10.15, Supplement 41.

(Continued)

*Primary Examiner*—N. M Minnifield
(74) *Attorney, Agent, or Firm*—Kenton Abel; Debra Condino

(57) ABSTRACT

Clostridial toxin substrates comprising a lanthanide donor complex, an acceptor, and a Clostridial toxin recognition sequence including a cleavage site; methods for determining the activity of a Clostridial toxin from a test sample using such Clostridial toxin substrates; cell compositions comprising such Clostridial toxin substrates and a Clostridial toxin receptor; and methods for determining the activity of a Clostridial toxin from a test sample using such cell compositions.

18 Claims, 10 Drawing Sheets

U.S. PATENT DOCUMENTS

| | | | |
|---|---|---|---|
| 2008/0146786 A1* | 6/2008 | Steward et al. | 530/409 |
| 2008/0176249 A1* | 7/2008 | Steward et al. | 435/7.4 |
| 2008/0176336 A1* | 7/2008 | Steward et al. | 436/172 |
| 2008/0220456 A1* | 9/2008 | Williams et al. | 435/7.32 |
| 2009/0042231 A1* | 2/2009 | Steward et al. | 435/23 |
| 2009/0053746 A1* | 2/2009 | Steward et al. | 435/23 |
| 2009/0117572 A1* | 5/2009 | Fernandez-Salas et al. | 435/6 |
| 2009/0208993 A1* | 8/2009 | Fournie-Zaluski et al. | 435/24 |

FOREIGN PATENT DOCUMENTS

| | | |
|---|---|---|
| WO | WO 95/33850 A1 | 12/1995 |
| WO | WO 97/34620 A1 | 9/1997 |
| WO | WO 99/29721 A1 | 6/1999 |
| WO | WO 99/55899 A1 | 11/1999 |
| WO | WO 00/34308 A2 | 6/2000 |
| WO | WO 01/18038 A2 | 3/2001 |
| WO | WO 02/25284 A2 | 3/2002 |
| WO | WO 03/020948 A2 | 3/2003 |
| WO | WO 2004/029576 | 4/2004 |
| WO | WO 2004/031355 A2 | 4/2004 |
| WO | WO 2004/031773 | 4/2004 |
| WO | WO 2005/076785 * | 8/2005 |
| WO | WO 2005/076785 A2 | 8/2005 |
| WO | WO 2006/107921 * | 10/2006 |
| WO | WO 2009/035476 A1 * | 3/2009 |

OTHER PUBLICATIONS

Ausubel et al., *Current Protocols in Molecular Biology*, John Wiley & Sons, Inc.: New York (2000), Chapter 16.6.

Ausubel et al., *Current Protocols in Molecular Biology*, John Wiley & Sons, Inc.: New York (2000), Chapter 16.7.

Autofluorescent Proteins, *AFP's Applications Manual*, pp. 1-25 (Nov. 1998).

Bark, "Structure of the chicken gene for SNAP-25 reveals duplicated exon encoding distinct isoforms of the protein ," *J. Mol. Biol.* 233(1):67-76 (1993).

BD Biosciences Clontech Product List, BD Living Colors™ Fluorescent Proteins, pp. 1-9 (Apr. 2004).

Blasi et al., "Botulinum neurotoxin C1 blocks neurotransmitter release by means of cleaving HPC-1/syntaxin," *EMBO J.* 12(12):4821-4828 (1993).

Bronstein et al., "Chemiluminescent and bioluminescent reporter gene assays," *Anal. Biochem.* 219:169-181 (2001).

Burnett et al., "Novel small molecule inhibitors of botulinum neurotoxin A metalloprotease activity," *Biochem. Biophys. Res. Commun.* 310(1):84-93 (2003).

Calbiochem, "SNAPtide® Botulinum Toxin A Substrate, Fluorogenic," www.calbiochem.com. printed on Dec. 17, 2002.

Catsicas et al., "Expression of a conserved cell-type-specific protein in nerve terminals coincides with synaptogenesis ," *Proc. Natl. Acad. Sci. U.S.A.* 88(3):785-789 (1991).

Chen and Selvin, "Thiol-reactive Luminescent Chelates of Terbium and Europium," *Bioconjugate Chem.* 10(2):311-315 (1999).

Chen, Jiyan, et al., *Thiol-Reactive Luminescent Chelates of Terbium and Europium*, Bioconjugate Chem., 1999, 10, pp. 311-315.

CIS Bio International, "Homogeneous Time Resolved Fluorescence—Methodological aspects," Application Note 1, pp. 1-4, CIS bio international: France (2003).

Clark et al., "A novel peptide designed for sensitization of terbium (III) luminescence," *FEBS Lett.* 333(1-2):96-98 (1993).

Clark et al., "A study of sensitized lanthanide luminescence in an engineered calcium-binding protein," *Anal. Biochem.* 210(1):1-6 (1993).

Clegg, "Fluorescence resonance energy transfer," *Curr. Opin. Biotechnol.* 6(1):103-110 (1995).

Collins, "Generation and initial analysis of more than 15,000 full-length human and mouse cDNA sequences," *Proc. Natl. Acad. Sci. U.S.A.* 99(26):16899-16903 (2002).

Cooper and Sammes, "Synthesis and spectral properties of a new luminescent europium(III) terpyridyl chelate," *J. Chem. Soc., Perkin Trans. 2* 8:1695-1700 (2000).

Cornille et al., "Solid-Phase Synthesis, Conformational Analysis and In Vitro Cleavage of Synthetic Human Synaptobrevin II 1-93 by Tetanus Toxin L Chain," *Eur. J. Biochem.* 222:173-181 (1994).

Criado et al. "A single amino acid near the C terminus of the synaptosomeassociated protein of 25 kDa (SNAP-25) is essential for exocytosis in chromaffin cells," *Proc. Natl. Acad. Sci. U.S.A.* 96(13):7256-7261 (1999).

Deloukas et al., "The DNA sequence and comparative analysis of human chromosome 20," *Nature* 414(6866):865-871 (2001).

Diamandis and Christopoulos, "Europium chelate labels in time-resolved fluorescence immunoassays and DNA hybridization assays," *Anal. Chem.* 62(22):1149A-1157A (1990).

Diamandis, "Immunoassays with time-resolved fluorescence spectroscopy: Principles and applications," *Clin. Biochem.* 21(3):139-150 (1988).

Ekong et al., "Recombinant SNAP-25 is an Effective Substrate for *Clostridium botulinum* Type A Toxin Endopeptidase Activity in vitro," *Microbiology* 143:3337-3347 (1997).

Ellenberg et al., "Two-color green fluorescent protein time-lapse imaging," *Biotechniques* 25(5):838-842, 844-846 (1998).

Enzelberger et al., "Designing new metal affinity peptides by random mutagenesis of a natural metal-binding site," *J. Chromatogr. A.* 898(1):83-94 (2000).

Fernandez-Salas et al, "Plasma membrane localization signals in the light chain of botulinum neurotoxin", PNAS, vol. 101, No. 9, Mar. 2, 1994, pp. 3208-3213.

Florentin et al., "A Highly Sensitive Fluorometric Assay for 'Enkephalinase,' a Neutral Metalloendopeptidase That Releases Tyrosine-Glycine-Glycine from Enkephalins," *Analytical Biochemistry* 141:62-69 (1984).

Foran et al., "Differences in the Protease Activities of Tetanus and Botulinum B Toxins Revealed by the Cleavage of Vesicle-Associated Membrane Protein and Various Sized Fragments," *Biochemistry* 33:15365-15374 (1994).

Foran et al., "Botulinum neurotoxin C1 cleaves both syntaxin and SNAP-25 in intact and permeabilized chromaffin cells: Correlation with its blockade of catecholamine release," *Biochemistry* 35(8):2630-2636 (1996).

Geoghegan et al., "Fluorescence-based Continuous Assay for the Aspartyl Protease of Human Immunodeficiency Virus-1," *FEBS* 262:119-122 (1990).

Gil et al., "Modifications in the C terminus of the synaptosome-associated protein of 25 kDa (SNAP-25) and in the complementary region of synaptobrevin affect the final steps of exocytosis," *J. Biol. Chem.* 277(12):9904-9910(2002).

Graham et al., "A method to measure the interaction of Rac/Cdc42 with their binding partners using fluorescence resonance energy transfer between mutants of green fluorescent protein," *Analytical Biochem.* 296:208-217 (2001).

Griesbeck et al., "Reducing the environmental sensitivity of yellow fluorescent protein. Mechanism and applications," *J. Biol. Chem.* 276(31):29188-29194 (2001).

Grisshammer and Tucker, "Quantitative evaluation of neurotensin receptor purification by immobilized metal affinity chromatography," *Prot. Expr. Purif.* 11:53-60 (1997).

Hallis et al., "Development of Novel Assays for Botulinum Type A and B Neurotoxins Based on Their Endopeptidase Activities," *J. Clin. Microbiol.* 34:1934-1938 (1996).

Hanson and Stevens, "Cocrystal Structure of Synaptobrevin-II Bound to Botulinum Neurotoxin Type B at 2.0 Å Resolution," *Nature Structural Biology* 7:687-692 (2000).

Heim and Tsien, "Engineering green fluorescent protein for improved brightness, longer wavelengths and fluorescence resonance energy transfer," *Curr. Biol.* 6(2):178-182 (1996).

Heim et al., "Wavelength mutations and posttranslational autoxidation of green fluorescent protein," *Proc Natl Acad Sci U S A.* 91(26):12501-12504 (1994).

Heyduk, "Measuring protein conformational changes by FRET/LRET," *Curr. Opin. Biotechnol.* 13:292-296 (2002).

Hodel, "Molecules in Focus: SNAP-25," *Int. J. Biochem. & Cell Biol.* 30:1069-1073 (1998).

Holskin et al., "A Continuous Fluorescence-Based Assay of Human Cytomegalovirus Protease Using a Peptide Substrate," *Analytical Biochemistry* 226:148-155 (1995).

Huang et al., "$Ca^{2+}$ influx and cAMP elevation overcame botulinum toxin A but not tetanus toxin inhibition of insulin exocytosis," *Am. J. Physiol. Cell Physiol.* 281:C740-C750 (2001).

Humeau et al., "How Botulinum and Tetanus Neurotoxins Block Neurotransmitter Release," *Biochimie* 82:427-446 (2000).

Jacobsson et al., "Differential subcellular localization of SNAP-25a and SNAP-25b RNA transcripts in spinal motoneurons and plasticity in expression after nerve injury," *Brain Res. Mol. Brain Res.* 37(1-2):49-62 (1996).

Jagadish et al., "Insulin-responsive tissues contain the core complex protein SNAP-25 (synaptosomal-associated protein 25) A and B isoforms in addition to syntaxin 4 and synaptobrevins 1 and 2," *Biochem. J.* 317(Pt 3):945-954 (1996).

Kakiuchi et al., "A High Throughput Assay of the Hepatitis C Virus Nonstructural Protein 3 Serine Proteinase," *Journal of Virological Methods* 80:77-84 (1999).

Kalandakanond and Coffield, "Cleavage of SNAP-25 by botulinum toxin type A requires receptor-mediated endocytosis, pH-dependent translocation, and zinc ," *J. Pharmacol. Exp. Ther.* 296(3):980-986 (2001).

Kam et al., "Probing molecular processes in live cells by quantitative multidimensional microscopy," *Trends in Cell Biology* 11:329-334 (2001).

Kawasaki and Kretsinger, "Calcium Binding Proteins 1: EF-hands," *Protein Profile* 1(4):343-517, Sheterline et al. (eds.), Academic Press: London (1994).

Knapp et al., "The Crystal Structure of Botulinum Toxin A zinc Protease Domain" abstract of presentation, *37th Annual Meeting of the Interagency Botulism Research Coordinating Committee* Asilomar, CA (2000).

Kolb et al., "Use of a novel homogenous fluorescent technology in high throughput screening," *J. Biomol. Screening* 1:203-210 (1996).

Kolb et al., in Devlin (ed.), *High Throughput Screening: The Discovery of Bioactive Substances*, pp. 345-360, New York: Marcel Dekker (1997).

Lacy et al., "Crystal Structure of Botulinum Neurotoxin Type A and Implications for Toxicity," *Nature Structural Biology* 5:898-902 (1998).

Le Bonniec et al., "Characterization of the $P_2'$ and $P_3'$ Specificities of Thrombin Using Fluorescence-Quenched Substrates and Mapping of the Subsites by Mutagenesis," *Biochemistry* 35:7114-7122 (1996).

Lewit-Bentley, "EF-hand calcium-binding proteins," *Curr. Opin. Struct. Biol.* 10(6):637-643 (2000).

Li and Selvin, "Luminescent Lanthanide Polyaminocarboxylate Chelates: The Effect of Chelate Structure," *J. Am. Chem. Soc.* 117:8132-8138 (1995).

Li and Selvin, "Amine-Reactive Forms of a Luminescent Diethylenetriaminepentaacetic Acid Chelate of Terbium and Europium: Attachment to DNA and Energy Transfer Measurements," *Bioconjugate Chem.* 8:127-132 (1997).

Lippincott-Schwartz and Patterson, "Development and use of fluorescent protein markers in living cells," *Science* 300:87-91 (2003).

List Biological Laboratories, "SNAPtide for Fluorometric Measurement of Botulinum Toxin Type A Activity," www.listlabs.com, printed on Dec. 23, 2002.

List Biological Laboratories, Inc., "Botulinum Neurotoxins," web page: http://www.listlabs.com/Literature/130.htm (Printed: Dec. 10, 2004).

List Biological Laboratories, Inc., "What's new?," web page: http://www.listlabs.com/listopener.htm (Printed: Dec. 9, 2004).

MacManus et al., "A new member of the troponin C superfamily: Comparison of the primary structures of rat oncomodulin and rat parvalbumin," *Biosci. Rep.* 3(11):1071-1075 (1983).

Mahajan et al., "Novel Mutant Green Fluorescent Protein Protease Substrates Reveal the Activation of Specific Caspases During Apoptosis," *Chemistry & Biology* 6:401-409 (1999).

Mathis, "Homogeneous immunoassay and other applications of a novel fluorescence energy transfer technology using rare earth cryptates," *J. Clin. Ligand Assay* 20:141-147 (1997).

Mathis, "Probing molecular interactions with homogeneous techniques based on rare earth cryptates and fluorescence energy transfer," *Clin. Chem.* 41(9):1391-137 (1995).

Matayoshi et al., "Novel Fluorogenic Substrates for Assaying Retroviral Proteases by Resonance Energy Transfer," *Science* 247:954-958 (1990).

Matsumoto et al., "A High-Throughput Screening Utilizing Intramolecular Fluorescence Resonance Energy Transfer for the Discovery of the Molecules that Bind HIV-1 TAR RNA Specifically," *Bioorganic & Medicinal Chemistry Letters* 10:1857-1861 (2000).

Mohanty and Weiner, "Membrane protein expression and production: Effects of polyhistidine tag length and position," *Protein Expr. Purif.* 33:311-325 (2004).

Molecular Probes, "Section 10.4—Detecting Peptidases and Proteases," *Molecular Probes Handbook*, web page http://www.probes.com/handbook/sections/1004.html Updated Aug. 3, 2003.

Montecucco and Schiavo, "Structure and Function of Tetanus and Botulinum Neurotoxins," *Quarterly Reviews of Biophysics* 28:423-472 (1995).

Moore et al., "Reactivation of 3-Dehydroquinate Synthase by Lanthanide Cations," *J. Am. Chem. Soc.* 120:7105-7106 (1998).

Nagai et al., "A variant of yellow fluorescent protein with fast and efficient maturation for cell-biological applications," *Nat. Biotechnol.* 20(1):87-90 (2002).

Nakayama and Kretsinger, "Evolution of the EF-hand family of proteins," *Annu. Rev. Biophys. Biomol. Struct.* 23:473-507 (1994).

Neale et al., "Botulinum neurotoxin A blocks synaptic vesicle exocytosis but not endocytosis at the nerve terminal," *J. Cell Biology* 147:1249-1260 (1999).

Niemann et al., "Clostridial Neurotoxins: New Tools for Dissecting Exocytosis," *Trends in Cell Biology* 4:179-185 (1994).

Nitz et al., "A powerful combinatorial screen to identify high-affinity terbium(III)-binding peptides," *Chembiochem* 4(4):272-276 (2003).

Nitz et al., "Structural origin of the high affinity of a chemically evolved lanthanide-binding peptide," *Angew Chem. Int. Ed. Engl.* 43(28):3682-3685 (2004).

Olsen et al., "High-throughput Screening of Enzyme Libraries," *Curr. Opin. Biotechnol.* 11:331-337 (2000).

Ormo et al. "Crystal structure of the *Aequorea victoria* green fluorescent protein," *Science* 273(5280):1392-1395 (1996).

Oyler et al., "The identification of a novel synaptosomal-associated protein, SNAP-25, differentially expressed by neuronal subpopulations ," *J. Cell Biol.* 109 (6, Pt. 1):3039-3052 (1989).

Pellizzari et al., "Tetanus and Botulinum Neurotoxins: Mechanism of Action and Therapeutic Uses," *Phil. Trans. R. Soc. Lond.* 354:259-268 (1999).

PerkinElmer Life Sciences, "Applications of time-resolved fluorometry with the DELFIA® method," pp. 1-23 (2002).

Perpetuo et al., "Development of an operational synaptobrevin-based fluorescent substrate for tetanus neurotoxin quantification," *Biotechnol. Appl. Biochem.* 36:155-161 (2002).

Petoud et al., "Stable lanthanide luminescence agents highly emissive in aqueous solution: Multidentate 2-hydroxyisophthalamide complexes of Sm(3+), Eu(3+), Tb(3+), Dy(3+)," *J. Am. Chem. Soc.* 125(44):13324-13325 (2003).

Pidcock and Moore, "Structural characteristics of protein binding sites for calcium and lanthanide ions," *J. Biol. Inorg. Chem.* 6(5-6):479-489 (2001).

Plafker and Macara, "Fluorescence resonance energy transfer biosensors that detect Ran conformational changes and a Ran•GDP-importin-β-RanBP1 complex in vitro and in intact cells," *J. Biol. Chem.* 277(33):30121-30127 (2002).

Reifenberger et al., "Emission Polarization of Europium and Terbium Chelates," *J. Phys. Chem. B* 107:12862-12873 (2003).

Risinger and Larhammar, "Multiple loci for synapse protein SNAP-25 in the tetraploid goldfish," *Proc. Natl. Acad. Sci. U.S.A.* 90(22):10598-10602 (1993).

Risinger et al., "Cloning of two loci for synapse protein Snap25 in zebrafish: Comparison of paralogous linkage groups suggests loss of one locus in the mammalian lineage ," *J. Neurosci. Res.* 54:563-573 (1998).

Rossetto et al., "Tetanus and Botulinum Neurotoxins: Turning Bad Guys Into Good by Research," *Toxicon* 39:27-41 (2001).

Schiavo et al., "Botulinum neurotoxin type C cleaves a single Lys-Ala bond within the carboxyl-terminal region of syntaxins," *J. Biol. Chem.* 270(18):10566-10570 (1995).

Schiavo et al, "Botulinum neurotoxins serotypes A and E cleave SNAP-25 at distinct COOH-terminal peptide bonds", FEBS Letters, vol. 335, No. 1, Nov. 1993, pp. 99-103 XP-002976174.

Schmidt and Bostian, "Endoproteinase Activity of Type A Botulinum Neurotoxin: Substrate Requirements and Activation by Serum Albumin," *J. Protein Chem.* 16(1):19-26 (1997).

Schmidt and Stafford, "A high-affinity competitive inhibitor of type A botulinum neurotoxin protease activity," *FEBS Lett.* 532(3):423-426 (2002).

Schmidt and Stafford, "Fluorigenic substrates for the protease activities of botulinum neurotoxins, serotypes A, B, and F," *Appl. Environ. Microbiol.* 69(1):297-303 (2003); Erratum in: *Appl Environ Microbiol.* 69(5):3025 (May 2003).

Schmidt et al., "Type A Botulinum Neurotoxin Proteolytic Activity: Development of Competitive Inhibitors and Implications for Substrate Specificity at the $Si_1'$ Binding Subsite," *FEBS Lett.* 435:61-64 (1998).

Schmidt et al., "High-throughput assays for botulinum neurotoxin proteolytic activity: Serotypes A, B, D, and F," *Analytical Biochem.* 296:130-137 (2001).

Schmidt and Skerra, "The random peptide library-assisted engineering of a C-terminal affinity peptide, useful for the detection and purification of a functional Ig Fv fragment," *Protein Eng.* 6(1):109-122 (1993).

Selvin et al. "Luminescence resonance energy transfer," *J. Am. Chem. Soc.* 116:6029-6030 (1994).

Selvin, "Fluorescence resonance energy transfer," *Methods Enzymol.* 246:300-334 (1995).

Selvin, "The Renaissance of Fluorescence Resonance Energy Transfer," *Nature Structural Biology* 7(9):730-734 (2000).

Selvin, "Principles and biophysical applications of lanthanide-based probes," *Annu. Rev. Biophys. Biomol. Struct.* 31:275-302 (2002).

Shavaleev et al., "Sensitized near-infrared emission from complexes of YbIII, NdIII and ErIII by energy-transfer from covalently attached PtII-based antenna units," *Chem. Eur. J.* 9(21):5283-5291 (2003).

Shine et al., "Sensitive method for detection of botulinum toxin type A," abstract, The 38th Interagency Botulism Research Coordinating Committee Meeting, Oct. 17-19 (2001).

Shine et al., "A continuous fluorimetric assay for high-throughput screening for botulinum toxin type A inhibitors," *Naunyn Schmiedebergs Arch. Pharmacol.* 365(Supp. 2):R40 (Jun. 2002).

Shone et al., "Proteolytic Cleavage of Synthetic Fragments of Vesicle-Associated Membrane Protein, Isoform-2 by Botulinum Type B Neurotoxin," *Eur. J. Biochem.* 217:965-971 (1993).

Siegel R. et al, "Measurement of molecular interactions in living cells by fluorescence resonance energy transfer between variants of green fluorescent protein", STKE, Jun. 27, 2000, pp. 1-6.

Sigma Genosys, "Strep-Tag II Protein Expression and Purification System," web page: http://www.sigma-genosys.com/molbio_strep_generalinfo.asp date printed Aug. 5, 2004.

Sittampalam et al., "High-Throughput Screening: Advances in Assay Technologies," *Current Opinion in Chemical Biology* 1:384-391 (1997).

Smith, "Purification of gluthation-S-transferase fusion proteins," *Methods Mol. Cell Biol.* 4:220-229 (1993).

Strynadka and James, "Crystal structures of the helix-loop-helix calcium-binding proteins," *Annu. Rev. Biochem.* 58:951-998 (1989).

Swaminathan and Eswaramoorthy, "Structural Analysis of the Catalytic and Binding Sites of *Clostridium botulinum* Neurotoxin B," *Nature Structural Biology* 7:693-699 (2000).

Tawa et al., "Quantitative Analysis of Fluorescent Caspase Substrate Cleavage in Intact Cells and Identification of Novel Inhibitors of Apoptosis," *Cell Death and Differentiation* 8:30-37 (2001).

Tomchick et al., "Adaptation of an enzyme to regulatory function: Structure of Bacillus subtilis PyrR, a pyr RNA-binding attenuation protein and uracil phosphoribosyltransferase," *Structure* 6(3):337-350 (1998).

Trinquet et al., "New europium cryptates to probe molecular interactions using HTRF®," Application Note 7, pp. 1-3, CIS bio international: France (2003).

Vadakkanchery V. et al, "Proteolysis of SNAP-25 isoforms by botulinum neurotoxin types A, C, and E: Domains and amino acid residues controlling the formation of enzyme-substrate complexes and cleavage", J. Neurochem, vol. 72, 1999, pp. 327-337.

Vazquez-Ibar, et al., "Engineering a terbium-binding site into an integral membrane protein for luminescence energy transfer," *Proc. Natl. Acad. Sci. U.S.A.* 99(6):3487-3492 (2002).

Wagman, Jack, et al., Botulinum A Toxin: Properties of a Toxic Dissociation Product, Archives of Biochemistry and Biophysics, vol. 45, No. 2, Aug. 1953, pp. 375-383.

Wang et al., "A Continuous Fluorescence Assay of Renin Activity," *Analytical Biochemistry* 210:351-359 (1993).

Ward et al., "Spectral perturbations of the Aequorea green fluorescent protein," *Photochem. Photobiol.* 35:803-808 (1982).

Wedin, "One-step fluorescence HTS assays are getting faster, cheaper, smaller, and more sensitive," *Modern Drug Discovery* 2(3):61, 63-64, 66, 68, 71 (1999).

Welch et al., "Lanthanide-binding helix-turn-helix peptides: Solution structure of a designed metallonuclease," *Proc. Natl. Acad. Sci. U.S.A.* 100(7):3725-3730 (2003).

Wu and Brand, "Resonance Energy Transfer: Methods and Applications," *Analytical Biochemistry* 218:1-13 (1994).

Xia and Liu, "Reliable and global measurement of fluorescence resonance energy transfer using fluorescence microscopes," *Biophys. J.* 81(4):2395-2402 (2001).

Xia et al., "Stable SNARE complex prior to evoked synaptic vesicle fusion revealed by fluorescence resonance energy transfer," *J. Biol. Chem.* 276(3):1766-1771 (2001).

Yamasaki et al., "Cleavage of Members of the Synaptobrevin/VAMP Family by Types D and F Botulinal Neurotoxins and Tetanus Toxin," *J. Biol. Chem.* 269:12764-12772 (1994).

Yuan et al., "Synthesis of a terbium fluorescent chelate and its application to time-resolved fluoroimmunoassay," *Anal. Chem.* 73(8):1869-1876 (2001).

Zhang et al., "Creating new fluorescent probes for cell biology," *Nat. Rev. Mol. Cell Biol.* 3(12):906-918 (2002).

Zhao et al., "Cloning and sequence analysis of the human SNAP25 cDNA," *Gene* 145(2):313-314 (1994).

Zimmer, "Green flourescent protein (GFP): Applications, structure, and related photophysical behavior," *Chem. Rev.* 102(3):759-781 (2002).

Zlokarnik et al., "Quantitation of Transcription and Clonal Selection of Single Living Cells with β-Lactamase as Reporter," *Science* 279(5347):84-88 (1998).

Office Action Date Mailed Jun. 20, 2008 in U.S. Appl. No. 10/598,073.

Keller, James E. et al, FEBS Letters, vol. 456, 1999, pp. 137-142, Persistence of botulinum neurotoxin action in cultured spinal cord cells.

Kretsinger, Annu Rev Biochem.-45-239-66, 1976-Abstract—PubMed.

Kretsinger et al, Carp Muscle Calcium-binding Protein, The Journal of Biological Chemistry, vol. 248, No. 9, 3313-3326, 1973.

* cited by examiner

FRET when donor fluorophore is a fluorescent molecule
LRET when donor fluorophore is a lanthanide donor complex Donor Fluorophore Emission
No Acceptor Fluorophore Excitation FRET when donor fluorophore is a fluorescent molecule
LRET when donor fluorophore is a lanthanide donor complex Donor Fluorophore Emission
No Acceptor Fluorophore Excitation

SNAP-25

VAMP

Syntaxin

FIG. 4.

Neuro-2A

Neuro-2A

SH-SY5Y

LUMINESCENCE RESONANCE ENERGY TRANSFER (LRET) ASSAYS FOR CLOSTRIDIAL TOXIN ACTIVITY

This application is a continuation and claims priority pursuant to 35 U.S.C. §120 to U.S. patent application Ser. No. 11/752,596, filed May 23, 2007, a continuation-in-part application which claims priority pursuant to 35 U.S.C. §120 to U.S. patent application Ser. No. 09/942,098, filed Aug. 28, 2001, now U.S. Pat. No. 7,332,567, and U.S. patent application Ser. No. 10/947,071, filed Sep. 21, 2004, now abandoned, each of which is hereby incorporated by reference in its entirety.

All patents and publications cited in this application are hereby incorporated by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochangmyeon, South Korea) BTX-A (Lanzhou Institute Biological Products, China) and Xeomin® (Merz Pharmaceuticals, GmbH., Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

The growing clinical and therapeutic use of Clostridial toxins necessitates the pharmaceutical industry to use accurate assays for Clostridial toxin activity in order to, for example, ensure accurate pharmaceutical formulations and monitor established quality control standards. In addition, given the potential danger associated with small quantities of Clostridial toxins in foodstuffs, the food industry requires Clostridial toxin assays, for example, to validate new food packaging methods and to ensure food safety. The present invention provides novel Clostridial toxin substrates and assays for determining the presence or activity of a Clostridial toxin useful for various industries, such as, e.g., the pharmaceutical and food industries, and provides related advantages as well.

BRIEF DESCRIPTION OF THE DRAWINGS

FIG. 1 shows a schematic of a Clostridial toxin activity assays which relies on a Clostridial toxin substrate disclosed in the present specification. FIG. 1a illustrates a scenario where the test sample lacks any Clostridial toxin activity and only the presence of an uncleaved Clostridial toxin substrate is detected. Upon excitation, the donor fluorophore emits fluorescent light at a characteristic wavelength. However, because the substrate is uncleaved, the close proximity between donor fluorophore and the acceptor fluorophore allows efficient resonance energy transfer. In the case where the donor fluorophore is a fluorescent molecule, the resonance transfer energy is FRET. In the case where the donor fluorophore is a lanthanide donor complex, the resonance transfer energy is LRET. The emission of the donor fluorophore excites the acceptor fluorophore which in turn emits light energy at its characteristic wavelength. Detection of fluorescence from the acceptor fluorophore emissions is indicative of resonance energy transfer and the presence an uncleaved Clostridial toxin substrate. FIG. 1b illustrates a scenario where the test sample has Clostridial toxin activity and the presence of cleaved Clostridial toxin substrate is detected. Upon excitation, the donor fluorophore emits fluorescent light at a characteristic wavelength. However, because the cleavage product of the Clostridial toxin substrate is released into the cytoplasm, the distance between the donor fluorophore and the acceptor fluorophore exceeds the maximal distance allowed for efficient energy transfer. Thus, the emission from the donor fluorophore does not excite the acceptor fluorophore and energy transfer does not occur. A decrease in acceptor fluorophore emissions is indicative of a decrease of energy transfer, a decrease in uncleaved Clostridial toxin substrate and, conversely, an increase in cleaved Clostridial toxin substrate. FIG. 1c illustrates a scenario where the test sample lacks any Clostridial toxin activity and only the presence of an uncleaved Clostridial toxin substrate is detected. Upon excitation, the donor fluorophore emits fluorescent light at a characteristic wavelength. However, because the substrate is uncleaved, the close proximity between donor fluorophore and the acceptor fluorophore allows efficient resonance energy transfer. In the case where the donor fluorophore is a fluorescent molecule, the resonance transfer energy is FRET. In the case where the donor fluorophore is a lanthanide donor complex, the resonance transfer energy is LRET. The emission of the donor fluorophore excites the acceptor fluorophore which in turn emits light energy at its characteristic wavelength. Detection of fluorescence from the acceptor fluorophore emissions is indicative of resonance energy transfer and the presence an uncleaved Clostridial toxin substrate. FIG. 1d illustrates a scenario where the test sample has Clostridial toxin activity and the presence of cleaved Clostridial toxin substrate is detected. Upon excitation, the donor fluorophore emits fluorescent light at a characteristic wavelength. However, because the cleavage product of the Clostridial toxin substrate is released into the reaction solution, the distance between the donor fluorophore and the acceptor fluorophore exceeds the maximal distance allowed for efficient energy transfer. Thus, the emission from the donor fluorophore does not excite the acceptor fluorophore and energy transfer does not occur. A decrease in acceptor fluorophore emissions is indicative of a decrease of energy transfer, a decrease in uncleaved Clostridial toxin substrate and, conversely, an increase in cleaved Clostridial toxin substrate.

FIG. 3 shows a schematic of SNARE proteins.

FIG. 4 shows a schematic of the subcellular localization and cleavage sites of SNAP-25, VAMP and Syntaxin. VAMP is localized to synaptic vesicle membrane, whereas SNAP-25 and Syntaxin are localized to the plasma membrane. BoNT/A and BoNT/E cleave SNAP-25 close to the carboxyl-terminus, releasing nine or 26 residues, respectively. BoNT/B, BoNT/D, BoNT/F, BoNT/G and TeNT act on the conserved central portion of VAMP (white box) and release the amino-terminal cytosolic half of VAMP into the cytosol. BoNT/C1 cleaves SNAP-25 close to the carboxyl-terminus as well as cleaving Syntaxin at a single site near the cytosolic membrane surface. The action of BoNT/C1 results in release of a large portion of the cytosolic domain of Syntaxin, while only a small portion of SNAP-25 is released by selective proteolysis of BoNT/C1.

FIG. 6 shows Western blot analysis identifying cells with high affinity uptake for a Clostridial toxin.

FIG. 7 shows Western blot analysis identifying cells with high affinity uptake for a Clostridial toxin.

FIG. 8 shows Western blot analysis evaluating the effects of treatments used to increase uptake of a Clostridial toxin.

FIG. 9 shows Western blot analysis evaluating the effects of treatments used to increase uptake of a Clostridial toxin.

DETAILED DESCRIPTION

Figure 1A:
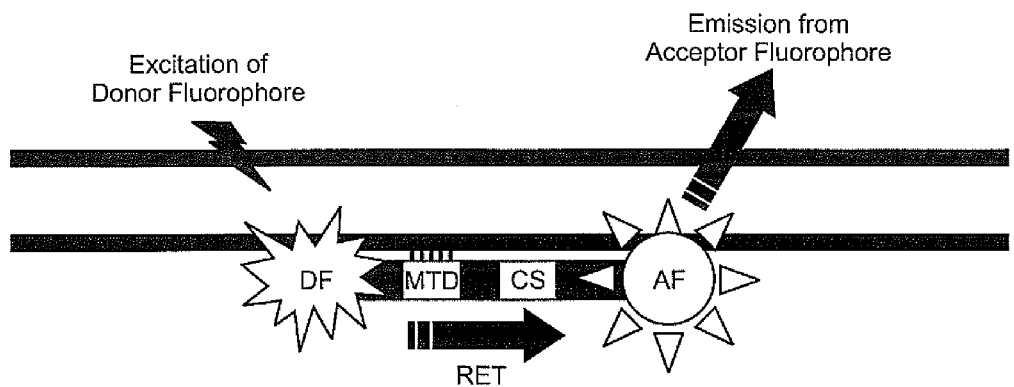
FIGS. 1a and 1b show a cell-based assay scenario which utilizes a Clostridial toxin substrate comprising a donor fluorophore (DF), an acceptor fluorophore (AF), a Clostridial toxin recognition sequence including a cleavage site that intervenes between the donor fluorophore and the acceptor fluorophore (CS), and a membrane targeting domain (MTD).
Figure 1B:
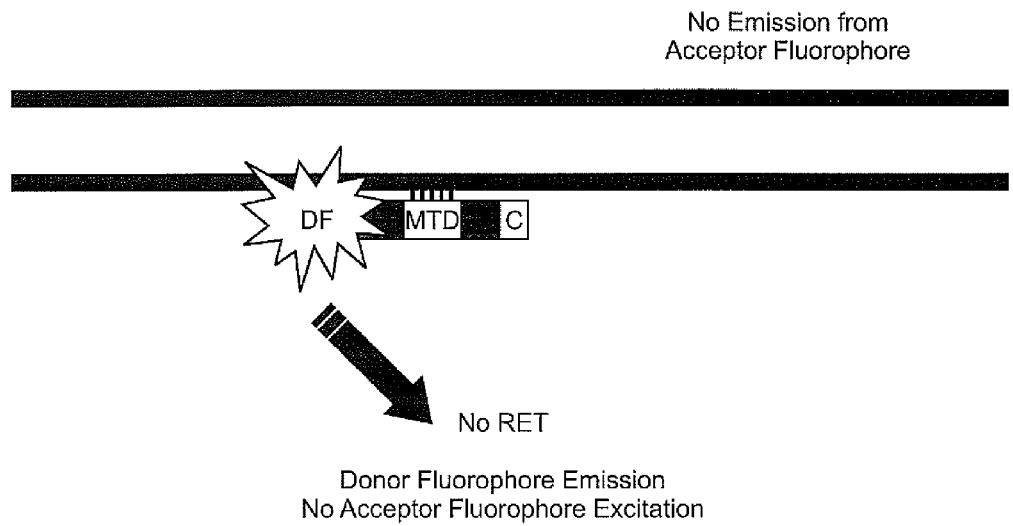
Figure 1B:
Figure 1C:
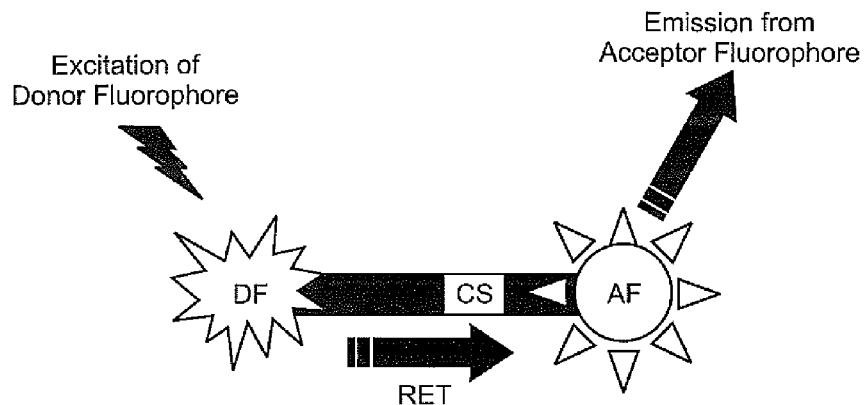
FIG. 1c and 1d show an in vitro-based assay scenario which utilizes a Clostridial toxin substrate comprising a donor fluorophore (DF), an acceptor fluorophore (AF), and a Clostridial toxin recognition sequence including a cleavage site that intervenes between the donor fluorophore and the acceptor fluorophore (CS). In an in vitro assay, the presence of the membrane targeting domain (MTD) is optional.
Figure 1D:
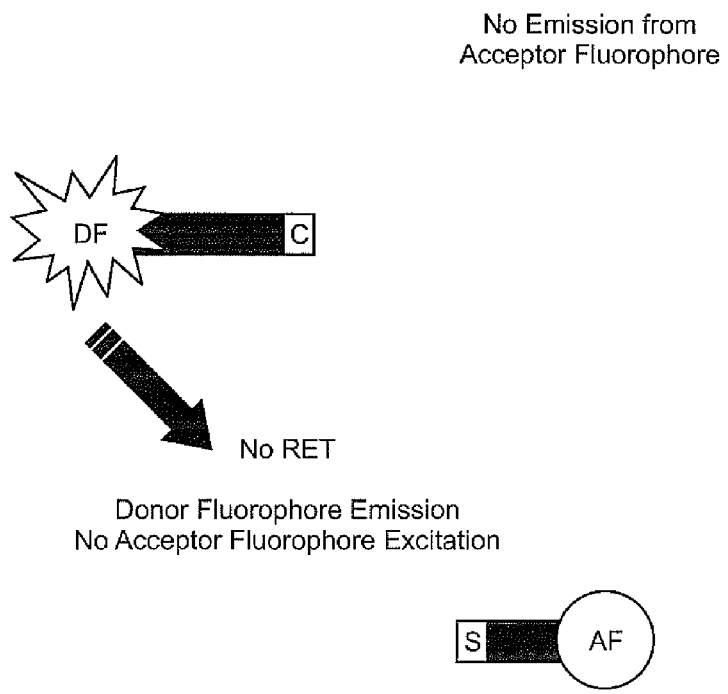

The present invention provides novel substrates and resonance energy transfer activity assays for determining the presence or absence of Clostridial toxin activity. The novel substrates, cells and methods of the present invention reduce the need for animal toxicity studies, yet serve to analyze the multiple steps encompassing the cellular intoxication mechanism, namely, cell binding of the toxin, cellular uptake of the toxin, translocation of the enzymatic domain into the cell cytosol, and proteolytic cleavage of a target substrate. As discussed further below, the novel substrates, cells and methods of the invention can be used to analyze the activity of Clostridial toxins from crude, bulk, refined or formulated samples and are further amenable to automated high throughput assay formats.

Thus, aspects of the present invention provide a Clostridial toxin substrate comprising a lanthanide donor complex, an acceptor and a Clostridial toxin recognition sequence including a cleavage site that intervenes between the lanthanide donor complex and the acceptor; wherein the acceptor has an absorbance spectrum overlapping the emission spectrum of the lanthanide donor complex; and wherein, under the appropriate conditions, resonance energy transfer is exhibited between the lanthanide donor complex and the acceptor. In is envisioned that any and all Clostridial toxin recognition sequences including a Clostridial toxin cleavage site can be used, including, without limitation, a BoNT/A recognition sequence including a BoNT/A cleavage site, a BoNT/B recognition sequence including a BoNT/B cleavage site, a BoNT/C1 recognition sequence including a BoNT/C1 cleavage site, a BoNT/D recognition sequence including a BoNT/D cleavage site, a BoNT/E recognition sequence including a BoNT/E cleavage site, a BoNT/F recognition sequence including a BoNT/F cleavage site, a BoNT/G recognition sequence including a BoNT/G cleavage site, or a TeNT recognition sequence including a TeNT cleavage site. It is also envisioned that any and all lanthanide donor complexes can be used, including, without exception, complexes that comprise a lanthanide biding site and lanthanide ion and complexes that comprise a lanthanide biding site, lanthanide ion and an antennae. It is further envisioned that any and all lanthanide donor complexes can be used, including, without exception, small molecules, proteins and peptidomimetics. It is also envisioned that any and all acceptors can be used, including, without exception, fluorescent molecules, such as, e.g., fluorescent proteins, fluorophore binding proteins and fluorescent dyes; and non-fluorescent molecules, such as, e.g., quenchers.

Other aspects of the present invention provide a cell comprising (a) a Clostridial toxin substrate comprising a lanthanide donor complex, an acceptor and a Clostridial toxin recognition sequence including a cleavage site that intervenes between the lanthanide donor complex and the acceptor; and (b) a Clostridial toxin receptor capable of initiating the intoxication process by selectively binding a Clostridial toxin; wherein the acceptor has an absorbance spectrum overlapping the emission spectrum of the lanthanide donor complex; and wherein, under the appropriate conditions, resonance energy transfer is exhibited between the lanthanide donor complex and the acceptor. It is envisioned that any and all cells capable of selectively binding a binding domain of a Clostridial toxin and expressing a Clostridial toxin substrate can be used, including, a neuronal cell and a non-neuronal cell.

Other aspects of the present invention provide a method of detecting activity of a Clostridial toxin, the method comprising the steps of (a) treating with a test sample, under conditions suitable for Clostridial toxin protease activity, a Clostridial toxin substrate comprising (1) a lanthanide donor complex, (2) an acceptor and (3) a Clostridial toxin recognition sequence including a cleavage site that intervenes between the lanthanide donor complex and the acceptor; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; and (c) detecting resonance energy transfer of the treated substrate from the test sample.

Other aspects of the present invention provide a method of detecting activity of a Clostridial toxin, the method comprising the steps of (a) treating with a test sample, under conditions suitable for Clostridial toxin protease activity, a Clostridial toxin substrate comprising (1) a lanthanide donor complex, (2) an acceptor and (3) a Clostridial toxin recognition sequence including a cleavage site that intervenes between the lanthanide donor complex and the acceptor; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; (c) detecting resonance energy transfer of the treated substrate from the test sample, and (d) comparing the resonance energy transfer detected from the test sample with the resonance energy transfer detected from a control sample subjected to steps (a)-(c), wherein a difference in fluorescence resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Other aspects of the present invention provide a method of determining activity of a Clostridial toxin, the method comprising the steps of (a) contacting with a test sample a cell comprising (1) a Clostridial toxin substrate comprising a lanthanide donor complex, an acceptor and a Clostridial toxin recognition sequence including a cleavage site that intervenes between the lanthanide donor complex and the acceptor; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; and (c) detecting resonance energy transfer of the treated substrate from the test sample.

Other aspects of the present invention provide a method of determining activity of a Clostridial toxin, the method comprising the steps of (a) contacting with a test sample a cell comprising (1) a Clostridial toxin substrate comprising a lanthanide donor complex, an acceptor and a Clostridial toxin recognition sequence including a cleavage site that intervenes between the lanthanide donor complex and the acceptor; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; (c) detecting resonance energy transfer of the treated substrate from the test sample; and (d) comparing the resonance energy transfer detected from the test sample with the resonance energy transfer detected from a control sample subjected to steps (a)-(c), wherein a difference in resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Yet other aspects of the present invention provide, in part, a membrane-associated Clostridial toxin substrate comprising a donor fluorophore, an acceptor, a Clostridial toxin recognition sequence including a Clostridial toxin cleavage site that intervenes between the donor fluorophore and the acceptor and a membrane targeting domain. In is envisioned that any and all Clostridial toxin recognition sequences including a Clostridial toxin cleavage site can be used, including, without limitation, a BoNT/A recognition sequence including a BoNT/A cleavage site, a BoNT/B recognition sequence including a BoNT/B cleavage site, a BoNT/C1 recognition sequence including a BoNT/C1 cleavage site, a BoNT/D recognition sequence including a BoNT/D cleavage site, a BoNT/E recognition sequence including a BoNT/E cleavage site, a BoNT/F recognition sequence including a BoNT/F cleavage site, a BoNT/G recognition sequence including a BoNT/G cleavage site, or a TeNT recognition sequence including a TeNT cleavage site. It is also envisioned that any and all donor fluorophores can be used, including, without exception, fluorescent proteins, fluorescent binding proteins, and fluorescent dyes. It is also envisioned that any and all acceptors can be used, including, without exception, fluorescent molecules, such as, e.g., fluorescent proteins, fluorophore binding proteins and fluorescent dyes; and non-fluorescent molecules, such as, e.g., quenchers.

Yet other aspects of the present invention provide, in part, a cell comprising (a) a membrane-associated Clostridial toxin substrate comprising a donor fluorophore, an acceptor, a Clostridial toxin recognition sequence including a Clostridial toxin cleavage site that intervenes between the donor fluorophore and the acceptor and a membrane targeting domain; and (b) a Clostridial toxin receptor capable of initiating the intoxication process by selectively binding a Clostridial toxin; wherein the acceptor has an absorbance spectrum overlapping the emission spectrum of the lanthanide donor complex; and wherein, under the appropriate conditions, resonance energy transfer is exhibited between the lanthanide donor complex and the acceptor. It is envisioned that any and all cells capable of selectively binding a Clostridial toxin and expressing a Clostridial toxin substrate can be used, including, a neuronal cell and a non-neuronal cell. It is also envisioned that any and all donor fluorophores can be used, including, without exception, fluorescent proteins, fluorescent binding proteins, and fluorescent dyes. It is also envisioned that any and all acceptors can be used, including, without exception, fluorescent molecules, such as, e.g., fluorescent proteins, fluorescent binding proteins and fluorescent dyes; and non-fluorescent molecules, such as, e.g., quenchers. It is envisioned that any and all cells capable of selectively binding a binding domain of a Clostridial toxin and expressing a Clostridial toxin substrate can be used, including, a neuronal cell and a non-neuronal cell.

Other aspects of the present invention provide a method of detecting activity of a Clostridial toxin, the method comprising the steps of (a) treating with a test sample, under conditions suitable for Clostridial toxin protease activity, a Clostridial toxin substrate comprising (1) a donor fluorophore, (2) an acceptor, (3) a Clostridial toxin recognition sequence including a cleavage site that intervenes between the donor fluorophore and the acceptor and (4) a membrane targeting domain; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the donor fluorophore; and (c) detecting resonance energy transfer of the treated substrate from the test sample.

Other aspects of the present invention provide a method of detecting activity of a Clostridial toxin, the method comprising the steps of (a) treating with a test sample, under conditions suitable for Clostridial toxin protease activity, a Clostridial toxin substrate comprising (1) a donor fluorophore, (2) an acceptor, (3) a Clostridial toxin recognition sequence including a cleavage site that intervenes between the donor fluorophore and the acceptor and (4) a membrane targeting domain; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the lanthanide donor complex; (c) detecting resonance energy transfer of the treated substrate from the test sample, and (d) comparing the resonance energy transfer detected from the test sample with the resonance energy transfer detected from a control sample subjected to steps (a)-(c), wherein a difference in fluorescence resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Other aspects of the present invention provide a method of determining activity of a Clostridial toxin, the method comprising the steps of (a) contacting with a test sample a cell comprising (1) a Clostridial toxin substrate comprising a donor fluorophore, an acceptor, a Clostridial toxin recognition sequence including a cleavage site that intervenes between the donor fluorophore and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the donor fluorophore; and (c) detecting resonance energy transfer of the treated substrate from the test sample.

Other aspects of the present invention provide a method of determining activity of a Clostridial toxin, the method comprising the steps of (a) contacting with a test sample a cell comprising (1) a Clostridial toxin substrate comprising a donor fluorophore, an acceptor, a Clostridial toxin recognition sequence including a cleavage site that intervenes between the donor fluorophore and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the donor fluorophore; (c) detecting resonance energy transfer of the treated substrate from the test sample; and (d) comparing the resonance energy transfer detected from the test sample with the resonance energy transfer detected from a control sample subjected to steps (a)-(c), wherein a difference in resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Bacteria of the genus Clostridia are strictly anaerobic to aero-tolerant spore-forming bacilli found in soil, freshwater and saltwater sediments, household dust, the surface of foods, feces as well as in the normal intestinal flora of humans and animals. While the majority of isolates are gram-positive, a few gram-negative species exist. Members of this genus produce sophisticated exotoxins that are among the most potent toxins known in the world. Exposure to these toxins during the course of Clostridia infection is the primary cause underlying disease pathogenesis. Clostridia are a major threat to human and animal health, being responsible for many diseases including botulism, tetanus, gas gangrene, pseudomembranous colitis and food poisoning. For example, *Clostridium argentinense, C. bifermentans, C. histolyticum, C. novyi, C. septicum, C. sporogenes* and *C. tertium* are etiological agents for gas gangrene. *C. perfringens* is responsible for foodborne illness, enteritis necroticans where as *C. difficile* is responsible for pseudomembranous enterocolitis. Both *C. baratii* and *C. butyricum* are causative agents for a form of foodborne, intestinal and wound botulism. Interestingly, only a few species of these bacteria are pathogenic for humans, most are saprophytic. Thus, in most cases, Clostridia are opportunistic pathogens that infect a host whose health is compromised.

Of all Clostridia, *Clostridium botulinum* and *Clostridium tetani* produce the most potent biological toxins known and are the causative agents of the neuroparalytic syndromes botulism and tetanus. Seven antigenically-distinct types of Botulinum toxins (BoNTs) have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. The amino acid sequences of eight Clostridial toxin serotypes have been derived from the corresponding genes (Niemann, "Molecular Biology of Clostridial Neurotoxins" in Sourcebook of Bacterial Protein Toxins Alouf and Freer (Eds.) pp. 303-348 London: Academic Press 1991). It is recognized by those of skill in the art that within each type of Clostridial toxin there can be various strains differing somewhat in their amino acid sequence, and also in the polynucleotides encoding these proteins. While all seven BoNT serotypes have similar structure and pharmacological properties, each also displays heterogeneous bacteriological characteristics. In contrast, tetanus toxin (TeNT) is produced by a uniform group of *C. tetani*. Two other species of clostridia, *C. baratii* and *C. butyricum*, also produce toxins similar to BoNT/F and BoNT/E, respectively.

Clostridia toxins (CoNTs) are each translated as a single chain polypeptide of approximately 150 kDa that is subsequently cleaved by proteolytic scission within a disulphide loop by bacterial or tissue proteases. This posttranslational processing yields a di-chain molecule comprising an approximately 50 kDa light chain (LC) and an approximately 100 kDa heavy chain (HC) held together by a single disulphide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the toxin from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell.

Figure 2:
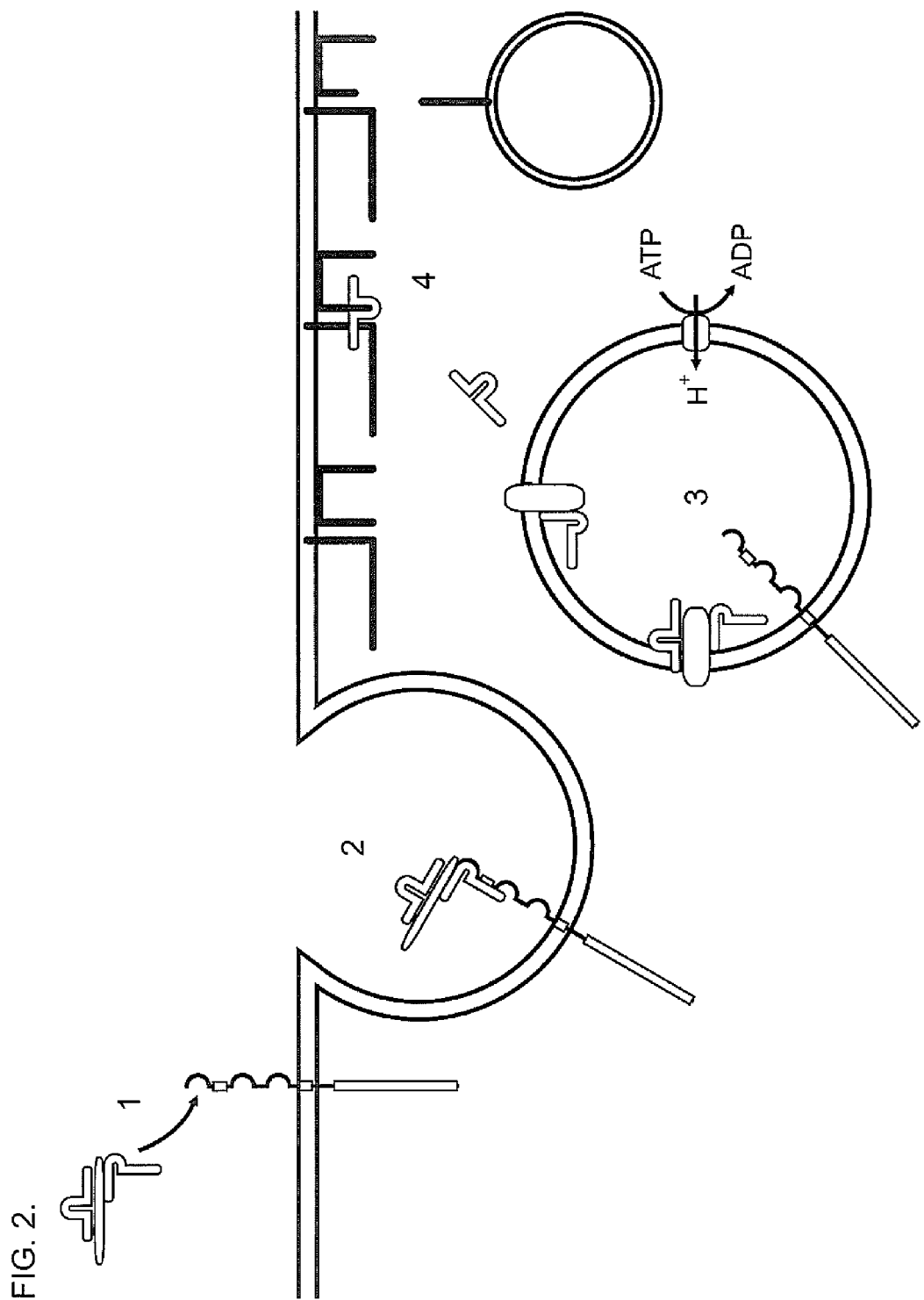
FIG. 2 shows a schematic of the current paradigm of the intoxication mechanism for Clostridial toxins in a central or peripheral neuron. This intoxication process can be described as comprising four steps: 1) receptor binding, where Clostridial toxin binding to a Clostridial receptor system initiates the intoxication process; 2) complex internalization, where after toxin binding, a vesicle containing a toxin/receptor system complex is endocytosised into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, enzymatic activation of the light chain; and release of the activated light chain and 4) enzymatic target modification, where the light chain of Clostridial toxin proteolytically cleaves its target SNARE substrates, such as, e.g., SNAP-25, VAMP or Syntaxin.
Figure 3A:
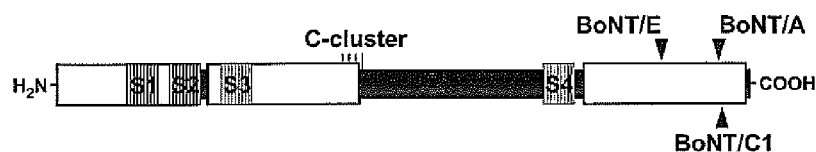
FIG. 3a shows the general domain organization of SNAP-25, VAMP and Syntaxin depicting approximate locations of the α-helical regions (white boxes), SNARE motifs (Hatched boxes with S1, S2, S3, S4, V1, V2, X1 or X2 designations) and the membrane anchoring domains (white boxes designated MA).
Figure 3A:
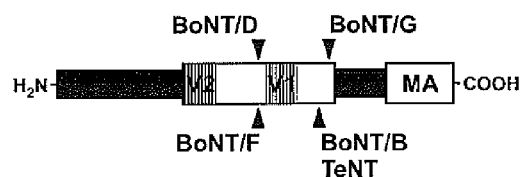
Figure 3A:
Figure 3B:
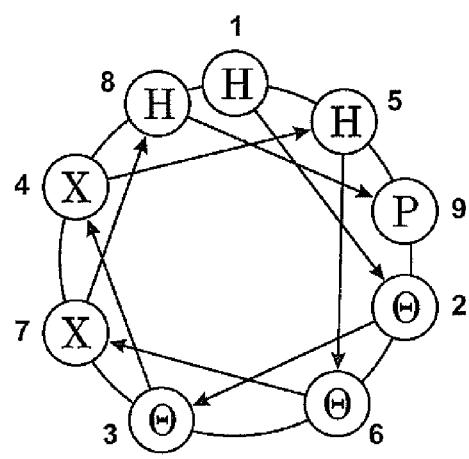
FIG. 3b shows the helical organization of a SNARE motif.

The binding, translocation and enzymatic activity of these three functional domains are all necessary for toxicity. While all details of this process are not yet precisely known, the overall cellular intoxication mechanism whereby CoNTs enter a neuron and inhibit neurotransmitter release is similar, regardless of type. Although the applicants have no wish to be limited by the following description, the intoxication mechanism can be described as comprising four steps: 1) receptor binding, 2) complex internalization, 3) light chain translocation, and 4) enzymatic target modification (see FIG. 2). The process is initiated when the $H_C$ domain of a CoNT binds to CoNT-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the CoNT/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. The light chain of the toxin is released from the intracellular vesicle into the cytosol where it specifically targets one of three known core components of the neurotransmitter release apparatus. There of these core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family (see FIG. 3). The selective proteolysis of synaptic SNAREs accounts for the total block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); M. Zouhair Atassi, *Basic and Therapeutic Aspects of Botulinum and Tetanus Toxins*, (Dirk W. Dressler & Joseph J. Jankovic eds., 2003); Giovanna Lalli et al., *The Journey of Tetanus and Botulinum Neurotoxins in Neurons*, 11 (9) Trends Microbiol. 431-437, (2003).

TeNT and BoNT/B, BoNT/D, BoNT/F, and BoNT/G specifically recognize VAMP (also known as synaptobrevin), an integral protein of the synaptic vesicle membrane. VAMP is cleaved at distinct bonds depending on the toxin. BoNT/A and /E recognize and specifically cleave SNAP-25, a protein of the presynaptic membrane, at two different sites in the carboxyl-terminal portion of the protein. BoNT/C1 cleaves Syntaxin, a protein of the nerve plasmalemma, in addition to SNAP-25. The three protein targets of the CoNTs are conserved from yeast to humans although cleavage sites and toxin susceptibility are not necessarily conserved, see below; see, also, e.g., Humeau, supra, (2000); Heiner Niemann et al., Clostridial neurotoxins: new tools for dissecting exocytosis, 4(5) Trends Cell Biol. 179-185 (1994); and Rossella Pellizzari et al., Tetanus and botulinum neurotoxins: mechanism of action and therapeutic uses, 354(1381) Philos. Trans. R. Soc. Lond. B Biol. Sci. 259-268 (1999).

The natural targets of the Clostridial toxins include VAMP, SNAP-25, and Syntaxin. VAMP is associated with the synaptic vesicle membrane, whereas SNAP-25 and Syntaxin are associated with the plasma membrane (see FIG. 4). BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves Syntaxin at a single site near the cytosolic membrane surface. Thus, BoNT/B, BoNT/C1, BoNT/D, BoNT/F, BoNT/G or TeNT proteolysis results in release of a large portion of the cytosolic domain of VAMP or Syntaxin, while only a small portion of SNAP-25 is released by BoNT/A, BoNT/C1 or BoNT/E cleavage, see, e.g., Humeau et al., supra, (2000); Turton et al., supra, (2002); Lalli et al., supra (2003).

Figure 4:
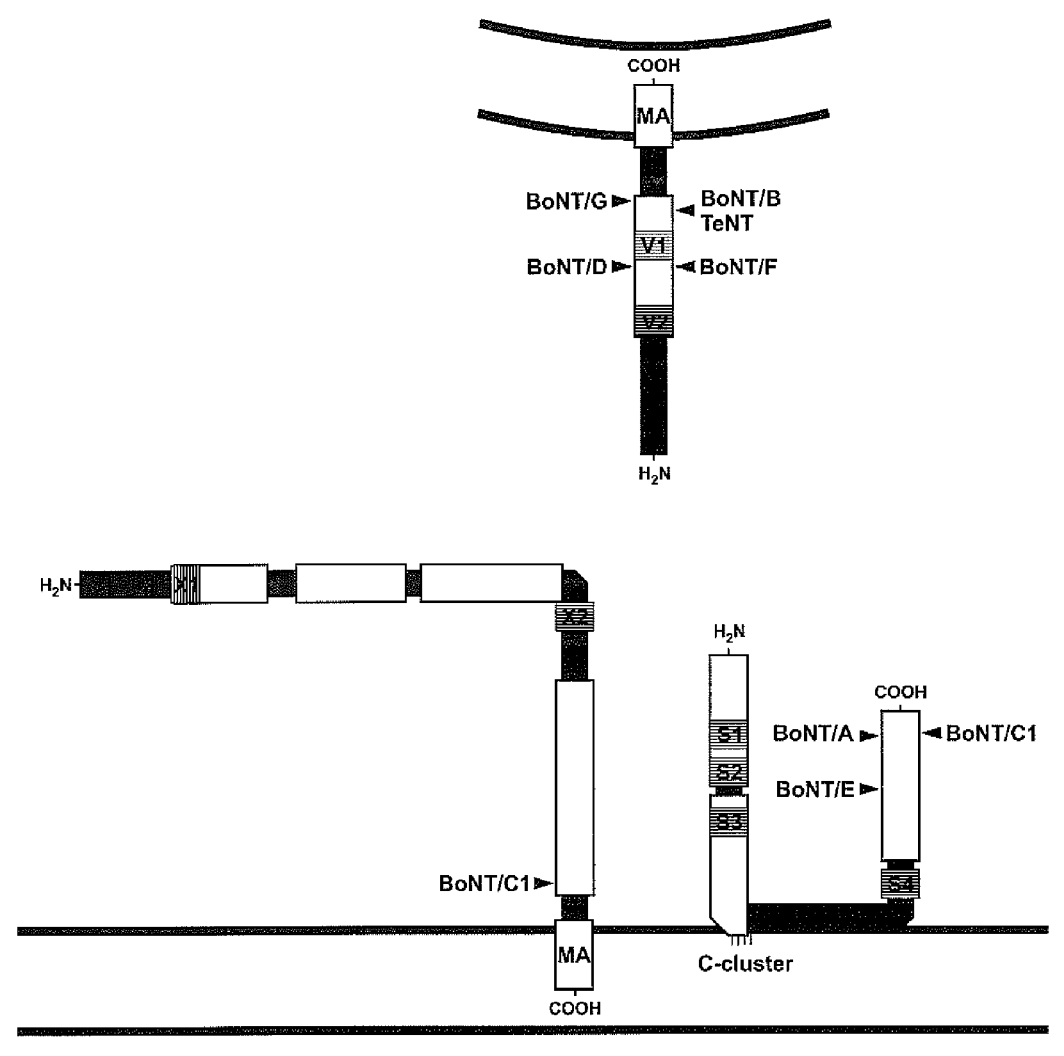

Naturally occurring SNAP-25, a protein of about 206 residues lacking a transmembrane segment, is associated with the cytosolic surface of the nerve plasmalemma (see FIG. 4). SNAP-25 is required for axonal growth during development and may be required for nerve terminal plasticity in the mature nervous system. SNAP-25 has been isolated from a variety of vertebrate and invertebrate species including, e.g., species belonging to the genera *Homo, Macaca, Bos, Rattus, Mus, Gallus, Carassius, Danio, Torpedo, Xenopus, Strongylocentrotus, Drosophila, Hirudo, Loligo, Lymnaea* and *Caenorhabditis*. In humans, at least two isoforms are differentially expressed during development; isoform a is constitutively expressed during fetal development, while isoform b appears at birth and predominates in adult life. SNAP-25 analogues such as SNAP-23 also are expressed outside the nervous system, for example, in pancreatic cells.

Naturally occurring VAMP is a protein of about 120 residues, with the exact length depending on the species and isoform. As shown in FIG. 4, VAMP contains a short carboxyl-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP colocalizes with synaptophysin on synaptic vesicle membranes. VAMP has been isolated from a variety of vertebrate and invertebrate species including, e.g., species belonging to the genera *Homo, Macaca, Bos, Rattus, Mus, Gallus, Danio, Torpedo, Xenopus, Strongylocentrotus, Drosophila, Hirudo, Loligo, Lymnaea, Aplysia* and *Caenorhabditis*. In addition, multiple isoforms of VAMP have been identified including VAMP-1, VAMP-2 and VAMP-3/cellubrevin, and forms insensitive to toxin cleavage have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 orthologs have a valine in place of the glutamine present in human and mouse VAMP-1 at the TeNT or BoNT/B cleavage site. The substitution does not affect BoNT/D, /F or /G, which cleave both VAMP-1 and VAMP-2 with similar rates.

Naturally occurring Syntaxin is located on the cytosolic surface of the nerve plasmalemma and is membrane-anchored via a carboxyl-terminal segment, with most of the protein exposed to the cytosol (see FIG. 4). Syntaxin colocalizes with calcium channels at the active zones of the presynaptic membrane, where neurotransmitter release takes place. In addition, Syntaxin interacts with synaptotagmin, a protein of the SSV membrane that forms a functional bridge between the plasmalemma and the vesicles. Syntaxin has been isolated from a variety of vertebrate and invertebrate species including, e.g., species belonging to the genera *Homo, Bos, Rattus, Mus, Gallus, Danio, Strongylocentrotus, Drosophila, Hirudo, Loligo, Lymnaea* and *Aplysia*. Three isoforms of slightly different length (285 and 288 residues) have been identified in nerve cells (isoforms 1A, 1B1 and 1B2), with isoforms 2, 3, 4 and 5 expressed in other tissues. The different isoforms have varying sensitivities to BoNT/C1, with the 1A, 1B1, 1B2, 2 and 3 Syntaxin isoforms cleaved by this toxin.

The present specification provides, in part, a Clostridial toxin substrate. By definition, a Clostridial toxin substrate is susceptible to cleavage by at least one Clostridial toxin under conditions suitable for Clostridial toxin protease activity. A variety of Clostridial toxin substrates are discussed herein below. Additional Clostridial toxin substrates are described in, e.g., Lance E. Steward, et al., FRET Protease Assays for Clostridial Toxins, U.S. Pat. No. 7,208,285 (Apr. 24, 2007); Lance E. Steward, et al., FRET Protease Assays for Botulinum Serotype A/E Toxins, U.S. Patent Publication 2003/0143650 (Jul. 31, 2003); Ester Fernandez-Salas, et al., Cell-based Fluorescence Resonance Energy Transfer (FRET) Assays for Clostridial Toxins, U.S. Pat. No. 7,183,066 (Feb. 27, 2007); and Dudley J. Williams et al., Lanthanide-based Substrates and Methods for Determining Clostridial Toxin Activity, U.S. Patent Publication 2006/0063221 (Mar. 23, 2006), each of which is hereby incorporated by reference in its entirety. In aspects of this embodiment, a Clostridial toxin substrate useful in the invention is a peptide or peptidomimetic having a defined length. A Clostridial toxin substrate can be, for example, a peptide or peptidomimetic having at least 100, at least 150, at least 200, at least 250, at least 300, at least 350, at least 400 residues, at least 500 residues, at least 600 residues, at least 700 residues or at least 800 residues. In other embodiments, a Clostridial toxin substrate has at most 20 residues, at most 30 residues, at most 40 residues, at most 50 residues, at most 100 residues, at most 150 residues, at most 200 residues, at most 250 residues, at most 300 residues, at most 350 residues, at most 400 residues at most 500 residues, at most 600 residues, at most 700 residues or at most 800 residues.

The Clostridial toxin substrates disclosed in the present specification comprise, in part, a Clostridial toxin recognition sequence including a Clostridial toxin cleavage site. As used herein, the term "Clostridial toxin recognition sequence" means a scissile bond together with adjacent or non-adjacent recognition elements, or both, sufficient for detectable proteolysis at the scissile bond by a Clostridial toxin under conditions suitable for Clostridial toxin protease activity. It is envisioned that a Clostridial toxin recognition sequence can be of any length, with the proviso that the Clostridial toxin recognition sequence can be cleaved by a Clostridial toxin. In aspects of this embodiment, a Clostridial toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, at least 200 residues, at least 250 residues or at least 300 residues. In other embodiments, a Clostridial toxin recognition sequence has at most 20 residues, at most 30 residues, at most 40 residues, at most 50 residues, at most 100 residues, at most 150 residues, at most 200 residues, at most 250 residues or at most 300 residues. A variety of Clostridial toxin recognition sequences are discussed herein below.

Clostridial toxin substrates useful in aspects of the invention include peptides and peptidomimetics as well as derivative forms thereof. A peptide comprises at least two amino acids covalently linked together. As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as, without limitation, 4-hydroxyproline, hydroxylysine, desmosine, isodesmosine, homocysteine, citrulline and ornithine. Non-naturally occurring amino acids include, but are not limited to, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups or moieties on the amino acid or by derivatization of the amino acid.

As used herein, the term "peptidomimetic" is used broadly to mean a peptide-like molecule that is cleaved by the same Clostridial toxin as the peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and are cleaved by the same Clostridial toxin as the peptide substrate upon which the peptidomimetic is derived, see, e.g., Goodman & Ro, Peptidomimetics for Drug Design, pp. 803-861, in "Burger's Medicinal Chemistry and Drug Discovery" Vol. 1 (ed. M. E. Wolff; John Wiley & Sons 1995).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β, β-dimethyl or β-methyl amino acid; a β-substituted-2,3-methano amino acid; an $NC^\delta$ or $C^\alpha$-$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

A wide variety of Clostridial toxin recognition sequences are useful in aspects of the invention. Specific and distinct cleavage sites for different Clostridial toxins are well known in the art. BoNT/A cleaves a Gln-Arg bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table 1). In standard nomenclature, the sequence surrounding a Clostridial toxin cleavage site is denoted $P_5$-$P_4$-$P_3$-$P_2$-$P_1$-$P_1'$-$P_2'$-$P_3'$-$P_4'$-$P_5'$ with $P_1$-$P_1'$ representing the scissile bond. It is understood that a $P_1$ or $P_1'$ site, or both, can be substituted with another amino acid or amino acid mimetic in place of the naturally occurring residue. As an example, BoNT/A substrates have been prepared in which the $P_1$ position (Gln) is modified to be an alanine, 2-aminobutyric acid or asparagine residue; these substrates were hydrolyzed by BoNT/A at the $P_1$-Arg bond, see, e.g., James J. Schmidt & Karen A Bostian, Endoproteinase activity of type A botulinum neurotoxin: substrate requirements and activation by serum albumin, 16(1) J. Protein Chem. 19-26 (1997). While it is recognized that substitutions can be introduced at the $P_1$ position of the scissile bond, for example, a BoNT/A scissile bond, it is further recognized that conservation of the $P_1'$ residue can be advantageous, see, e.g., Vadakkanchery V. Vaidyanathan et al., Proteolysis of SNAP-25 isoforms by botulinum neurotoxin types A, C, and E: domains and amino acid residues controlling the formation of enzyme-substrate complexes and cleavage, 72(1) J. Neurochem. 327-337 (1999).

TABLE 1

| Bonds Cleaved in Human VAMP-2, SNAP-25 or Syntaxin-1 | | | |
| --- | --- | --- | --- |
| Toxin | Target | $P_4$-$P_3$-$P_2$-$P_1$-$P_1'$-$P_2'$-$P_3'$-$P_4'$ | SEQ ID NO: |
| BoNT/A | SNAP-25 | Glu-Ala-Asn-Gln-Arg*-Ala-Thr-Lys | 96 |
| BoNT/B | VAMP-2 | Gly-Ala-Ser-Gln-Phe*-Glu-Thr-Ser | 97 |

TABLE 1-continued

Bonds Cleaved in Human VAMP-2, SNAP-25 or Syntaxin-1

| Toxin | Target | $P_4$-$P_3$-$P_2$-$P_1$-$P_1$'-$P_2$'-$P_3$'-$P_4$' | SEQ ID NO: |
|---|---|---|---|
| BoNT/C1 | Syntaxin-1 | Asp-Thr-Lys-Lys-Ala*-Val-Lys-Tyr | 98 |
| BoNT/C1 | SNAP-25 | Ala-Asn-Gln-Arg-Ala*-Thr-Lys-Met | 99 |
| BoNT/D | VAMP-2 | Arg-Asp-Gln-Lys-Leu*-Ser-Glu-Leu | 100 |
| BoNT/E | SNAP-25 | Gln-Ile-Asp-Arg-Ile*-Met-Glu-Lys | 101 |
| BoNT/F | VAMP-2 | Glu-Arg-Asp-Gln-Lys*-Leu-Ser-Glu | 102 |
| BoNT/G | VAMP-2 | Glu-Thr-Ser-Ala-Ala*-Lys-Leu-Lys | 103 |
| TeNT | VAMP-2 | Gly-Ala-Ser-Gln-Phe*-Glu-Thr-Ser | 104 |

*Scissile bond shown in bold

Thus, an embodiment, a Clostridial toxin substrate comprises, in part, a Clostridial toxin recognition sequence comprising a cleavage site. In an aspect of this embodiment, a Clostridial toxin substrate comprises a Clostridial toxin recognition sequence in which the $P_1$' residue is not modified or substituted relative to the naturally occurring residue in a target protein cleaved by the Clostridial toxin. In another aspect of this embodiment, a Clostridial toxin substrate comprises a Clostridial toxin recognition sequence in which the $P_1$ residue is modified or substituted relative to the naturally occurring residue in a target protein cleaved by the Clostridial toxin; such a Clostridial toxin substrate retains susceptibility to peptide bond cleavage between the $P_1$ and $P_1$' residues.

In another embodiment, a Clostridial toxin substrate comprises a Clostridial toxin recognition sequence in which the residue at position $P_1$, $P_2$, $P_3$, $P_4$, $P_5$ or $P_{>5}$ is substituted with an amino acid conjugated to a donor fluorophore or acceptor, and in which the residue at position $P_1$', $P_2$', $P_3$', $P_4$', $P_5$' or $P_{>5}$' is substituted with an amino acid conjugated to a donor fluorophore or acceptor. In an aspect of this embodiment, a Clostridial toxin substrate comprises a Clostridial toxin recognition sequence in which the residue at position $P_1$, $P_3$, $P_4$ or $P_{>5}$ is substituted with an amino acid conjugated to a donor fluorophore or acceptor, and in which the residue at position $P_2$', $P_3$', $P_5$' or $P_{>5}$' is substituted with an amino acid conjugated to a donor fluorophore or acceptor. In an aspect of this embodiment, a Clostridial toxin substrate comprises a Clostridial toxin recognition sequence in which the residue at $P_3$, $P_4$ or $P_{>5}$ is substituted with an amino acid conjugated to a donor fluorophore or acceptor, and in which the residue at position $P_2$', $P_3$', $P_5$' or $P>5$' is substituted with an amino acid conjugated to a donor fluorophore or acceptor. It is understood that the amino acid side chain of the residue conjugated to a donor fluorophore or acceptor can be otherwise identical to the residue present in the corresponding position of the naturally occurring target protein, or can contain, for example, a different side chain.

In another embodiment, a Clostridial toxin substrate comprises a Clostridial toxin recognition sequence in which one of the residue substituted with an amino acid conjugated to a donor fluorophore or acceptor is excluded from $P_5$-$P_4$-$P_3$-$P_2$-$P_1$-$P_1$'-$P_2$'-$P_3$'-$P_4$'-$P_5$' sequence. In another embodiment, a Clostridial toxin substrate comprises a Clostridial toxin recognition sequence in which both residues substituted with an amino acid conjugated to a donor fluorophore or acceptor are excluded from $P_5$-$P_4$-$P_3$-$P_2$-$P_1$-$P_1$'-$P_2$'-$P_3$'-$P_4$'-$P_5$' sequence. It is envisioned that the excluded residue or residues can be distance from the $P_1$-$P_1$' cleavage site with the proviso that the substrate can be cleaved by a Clostridial toxin and, where under the appropriate conditions, resonance energy transfer is exhibited between the donor fluorophore and acceptor. In aspects of this embodiment, the excluded residue or residues substituted with an amino acid conjugated to a donor fluorophore or acceptor can be, e.g., at least five residues away from the $P_1$-$P_1$' cleavage site, at least six residues away from the $P_1$-$P_1$' cleavage site, at least seven residues away from the $P_1$-$P_1$' cleavage site, at least eight residues away from the $P_1$-$P_1$' cleavage site, at least nine residues away from the $P_1$-$P_1$' cleavage site or at least ten residues away from the $P_1$-$P_1$' cleavage site. In other aspects of this embodiment, the excluded residue or residues substituted with an amino acid conjugated to a donor fluorophore or acceptor can be, e.g., at least 15 residues away from the $P_1$-$P_1$' cleavage site, at least 20 residues away from the $P_1$-$P_1$' cleavage site, at least 25 residues away from the $P_1$-$P_1$' cleavage site, at least 30 residues away from the $P_1$-$P_1$' cleavage site, at least 40 residues away from the $P_1$-$P_1$' cleavage site or at least 50 residues away from the $P_1$-$P_1$' cleavage site. In still other aspects of this embodiment, the excluded residue or residues substituted with an amino acid conjugated to a donor fluorophore or acceptor can be, e.g., at least 75 residues away from the $P_1$-$P_1$' cleavage site, at least 100 residues away from the $P_1$-$P_1$' cleavage site, at least 125 residues away from the $P_1$-$P_1$' cleavage site, at least 150 residues away from the $P_1$-$P_1$' cleavage site, at least 175 residues away from the $P_1$-$P_1$' cleavage site or at least 200 residues away from the $P_1$-$P_1$' cleavage site.

In other aspects of this embodiment, the excluded residue or residues substituted with an amino acid conjugated to a donor fluorophore or acceptor can be, e.g., at most five residues away from the $P_1$-$P_1$' cleavage site, at most six residues away from the $P_1$-$P_1$' cleavage site, at most seven residues away from the $P_1$-$P_1$' cleavage site, at most eight residues away from the $P_1$-$P_1$' cleavage site, at most nine residues away from the $P_1$-$P_1$' cleavage site or at most ten residues away from the $P_1$-$P_1$' cleavage site. In other aspects of this embodiment, the excluded residue or residues substituted with an amino acid conjugated to a donor fluorophore or acceptor can be, e.g., at most 15 residues away from the $P_1$-$P_1$' cleavage site, at most 20 residues away from the $P_1$-$P_1$' cleavage site, at most 25 residues away from the $P_1$-$P_1$' cleavage site, at most 30 residues away from the $P_1$-$P_1'$ cleavage site, at most 40 residues away from the $P_1$-$P_1'$ cleavage site or at most 50 residues away from the $P_1$-$P_1'$ cleavage site. In still other aspects of this embodiment, the excluded residue substituted with an amino acid conjugated to a donor fluorophore or acceptor can be, e.g., at most 75 residues away from the $P_1$-$P_1'$ cleavage site, at most 100 residues away from the $P_1$-$P_1'$ cleavage site, at most 125 residues away from the $P_1$-$P_1'$ cleavage site, at most 150 residues away from the $P_1$-$P_1'$ cleavage site, at most 175 residues away from the $P_1$-$P_1'$ cleavage site or at most 200 residues away from the $P_1$-$P_1'$ cleavage site.

It is understood that the donor fluorophore, acceptor, or both, can be located within or without of the active site cavity of a Clostridial toxin. Thus, a clostridial toxin substrate useful in the present invention can be designed such that, when bound by a toxin, the donor fluorophore, acceptor, or both, is excluded from the active site cavity of the Clostridial toxin. Non-limiting examples of a peptide region from a clostridial toxin substrate thought to be bound within the active site cavity of a Clostridial toxin include SNAP-25 amino acids 174-185 of SEQ ID NO: 1, SNAP-25 amino acids 191-202 of SEQ ID NO: 1, SNAP-25 amino acids 192-203 of SEQ ID NO: 1, VAMP-1 amino acids 54-65 of SEQ ID NO: 28, VAMP-1 amino acids 55-66 of SEQ ID NO: 28, VAMP-1 amino acids 72-83 of SEQ ID NO: 28, VAMP-1 amino acids 77-88 of SEQ ID NO: 28, and Syntaxin-1 amino acids 247-258 of SEQ ID NO: 66. A person of ordinary skill in the art would understand that alignment of amino acid sequences of other Clostridial toxin substrates centered on the cleavage site would reveal additional peptide region from a clostridial toxin substrate thought to be bound within the active site cavity of a Clostridial toxin.

Aspects of the present invention provide, in part, a substrate, cell or method that incorporates a BoNT/A, BoNT/B, BoNT/C1, BoNT/D, BoNT/E, BoNT/F, BoNT/G or TeNT substrate in which, when bound by toxin, the donor fluorophore, acceptor, or both, is excluded from the active site cavity of toxin holoenzyme.

In one embodiment, a BoNT/A substrate comprises at least six residues of human SNAP 25, where the six residues include $Gln_{197}$-$Arg_{198}$, and further contains a donor fluorophore, acceptor, or both, which is positioned outside of residues $Arg_{191}$ to $Met_{202}$ of SNAP-25, which can be within the active site cavity of BoNT/A. In another embodiment, a BoNT/B substrate comprises at least six residues of VAMP-2, where the six residues include $Gln_{76}$-$Phe_{77}$, and further contains a donor fluorophore, acceptor, or both, which is positioned outside of residues $Leu_{70}$ to $Ala_{81}$ of VAMP-2, which can be within the active site cavity of BoNT/B. In another embodiment, a BoNT/C1 substrate comprises at least six residues of human SNAP 25, where the six residues include $Arg_{198}$-$Ala_{199}$, and further contains a donor fluorophore, acceptor, or both, which is positioned outside of residues $Ile_{192}$ to $Leu_{203}$ of SNAP-25, which can be within the active site cavity of BoNT/C1. In still another embodiment, a BoNT/C1 substrate comprises at least six residues of human Syntaxin-1, where the six residues include $Lys_{253}$-$Ala_{254}$, and further contains a donor fluorophore, acceptor, or both, which is positioned outside of residues $Ala_{247}$ to $Gln_{258}$ of Syntaxin-1, which can be within the active site cavity of BoNT/C1. In still another embodiment, a BoNT/D substrate comprises at least six residues of VAMP-2, where the six residues include $Lys_{59}$-$Leu_{60}$, and further contains a donor fluorophore, acceptor, or both, which is positioned outside of residues $Val_{53}$ to $Asp_{64}$ of VAMP-2, which can be within the active site cavity of BoNT/D. In still another embodiment, a BoNT/E substrate comprises at least six residues of SNAP 25, where the six residues include $Arg_{180}$-$Ile_{181}$, and further contains a donor fluorophore, acceptor, or both, which is positioned outside of residues $Gln_{174}$ to $Ala_{185}$ of SNAP 25, which can be within the active site cavity of BoNT/E. In yet another embodiment, a BoNT/F substrate comprises at least six residues of VAMP-2, where the six residues include $Gln_{58}$-$Lys_{59}$, and further contains a donor fluorophore, acceptor, or both, which is positioned outside of residues $Lys_{52}$ to $Leu_{63}$ of VAMP-2, which can be within the active site cavity of BoNT/F. In yet another embodiment, a BoNT/G substrate comprises at least six residues of VAMP-2, where the six residues include $Ala_{81}$-$Ala_{82}$, and further contains a donor fluorophore, acceptor, or both, which is positioned outside of residues $Ser_{75}$ to $Arg_{86}$ of VAMP-2, which can be within the active site cavity of BoNT/G. In yet another embodiment, a TeNT substrate comprises at least six residues of VAMP-2, where the six residues include $Gln_{76}$-$Phe_{77}$, and further contains a donor fluorophore, acceptor, or both, which is positioned outside of residues $Leu_{70}$ to $Ala_{81}$ of VAMP-2, which can be within the active site cavity of TeNT.

In a complex of a VAMP substrate and the light chain of BoNT/B (LC/B), nearly all VAMP residues with side chains containing hydrogen bond acceptors or donors were hydrogen bonded with the LC/B. Thus, it is understood that a clostridial toxin substrate useful in the invention can be prepared, if desired, in which the potential for hydrogen bonding, for example, by Ser, Thr, Tyr, Asp, Glu, Asn or Gln residues is not diminished in the clostridial toxin substrate as compared to a native protein sensitive to cleavage by the toxin. In particular embodiments, the present invention provides a substrate composition, cell or method incorporating a clostridial toxin substrate in which the potential for hydrogen-bonding is not diminished in the substrate as compared to a native protein sensitive to cleavage by the corresponding clostridial toxin.

Any of a variety of Clostridial toxin recognition sequences are useful in the cells of the invention including, without limitation, botulinum toxin recognition sequences such as BoNT/A recognition sequences, BoNT/B recognition sequences, BoNT/C1 recognition sequences, BoNT/D recognition sequences, BoNT/E recognition sequences, BoNT/F recognition sequences, BoNT/G recognition sequences and TeNT recognition sequences.

A variety of BoNT/A recognition sequences are well known in the art and are useful in the invention, see, e.g., Mark A. Breidenbach & Axel T. Brunger, Substrate recognition strategy for botulinum neurotoxin serotype A, 432(7019) Nature 925-929 (2004). A BoNT/A recognition sequence can have, for example, residues 46-206, residues 134 to 206, residues 137 to 206 or 146-206 of human SNAP-25, see, e.g., Teresa A. Ekong et al., Recombinant SNAP-25 is an effective substrate for *Clostridium botulinum* type A toxin endopeptidase activity in vitro, 143 (Pt 10) Microbiology 3337-3347 (1997); Clifford C. Shone et al., Toxin Assays, U.S. Pat. No. 5,962,637 (Oct. 5, 1999); and Vaidyanathan et al., supra, (1999). A BoNT/A recognition sequence also can include, without limitation, the sequence Thr-Arg-Ile-Asp-Glu-Ala-Asn-Gln-Arg-Ala-Thr-Lys-Met (SEQ ID NO: 105) or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 106) or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 107) or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 108) or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 109) or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 110) or a peptidomimetic thereof, which corresponds to residues 186 to 203 of human SNAP-25. See, for example, James J. Schmidt & Karen A Bostian, *Proteolysis of synthetic peptides by type A botulinum neurotoxin,* 14(8) J. Protein Chem. 703-708 (1995); Schmidt & Bostian, supra, (1997); James J. Schmidt et al., *Type A botulinum neurotoxin proteolytic activity: development of competitive inhibitors and implications for substrate specificity at the S1' binding subsite,* 435(1) FEBS Lett. 61-64 (1998); and James J. Schmidt & Karen A Bostian, *Assay for the proteolytic activity of serotype A from clostridium botulinum,* U.S. Pat. No. 5,965,699 (Oct. 12, 1999).

TABLE 2

Cleavage of SNAP-25 and Related Proteins[a, b, c]

| Organism | Isoform | | BoNT/E ▼ | | BoNT/A ▼ | BoNT/C1 ▼ | | Cleaved Susceptibility |
|---|---|---|---|---|---|---|---|---|
| Primate | SNAP-25A SNAP-25B | MALDMGNEIDTQNRQIDR | * | IMEKADSNKTRIDEANQ | * | R | * | ATKMLGSG | BoNT/A; BoNT/C1; BoNT/E |
| Primate | SNAP-23A SNAP-23B | MALNIGNEIDAQNEQIKR | — | ITDKADTNRDRIDIANA | — | R | — | AKKLIDS | None[b] |
| Rodent | SNAP-25A SNAP-25B | MALDMGNEIDTQNRQIDR | * | IMEKADSNKTRIDEANQ | * | R | * | ATKMLGSG | BoNT/A; BoNT/C1; BoNT/E |
| Rodent | SNAP-23 | MALDMGNEIDAQNQQIQK | * | ITEKADTNKNRIDIANI | — | R | — | AKKLIDS | BoNT/E |
| Bird | SNAP-25B | MALDMGNEIDTQNRQIDR | * | IMEKADSNKTRIDEANQ | — | R | — | ATKMLGSG | BoNT/E |
| Amphibian | SNAP-25A SNAP-25B | MALDMGNEIDTQNRQIDR | ND | IMEKADSNKARIDEANK | ND | H | ND | ATKMLGSG | ND |
| Amphibian | SNAP-23 | MAIDMGNELESHNQQIGR | ND | INEKAETNKTRIDEANI | ND | K | ND | AKKLIE | ND |
| Fish | SNAP-25A | MALDMGNEIDTQNRQIDR | * | IMEKADSNKTRIDEANQ | * | R | * | ATKMLGSG | BoNT/A; BoNT/C1; BoNT/E |
| | SNAP-25B | MALDMGNEIDTQNRQIDR | * | IMDMADSNKTRIDEANQ | * | R | * | ATKMLGSG | |
| Fish | SNAP-23 | LALDMGNEIDKQNKTIDR | ND | ITDKADMNKARIDEANQ | ND | R | ND | ANKLL | ND |
| Ray | SNAP-25 | MALDMSNEIGSQNAQIDR | —[c] | IVMKGDMNKARIDEANK | * | H | ND | ATKML | BoNT/A |
| Sea urchin | SNAP-25 | MAIDMQSEIGAQNSQVGR | ND | ITSKAESNEGRINSADK | ND | R | ND | AKNILRNK | ND |
| Insect | SNAP-25 | MALDMGSELENQNRQIDR | — | INRKGESNEARIAVANQ | — | R | * | AHQLLK | BoNT/C1 |
| Insect | SNAP-24 | MALDMGSELENQNKQVDR | ND | INAKGDANNIRMDGVNK | ND | R | ND | ANNLLKS | ND |
| Segmented worm | SNAP-25 | MAVDMGSEIDSQNRQVDR | ND | INNKMTSNQLRISDANK | — | R | ND | ASKLLKE | ND |
| Cephalopod | SNAP-25 | MAIDMGNEIGSQNRQVDR | ND | IQQKAESNESRIDEANK | ND | K | ND | ATKLLKN | ND |

TABLE 2-continued

Cleavage of SNAP-25 and Related Proteins[a, b, c]

| Organism | Isoform | | Cleavage Sites | | | | | |
|---|---|---|---|---|---|---|---|---|
| | | | BoNT/E ▼ | | BoNT/A ▼ | BoNT/C1 ▼ | | Cleaved Susceptibility |
| Gastropod | SNAP-25 | MAVDMGNEIESQNKQLDR | ND | INQKGGSLNVRVDEAN[K] | ND | R | ND | ANRILRKQ | ND |
| Round worm | SNAP-25 | MAIDMSTEVSNQNRQLDR | * | IHDKAQSNEVRVESAN[K] | — | R | — | AKNLITK | BoNT/E |

Proteolytic cleavage occurs at this site (*); Proteolytic cleavage not detected at this site (—); Proteolytic cleavage not determined at this site (ND)
[a]= In vitro cleavage of SNAP-25 requires 1000-fold higher BoNT/C concentration than BoNT/A or /E.
[b]= Substitution of P182R, or K185DD (boxes) induces susceptibility toward BoNT/E.
[c]= Resistance to BoNT/E possibly due to D189 or E189 substitution by V189, see box.

Table 2—Cleavage of SNAP-25 and related proteins. Primate: Human SNAP-25A residues 163-206 of SEQ ID NO: 1; Human SNAP-25B residues 163-206 of SEQ ID NO: 2; Human SNAP-23A residues 169-211 of SEQ ID NO: 3; Human SNAP-23B residues 116-158 of SEQ ID NO: 4; Monkey SNAP-25B residues 163-206 of SEQ ID NO: 5; Rodent: Rat SNAP-25A residues 163-206 of SEQ ID NO: 6; Rat SNAP-25B residues 163-206 of SEQ ID NO: 7; Mouse SNAP-25B residues 163-206 of SEQ ID NO: 8; Rat SNAP-23 residues 168-210 of SEQ ID NO: 9; Mouse SNAP-23 residues 168-210 of SEQ ID NO: 10; Bird: Chicken SNAP-25B residues 163-206 of SEQ ID NO: 11; Fish: Goldfish SNAP-25A residues 161-204 of SEQ ID NO: 12; Goldfish SNAP-25B residues 160-203 of SEQ ID NO: 13; Zebrafish SNAP-25A residues 161-204 of SEQ ID NO: 14; Zebrafish SNAP-25B residues 160-203 of SEQ ID NO: 15; Zebrafish SNAP-23 residues 174-214 of SEQ ID NO: 16; Ray: marbled electric ray SNAP-25 residues 170-210 of SEQ ID NO: 17; Amphibian: Frog SNAP-25A residues 163-206 of SEQ ID NO: 18; Frog SNAP-25B residues 163-206 of SEQ ID NO: 19; Frog SNAP-23 residues 163-204 of SEQ ID NO: 20; Sea urchin SNAP-25 residues 169-212 of SEQ ID NO: 21; Insect: Fruit fly SNAP-25 residues 171-212 of SEQ ID NO: 22 212; Fruit fly SNAP-24 residues 170-212 of SEQ ID NO: 23; Segmented worm: Leech SNAP-25 residues 170-212 of SEQ ID NO: 24; Cephalopod: squid SNAP-25 residues 245-267 of SEQ ID NO: 25; Gastropod: Pond snail SNAP-25 residues 244-266 of SEQ ID NO: 26; Round worm: Nematode worm SNAP-25 residues 165-207 of SEQ ID NO: 27.

A BoNT/A recognition sequence useful in aspects of the invention can correspond to a segment of a protein that is sensitive to cleavage by botulinum toxin serotype A, or can be substantially similar to a segment of a BoNT/A-sensitive protein. As shown in Table 2, a variety of naturally occurring proteins sensitive to cleavage by BoNT/A are known in the art and include, for example, human, rat, mouse, Danio, Carassius, SNAP-25A and SNAP-25B; and Torpedo SNAP-25. Thus, a BoNT/A recognition sequence can correspond, for example, to a segment of human SNAP-25A or SNAP-25B; bovine SNAP-25A or SNAP-25B; rat SNAP-25A or SNAP-25B; mouse SNAP-25A or SNAP-25B; Xenopus SNAP-25A or SNAP-25B; Danio SNAP-25A or SNAP-25B; Carassius SNAP-25A or SNAP-25B; Torpedo SNAP-25; Strongylocentrotus SNAP-25; Loligo SNAP-25; Lymnaea SNAP-25; Aplysia SNAP-25, isoforms thereof, or another naturally occurring protein sensitive to cleavage by BoNT/A. Furthermore, comparison of native SNAP-25 amino acid sequences cleaved by BoNT/A reveals that such sequences are not absolutely conserved (see Table 2), indicating that a variety of amino acid substitutions and modifications relative to a naturally occurring BoNT/A-sensitive SNAP-25 sequence can be tolerated in a BoNT/A recognition sequence useful in the invention. It is understood that a similar BoNT/A recognition sequence can be prepared, if desired, from a corresponding (homologous) segment of another BoNT/A-sensitive SNAP-25 isoform, paralog or ortholog, such as, the BoNT/A recognition sequence contain in the SNAP-25 proteins identified in the organisms listed above and in Table 2.

A Clostridial toxin substrate, such as a substrate containing a BoNT/A recognition sequence, can have one or multiple modifications as compared to a naturally occurring sequence that is cleaved by the corresponding Clostridial toxin. As an example, as compared to a 17-mer corresponding to residues 187 to 203 of human SNAP-25, substitution of Asp193 with Asn in the BoNT/A substrate resulted in a relative rate of proteolysis of 0.23; substitution of Glu194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table 3). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively, see, e.g., Schmidt & Bostian, supra, (1997). These results indicate that a variety of residues can be substituted in a Clostridial toxin substrate as compared to a naturally occurring toxin-sensitive sequence. In the case of BoNT/A, these results indicate that residues including but not limited to Glu194, Ala195, Gln197, Ala199, Thr200 and Met202, Leu203, Gly204, Ser205, and Gly206, as well as residues more distal from the Gln-Arg scissile bond, can be substituted or conjugated to a fluorophore, bulking group, donor fluorophore or acceptor in a BoNT/A substrate useful in the invention. Such a BoNT/A substrate is detectably proteolyzed at the scissile bond by BoNT/A under conditions suitable for Clostridial toxin protease activity. Thus, a BoNT/A substrate can include, if desired, one or several amino acid substitutions, additions or deletions relative to a naturally occurring SNAP-25 sequence.

TABLE 3

Kinetic Parameters of BoNT/A
Synthetic Peptide Substrates

| Peptide | Sequence[a] | SEQ ID NO: | Relative Rate[b] |
|---|---|---|---|
| [1-15] | SNKTRIDEANQRATK | 106 | 0.03 |
| [1-16] | SNKTRIDEANQRATKM | 107 | 1.17 |
| [1-17] | SNKTRIDEANQRATKML | 108 | 1.00 |
| M16A | SNKTRIDEANQRATKAL | 111 | 0.38 |
| M16X | SNKTRIDEANQRATKXL | 112 | 1.20 |
| K15A | SNKTRIDEANQRATAML | 113 | 0.12 |
| T14S | SNKTRIDEANQRASKML | 114 | 0.26 |
| T14B | SNKTRIDEANQRABKML | 115 | 1.20 |
| A13B | SNKTRIDEANQRBTKML | 116 | 0.79 |
| Q11A | SNKTRIDEANARATKML | 117 | 0.19 |
| Q11B | SNKTRIDEANBRATKML | 118 | 0.25 |
| Q11N | SNKTRIDEANNRATKML | 119 | 0.66 |
| N10A | SNKTRIDEAAQRATKML | 120 | 0.06 |
| A9B | SNKTRIDEBNQRATKML | 121 | 0.38 |
| E8Q | SNKTRIDQANQRATKML | 122 | 2.08 |
| D7N | SNKTRINEANQRATKML | 123 | 0.23 |

[a]Nonstandard abbreviations: B, 2-aminobutyric acid; X, 2-aminohexanoic acid (norleucine)
[b]Initial hydrolysis rates relative to peptide [1-17]. Peptide concentrations were 1.0 mM.

Thus, in an embodiment, a cell comprises, in part, a BoNT/A substrate comprising a donor fluorophore, an acceptor and a BoNT/A recognition sequence including a cleavage site. As used herein, the term "botulinum toxin serotype A recognition sequence" is synonymous with "BoNT/A recognition sequence" and means a scissile bond together with adjacent or non-adjacent recognition elements, or both, sufficient for detectable proteolysis at the scissile bond by a BoNT/A under conditions suitable for Clostridial toxin protease activity. A scissile bond cleaved by BoNT/A can be, for example, Gln-Arg. It is envisioned that a BoNT/A recognition sequence can be of any length, with the proviso that the BoNT/A recognition sequence can be cleaved by a BoNT/A.

In an aspect of this embodiment, the Clostridial toxin substrate includes, in part, a BoNT/A recognition sequence comprising a BoNT/A recognition sequence containing at least six consecutive residues of SNAP-25 including Gln-Arg. In another aspect of this embodiment, the Clostridial toxin substrate includes, in part, a BoNT/A recognition sequence comprising the BoNT/A recognition sequence Glu-Ala-Asn-Gln-Arg-Ala-Thr-Lys (SEQ ID NO: 96). In other aspects of this embodiment, the Clostridial toxin substrate includes, in part, a BoNT/A recognition sequence comprising a portion of SNAP-25 such as, e.g., residues 1 to 206 of SEQ ID NO: 1; residues 46 to 206 of SEQ ID NO: 1; residues 134 to 206 of SEQ ID NO: 1; residues 137 to 206 of SEQ ID NO: 1; residues 146 to 206 of SEQ ID NO: 1, or a peptidomimetic thereof. In still other aspects of this embodiment, the Clostridial toxin substrate includes, in part, a BoNT/A recognition sequence comprising SEQ ID NO: 105, SEQ ID NO: 106, SEQ ID NO: 107, SEQ ID NO: 108, SEQ ID NO: 109, or SEQ ID NO: 110, or a peptidomimetic thereof.

In other aspects of this embodiment, a BoNT/A toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, at least 200 residues, at least 250 residues or at least 300 residues. In other embodiments, a BoNT/A toxin recognition sequence has at most 20 residues, at most 30 residues, at most 40 residues, at most 50 residues, at most 100 residues, at most 150 residues, at most 200 residues, at most 250 residues or at most 300 residues.

A variety of BoNT/B recognition sequences are well known in the art or can be defined by routine methods. Such BoNT/B recognition sequences can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 31), or residues 60 to 94 of human VAMP-1-1 (SEQ ID NO: 28), VAMP-1-2 (SEQ ID NO: 29) and VAMP-1-3 (SEQ ID NO: 30) see, e.g., Shone et al., Eur. J. Biochem. 217: 965-971 (1993); and Shone et al., supra, (Oct. 5, 1999). A BoNT/B recognition sequence also can include, without limitation, the sequence Leu-Ser-Glu-Leu-Asp-Asp-Arg-Ala-Asp-Ala-Leu-Gln-Ala-Gly-Ala-Ser-Gln-Phe-Glu-Thr-Ser-Ala-Ala-Lys-Leu-Lys-Arg-Lys-Tyr-Trp-Trp-Lys-Asn-Leu-Lys (SEQ ID NO: 124) or a peptidomimetic thereof, which corresponds to residues 60 to 94 of human VAMP-2, see, e.g., James J. Schmidt & Robert G. Stafford, High Throughput Assays for the Proteolytic Activities of Clostridial Neurotoxins, U.S. Pat. No. 6,762,280 (Jul. 13, 2004) and the BoNT/B recognition sequence Leu-Ser-G lu-Leu-Asp-Asp-Arg-Ala-Asp-Ala-Leu-Gln-Ala-Gly-Ala-Ser-Gln-Phe-Glu-Ser-Ser-Ala-Ala-Lys-Leu-Lys-Arg-Lys-Tyr-Trp-Trp-Lys-Asn-Cys-Lys (SEQ ID NO: 125) or a peptidomimetic thereof, which corresponds to residues 62 to 96 of human VAMP-1.

A BoNT/B recognition sequence useful in aspects of the invention can correspond to a segment of a protein that is sensitive to cleavage by botulinum toxin serotype B, or can be substantially similar to a segment of a BoNT/B-sensitive protein. As shown in Table 4, a variety of naturally occurring proteins sensitive to cleavage by BoNT/B are known in the art and include, for example, human and mouse VAMP-1, VAMP-2 and VAMP-3/cellubrevin; bovine VAMP-2; rat VAMP-2 and VAMP-3; chicken VAMP-2; Torpedo VAMP-1; *Strongylocentrotus* VAMP; *Drosophila* sybA, synB, synC, synD and synE; *Hirudo* VAMP; and *Caenorhabditis* SNB1-like. Thus, a BoNT/B recognition sequence can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD or synE; *Hirudo* VAMP; *Loligo* VAMP; *Lymnaea* VAMP; *Aplysia* VAMP; *Caenorhabditis* SNB1, isoforms thereof, or another naturally occurring protein sensitive to cleavage by BoNT/B. Furthermore, as shown in Table 4, comparison of native VAMP amino acid sequences cleaved by BoNT/B reveals that such sequences are not absolutely conserved, indicating that a variety of amino acid substitutions and modifications relative to a naturally occurring VAMP sequence can be tolerated in a BoNT/B substrate of the invention. It is understood that a similar BoNT/B recognition sequence can be prepared, if desired, from a corresponding (homologous) segment of another BoNT/B-sensitive VAMP-1 or VAMP-2 isoform, paralog or ortholog, such as, the BoNT/B recognition sequence contain in the VAMP-1 and VAMP-2 proteins identified in the organisms listed above and in Table 4.

Thus, in an embodiment, a cell comprises, in part, a BoNT/B substrate comprising a donor fluorophore, an acceptor and a BoNT/B recognition sequence including a cleavage site. As used herein, the term "botulinum toxin serotype B recognition sequence" is synonymous with "BoNT/B recognition sequence" and means a scissile bond together with adjacent or non-adjacent recognition elements, or both, sufficient for detectable proteolysis at the scissile bond by a BoNT/B under appropriate conditions. A scissile bond cleaved by BoNT/B can be, for example, Gln-Phe. It is envisioned that a BoNT/B recognition sequence can be of any length, with the proviso that the BoNT/B recognition sequence can be cleaved by a BoNT/B.

In an aspect of this embodiment, the Clostridial toxin substrate includes, in part, a BoNT/B recognition sequence comprising a BoNT/B recognition sequence containing at least six consecutive residues of VAMP including Gln-Phe. In another aspect of this embodiment, the Clostridial toxin substrate includes, in part, a BoNT/B recognition sequence comprising the BoNT/B recognition sequence Gly-Ala-Ser-Gln-Phe-Glu-Thr-Ser (SEQ ID NO: 97). In other aspects of this embodiment, the Clostridial toxin substrate includes, in part, a BoNT/B recognition sequence comprising a portion of VAMP-1-1 such as, e.g., residues 1 to 118 of SEQ ID NO: 28; residues 62 to 96 of SEQ ID NO: 28, or a peptidomimetic thereof. In other aspects of this embodiment, the Clostridial toxin substrate includes, in part, a BoNT/B recognition sequence comprising a portion of VAMP-1-2 such as, e.g., residues 1 to 117 of SEQ ID NO: 29; residues 62 to 96 of SEQ ID NO: 29, or a peptidomimetic thereof. In other aspects of this embodiment, the Clostridial toxin substrate includes, in part, a BoNT/B recognition sequence comprising a portion of VAMP-1-3 such as, e.g., residues 1 to 116 of SEQ ID NO: 30; residues 62 to 96 of SEQ ID NO: 30, or a peptidomimetic thereof. In other aspects of this embodiment, the Clostridial toxin substrate includes, in part, a BoNT/B recognition sequence comprising a portion of VAMP-2 such as, e.g., residues 1 to 116 of SEQ ID NO: 31; residues 33 to 94 of SEQ ID NO: 31; residues 45 to 94 of SEQ ID NO: 31; residues 55 to 94 of SEQ ID NO: 31; residues 60 to 94 of SEQ ID NO: 31; residues 65 to 94 of SEQ ID NO: 31; residues 60 to 88 of SEQ ID NO: 31; residues 65 to 88 of SEQ ID NO: 31, or a peptidomimetic thereof.

In other aspects of this embodiment, a BoNT/B toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, or at least 200 residues. In other embodiments, a BoNT/B toxin recognition sequence has at most 20 residues, at most 30 residues, at most 40 residues, at most 50 residues, at most 100 residues, at most 150 residues, or at most 200 residues.

TABLE 4

Cleavage of VAMP and Related Proteins

| Organism | Isoform | | Cleavage Sites | | | |
|---|---|---|---|---|---|---|
| | | | BonT/F ▼ | | BonT/D ▼ | |
| Primate | VAMP1-1 VAMP1-2 VAMP1-3 | RVNVDKVLERDQ | * | K | * | LSELDDRADALQAGASQ |
| Primate | VAMP2 | RVNVDKVLERDQ | * | K | * | LSELDDRADALQAGASQ |
| Primate | VAMP3 | RVNVDKVLERDQ | * | K | * | LSELDDRADALQAGASQ |
| Bovine | VAMP2 | RVNVDKVLERDQ | * | K | * | LSELDDRADALQAGASQ |
| Rodent | VAMP1/1b | RVNVDKVLERDQ | * | K | * | LSELDDRADALQAGASV |
| | VAMP1 | RVNVDKVLERDQ | * | K | * | LSELDDRADALQAGASQ |
| Rodent | VAMP2 VAMP2-b | RVNVDKVLERDQ | * | K | * | LSELDDRADALQAGASQ |
| Rodent | VAMP3 | RVNVDKVLERDQ | * | K | * | LSELDDRADALQAGASQ |
| Bird | VAMP1 | RVNVDKVLERDQ | * | K | * | LSELDDRADALQAGASV |
| Bird | VAMP2 | RMNVDKVLERDQ | * | K | * | LSELDNRADALQAGASQ |
| Bird | VAMP3 | RVNVDKVLERDQ | ND | K | ND | LSELDDRADALQAGASQ |
| Amphibian | VAMP2 | RVNVDKVLERDI | ND | K | ND | LSELDDRADALQAGASQ |
| Amphibian | VAMP3 | RVNVDKVLERDQ | ND | K | ND | LSELDDRADALQAGASQ |
| Fish | VAMP1 | RVNVDKVLERDQ | ND | K | ND | LSELDDRADALQAGASQ |
| Fish | VAMP2 | RVNVDKVLERDQ | ND | K | ND | LSELDDRADALQAGASQ |
| Fish | VAMP-3 | RVNVDKVLERDQ | ND | K | ND | LSELDDRADALQAGASQ |
| Ray | VAMP1 | RVNVDKVLERDQ | * | K | * | LSELDDRADALQAGASQ |
| Sea urchin | VAMP | RVNVDKVLERDQ | — | A | — | LSVLDDRADALQQGASQ |

TABLE 4-continued

Cleavage of VAMP and Related Proteins

| Organism | Protein | Sequence 1 | | | | Sequence 2 |
|---|---|---|---|---|---|---|
| Insect | Syn-A1<br>Syn-B1 | RVNVEKVLERDQ | * | K | * | LSELGERADQLEQGASQ |
| Insect | Syn-A2<br>Syn-B2 | RVNVEKVLERDQ | * | K | * | LSELGERADQLEQGASQ |
| Insect | Syn-C<br>Syn-D<br>Syn-E | RTNVEKVLERD[S] | — | K | * | LSELDDRADALQQGASQ |
| Segmented worm | VAMP | RVNVDKVLEKDQ | * | K | * | LAELDGRADALQAGASQ |
| Cephalopod | VAMP | RTNVEKVLERD[S] | ND | K | ND | [I]SELDDRADALQAGASQ |
| Gastropod | VAMP | RVNVEKVLDRDQ | ND | K | ND | [I]SQLDDRAEALQAGASQ |
| Round worm | SNB1<br>SNB-like | KVNVEKVLERDQ<br>RNNVNKVMERD[V] | ND<br>— | K<br>[Q] | ND<br>— | LSQLDDRADALQEGASQ<br>LNSLDHRAEVLQNGASQ |

| | Cleavage Sites | | | | |
|---|---|---|---|---|---|
| Organism | TeNT<br>BonT/B ▼ | | BonT/G ▼ | | Cleaved Susceptibility |
| Primate | * | FESSA | * | AKLKRKYWW | BoNT/B; BoNT/D;<br>BoNT/F; BoNT/G; TeNT |
| Primate | * | FETSA | * | AKLKRKYWW | BoNT/B; BoNT/D;<br>BoNT/F; BoNT/G; TeNT |
| Primate | * | FETSA | * | AKLKRKYWW | BoNT/B; BoNT/D;<br>BoNT/F; BoNT/G; TeNT |
| Bovine | * | FETSA | * | AKLKRKYWW | BoNT/B; BoNT/D;<br>BoNT/F; BoNT/G; TeNT |
| Rodent | —[a] | FESSA | * | AKLKRKYWW | BoNT/B; BoNT/D; |
| | * | FESSA | * | AKLKRKYWW | BoNT/F; BoNT/G; TeNT |
| Rodent | * | FETSA | * | AKLKRKYWW | BoNT/B; BoNT/D;<br>BoNT/F; BoNT/G; TeNT |
| Rodent | * | FETSA | * | AKLKRKYWW | BoNT/B; BoNT/D;<br>BoNT/F; BoNT/G; TeNT |
| Bird | — | FESSA | * | AKLKRKYWW | BoNT/D; BoNT/F;<br>BoNT/G |
| Bird | * | FETSA | * | AKLKRKYWW | BoNT/B; BoNT/D;<br>BoNT/F; BoNT/G; TeNT |
| Bird | ND | FETSA | ND | AKLKRKYWW | ND |
| Amphibian | ND | FETSA | ND | AKLKRKYWW | ND |
| Amphibian | ND | FETSA | ND | AKLKRKYWW | ND |
| Fish | ND | FESSA | ND | AKLKNKYWW | ND |
| Fish | ND | FETSA | ND | AKLKNKYWW | ND |
| Fish | ND | FETSA | ND | AKLKRKYWW | ND |
| Ray | * | FESSA | * | AKLKRKYWW | BoNT/B; BoNT/D;<br>BoNT/F; BoNT/G; TeNT |
| Sea urchin | * | FETNA | — | [G]KLKRKYWW | BoNT/B; TeNT |
| Insect | * | FEQQA | — | [G]KLKRKQWW | BoNT/B; BoNT/D;<br>BoNT/F; TeNT |
| Insect | — | [S]EQQA | — | [G]KLKRKQWW | BoNT/D; BoNT/F |
| Insect | * | FEQQA | — | [G]KLKRKFWL | BoNT/B; BoNT/D;<br>TeNT |
| Segmented worm | * | FEASA | — | [G]KLKRKFWW | BoNT/B; BoNT/D;<br>BoNT/F;<br>TeNT |
| Cephalopod | ND | FEASA | ND | [G]KLKRKFWW | ND |
| Gastropod | ND | FEASA | ND | [G]KLKRKYWW | ND |

TABLE 4-continued

Cleavage of VAMP and Related Proteins

| | | | | | |
|---|---|---|---|---|---|
| Round worm | ND | FEKSA | ND | ATLKRKTWW | BoNT/B; TeNT; |
| | * | FQQS[S] | — | [R]TLRQKYWW | |

Proteolytic cleavage occurs at this site (*); Proteolytic cleavage not detected at this site (—); Proteolytic cleavage not determined at this site (ND)
$^a$= Rat VAMP1 resistance to BoNT/B and TeNT possibly due to Q189V substitution, see box.

Table 4—Cleavage of VAMP and related proteins. Primate: Human VAMP-1-1 residues 49-92 of SEQ ID NO: 28; Human VAMP-1-2 residues 49-92 of SEQ ID NO: 29; Human VAMP-1-3 residues 49-92 of SEQ ID NO: 30; Human VAMP-2 residues 47-90 of SEQ ID NO: 31; Monkey VAMP-2 residues 47-90 of SEQ ID NO: 32; Human VAMP-3/cellubrevin residues 30-73 of SEQ ID NO: 33; Bovine: Cow VAMP-2 residues 47-90 of SEQ ID NO: 34; Rodent: Rat VAMP-1 residues 49-92 of SEQ ID NO: 35; Rat VAMP-1-b residues 49-92 of SEQ ID NO: 36; Mouse VAMP-1 residues 49-92 of SEQ ID NO: 37; Rat VAMP-2 residues 47-90 of SEQ ID NO: 38; Rat VAMP-2-b residues 47-90 of SEQ ID NO: 39; Mouse VAMP-2 residues 47-90 of SEQ ID NO: 40; Rat VAMP-3/cellubrevin residues 34-77 of SEQ ID NO: 41; Mouse VAMP-3/cellubrevin residues 34-77 of SEQ ID NO: 42; Bird: Chicken VAMP-1 residues 190-233 of SEQ ID NO: 43; Chicken VAMP-2 residues 47-88 of SEQ ID NO: 44; Chicken VAMP-3/cellubrevin residues 34-77 of SEQ ID NO: 45; Fish: Zebrafish VAMP-1 residues 50-93 of SEQ ID NO: 46; Zebrafish VAMP-2 residues 41-84 of SEQ ID NO: 47; Zebrafish VAMP-3 residues 33-60 of SEQ ID NO: 48; Ray: marbled electric ray VAMP-1 residues 51-94 of SEQ ID NO: 49; Amphibian: Frog VAMP-2 residues 45-88 of SEQ ID NO: 50; Frog VAMP-3 residues 32-75 of SEQ ID NO: 51; Sea urchin VAMP residues 31-74 of SEQ ID NO: 52; Insect: Fruit fly SynA1 residues 40-83 of SEQ ID NO: 53; Fruit fly SynA2 residues 63-106 of SEQ ID NO: 54; Fruit fly SynB1 residues 63-106 of SEQ ID NO: 55; Fruit fly SynB2 residues 63-106 of SEQ ID NO: 56; Fruit fly SynC residues 57-100 of SEQ ID NO: 57; Fruit fly SynD residues 66-109 of SEQ ID NO: 58; Fruit fly SynE residues 57-100 of SEQ ID NO: 59; Segmented worm: Leech VAMP residues 45-88 of SEQ ID NO: 60; Cephalopod: squid VAMP residues 56-99 of SEQ ID NO: 61; Gastropod: Pond snail VAMP residues 49-92 of SEQ ID NO: 62; sea hare VAMP residues 37-80 of SEQ ID NO: 63; Round worm: Nematode worm SNB1 residues 72-115 of SEQ ID NO: 64; Nematode worm SNB-like residues 82-115 of SEQ ID NO: 65.

It is understood that a BoNT/C1 recognition sequence can correspond to a segment of a protein that is sensitive to cleavage by botulinum toxin serotype C1, or can be substantially similar to a segment of a BoNT/C1-sensitive protein. As further shown in Table 5, a variety of naturally occurring proteins sensitive to cleavage by BoNT/C1 are known in the art and include, for example, human and mouse Syntaxin 1A, Syntaxin 1B1 and Syntaxin 1B2; bovine and rat Syntaxin 1A and Syntaxin 1B2; rat Syntaxin 2 and Rat Syntaxin 3; Strongylocentrotus Syntaxin; Drosophila Syntaxin 1A; Hirudo Syntaxin 1A; Loligo Syntaxin 1A; Aplysia Syntaxin 1A. Thus, a BoNT/C1 recognition sequence can correspond, for example, to a segment of human Syntaxin 1A, Syntaxin 1B1, Syntaxin 1B2, Syntaxin 2-1, Syntaxin 2-2, Syntaxin 2-3 or Syntaxin 3A; bovine Syntaxin 1A, Syntaxin 1B1 or Syntaxin 1B2; rat Syntaxin 1A, Syntaxin 1B1, Syntaxin 1B2, Syntaxin 2 or Syntaxin 3A; mouse Syntaxin 1A, Syntaxin 1B1, Syntaxin 1B2, Syntaxin 2, Syntaxin 3A, Syntaxin 3B or Syntaxin 3C; chicken Syntaxin 1A or Syntaxin 2; *Xenopus* Syntaxin 1A or Syntaxin 1B; *Danio* Syntaxin 1A, Syntaxin 1B or Syntaxin 3; *Torpedo* Syntaxin 1A or Syntaxin 1B; *Strongylocentrotus* Syntaxin 1A or Syntaxin 1B; *Drosophila* Syntaxin 1A or Syntaxin 1B; Hirudo Syntaxin 1A or Syntaxin 1B; *Loligo* Syntaxin 1A or Syntaxin 1B; *Lymnaea* Syntaxin 1A or Syntaxin 1B, isoforms thereof, or another naturally occurring protein sensitive to cleavage by BoNT/C1. Furthermore, comparison of native Syntaxin amino acid sequences cleaved by BoNT/C1 reveals that such sequences are not absolutely conserved (see Table 5), indicating that a variety of amino acid substitutions and modifications relative to a naturally occurring BoNT/C1-sensitive Syntaxin sequence can be tolerated in a BoNT/C1 substrate useful in the invention. It is understood that a similar BoNT/C1 recognition sequence can be prepared, if desired, from a corresponding (homologous) segment of another BoNT/C1-sensitive Syntaxin isoform, paralog or ortholog, such as, the BoNT/C1 recognition sequence contain in the Syntaxin proteins identified in the organisms listed above and in Table 5.

TABLE 5

Cleavage of Syntaxin and Related Proteins

| | | Cleavage Site | | | |
|---|---|---|---|---|---|
| Organism | Isoform | | BoNT/C1 ▼ | | Cleaved Susceptibility |
| Primate | Syntaxin1A Syntaxin1B1 Syntaxin1B2 | DYVERAVSDTKK | * | AVKYQSKARRK | BoNT/C1 |
| Primate | Syntaxin2-1 Syntaxin2-2 Syntaxin2-3 | DYVEHAKEETKK | ND | AIKYQSKARRK | ND |
| Primate | Syntaxin3A | DHVEKARDESKK | ND | AVKYQSARRK | ND |
| Bovine | Syntaxin1A Syntaxin1B2 | DYVERAVSDTKK | * | AVKYQSKARRK | BoNT/C1 |

TABLE 5-continued

Cleavage of Syntaxin and Related Proteins

| Organism | Isoform | Cleavage Site BoNT/C1 ▼ | | | Cleaved Susceptibility |
|---|---|---|---|---|---|
| Rodent | Syntaxin1A Syntaxin1B1 Syntaxin1B2 | DYVERAVSDTKK | * | AVKYQSKARRK | BoNT/C1 |
| Rodent | Syntaxin2 | DYVEHAKEETKK | * | AIKYQSKARRK | BoNT/C1 |
| Rodent | Syntaxin3A | DHVEKARDETKR | * | AMKYQGQARKK | BoNT/C1 |
| Rodent | Syntaxin3B Syntaxin3C | GFVERAVADTKK | ND | AVKYQSEARRK | ND |
| Bird | Syntaxin1B | DYVEPVVFVTKS | ND | AVMYQCKSRRK | ND |
| Bird | Syntaxin2 | DYVEHAKEETKK | ND | AVKYQSKARRK | ND |
| Fish | Syntaxin1B | DYVERAVSDTKK | * | AVKYQSQARKK | BoNT/C1 |
| Fish | Syntaxin3 | DHVEAARDETKK | ND | AVRYQSKARKK | ND |
| Sea urchin | Syntaxin1B | DYVRRQNDTKK | * | AVKYQSKARRK | BoNT/C1 |
| Insect | Syntaxin1A | DYVQTATQDTKK | * | ALKYQSKARRK | BoNT/C1 |
| Segmented worm | Syntaxin1A | DYVETAAADTKK | * | AMKYQSAARKK | BoNT/C1 |
| Cephalopod | Syntaxin1A | DYIETAKVDTKK | * | AVKYQSKARQK | BoNT/C1 |
| Gastropod | Syntaxin1A | DYIETAKMDTKK | * | AVKYQSKARRK | BoNT/C1 |

Proteolytic cleavage occurs at this site (*); Proteolytic cleavage not detected at this site (—); Proteolytic cleavage not determined at this site (ND)

Table 5—Cleavage of Syntaxin and related proteins. Primate: Human Syntaxin1A residues 242-264 of SEQ ID NO: 66; Human Syntaxin1B1 residues 241-263 of SEQ ID NO: 67; Human Syntaxin1B2 residues 241-263 of SEQ ID NO: 68; Human Syntaxin2-1 residues 241-263 of SEQ ID NO: 69; Human Syntaxin2-2 residues 241-263 of SEQ ID NO: 70; Human Syntaxin2-3 residues 241-263 of SEQ ID NO: 71; Human Syntaxin3 residues 241-263 of SEQ ID NO: 72; Bovine: Cow Syntaxin1A residues 242-264 of SEQ ID NO: 73; Cow Syntaxin1B2 residues 241-263 of SEQ ID NO: 74; Rodent: Rat Syntaxin1A residues 242-264 of SEQ ID NO: 75; Rat Syntaxin1B2 residues 241-263 of SEQ ID NO: 76; Mouse Syntaxin1A residues 242-264 of SEQ ID NO: 77; Mouse Syntaxin1B1 residues 241-263 of SEQ ID NO: 78; Mouse Syntaxin1B2 residues 241-263 of SEQ ID NO: 79; Rat Syntaxin2 residues 243-265 of SEQ ID NO: 80; Mouse Syntaxin2 residues 242-264 of SEQ ID NO: 81; Rat Syntaxin3A residues 241-263 of SEQ ID NO: 82; Mouse Syntaxin3A residues 241-263 of SEQ ID NO: 83; Mouse Syntaxin3B residues 241-263 of SEQ ID NO: 84; Mouse Syntaxin3C residues 223-245 of SEQ ID NO: 85; Bird: Chicken Syntaxin1B residues 235-257 of SEQ ID NO: 86; Chicken Syntaxin2 residues 240-262 of SEQ ID NO: 87; Fish: Zebrafish Syntaxin1B residues 241-263 of SEQ ID NO: 88; Zebrafish Syntaxin3 residues 239-261 of SEQ ID NO: 89; sea urchin Syntaxin1B residues 241-263 of SEQ ID NO: 90; Insect: Fruit fly Syntaxin1A residues 245-267 of SEQ ID NO: 91; Segmented worm: leech Syntaxin1A residues 248-270 of SEQ ID NO: 92; Cephalopod: squid Syntaxin1A residues 245-267 of SEQ ID NO: 93; Gastropod: Pond snail Syntaxin1A residues 244-266 of SEQ ID NO: 94; sea hare Syntaxin1A residues 244-266 of SEQ ID NO: 95.

As further shown in Table 2, a variety of naturally occurring proteins sensitive to cleavage by BoNT/C1 are known in the art and include, for example, human, rat, mouse, Danio, Carassius SNAP-25A and SNAP-25B; and *Drosophila* SNAP-25. Thus, a BoNT/C1 recognition sequence can correspond, for example, to a segment of human SNAP-25A or SNAP-25B; bovine SNAP-25A or SNAP-25B; rat SNAP-25A or SNAP-25B; mouse SNAP-25A or SNAP-25B; *Xenopus* SNAP-25A or SNAP-25B; Danio SNAP-25A or SNAP-25B; Carassius SNAP-25A or SNAP-25B; Torpedo SNAP-25; Strongylocentrotus SNAP-25; *Drosophila* SNAP-25 or SNAP-24; Hirudo SNAP-25; Loligo SNAP-25; *Lymnaea* SNAP-25, isoforms thereof, or another naturally occurring protein sensitive to cleavage by BoNT/C1. As discussed above in regard to variants of naturally occurring Syntaxin sequences, comparison of native SNAP-25 amino acid sequences cleaved by BoNT/C1 reveals significant sequence variability (Table 2), indicating that a variety of amino acid substitutions and modifications relative to a naturally occurring BoNT/C1-sensitive SNAP-25 sequence can be tolerated in a BoNT/C1 substrate useful in the invention. It is understood that a similar BoNT/C1 recognition sequence can be prepared, if desired, from a corresponding (homologous) segment of another BoNT/C1-sensitive SNAP-25 isoform, paralog or ortholog, such as, the BoNT/A recognition sequence contain in the SNAP-25 proteins identified in the organisms listed above and in Table 2.

Thus, in an embodiment, a cell comprises, in part, a BoNT/C1 substrate comprising a donor fluorophore, an acceptor and a BoNT/C1 recognition sequence including a cleavage site. As used herein, the term "botulinum toxin serotype C1 recognition sequence" is synonymous with "BoNT/C1 recognition sequence" and means a scissile bond together with adjacent or non-adjacent recognition elements, or both, sufficient for detectable proteolysis at the scissile bond by a BoNT/C1 under appropriate conditions. A scissile bond cleaved by BoNT/C1 can be, for example, Lys-Ala or Arg-Ala. It is envisioned that a BoNT/C1 recognition sequence can be of any length, with the proviso that the BoNT/C1 recognition sequence can be cleaved by a BoNT/C1.

In an aspect of this embodiment, the encoded Clostridial toxin substrate includes, in part, a BoNT/C1 recognition sequence comprising a BoNT/C1 recognition sequence containing at least six consecutive residues of Syntaxin including Lys-Ala. In another aspect of this embodiment, the Clostridial toxin substrate includes, in part, a BoNT/C1 recognition sequence comprising the BoNT/C1 recognition sequence Asp-Thr-Lys-Lys-Ala-Val-Lys-Tyr (SEQ ID NO: 98). In another aspect of this embodiment, the Clostridial toxin substrate includes, in part, a BoNT/C1 recognition sequence comprising a BoNT/C1 recognition sequence containing at least six consecutive residues of SNAP-25 including Arg-Ala. In another aspect of this embodiment, the Clostridial toxin substrate includes, in part, a BoNT/C1 recognition sequence comprising the BoNT/C1 recognition sequence Ala-Asn-Gln-Arg-Ala-Thr-Lys-Met (SEQ ID NO: 99). In yet another aspect of this embodiment, the Clostridial toxin substrate includes, in part, a BoNT/C1 recognition sequence comprising a BoNT/C1 recognition sequence containing at least six consecutive residues of Syntaxin including Lys-Ala and a BoNT/C1 recognition sequence comprising a BoNT/C1 recognition sequence containing at least six consecutive residues of SNAP-25 including Arg-Ala.

In other aspects of this embodiment, the Clostridial toxin substrate includes, in part, a BoNT/C1 recognition sequence comprising a portion of Syntaxin-1A such as, e.g., residues 1 to 288 of SEQ ID NO: 66, or a peptidomimetic thereof. In other aspects of this embodiment, the Clostridial toxin substrate includes, in part, a BoNT/C1 recognition sequence comprising a portion of Syntaxin-1B1 such as, e.g., residues 1 to 288 of SEQ ID NO: 67, or a peptidomimetic thereof. In other aspects of this embodiment, the Clostridial toxin substrate includes, in part, a BoNT/C1 recognition sequence comprising a portion of Syntaxin-1B2 such as, e.g., residues 1 to 288 of SEQ ID NO: 68, or a peptidomimetic thereof. In other aspects of this embodiment, the Clostridial toxin substrate includes, in part, a BoNT/C1 recognition sequence comprising a portion of Syntaxin 2-1 such as, e.g., residues 1 to 287 of SEQ ID NO: 69, or a peptidomimetic thereof. In other aspects of this embodiment, the Clostridial toxin substrate includes, in part, a BoNT/C1 recognition sequence comprising a portion of Syntaxin-2-2 such as, e.g., residues 1 to 288 of SEQ ID NO: 70, or a peptidomimetic thereof. In other aspects of this embodiment, the Clostridial toxin substrate includes, in part, a BoNT/C1 recognition sequence comprising a portion of Syntaxin-2-3 such as, e.g., residues 1 to 289 of SEQ ID NO: 71, or a peptidomimetic thereof. In other aspects of this embodiment, the Clostridial toxin substrate includes, in part, a BoNT/C1 recognition sequence comprising a portion of Syntaxin-3A such as, e.g., residues 1 to 289 of SEQ ID NO: 83, or a peptidomimetic thereof. In other aspects of this embodiment, the Clostridial toxin substrate includes, in part, a BoNT/C1 recognition sequence comprising a portion of Syntaxin-3B such as, e.g., residues 1 to 283 of SEQ ID NO: 84, or a peptidomimetic thereof. In other aspects of this embodiment, the Clostridial toxin substrate includes, in part, a BoNT/C1 recognition sequence comprising a portion of Syntaxin-3C such as, e.g., residues 1 to 269 of SEQ ID NO: 85, or a peptidomimetic thereof.

In other aspects of this embodiment, the Clostridial toxin substrate includes, in part, a BoNT/C1 recognition sequence comprising a portion of SNAP-25 such as, e.g., residues 1 to 206 of SEQ ID NO: 1; residues 93 to 206 of SEQ ID NO: 1; residues 134 to 206 of SEQ ID NO: 1; residues 137 to 206 of SEQ ID NO: 1; residues 146 to 206 of SEQ ID NO: 1; residues 137 to 202 of SEQ ID NO: 1, or a peptidomimetic thereof. In still other aspects of this embodiment, the Clostridial toxin substrate includes, in part, a BoNT/C1 recognition sequence comprising SEQ ID NO: 105, SEQ ID NO: 106, SEQ ID NO: 107, SEQ ID NO: 108, SEQ ID NO: 109, or SEQ ID NO: 110, or a peptidomimetic thereof.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2, see, e.g., Shinji Yamasaki et al., Cleavage of members of the synaptobrevin/VAMP family by types D and F botulinum neurotoxins and tetanus toxin, 269(17) J. Biol. Chem. 12764-12772 (1994). Thus, a BoNT/D recognition sequence can include, for example, residues 27 to 69 or residues 37 to 69 of rat VAMP-2. A BoNT/D recognition sequence also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 126) or a peptidomimetic thereof, which corresponds to residues 37 to 75 of human VAMP-2, see, e.g., Schmidt & Stafford, supra, (Jul. 13, 2004) and the BoNT/D recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 127) or a peptidomimetic thereof, which corresponds to residues 39 to 77 of the human VAMP-1 isoforms, VAMP-1-1, VAMP-1-2 and VAMP-1-3.

In other aspects of this embodiment, a BoNT/C1 toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, at least 200 residues, at least 250 residues or at least 300 residues. In other embodiments, a BoNT/C1 toxin recognition sequence has at most 20 residues, at most 30 residues, at most 40 residues, at most 50 residues, at most 100 residues, at most 150 residues, at most 200 residues, at most 250 residues or at most 300 residues.

A BoNT/D recognition sequence can correspond to a segment of a protein that is sensitive to cleavage by botulinum toxin serotype D, or can be substantially similar to a segment of a BoNT/D-sensitive protein. As shown in Table 4, a variety of naturally occurring proteins sensitive to cleavage by BoNT/D are known in the art and include, for example, human, rat and mouse VAMP-1, VAMP-2 and VAMP-3/cellubrevin; bovine VAMP-2; chicken VAMP-1, VAMP-2 and VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD, synE; *Hirudo* VAMP; *Loligo* VAMP; *Lymnaea* VAMP; *Aplysia* VAMP; and *Caenorhabditis* SNB1. Thus, a BoNT/D recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD, synE; Hirudo VAMP; Loligo VAMP; *Lymnaea* VAMP; Aplysia VAMP; *Caenorhabditis* SNB1, isoforms thereof, or another naturally occurring protein sensitive to cleavage by BoNT/D. Furthermore, as shown in Table 4 above, comparison of native VAMP amino acid sequences cleaved by BoNT/D reveals significant sequence variability, indicating that a variety of amino acid substitutions and modifications relative to a naturally occurring BoNT/D-sensitive VAMP sequence can be tolerated in a BoNT/D substrate useful in the invention. It is understood that a similar BoNT/D recognition sequence can be prepared, if desired, from a corresponding (homologous) segment of another BoNT/D-sensitive VAMP-1 or VAMP-2 isoform, paralog or ortholog, such as, the BoNT/B recognition sequence contain in the VAMP-1 and VAMP-2 proteins identified in the organisms listed above and in Table 4.

Thus, in an embodiment, a cell comprises, in part, a BoNT/D substrate comprising a donor fluorophore, an acceptor and a BoNT/D recognition sequence including a cleavage site. The term "botulinum toxin serotype D recognition sequence" is synonymous with "BoNT/D recognition sequence" and means a scissile bond together with adjacent or non-adjacent recognition elements, or both, sufficient for detectable proteolysis at the scissile bond by a BoNT/D under appropriate conditions. A scissile bond cleaved by BoNT/D can be, for example, Lys-Leu. It is envisioned that a BoNT/D recognition sequence can be of any length, with the proviso that the BoNT/D recognition sequence can be cleaved by a BoNT/D.

In an aspect of this embodiment, the Clostridial toxin substrate includes, in part, a BoNT/D recognition sequence comprising a BoNT/D recognition sequence containing at least six consecutive residues of VAMP including Lys-Leu. In another aspect of this embodiment, the Clostridial toxin substrate includes, in part, a BoNT/D recognition sequence comprising the BoNT/D recognition sequence Arg-Asp-Gln-Lys-Leu-Ser-Glu-Leu (SEQ ID NO: 100). In other aspects of this embodiment, the Clostridial toxin substrate includes, in part, a BoNT/D recognition sequence comprising a portion of VAMP-1-1 such as, e.g., residues 1 to 118 of SEQ ID NO: 28; residues 39 to 77 of SEQ ID NO: 28, or a peptidomimetic thereof. In other aspects of this embodiment, the Clostridial toxin substrate includes, in part, a BoNT/D recognition sequence comprising a portion of VAMP-1-2 such as, e.g., residues 1 to 117 of SEQ ID NO: 29; residues 39 to 77 of SEQ ID NO: 29, or a peptidomimetic thereof. In other aspects of this embodiment, the Clostridial toxin substrate includes, in part, a BoNT/D recognition sequence comprising a portion of VAMP-1-3 such as, e.g., residues 1 to 116 of SEQ ID NO: 30; residues 39 to 77 of SEQ ID NO: 30, or a peptidomimetic thereof. In other aspects of this embodiment, the Clostridial toxin substrate includes, in part, a BoNT/D recognition sequence comprising a portion of VAMP-2 such as, e.g., residues 1 to 116 of SEQ ID NO: 31; residues 1 to 86 of SEQ ID NO: 31; residues 1 to 76 of SEQ ID NO: 31; residues 1 to 69 of SEQ ID NO: 31; residues 27 to 116 of SEQ ID NO: 31; residues 37 to 116 of SEQ ID NO: 31; residues 27 to 68 of SEQ ID NO: 31; residues 37 to 69 of SEQ ID NO: 31, or a peptidomimetic thereof.

In other aspects of this embodiment, a BoNT/D toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, or at least 200 residues. In other embodiments, a BoNT/D toxin recognition sequence has at most 20 residues, at most 30 residues, at most 40 residues, at most 50 residues, at most 100 residues, at most 150 residues, or at most 200 residues.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A BoNT/E recognition sequence can have, for example, residues 46-206, residues 92 to 206, residues, residues 134 to 206, residues, 137 to 206; 146-206 or 156-206 of human SNAP-25, see, e.g., Vaidyanathan et al., supra, (1999); and Schmidt & Stafford, supra, (Jul. 13, 2004).

A BoNT/E recognition sequence useful in aspects of the invention can correspond to a segment of a protein that is sensitive to cleavage by botulinum toxin serotype E, or can be substantially similar to a segment of a BoNT/E-sensitive protein. As shown in Table 2, a variety of naturally occurring proteins sensitive to cleavage by BoNT/E are known in the art and include, for example, human, chicken, *Danio, Carassius* SNAP-25A and SNAP-25B; rat and mouse SNAP-25A, SNAP-25B and SNAP-23; and *Caenorhabditis* SNAP-25. Thus, a BoNT/E recognition sequence can correspond, for example, to a segment of human SNAP-25A or SNAP-25B; bovine SNAP-25A or SNAP-25B; rat SNAP-25A, SNAP-25B or SNAP-23; mouse SNAP-25A, SNAP-25B or SNAP-23; *Xenopus* SNAP-25A or SNAP-25B; *Danio* SNAP-25A or SNAP-25B; *Carassius* SNAP-25A or SNAP-25B; *Strongylocentrotus* SNAP-25; *Drosophila* SNAP-24; *Hirudo* SNAP-25; *Loligo* SNAP-25; *Lymnaea* SNAP-25; *Caenorhabditis* SNAP-25, isoforms thereof, or another naturally occurring protein sensitive to cleavage by BoNT/C1. Furthermore, as shown in Table 2, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a BoNT/E substrate useful in the invention. It is understood that a similar BoNT/E recognition sequence can be prepared, if desired, from a corresponding (homologous) segment of another BoNT/E-sensitive SNAP-25 isoform, paralog or ortholog, such as, the BoNT/E recognition sequence contain in the SNAP-25 proteins identified in the organisms listed above and in Table 2.

Thus, in an embodiment, a cell comprises, in part, a BoNT/E substrate comprising a donor fluorophore, an acceptor and a BoNT/E recognition sequence including a cleavage site. As used herein, the term "botulinum toxin serotype E recognition sequence" is synonymous with "BoNT/E recognition sequence" and means a scissile bond together with adjacent or non-adjacent recognition elements, or both, sufficient for detectable proteolysis at the scissile bond by a BoNT/E under appropriate conditions. A scissile bond cleaved by BoNT/E can be, for example, Arg-Ile. It is envisioned that a BoNT/E recognition sequence can be of any length, with the proviso that the BoNT/E recognition sequence can be cleaved by a BoNT/E.

In an aspect of this embodiment, the Clostridial toxin substrate includes, in part, a BoNT/E recognition sequence comprising a BoNT/E recognition sequence containing at least six consecutive residues of SNAP-25 including Arg-Ile. In another aspect of this embodiment, the Clostridial toxin substrate includes, in part, a BoNT/E recognition sequence comprising the BoNT/E recognition sequence Gln-Ile-Asp-Arg-Ile-Met-Glu-Lys (SEQ ID NO: 101). In other aspects of this embodiment, the Clostridial toxin substrate includes, in part, a BoNT/E recognition sequence comprising a portion of SNAP-25 such as, e.g., residues 1 to 206 of SEQ ID NO: 1; residues 46 to 206 of SEQ ID NO: 1; residues 92 to 206 of SEQ ID NO: 1; residues 134 to 206 of SEQ ID NO: 1; residues 137 to 206 of SEQ ID NO: 1, residues 146 to 206 of SEQ ID NO: 1; residues 156 to 206 of SEQ ID NO: 1, or a peptidomimetic thereof.

In other aspects of this embodiment, a BoNT/E toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, at least 200 residues, at least 250 residues or at least 300 residues. In other embodiments, a BoNT/E toxin recognition sequence has at most 20 residues, at most 30 residues, at most 40 residues, at most 50 residues, at most 100 residues, at most 150 residues, at most 200 residues, at most 250 residues or at most 300 residues.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2, see, e.g., Yamasaki et al., supra, (1994). A BoNT/F recognition sequence also can include, for example, residues 27 to 69 or residues 37 to 69 of rat VAMP-2. It is understood that a similar BoNT/F recognition sequence can be prepared, if desired, from a corresponding (homologous) segment of another BoNT/F-sensitive VAMP isoform, paralog or ortholog, such as, e.g., human VAMP-1 or human VAMP-2. A BoNT/F recognition sequence also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 126) or a peptidomimetic thereof, which corresponds to residues 37 to 75 of human VAMP-2, see, e.g., Schmidt & Stafford, supra, (Jul. 13, 2004) and the BoNT/F recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 127) or a peptidomimetic thereof, which corresponds to residues 39 to 77 of human VAMP-1.

A BoNT/F recognition sequence can correspond to a segment of a protein that is sensitive to cleavage by botulinum toxin serotype F, or can be substantially similar to a segment of a BoNT/F-sensitive protein. As shown in Table 4, a variety of naturally occurring proteins sensitive to cleavage by BoNT/F are known in the art and include, for example, human, rat and mouse VAMP-1, VAMP-2 and VAMP-3/cellubrevin; bovine VAMP-2; chicken VAMP-1 and VAMP-2; *Torpedo* VAMP-1; and *Drosophila* sybA and synB. Thus, a BoNT/F recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Drosophila* sybA and synB; *Hirudo* VAMP; *Loligo* VAMP; *Lymnaea* VAMP; *Aplysia* VAMP; *Caenorhabditis* SNB1, isoforms thereof, or another naturally occurring protein sensitive to cleavage by BoNT/F. Thus, a BoNT/F recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, *Drosophila* syb, leech VAMP, or another naturally occurring protein sensitive to cleavage by BoNT/F. Furthermore, as shown in Table 4 above, comparison of native VAMP amino acid sequences cleaved by BoNT/F reveals that such sequences are not absolutely conserved, indicating that a variety of amino acid substitutions and modifications relative to a naturally occurring BoNT/F-sensitive VAMP sequence can be tolerated in a BoNT/F substrate useful in the invention. It is understood that a similar BoNT/F recognition sequence can be prepared, if desired, from a corresponding (homologous) segment of another BoNT/F-sensitive VAMP-1 or VAMP-2 isoform, paralog or ortholog, such as, the BoNT/F recognition sequence contain in the VAMP-1 and VAMP-2 identified in the organisms listed above and in Table 4.

Thus, in an embodiment, a cell comprises, in part, a BoNT/F substrate comprising a donor fluorophore, an acceptor and a BoNT/F recognition sequence including a cleavage site. The term "botulinum toxin serotype F recognition sequence," as used herein, is synonymous with "BoNT/F recognition sequence" and means a scissile bond together with adjacent or non-adjacent recognition elements, or both, sufficient for detectable proteolysis at the scissile bond by a BoNT/F under appropriate conditions. A scissile bond cleaved by BoNT/F can be, for example, Gln-Lys. It is envisioned that a BoNT/F recognition sequence can be of any length, with the proviso that the BoNT/F recognition sequence can be cleaved by a BoNT/F.

In an aspect of this embodiment, the Clostridial toxin substrate includes, in part, a BoNT/F recognition sequence comprising a BoNT/F recognition sequence containing at least six consecutive residues of VAMP including Gln-Lys. In another aspect of this embodiment, the Clostridial toxin substrate includes, in part, a BoNT/F recognition sequence comprising the BoNT/F recognition sequence Glu-Arg-Asp-Gln-Lys-Leu-Ser-Glu (SEQ ID NO: 102). In other aspects of this embodiment, the Clostridial toxin substrate includes, in part, a BoNT/F recognition sequence comprising a portion of VAMP-1-1 such as, e.g., residues 1 to 118 of SEQ ID NO: 28; residues 39 to 77 of SEQ ID NO: 28, or a peptidomimetic thereof. In other aspects of this embodiment, the Clostridial toxin substrate includes, in part, a BoNT/F recognition sequence comprising a portion of VAMP-1-2 such as, e.g., residues 1 to 117 of SEQ ID NO: 29; residues 39 to 77 of SEQ ID NO: 29, or a peptidomimetic thereof. In other aspects of this embodiment, the Clostridial toxin substrate includes, in part, a BoNT/F recognition sequence comprising a portion of VAMP-1-3 such as, e.g., residues 1 to 116 of SEQ ID NO: 30; residues 39 to 77 of SEQ ID NO: 30, or a peptidomimetic thereof. In other aspects of this embodiment, the Clostridial toxin substrate includes, in part, a BoNT/F recognition sequence comprising a portion of VAMP-2 such as, e.g., residues 1 to 116 of SEQ ID NO: 31; residues 1 to 86 of SEQ ID NO: 31; residues 1 to 76 of SEQ ID NO: 31; residues 1 to 69 of SEQ ID NO: 31; residues 27 to 116 of SEQ ID NO: 31; residues 37 to 116 of SEQ ID NO: 31; residues 27 to 68 of SEQ ID NO: 31; residues 37 to 75 of SEQ ID NO: 31; residues 37 to 69 of SEQ ID NO: 31, or a peptidomimetic thereof.

In other aspects of this embodiment, a BoNT/F toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, or at least 200 residues. In other embodiments, a BoNT/F toxin recognition sequence has at most 20 residues, at most 30 residues, at most 40 residues, at most 50 residues, at most 100 residues, at most 150 residues, or at most 200 residues.

A BoNT/G recognition sequence can correspond to a segment of a protein that is sensitive to cleavage by botulinum toxin serotype G, or can be substantially similar to such a BoNT/G-sensitive segment. As shown in Table 4, a variety of naturally occurring proteins sensitive to cleavage by BoNT/G are known in the art and include, for example, human, rat and mouse VAMP-1, VAMP-2 and VAMP-3/cellubrevin; bovine VAMP-2; chicken VAMP-1, and VAMP-2; and Torpedo VAMP-1. Thus, a BoNT/G recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; Xenopus VAMP-2 or VAMP-3; Danio VAMP-1 or VAMP-2; Torpedo VAMP-1; Caenorhabditis SNB1, isoforms thereof, or another naturally occurring protein sensitive to cleavage by BoNT/G. Furthermore, as shown in Table 4 above, comparison of native VAMP amino acid sequences cleaved by BoNT/G reveals that such sequences are not absolutely conserved, indicating that a variety of amino acid substitutions and modifications relative to a naturally occurring BoNT/G-sensitive VAMP sequence can be tolerated in a BoNT/G substrate useful in the invention. It is understood that a similar BoNT/G recognition sequence can be prepared, if desired, from a corresponding (homologous) segment of another BoNT/G-sensitive VAMP-1 or VAMP-2 isoform, paralog or ortholog, such as, the BoNT/G recognition sequence contain in the VAMP-1 and VAMP-2 identified in the organisms listed above and in Table 4.

Thus, in an embodiment, a cell comprises, in part, a BoNT/G substrate comprising a donor fluorophore, an acceptor and a BoNT/G recognition sequence including a cleavage site. As used herein, the term "botulinum toxin serotype G recognition sequence" is synonymous with "BoNT/G recognition sequence" and means a scissile bond together with adjacent or non-adjacent recognition elements, or both, sufficient for detectable proteolysis at the scissile bond by a BoNT/G under appropriate conditions. A scissile bond cleaved by BoNT/G can be, for example, Ala-Ala. It is envisioned that a BoNT/G recognition sequence can be of any length, with the proviso that the BoNT/G recognition sequence can be cleaved by a BoNT/G.

In an aspect of this embodiment, the Clostridial toxin substrate includes, in part, a BoNT/G recognition sequence comprising a BoNT/G recognition sequence containing at least six consecutive residues of VAMP including Ala-Ala. In another aspect of this embodiment, the Clostridial toxin substrate includes, in part, a BoNT/G recognition sequence comprising the BoNT/G recognition sequence Glu-Thr-Ser-Ala-Ala-Lys-Leu-Lys (SEQ ID NO: 103). In other aspects of this embodiment, the Clostridial toxin substrate includes, in part, a BoNT/G recognition sequence comprising a portion of VAMP-1-1 such as, e.g., residues 1 to 118 of SEQ ID NO: 28, or a peptidomimetic thereof. In other aspects of this embodiment, the Clostridial toxin substrate includes, in part, a BoNT/G recognition sequence comprising a portion of VAMP-1-2 such as, e.g., residues 1 to 117 of SEQ ID NO: 29, or a peptidomimetic thereof. In other aspects of this embodiment, the Clostridial toxin substrate includes, in part, a BoNT/G recognition sequence comprising a portion of VAMP-1-3 such as, e.g., residues 1 to 116 of SEQ ID NO: 30, or a peptidomimetic thereof. In other aspects of this embodiment, the Clostridial toxin substrate includes, in part, a BoNT/G recognition sequence comprising a portion of VAMP-2 such as, e.g., residues 1 to 116 of SEQ ID NO: 31, or a peptidomimetic thereof.

In other aspects of this embodiment, a BoNT/G toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, or at least 200 residues. In other embodiments, a BoNT/G toxin recognition sequence has at most 20 residues, at most 30 residues, at most 40 residues, at most 50 residues, at most 100 residues, at most 150 residues, or at most 200 residues.

A variety of TeNT recognition sequences are well known in the art or can be defined by routine methods and include sequences corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 31; F. Cornille et al., Solid-phase synthesis, conformational analysis and in vitro cleavage of synthetic human synaptobrevin II 1-93 by tetanus toxin L chain, 222(1) Eur. J. Biochem. 173-181 (1994); Patrick Foran et al., Differences in the protease activities of tetanus and botulinum B toxins revealed by the cleavage of vesicle-associated membrane protein and various sized fragments, 33(51) Biochemistry 15365-15374 (1994); residues 51 to 93 or residues 1 to 86 of rat VAMP-2, see, e.g., Yamasaki et al., supra, (1994); or residues 33 to 94 of human VAMP-1-1 (SEQ ID NO: 28), residues 33 to 94 of human VAMP-1-2 (SEQ ID NO: 29) and residues 33 to 94 of human VAMP-1-3 (SEQ ID NO: 30). A TeNT recognition sequence also can include, for example, residues 25 to 86, residues 33 to 86 or residues 51 to 86 of human VAMP-2 (SEQ ID NO: 31) or rat VAMP-2 (SEQ ID NO: 38). It is understood that a similar TeNT recognition sequence can be prepared, if desired, from a corresponding (homologous) segment of another TeNT-sensitive VAMP isoform or species homolog such as human VAMP-1 or sea urchin or Aplysia VAMP.

Thus, a TeNT recognition sequence can correspond to a segment of a protein that is sensitive to cleavage by tetanus toxin, or can be substantially similar to a segment of a TeNT-sensitive protein. As shown in Table 4, a variety of naturally occurring proteins sensitive to cleavage by TeNT are known in the art and include, for example, human and mouse VAMP-1, VAMP-2 and VAMP-3/cellubrevin; bovine VAMP-2; rat VAMP-2 and VAMP-3; chicken VAMP-2; Torpedo VAMP-1; Strongylocentrotus VAMP; Drosophila sybA, synB, synC, synD and synE; Hirudo VAMP; and Caenorhabditis SNB1-like. Thus, a TeNT recognition sequence can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; Xenopus VAMP-2 or VAMP-3; Danio VAMP-1 or VAMP-2; Torpedo VAMP-1; Strongylocentrotus VAMP; Drosophila sybA, synB, synC, synD or synE; Hirudo VAMP; Loligo VAMP; Lymnaea VAMP; Aplysia VAMP; Caenorhabditis SNB1 and SNB-like, isoforms thereof, or another naturally occurring protein sensitive to cleavage by TeNT. Furthermore, comparison of native VAMP amino acid sequences cleaved by TeNT reveals that such sequences are not absolutely conserved (Table 4). This finding indicates that a variety of amino acid substitutions and modifications relative to a naturally occurring TeNT-sensitive VAMP sequence can be tolerated in a TeNT substrate useful in the invention. It is understood that a similar TeNT recognition sequence can be prepared, if desired, from a corresponding (homologous) segment of another TeNT-sensitive VAMP-1 or VAMP-2 isoform, paralog or ortholog, such as, the TeNT recognition sequence contain in the VAMP-1 and VAMP-2 identified in the organisms listed above and in Table 4.

Thus, in an embodiment, a cell comprises, in part, a TeNT substrate comprising a donor fluorophore, an acceptor and a TeNT recognition sequence including a cleavage site. As used herein, the term "tetanus toxin recognition sequence" means a scissile bond together with adjacent or non-adjacent recognition elements, or both, sufficient for detectable proteolysis at the scissile bond by a tetanus toxin under appropriate conditions. A scissile bond cleaved by TeNT can be, for example, Gln-Phe. It is envisioned that a TeNT recognition sequence can be of any length, with the proviso that the TeNT recognition sequence can be cleaved by a TeNT.

In an aspect of this embodiment, the Clostridial toxin substrate includes, in part, a TeNT recognition sequence comprising a TeNT recognition sequence containing at least six consecutive residues of VAMP including Gln-Phe. In another aspect of this embodiment, the Clostridial toxin substrate includes, in part, a TeNT recognition sequence comprising the TeNT recognition sequence Gly-Ala-Ser-Gln-Phe-Glu-Thr-Ser (SEQ ID NO: 104). In other aspects of this embodiment, the Clostridial toxin substrate includes, in part, a TeNT recognition sequence comprising a portion of VAMP-1-1 such as, e.g., residues 1 to 118 of SEQ ID NO: 28 or residues 33 to 94 of SEQ ID NO: 28. In other aspects of this embodiment, the Clostridial toxin substrate includes, in part, a TeNT recognition sequence comprising a portion of VAMP-1-2 such as, e.g., residues 1 to 117 of SEQ ID NO: 29 or residues 33 to 94 of SEQ ID NO: 29. In other aspects of this embodiment, the Clostridial toxin substrate includes, in part, a TeNT recognition sequence comprising a portion of VAMP-1-3 such as, e.g., residues 1 to 116 of SEQ ID NO: 30 or residues 33 to 94 of SEQ ID NO: 30. In other aspects of this embodiment, the Clostridial toxin substrate includes, in part, a TeNT recognition sequence comprising a portion of VAMP-2 such as, e.g., residues 1 to 116 of SEQ ID NO: 31; residues 25 to 94 of SEQ ID NO: 31; residues 33 to 94 of SEQ ID NO: 31; residues 51 to 93 of SEQ ID NO: 31; residues 1 to 86 of SEQ ID NO: 31; residues 25 to 86 of SEQ ID NO: 31; residues 33 to 86 of SEQ ID NO: 31; residues 51 to 86 of SEQ ID NO: 31, or a peptidomimetic thereof.

In other aspects of this embodiment, a TeNT toxin recognition sequence can be, e.g., a peptide or peptidomimetic having at least 10, at least 15, at least 20, at least 25, at least 30, at least 35, at least 40 residues, at least 50 residues, at least 60 residues, at least 70 residues, at least 80 residues, at least 90 residues, at least 100 residues, at least 125 residues, at least 150 residues, at least 175 residues, or at least 200 residues. In other embodiments, a TeNT toxin recognition sequence has at most 20 residues, at most 30 residues, at most 40 residues, at most 50 residues, at most 100 residues, at most 150 residues, or at most 200 residues.

SNAP-25, VAMP and Syntaxin share a short motif usually located within regions predicted to adopt an α-helical conformation called the SNARE motif. This motif usually comprises a nine amino acid motif with the general formula of H-⊖-⊖-X—H-⊖-X—H—P (see FIG. 3b), where H is a aliphatic residue, ⊖ is a carboxylate residue, P is a polar residue and X is any amino acid, see e.g., Ornella Rossetto et al., SNARE motif and neurotoxins, 372(6505) Nature 415-416 (1994); Rossella Pellizzari et al., Structural determinants of the specificity for synaptic vesicle-associated membrane protein/synaptobrevin of tetanus and botulinum type B and G neurotoxins, 271(34) J. Biol. Chem. 20353-20358 (1996); Rossella Pellizzari et al., The interaction of synaptic vesicle-associated membrane protein/synaptobrevin with botulinum neurotoxins D and F, 409(3) FEBS Lett. 339-342 (1997); and Philip Washbourne et al., Botulinum neurotoxin types A and E require the SNARE motif in SNAP-25 for proteolysis, 418(1-2) FEBS Lett. 1-5 (1997). This motif is present in SNAP-25, VAMP and Syntaxin isoforms expressed in animals sensitive to the toxins. In contrast, Drosophila and yeast SNAP-25 proteins are resistant to these toxins. In addition, VAMP and Syntaxin isoforms not involved in exocytosis contain sequence variations in these α-helical motif regions.

Multiple repetitions of the α-helical motif are present in proteins sensitive to cleavage by Clostridial toxins: Four copies are naturally present in SNAP-25, designated S1-S4; two copies are naturally present in VAMP, designated V1 and V2; and two copies are naturally present in Syntaxin, designated X1 and X2, see, e.g., Humeau et al., supra, (2000). Furthermore, peptides corresponding to the specific sequence of the α-helical motifs can inhibit toxin activity in vitro and in vivo, and such peptides can cross-inhibit different toxins. In addition, antibodies raised against such peptides can cross-react among the three target proteins, indicating that this α-helical motif is exposed on the protein surface and adopts a similar configuration in each of the three target proteins. Consistent with these findings, SNAP-25-specific, VAMP-specific and Syntaxin-specific toxins cross-inhibit each other by competing for the same binding site, although they do not cleave targets non-specifically. These results indicate that a Clostridial toxin recognition sequence can include, if desired, at least one α-helical motif. It is recognized that an α-helical motif is not required for cleavage by a Clostridial toxin, as evidenced by 16-mer and 17-mer substrates for BoNT/A known in the art, see, e.g., Schmidt & Bostian, supra, (1997); Schmidt & Bostian, supra, (Oct. 12, 1999); and Schmidt & Stafford, supra, (Jul. 13, 2004).

Although multiple α-helical motifs are found in the naturally occurring SNAP-25, VAMP and Syntaxin target proteins, a Clostridial toxin recognition sequence useful in a Clostridial toxin substrate can have a single α-helical motif. In particular embodiments, a method of the invention relies on a Clostridial toxin recognition sequence including two or more α-helical motifs. A BoNT/A or BoNT/E recognition sequence can include, for example, the S4 α-helical motif, alone or combined with one or more additional α-helical motifs; a BoNT/B, BoNT/G or TeNT recognition sequence can include, for example, the V2 α-helical motif, alone or combined with one or more additional α-helical motifs; a BoNT/C1 recognition sequence can include, for example, the S4 α-helical motif, alone or combined with one or more additional α-helical motifs, or the X2 α-helical motif, alone or combined with one or more additional α-helical motifs; and a BoNT/D or BoNT/F recognition sequence can include, for example, the V1 α-helical motif, alone or combined with one or more additional α-helical motifs. Representative SNARE motifs are presented in Tables 6, 7 and 8.

TABLE 6

SNARE motifs of SNAP-25 and Related Proteins

| Organism | Isoform | S1 | S2 | S3 | S4 |
|---|---|---|---|---|---|
| Primate | SNAP-25A | ADESLESTR | VEESKDAGI | LDEQGEQLD | MDENLEQVS |
|  | SNAP-25B |  |  | LDEQGEQLE |  |

TABLE 6-continued

SNARE motifs of SNAP-25 and Related Proteins

| Organism | Isoform | S1 | S2 | S3 | S4 |
|---|---|---|---|---|---|
| Primate | SNAP-23A SNAP-23B | TDESLESTR | AIESQDAGI | LDEQKEQLN | MEENLTQVG |
| Rodent | SNAP-25A SNAP-25B | ADESLESTR | VEESKDAGI | LDEQGEQLD LDEQGEQLE | MDENLEQVS |
| Rodent | SNAP-23 | TDESLESTR | AIESQDAGI | LDEQGEQLN | MEENLTQVG |
| Bird | SNAP-25B | ADESLESTR | VEESKDAGI | LDEQGEQLE | MDENLEQVS |
| Amphibian | SNAP-25A SNAP-25B | ADESLESTR | VEGSKDAGI | LDEQGEQLD LDEQGEQLE | MDENLEQVG |
| Amphibian | SNAP-23 | ADESLESTR | ALESQDAGI | LDEQGEQLD | MDENLVQVG |
| Fish | SNAP-25A SNAP-25B | ADESLESTR GDESLESTR | VEESKDAGI | LDEQGEQLE | MDENLEQVG MDENLEQVG |
| Fish | SNAP-23 | TDESLESTR | AEESRETGV | LDEQGEQLR | MEENLDQVG |
| Ray | SNAP-25 | TDESLESTR | VEESKDAGI | LDEQGEQLE | MEENLDQVG |
| Sea urchin | SNAP-25 | TDESLESTR | AEESKEAGI | LDEQGEQLD | MDENLTQVS |
| Insect | SNAP-25 | ADESLESTR | CEESKEAGI | LDDQGEQLD | MEENMGQVN |
| Insect | SNAP-24 | ADESLESTR | MDESKEAGI | LDDQGEQLD | MDENLGQVN |
| Segmented worm | SNAP-25 | TDDSLESTR | CEESKDAGI | LDEQGEQLD | MEQNMGEVS |
| Cephalopod | SNAP-25 | TDDSLESTR | CEESKEAGI | LDEQGEQLD | MENNMKEVS |
| Gastropod | SNAP-25 | TNESLESTR | CEESKEAGI | LDEQGEQLD | MEQNIGEVA |
| Round worm | SNAP-25 | TDDSLESTR | CEESKEAGI | LDDQGEQLE | MDENVQQVS |

Proteolytic cleavage occurs at this site (*); Proteolytic cleavage not detected at this site (-); Proteolytic cleavage not determined at this site (ND)

Table 6—SNARE motifs of SNAP-25 and Related Proteins. Primate: Human SNAP-25A residues 22-30, 36-44, 50-58 and 146-154 of SEQ ID NO: 1; Human SNAP-25B residues 22-30, 36-44, 50-58 and 146-154 of SEQ ID NO: 2; Human SNAP-23A residues 17-25, 31-39, 45-53, and 152-160 of SEQ ID NO: 3; Human SNAP-23B residues 17-25, 31-39, 45-53 and 152-160 of SEQ ID NO: 4; Monkey SNAP-25B residues 22-30, 36-44, 50-58 and 146-154 of SEQ ID NO: 5; Rodent: Rat SNAP-25A residues 22-30, 36-44, 50-58 and 146-154 of SEQ ID NO: 6; Rat SNAP-25B residues 22-30, 36-44, 50-58 and 146-154 of SEQ ID NO: 7; Mouse SNAP-25B residues 22-30, 36-44, 50-58 and 146-154 of SEQ ID NO: 8; Rat SNAP-23 residues 17-25, 31-39, 45-53 and 151-159 of SEQ ID NO: 9; Mouse SNAP-23 residues 17-25, 31-39, 45-53 and 151-159 of SEQ ID NO: 10; Bird: Chicken SNAP-25B residues 22-30, 36-44, 50-58 and 146-154 of SEQ ID NO: 11; Fish: Goldfish SNAP-25A residues 22-30, 36-44, 50-58 and 144-152 of SEQ ID NO: 12; Goldfish SNAP-25B residues 22-30, 36-44, 50-58 and 143-151 of SEQ ID NO: 13; Zebrafish SNAP-25A residues 22-30, 36-44, 50-58 and 144-152 of SEQ ID NO: 14; Zebrafish SNAP-25B residues 22-30, 36-44, 50-58 and 143-151 of SEQ ID NO: 15; Zebrafish SNAP-23 residues 17-25, 31-39, 45-53 and 157-165 of SEQ ID NO: 16; Ray: marbled electric ray SNAP-25 residues 26-34, 40-48, 54-62 and 153-161 of SEQ ID NO: 17; Amphibian: Frog SNAP-25A residues 22-30, 36-44, 50-58 and 146-154 of SEQ ID NO: 18; Frog SNAP-25B residues 22-30, 36-44, 50-58 and 146-154 of SEQ ID NO: 19; Frog SNAP-23 residues 17-25, 31-39, 45-53, and 146-154 of SEQ ID NO: 20; Sea urchin SNAP-25 residues 24-32, 38-46, 52-60 and 152-160 of SEQ ID NO: 21; Insect: Fruit fly SNAP-25 residues 29-37, 43-51, 57-65 and 154-163 of SEQ ID NO: 22 212; Fruit fly SNAP-24 residues 24-32, 38-46, 52-60 and 153-162 of SEQ ID NO: 23; Segmented worm: Leech SNAP-25 residues 30-38, 44-52, 58-66 and 153-161 of SEQ ID NO: 24; Cephalopod: squid SNAP-25 residues 25-33, 39-47, 53-61 and 153-161 of SEQ ID NO: 25; Gastropod: Pond snail SNAP-25 residues 32-40, 46-54, 60-68 and 160-168 of SEQ ID NO: 26; Round worm: Nematode worm SNAP-25 residues 22-30, 36-44, 50-58 and 148-156 of SEQ ID NO: 27.

TABLE 7

SNARE motifs of VAMP and Related Proteins

| Organism | Isoform | V1 | V2 |
|---|---|---|---|
| Primate | VAMP1-1 VAMP1-2 VAMP1-3 | VEEVVDIIR | LDDRADALQ |

TABLE 7-continued

SNARE motifs of VAMP and Related Proteins

| Organism | Isoform | Motif V1 | Motif V2 |
|---|---|---|---|
| Primate | VAMP2 | VDEVVDIMR | LDDRADALQ |
| Primate | VAMP3 | VDEVVDIMR | LDDRADALQ |
| Bovine | VAMP2 | VDEVVDIMR | LDDRADALQ |
| Rodent | VAMP1 | VEEVVDIIR | LDDRADALQ |
|  | VAMP1/1b | VEEVVDIMR |  |
| Rodent | VAMP2 | VDEVVDIMR | LDDRADALQ |
|  | VAMP2-b |  |  |
| Rodent | VAMP3 | VDEVVDIMR | LDDRADALQ |
| Bird | VAMP1 | VEEVVDIMR | LDDRADALQ |
| Bird | VAMP2 | VDEVVDIMR | LDNRADALQ |
| Bird | VAMP3 | VDEVVDIMR | LDDRADALQ |
| Amphibian | VAMP2 | VDEVVDIMR | LDDRADALQ |
| Amphibian | VAMP3 | VDEVVDIMR | LDDRADALQ |
| Fish | VAMP1 | VDEVVDIMR | LDDRADALQ |
| Fish | VAMP2 | VDEVVDIMR | LDDRADALQ |
| Fish | VAMP-3 | VDEVVDIMR | LDDRADALQ |
| Ray | VAMP1 | VEEVVDIIR | LDDRADALQ |
| Sea urchin | VAMP | VDEVVDIMR | LDDRADALQ |
| Insect | Syn-A1 Syn-B1 | VDEVVGIMR | LGERADQLE |
| Insect | Syn-A2 Syn-B2 | VDEVVGIMR | LGERADQLE |
| Insect | Syn-C Syn-D Syn-E | VDEVVDIMR | LDDRADALQ |
| Segmented worm | VAMP | VDEVVGMMR | LDGRADALQ |
| Cephalopod | VAMP | VEEVVGIMR | LDDRADALQ |
| Gastropod | VAMP | VDEVVGIMR | LDDRAEALQ |
| Round worm | SNB1 | VDEVVGIMK | LDDRADALQ |
|  | SNB-like | VNEVIDVMR | LDHRAEVLQ |

Table 7—SNARE motifs of VAMP and Related Proteins. Primate: Human VAMP-1-1 residues 40-48 and 56-64 of SEQ ID NO: 28; Human VAMP-1-2 residues 40-48 and 56-64 of SEQ ID NO: 29; Human VAMP-1-3 residues 40-48 and 56-64 of SEQ ID NO: 30; Human VAMP-2 residues 39-47 and 63-71 of SEQ ID NO: 31; Monkey VAMP-2 residues 39-47 and 63-71 of SEQ ID NO: 32; Human VAMP-3/cellubrevin residues 22-30 and 46-54 of SEQ ID NO: 33; Bovine: Cow VAMP-2 residues 39-47 and 63-71 of SEQ ID NO: 34; Rodent: Rat VAMP-1 residues 40-48 and 56-64 of SEQ ID NO: 35; Rat VAMP-1-b residues 40-48 and 56-64 of SEQ ID NO: 36; Mouse VAMP-1 residues 40-48 and 56-64 of SEQ ID NO: 37; Rat VAMP-2 residues 39-47 and 63-71 of SEQ ID NO: 38; Rat VAMP-2-b residues 39-47 and 63-71 of SEQ ID NO: 39; Mouse VAMP-2 residues 39-47 and 63-71 of SEQ ID NO: 40; Rat VAMP-3/cellubrevin residues 26-34 and 50-58 of SEQ ID NO: 41; Mouse VAMP-3/cellubrevin residues 26-34 and 50-58 of SEQ ID NO: 42; Bird: Chicken VAMP-1 residues 182-190 and 198-206 of SEQ ID NO: 43; Chicken VAMP-2 residues 37-45 and 61-69 of SEQ ID NO: 44; Chicken VAMP-3/cellubrevin residues 26-34 and 50-58 of SEQ ID NO: 45; Fish: Zebrafish VAMP-1 residues 41-49 and 57-65 of SEQ ID NO: 46; Zebrafish VAMP-2 residues 33-41 and 57-65 of SEQ ID NO: 47; Zebrafish VAMP-3 residues 25-33 and 49-57 of SEQ ID NO: 48; Ray: marbled electric ray VAMP-1 residues 42-50 and 58-66 of SEQ ID NO: 49; Amphibian: Frog VAMP-2 residues 37-45 and 61-69 of SEQ ID NO: 50; Frog VAMP-3 residues 24-32 and 48-56 of SEQ ID NO: 51; Sea urchin VAMP residues 23-31 and 39-47 of SEQ ID NO: 52; Insect: Fruit fly SynA1 residues 31-39 and 47-55 of SEQ ID NO: 53; Fruit fly SynA2 residues 54-62 and 70-78 of SEQ ID NO: 54; Fruit fly SynB1 residues 54-62 and 70-78 of SEQ ID NO: 55; Fruit fly SynB2 residues 54-62 and 70-78 of SEQ ID NO: 56; Fruit fly SynC residues 48-56 and 64-72 of SEQ ID NO: 57; Fruit fly SynD residues 67-75 and 83-91 of SEQ ID NO: 58; Fruit fly SynE residues 67-75 and 83-91 of SEQ ID NO: 59; Segmented worm: Leech VAMP residues 37-45 and 53-61 of SEQ ID NO: 60; Cephalopod: squid VAMP residues 47-55 and 63-71 of SEQ ID NO: 61; Gastropod: Pond snail VAMP residues 40-48 and 56-64 of SEQ ID NO: 62; sea hare VAMP residues 30-38 and 46-54 of SEQ ID NO: 63; Round worm: Nematode worm SNB1 residues 34-42 and 50-58 of SEQ ID NO: 64; Nematode worm SNB-like residues 40-48 and 56-64 of SEQ ID NO: 65.

TABLE 8

SNARE motifs of Syntaxin and Related Proteins

| Organism | Isoform | Motif X1 | Motif X2 |
|---|---|---|---|
| Primate | Syntaxin1A | MDEFFEQVE | LEDMLESGN |
|  | Syntaxin1B1 | MDEFFEQEE | LEDMLESGK |
|  | Syntaxin1B2 | MDEFFEQVE | LEDMLESGK |
| Primate | Syntaxin2-1 | MDDFFHQVE | LEEMLESGK |
|  | Syntaxin2-2 |  |  |
|  | Syntaxin2-3 |  |  |
| Primate | Syntaxin3A | MDEFFSEIE | LEEMLESGN |
| Bovine | Syntaxin1A | MDEFFEQVE | LEDMLESGN |
|  | Syntaxin1B2 |  | LEDMLESGK |
| Rodent | Syntaxin1A | MDEFFEQVE | LEDMLESGN |
|  | Syntaxin1B1 | MAEFFEQVE | LEDMLESGK |
|  | Syntaxin1B2 | MDEFFEQVE | LEDMLESGK |
| Rodent | Syntaxin2 | MDGFFHQVE | LEEMLESGK |
| Rodent | Syntaxin3A | MDEFFSEIE | LEEMLESGN |
|  | Syntaxin3B |  |  |
| Rodent | Syntaxin3C | MDEFFSENF | LEEMLESGN |
| Bird | Syntaxin1B | MDEFFEQVE | LEDMLESGK |
| Bird | Syntaxin2 | MDDFFQQVE | LEEMLESGN |
| Fish | Syntaxin1B | MDEFFEQVE | LEDMLESGK |
| Fish | Syntaxin3 | MDEFFSQIE | LEEMLEGGN |
| Sea urchin | Syntaxin1B | MEEFFEQVE | LEDMLESGN |
| Insect | Syntaxin1A | MDDFFAQVE | LEKMLEEGN |

TABLE 8-continued

SNARE motifs of Syntaxin and Related Proteins

| | | Motif | |
|---|---|---|---|
| Organism | Isoform | X1 | X2 |
| Segmented worm | Syntaxin1A | MEEFFEQVN | LEDMLESGN |
| Cephalopod | Syntaxin1A | MEEFFEQVE | LEDMLESGN |
| Gastropod | Syntaxin1A | MEEFFEQVD | LEDMIESGN |

Table 8—SNARE motifs of Syntaxin and Related Proteins. Primate: Human Syntaxin1A residues 30-38 and 165-173 of SEQ ID NO: 66; Human Syntaxin1B1 residues 29-37 and 164-172 of SEQ ID NO: 67; Human Syntaxin1B2 residues 29-37 and 164-172 of SEQ ID NO: 68; Human Syntaxin2-1 residues 29-37 and 168-176 of SEQ ID NO: 69; Human Syntaxin2-2 residues 29-37 and 168-176 of SEQ ID NO: 70; Human Syntaxin2-3 residues 29-37 and 168-176 of SEQ ID NO: 71; Human Syntaxin3 residues 32-40 and 165-173 of SEQ ID NO: 72; Bovine: Cow Syntaxin1A residues 30-38 and 165-173 of SEQ ID NO: 73; Cow Syntaxin1B2 residues 29-37 and 164-172 of SEQ ID NO: 74; Rodent: Rat Syntaxin1A residues 30-38 and 165-173 of SEQ ID NO: 75; Rat Syntaxin1B2 residues 29-37 and 164-172 of SEQ ID NO: 76; Mouse Syntaxin1A residues 30-38 and 165-173 of SEQ ID NO: 77; Mouse Syntaxin1B1 residues 29-37 and 164-172 of SEQ ID NO: 78; Mouse Syntaxin1B2 residues 29-37 and 164-172 of SEQ ID NO: 79; Rat Syntaxin2 residues 31-39 and 170-178 of SEQ ID NO: 80; Mouse Syntaxin2 residues 30-38 and 169-177 of SEQ ID NO: 81; Rat Syntaxin3A residues 32-40 and 165-173 of SEQ ID NO: 82; Mouse Syntaxin3A residues 32-40 and 165-173 of SEQ ID NO: 83; Mouse Syntaxin3B residues 32-40 and 165-173 of SEQ ID NO: 84; Mouse Syntaxin3C residues 32-40 and 147-155 of SEQ ID NO: 85; Bird: Chicken Syntaxin1B residues 29-37 and 157-165 of SEQ ID NO: 86; Chicken Syntaxin2 residues 28-36 and 167-175 of SEQ ID NO: 87; Fish: Zebrafish Syntaxin1B residues 29-37 and 164-172 of SEQ ID NO: 88; Zebrafish Syntaxin3 residues 29-37 and 163-171 of SEQ ID NO: 89; sea urchin Syntaxin1B residues 29-37 and 164-172 of SEQ ID NO: 90; Insect: Fruit fly Syntaxin1A residues 33-41 and 168-176 of SEQ ID NO: 91; Segmented worm: leech Syntaxin1A residues 36-44 and 171-179 of SEQ ID NO: 92; Cephalopod: squid Syntaxin1A residues 33-41 and 168-176 of SEQ ID NO: 93; Gastropod: Pond snail Syntaxin1A residues 32-40 and 167-175 of SEQ ID NO: 94; sea hare Syntaxin1A residues 32-40 and 167-175 of SEQ ID NO: 95.

Thus, in an embodiment, a Clostridial toxin recognition sequence can comprise an α-helical motif. In an aspect of this embodiment, a Clostridial toxin recognition sequence can comprise a S1 α-helical motif, a S2 α-helical motif, a S3 α-helical motif, a S4 α-helical motif or any combination thereof. In another aspect of this embodiment, a Clostridial toxin recognition sequence can comprise a V1 α-helical motif, a V2 α-helical motif, or any combination thereof. In yet another aspect of this embodiment, a Clostridial toxin recognition sequence can comprise a X1 α-helical motif, a X2 α-helical motif, or any combination thereof. In still another aspect of this embodiment, a Clostridial toxin recognition sequence can comprise a S1 α-helical motif, a S2 α-helical motif, a S3 α-helical motif, a S4 α-helical motif, a V1 α-helical motif, a V2 α-helical motif, a X1 α-helical motif, a X2 α-helical motif or any combination thereof.

As discussed above, the SNARE complex is comprised of the t-SNARE SNAP-25 along with another t-SNARE, Syntaxin 1 and a v-SNARE VAMP/synaptobrevin. Members of the SNAP-25 family of proteins can be divided into three structural domains and amino-terminal α-helix of approximately 84 residues, an approximately 36 amino acid interhelical loop and a carboxyl-terminal α-helix of approximately 86 residues, depending on the individual member. As will be discussed below, all three of these regions may be used to target SNAP-25 to the plasma membrane either alone or in any combination of the three.

The interhelical loop of SNAP-25 appears to be important for conferring targeting specificity of this SNARE protein to the membrane. For example, in one study a membrane-targeting domain comprising residues 85-120 of SNAP-25 was shown to localize to the cell membrane Susana Gonzalo et al., SNAP-25 is targeted to the plasma membrane through a novel membrane-binding domain, 274(30) J. Biol. Chem. 21313-21318 (1999). This region represents two-thirds of the interhelical loop that connects the amino- and carboxyl-terminal α-helices of SNAP-25. The function of this targeting domain appears to be independent of SNARE protein-protein interactions since remove of the SNAP-25 regions that associate with either Syntaxin or synaptobrevin did not interfere with proper targeting of SNAP-25 to the membrane.

Alignment of SNAP-25 family members revealed two conserved motifs present within the interhelical loop region responsible for membrane targeting. The first is a cysteine-rich region present at the amino-terminal boundary of the membrane-targeting interhelical loop domain. One or more of the cysteines present in this motif is fatty acylated via a thioester linkage of palmitate. Palmitoylation of this cysteine-rich may be important for membrane insertion because elimination of these cysteine residues results in a loss of SNAP-25 membrane-targeting.

The second is a five-amino acid motif located at the carboxyl-terminal boundary of the membrane-targeting interhelical loop domain (QPXR(V/I)). This motif is believed to play a role in membrane association, see, e.g., Gonzalo et al., supra, (1999); Philip Washbourne et al., Cysteine residues of SNAP-25 are required for SNARE disassembly and exocytosis, but not for membrane targeting, 357(3) Biochem. J. 625-634 (2001).

The α-helices of the various SNARE complex members seem to be involved in protein-protein interactions between members. For example, solution of the crystal structure of the SNARE complex reveals that SNAP-25, Syntaxin and synaptobrevin appear to favor a heterotrimeric, parallel four-helix bundle association, see, e.g., R. Bryan Sutton et al., Crystal structure of a SNARE complex involved in synaptic exocytosis at 2.4 Å resolution, 395(6700) Nature 347-353 (1998). This analysis indicated an extensive intertwining of the α-helices with the amino-terminal region of the bundle comprising interactions between the amino-terminal α-helix of SNAP-25 with Syntaxin, several central associations amongst all three members and an association between Syntaxin and synaptobrevin at the carboxyl-terminal portion of the four-helix bundle.

Protein-protein interactions between the α-helices of SNARE complex members appear to be another way of localizing SNAP-25 to the membrane. For example, co-expression of SNAP-25 with Syntaxin results in targeting SNAP-25 to the membrane in the absence of a functional interhelical loop suggesting that protein-protein interactions between these two t-SNAREs can target Clostridial toxin substrates to the membrane, see, e.g., Washbourne et al., supra, (2001).

Members of the Syntaxin family of proteins can be divided into several structural domains. In the amino-terminal half of the protein contains an Habc region comprising three α-helix domains located at amino acids 30-60, 69-104 and 110-154. The carboxyl-terminal half of Syntaxin-1 contains an α-helix of approximately 52-69 residues, depending on the individual member and an approximately 23 amino acid membrane anchoring domain. As will be discussed below, regions comprising the membrane anchoring domain of Syntaxin may be used to target Clostridial toxin substrates to the plasma membrane.

The Clostridial toxin substrates disclosed in the present specification include, in part, a membrane targeting domain. As used herein, the term "membrane targeting domain" is synonymous with "MTD" and means a SNAP-25 or Syntaxin peptide which directs a Clostridial toxin substrate to the cell membrane. Any and all SNAP-25 or Syntaxin membrane targeting domains can be used in aspects of the present invention, with the proviso that the Clostridial toxin substrate maintains the property to be cleaved by a Clostridial toxin. Examples include, without limitation, naturally occurring membrane targeting domains present in SNAP-25, naturally occurring SNAP-25 MTD variants, and non-naturally occurring SNAP-25 MTD variants, such as, e.g., genetically engineered SNAP-25 MTD variants, produced, e.g., by random mutagenesis or rational designed and SNAP-25 MTD peptidomimetics; and naturally occurring membrane targeting domains present in Syntaxin, naturally occurring Syntaxin MTD variants, and non-naturally occurring Syntaxin MTD variants, such as, e.g., genetically engineered Syntaxin MTD variants, produced, e.g., by random mutagenesis or rational designed and Syntaxin MTD peptidomimetics.

Thus, aspects of the present invention provide, in part, a membrane-associated Clostridial toxin substrate comprising a donor fluorophore, an acceptor, a Clostridial toxin recognition sequence including a Clostridial toxin cleavage site and a membrane targeting domain. In is envisioned that any and all Clostridial toxin recognition sequences including a Clostridial toxin cleavage site can be used, including, without limitation, a BoNT/A recognition sequence including a BoNT/A cleavage site, a BoNT/B recognition sequence including a BoNT/B cleavage site, a BoNT/C1 recognition sequence including a BoNT/C1 cleavage site, a BoNT/D recognition sequence including a BoNT/D cleavage site, a BoNT/E recognition sequence including a BoNT/E cleavage site, a BoNT/F recognition sequence including a BoNT/F cleavage site, a BoNT/G recognition sequence including a BoNT/G cleavage site, or a TeNT recognition sequence including a TeNT cleavage site. It is also envisioned that any and all donor fluorophores can be used, including, without exception, fluorescent proteins, fluorescent binding proteins, fluorescent dyes, and quenchers. It is also envisioned that any and all acceptors can be used, including, without exception, fluorescent molecules, such as, e.g., fluorescent proteins, fluorescent binding proteins and fluorescent dyes; and non-fluorescent molecules, such as, e.g., quenchers. It is envisioned that any and all cells capable of selectively binding a binding domain of a Clostridial toxin and expressing a Clostridial toxin substrate can be used, including, a neuronal cell and a non-neuronal cell.

Other aspects of the present invention provide, in part, a cell comprising (a) a membrane-associated Clostridial toxin substrate comprising a donor fluorophore, an acceptor, a Clostridial toxin recognition sequence including a Clostridial toxin cleavage site that intervenes between the donor fluorophore and the acceptor and a membrane targeting domain; and (b) a Clostridial toxin receptor capable of initiating the intoxication process by selectively binding a Clostridial toxin; wherein the acceptor has an absorbance spectrum overlapping the emission spectrum of the donor fluorophore; and wherein, under the appropriate conditions, resonance energy transfer is exhibited between the donor fluorophore and the acceptor. It is envisioned that any and all cells capable of selectively binding a Clostridial toxin and expressing a Clostridial toxin substrate can be used, including, a neuronal cell and a non-neuronal cell.

Other aspects of the present invention provide a method of detecting activity of a Clostridial toxin, the method comprising the steps of (a) treating with a test sample, under conditions suitable for Clostridial toxin protease activity, a clostridial toxin substrate comprising (1) a donor fluorophore, (2) an acceptor, (3) a Clostridial toxin recognition sequence including a cleavage site that intervenes between the donor fluorophore and the acceptor and (4) a membrane targeting domain; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the donor fluorophore; and (c) detecting resonance energy transfer of the treated substrate from the test sample.

Other aspects of the present invention provide a method of detecting activity of a Clostridial toxin, the method comprising the steps of (a) treating with a test sample, under conditions suitable for Clostridial toxin protease activity, a Clostridial toxin substrate comprising (1) a donor fluorophore, (2) an acceptor, (3) a Clostridial toxin recognition sequence including a cleavage site that intervenes between the lanthanide donor complex and the acceptor and (4) a membrane targeting domain; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the lanthanide donor complex; (c) detecting resonance energy transfer of the treated substrate from the test sample, and (d) comparing the resonance energy transfer detected from the test sample with the resonance energy transfer detected from a control sample subjected to steps (a)-(c), wherein a difference in fluorescence resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Other aspects of the present invention provide a method of determining activity of a Clostridial toxin, the method comprising the steps of (a) contacting with a test sample a cell comprising (1) a Clostridial toxin substrate comprising a donor fluorophore, an acceptor, a Clostridial toxin recognition sequence including a cleavage site that intervenes between the donor fluorophore and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b)

exciting the donor fluorophore; and (c) detecting resonance energy transfer of the treated substrate from the test sample.

Other aspects of the present invention provide a method of determining activity of a Clostridial toxin, the method comprising the steps of (a) contacting with a test sample a cell comprising (1) a Clostridial toxin substrate comprising a donor fluorophore, an acceptor, a Clostridial toxin recognition sequence including a cleavage site that intervenes between the donor fluorophore and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the donor fluorophore; and wherein, under the appropriate conditions, fluorescence resonance energy transfer is exhibited between the donor fluorophore and the acceptor; (b) exciting the donor fluorophore; (c) detecting resonance energy transfer of the treated substrate from the test sample; and (d) comparing the resonance energy transfer detected from the test sample with the resonance energy transfer detected from a control sample subjected to steps (a)-(c), wherein a difference in resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Thus, aspects of the present invention provide, in part, a membrane-associated Clostridial toxin substrate comprising a lanthanide donor complex, an acceptor, a Clostridial toxin recognition sequence including a Clostridial toxin cleavage site and a membrane targeting domain. In is envisioned that any and all Clostridial toxin recognition sequences including a Clostridial toxin cleavage site can be used, including, without limitation, a BoNT/A recognition sequence including a BoNT/A cleavage site, a BoNT/B recognition sequence including a BoNT/B cleavage site, a BoNT/C1 recognition sequence including a BoNT/C1 cleavage site, a BoNT/D recognition sequence including a BoNT/D cleavage site, a BoNT/E recognition sequence including a BoNT/E cleavage site, a BoNT/F recognition sequence including a BoNT/F cleavage site, a BoNT/G recognition sequence including a BoNT/G cleavage site, or a TeNT recognition sequence including a TeNT cleavage site. It is also envisioned that any and all lanthanide donor complexes can be used, including, without exception, a lanthanide donor complex comprising a small molecule lanthanide binding site, such as, e.g., a chelate or a cryptate; and a lanthanide donor complex comprising a peptide or peptidomemetic lanthanide binding site, such as, e.g., a EF-hand. It is also envisioned that any and all acceptors can be used, including, without exception, fluorescent molecules, such as, e.g., fluorescent proteins, fluorescent binding proteins and fluorescent dyes; and non-fluorescent molecules, such as, e.g., quenchers. It is envisioned that any and all cells capable of selectively binding a binding domain of a Clostridial toxin and expressing a Clostridial toxin substrate can be used, including, a neuronal cell and a non-neuronal cell.

Other aspects of the present invention provide, in part, a cell comprising (a) a membrane-associated Clostridial toxin substrate comprising a lanthanide donor complex, an acceptor, a Clostridial toxin recognition sequence including a Clostridial toxin cleavage site that intervenes between the lanthanide donor complex and the acceptor and a membrane targeting domain; and (b) a Clostridial toxin receptor capable of initiating the intoxication process by selectively binding a Clostridial toxin; wherein the acceptor has an absorbance spectrum overlapping the emission spectrum of the lanthanide donor complex; and wherein, under the appropriate conditions, resonance energy transfer is exhibited between the lanthanide donor complex and the acceptor. It is envisioned that any and all cells capable of selectively binding a Clostridial toxin and expressing a Clostridial toxin substrate can be used, including, a neuronal cell and a non-neuronal cell.

Other aspects of the present invention provide a method of detecting activity of a Clostridial toxin, the method comprising the steps of (a) treating with a test sample, under conditions suitable for Clostridial toxin protease activity, a clostridial toxin substrate comprising (1) a lanthanide donor complex, (2) an acceptor, (3) a Clostridial toxin recognition sequence including a cleavage site that intervenes between the lanthanide donor complex and the acceptor and (4) a membrane targeting domain; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; and (c) detecting resonance energy transfer of the treated substrate from the test sample.

Other aspects of the present invention provide a method of detecting activity of a Clostridial toxin, the method comprising the steps of (a) treating with a test sample, under conditions suitable for Clostridial toxin protease activity, a clostridial toxin substrate comprising (1) a lanthanide donor complex, (2) an acceptor, (3) a Clostridial toxin recognition sequence including a cleavage site that intervenes between the lanthanide donor complex and the acceptor and (4) a membrane targeting domain; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; (c) detecting resonance energy transfer of the treated substrate from the test sample, and (d) comparing the resonance energy transfer detected from the test sample with the resonance energy transfer detected from a control sample subjected to steps (a)-(c), wherein a difference in fluorescence resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

Other aspects of the present invention provide a method of determining activity of a Clostridial toxin, the method comprising the steps of (a) contacting with a test sample a cell comprising (1) a Clostridial toxin substrate comprising a lanthanide donor complex, an acceptor, a Clostridial toxin recognition sequence including a cleavage site that intervenes between the lanthanide donor complex and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; and (c) detecting resonance energy transfer of the treated substrate from the test sample.

Other aspects of the present invention provide a method of determining activity of a Clostridial toxin, the method comprising the steps of (a) contacting with a test sample a cell comprising (1) a Clostridial toxin substrate comprising a lanthanide donor complex, an acceptor, a Clostridial toxin recognition sequence including a cleavage site that intervenes between the lanthanide donor complex and the acceptor, and a membrane targeting domain; and (2) a Clostridial toxin receptor capable of initiating the intoxication process by selectively binding a Clostridial toxin; wherein the cell is capable of intoxication by the Clostridial toxin; wherein the acceptor has an absorbance spectrum overlapping the emission spectrum of the lanthanide donor complex; and wherein, under the appropriate conditions, fluorescence resonance energy transfer is exhibited between the lanthanide donor complex and the acceptor; (b) exciting the lanthanide donor complex; (c) detecting resonance energy transfer of the treated substrate from the test sample; and (d) comparing the resonance energy transfer detected from the test sample with the resonance energy transfer detected from a control sample subjected to steps (a)-(c), wherein a difference in resonance energy transfer of the test sample as compared to a control sample is indicative of activity from a Clostridial toxin, the Clostridial toxin activity comprising cell binding of the toxin to the Clostridial receptor, cellular uptake of the toxin, translocation of the enzymatic domain into the cell cytoplasm, and proteolytic cleavage of a Clostridial toxin substrate.

It is envisioned that a membrane-associated Clostridial toxin substrate disclosed in the present specification can comprise a MTD in any and all locations with the proviso that Clostridial toxin substrate is capable of being cleaved by a Clostridial toxin. Non-limiting examples include, locating a MTD at the amino terminus of a Clostridial toxin substrate; locating a MTD between a donor fluorophore and a Clostridial toxin recognition site; locating a MTD between an acceptor and a Clostridial toxin recognition site; and locating a MTD at the carboxyl terminus of a Clostridial toxin substrate. Where a MTD is in the amino-terminal position, an amino acid sequence comprising a start methionine should be placed in front of the amino-terminal MTD. In addition, it is known in the art that when adding a polypeptide that is operably-linked to the amino terminus of another polypeptide comprising the start methionine that the original methionine residue can be deleted.

Thus, in an embodiment, a membrane-associated Clostridial toxin substrate can comprise an amino to carboxyl single polypeptide linear order comprising a MTD, a donor fluorophore, Clostridial toxin recognition sequence including a Clostridial toxin cleavage site, and an acceptor. In another embodiment, a membrane-associated Clostridial toxin substrate can comprise an amino to carboxyl single polypeptide linear order comprising a donor fluorophore, a MTD, Clostridial toxin recognition sequence including a Clostridial toxin cleavage site, and an acceptor. In yet another embodiment, a membrane-associated Clostridial toxin substrate can comprise an amino to carboxyl single polypeptide linear order comprising a donor fluorophore, Clostridial toxin recognition sequence including a Clostridial toxin cleavage site, a MTD, and an acceptor. In still another embodiment, a membrane-associated Clostridial toxin substrate can comprise an amino to carboxyl single polypeptide linear order comprising a donor fluorophore, Clostridial toxin recognition sequence including a Clostridial toxin cleavage site, an acceptor and a MTD.

In another embodiment, a membrane-associated Clostridial toxin substrate can comprise an amino to carboxyl single polypeptide linear order comprising a MTD, an acceptor, Clostridial toxin recognition sequence including a Clostridial toxin cleavage site, and a donor fluorophore. In another embodiment, a membrane-associated Clostridial toxin substrate can comprise an amino to carboxyl single polypeptide linear order comprising an acceptor, a MTD, Clostridial toxin recognition sequence including a Clostridial toxin cleavage site, and a donor fluorophore. In yet another embodiment, a membrane-associated Clostridial toxin substrate can comprise an amino to carboxyl single polypeptide linear order comprising an acceptor, Clostridial toxin recognition sequence including a Clostridial toxin cleavage site, a MTD, and a donor fluorophore. In still another embodiment, a membrane-associated Clostridial toxin substrate can comprise an amino to carboxyl single polypeptide linear order comprising an acceptor, Clostridial toxin recognition sequence including a Clostridial toxin cleavage site, a donor fluorophore and a MTD.

In yet another embodiment, a membrane-associated Clostridial toxin substrate can comprise an amino to carboxyl single polypeptide linear order comprising a MTD, a lanthanide donor complex, Clostridial toxin recognition sequence including a Clostridial toxin cleavage site, and an acceptor. In another embodiment, a membrane-associated Clostridial toxin substrate can comprise an amino to carboxyl single polypeptide linear order comprising a lanthanide donor complex, a MTD, Clostridial toxin recognition sequence including a Clostridial toxin cleavage site, and an acceptor. In yet another embodiment, a membrane-associated Clostridial toxin substrate can comprise an amino to carboxyl single polypeptide linear order comprising a lanthanide donor complex, Clostridial toxin recognition sequence including a Clostridial toxin cleavage site, a MTD, and an acceptor. In still another embodiment, a membrane-associated Clostridial toxin substrate can comprise an amino to carboxyl single polypeptide linear order comprising a lanthanide donor complex, Clostridial toxin recognition sequence including a Clostridial toxin cleavage site, an acceptor and a MTD.

In still another embodiment, a membrane-associated Clostridial toxin substrate can comprise an amino to carboxyl single polypeptide linear order comprising a MTD, an acceptor, Clostridial toxin recognition sequence including a Clostridial toxin cleavage site, and a lanthanide donor complex. In another embodiment, a membrane-associated Clostridial toxin substrate can comprise an amino to carboxyl single polypeptide linear order comprising an acceptor, a MTD, Clostridial toxin recognition sequence including a Clostridial toxin cleavage site, and a lanthanide donor complex. In yet another embodiment, a membrane-associated Clostridial toxin substrate can comprise an amino to carboxyl single polypeptide linear order comprising an acceptor, Clostridial toxin recognition sequence including a Clostridial toxin cleavage site, a MTD, and a lanthanide donor complex. In still another embodiment, a membrane-associated Clostridial toxin substrate can comprise an amino to carboxyl single polypeptide linear order comprising an acceptor, Clostridial toxin recognition sequence including a Clostridial toxin cleavage site, a lanthanide donor complex and a MTD.

Thus, in an embodiment a Clostridial toxin substrate comprises, in part, the membrane targeting domain comprising a region from SNAP-25 sufficient to target a toxin substrate disclosed in the present specification to the membrane. In an aspect of this embodiment, the membrane targeting domain comprising a region from the interhelical region of SNAP-25 sufficient to target a toxin substrate disclosed in the present specification to the membrane. In an aspect of this embodiment the membrane targeting domain comprises the amino acids 85-120 of SEQ ID NO: 1. It is envisioned that an interhelical loop region from SNAP-25 of any and all lengths can comprise the membrane targeting domain with the proviso that the loop region is sufficient to target a toxin substrate disclosed in the present specification to the membrane. Thus, aspects of this embodiment may include an interhelical loop region comprising, e.g., at least 35 residues from amino acids 85-120 of SEQ ID NO: 1, at least 30 residues from amino acids 85-120 of SEQ ID NO: 1, at least 25 residues from amino acids 85-120 of SEQ ID NO: 1, at least 20 residues from amino acids 85-120 of SEQ ID NO: 1, at least 15 residues from amino acids 85-120 of SEQ ID NO: 1, at least 10 residues from amino acids 85-120 of SEQ ID NO: 1 or at least 5 residues from amino acids 85-120 of SEQ ID NO: 1. Further aspects of this embodiment may include an interhelical loop region comprising, e.g., at most 35 residues from amino acids 85-120 of SEQ ID NO: 1, at most 30 residues from amino acids 85-120 of SEQ ID NO: 1, at most 25 residues from amino acids 85-120 of SEQ ID NO: 1, at most 20 residues from amino acids 85-120 of SEQ ID NO: 1, at most 15 residues from amino acids 85-120 of SEQ ID NO: 1, at most 10 residues from amino acids 85-120 of SEQ ID NO: 1 or at most 5 residues from amino acids 85-120 of SEQ ID NO: 1.

In another aspect of this embodiment a Clostridial toxin substrate comprises, in part, the membrane targeting domain comprises amino acids CGLCVCPCNK (SEQ ID NO: 128). In another aspect of this embodiment the membrane targeting domain comprises amino acids CGLFICPCNK (SEQ ID NO: 129). In another aspect of this embodiment the membrane targeting domain comprises amino acids CGLCSCPCNK (SEQ ID NO: 130). In another aspect of this embodiment the membrane targeting domain comprises amino acids CGLCPCPCNK(SEQ ID NO: 131). In another aspect of this embodiment the membrane targeting domain comprises amino acids CGICVCPWKK(SEQ ID NO: 132). In another aspect of this embodiment the membrane targeting domain comprises amino acids CGICVLPCNK(SEQ ID NO: 133). In another aspect of this embodiment the membrane targeting domain comprises amino acids CGLCVLPWNK(SEQ ID NO: 134).

In another embodiment a Clostridial toxin substrate comprises, in part, the membrane targeting domain comprises the amino acids QPXRV (SEQ ID NO: 135), where X is any amino acid. In another aspect of this embodiment the membrane targeting domain comprises amino acids QPXRI (SEQ ID NO: 136), where X is any amino acid. In another aspect of this embodiment the membrane targeting domain comprises amino acids QPARV (SEQ ID NO: 137). In another aspect of this embodiment the membrane targeting domain comprises amino acids QPQRV (SEQ ID NO: 138). In another aspect of this embodiment the membrane targeting domain comprises amino acids QPGRV (SEQ ID NO: 139). In another aspect of this embodiment the membrane targeting domain comprises amino acids QPSRI (SEQ ID NO: 140). In another aspect of this embodiment the membrane targeting domain comprises amino acids QPMRM (SEQ ID NO: 141). In another aspect of this embodiment the membrane targeting domain comprises amino acids QPRI (SEQ ID NO: 142).

In another embodiment a Clostridial toxin substrate comprises, in part, the membrane targeting domain comprises amino acids from the amino-terminal α-helix of SNAP-25 sufficient to target a toxin substrate disclosed in the present specification to the membrane. In an aspect of this embodiment the membrane targeting domain comprises the amino acids 1-84 of SEQ ID NO: 1. It is envisioned that an amino-terminal α-helix from SNAP-25 of any and all lengths can comprise the membrane targeting domain with the proviso that the loop region is sufficient to target a toxin substrate disclosed in the present specification to the membrane. Thus, aspects of this embodiment may include an amino-terminal α-helix region comprising, e.g., at least 80 residues from amino acids 1-84 of SEQ ID NO: 1, at least 75 residues from amino acids 1-84 of SEQ ID NO: 1, at least 70 residues from amino acids 1-84 of SEQ ID NO: 1, at least 65 residues from amino acids 1-84 of SEQ ID NO: 1, at least 60 residues from amino acids 1-84 of SEQ ID NO: 1, at least 55 residues from amino acids 1-84 of SEQ ID NO: 1, at least 50 residues from amino acids 1-84 of SEQ ID NO: 1, at least 45 residues from amino acids 1-84 of SEQ ID NO: 1, at least 40 residues from amino acids 1-84 of SEQ ID NO: 1, at least 35 residues from amino acids 1-84 of SEQ ID NO: 1, at least 30 residues from amino acids 1-84 of SEQ ID NO: 1, at least 25 residues from amino acids 1-84 of SEQ ID NO: 1, at least 20 residues from amino acids 1-84 of SEQ ID NO: 1, at least 15 residues from amino acids 1-84 of SEQ ID NO: 1, at least 10 residues from amino acids 1-84 of SEQ ID NO: 1 or at least 5 residues from amino acids 1-84 of SEQ ID NO: 1. Further aspects of this embodiment may include an amino-terminal α-helix region comprising, e.g., at most 80 residues from amino acids 1-84 of SEQ ID NO: 1, at most 75 residues from amino acids 1-84 of SEQ ID NO: 1, at most 70 residues from amino acids 1-84 of SEQ ID NO: 1, at most 65 residues from amino acids 1-84 of SEQ ID NO: 1, at most 60 residues from amino acids 1-84 of SEQ ID NO: 1, at most 55 residues from amino acids 1-84 of SEQ ID NO: 1, at most 50 residues from amino acids 1-84 of SEQ ID NO: 1, at most 45 residues from amino acids 1-84 of SEQ ID NO: 1, at most 40 residues from amino acids 1-84 of SEQ ID NO: 1, at most 35 residues from amino acids 1-84 of SEQ ID NO: 1, at most 30 residues from amino acids 1-84 of SEQ ID NO: 1, at most 25 residues from amino acids 1-84 of SEQ ID NO: 1, at most 20 residues from amino acids 1-84 of SEQ ID NO: 1, at most 15 residues from amino acids 1-84 of SEQ ID NO: 1, at most 10 residues from amino acids 1-84 of SEQ ID NO: 1 or at most 5 residues from amino acids 1-84 of SEQ ID NO: 1.

In yet another embodiment a Clostridial toxin substrate comprises, in part, the membrane targeting domain comprises amino acids from the carboxyl-terminal α-helix of SNAP-25 sufficient to target a toxin substrate disclosed in the present specification to the membrane. In an aspect of this embodiment the membrane targeting domain comprises the amino acids 121-206 of SEQ ID NO: 1. It is envisioned that an carboxyl-terminal α-helix from SNAP-25 of any and all lengths can comprise the membrane targeting domain with the proviso that the loop region is sufficient to target a toxin substrate disclosed in the present specification to the membrane. Thus, aspects of this embodiment may include an carboxyl-terminal α-helix region comprising, e.g., at least 80 residues from amino acids 121-206 of SEQ ID NO: 1; at least 75 residues from amino acids 121-206 of SEQ ID NO: 1, at least 70 residues from amino acids 121-206 of SEQ ID NO: 1, at least 65 residues from amino acids 121-206 of SEQ ID NO: 1, at least 60 residues from amino acids 121-206 of SEQ ID NO: 1, at least 55 residues from amino acids 121-206 of SEQ ID NO: 1, at least 50 residues from amino acids 121-206 of SEQ ID NO: 1, at least 45 residues from amino acids 121-206 of SEQ ID NO: 1, at least 40 residues from amino acids 121-206 of SEQ ID NO: 1, at least 35 residues from amino acids 121-206 of SEQ ID NO: 1, at least 30 residues from amino acids 121-206 of SEQ ID NO: 1, at least 25 residues from amino acids 121-206 of SEQ ID NO: 1, at least 20 residues from amino acids 121-206 of SEQ ID NO: 1, at least 15 residues from amino acids 121-206 of SEQ ID NO: 1, at least 10 residues from amino acids 121-206 of SEQ ID NO: 1 or at least 5 residues from amino acids 121-206 of SEQ ID NO: 1. Further aspects of this embodiment may include a carboxyl-terminal α-helix region comprising, e.g., at most 85 residues from amino acids 121-206 of SEQ ID NO: 1; at most 80 residues from amino acids 121-206 of SEQ ID NO: 1; at most 75 residues from amino acids 121-206 of SEQ ID NO: 1, at most 70 residues from amino acids 121-206 of SEQ ID NO: 1, at most 65 residues from amino acids 121-206 of SEQ ID NO: 1, at most 60 residues from amino acids 121-206 of SEQ ID NO: 1, at most 55 residues from amino acids 121-206 of SEQ ID NO: 1, at most 50 residues from amino acids 121-206 of SEQ ID NO: 1, at most 45 residues from amino acids 121-206 of SEQ ID NO: 1, at most 40 residues from amino acids 121-206 of SEQ ID NO: 1, at most 35 residues from amino acids 121-206 of SEQ ID NO: 1, at most 30 residues from amino acids 121-206 of SEQ ID NO: 1, at most 25 residues from amino acids 121-206 of SEQ ID NO: 1, at most 20 residues from amino acids 121-206 of SEQ ID NO: 1, at most 15 residues from amino acids 121-206 of SEQ ID NO: 1, at most 10 residues from amino acids 121-206 of SEQ ID NO: 1 or at most 5 residues from amino acids 121-206 of SEQ ID NO: 1.

In another embodiment a Clostridial toxin substrate comprises, in part, the membrane targeting domain comprising a region from Syntaxin sufficient to target a toxin substrate disclosed in the present specification to the membrane. In an aspect of this embodiment, the membrane targeting domain comprising a region from the membrane anchoring domain of Syntaxin sufficient to target a toxin substrate disclosed in the present specification to the membrane. In an aspect of this embodiment the membrane targeting domain comprises the amino acids 266-288 of SEQ ID NO: 66. It is envisioned that an membrane anchoring domain from Syntaxin of any and all lengths can comprise the membrane targeting domain with the proviso that the loop region is sufficient to target a toxin substrate disclosed in the present specification to the membrane. Thus, aspects of this embodiment may include an interhelical loop region comprising, e.g., at least 20 residues from amino acids 266-288 of SEQ ID NO: 66; at least 15 residues from amino acids 266-288 of SEQ ID NO: 66, Or at least 10 residues from amino acids 266-288 of SEQ ID NO: 66. Further aspects of this embodiment may include an membrane anchoring domain comprising, e.g., at most 20 residues from amino acids 266-288 of SEQ ID NO: 66; at most 15 residues from amino acids 266-288 of SEQ ID NO: 66 or at most 10 residues from amino acids 266-288 of SEQ ID NO: 66.

In an aspect of this embodiment, a Clostridial toxin substrate comprises, in part, the membrane targeting domain of human Syntaxin-1A of SEQ ID NO: 66. In another aspect of this embodiment, a Clostridial toxin substrate comprises, in part, the membrane targeting domain comprising amino acids IMIIICCVILGIVIASTVGGIFA, which corresponds to residues 266-288 of SEQ ID NO: 66. In another aspect of this embodiment, a Clostridial toxin substrate comprises, in part, the membrane targeting domain of human Syntaxin-1B1 of SEQ ID NO: 67. In another aspect of this embodiment, a Clostridial toxin substrate comprises, in part, the membrane targeting domain comprising amino acids IIIIICCWLGW-LASSIGCTLGL, which corresponds to residues 265-288 of SEQ ID NO: 67. In another aspect of this embodiment, a Clostridial toxin substrate comprises, in part, the membrane targeting domain of human Syntaxin-1B2 of SEQ ID NO: 68. In another aspect of this embodiment, a Clostridial toxin substrate comprises, in part, the membrane targeting domain comprising amino acids IMIIICCWLGWLASSIGGTLGL, which corresponds to residues 265-288 of SEQ ID NO: 68. In another aspect of this embodiment, a Clostridial toxin substrate comprises, in part, the membrane targeting domain of human Syntaxin-2-1 of SEQ ID NO: 69. In another aspect of this embodiment, a Clostridial toxin substrate comprises, in part, the membrane targeting domain comprising amino acids LMFIIICVIVLLVILGIILATTLS, which corresponds to residues 264-287 of SEQ ID NO: 69. In another aspect of this embodiment, a Clostridial toxin substrate comprises, in part, the membrane targeting domain of human Syntaxin-2-2 of SEQ ID NO: 70. In another aspect of this embodiment, a Clostridial toxin substrate comprises, in part, the membrane targeting domain comprising amino acids WIIIAVSVVLWI-IVLIIGLSVGK, which corresponds to residues 264-288 of SEQ ID NO: 70. In another aspect of this embodiment, a Clostridial toxin substrate comprises, in part, the membrane targeting domain of human Syntaxin-2-3 of SEQ ID NO: 71. In another aspect of this embodiment, a Clostridial toxin substrate comprises, in part, the membrane targeting domain comprising amino acids WIIIAVSWLVAIIALIIGLSVGK, which corresponds to residues 264-288 of SEQ ID NO: 71. In another aspect of this embodiment, a Clostridial toxin substrate comprises, in part, the membrane targeting domain of human Syntaxin-3 of SEQ ID NO: 72. In another aspect of this embodiment, a Clostridial toxin substrate comprises, in part, the membrane targeting domain comprising amino acids LIIIIVLWVLLGILALIIGISVGLN, which corresponds to residues 264-289 of SEQ ID NO: 72.

In another aspect of this embodiment, a Clostridial toxin substrate comprises, in part, the membrane targeting domain of cow Syntaxin-1A of SEQ ID NO: 73. In another aspect of this embodiment, a Clostridial toxin substrate comprises, in part, the membrane targeting domain comprising amino acids IMIVICCVVLGIVIASTFGGIFG, which corresponds to residues 266-288 of SEQ ID NO: 73.

In an aspect of this embodiment, a Clostridial toxin substrate comprises, in part, the membrane targeting domain of rat Syntaxin-1A of SEQ ID NO: 75. In another aspect of this embodiment, a Clostridial toxin substrate comprises, in part, the membrane targeting domain comprising amino acids IMIIICCVILGIIIASTIGGIFG, which corresponds to residues 266-288 of SEQ ID NO: 75. In an aspect of this embodiment, a Clostridial toxin substrate comprises, in part, the membrane targeting domain of rat Syntaxin-1B2 of SEQ ID NO: 76. In another aspect of this embodiment, a Clostridial toxin substrate comprises, in part, the membrane targeting domain comprising amino acids IMIIICCWLGWLASSIG-GTLGL, which corresponds to residues 265-288 of SEQ ID NO: 76. In an aspect of this embodiment, a Clostridial toxin substrate comprises, in part, the membrane targeting domain of rat Syntaxin-2 of SEQ ID NO: 80. In another aspect of this embodiment, a Clostridial toxin substrate comprises, in part, the membrane targeting domain comprising amino acids WIIAVWAVIAVLALIIGLSVGK, which corresponds to residues 267-290 of SEQ ID NO: 80. In an aspect of this embodiment, a Clostridial toxin substrate comprises, in part, the membrane targeting domain of mouse Syntaxin-2 of SEQ ID NO: 81. In another aspect of this embodiment, a Clostridial toxin substrate comprises, in part, the membrane targeting domain comprising amino acids WIIAAVAVAVIA-VLALIIGLSVGK, which corresponds to residues 266-289 of SEQ ID NO: 81. In an aspect of this embodiment, a Clostridial toxin substrate comprises, in part, the membrane targeting domain of rat Syntaxin-3A of SEQ ID NO: 82. In another aspect of this embodiment, a Clostridial toxin substrate comprises, in part, the membrane targeting domain comprising amino acids LIIIIVIWVLLGILALIIGISVGLK, which corresponds to residues 264-289 of SEQ ID NO: 82. In an aspect of this embodiment, a Clostridial toxin substrate comprises, in part, the membrane targeting domain of mouse Syntaxin-3A of SEQ ID NO: 83. In another aspect of this embodiment, a Clostridial toxin substrate comprises, in part, the membrane targeting domain comprising amino acids LII-IIVVVVVLLGILALIIGLSVGLK, which corresponds to residues 264-289 of SEQ ID NO: 83. In an aspect of this embodiment, a Clostridial toxin substrate comprises, in part, the membrane targeting domain of mouse Syntaxin-3B of SEQ ID NO: 84. In another aspect of this embodiment, a Clostridial toxin substrate comprises, in part, the membrane targeting domain comprising amino acids IMIMICCIILAI-ILASTIG, which corresponds to residues 265-283 of SEQ ID NO: 84. In an aspect of this embodiment, a Clostridial toxin substrate comprises, in part, the membrane targeting domain of mouse Syntaxin-3C of SEQ ID NO: 85. In another aspect of this embodiment, a Clostridial toxin substrate comprises, in part, the membrane targeting domain comprising amino acids IMIMICCIILAIILASTIGGIFA, which corresponds to residues 247-269 of SEQ ID NO: 85.

In an aspect of this embodiment, a Clostridial toxin substrate comprises, in part, the membrane targeting domain of chicken Syntaxin-1A of SEQ ID NO: 86. In another aspect of this embodiment, a Clostridial toxin substrate comprises, in part, the membrane targeting domain comprising amino acids IMIIIFWVLGWLSPVICGTLGL, which corresponds to residues 259-282 of SEQ ID NO: 86. In an aspect of this embodiment, a Clostridial toxin substrate comprises, in part, the membrane targeting domain of chicken Syntaxin-2 of SEQ ID NO: 87. In another aspect of this embodiment, a Clostridial toxin substrate comprises, in part, the membrane targeting domain comprising amino acids WIIIIVSLVLIA-VIGIIIGLSVGIR, which corresponds to residues 263-288 of SEQ ID NO: 87.

In an aspect of this embodiment, a Clostridial toxin substrate comprises, in part, the membrane targeting domain of zebrafish Syntaxin-1A of SEQ ID NO: 88. In another aspect of this embodiment, a Clostridial toxin substrate comprises, in part, the membrane targeting domain comprising amino acids IMIIICCVILGVVLRSSIGGTLGF, which corresponds to residues 265-288 of SEQ ID NO: 88. In an aspect of this embodiment, a Clostridial toxin substrate comprises, in part, the membrane targeting domain of zebrafish Syntaxin-3 of SEQ ID NO: 89. In another aspect of this embodiment, a Clostridial toxin substrate comprises, in part, the membrane targeting domain comprising amino acids IIIIVSWLVILAI-IALIVGISVGLKR, which corresponds to residues 262-288 of SEQ ID NO: 89.

In an aspect of this embodiment, a Clostridial toxin substrate comprises, in part, the membrane targeting domain of sea urchin Syntaxin-1A of SEQ ID NO: 90. In another aspect of this embodiment, a Clostridial toxin substrate comprises, in part, the membrane targeting domain comprising amino acids YIAICCGVALGILILVLIIVLA, which corresponds to residues 264-286 of SEQ ID NO: 90.

In an aspect of this embodiment, a Clostridial toxin substrate comprises, in part, the membrane targeting domain of fruit fly Syntaxin-1A of SEQ ID NO: 91. In another aspect of this embodiment, a Clostridial toxin substrate comprises, in part, the membrane targeting domain comprising amino acids IMILICLTVLGILAASYVSSYFM, which corresponds to residues 269-291 of SEQ ID NO: 91.

In an aspect of this embodiment, a Clostridial toxin substrate comprises, in part, the membrane targeting domain of leech Syntaxin-1A of SEQ ID NO: 92. In another aspect of this embodiment, a Clostridial toxin substrate comprises, in part, the membrane targeting domain comprising amino acids IIILICVSVLILIVGGSLLGIFIP, which corresponds to residues 272-295 of SEQ ID NO: 92.

In an aspect of this embodiment, a Clostridial toxin substrate comprises, in part, the membrane targeting domain of squid Syntaxin-1A of SEQ ID NO: 93. In another aspect of this embodiment, a Clostridial toxin substrate comprises, in part, the membrane targeting domain comprising amino acids IAILVCLVILVLVIVSTVGGVFGG, which corresponds to residues 269-292 of SEQ ID NO: 93.

In an aspect of this embodiment, a Clostridial toxin substrate comprises, in part, the membrane targeting domain of snail Syntaxin-1A of SEQ ID NO: 94. In another aspect of this embodiment, a Clostridial toxin substrate comprises, in part, the membrane targeting domain comprising amino acids IMIIICVCVLIIILVGILGGTFG, which corresponds to residues 268-290 of SEQ ID NO: 94.

In an aspect of this embodiment, a Clostridial toxin substrate comprises, in part, the membrane targeting domain of sea hare Syntaxin-1A of SEQ ID NO: 95. In another aspect of this embodiment, a Clostridial toxin substrate comprises, in part, the membrane targeting domain comprising amino acids IMILVCLAILIIILVGVIGGTLG, which corresponds to residues 268-290 of SEQ ID NO: 95.

The Clostridial toxin substrates disclosed in the present specification include, in part, donor fluorophore. As used herein, the term "fluorophore" is synonymous with the term "fluorochrome" or "fluorescent molecule." As used herein, the term "donor fluorophore" means a molecule that, when irradiated with light of a certain wavelength, emits light of a different wavelength, also denoted as fluorescence. Thus, a donor fluorophore can be a fluorescent molecule.

The Clostridial toxin substrates disclosed in the present specification include, in part, acceptor. As used herein, the term "acceptor" means a molecule that can absorb energy from a donor fluorophore and is a term that encompasses fluorescent molecules as well as non-fluorescent molecules. As used herein, the term "acceptor fluorophore" means an acceptor comprising a fluorescent molecule. In is envisioned that any and all fluorescent molecules.

It is envisioned that any and all fluorescent molecules can serve as a donor fluorophore or an acceptor fluorophore, including, without limitation, a fluorescent protein, a fluorophore binding protein and a fluorescent dye.

A donor fluorophore or an acceptor fluorophore disclosed in the present specification can be, in part, a fluorescent protein. As used herein, the term "fluorescent protein" means a peptide which absorbs light energy of a certain wavelength and emits light energy of a different wavelength and encompasses those which emit in a variety of spectra, including violet, blue, cyan, green, yellow, orange and red, see Table 9. It is envisioned that fluorescent proteins derived from any of a variety of species can be useful in aspects of the present invention including, but not limited to, *Aequorea* fluorescent proteins, *Anemonia* fluorescent proteins, *Anthozoa* fluorescent proteins, *Discosoma* fluorescent proteins, *Entacmeae* fluorescent proteins, *Heteractis* fluorescent proteins, *Montastrea* fluorescent proteins, *Renilla* fluorescent proteins, *Zoanthus* fluorescent proteins, and fluorescent proteins from other organisms. Fluorescent proteins useful in the invention encompass, without limitation, wild type fluorescent proteins, naturally occurring variants, and genetically engineered variants, produced, e.g., by random mutagenesis or rational designed, and active peptide fragments derived from an organism. Fluorescent proteins useful in aspects of the invention include, e.g., those which have been genetically engineered for superior performance such as, without limitation, altered excitation or emission wavelengths; enhanced brightness, pH resistance, stability or speed of fluorescent protein formation; photoactivation; or reduced oligomerization or photobleaching, see, e.g., Brendan P. Cormack et al., FACS-optimized Mutants of the Green Fluorescent Protein (GFP), U.S. Pat. No. 5,804,387 (Sep. 8, 1998); Roger Y. Tsien & Roger Heim, Modified Green Fluorescent Proteins, U.S. Pat. No. 6,800,733 (Oct. 5, 2004); Roger Y. Tsien et al., Long Wavelength Engineered Fluorescent Proteins, U.S. Pat. No. 6,780,975 (Aug. 24, 2004); and Roger Y. Tsien et al., Fluorescent Protein Sensors For Measuring the pH of a Biological Sample, U.S. Pat. No. 6,627,449 (Sep. 30, 2003). It is understood that a fluorescent protein can be engineered for improved protein expression by converting wild type codons to other codons more efficiently utilized in the cells which serve to express the Clostridial toxin substrate, see, e.g., Brian Seed and Jurgen Haas, High Level Expression of Proteins, U.S. Pat. No. 5,795,737 (Aug. 18, 1998). A fluorescent protein can be operably-linked to a Clostridial toxin recognition sequence to create a fusion protein using standard molecular genetic techniques. Additionally, a fluorescent protein can be specifically linked to the amino- or carboxyl-terminus of a Clostridial toxin recognition sequence using well known chemical methods, see, e.g., *Chemical Approaches to Protein Engineering*, in *Protein Engineering: A Practical Approach* (Eds. Rees et al., Oxford University Press, 1992).

It is also envisioned that any of a variety of active protein fragments can be useful in aspects of the present invention with the proviso that these active fragments retain the ability to emit light energy in a range suitable for the proper operation of aspects of the present invention, such as, e.g. 420-460 nm for blue emitting fluorescent proteins, 460-500 nm for cyan emitting fluorescent proteins, 500-520 nm for green emitting fluorescent proteins, 520-550 nm for yellow emitting fluorescent proteins and for 550-740 nm for red emitting fluorescent proteins. Thus, aspects of this embodiment can include active fragments of fluorescent proteins that retain the ability to emit light energy in a range suitable for the proper operation of aspects of the present invention having a length of, e.g., at least 50 amino acids, at least 60 amino acids, at least 70 amino acids, at least 80 amino acids, at least 90 amino acids, at least 100 amino acids, at least 125 amino acids, at least 150 amino acids, at least 175 amino acids and at least 200 amino acids. Other aspects of this embodiment, can include active fragments of fluorescent proteins that retain the ability to emit light energy in a range suitable for the proper operation of aspects of the present invention having a length of, e.g., at most 50 amino acids, at most 60 amino acids, at most 70 amino acids, at most 80 amino acids, at most 90 amino acids, at most 100 amino acids, at most 125 amino acids, at most 150 amino acids, at most 175 amino acids and at most 200 amino acids.

TABLE 9

Excitation and Emission Maxima of Exemplary Fluorescent Proteins

| Fluorescent protein | Excitation maxima (nm) | Emission maxima (nm) |
|---|---|---|
| EBFP | 380 | 440 |
| ECFP | 439 | 476 |
| AmCyan | 458 | 489 |
| AcGFP | 475 | 505 |
| ZsGreen | 493 | 505 |
| Vitality ® hrGFP | 500 | 506 |
| EGFP | 484 | 510 |
| Monster Green ® | 505 | 515 |
| EYFP | 512 | 529 |
| ZsYellow | 529 | 539 |
| DsRed-Express | 557 | 579 |
| DsRed2 | 563 | 582 |
| DsRed | 558 | 583 |
| AsRed2 | 576 | 592 |
| HcRed1 | 588 | 618 |

Non-limiting examples of fluorescent proteins that may be operably-linked to a CoNT substrate disclosed in the specification include, e.g., photoproteins, such as, e.g., aequorin; obelin; Aequorea fluorescent proteins, such, e.g., green fluorescent proteins (GFP, EGFP, AcGFP1), cyan fluorescent proteins (CFP, ECFP), blue fluorescent proteins (BFP, EBFP), red fluorescent proteins (RFP), yellow fluorescent proteins (YFP, EYFP), ultraviolet fluorescent protein (GFPuv), their fluorescence-enhancement variants, their peptide destabilization variants, and the like; coral reef fluorescent proteins, such, e.g., Discosoma red fluorescent proteins (DsRed, DsRed1, DsRed2, and DsRed-Express), Anemonia red fluorescent proteins (AsRed and AsRed2), Heteractis far-red fluorescent proteins (HcRed, HcRed1), Anemonia cyan fluorescent proteins (AmCyan, AmCyan1), Zoanthus green fluorescent proteins (ZsGreen, ZsGreen1), Zoanthus yellow fluorescent proteins (ZsYellow, ZsYellow1), their fluorescence-enhancement variants, their peptide destabilization variants, and the like; *Renilla reniformis* green fluorescent protein (Vitality hrGFP), its fluorescence-enhancement variants, its peptide destabilization variants, and the like; and Great Star Coral fluorescent proteins, such, e.g., *Montastrea cavernosa* fluorescent protein (Monster Greene® Fluorescent Protein), its fluorescence-enhancement variants, its peptide destabilization variants, and the like. One skilled in the art understands that these and a variety of other fluorescent proteins can be useful as a fluorescent protein in aspects of the invention, see, e.g., Jennifer Lippincott-Schwartz & George H. Patterson, Development and Use of Fluorescent Protein Markers in Living Cells, 300(5616) Science 87-91 (2003); and Jin Zhang et al., 3(12) Nat. Rev. Mol. Cell. Biol. 906-918 (2002). One skilled in the art understands that these and many other fluorescent proteins, including species orthologs and paralogs of the above described naturally occurring fluorescent proteins as well as engineered fluorescent proteins can be useful as a fluorescent protein disclosed in aspects of the present specification. CoNT substrates disclosed in the present specification containing, in part, such fluorescent proteins can be prepared and expressed using standard methods see, e.g., Living Colors® User Manual PT2040-1 (PRI1Y691), BD Biosciences-Clontech, (Nov. 26 2001); BD Living Color S™ User Manual Volume II: Reef Coral Fluorescent Proteins, PT3404-1 (PR37085), BD Biosciences-Clontech, (Jul. 17, 2003); Monster Green Florescent Protein pHMCFP Vector, TB320, Promega Corp., (May, 2004); and Vitality hrGFP Mammalian Expression Vectors, Instruction Manual (rev.

064007g), Stratagene, Inc. Expression vectors suitable for bacterial, mammalian and other expression of fluorescent proteins are available from a variety of commercial sources including BD Biosciences Clontech (Palo Alto, Calif.); Promega Corp. (Madison, Wis.) and Stratagene, Inc. (La Jolla, Calif.).

Thus, in an embodiment, a donor fluorophore is a blue fluorescent protein, a cyan fluorescent protein, a green fluorescent protein, a yellow fluorescent protein, a red fluorescent protein or an ultraviolet fluorescent protein. In another embodiment, an acceptor fluorophore is a blue fluorescent protein, a cyan fluorescent protein, a green fluorescent protein, a yellow fluorescent protein, a red fluorescent protein or an ultraviolet fluorescent protein.

In another embodiment, a donor fluorophore or an acceptor fluorophore is a green fluorescent protein. As used herein, the term "green fluorescent protein" is synonymous with "GFP" and means a protein which absorbs light of a certain wavelength and emits peak light energy of wavelengths in the range of 500-520 nm. Green fluorescent proteins useful in the invention include, without limitation, the AcGFP1 of SEQ ID NO: 143, genetically engineered AcGFP1 variants and active AcGFP1 fragments thereof that retain the ability to emit peak light energy in the range of 500-520 nm, the ZsGreen of SEQ ID NO: 144, genetically engineered ZsGreen variants and active ZsGreen fragments thereof that retain the ability to emit peak light energy in the range of 500-520 nm, the EGFP of SEQ ID NO: 145, genetically engineered ECFP variants and active ECFP fragments thereof that retain the ability to emit peak light energy in the range of 500-520 nm, the Monster Green Fluorescent Protein (MGFP) of SEQ ID NO: 146, genetically engineered MGFP variants and active MGFP fragments thereof that retain the ability to emit peak light energy in the range of 500-520 nm, the Vitality® hrGFP of SEQ ID NO: 147, genetically engineered hrGFP variants and active hrGFP fragments thereof that retain the ability to emit peak light energy in the range of 500-520 nm, as well as, naturally-occurring GFPs, naturally occurring GFP variants, genetically engineered GFP variants and active GFP fragments thereof that retain the ability to emit peak light energy in the range of 500-520 nm. As non-limiting examples, *Renilla*-derived fluorescent proteins such as, e.g., the dimeric *Renilla muleri* GFP, which has narrow excitation (498 nm) and emission (509 nm) peaks, see, e.g., Beau Peelle et al., Characterization and use of green fluorescent proteins from *Renilla mulleri* and *Ptilosarcus guernyi* for the human cell display of functional peptides, 20(6) J. Protein Chem. 507-519 (2001); and Aequorea-derived fluorescent proteins as described in, e.g., Roger Y. Tsien & Roger Heim, Modified Green Fluorescent Proteins, U.S. Pat. No. 5,625,048 (Apr. 29, 1997), U.S. Pat. No. 6,319,669 (Nov. 20, 2001), U.S. Pat. No. 6,066,476 (May 23, 2000) and U.S. Pat. No. 6,800,733 (Oct. 5, 2004).

Thus, in aspects of this embodiment, a donor fluorophore or an acceptor fluorophore can be a GFP that emits peak light in the range of 500-520 nm which has, e.g., at least 70% amino acid identity with the AcGFP1 of SEQ ID NO: 143, at least 75% amino acid identity with the AcGFP1 of SEQ ID NO: 143, at least 80% amino acid identity with the AcGFP1 of SEQ ID NO: 143, at least 85% amino acid identity with the AcGFP1 of SEQ ID NO: 143, at least 90% amino acid identity with the AcGFP1 of SEQ ID NO: 143 or at least 95% amino acid identity with the AcGFP1 of SEQ ID NO: 143. In other aspects of this embodiment, a donor fluorophore or an acceptor fluorophore is a GFP that emits light in the range of 500-520 nm which has, e.g., at most one, two, three, four, five, six, seven, eight, nine, or ten amino acid substitutions relative to the AcGFP1 of SEQ ID NO: 143.

In other aspects of this embodiment, a donor fluorophore or an acceptor fluorophore can be a GFP that emits light in the range of 500-520 nm which has, e.g., at least 70% amino acid identity with the ZsGreen of SEQ ID NO: 144, at least 75% amino acid identity with the ZsGreen of SEQ ID NO: 144, at least 80% amino acid identity with the ZsGreen of SEQ ID NO: 144, at least 85% amino acid identity with the ZsGreen of SEQ ID NO: 144, at least 90% amino acid identity with the ZsGreen of SEQ ID NO: 144 or at least 95% amino acid identity with the ZsGreen of SEQ ID NO: 144. In still other aspects of this embodiment, a donor fluorophore or an acceptor fluorophore is a GFP that emits light in the range of 500-520 nm which has, e.g., at most one, two, three, four, five, six, seven, eight, nine, or ten amino acid substitutions relative to the ZsGreen of SEQ ID NO: 144.

In other aspects of this embodiment, a donor fluorophore or an acceptor fluorophore can be a GFP that emits light in the range of 500-520 nm which has, e.g., at least 70% amino acid identity with the EGFP of SEQ ID NO: 145, at least 75% amino acid identity with the EGFP of SEQ ID NO: 145, at least 80% amino acid identity with the EGFP of SEQ ID NO: 145, at least 85% amino acid identity with the EGFP of SEQ ID NO: 145, at least 90% amino acid identity with the EGFP of SEQ ID NO: 145 or at least 95% amino acid identity with the EGFP of SEQ ID NO: 145. In still other aspects of this embodiment, a donor fluorophore or an acceptor fluorophore is a GFP that emits light in the range of 500-520 nm which has, e.g., at most one, two, three, four, five, six, seven, eight, nine, or ten amino acid substitutions relative to the EGFP of SEQ ID NO: 145.

In other aspects of this embodiment, a donor fluorophore or an acceptor fluorophore can be a GFP that emits light in the range of 500-520 nm which has, e.g., at least 70% amino acid identity with the MGFP of SEQ ID NO: 146, at least 75% amino acid identity with the MGFP of SEQ ID NO: 146, at least 80% amino acid identity with the MGFP of SEQ ID NO: 146, at least 85% amino acid identity with the MGFP of SEQ ID NO: 146, at least 90% amino acid identity with the MGFP of SEQ ID NO: 146 or at least 95% amino acid identity with the MGFP of SEQ ID NO: 146. In still other aspects of this embodiment, a donor fluorophore or an acceptor fluorophore is a GFP that emits light in the range of 500-520 nm which has, e.g., at most one, two, three, four, five, six, seven, eight, nine, or ten amino acid substitutions relative to the MGFP of SEQ ID NO: 146.

In other aspects of this embodiment, a donor fluorophore or an acceptor fluorophore can be a GFP that emits light in the range of 500-520 nm which has, e.g., at least 70% amino acid identity with the hrGFP of SEQ ID NO: 147, at least 75% amino acid identity with the hrGFP of SEQ ID NO: 147, at least 80% amino acid identity with the hrGFP of SEQ ID NO: 147, at least 85% amino acid identity with the hrGFP of SEQ ID NO: 147, at least 90% amino acid identity with the hrGFP of SEQ ID NO: 147 or at least 95% amino acid identity with the hrGFP of SEQ ID NO: 147. In still other aspects of this embodiment, a donor fluorophore or an acceptor fluorophore is a GFP that emits light in the range of 500-520 nm which has, e.g., at most one, two, three, four, five, six, seven, eight, nine, or ten amino acid substitutions relative to the hrGFP of SEQ ID NO: 147.

In another embodiment, a donor fluorophore or acceptor fluorophore is a cyan fluorescent protein. As used herein, the term "cyan fluorescent protein" is synonymous with "CFP" and means a protein which absorbs light of a certain wavelength and emits peak light energy of wavelengths in the range of 460-500 nm. Cyan fluorescent proteins useful in the invention include, without limitation, the ECFP of SEQ ID NO: 148, genetically engineered ECFP variants and active ECFP fragments thereof that retain the ability to emit peak light energy in the range of 460-500 nm, the AmCyan of SEQ ID NO: 149, genetically engineered AmCyan variants and active AmCyan fragments thereof that retain the ability to emit peak light energy in the range of 460-500 nm, as well as, naturally-occurring cyan fluorescent proteins, naturally occurring CFP variants, genetically engineered CFP variants and active CFP fragments thereof that retain the ability to emit peak light energy in the range of 460-500 nm. As a non-limiting example, the CFP variant known as "CGFP" contains a Thr203Tyr substitution that changes the excitation and emission wavelengths of the ECFP of SEQ ID NO: 148 to a range between CFP and EGFP; and Aequorea-derived fluorescent proteins as described in, e.g., Roger Y. Tsien & Roger Heim, Modified Green Fluorescent Proteins, U.S. Pat. Nos. 5,625,048 (Apr. 29, 1997), U.S. Pat. No. 6,319,669 (Nov. 20, 2001), U.S. Pat. No. 6,066,476 (May 23, 2000) and U.S. Pat. No. 6,800,733 (Oct. 5, 2004).

Thus, in aspects of this embodiment, a donor fluorophore or an acceptor fluorophore is a CFP that emits light in the range of 460-500 nm which has, e.g., at least 70% amino acid identity with the ECFP of SEQ ID NO: 148, at least 75% amino acid identity with the ECFP of SEQ ID NO: 148, at least 80% amino acid identity with the ECFP of SEQ ID NO: 148, at least 85% amino acid identity with the ECFP of SEQ ID NO: 148, at least 90% amino acid identity with the ECFP of SEQ ID NO: 148 or at least 95% amino acid identity with the ECFP of SEQ ID NO: 148. In other aspects of this embodiment, a donor fluorophore or an acceptor fluorophore is a CFP that emits light in the range of 460-500 nm which has, e.g., at most one, two, three, four, five, six, seven, eight, nine, or ten amino acid substitutions relative to the ECFP of SEQ ID NO: 148.

In other aspects of this embodiment, a donor fluorophore or an acceptor fluorophore is a CFP that emits light in the range of 460-500 nm which has, e.g., at least 70% amino acid identity with the AmCyan of SEQ ID NO: 149, at least 75% amino acid identity with the AmCyan of SEQ ID NO: 149, at least 80% amino acid identity with the AmCyan of SEQ ID NO: 149, at least 85% amino acid identity with the AmCyan of SEQ ID NO: 149, at least 90% amino acid identity with the AmCyan of SEQ ID NO: 149 or at least 95% amino acid identity with the AmCyan of SEQ ID NO: 149. In still other aspects of this embodiment, a donor fluorophore or an acceptor fluorophore is a CFP that emits light in the range of 460-500 nm which has, e.g., at most one, two, three, four, five, six, seven, eight, nine, or ten amino acid substitutions relative to the AmCyan of SEQ ID NO: 149.

In yet another embodiment, a donor fluorophore or an acceptor fluorophore is a blue fluorescent protein. As used herein, the term "blue fluorescent protein" is synonymous with "BFP" and means a protein which absorbs light of a certain wavelength and emits peak light energy of wavelengths in the range of 420-460 nm. Blue fluorescent proteins useful in the invention include, without limitation, the EBFP of SEQ ID NO: 150, genetically engineered EBFP variants and active EBFP fragments thereof that retain the ability to emit peak light energy in the range of 420-460 nm, as well as, naturally-occurring blue fluorescent proteins, naturally occurring BFP variants, genetically engineered BFP variants and active BFP fragments thereof that retain the ability to emit peak light energy in the range of 420-460 nm. As non-limiting examples, see Aequorea-derived fluorescent proteins as described in, e.g., Roger Y. Tsien & Roger Heim, Modified Green Fluorescent Proteins, U.S. Pat. No. 5,625,048 (Apr. 29, 1997), U.S. Pat. No. 6,319,669 (Nov. 20, 2001), U.S. Pat. No. 6,066,476 (May 23, 2000) and U.S. Pat. No. 6,800,733 (Oct. 5, 2004).

Thus, in aspects of this embodiment, a donor fluorophore or an acceptor fluorophore is a BFP that emits light in the range of 420-460 nm which has, e.g., at least 70% amino acid identity with the EBFP of SEQ ID NO: 150, at least 75% amino acid identity with the EBFP of SEQ ID NO: 150, at least 80% amino acid identity with the EBFP of SEQ ID NO: 150, at least 85% amino acid identity with the EBFP of SEQ ID NO: 150, at least 90% amino acid identity with the EBFP of SEQ ID NO: 150 or at least 95% amino acid identity with the EBFP of SEQ ID NO: 150. In other aspects of this embodiment, a donor fluorophore or an acceptor fluorophore is a BFP that emits light in the range of 420-460 nm which has, e.g., at most one, two, three, four, five, six, seven, eight, nine, or ten amino acid substitutions relative to the EBFP of SEQ ID NO: 150.

In yet another embodiment, a donor fluorophore or an acceptor fluorophore is a yellow fluorescent protein. As used herein, the term "yellow fluorescent protein" is synonymous with "YFP" and means a protein which absorbs light of a certain wavelength and emits peak light energy of wavelengths in the range of 520-550 nm. Yellow fluorescent proteins useful in the invention include, without limitation, the EYFP of SEQ ID NO: 151, genetically engineered EYFP variants and active EYFP fragments thereof that retain the ability to emit peak light energy in the range of 520-550 nm, the ZsYellow of SEQ ID NO: 152, genetically engineered ZsYellow variants and active ZsYellow fragments thereof that retain the ability to emit peak light energy in the range of 520-550 nm, as well as, naturally-occurring YFPs, naturally occurring YFP variants, genetically engineered YFP variants and active YFP fragments thereof that retain the ability to emit peak light energy in the range of 520-550 nm. As non-limiting examples, the YFP variants "Citrine," which contain Val68Leu and Gln69Met substitutions in the YFP of SEQ ID NO: 151, and "Venus," which contain Phe46Leu, Met153Thr, Val163Ala and Ser175Gly substitutions in the YFP of SEQ ID NO: 151, are extremely bright and fast-maturing YFPs, see, e.g., Oliver Griesbeck et al., Reducing the environmental sensitivity of yellow fluorescent protein. Mechanism and applications, 276(31) J. Biol. Chem. 29188-29194 (2001); and Takeharu Nagai et al., A variant of yellow fluorescent protein with fast and efficient maturation for cell-biological applications, 20(1) Nat. Biotechnol. 87-90 (2002); and Aequorea-derived fluorescent proteins as described in, e.g., Roger Y. Tsien et al., Long Wavelength Engineered Fluorescent Proteins, U.S. Pat. No. 6,124,128 (Sep. 26, 2000), U.S. Pat. No. 6,054,321 (Apr. 25, 2000), U.S. Pat. No. 6,077,707 (Jun. 20, 2000), U.S. Pat. No. 6,403,374 (Jun. 11, 2002) and U.S. Pat. No. 6,780,975 (Aug. 24, 2004).

Thus, in aspects of this embodiment, a donor fluorophore or an acceptor fluorophore is a YFP that emits light in the range of 520-550 nm which has, e.g., at least 70% amino acid identity with the YFP of SEQ ID NO: 151, at least 75% amino acid identity with the YFP of SEQ ID NO: 151, at least 80% amino acid identity with the YFP of SEQ ID NO: 151, at least 85% amino acid identity with the YFP of SEQ ID NO: 151, at least 90% amino acid identity with the YFP of SEQ ID NO: 151 or at least 95% amino acid identity with the YFP of SEQ ID NO: 151. In other aspects of this embodiment, a donor fluorophore or an acceptor fluorophore is a YFP that emits light in the range of 520-550 nm which has, e.g., at most one, two, three, four, five, six, seven, eight, nine, or ten amino acid substitutions relative to the YFP of SEQ ID NO: 151.

In other aspects of this embodiment, a donor fluorophore or an acceptor fluorophore is a YFP that emits light in the range of 520-550 nm which has, e.g., at least 70% amino acid identity with the ZsYellow of SEQ ID NO: 152, at least 75% amino acid identity with the ZsYellow of SEQ ID NO: 152, at least 80% amino acid identity with the ZsYellow of SEQ ID NO: 152, at least 85% amino acid identity with the ZsYellow of SEQ ID NO: 152, at least 90% amino acid identity with the ZsYellow of SEQ ID NO: 152 or at least 95% amino acid identity with the ZsYellow of SEQ ID NO: 152. In still other aspects of this embodiment, a donor fluorophore or an acceptor fluorophore is a YFP that emits light in the range of 520-550 nm which has, e.g., at most one, two, three, four, five, six, seven, eight, nine, or ten amino acid substitutions relative to the ZsYellow of SEQ ID NO: 152.

In yet embodiment, a donor fluorophore or an acceptor fluorophore is a red fluorescent protein. As used herein, the term "red fluorescent protein" is synonymous with "RFP" and means a protein which absorbs light of a certain wavelength and emits peak light energy of wavelengths in the range of 550-740 nm. Red fluorescent proteins useful in the invention include, without limitation, the Discosoma striate RFP DsRed of SEQ ID NO: 153, DsRed1 of SEQ ID NO: 154, DsRed2 of SEQ ID NO: 155 and DsRed Express of SEQ ID NO: 156, genetically engineered DsRed, DsRed1, DsRed2 and DsRed Express variants and active DsRed, DsRed1, DsRed2 and DsRed Express fragments thereof that retain the ability to emit peak light energy in the range of 550-740 nm; the Heteractis crispa RFP HcRed of SEQ ID NO: 157, genetically engineered HcRed variants and active HcRed fragments thereof that retain the ability to emit peak light energy in the range of 550-740 nm; the Anemonia sulcata RFP AsRed of SEQ ID NO: 158, genetically engineered AsRed variants and active AsRed fragments thereof that retain the ability to emit peak light energy in the range of 550-740 nm, as well as, naturally-occurring RFPs, naturally occurring RFP variants, genetically engineered RFP variants and active RFP fragments thereof that retain the ability to emit peak light energy in the range of 550-740 nm. As a non-limiting example, Entacmeae quadricolor fluorescent proteins including red fluorescent proteins such as, e.g., eqFP611, see, e.g., Jörg Wiedenmann et al., A far-red fluorescent protein with fast maturation and reduced oligomerization tendency from Entacmaea quadricolor Anthozoa, Actinaria), 99(18) Proc. Natl. Acad. Sci. U.S.A. 11646-11651 (2002).

Thus, in aspects of this embodiment, a donor fluorophore or an acceptor fluorophore can be a RFP that emits light in the range of 550-740 nm which has, e.g., at least 70% amino acid identity with the DsRed of SEQ ID NO: 153, at least 75% amino acid identity with the DsRed of SEQ ID NO: 153, at least 80% amino acid identity with the DsRed of SEQ ID NO: 153, at least 85% amino acid identity with the DsRed of SEQ ID NO: 153, at least 90% amino acid identity with the DsRed of SEQ ID NO: 153 or at least 95% amino acid identity with the DsRed of SEQ ID NO: 153. In other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the DsRed of SEQ ID NO: 153.

In other aspects of this embodiment, a donor fluorophore or an acceptor fluorophore can be a RFP that emits light in the range of 550-740 nm which has, e.g., at least 70% amino acid identity with the DsRed1 of SEQ ID NO: 154, at least 75% amino acid identity with the DsRed1 of SEQ ID NO: 154, at least 80% amino acid identity with the DsRed1 of SEQ ID NO: 154, at least 85% amino acid identity with the DsRed1 of SEQ ID NO: 154, at least 90% amino acid identity with the DsRed1 of SEQ ID NO: 154 or at least 95% amino acid identity with the DsRed1 of SEQ ID NO: 154. In still other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the DsRed1 of SEQ ID NO: 154.

In other aspects of this embodiment, a donor fluorophore or an acceptor fluorophore can be a RFP that emits light in the range of 550-740 nm which has, e.g., at least 70% amino acid identity with the DsRed2 of SEQ ID NO: 155, at least 75% amino acid identity with the DsRed2 of SEQ ID NO: 155, at least 80% amino acid identity with the DsRed2 of SEQ ID NO: 155, at least 85% amino acid identity with the DsRed2 of SEQ ID NO: 155, at least 90% amino acid identity with the DsRed2 of SEQ ID NO: 155 or at least 95% amino acid identity with the DsRed2 of SEQ ID NO: 155. In still other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the DsRed2 of SEQ ID NO: 155.

In other aspects of this embodiment, a donor fluorophore or an acceptor fluorophore can be a RFP that emits light in the range of 550-740 nm which has, e.g., at least 70% amino acid identity with the DsRed2 of SEQ ID NO: 156, at least 75% amino acid identity with the DsRed Express of SEQ ID NO: 156, at least 80% amino acid identity with the DsRed Express of SEQ ID NO: 156, at least 85% amino acid identity with the DsRed Express of SEQ ID NO: 156, at least 90% amino acid identity with the DsRed Express of SEQ ID NO: 156 or at least 95% amino acid identity with the DsRed Express of SEQ ID NO: 156. In still other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the DsRed Express of SEQ ID NO: 156.

In other aspects of this embodiment, a donor fluorophore or an acceptor fluorophore can be a RFP that emits light in the range of 550-740 nm which has, e.g., at least 70% amino acid identity with the AsRed of SEQ ID NO: 158, at least 75% amino acid identity with the AsRed of SEQ ID NO: 158, at least 80% amino acid identity with the AsRed of SEQ ID NO: 158, at least 85% amino acid identity with the AsRed of SEQ ID NO: 158, at least 90% amino acid identity with the AsRed of SEQ ID NO: 158 or at least 95% amino acid identity with the AsRed of SEQ ID NO: 158. In still other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the AsRed of SEQ ID NO: 158.

In other aspects of this embodiment, a donor fluorophore or an acceptor fluorophore can be a RFP that emits light in the range of 550-740 nm which has, e.g., at least 70% amino acid identity with the HcRed of SEQ ID NO: 157, at least 75% amino acid identity with the HcRed of SEQ ID NO: 157, at least 80% amino acid identity with the HcRed of SEQ ID NO: 157, at least 85% amino acid identity with the HcRed of SEQ ID NO: 157, at least 90% amino acid identity with the HcRed of SEQ ID NO: 157 or at least 95% amino acid identity with the HcRed of SEQ ID NO: 157. In still other aspects of this embodiment, a donor fluorophore or an acceptor fluorophore is a RFP that emits light in the range of 550-740 nm which has, e.g., at most one, two, three, four, five, six, seven, eight, nine, or ten amino acid substitutions relative to the HcRed of SEQ ID NO: 157.

A donor fluorophore or an acceptor fluorophore disclosed in the present specification can be, in part, a fluorophore binding protein that is subsequently labeled with a fluorophore. A fluorophore binding protein establishes a covalent bond, or strong non-covalent interaction, with the fluorophore in a selective chemical or biochemical reaction. Non-limiting examples of such fluorophore binding proteins and corresponding fluorophores include the bis-arsenical tetracysteine system, see, e.g., B. Albert Griffin et al., Specific covalent labeling of recombinant protein molecules inside live cells, 281(5374) Science 269-272 (1998); and B. Albert Griffin et al., Fluorescent labeling of recombinant proteins in living cells with FIAsH, 327 Methods Enzymol. 565-578 (2000); the alkylguanine-DNA-alkyltransferase (AGT) system, see, e.g., Antje Keppler et al, *A General Method for the Covalent Labeling of Fusion proteins with Small Molecules in vivo*, 21 (1) Nat. Biotech 86-89 (2003); Antje Keppler et al, *Labeling of fusion proteins of O6-alkylguanine-DNAalkyltransferase with small molecules in vivo and in vitro*, 32(4) Methods 437-444 (2004); and Antje Keppler et al, *Labeling of Fusion Proteins with Synthetic Fluorophores in Live Cells*, 101(27) Proc. Natl. Acad. Sci. USA 9955-9959 (2004); and the dehalogenase system. In addition, non-limiting examples of fluorophore binding proteins and corresponding fluorophores, as well as well-characterized reagents, conditions and protocols are readily available from commercial vendors that include, without limitation, TC-FIAsH™ TC-ReAsH™ In-Cell Tetracysteine Tag Detection Kit (Invitrogen Corp., Carlsbad, Calif.); SNAP-tag™ multi-purpose protein tag system (Covalys Biosciences AG, Switzerland); and HaloTag™ Interchangeable Labeling Technology (Promega Corp., Madison Wis.). These protocols are routine procedures well within the scope of one skilled in the art and from the teaching herein. A fluorophore binding protein can be operably-linked to a Clostridial toxin recognition sequence to create a fusion protein using standard molecular genetic techniques. Additionally, a fluorophore binding protein can be specifically linked to the amino- or carboxyl-terminus of a Clostridial toxin recognition sequence using well known chemical methods, see, e.g., *Chemical Approaches to Protein Engineering*, in PROTEIN ENGINEERING: A PRACTICAL APPROACH (Eds. Rees et al., Oxford University Press, 1992).

TABLE 10

Excitation and Emission Maxima of Exemplary Fluorophores for Fluorophore Binding Proteins

| Name | Dye | Excitation maxima (nm) | Emission maxima (nm) |
|---|---|---|---|
| bis-Arsenical Tetracysteine System | | | |
| FlAsH | fluorescein arsenical hairpin binding dye | 508 | 528 |
| ReAsH | resorufin arsenical hairpin binding dye | 593 | 608 |
| AGT/SNAP-Tag System | | | |
| BG-430 | para-benzyl guanine diethylaminocoumarin | 421 | 444 and 484 |
| BG-DAF | para-benzyl guanine diacetylfluorescein | 500 | 524 |
| BG-505 | para-benzyl guanine dyomic DY-505-05 | 504 | 532 |
| BG-488 | para-benzyl guanine ATTO 488 | 506 | 526 |
| BG-532 | para-benzyl guanine ATTO 532 | 536 | 554 |
| BG-547 | para-benzyl guanine dyomic DY-547 | 554 | 568 |
| TMR-Star | para-benzyl guanine tetramethylrhodamine | 554 | 580 |
| BG-600 | para-benzyl guanine ATTO 600 | 606 | 626 |
| BG-632 | para-benzyl guanine dyomic DY-632 | 636 | 656 |
| BG-647 | para-benzyl guanine dyomic DY-647 | 660 | 673 |
| BG-732 | para-benzyl guanine dyomic DY-732 | 732 | 747 |
| BG-747 | para-benzyl guanine dyomic DY-747 | 752 | 763 |
| Dehalogenase/HaloTag ™ System | | | |
| HaloTag Coumarian | Coumarian derivative | 353 | 434 |
| HaloTag diAcFAM | nonfluorescent diacetyl fluorescein derivative | 494 | 526 |
| HaloTag TMR | tetramethyl rhodamine derivative | 555 | 585 |

The bis-arsenical tetracysteine system comprises a fusion protein including the protein of interest and a tetracysteine hexapeptide comprising the amino acid sequence C—C—X—X—C—C (SEQ ID NO: 159) and a bis-arsenical fluorophore complexed with two dithiol residues. In the labeling reaction, the tetracysteine peptide displaces the dithiols from the arsenic residues of the fluorophore. This interaction strongly couples the fluorophore with the fluorophore binding protein and significantly increases the signal by reducing the quenching of the fluorophore. Non-limiting examples of bis-arsenical fluorophores include nonfluorescent biarsenical derivatives of fluorescein, such as, e.g., FIAsH and nonfluorescent biarsenical derivatives of resorufin, such as, e.g., ReAsH.

The AGT system comprises a fusion protein including the protein of interest and a modified AGT 22 kDa polypeptide (SEQ ID NO: 160) and a benzyl guanine modified in the para-position by a fluorescent label. In the labeling reaction, the O6-position of the para-substituted benzyl guanine irreversibly binds to a reactive cysteine in the active center of AGT. Non-limiting examples of modified benzylguanine fluorophores listed in Table 10.

The dehalogenase system comprises a fusion protein including the protein of interest and a modified dehalogenase and a modified fluorophore comprising an alkyl residue. In the labeling reaction, the modified fluorophore strongly interacts with the active site of the modified dehalogenase. The modified dehalogenase is a 33 kDa polypeptide (SEQ ID NO: 161) comprising a mutation in the active center that significantly slows the catalytic activity of the enzyme, effectively creating an irreversible interaction. Non-limiting examples of modified benzylguanine fluorophores listed in Table 10.

Thus in an embodiment, a donor fluorophore or an acceptor fluorophore is a fluorophore binding protein which strongly interacts with a fluorophore. In another embodiment, a donor fluorophore or an acceptor fluorophore is a tetracysteine peptide which strongly interacts with a fluorophore. In an aspect of this embodiment, a donor fluorophore or an acceptor fluorophore is a tetracysteine peptide comprises SEQ ID NO: 159 which strongly interacts with a fluorophore. In another aspect of this embodiment, a donor fluorophore or an acceptor fluorophore is a tetracysteine peptide that strongly interacts with a nonfluorescent biarsenical derivatives of fluorescein. In another aspect of this embodiment, a donor fluorophore or an acceptor fluorophore is a tetracysteine peptide that strongly interacts with a nonfluorescent biarsenical derivatives of resorufin.

Thus, in an embodiment, a donor fluorophore or an acceptor fluorophore is an AGT polypeptide which strongly interacts with a fluorophore. In an aspect of this embodiment, a donor fluorophore or an acceptor fluorophore is an AGT which strongly interacts with a fluorophore comprises SEQ ID NO: 160. In other aspects of this embodiment, a donor fluorophore or an acceptor fluorophore can be a AGT which strongly interacts with a fluorophore that has, e.g., at least 70% amino acid identity with the AGT of SEQ ID NO: 160, at least 75% amino acid identity with the AGT of SEQ ID NO: 160, at least 80% amino acid identity with the AGT of SEQ ID NO: 160, at least 85% amino acid identity with the AGT of SEQ ID NO: 160, at least 90% amino acid identity with the AGT of SEQ ID NO: 160 or at least 95% amino acid identity with the AGT of SEQ ID NO: 160. In still other aspects of this embodiment, a donor fluorophore or an acceptor fluorophore is a AGT which strongly interacts with a fluorophore that has, e.g., at most one, two, three, four, five, six, seven, eight, nine, or ten amino acid substitutions relative to the AGT of SEQ ID NO: 160. In other aspects of this embodiment, a donor fluorophore or an acceptor fluorophore is an AGT that strongly interacts with a para-substituted benzyl guanine derivative comprising a diethylaminocoumarin, a diacetylfluorescein, a dyomic DY-505-05, an ATTO 488, an ATTO 532, a DY-547, a tetramethylrhodamine, an ATTO 600, a dyomic DY-632, a dyomic DY-647, a dyomic DY-732 or a dyomic DY-747.

Thus, in an embodiment, a donor fluorophore or an acceptor fluorophore is a dehalogenase polypeptide which strongly interacts with a fluorophore. In an aspect of this embodiment, a donor fluorophore or an acceptor fluorophore is a dehalogenase which strongly interacts with a fluorophore comprises SEQ ID NO: 161. In other aspects of this embodiment, a donor fluorophore or an acceptor fluorophore can be a dehalogenase which strongly interacts with a fluorophore that has, e.g., at least 70% amino acid identity with the dehalogenase of SEQ ID NO: 161, at least 75% amino acid identity with the dehalogenase of SEQ ID NO: 161, at least 80% amino acid identity with the dehalogenase of SEQ ID NO: 161, at least 85% amino acid identity with the dehalogenase of SEQ ID NO: 161, at least 90% amino acid identity with the dehalogenase of SEQ ID NO: 161 or at least 95% amino acid identity with the dehalogenase of SEQ ID NO: 161. In still other aspects of this embodiment, a donor fluorophore or an acceptor fluorophore is a dehalogenase which strongly interacts with a fluorophore that has, e.g., at most one, two, three, four, five, six, seven, eight, nine, or ten amino acid substitutions relative to the dehalogenase of SEQ ID NO: 161. In other aspects of this embodiment, a donor fluorophore or an acceptor fluorophore is a dehalogenase that strongly interacts with a coumarian derivative such as HaloTag Coumarian, a fluorescein derivative such as HaloTag diAcFAM or a tetramethyl rhodamine derivative such as HaloTag TMR.

A donor fluorophore or an acceptor fluorophore disclosed in the present specification can be, in part, a fluorescent dye. As used herein, the term "fluorescent dye" means a molecule which absorbs light energy of a certain wavelength, including, e.g., violet, blue, cyan, green, yellow-green, yellow, orange, red-orange, red, far-red or infrared, and emits light energy of a different wavelength and encompass those which emit in a variety of spectra, including violet, blue, cyan, green, yellow-green, yellow, orange, red-orange, red, far-red or infrared, see Table 11 for non-limiting examples. Non-limiting examples of a fluorescent dye include dyes derived from, e.g., a coumarin, a cyanine, a fluorescein, an isocyanate, an isothiocyanate, an indocarbocyanine, an indodicarbocyanine, a pyridyloxazole, a phycoerythrin, a phycocyanin, an o-phthaldehyde and a rhodamine. As another non-limiting example, a fluorescent dye can be a blue fluorescent dye, such as, e.g., 7-amino-4-methylcoumarin-3-acetic acid (AMCA), Cascade Blue, Alexa Fluor® 350 and Alexa Fluor® 405. As still another non-limiting example, a fluorescent dye can be a green fluorescent dye, such as, e.g., fluorescein, fluorescamine, carboxyfluorescein (FAM), fluorescein isothiocyanate (FITC), Cy2, BODIPY FL, BODIPY 493/503, BODIPY 499/508, Alexa Fluor® 488, Oregon Green® 488 and Alexa Fluor® 500. As yet another non-limiting example, a fluorescent dye can be a yellow-green fluorescent dye, such as, e.g., rhodamine 6G, BODIPY R6G, Alexa Fluor® 430 and Alexa Fluor® 514. As a further non-limiting example, a fluorescent dye can be a yellow fluorescent dye, such as, e.g., Lucifer Yellow, BODIPY 507/545, BODIPY 530/550, Alexa Fluor® 532. As a still further non-limiting example, a fluorescent dye can be an orange fluorescent dyes, such as, e.g., tetramethyl rhodamine (TAMRA), tetramethyl rhodamine-5-isothiocyanate (5-TRITC), tetramethyl rhodamine-6-isothiocyanate (6-TRITC), Cy3, BODIPY TMR, BODIPY 581/591, Alexa Fluor® 546. As a yet further non-limiting example, a fluorescent dye can be a red-orange fluorescent dye, such as, e.g., Lissamine Rhodamine B, Alexa Fluor® 555 and Alexa Fluor® 568. As another non-limiting example, a fluorescent dye can be a red fluorescent dye, such as, e.g., Texas Red, BODIPY TR, BODIPY 577/618, Alexa Fluor® 594 and Alexa Fluor® 610. As still another non-limiting example, a fluorescent dye can be a far-red fluorescent dye, such as, e.g., Cy5, BODIPY 630/650, BODIPY 650/665, Alexa Fluor® 633, Alexa Fluor® 635 and Alexa Fluor® 647; and near infrared fluorescent dyes, such as, e.g., allophycocyanin (APC), Cy5.5, Cy7, Alexa Fluor® 660, Alexa Fluor® 680, Alexa Fluor® 700 and Alexa Fluor® 750.

A fluorescent dye disclosed in the present specification can be attached to a Clostridial toxin substrate using standard conjugation chemistry methods known in the art, see, e.g., Richard P. Haugland, *A Guide to Fluorescent Probes and Labeling Technologies*, (Michelle T. Z. Spence ed., Invitrogen Corp., 10th ed., 2005). A variety of reactive groups can be used to couple a donor fluorophore or acceptor to the desired position in a peptide or peptidomimetic to produce a clostridian toxin substrate disclosed in the present specification. One method of labeling a Clostridila toxin substrate disclosed in the present specification is to attach a fluorescent dye to a free amine group present in lysine residues and at the amino-terminus of a peptide. Amine-reactive dyes are mostly acylating reagents that form carboxamides, sulfonamides or thioureas upon reaction with the amines. Reactive groups usually present on amine-reactive fluorescent dyes, include, without limitation, a succinimidyl ester group, a sulfosuccinimidyl ester group, a tetrafluorophenyl ester group, a carbonyl azide group, an isocyanate group, a sulfonyl chloride group or an aldehyde-containing group, such as, e.g., o-phthaldialdehyde (OPA), naphthalenedicarboxaldehyde (NDA) and 3-acylquinolinecarboxaldehyde (ATTO-TAG). Another method of labeling a Clostridila toxin substrate disclosed in the present specification is to attach a fluorescent dye to a free thiol group (also called mercaptans or sulfhydryls) present in cysteine residues. Reactive groups usually present on thiol-reactive fluorescent dyes, include, without limitation, a maleimide group, an iodoacetamide group, a phenylmercury group, a thiosulfate group or a methyl bromide group. Yet another method of labeling a Clostridila toxin substrate disclosed in the present specification is to attach a fluorescent dye to a free carboxylic acid group. Reactive groups usually present on carboxylic acid-reactive fluorescent dyes, include, without limitation, a hydrazide group, a hydroxylamine group, a cadaverine group or an amine group. A fluorescent dye can also be attached using a cross-linker moiety, including, without limitation, homo- and hetero-bifunctional cross-linkers, such as, e.g., BMH and SPDP.

Thus, in an embodiment, a donor fluorophore is a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye. In another embodiment, an acceptor fluorophore is a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye or an infrared fluorescent dye.

TABLE 11

Excitation and Emission Maxima of Exemplary Fluorescent Dyes

| Dye | Excitation maxima (nm) | Emission maxima (nm) |
| --- | --- | --- |
| Alexa Fluor ® 350 | 346 | 440 |
| Alexa Fluor ® 405 | 402 | 421 |
| Alexa Fluor ® 430 | 430 | 540 |
| Alexa Fluor ® 488 | 495 | 519 |
| Alexa Fluor ® 500 | 503 | 525 |
| Alexa Fluor ® 514 | 518 | 540 |
| Alexa Fluor ® 532 | 532 | 553 |
| Alexa Fluor ® 546 | 556 | 575 |
| Alexa Fluor ® 555 | 555 | 565 |
| Alexa Fluor ® 568 | 578 | 603 |
| Alexa Fluor ® 594 | 590 | 617 |
| Alexa Fluor ® 610 | 612 | 628 |
| Alexa Fluor ® 633 | 632 | 647 |
| Alexa Fluor ® 647 | 650 | 665 |
| Alexa Fluor ® 660 | 663 | 690 |
| Alexa Fluor ® 680 | 679 | 702 |
| Alexa Fluor ® 700 | 696 | 719 |
| Alexa Fluor ® 750 | 749 | 775 |
| BODIPY FL | 505 | 513 |
| BODIPY TMR | 544 | 570 |
| BODIPY 493/503 | 493 | 503 |
| BODIPY 499/508 | 499 | 508 |
| BODIPY 507/545 | 508 | 543 |
| BODIPY 530/550 | 534 | 554 |
| BODIPY 577/618 | 577 | 618 |
| BODIPY 581/591 | 584 | 592 |
| BODIPY 630/650 | 625 | 640 |

TABLE 11-continued

Excitation and Emission Maxima of Exemplary Fluorescent Dyes

| Dye | Excitation maxima (nm) | Emission maxima (nm) |
| --- | --- | --- |
| BODIPY 650/665 | 646 | 660 |
| Cy-2 | 492 | 510 |
| Cy-3 | 550 | 570 |
| Cy-5 | 650 | 670 |
| Cy-7 | 740 | 760 |
| Eosin | 524 | 544 |
| Fluo-4 | 494 | 516 |
| Fluorescein | 494 | 518 |
| Lucifer yellow | 426 | 531 |
| NBD | 478 | 541 |
| Oregon Green 488 | 496 | 524 |
| PyMPO | 415 | 570 |
| Rhodamine Red | 570 | 590 |
| Sulfonerhodamine | 555 | 580 |
| Tetramethylrhodamine | 555 | 580 |
| Texas Red | 595 | 615 |

In yet another embodiment, a donor fluorophore or an acceptor fluorophore is a fluorescent dye which absorbs light of a certain wavelength and emits peak light energy of wavelengths in the range of 420-460 nm. In aspects of this embodiment, the donor fluorophore or the acceptor fluorophore is Alexa Fluor® 350 or Alexa Fluor® 405. In another embodiment, the donor fluorophore or the acceptor fluorophore is a fluorescent dye that absorbs peak light energy in the range of 420-460 nm. In aspects of this embodiment, the donor fluorophore or the acceptor fluorophore is Alexa Fluor® 350, Alexa Fluor® 405, Alexa Fluor® 430, Lucifer Yellow or PyMPO.

In yet another embodiment, a donor fluorophore or an acceptor fluorophore is a fluorescent dye which absorbs light of a certain wavelength and emits peak light energy of wavelengths in the range of 460-500 nm. In another embodiment, the donor fluorophore or the acceptor fluorophore is a fluorescent dye that absorbs peak light energy in the range of 460-500 nm. In aspects of this embodiment, the donor fluorophore or the acceptor fluorophore is Alexa Fluor® 488, BODIPY 493/503, BODIPY 499/508, Cy-2, Fluo-4, Fluorescein, NBD or Oregon Green 488.

In still another embodiment, a donor fluorophore or an acceptor fluorophore is a fluorescent dye which absorbs light of a certain wavelength and emits peak light energy of wavelengths in the range of 500-520 nm. In aspects of this embodiment, the donor fluorophore or the acceptor fluorophore is Alexa Fluor® 488, BODIPY FL, BODIPY 493/503, BODIPY 499/508, Cy-2, Fluo-4 or Fluorescein. In another embodiment, the donor fluorophore or the acceptor fluorophore is a fluorescent dye that absorbs peak light energy in the range of 500-520 nm. In aspects of this embodiment, the donor fluorophore or the acceptor fluorophore is Alexa Fluor® 500, Alexa Fluor® 514, BODIPY FL or BODIPY 507/545.

In still another embodiment, a donor fluorophore or an acceptor fluorophore is a fluorescent dye which absorbs light of a certain wavelength and emits peak light energy of wavelengths in the range of 520-550 nm. In aspects of this embodiment, the donor fluorophore or the acceptor fluorophore is Alexa Fluor® 430, Alexa Fluor® 500, Alexa Fluor® 514, BODIPY 507/545, Eosin, Lucifer Yellow, NBD or Oregon Green 488. In another embodiment, the donor fluorophore or the acceptor fluorophore is a fluorescent dye that absorbs peak light energy in the range of 520-550 nm. In aspects of this embodiment, the donor fluorophore or the acceptor fluorophore is Alexa Fluor® 532, BODIPY 530/550, Cy-3 or Eosin.

In still another embodiment, a donor fluorophore or an acceptor fluorophore is a fluorescent dye which absorbs light of a certain wavelength and emits peak light energy of wavelengths in the range of 550-740 nm. In aspects of this embodiment, the donor fluorophore or the acceptor fluorophore is Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, BODIPY TMR, BODIPY 530/550, BODIPY 577/618, BODIPY 581/591, BODIPY 630/650, BODIPY 650/665, Cy-3, Cy-5, Cy-7, PyMPO, Rhodamine Red, Sulfonerhodamine, Tetramethylrhodamine or Texas Red. In another embodiment, the donor fluorophore or the acceptor fluorophore is a fluorescent dye that absorbs peak light energy in the range of 550-740 nm. In aspects of this embodiment, the donor fluorophore or the acceptor fluorophore is Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, BODIPY TMR, BODIPY 577/618, BODIPY 581/591, BODIPY 630/650, BODIPY 650/665, Cy-5, Cy-7, Rhodamine Red, Sulfonerhodamine, Tetramethylrhodamine or Texas Red.

Aspects of the present invention can rely on a Clostridial toxin substrate which contains a donor fluorophore comprising a lanthanide donor complex. In other aspects, a donor fluorophore is a lanthanide donor complex. A Clostridial toxin substrate comprising a lanthanide donor complex exploits the remarkable luminescent properties of lanthanides, which are their long, millisecond to submillisecond lifetimes, narrow and multiple emission bands in the visible spectrum, and unpolarized emission. A useful lanthanide donor complex/acceptor pair also can be the lanthanide donor complex). In one embodiment, a lanthanide donor complex comprises a lanthanide binding site and a lanthanide ion. In another embodiment, a lanthanide donor complex comprises a lanthanide binding site, a lanthanide ion and an antennae.

A lanthanide donor complex includes a lanthanide ion such as, without limitation, a terbium ion, europium ion, samarium ion or dysprosium ion. Lanthanide ions, or "rare earth" elements, are a group of elements whose trivalent cations emit light at well-defined wavelengths and with long decay times. Lanthanides include, without limitation, elements with atomic numbers 57 through 71: lanthanide (La); cerium (Ce); praseodymium (Pr); neodymium (Nd); promethium (Pm); samarium (Sm); europium (Eu); gadolinium (Gd); terbium (Tb); dysprosium (Dy); holmium (Ho); erbium (Er); thulium (Tm); ytterbium (Yb); and lutetium (Lu). Lanthanides can further include, without limitation, yttrium (Y; atomic number 39) and scandium (Sc; atomic number 21). Lanthanide ions have unique photophysical and spectral properties based on their special electronic configuration which partly shields optically active electrons, thereby allowing lanthanide ions to emit light at well-defined wavelengths. A characteristic of this lanthanide luminescence is the long decay times which results in very long emission lifetimes (in the micro to millisecond range).

The lanthanides usually exist as trivalent cations, in which case their electronic configuration is (Xe) 4f$^n$, with n varying from 1 ($Ce^{3+}$) to 14 ($Lu^{3+}$). The transitions of the f-electrons are responsible for the interesting photophysical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are forbidden, leading to long excited state lifetimes, in the micro- to millisecond range.

Many compounds and proteins present in biological samples are naturally fluorescent; thus, the use of conventional fluorophores can lead to significant limitations in sensitivity. However, non-specific background fluorescence is short-lived, typically having a decay time of only about 10 nanoseconds and therefore dying away much earlier than sample fluorescence. Thus, most background signals can be readily differentiated using time-resolved fluorescence (TRF), which is a quick and convenient assay based on the long-lived fluorescence of the lanthanide ions. In time-resolved fluorescence, the detector is gated for a short period of time such that the initial burst of fluorescence, including most of the background fluorescence, is not measured. After the gating period, the longer lasting fluorescence in the sample is measured, substantially enhancing sensitivity. As a non-limiting example, a pulsed excitation source for exciting the antenna of a lanthanide donor complex can be generated using a nitrogen laser (337 nm). Typically, a pulse-width of about 5 nanoseconds is utilized with a 20 to 50-Hz repetition rate. For lifetime measurements, a photomultiplier tube with suitable color filters and counting electronics can be used. For time-delayed spectra, a spectrometer, generally utilizing diffraction gratings, and either a time-gated photomultiplier tube or a CCD, gated electronically or with a mechanical chopper are used. Such instruments are commercially available and are well known in the art as described, for example, in Ming Xiao and Paul R. Selvin, *An Improved Instrument for Measuring Time-resolved Lanthanide Emission and Resonance Energy Transfer,* 70(10) Rev. Sci. Inst. 3877-3881 (1999); and Ming Xiao and Paul R. Selvin, *Quantum Yields of Luminescent Lanthanide Chelates and Far-Red Dyes Measured by Resonance Energy Transfer,* 123(29) J. Am. Chem. Soc. 7067-7073 (2001).

Lanthanide ions useful in the invention include, without limitation, terbium (Tb), europium (Eu), dysprosium (Dy) and samarium (Sm) ions, which are lanthanides that emit in the visible spectra. In one embodiment, a lanthanide ion is a Tb or Eu ion, which has a high emission quantum yield and emits with stronger intensity than a Dy or Sm ion. Excitation of an antenna for Tb or Eu is in the ultraviolet range and can be achieved, for example, using a nitrogen laser at 337 nm, or a flash lamp. Terbium emission is in the green spectra, while europium emission is in the red spectra, both providing a contrast to the excitation light.

A lanthanide-binding site functions to retain the lanthanide ion and may optionally act as a scaffold for attachment of an antenna and a reactive group suitable for coupling the lanthanide donor complex to the remainder of the Clostridial toxin substrate. As used herein, the term "lanthanide-binding site" means a moiety that constrains a lanthanide ion. A variety of lanthanide-binding sites are useful in the Clostridial toxin substrates of the invention, including, without limitation, a small molecule, a peptide or peptidomimetic.

A lanthanide-binding site useful in a lanthanide donor complex can be a small molecule, such as, e.g., a chelate. Exemplary chelate lanthanide-binding sites include, without limitation, thiol-reactive chelators, such as, e.g., a N,N,N(1),N(1)-[2,6-bis(3'-aminomethyl-1'-pyrazolyl)-4-phenylpyridine]tetrakis(acetic acid) (BPTA) chelate, a 4,7-bis(chlorosulfophenyl)-1,10-phenantroline-2,9-dicarboxylate (BCPDA) chelate, a 4,4'-Bis (1',1',1',2',2',3',3',-heptafluoro-4',6',-hexanedion-6'-il)chlorosulfo-o-terphenyl (BHHCT) chelate, a 5-(4-chlorosulfo-1',1-diphenyl-4'-yl)-1,1,1,2,2- pentafluoro-3,5-pentanedione (CDPP) chelate, a 1,4,7,10-Tetraazacyclododecane (Cyclen) chelate, a 1,4,7,10-Tetraazaciclododecane-1,4,7,10-tetraacetic acid (DOTA) chelate, a (1R,4R,7R,10R)-a,a',a",a'''-Tetramethyl-1,4,7,10-tetraazacyclododecane-1,4,7,10-tetraaetic acid (DOTMA) chelate, a 1,4,7,10-Tetraazacyclododecane-1,4,7,10-tetra (methylene phosphonic acid))(DOTP) chelate, A DO2A chelate, a DO3A chelate, a diethylenetriaminepentacetic acid (DTPA) chelate, a 1,4,8,11-Tetraazacyclododecane-1,4,8,11-tetraacetic acid (TETA) chelate, a triethylenetetraaminehexaacetic acid (TTHA) chelate, a polyphenol chelate, a β-diketone chelate, a polyaminopolycarboxylic acid chelate, a pyridine chelate, a polypyridine chelate, a porphyrin chelate, and a calixarene chelate. These and other lanthanide chelates are known in the art as described in, e.g., Paul R. Selvin et al., *Luminescence Resonance Energy Transfer,* 116 J. of the American Chemical Soc. 6029-6030 (1994); Paul R. Selvin, *Fluorescence Resonance Energy Transfer,* in *Methods in Enzymology* (Vol. 246, Biochemical Spectroscopy, ed. Kenneth Sauer) Ch 13, 300-334 (1995); Min Li and Paul R. Selvin, *Amine-reactive Forms of a Luminescent DTPA Chelate of Terbium and Europium: Attachment to DNA and Energy Transfer Measurements,* 8(2) Bioconj. Chem. 127-132 (1997); Jiyan Chen, Paul R. Selvin, *Thiol-reactive Luminescent Chelates of Terbium and Europium,* 10(2) Bioconj. Chem. 311-315 (1999); Paul R. Selvin, *The Renaissance of Fluorescence Resonance Energy Transfer,* 7(9) Nature Struc. Biol. 730-734 (2000); and Jingli Yuan et al., *Synthesis of a Terbium Fluorescent Chelate and its Application to Time-Resolved Fluoroimmunoassay,* 73(8) Anal. Chem. 1869-1876 (2001).

Lanthanide-binding sites useful in a lanthanide donor complex further include 2-hydroxyisophthalamide, a molecule which forms luminescent and highly stable complexes with lanthanides such as $Sm^{3+}$, $Eu^{3+}$, $Tb^{3+}$ and $Dy^{3+}$, see, e.g., Stephane Petoud et al., *Stable Lanthanide Luminescence Agents Highly Emissive in Aqueous Solution: Multidentate 2-Hydroxyisophthalamide Complexes of Sm(3+), Eu(3+), Tb(3+), Dy(3+),* 125(44).J. Am. Chem. Soc. 13324-13325 (2003). The 2-hydroxyisophthalamide group is a very good ligand for lanthanide ions, providing, for example, excellent sensitization of $Tb^{3+}$ through a particularly efficient ligand-to-lanthanide energy transfer process. The quantum yields of 2-hydroxyisophthalamide lanthanide chelates can be quite high ($\phi>0.5$), and complexes formed with 2-hydroxyisophthalamides are generally highly soluble and stable in water at physiological pH (Petoud, supra, 2003).

A lanthanide-binding site useful in a lanthanide donor complex also can be a β-diketonate such as, without limitation, a $Eu^{3+}$-β-diketonate (2-naphthoyltrifluoroacetonate)-trioctylphosphine oxide ternary fluorescent complex. Such lanthanide-binding sites are well known in the art as described, for example, in Eleftherios P. Diamandis, *Immunoassays with Time-Resolved Fluorescence Spectroscopy: Principles and Applications,* 21(3) Clin. Biochem. 139-150 (1988), and are commercially available, for example, as part of the DELFIA® system (Perkin-Elmer).

Thus, in aspects of this embodiment, a donor lanthanide complex comprises a BPTA-$Tb^{3+}$, a DOTA-$Tb^{3+}$, a DTPA-$Tb^{3+}$, a BHHCT-$Eu^{3+}$, a BHHCT-$Sm^{3+}$, a BCPDA-$Eu^{3+}$, or a CDPP-$Eu^{3+}$.

A lanthanide-binding site useful in a lanthanide donor complex can be a small molecule, such as, e.g., a cryptate. A cryptate is a macropolycyclic compound that acts as a cage, trapping a lanthanide ion and protecting it from solvent. Such cryptates, which are tightly associated with their ions, are highly stable in biological media. The cryptate cage itself acts as an antenna for the trapped lanthanide ion, specifically by absorbing excitation light and transferring the energy to the ion and by protecting it from quenching by water. A variety of lanthanide cryptates are useful in the invention including, but not limited to, trisbipyridine (TBP) cryptates, trisbipyridine tetracarboxylate (TBP4COOH) cryptates, trisbipyridine pentacarboxylate (TBP5COOH) cryptates and pyridine bipyridine tetracarboxylate (PBP4COOH) cryptates. One skilled in the art understands that cryptate derivatives containing multiple carboxylic groups such as TBP4COOH or PBP4COOH can be significantly more luminescent than their parent cryptate. These and other lanthanide cryptates are well known in the art, as described, for example, in Paul R. Selvin, *Principles and Biophysical Applications of Lanthanide-Based Probes,* 31 Ann. Rev. Biomol. Struct. 275-302 (2002); Gérard Mathis, *Probing Molecular Interactions with Homogeneous Techniques Based on Rare Earth Cryptates and Fluorescence Energy Transfer,* 41(9) Clin. Chem. 1391-1397 (1995); and Gérard Mathis, 20 J. Clin. Ligand Assay 141-147 (1997).

A lanthanide-binding site useful in a lanthanide donor complex can be a peptide or peptidomimetic, such as, e.g., an EF-hand motif. As used herein, the term "EF-hand motif" means two α-helices flanking the coordination site of an EF-hand motif. A variety of naturally occurring EF-hands are known in the art, as described, e,g., Hiroshi Kawasaki and Robert H. Kretsinger, *Calcium-Binding Proteins 1: EF-Hands,* 1(4) Protein Profile 343-517 (1994); and Susumu Nakayama and Robert H. Kretsinger, Evolution of the EF-Hand Family of Proteins, 23 Annu. Rev. Biophys. Biomol. Struct. 473-507 473-507 (1994); Hiroshi Kawasaki et al., *Classification and Evolution of EF-Hand Proteins,* 11(4) Biometals 277-295 (1998); and Yubin Zhou et al., *Prediction of EF-Hand Calcium-Binding Proteins and Analysis of Bacterial Proteins* 65(3) Proteins 643-655 (2006).

An EF-hand motif useful in the invention can be, without limitation, an EF-hand derived from one of the following subfamilies: the S100 subfamily, the Calmodulin subfamily, the Myosin Light Chain subfamily, the Parvalbumin subfamily, the Spectrin α-chain subfamily, the Calcineurin B subfamily, the Calbindin D28k subfamily, the Neuronal Calcium Sensor subfamily, the Calpain subfamily, the Sarcoplasmic Calcium-Binding Protein subfamily, and the BM-40 subfamily. Exemplary examples of EF-hand motif containing proteins from the S100 subfamily include, without limitation, a S100A1, a S100A10/p11, a S100A12/calgranulin C, a S100A2/S100L, a S100A3/S100E, a S100A4/placental calcium-binding protein, a S100A5/S100D, a S100A6/calcyclin, a S100A7/psoriasin, a S100A8/MRP-8, a S100A9/MRP-14, a S100B, a S100C, a S100P and a calbindin D9k. Exemplary examples of EF-hand motif containing proteins from the Calmodulin subfamily include, without limitation, a calcium-dependent protein kinase, a calmodulin, a calmodulin-like protein, a caltractin, a squidulin, a troponin C, and a nonvertebrate a troponin. Exemplary examples of EF-hand motif containing proteins from the Myosin Light Chain subfamily include, without limitation, a myosin essential light chain (ELC), and a myosin regulatory light chain (RLC). Exemplary examples of EF-hand motif containing proteins from the Parvalbumin subfamily include, without limitation, a parvalbumin (oncomodulin). Exemplary examples of EF-hand motif containing proteins from the Spectrin subfamily include, without limitation, a spectrin (brain actin-binding protein (BABP), calspectin). Exemplary examples of EF-hand motif containing proteins from the Calcineurin B subfamily include, without limitation, a calcineurin B. Exemplary examples of EF-hand motif containing proteins from the Calbindin D28k subfamily include, without limitation, a calbindin D28k and a calretinin. Exemplary examples of EF-hand motif containing proteins from the Neuronal Calcium Sensor subfamily include, without limitation, a neuronal calcium sensor-1 (NCS-1), a hippocalcin and a recoverin (visinin). Exemplary examples of EF-hand motif containing proteins from the Calpain-like subfamily include, without limitation, a ALG-2, a calpain, a grancalcin and a sorcin. Exemplary examples of EF-hand motif containing proteins from the Sarcoplasmic Calcium-Binding Protein subfamily include, without limitation, a sarcoplasmic calcium-binding protein. Exemplary examples of EF-hand motif containing proteins from the BM-40 subfamily members include, without limitation, a BM-40 (secreted protein rich in cysteines (SPARC), osteonectin). Other EF-hand motif containing proteins include, without limitation, a LAV1, a EHF5, p24 thyroid protein, a diacylglycerol kinase (DGK), an α-actinin, a SPEC, a SPEC resembling protein (LPS), an Aequorin binding protein, a luciferin binding protein, a calcium vector protein (CVP), a 1F8 and a TB17. Table 12 lists representative EF-hand motifs from various subfamilies.

Figure 5:
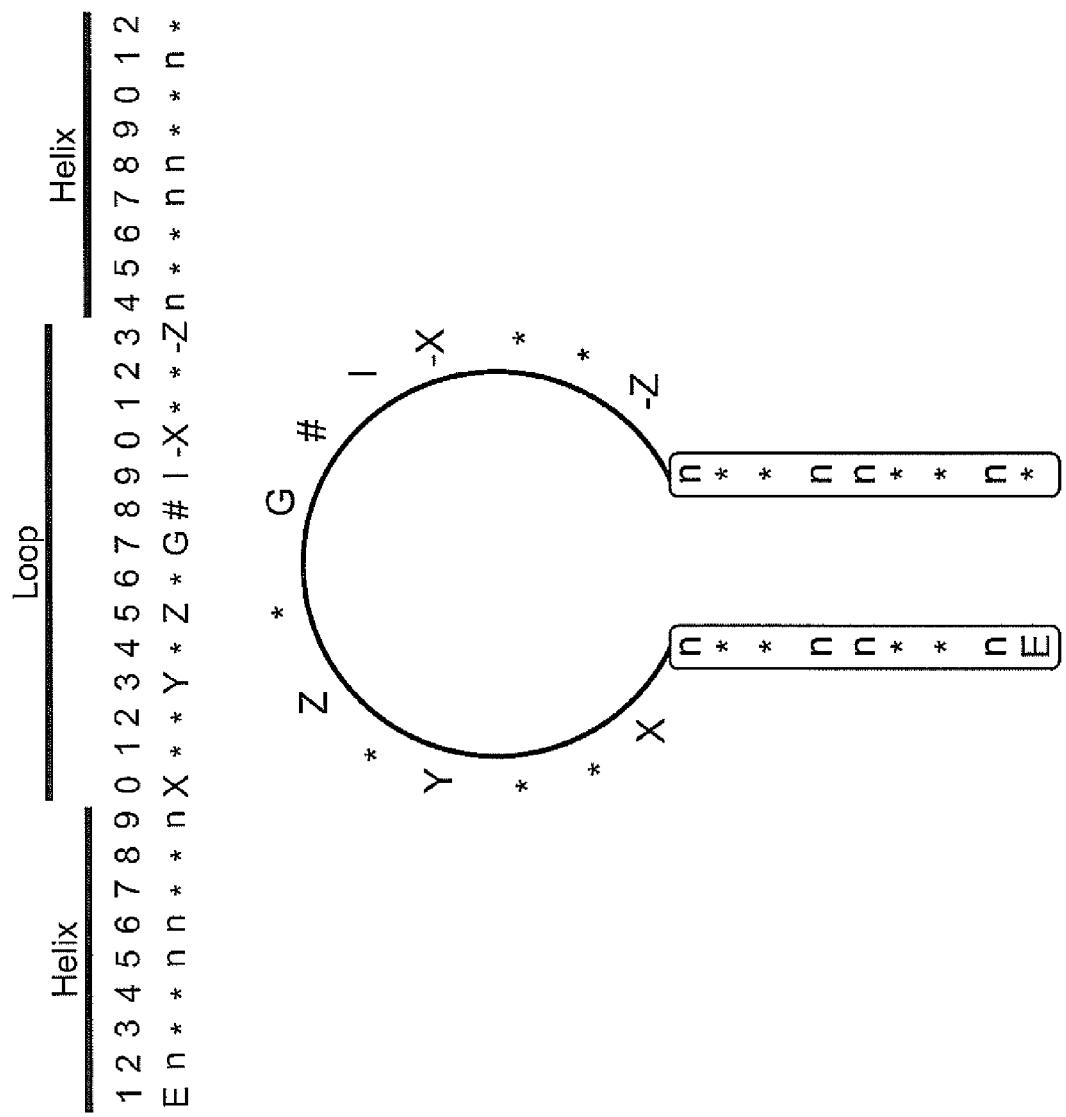
FIG. 5 shows a canonical EF-hand containing a first α-helix (residues 1-9), a lanthanide-binding loop (Loop, residues 10-23), and a second α-helix (residues 24-32). Residues specifically indicated reflect a strong consensus but are not invariant. E indicates an acidic residue, usually a glutamate; I indicates an aliphatic residue such as, e.g., an isoleucine, a leucine or a valine; G indicates a glycine, which at position 17 permits a sharp bend in the lanthanide-binding loop; n indicates a hydrophobic residue; * indicates any amino acid, but which are often hydrophilic; X indicates the first residue to coordinate the lanthanide ion; Y indicates the second residue to coordinate the lanthanide ion; Z indicates the third residue to coordinate the lanthanide ion; # indicates the four residue to coordinate the lanthanide ion; —X indicates the fifth residue to coordinate the lanthanide ion; —Z indicates the sixth residue to coordinate the lanthanide ion and is typically a glutamate or aspartate residue. The lanthanide ion is coordinated by an oxygen atom, or bridging water molecule, of the side chains of residues 10 (X), 13 (Y), 15 (Z), and 20 (—X), the carbonyl oxygen of residue 18 (#) and residue 23 (—Z).

An EF-hand motif useful in the invention also can be a canonical EF-hand motif as shown in FIG. 5 or a peptide having significant amino acid homology to a naturally occurring EF-hand. Methods of genetically engineering an EF-hand motif or the coordination site of an EF-hand motif are well known in the art, see, e.g., Vazquez-lbar, supra, 2002. Thus in an embodiment, an EF-hand motif can comprise a genetically altered EF-hand motif. In aspects of this embodiment, a genetically altered EF-hand motif comprises a polypeptide having, e.g., at least 70% amino acid identity with the amino acid sequence selected from the group consisting of SEQ ID NO: 186 through SEQ ID NO: 303, at least 75% amino acid identity with the amino acid sequence selected from the group consisting of SEQ ID NO: 186 through SEQ ID NO: 303, at least 80% amino acid identity with the amino acid sequence selected from the group consisting of SEQ ID NO: 186 through SEQ ID NO: 303, at least 85% amino acid identity with the amino acid sequence selected from the group consisting of SEQ ID NO: 186 through SEQ ID NO: 303, at least 90% amino acid identity with the amino acid sequence selected from the group consisting of SEQ ID NO: 186 through SEQ ID NO: 303 or at least 95% amino acid identity with the amino acid sequence selected from the group consisting of SEQ ID NO: 186 through SEQ ID NO: 303. In yet other aspects of this embodiment, a genetically altered EF-hand motif comprises a polypeptide having, e.g., at most 70% amino acid identity with the amino acid sequence selected from the group consisting of SEQ ID NO: 186 through SEQ ID NO: 303, at most 75% amino acid identity with the amino acid sequence selected from the group consisting of SEQ ID NO: 186 through SEQ ID NO: 303, at most 80% amino acid identity with the amino acid sequence selected from the group consisting of SEQ ID NO: 186 through SEQ ID NO: 303, at most 85% amino acid identity with the amino acid sequence selected from the group consisting of SEQ ID NO: 186 through SEQ ID NO: 303, at most 90% amino acid identity with the amino acid sequence selected from the group consisting of SEQ ID NO: 186 through SEQ ID NO: 303 or at most 95% amino acid identity with the amino acid sequence selected from the group consisting of SEQ ID NO: 186 through SEQ ID NO: 303.

In another embodiment, a genetically altered EF-hand motif comprises a polypeptide having, e.g., at most one, two, three, four, five, six, seven, eight, nine, or 10 non-contiguous amino acid substitutions relative to a naturally occurring EF-hand motif. In other aspects of this embodiment, a genetically altered EF-hand motif comprises a polypeptide having, e.g., at most one, two, three, four, five, six, seven, eight, nine, or 10 non-contiguous amino acid substitutions relative to the amino acid sequence selected from the group consisting of SEQ ID NO: 186 through SEQ ID NO: 303. In another embodiment, a genetically altered EF-hand motif comprises a polypeptide having, e.g., at least one, two, three, four, five, six, seven, eight, nine, or 10 non-contiguous amino acid substitutions relative to a naturally occurring EF-hand motif. In other aspects of this embodiment, a genetically altered EF-hand motif comprises a polypeptide having, e.g., at least one, two, three, four, five, six, seven, eight, nine, or 10 non-contiguous amino acid substitutions relative to the amino acid sequence selected from the group consisting of SEQ ID NO: 186 through SEQ ID NO: 303. In yet another embodiment, a genetically altered EF-hand motif comprises a polypeptide having, e.g., at most one, two, three, four, five, six, seven, eight, nine, or 10 non-contiguous amino acid deletions relative to a naturally occurring EF-hand motif. In yet other aspects of this embodiment, a genetically altered EF-hand motif comprises a polypeptide having, e.g., at most one, two, three, four, five, six, seven, eight, nine, or 10 non-contiguous amino acid deletions relative to the amino acid sequence selected from the group consisting of SEQ ID NO: 186 through SEQ ID NO: 303. In yet another embodiment, a genetically altered EF-hand motif comprises a polypeptide having, e.g., at least one, two, three, four, five, six, seven, eight, nine, or 10 non-contiguous amino acid deletions relative to a naturally occurring EF-hand motif. In other aspects of this embodiment, a genetically altered EF-hand motif comprises a polypeptide having, e.g., at least one, two, three, four, five, six, seven, eight, nine, or 10 non-contiguous amino acid deletions relative to the amino acid sequence selected from the group consisting of SEQ ID NO: 186 through SEQ ID NO: 303. In still another embodiment, a genetically altered EF-hand motif comprises a polypeptide having, e.g., at most one, two, three, four, five, six, seven, eight, nine, or 10 non-contiguous amino acid additions relative to a naturally occurring EF-hand motif. In still other aspects of this embodiment, a genetically altered EF-hand motif comprises a polypeptide having, e.g., at most one, two, three, four, five, six, seven, eight, nine, or 10 non-contiguous amino acid additions relative to the amino acid sequence selected from the group consisting of SEQ ID NO: 186 through SEQ ID NO: 303. In still another embodiment, a genetically altered EF-hand motif comprises a polypeptide having, e.g., at least one, two, three, four, five, six, seven, eight, nine, or 10 non-contiguous amino acid additions relative to a naturally occurring EF-hand motif. In other aspects of this embodiment, a genetically altered EF-hand motif comprises a polypeptide having, e.g., at least one, two, three, four, five, six, seven, eight, nine, or 10 non-contiguous amino acid additions relative to the amino acid sequence selected from the group consisting of SEQ ID NO: 186 through SEQ ID NO: 303.

In another embodiment, a genetically altered EF-hand motif comprises a polypeptide having, e.g., at most one, two, three, four, five, six, seven, eight, nine, or 10 contiguous amino acid substitutions relative to a naturally occurring EF-hand motif. In other aspects of this embodiment, a genetically altered EF-hand motif comprises a polypeptide having, e.g., at most one, two, three, four, five, six, seven, eight, nine, or 10 contiguous amino acid substitutions relative to the amino acid sequence selected from the group consisting of SEQ ID NO: 186 through SEQ ID NO: 303. In another embodiment, a genetically altered EF-hand motif comprises a polypeptide having, e.g., at least one, two, three, four, five, six, seven, eight, nine, or 10 contiguous amino acid substitutions relative to a naturally occurring EF-hand motif. In other aspects of this embodiment, a genetically altered EF-hand motif comprises a polypeptide having, e.g., at least one, two, three, four, five, six, seven, eight, nine, or 10 contiguous amino acid substitutions relative to the amino acid sequence selected from the group consisting of SEQ ID NO: 186 through SEQ ID NO: 303. In yet another embodiment, a genetically altered EF-hand motif comprises a polypeptide having, e.g., at most one, two, three, four, five, six, seven, eight, nine, or 10 contiguous amino acid deletions relative to a naturally occurring EF-hand motif. In yet other aspects of this embodiment, a genetically altered EF-hand motif comprises a polypeptide having, e.g., at most one, two, three, four, five, six, seven, eight, nine, or 10 contiguous amino acid deletions relative to the amino acid sequence selected from the group consisting of SEQ ID NO: 186 through SEQ ID NO: 303. In yet another embodiment, a genetically altered EF-hand motif comprises a polypeptide having, e.g., at least one, two, three, four, five, six, seven, eight, nine, or 10 contiguous amino acid deletions relative to a naturally occurring EF-hand motif. In other aspects of this embodiment, a genetically altered EF-hand motif comprises a polypeptide having, e.g., at least one, two, three, four, five, six, seven, eight, nine, or 10 contiguous amino acid deletions relative to the amino acid sequence selected from the group consisting of SEQ ID NO: 186 through SEQ ID NO: 303. In still another embodiment, a genetically altered EF-hand motif comprises a polypeptide having, e.g., at most one, two, three, four, five, six, seven, eight, nine, or contiguous amino acid additions relative to a naturally occurring EF-hand motif. In still other aspects of this embodiment, a genetically altered EF-hand motif comprises a polypeptide having, e.g., at most one, two, three, four, five, six, seven, eight, nine, or 10 contiguous amino acid additions relative to the amino acid sequence selected from the group consisting of SEQ ID NO: 186 through SEQ ID NO: 303. In still another embodiment, a genetically altered EF-hand motif comprises a polypeptide having, e.g., at least one, two, three, four, five, six, seven, eight, nine, or 10 contiguous amino acid additions relative to a naturally occurring EF-hand motif. In other aspects of this embodiment, a genetically altered EF-hand motif comprises a polypeptide having, e.g., at least one, two, three, four, five, six, seven, eight, nine, or 10 contiguous amino acid additions relative to the amino acid sequence selected from the group consisting of SEQ ID NO: 186 through SEQ ID NO: 303.

TABLE 12

EF-Hand Motifs

| Sub-Family | Protein Members | EF1 Helix-Loop-Helix | SEQ ID NO: | EF2 Helix-Loop-Helix | SEQ ID NO: |
|---|---|---|---|---|---|
| S100 | CALB9 | ELKGIFEKY-AAKEGDPNQLSKEE-LKLLLQTE | 186 | TLDELFEEL-DKNGDGEVSFEE-FQVLVKKIS | 187 |
| | CALCYC | LLIGIFHKY-SGKEGDKHTLSKKE-LKELIQKE | 188 | EIVKLMDDL-DRNKDQEVNFQE-YITFLGALA | 189 |
| | MRP-8 | SIIDVYHKY-SLIKGNPHAVYRDD-LKKLLETE | 190 | GADVWFKEL-DINTDGAVNFQE-FLILVIKMG | 191 |
| | MRP-14 | TIINTFHQY-SVKLGHPDTLNQGE-FKELVRKD | 192 | VIEHIMEDL-DTNADKQLSFEE-FIMLMARLT | 193 |
| | CALGRAN-C | GIINIFHQY-SVRLGHYDTLTKRE-LKQLITKE | 194 | TIDKIFQNL-DANQDEQVSFKE-FVVLVTDVL | 195 |
| | p11 | TMMFTFHKE-AGDKGY---LTKED-LRVLMEKE | 196 | AVDKIMKDL-DQCRDGKVGFQS-FFSLIAGLT | 197 |
| | S100A | TLINVFHAH-SGKEGDKYKLSKKE-LKELLQTE | 198 | AVDKVMKEL-DENGDGEVDFQE-YVVLVAALT | 199 |
| | S100B | ALIDVFHQY-SGREGDKHKLKKSE-LKELINNE | 200 | VVDKVMETL-DSDGDGECDFQE-FMAFVAMIT | 201 |
| | S100C | SLIAIFQKH-AGRDGNNTKISKTE-FLIFMNTE | 202 | VLDRMMKKL-DLDSDGQLDFQE-FLNLIGGLA | 203 |
| | S100D | TMVTTFHKY-SGREGSKLTLSRKE-LKELIKKE | 204 | SIDDLMKSL-DKNSDQEIDFKE-YSVFLTMLC | 205 |
| | S100E | AIVCTFQEY-AGRCGDKYKLCQAE-LKELLQKE | 206 | DYNKFMSVL-DTNKDCEVDFVE-YVRSLACLC | 207 |
| | S100L | VMVATFHKY-SGQEGDKFKLSKGE-MKELLHKE | 208 | GLKKLMGDL-DENSDQQVDFQE-YAVFLALIT | 209 |
| | S100P | MIIDVFSRY-SGSEGSTQTLTKGE-LKVLMEKE | 210 | AVDKLLKDL-DANGDAQVDFSE-FIVFVAAIT | 211 |
| | CAPL | VMVSTFHKY-SGKEGDKFKLNKSE-LKELLTRE | 212 | AFQKLMSNL-DSNRDNEVDFQE-YCVFLSCIA | 213 |
| Calmodulin | CALMOD-I | EFKEAFSLF-DKDGDGTITTKE-LGTVMRSL | 214 | ELQDMINEV-DADGNGTIDFPE-FLTMMARK | 215 |
| | CALMOD-II | EIREAFRVF-DKDGNGYISAAE-LRHVMTNL | 216 | EVDEMIREA-DIDGDGQVNYEE-FVQMMTAK | 217 |
| | CALTRCT-I | EIREAFDLF-DTDGSGTIDAKE-LKVAMRAL | 218 | EIKKMISEI-DKDGSGTIDFEE-FLTMMTAK | 219 |
| | CALTRCT-II | EILKAFRLF-DDDNSGTITIKD-LRRVAKEL | 220 | ELQEMIAEA-DRNDDNEIDEDE-FIRIMKKT | 221 |
| | TROPC-I | EFKAAFDMF-DADGGGDISTKE-LGTVMRML | 222 | ELDAIIEEV-DEDGSGTIDFEE-FLVMMVRQ | 223 |
| | TROPC-II | ELANCFRIF-DKNADGFIDIEE-LGEILRAT | 224 | DIEDLMKDS-DKNNDGRIDFDE-FLKMMEGV | 225 |
| | CALL-I | EFKEAFSLF-DKDGDGCITTRE-LGTVMRSL | 226 | ELRDMMSEI-DRDGNGTVDFPE-FLGMMARK | 227 |
| | CALL-II | EIREAFRVF-DKDGNGFVSAAE-LRHVMTRL | 228 | EVDEMIRAA-DTDGDGQVNYEE-FVRVLVSK | 229 |
| | CDPK-I | GLKELFKMI-DTDNSGTITFDE-LKDGLKRG | 230 | EIKDLMDAA-DIDKSGTIDYGE-FIAATVHL | 231 |
| | CDPK-II | NLVSAFSYF-DKDGSGYITLDE-IQQACKDF | 232 | HIDDMIKEI-DQDNDGQIDYGE-FAAMMRKG | 233 |
| | SQUID-I | EIKDAFDMF-DIDGDGQITSKE-LRSVMKSL | 234 | ELEEMIREV-DTDGNGTIEYAE-FVEMMAKQ | 235 |
| | SQUID-II | EMREAFRVF-DKDGNGLITAAE-LRQVMANF | 236 | EISEMIREA-DIDGDGMVNYEE-FVKMMTPK | 237 |
| Myosin Light Chains | MYO ELC-I | DLKDVFELF-DFWDGRDGAVDAFK-LGDVCRCL | 238 | EDVFAVGGT-HKMGEKSLPFEE-FLPAYEGL | 239 |
| | MYO ELC-II | DYMEAFKTF-DREGQGFISGAE-LRHVLTAL | 240 | DEIIKLTDL-QEDLEGNVKYED-FVKKVMAG | 241 |
| | MYO RLC-I | EMKEAFSMI-DVDRDGFVSKED-IKAISEQL | 242 | ELTAML----KE-APGPLNFTM-FLSIFSDK | 243 |
| | MYO RLC-II | TIRNAFAMF-DEQETKKLNIEY-IKDLLENM | 244 | EMRMTFKEA-PV-EGGKFDYVK-FTAMTKGS | 245 |
| Parvalbumin | PARV | DVKKVFKAI-DADASGFIEEEE-LKFVLKSF | 246 | ETKAFLKAA-DKDGDGKIGIDE-FETLVHEA | 247 |
| Spectrin | SPECTRIN | EFSMMFKHF-DKDKSGRLDHQE-FKSCLRSL | 248 | EFESILDTV-DPNRDGHVSLQE-YMAFMISR | 249 |
| Calcineurin B | CALCIN-I | RLGKRFKKL-DLDNSGSLSVEE-FMSLP-EL | 250 | LVQRVIDIF-DTDGNGEVDFKE-FIEGVSQF | 251 |
| | CALCIN-II | KLRFAFRIY-DMDKDGYISNGE-LFQVLKMM | 252 | IVDKTIINA-D-DGDGRISFEE-FCAVVGGL | 253 |

TABLE 12-continued

EF-Hand Motifs

| Sub-Family | Protein Members | EF1 Helix-Loop-Helix | SEQ ID NO: | EF2 Helix-Loop-Helix | SEQ ID NO: |
|---|---|---|---|---|---|
| Calbindin D28k | CALB28-I | QFFEIWLHF-DADGSGYLEGKE-LQNLIQEL | 254 | EMKTFVDQY-GQRDDGKIGIVE-LAHVLPTEE | 255 |
|  | CALB28-II | EFMKTWRKY-DTDHSGFIETEE-LKNFLKDL | 256 | YTDLMLKLF-DSNNDGKLELTE-MARLLPVQE | 257 |
|  | CALB28-III | EFNKAFELY-DQDGNGYIDENE-LDALLKDL | 258 | ITTYKKNIM-ALSDGGKLYRTD-LALILCAGD | 259 |
|  | CALRET-I | QFLEIWKHF-DADGNGYIEGKE-LENFFQEL | 260 | KMKEFMQKY-DKNSDGKIEMAE-LAQILPTEE | 261 |
|  | CALRET-II | EFMEAWRKY-DTDRSGYIEANE-LKGFLSDL | 262 | YTQTILRMF-DLNGDGKLGLSE-MSRLLPVQE | 263 |
|  | CALRET-III | EFNAIFTFY-DKDRSGYIDEHE-LDALLKDL | 264 | NYRKSVMSL-AEAGKLYRKDLE-IVLCSEPPM | 265 |
| Neuronal | HIPP-I | LQEWYKGFL-KDCPTGILNVDE-FKKIYANF | 266 | FAEHVFRTF-DTNSDGTIDFRE-FIIALSVTS | 267 |
|  | HIPP-II | KLMWAFSMY-DLDGNGYISREE-MLEIVQAI | 268 | RTEKIFRQM-DTNNDGKLSLEE-FIRGAKSDP | 269 |
|  | RECOV-I | LSSWYQSFL-KECPSGRITRQE-FQTIYSKF | 270 | YAQHVFRSF-DANSDGTLDFKE-YVIALHMTS | 271 |
|  | RECOV-II | KLEWAFSLY-DVDGNGTISKNE-VLEIVTAI | 272 | EKRAEKIWG-FFGKKDDDKLTE-KEFIEGTLA | 273 |
| Calpain | CANPI-I | ENFKALFRQ-LAGEDMEISVKE-LRTILNRI | 274 | SCRSMVNLM-DRDGNGKLGLVE-FNILWNR | 275 |
|  | CANPI-II | NYLSIFRKF-DLDKSGSMSAYE-MRMAIESA | 276 | KLYELIITR-YSEPDLAVDFDN-FVCCLVR | 277 |
|  | CANPI-III | TMFRFFKTL-DTDLDGVVTFDL-FKWLQLTM | 278 | — | — |
|  | CANPII-I | DGVRRLFAQ-LAGEDAEISAFE-LQTILRRV | 279 | TCKIMVDML-DSDGSGKLGLKE-FYILWTK | 280 |
|  | CANPII-II | KYQKIYREI-DVDRSGTMNSYE-MRKALEEA | 281 | QLHQVIVAR-FADDQLIIDFDN-FVRCLVR | 282 |
|  | CANPII-III | TLFKIFKQL-DPENTGTIELDL-ISWLCFSV | 283 | — | — |
|  | CANPIII-I | QQFRNIFKQ-IAGDDMEICADE-LKKVLNTV | 284 | SCRSMIALM-DTDGSGKLNLQE-FHHLWNK | 285 |
|  | CANPIII-II | AWQKIFKHY-DTDQSGTINSYE-MRNAVNDA | 286 | QLYDIITMR-YADKHMNIDFDS-FICCFVR | 287 |
|  | CANPIII-III | GMFRAFHAF-DKDGDGIIKLNV-LEWLQLTM | 288 | — | — |
|  | smCANP-I | RQFRRLFAQ-LAGDDMEVSATE-LMNILNKV | 289 | TCRSMVAVM-DSDTTGKLGFEE-FKYLWNN | 290 |
|  | smCANP-II | RWQAIYKQF-DTDRSGTICSSE-LPGAFEAA | 291 | HLYNMIIRR-YSDESGNMDFDN-FISCLVR | 292 |
|  | smCANP-III | AMFRAFKSL-DKDGTGQIQVNI-QEWLQLTM | 293 | — | — |
| Sarcoplasmic CaBP | AMP SARC-I | IKFTFDFFL-DMNHDGSIQDND-FEDMMTRY | 294 | EWRDLKGRA-DINKDDVVSWEE-YLAMWEKT | 295 |
|  | AMP SARC-II | RIPFLFKGM-DVSGDGIVDLEE-FQNYCKNF | 296 | VYNVITDGG-KVTFDLNRYKE-LYYRLLTSP | 297 |
|  | NER SARC-I | KMKTYFNRI-DFDKDGAITRMD-FESMAERF | 298 | SLTGVWDNF-LTAVAGGKGIDE-TTFINSM- | 299 |
|  | NER SARC-II | PLPLFFRAV-DTNEDNNISRDE-YGIFFGML | 300 | MAPASFDAI-DTNNDGLLSLEE-FVIAGSDF | 301 |
| BM40 | BM40 | PVHWQFGQL-DQHPIDGYLSHTE-LAPLRAPL | 302 | CTTRFFETC-DLDNDKYIALDE-WAGCFGIK | 303 |

In nature, the two α-helices of an EF-hand motif are connected by a loop of about 12 residues which contains the metal coordination site of the motif (FIG. 5). The residues which serve as ligands are highly conserved within a contiguous sequence of twelve residues spanning the loop and the beginning of the second α-helix. In particular, residues X, Y, Z, #, -X and -Z of the loop region and possibly a coordinating water molecule provide seven coordination oxygens for the lanthanide ion. Acidic amino acids are frequently present at most or all of the coordinating positions with the exception of Trp at position #, where the coordination oxygen is provided by the main chain, see, e.g., José Luis Vasquez-Ibar et al., *Engineering a Terbium-Binding Site into an Integral Membrane Protein for Luminescence Energy Transfer*, 99(6) Proc Natl Acad Sci USA. 3487-3492 (2002). Loop residues X, Y, Z and -Z contribute monodentate (X, Y and Z) or bidentate (-Z) ligands through side chain oxygens; residue # (tryptophan) ligands through its backbone carbonyl oxygen. An invariant glycine residue is present next to the # residue to allow the sharp bend necessary to ligate the lanthanide through the oxygen of residue flanking either side of the glycine. In addition, residue -X provides a ligand either directly though an oxygen of its side chain or indirectly via a water molecule. Residue -X is usually a glutamate (Glu), while residue X is typically aspartate (Asp). See Anita Lewit-Bentley and Stéphane Réty, *EF-Hand Calcium-Binding Proteins*, 10(6) Curr. Opin. Struct. Biol. 637-643 (2000); and *Molecular Biology and Biotechnology: A Comprehensive Desk Reference*, (R. A. Meyers, ed., VCH Publishers, New York, N.Y. (1995).

As used herein, the term "coordination site of an EF-hand motif" means a sequence of about 12 to about 14 residues of the loop region of an EF-motif comprising the metal binding site having a consensus sequences of X*Y*ZG#I-X**-Z, X*Y*Z*G#I-X-Z, XY*ZG#I-X-Z or XY*Z*G#I-X**-Z. In preferred compositions of these coordination sites, X is an aspartate, # is a tryptophan, -Z is a glutamate. Table 12 lists exemplary coordination sites. It is understood that a lanthanide-binding site which includes the coordination site of an EF-hand motif may or may not have homology to the α-helices of an EF-hand motif outside the coordination site of an EF-hand motif. In one embodiment, a lanthanide-binding site useful in the invention includes the coordination site of an EF-hand motif, which is a highly conserved domain in which two helices enclose a binding loop with high affinity for $Ca^{2+}$, $Tb^{3+}$ and other ions with similar ionic radii.

A sequence which includes the coordination site of an EF-hand motif can be, for example, the 14-mer peptide GDKNADGWIEFEEL (SEQ ID NO: 181) as described in, e.g., John P. MacManus et al., *A New Member of the Troponin C Superfamily: Comparison of the Primary Structures of Rat Oncomodulin and Rat Parvalbumin*, 3(11) Biosci. Rep. 1071-1075 (1983); and Natalie C. Strynadka and Michael N. James, Crystal Structures of the *Helix-Loop-Helix Calcium-Binding Proteins*, 58 Annu. Rev. Biochem. 951-998 (1989). The 14-mer SEQ ID NO: 97 functions as both a lanthanide-binding site and an antenna due to the inclusion of a tryptophan residue. Coordination sites of an EF-hand motif further include, without limitation, the peptide GDKNADGFICFEEL (SEQ ID NO: 182), where the indicated cysteine residue can be covalently labeled with iodoacetamidosalicylic acid or another antenna, see, e.g., Ian D. Clark et al., *A Novel Peptide Designed for Sensitization of Terbium (III)*

*Luminescence,* 333(102) FEBS Lett. 96-98 (1993), and the peptide DKNADGCIEFEE (SEQ ID NO: 183), where the indicated cysteine residue permits convenient covalent attachment of an antenna, see, e.g., Ian D. Clark et al., *Self-Association of Ca(2+)-Binding Peptides Induced by Lanthanide Ions: A Fluorescence Study,* 213(2) Anal. Biochem. 296-302 (1993). As non-limiting examples, 7-diethylamino-3-((4'-iodoacetylamino)phenyl)-4-methylcoumarin can be covalently attached to the cysteine in SEQ ID NO: 183, for example, as an antenna for $Eu^{3+}$, and 4-iodoacetamidosalicylic acid can be covalently attached to the cysteine in SEQ ID NO: 183, for example, as an antenna for $Tb^{3+}$.

A lanthanide-binding site which includes the coordination site of an EF-hand motif also can be a lanthanide-binding tag (LBT) such as one described in, e.g., Mark Nitz et al., *Structural Origin of the High Affinity of a Chemically Evolved Lanthanide-Binding Peptide,* 43(28) Angew. Chem. Int. Ed. Engl. 3682-3685 (2004). Such a lanthanide-binding site can include, without limitation, the 17-mer $YID_1TN_3ND_5GW_7YE_9GDE_{12}LLA$ (SEQ ID NO: 184), which includes the antenna tryptophan. Such a lanthanide-binding site can, for example, coordinate a terbium or other lanthanide ion through eight ligands, in particular, monodentate oxygen ligands of Asp1, Asn3 and Asp5, bidentate ligands from Glu9 and Glu12, and the backbone carbonyl of Trp 7. Furthermore, lanthanide-binding sites such as those described in Nitz, supra, 2004, can bind a terbium or other lanthanide ion with nanomolar affinities. As non-limiting examples, the lanthanide-binding site SEQ ID NO: 184 binds $Eu^{3+}$ with an apparent dissociation constant Kd of 62+/−4 nM; $Gd^{3+}$ with an apparent dissociation constant Kd of 84+/−6 nM; $Tb^{3+}$ with an apparent dissociation constant Kd of 57+/−3 nM; $Dy^{3+}$ with an apparent dissociation constant Kd of 71+/−5 nM; and $Er^{3+}$ with an apparent dissociation constant Kd of 78+/−6 nM.

Lanthanide-binding sites useful in a lanthanide donor complex further include those which bind a lanthanide ion exclusively through peptide-based ligands, excluding water molecules from the lanthanide ion coordination sphere. Such a lanthanide-binding site can include, for example, the 17-mer sequence YIDTNN DGWYEGDELLA (SEQ ID NO: 184; Nitz, supra, 2004).

Lanthanide-binding sites useful in a lanthanide donor complex further include chimeric helix-turn-helix/EF-hand peptides, which are helix-turn-helix DNA binding motifs redesigned to include a lanthanide binding site. Such lanthanide-binding sites include, without limitation, the peptide "P3W" (TERRQQLDKDGDGTIDEREIKIWFQNKRAKIK; SEQ ID NO: 185) as described in Joel T. Welch et al., *Lanthanide-Binding Helix-Turn-Helix Peptides: Solution Structure of a Designed Metallonuclease,* 100(7) Proc. Natl. Acad. Sci. U.S.A. 3725-3730 (2003).

Additional peptide lanthanide-binding sites are known in the art and include, yet are not limited to, those in which the lanthanide-binding site appears to be adventitious or is an intrinsic calcium-binding site. As non-limiting examples, lanthanide ions bind strongly to *Bacillus subtilus* PyrR, Diana R. Tomchick et al., *Adaptation of an Enzyme To Regulatory Function: Structure of Bacillus Subtilis Pyrr, a Pyr RNA-Binding Attenuation Protein and Uracil Phosphoribosyltransferase,* 6(3) Structure 337-350 (1998), and the cadherin NCD1, Elna Pidcock and Geoffrey R. Moore, *Structural Characteristics of Protein Binding Sites for Calcium and Lanthanide Ions,* 6(5-6) J. Biol. Inorg. Chem. 479-489 (2001). Peptide lanthanide-binding sites also include those identified using screening protocols based, for example, on terbium luminescence (Katherine J. Franz et al., *Lanthanide-Binding Tags as Versatile Protein Coexpression Probes,* 4(4) Chembiochem. 265-271 (2003); and Mark Nitz et al., *A Powerful Combinatorial Screen to Identify High-Affinity Terbium (III)-Binding Peptides,* 4(4) Chembiochem. 272-276 (2003), and those identified using similar screening assays.

Lanthanide-binding sites useful in a lanthanide donor complex further include, without limitation, those with an affinity for a lanthanide ion in the nanomolar to picomolar range. In particular embodiments, a lanthanide-binding site useful in the invention has Kd for a lanthanide ion of less than 10 µM, less than 5 µM, less than 1 µM, less than 500 nM, less than 250 nM, less than 100 nM, less than 50 nM, less than 10 nM, less than 1 nM or less than 0.1 nM. In further embodiments, a lanthanide-binding site useful in the invention has Kd for a lanthanide ion of less than 100 nM, less than 90 nM, less than 80 nM, less than 70 nM, less than 60 nM, less than 50 nM, less than 40 nM, less than 30 nM, less than 20 nM, or less than 10 nM. In still further embodiments, a lanthanide-binding site useful in the invention has Kd for a lanthanide ion of less than $1\times10^{-9}$ M, less than $1\times10^{-10}$ M, less than $1\times10^{-11}$ M, less than $1\times10^{-12}$ M, less than $1\times10^{-13}$ M, less than $1\times10^{-14}$ M, less than $1\times10^{-15}$ M, less than $1\times10^{-16}$ M, less than $1\times10^{-17}$ M, less than $1\times10^{-18}$ M, less than $1\times10^{-19}$ M or less than $1\times10^{-20}$ M.

One skilled in the art understands that these and other lanthanide-binding sites can be useful as part of a lanthanide donor complex in the clostridial toxin substrates and methods of the invention. Such lanthanide-binding sites encompass, but are not limited to, those containing 4,7-bis(chlorosulfodiphenyl)-1,10, phenanthroline-2,9-dicarboxylic acid ("FlAgen" system; Eleftherios P. Diamandis et al., *Europium Chelate Labels in Time-Resolved Fluorescence Immunoassays and DNA Hybridization Assays,* 62(22) Anal. Chem. 1149A-1157A (1990)) and those containing 5-fluorosalicylate-$Tb^{3+}$-EDTA ("enzyme-amplified time-resolved fluoroimmunoassay" system; Theodore K. Chrisopoulos and Eleftherios P. Diamandis, Enzymatically Amplified Time-Resolved Fluorescence Immunoassay with Terbium Chelates, 64(4) Anal. Chem. 342-346 (1992)). See, also, A. J. Kolb et al. *A Homogenous, Time-Resolved Fluorescence Method for Drug Discovery, pp.* 345-360 in, *High Throughput Screening: The Discovery of Bioactive Substances,* (J. P. Devlin, ed., Marcel Dekker, Inc., 1997). One skilled in the art understands that these and other peptide, peptidomimetic and small molecule lanthanide-binding sites can be incorporated into a lanthanide donor complex in a substrate of the invention.

A lanthanide donor complex can include an antenna which can be distinct from, or incorporated within, the lanthanide-binding site of the lanthanide donor complex. As used herein, the term "antenna" is synonymous with "sensitizer" and means a molecule such as an organic chromophore which absorbs excitation light and transfers the light energy to a lanthanide ion. It is difficult to generate luminescence by direct photoexcitation of a lanthanide ions because the forbidden nature of the f-f transitions results in low extinction coefficients. Given this weak ability to inherently absorb light, lanthanide ions are particularly useful in conjunction with a light-harvesting device ("antenna"), which can be, for example, a strongly absorbing organic chromophore, such as, e.g., a pyridyl, a phenyl or an indole group. The energy collected by the antenna is transferred by intramolecular nonradiative processes from the singlet to the triplet state of the moiety, then from the triplet to the emissive level of the lanthanide ion, which subsequently emits its characteristic long-lived luminescence. Thus, a lanthanide ion in conjunction with an antenna is useful as a luminescent probe, for example, in highly sensitive time-resolved assays, where it generates a long-lived fluorescent signal that can be readily distinguished from short-lived background fluorescence present in many biological samples. Lanthanides generally exist as trivalent cations, in which case their electronic configuration is (Xe)4fn, with n varying from 1 ($Ce^{3+}$) to 14 ($Lu^{3+}$). Without wishing to be bound by the following, the transitions of the f-electrons can be responsible for the special photophysical properties of the lanthanide ions such as long-lived luminescence and sharp absorption and emission lines. In particular, f-electrons can be shielded from external perturbations by filled 5s and 5p orbitals, resulting in characteristic line-like spectra. f-f electronic transitions are forbidden, leading to long excited state lifetimes in the microsecond to millisecond range.

In one embodiment, the antenna is carbostyril 124 (CS124), which absorbs light with an excitation of 337 nm. In another embodiment, the antenna is a tryptophan residue. In a further embodiment, the antenna is 2-hydroxyisophthalamide, which also acts as a lanthanide-binding site. It is understood that an antenna can be distinct from, or can make up part of a lanthanide binding-site. As non-limiting examples, an antenna which binds a lanthanide ion can be 2-hydroxyisophthalamide, a pyridine cryptate or other cryptate; a LANCE complex (Wallac; Perkin-Elmer); or a terpyridine complex. An antenna which is useful in conjunction with a polyaminocarboxylate lanthanide-binding site such as DTPA or TTHA can be, without limitation, CS124. In one embodiment, the antenna is incorporated within the lanthanide-binding site. In another embodiment, an antenna separate from the lanthanide-binding site is included in the lanthanide donor complex. In yet another embodiment, the invention provides a Clostridial toxin substrate incorporating a lanthanide donor complex which includes CS124 as the antenna. In still another embodiment, the invention provides a Clostridial toxin substrate in which the lanthanide donor complex is CS124-DTPA-EMCH-Tb.

Aspects of the present invention can rely on a Clostridial toxin substrate which contains a non-fluorescent acceptor. As used herein, the term "non-fluorescent acceptor" is synonymous with "quencher" and means a molecule which absorbs light energy of a certain wavelength, but has reduced ability to emit or cannot emit light energy. A non-fluorescent acceptor can be useful, e.g., in quench-release assays and in eliminating background fluorescence resulting from direct (nonsensitized) acceptor excitation. A variety of non-fluorescent acceptors are known in the art and include without limitation 2,4-dintrophenyl (DNP), 4-((4-(dimethylamino)phenyl)azo) benzoic acid (DABCYL), 4-dimethylaminoazobenzene-4'-sulfonyl (DABSYL), 4-dimethylaminophenylazophenyl (DABMI) Malachite green, QSY 7, QSY 9, QSY 21, QSY 35, BHQ-0, BHQ-1, BHQ-2, BHQ-3 and BHQ-10 (Table 13). These quenchers can be attached to a Clostridial toxin substrate using standard conjugation chemistry methods known in the art.

DABMI absorbs peak light energy in the range of 350-475 nm and can be useful in FRET applications as an energy transfer acceptor for donor fluorophores that emit light energy within this wavelength range, such as, e.g., BFP and CFP. For other useful donor fluorophore see Table 9, Table 10 and Table 11. DABCYL and DABSYL absorb peak light energy in the range of 400-525 nm and can be useful in FRET applications as an energy transfer acceptor for donor fluorophores that emit light energy within this wavelength range, such as, e.g., BFP, CFP, GFP and YFP. For other donor fluorophore useful in combination with DABMI, DABCYL and CABSYL see, e.g., Table 9, Table 10 and Table 11.

TABLE 13

Absorption Maxima of Exemplary Quencher Dyes

| Dye | Absorption maxima (nm) | Emission maxima (nm) |
|---|---|---|
| DABMI | 419 | — |
| DABCYL | 453 | — |
| DABSYL | 466 | — |
| QSY 35 | 475 | — |
| QSY 7 | 560 | — |
| QSY 9 | 562 | — |
| Malachite green | 628 | — |
| QSY 21 | 661 | — |
| DNP | | — |
| BHQ-0 | | — |
| BHQ-1 | 534 | — |
| BHQ-2 | 579 | — |
| BHQ-3 | 672 | — |
| BHQ-10 | | — |

QSY 35 absorbs peak light energy in the range of 425-525 nm and can be useful in FRET applications as an energy transfer acceptor for donor fluorophores that emit light energy within this wavelength range, such as, e.g., BFP, CFP, GFP and YFP. QSY 21 absorbs peak light energy in the range of 575-725 nm and can be useful in FRET applications as an energy transfer acceptor for donor fluorophores that emit light energy within this wavelength range, such as, e.g., YFP and RFP. QSY 7 and QSY 9 absorb peak light energy in the range of 500-600 nm and can be useful in FRET applications as an energy transfer acceptor for donor fluorophores that emit light energy within this wavelength range, such as, e.g., GFP, YFP and RFP. For other donor fluorophore useful in combination with QSY 35, QSY 7, QSY 9 and QSY 21 see, e.g., Table 9, Table 10 and Table 11.

BHQ-0 absorbs peak light energy in the range of 430-520 nm and can be useful in FRET applications as an energy transfer acceptor for donor fluorophores that emit light energy within this wavelength range, such as, e.g., BFP, CFP, GFP and YFP. BHQ-1 absorbs peak light energy in the range of 480-580 nm and can be useful in FRET applications as an energy transfer acceptor for donor fluorophores that emit light energy within this wavelength range, such as, e.g., CFP, GFP, YFP and RFP. BHQ-2 absorbs peak light energy in the range of 559-650 nm and can be useful in FRET applications as an energy transfer acceptor for donor fluorophores that emit light energy within this wavelength range, such as, e.g., YFP and RFP. Malachite green absorbs peak light energy in the range of 575-675 nm and can be useful in FRET applications as an energy transfer acceptor for donor fluorophores that emit light energy within this wavelength range, such as, e.g., YFP and RFP. BHQ-3 absorbs peak light energy in the range of 620-730 nm and can be useful in FRET applications as an energy transfer acceptor for donor fluorophores that emit light energy within this wavelength range, such as, e.g., RFP. For other donor fluorophore useful in combination with BHQ-0, BHQ-1, BHQO2 and BHQ-3 see, e.g., Table 9, Table 10 and Table 11.

Thus, an embodiment, a non-fluorescent acceptor can be a molecule that absorbs peak light energy in the range of 400-525 nm. In an aspect of this embodiment, the non-fluorescent acceptor is DABCYL. In another aspect of this embodiment, the non-fluorescent acceptor is DABSYL. In another embodiment, a non-fluorescent acceptor can be a molecule that absorbs peak light energy in the range of 425-525 nm. In an aspect of this embodiment, the non-fluorescent acceptor is QSY 35. In another embodiment, a non-fluorescent acceptor can be a molecule that absorbs peak light energy in the range of 430-520 nm. In an aspect of this embodiment, the non-fluorescent acceptor is BHQ-0.

In yet another embodiment, a non-fluorescent acceptor can be a molecule that absorbs peak light energy in the range of 480-580 nm. In an aspect of this embodiment, the non-fluorescent acceptor is BHQ-1. In yet another embodiment, a non-fluorescent acceptor can be a molecule that absorbs peak light energy in the range of 500-600 nm. In an aspect of this embodiment, the non-fluorescent acceptor is QSY 7. In another aspect of this embodiment, the non-fluorescent acceptor is QSY 9.

In still another embodiment, a non-fluorescent acceptor can be a molecule that absorbs peak light energy in the range of 559-650 nm. In an aspect of this embodiment, the non-fluorescent acceptor is BHQ-2. In still another embodiment, a non-fluorescent acceptor can be a molecule that absorbs peak light energy in the range of 575-675 nm. In an aspect of this embodiment, the non-fluorescent acceptor is Malachite green. In still another embodiment, a non-fluorescent acceptor can be a molecule that absorbs peak light energy in the range of 575-725 nm. In an aspect of this embodiment, the non-fluorescent acceptor is QSY 21. In still another embodiment, a non-fluorescent acceptor can be a molecule that absorbs peak light energy in the range of 620-730 nm. In an aspect of this embodiment, the non-fluorescent acceptor is BHQ-3.

Additionally, heme-containing proteins comprise a large family of proteins useful for fluorescence quenching-based analysis by resonance transfer energy because the heme group has a broad absorption spectrum and high optical extinction coefficient, see, e.g., C. Michael Hanbury et al., *Fiber-Optic Immunosensor for Measurement of Myoglobin*, 43(11) Clin. Chem. 2128-2136 (1997); Galina I. Lepesheva et al., *Conformational Dynamics and Molecular Interaction Reactions of Recombinant Cytochrome P450scc* (CYP11A1) *Detected by Fluorescence Energy Transfer*, 1434(1) Biochim. Biophys. Acta. 31-43 (1999); Galina P. Gorbenko, *Resonance Energy Transfer Study of Hemoglobin Complexes with Model Phospholipid Membranes*, 81(2) Biophys. Chem. 93-105 (1999); Galina P. Gorbenko, *Structure of Cytochrome c Complexes with Phospholipids as Revealed by Resonance Energy Transfer*, 1420(1-2) Biochim. Biophys. Acta 1-13 (1999); Dmitri Davydov et al., *Association of Cytochrome P450 with Their Reductases: Opposite Sign of the Electostatic Interactions in P450BM-3 as Compared with the Microsomal 2B4 System*, 39(21) Biochemistry 6489-6497 (2000); Esa K. J. Tuominen et al., *ATP Induces a Conformational Change in Lipid-bound Cytochrome c*, 276(22) J. Biol. Chem. 19356-19362 (2001); and Ross M. Taylor et al., *Cascade Blue as a Donor for Resonance Energy Transfer Studies of Heme-Containing Proteins*, 302(1) Anal. Biochem. 19-27 (2002). A heme-containing protein can be operably-linked to a Clostridial toxin recognition sequence to create a fusion protein using standard molecular genetic techniques.

An acceptor useful in the invention has an absorbance spectrum which overlaps the emission spectrum of the donor fluorophore. As used herein, the term "absorb" is synonymous with the term "excite" and the term "absorbance" is synonymous with the term "excitation." An acceptor useful in the invention generally has rather low absorption at a wavelength suitable for excitation of the donor fluorophore. As set forth above, an acceptor has an absorbance spectrum that overlaps the emission spectrum of the donor fluorophore. The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the emission spectrum of the donor fluorophore is higher than the low end of the range of the absorbance spectrum of the acceptor.

In a Clostridial toxin substrate useful in the invention, the donor fluorophore and acceptor are selected so that the donor fluorophore and acceptor exhibit resonance energy transfer when the donor fluorophore is excited. A fluorescence resonance energy transfer (FRET) pair comprises a donor fluorophore and an acceptor where the overlap between the emissions spectrum of the donor fluorophore and the absorbance spectrum of the acceptor is sufficient to enable FRET. A luminescence resonance energy transfer (LRET) pair comprises a lanthanide donor complex and an acceptor where the overlap between the emissions spectrum of the lanthanide donor complex and the absorbance spectrum of the acceptor is sufficient to enable LRET.

Aspects of the present invention rely, in part, on FRET, a physical process whereby energy is transferred non-radioactively from an excited donor fluorophore to an acceptor, which may be another fluorophore, through intramolecular long-range dipole-dipole coupling, see, e.g., Chapter 13 Energy Transfer, pp. 367-394, in Principles of Fluorescence Spectroscopy (Ed. Joseph R. Lakowicz, Kluwer Academic/Plenum Publisher, 2nd Ed.1999). When the donor fluorophore comprises a lanthanide donor complex, the present invention relies, in part, on luminescence resonance energy transfer (LRET), a physical process whereby energy non-radioactively from an excited lanthanide donor complex to an organic acceptor, which may be a fluorophore, through intramolecular long-range dipole-dipole coupling.

Both FRET and LRET are dependent on the inverse sixth power of the intramolecular separation of the donor fluorophore and acceptor, and for effective transfer, the donor fluorophore and acceptor are in close proximity, separated, for example, by about 10 A to about 100 A. Effective energy transfer is dependent on the spectral characteristics of the donor fluorophore and acceptor as well as their relative orientation. For effective transfer over 10 to 100 A, the quantum yield of the donor fluorophore generally is at least 0.1, and the absorption coefficient of the acceptor generally is at least 1000, see, e.g., Clegg, 6 Curr. Opin. Biotech. 103-110 (1995); and Selvin, 7 Nat. Struct. Biol. 730-734 (2000). One factor to be considered in choosing the donor fluorophore/acceptor pair is the efficiency of energy transfer between the donor fluorophore and acceptor.

As is well known in the art, the efficiency of energy transfer is dependent on the separation distance and the orientation of the donor fluorophore and acceptor as described by the Förster equation, as well as the fluorescent quantum yield of the donor fluorophore and the energetic overlap with the acceptor. In particular, the efficiency (E) of energy transfer can be determined as follows: $E=1-F_{DA}/F_D=1/(1+(R/R_0)^6)$, where $F_{DA}$ and $F_D$ are the fluorescence intensities of the donor fluorophore in the presence and absence of the acceptor, respectively, and R is the distance between the donor fluorophore and the acceptor.

The Förster radius ($R_o$) is the distance at which resonance energy transfer is 50% efficient, that is, 50% of excited donor fluorophores are deactivated by energy transfer, see, e.g. Lakowicz, supra, (1999). The magnitude of the Förster radius depends on the quantum yield of the donor fluorophore; the extinction coefficient of the acceptor; and the overlap between the donor fluorophore's emission spectrum and the acceptor's excitation spectrum.

$$R_O = [8.8 \times 10^{23} \cdot \kappa^2 \cdot n^{-4} \cdot QY_D \cdot J(\lambda)]^{1/6} \text{Å, where}$$

$\kappa^2$=dipole orientation factor (range 0 to 4; $\kappa^2$=2/3 for randomly oriented donors and acceptors)

$QY_D$=fluorescence quantum yield of the donor in the absence of the acceptor n=refractive index $J(\lambda)$=spectral overlap integral=$\int \epsilon_A(\lambda) \cdot F_D(\lambda) \cdot \lambda^4 d\lambda$ $cm^3 M^{-1}$, where $\epsilon_A$=extinction coefficient of acceptor $F_D$=fluorescence emission intensity of donor as a fraction of the total integrated intensity Any of a number of donor fluorophores and acceptors in various combinations can be included in a clostridial toxin substrate useful in the invention. A donor fluorophore generally is selected such that there is substantial spectral overlap between the emission spectrum of the donor fluorophore and the excitation spectrum of the acceptor. One skilled in the art understands that there are several considerations in selecting and positioning a donor fluorophore and acceptor in a Clostridial toxin substrate. The donor fluorophore and acceptor generally are positioned to minimize interference with substrate binding to, or proteolysis by, the Clostridial toxin. Thus, a donor fluorophore and acceptor can be selected and positioned, for example, so as to minimize the disruption of bonded and non-bonded interactions that are important for binding, and to minimize steric hindrance. In addition, the spatial distance between the donor fluorophore and acceptor generally is limited to achieve efficient energy transfer from the donor fluorophore to the acceptor. In addition, a donor fluorophore can be selected, for example, to have an excitation maximum near a convenient laser frequency such as Nitrogen 337 nm, Helium-Cadmium 442 nm or argon 488 nm, since laser light serves as a convenient and effective means to excite the donor fluorophore.

As discussed above, efficiency of energy transfer from a donor fluorophore to acceptor will be dependent, in part, on the spatial separation of the donor fluorophore and acceptor. As the distance between the donor fluorophore and acceptor increases, there is less energy transfer to the acceptor, and the donor fluorophore signal therefore increases, even prior to cleavage. The overall increase in fluorescence yield of the donor fluorophore, upon cleavage of the substrate, is dependent upon many factors, including the separation distance between the donor fluorophore and acceptor in the substrate, the spectral overlap between the donor fluorophore and acceptor, and the concentration of substrate used in an assay. One skilled in the art understands that, as the concentration of substrate increases, intermolecular quenching of the donor fluorophore, even after proteolytic cleavage, can become a factor. This phenomenon is denoted the "inner filter effect."

Thus, in one embodiment, the donor fluorophore is positioned carboxyl terminal of the cleavage site while the acceptor is positioned amino terminal of the cleavage site. In another embodiment, the donor fluorophore is positioned amino terminal of the cleavage site while the acceptor is positioned carboxyl terminal of the cleavage site.

In another an embodiment, the distance between the center of the donor fluorophore and the center of the acceptor is approximately 10 Å. In another embodiment, the distance between the center of the donor fluorophore and the center of the acceptor is approximately 50 Å. In another embodiment, the distance between the center of the donor fluorophore and the center of the acceptor is approximately 100 Å. In aspects of this embodiment, the distance between the center of the donor fluorophore and the center of the acceptor can be, e.g., at least 10 Å, at least 20 Å, at least 30 Å, at least 40 Å, at least 50 Å, at least 60 Å, at least 70 Å, at least 80 Å, at least 90 Å or at least 100 Å. In other aspects of this embodiment, the distance between the center of the donor fluorophore and the center of the acceptor can be, e.g., at most 10 Å, at most 20 Å, at most 30 Å, at most 40 Å, at most 50 Å, at most 60 Å, at most 70 Å, at most 80 Å, at most 90 Å or at most 100 Å. In other aspects of this embodiment, the distance between the center of the donor fluorophore and the center of the acceptor can be between, e.g., 10Å to 100Å, 10Å to 80Å, 10Å to 60Å, 10Å to 40Å, 10Å to 20Å, 20Å to 100Å, 20Å to 80Å, 20Å to 60Å, 20Å to 40Å, 40Å to 100Å, 40Å to 80Å or 40Å to 60Å.

In another embodiment, the efficiency of energy transfer between the donor fluorophore and acceptor is approximately 10%. In another embodiment, the efficiency of energy transfer between the donor fluorophore and acceptor is approximately 50%. In another embodiment, the efficiency of energy transfer between the donor fluorophore and acceptor is approximately 100%. In aspects of this embodiment, the efficiency of energy transfer between the donor fluorophore and acceptor can be, e.g., at least 10%, at least 20%, at least 30%, at least 40%, at least 50%, at least 60%, at least 70%, at least 80%, at least 90% or at least 100%. In other aspects of this embodiment, the efficiency of energy transfer between the donor fluorophore and acceptor can be, e.g., at most 10%, at most 20%, at most 30%, at most 40%, at most 50%, at most 60%, at most 70%, at most 80%, at most 90% or at most 100%.

In another embodiment, the wavelength maximum of the emission spectrum of the acceptor is approximately 10 nm greater than the wavelength maximum of the excitation spectrum of the donor fluorophore. In another embodiment, the wavelength maximum of the emission spectrum of the acceptor is approximately 50 nm greater than the wavelength maximum of the excitation spectrum of the donor fluorophore. In another embodiment, the wavelength maximum of the emission spectrum of the acceptor is approximately 100 nm greater than the wavelength maximum of the excitation spectrum of the donor fluorophore. In aspects of this embodiment, the wavelength maximum of the emission spectrum of the acceptor is greater than the wavelength maximum of the excitation spectrum of the donor fluorophore by, e.g., at least 10 nm, at least 20 nm, at least 30 nm, at least 40 nm, at least 50 nm, at least 60 nm, at least 70 nm, at least 80 nm, at least 90 nm or at least 100 nm. In other aspects of this embodiment, the wavelength maximum of the emission spectrum of the acceptor is greater than the wavelength maximum of the excitation spectrum of the donor fluorophore by, e.g., at most 10 nm, at most 20 nm, at most 30 nm, at most 40 nm, at most 50 nm, at most 60 nm, at most 70 nm, at most 80 nm, at most 90 nm or at most 100 nm.

In another embodiment, the spectral overlap between the donor fluorophore and acceptor is approximately 10%. In another embodiment, the spectral overlap between the donor fluorophore and acceptor is approximately 50%. In another embodiment, the spectral overlap between the donor fluorophore and acceptor is approximately 80%. In aspects of this embodiment, the spectral overlap between the donor fluorophore and acceptor can be, e.g., at least 10%, at least 20%, at least 30%, at least 40%, at least 50%, at least 60%, at least 70% or at least 80%. In other aspects of this embodiment, the spectral overlap between the donor fluorophore and acceptor can be, e.g., at most 10%, at most 20%, at most 30%, at most 40%, at most 50%, at most 60%, at most 70% or at most 80%.

In another embodiment, the difference between the peak light energy emitted by the donor fluorophore and the peak light energy absorbed by the acceptor can be, e.g., at least 25 nm, at least 50 nm, at least 75 nm or at least 100 nm. In another embodiment, the difference between the peak light energy emitted by the donor fluorophore and the peak light energy absorbed by the acceptor can be, e.g., at most 25 nm, at most 50 nm, at most 75 nm or at most 100 nm.

Non-limiting examples of FRET pairs include, e.g., any one of EBFP, HaloTag/Coumarian, Alexa Fluor® 350 or Alexa Fluor® 405 as a donor fluorophore and any one of ECFP, AmCyan, AGT/BG-430 or Alexa Fluor® 405, Lucifer Yellow or PyMPO as an acceptor fluorophore; any one of ECFP or AmCyan as a donor fluorophore and any one of AcGFP, ZsGreen, Vitalitye hrGFP, EGFP, Monster Green®, FlAsH, AGT/BG-DAF, AGT/BG-505, AGT/BG-488, Halo Tag/diAcFAM, Alexa Fluor® 488, Alexa Fluor® 500, BODIPY FL, BODIPY 493/503, BODIPY 499/508, Cy-2, Flu-4, Fluorescein, NDB or Oregon Green 488 as an acceptor fluorophore; EGFP as a donor fluorophore and any one of Vitalitye hrGFP, Monster Green®, EYFP, ZsYellow, FlAsH, AGT/BG-DAF, AGT/BG-505, AGT/BG-488, Alexa Fluor® 500, Alexa Fluor® 514, BODIPY FL, BODIPY 499/508 or BODIPY 507/545 as an acceptor fluorophore; any one of Alexa Fluor® 488, BODIPY FL, Cy-2, Fluo-4 or fluorescein as a donor fluorophore and any one of EYFP or Alexa Fluor® 514 as an acceptor fluorophore; ZsYellow as a donor fluorophore and any one of AGT/BG-532, AGT/BG-547, AGT/TMR-Star, Alexa Fluor® 532, Alexa Fluor® 546, Alexa Fluor® 555, BODIPY 530/550, Cy-3, sulfonerhodamine, tetramethylrhodamine or Texas Red as an acceptor fluorophore; any one of DsRed-Express, DsRed2 or DsRed as a donor fluorophore and any one of AsRed2, HcRed1, ReAsH, Alexa Fluor® 568, Alexa Fluor® 594, BODIPY 577/618 or BODIPY 581/591 as an acceptor fluorophore; AsRed2 as a donor fluorophore and any one of ReAsH, AGT/BG-600, Alexa Fluor® 594, Alexa Fluor® 610 or Texas Red as an acceptor fluorophore; HcRed1 as a donor fluorophore and any one of Alexa Fluor® 610, Alexa Fluor® 633 or BODIPY 630/650 as an acceptor fluorophore; and any one of AGT/BG-505, AGT/BG-532, Alexa Fluor® 430, Alexa Fluor® 500, Alexa Fluor® 514, BODIPY 507/545, Lucifer Yellow or NBD as a donor fluorophore and any one of ZsYellow DsRed-Express, DsRed2 or DsRed as an acceptor fluorophore. Other FRET pair combinations can be designed using the fluorescent molecules listed in Table 9, Table 10 and Table 11 or other fluorescent molecules known in the art by one of ordinary skill in the art.

Non-limiting examples of LRET pairs include, e.g., CS124-DTPA-EMCH-Tb or another terbium ion complex in combination with a green fluorescent protein or blue fluorescent protein as the acceptor, Eu-trisbipyridine cryptate (TBP-$Eu^{3+}$, $\lambda_{Ex}$ 337 nm) in combination with the 105 kDa phycobiliprotein acceptor fluorophore, allophycocyanin, Sittampalam et al., *Curr. Opin. Chem. Biol.* 1:384-391 (1997). The Eu-trisbipyridine cryptate has two bipyridyl groups that harvest light and channel it to the caged $Eu^{3+}$; $Eu^{3+}$ nonradiatively transfers energy to allophycocyanin when in close proximity to the acceptor, exhibiting greater than 50% transfer efficiency at a lanthanide ion-acceptor distance of 9.5 nm. Furthermore, both TBP-$Eu^{3+}$ and allophycocyanin and their spectroscopic characteristics are very stable in biological media, and allophycocyanin emits ($\lambda_{Em}$=665 nm) with the long lifetime of the lanthanide ion, allowing time-resolved detection (Kolb et al., *J. Biomol. Screening* 1:203-210 (1996)). Methods of preparing substrates containing such donor fluorophore-acceptor pairs are well known in the art as described, for example, in Kolb et al., supra, 1996, and Sittampalam et al., supra, 1997.

Non-limiting examples of quench-release pairs include, e.g., any one of EBFP, Halo Tag/Coumarian, Alexa Fluor® 350 or EDANS as a donor fluorophore and DABCYL as a quencher; any one of ECFP, AmCyan, as a donor fluorophore and any one of DABSYL or QSY 35; any one of ZsYellow, DsRed Express, AGT/BG-488, AGT/BG-547, Alexa Fluor® 555, BODIPY 530/550 or Cy-3 as a donor fluorophore and any one of QSY 7 or QSY 9 as a quencher; and any one of AGT/BG-632, AGT/BG-647, Alexa Fluor® 633, Alexa Fluor® 647, BODIPY 630/650, BODIPY 650/665 or Cy-5 as a donor fluorophore and QSY 21 as a quencher. Other quench-release pair combinations can be designed using the fluorescent molecules listed in Table 9, Table 10 and Table 11 and the non-fluorescent molecules listed in Table 13, or other fluorescent and non-fluorescent molecules known in the art by one of ordinary skill in the art.

It is understood that a Clostridial toxin substrate disclosed in the present specification can optionally include one or more additional components. As a non-limiting example of an optional component, a Clostridial toxin substrate can further comprise a flexible region comprising a flexible spacer. Non-limiting examples of a flexible spacer include, e.g., a G-spacer GGGGS (SEQ ID NO: 162) or an A-spacer EAAAK (SEQ ID NO: 163). A flexible region comprising flexible spacers can be used to adjust the length of a polypeptide region in order to optimize a characteristic, attribute or property of a polypeptide. Such a flexible region is operably-linked in-frame to the a Clostridial toxin substrate as a fusion protein. As a non-limiting example, a polypeptide region comprising one or more flexible spacers in tandem can be use to better expose a Clostridial toxin recognition sequence including a Clostridial toxin cleavage site thereby facilitating cleavage of that site by a Clostridial toxin. As another non-limiting example, a polypeptide region comprising one or more flexible spacers in tandem can be use to better present a donor fluorophore or acceptor, thereby facilitating the resonance transfer energy of the donor fluorophore and acceptor pair.

Thus, in an embodiment, a Clostridial toxin substrate disclosed in the present specification can further comprise a flexible region comprising a flexible spacer. In another embodiment, a Clostridial toxin substrate disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a Clostridial toxin substrate can comprise a flexible region comprising one or more copies of the same flexible spacers, one or more copies of different flexible-spacer regions, or any combination thereof.

In aspects of this embodiment, a Clostridial toxin substrate comprising a flexible spacer can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate.

It is envisioned that a Clostridial toxin substrate disclosed in the present specification can comprise a flexible spacer, such as, e.g., a G-spacer or an A-spacer, in any and all locations with the proviso that the Clostridial toxin substrate is capable of being cleaved by a Clostridial toxin. In aspects of this embodiment, a flexible spacer is positioned between, e.g., a donor fluorophore and a Clostridial toxin recognition sequence, an acceptor and a Clostridial toxin recognition sequence, a donor fluorophore and a membrane targeting domain, an acceptor and a membrane targeting domain, and a membrane targeting domain and a Clostridial toxin recognition sequence.

A useful Clostridial toxin substrate further can include, without limitation, one or more of the following: epitope-binding tags, such as. e.g., FLAG, Express™, human Influenza virus hemagluttinin (HA), human p62$^{c-MYc}$ protein (c-MYC), Vesicular Stomatitis Virus Glycoprotein (VSV-G), glycoprotein-D precursor of Herpes simplex virus (HSV), V5, and AU1; affinity-binding, such as. e.g., polyhistidine (HIS), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein; immunoglobulin hinge region; an N-hydroxysuccinimide linker; a peptide or peptidomimetic hairpin turn; or a hydrophilic sequence or another component or sequence that, for example, promotes the solubility or stability of the Clostridial toxin substrate. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998), which are hereby incorporated by reference. In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Aspects of the present invention provide, in part polynucleotide molecules encoding Clostridial toxin substrates disclosed in the present specification. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a Clostridial toxin substrate disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Thus, in an embodiment, a polynucleotide molecule encodes a Clostridial toxin substrate disclosed in the present specification. In aspects of this embodiment, a polynucleotide molecule encoding a Clostridial toxin substrate includes, e.g., a BoNT/A substrate, a BoNT/B substrate, a BoNT/C1 substrate, a BoNT/D substrate, a BoNT/E substrate, a BoNT/F substrate, a BoNT/G substrate, and a TeNT substrate. In other aspects of this embodiment, a polynucleotide molecule encodes a Clostridial toxin substrate comprising a lanthanide donor complex, an acceptor and a Clostridial toxin recognition sequence including a cleavage site that intervenes between the lanthanide donor complex and the acceptor; wherein the acceptor has an absorbance spectrum overlapping the emission spectrum of the lanthanide donor complex; and wherein, under the appropriate conditions, resonance energy transfer is exhibited between the lanthanide donor complex and the acceptor. In yet other aspects of this embodiment, a polynucleotide molecule encodes a Clostridial toxin substrate comprising a donor fluorophore, an acceptor, a Clostridial toxin recognition sequence including a Clostridial toxin cleavage site that intervenes between the donor fluorophore and the acceptor and a membrane targeting domain.

The compositions and methods of the present specification provide a cell, in part, capable of Clostridial toxin intoxication. As used herein, the term "cell," means any eukaryotic cell that expresses, or can be engineered to express, at least one receptor that binds a Clostridial toxin. The term cell encompasses cells from a variety of organisms, such as, e.g., murine, rat, porcine, bovine, equine, primate and human cells; from a variety of cell types such as, e.g., neural and non-neural; and can be isolated from or part of a heterogeneous cell population, tissue or organism. It is understood that cells useful in aspects of the invention can included, without limitation, primary cells; cultured cells; established cells; normal cells; transformed cells; tumor cells; infected cells; proliferating and terminally differentiated cells; and stably or transiently transfected cells, including stably and transiently transfected cells. It is further understood that cells useful in aspects of the invention can be in any state such as proliferating or quiescent; intact or permeabilized such as through chemical-mediated transfection such as, e.g., calcium phosphate-mediated, diethyl-laminoethyl (DEAE) dextran-mediated, lipid-mediated, polyethyleneimine (PEI)-mediated and polybrene-mediated; physical-mediated tranfection, such as, e.g., biolistic particle delivery, microinjection and electroporation; and viral-mediated transfection, such as, e.g., retroviral-mediated transfection. It is further understood that cells useful in aspects of the invention may include those which express a Clostridial toxin substrate under control of a constitutive, tissue-specific, cell-specific or inducible promoter element, enhancer element or both. It further is understood that cells useful in aspects of the invention may or may not express one or more endogenous Clostridial toxin target proteins such as, e.g., SNAP-25, VAMP and syntaxin.

The cell compositions disclosed in the present specification are capable of Clostridial toxin intoxication. As used herein, the term "cell capable of Clostridial toxin intoxication" means a cell that can enable the overall cellular mechanism whereby a Clostridial toxin proteolytically cleaves a substrate and encompasses the binding of a Clostridial toxin to a low or high affinity receptor, the internalization of the toxin/receptor complex, the translocation of the Clostridial toxin light chain into the cytoplasm and the enzymatic target modification of a Clostridial toxin substrate. By definition, a cell capable of Clostridial toxin intoxication must express one or more endogenous low or high affinity Clostridial toxin receptors for one or more Clostridial toxin serotypes; express one or more exogenous low or high affinity Clostridial toxin receptors for one or more Clostridial toxin serotypes; or express a combination of endogenous low or high affinity Clostridial toxin receptors and exogenous low or high affinity Clostridial toxin receptors for one or more Clostridial toxin serotypes.

Thus, in an embodiment, a cell capable of Clostridial toxin intoxication can be a cell expressing a Clostridial toxin receptor. In aspects of this embodiment, the Clostridial toxin receptor can be a low affinity Clostridial toxin receptor, a high affinity Clostridial toxin receptor, an endogenous Clostridial toxin receptor, an exogenous Clostridial toxin receptor, or any combination thereof. In other aspects of this embodiment, the Clostridial toxin receptor can be a BoNT/A receptor, a BoNT/B receptor, a BoNT/C1 receptor, a BoNT/D receptor, a BoNT/E receptor, a BoNT/F receptor, a BoNT/G receptor or a TeNT receptor.

In another embodiment, a cell capable of Clostridial toxin intoxication can be a cell expressing a plurality of Clostridial toxin receptors. In aspects of this embodiment, a plurality of Clostridial toxin receptor can comprise low affinity Clostridial toxin receptors, high affinity Clostridial toxin receptors, endogenous Clostridial toxin receptors, exogenous Clostridial toxin receptors, or any combination thereof. In aspects of this embodiment, a plurality of Clostridial toxin receptor can comprise, e.g., two or more Clostridial toxin receptors, three or more Clostridial toxin receptors, four or more Clostridial toxin receptors, five or more Clostridial toxin receptors, six or more Clostridial toxin receptors, seven or more Clostridial toxin receptors and eight or more Clostridial toxin receptors. In other aspects of this embodiment, cell capable of Clostridial toxin intoxication can express two or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express three or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express four or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express five or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express six or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express seven or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor.

Cells that express one or more endogenous or exogenous Clostridial toxin receptors can be identified by routine methods including direct and indirect assays for toxin uptake. Assays that determine Clostridial toxin binding or uptake properties can be used to assess whether a cell is expressing a Clostridial toxin receptor. Such assays include, without limitation, cross-linking assays using labeled Clostridial toxins, such as, e.g., [$^{125}$I] BoNT/A, [$^{125}$I] BoNT/B, [$^{125}$I] BoNT/C1, [1251] BoNT/D, [$^{125}$I] BoNT/E, [$^{125}$I] BoNT/F, [$^{125}$I] BoNT/G and [$^{125}$I] TeNT, see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type Cl, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004), that detect bound toxin using labeled or unlabeled antibodies. Antibodies useful for these assays include, without limitation, antibodies selected against a Clostridial toxin, such as, e.g., BoNT/A, BoNT/B, BoNT/C1, BoNT/D, BoNT/E, BoNT/F, BoNT/G or TeNT, antibodies selected against a CoNT receptor, such as, e.g., FGFR3 or synaptotagmin, and/or antibodies selected against a ganglioside, such as, e.g., GD1a, GD1b, GD3, GQ1b, or GT1b. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine Clostridial toxin uptake properties or characteristics can be useful in selecting a neuron or other cells useful in aspects of the invention.

Assays that monitor the release of a molecule after exposure to a Clostridial toxin can also be used to assess whether a cell is expressing a Clostridial toxin receptor. In these assays, inhibition of the molecule's release would occur in cells expressing a Clostridial toxin receptor after Clostridial toxin treatment. Well known assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and botulinum toxin type F, 90(3) Neuroscience 893-902 (1999); and Sara Stigliani et al., The sensitivity of catecholamine release to botulinum toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by botulinum toxin A or B, 236(3) Eur. J. Biochem. 877-886 (1996); and Patrick Foran et al., Botulinum neurotoxin C1 cleaves both syntaxin and SNAP-25 in intact and permeabilized chromaffin cells: correlation with its blockade of catecholamine release, 35(8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in selecting a neuron or other cells useful in aspects of the invention.

Assays that detect the cleavage of a Clostridial toxin substrate after exposure to a Clostridial toxin can also be used to assess whether a cell is expressing a Clostridial toxin receptor. In these assays, generation of a Clostridial toxin substrate cleavage-product would be detected in cells expressing a Clostridial toxin receptor after Clostridial toxin treatment. Non-limiting examples of specific Western blotting procedures, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for Clostridial toxin substrate cleavage can be useful in selecting a neuron or other cells useful in aspects of the invention.

As non-limiting examples, western blot analysis using an antibody that specifically recognizes BoNT/A SNAP-25-cleaved product can be used to assay for uptake of BoNT/A; western blot analysis using an antibody that specifically recognizes BoNT/C1 SNAP-25-cleaved product can be used to assay for uptake of BoNT/C1; and western blot analysis using an antibody that specifically recognizes a BoNT/E SNAP-25-cleaved product can be used to assay for uptake of BoNT/E. Examples of anti-SNAP-25 antibodies useful for these assays include, without limitation, rabbit polyclonal anti-SNAP25197 antiserum pAb anti-SNAP25197 #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody Cl 71.1 (Synaptic Systems, Goettingen, Germany), mouse monoclonal anti-SNAP-25 antibody Cl 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

As additional non-limiting examples, western blot analysis using an antibody that specifically recognizes a BoNT/B VAMP-cleaved product can be used to assay for uptake of BoNT/B; western blot analysis using an antibody that specifically recognizes BoNT/D VAMP-cleaved product can be used to assay for uptake of BoNT/D; western blot analysis using an antibody that specifically recognizes BoNT/F VAMP-cleaved product can be used to assay for uptake of BoNT/F; western blot analysis using an antibody that specifically recognizes BoNT/G VAMP-cleaved product can be used to assay for uptake of BoNT/G; and western blot analysis using an antibody that specifically recognizes TeNT. Examples of anti-VAMP antibodies useful for these assays include, without limitation, mouse monoclonal anti-VAMP-1 antibody Cl 10.1 (Synaptic Systems, Goettingen, Germany), mouse monoclonal anti-VAMP-1 antibody SP10 (Abcam, Cambridge, Mass.), mouse monoclonal anti-VAMP-1 antibody SP11 (Abcam, Cambridge, Mass.), rabbit polyclonal anti-VAMP-1 antiserum (Synaptic Systems, Goettingen, Germany), rabbit polyclonal anti-VAMP-1 antiserum (Abcam, Cambridge, Mass.), mouse monoclonal anti-VAMP-2 antibody Cl 69.1 (Synaptic Systems, Goettingen, Germany), rabbit polyclonal anti-VAMP-2 antiserum (Synaptic Systems, Goettingen, Germany), rabbit polyclonal anti-VAMP-2 antiserum (Abcam, Cambridge, Mass.), mouse monoclonal anti-VAMP-3 antibody Cl 10.1 (Synaptic Systems, Goettingen, Germany), rabbit polyclonal anti-VAMP-3 antiserum (Synaptic Systems, Goettingen, Germany) and rabbit polyclonal anti-VAMP-3 antiserum (Abcam, Cambridge, Mass.), As another non-limiting example, western blot analysis using an antibody that specifically recognizes BoNT/C1 Syntaxin-cleaved product can be used to assay for uptake of BoNT/C1. Examples of anti-Syntaxin antibodies useful for these assays include, without limitation, mouse monoclonal anti-Syntaxin-1 antibody Cl 78.2 (Synaptic Systems, Goettingen, Germany), mouse monoclonal anti-Syntaxin-1A antibody Cl 78.3 (Synaptic Systems, Goettingen, Germany), rabbit polyclonal anti-Syntaxin-1A antiserum (Synaptic Systems, Goettingen, Germany), rabbit polyclonal anti-Syntaxin-1B antiserum (Synaptic Systems, Goettingen, Germany), rabbit polyclonal anti-Syntaxin antiserum (Abcam, Cambridge, Mass.), rabbit polyclonal anti-Syntaxin-2 antiserum (Abcam, Cambridge, Mass.) and rabbit polyclonal anti-Syntaxin-3 antiserum (Abcam, Cambridge, Mass.), It is envisioned that an exogenous Clostridial toxin receptor can include, without limitation, a polynucleotide molecule, such as, e.g., DNA and RNA, that encodes a Clostridial toxin receptor disclosed in the present specification and peptide molecule or peptidomimetic comprising a Clostridial toxin receptor disclosed in the present specification. In is also envisioned that an exogenous Clostridial toxin receptor can be transiently or stably expressed in a cell useful in aspects of the invention. Thus, aspects of this embodiment include a cell that transiently contains a polynucleotide molecule, such as, e.g., DNA and RNA, that encode a Clostridial toxin receptor disclosed in the present specification and a cell that transiently contains a peptide molecule or peptidomimetic comprising Clostridial toxin receptor disclosed in the present specification. Other aspects of this embodiment include a cell that stably contains a polynucleotide molecule, such as, e.g., DNA and RNA, that encode a Clostridial toxin substrate disclosed in the present specification and a cell that stably contains a peptide molecule or peptidomimetic comprising Clostridial toxin substrate disclosed in the present specification. Stably-maintained polynucleotide molecules may be extra-chromosomal and replicate autonomously, or they may be integrated into the chromosomal material of the cell and replicate non-autonomously.

It is understood that the selection of a cell depends, in part, on which Clostridial toxin is to be assayed. As a non-limiting example, to assay for BoNT/A activity, one selects a cell that expresses or can be engineered to express a low or high affinity receptor for BoNT/A. As a further example, to assay for BoNT/B activity, one selects a cell that expresses or can be engineered to express a low or high affinity receptor for BoNT/B. As a still further example, to assay for BoNT/C1 activity, one selects a cell that expresses or can be engineered to express a low or high affinity receptor for BoNT/C1. As a still further example, to assay for BoNT/D activity, one selects a cell that expresses or can be engineered to express a low or high affinity receptor for BoNT/D. As a still further example, to assay for BoNT/E activity, one selects a cell that expresses or can be engineered to express a low or high affinity receptor for BoNT/E. As a still further example, to assay for BoNT/F activity, one selects a cell that expresses or can be engineered to express a low or high affinity receptor for BoNT/F. As a still further example, to assay for BoNT/G activity, one selects a cell that expresses or can be engineered to express a low or high affinity receptor for BoNT/G. As a still further example, to assay for TeNT activity, one selects a cell that expresses or can be engineered to express a low or high affinity receptor for TeNT.

As discussed above, it is understood that a cell useful in the invention expresses endogenous or exogenous low or high affinity Clostridial toxin receptors for one or more Clostridial toxins. Such a cell also generally exhibits inhibition of exocytosis upon exposure to Clostridial toxin with, for example, an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM. In particular embodiments, the invention provides a neuron containing a BoNT/A substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/A. In further embodiments, the invention provides a neuron containing a BoNT/B substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/B. In other embodiments, the invention provides a neuron containing a BoNT/C1 substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/C1. In still further embodiments, the invention provides a neuron containing a BoNT/D substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/D. In additional embodiments, the invention provides a neuron containing a BoNT/E substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/E. In yet further embodiments, the invention provides a neuron containing a BoNT/F substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/F. In further embodiments, the invention provides a neuron containing a BoNT/G substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/G. In still further embodiments, the invention provides a neuron containing a TeNT substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to TeNT. It is understood that the same neuron can express two or more receptors for different Clostridial toxin serotypes, with the same or a different $IC_{50}$ for each individual toxin serotype.

Cells useful in aspects of the invention include both neuronal and non-neuronal cells. Neuronal cells useful in aspects of the invention include, without limitation, primary neuronal cells; immortalized or established neuronal cells; transformed neuronal cells; neuronal tumor cells; stably and transiently transfected neuronal cells and further include, yet are not limited to, mammalian, murine, rat, primate and human neuronal cells. Non-limiting examples of neuronal cells useful in aspects of the invention include, e.g., peripheral neuronal cells, such as, e.g., motor neurons and sensory neurons; and CNS neuronal cells, such as, e.g., spinal cord neurons like embryonic spinal cord neurons, dorsal root ganglia (DRG) neurons, cerebral cortex neurons, cerebellar neurons, hippocampal neurons and motor neurons. Neuronal cells useful in the invention include, without limitation, those described herein below or tabulated in Table 14. Such neuronal cells can be, for example, central nervous system (CNS) neurons; neuroblastoma cells; motor neurons, hippocampal neurons or cerebellar neurons and further can be, without limitation, Neuro-2A, SH-SY5Y, NG108-15, N1E-115 or SK-N-DZ cells. The skilled person understands that these and additional primary and established neurons can be useful in the cells and methods of the invention.

Neurons useful in aspects of the invention include, without limitation, primary cultures such as primary cultures of embryonic dorsal root ganglion (DRG) neurons. As one example, primary cultures of embryonic rat DRG neurons are described in Mary J. Welch et al., Sensitivity of embryonic rat dorsal root ganglia neurons to *Clostridium botulinum* neurotoxins, 38(2) Toxicon 245 258 (2000); and primary cultures of fetal spinal cord neurons, for example, primary cultures of murine fetal spinal cord neurons are described in Elaine A. Neale et al., Botulinum neurotoxin A blocks synaptic vesicle exocytosis but not endocytosis at the nerve terminal, 147(6) J. Cell Biol. 1249-1260 (1999), and John A. Chaddock et al., Inhibition of vesicular secretion in both neuronal and non-neuronal cells by a retargeted endopeptidase derivative of *Clostridium botulinum* neurotoxin type A, 68(5) Infect. Immun. 2587-2593 (2000). Thus, in an embodiment, a cell capable of Clostridial toxin intoxication can be a neuron. In aspects of this embodiment, a neuron can be a neuron from, e.g., a primary culture, an embryonic dorsal root ganglion primary culture or a fetal spinal cord primary culture. As non-limiting examples, cells useful for determining Clostridial toxin activity according to a method disclosed in the present specification can include, a primary neuronal cell, such as, e.g., rat embryonic dorsal root ganglion (DRG) neurons or murine fetal spinal cord neurons, that include a Clostridial toxin substrate comprising a SNAP-25 recognition sequence; such as, e.g., a BoNT/A recognition sequence or a BoNT/E recognition sequence; a primary neuronal cell, such as, e.g., rat embryonic dorsal root ganglion (DRG) neurons or murine fetal spinal cord neurons, that include a Clostridial toxin substrate comprising a VAMP recognition sequence; such as, e.g., a BoNT/B recognition sequence or a TeNT recognition sequence; and a primary neuronal cell, such as, e.g., rat embryonic dorsal root ganglion (DRG) neurons or murine fetal spinal cord neurons, that include a Clostridial toxin substrate comprising a Syntaxin recognition sequence; such as, e.g., a BoNT/C1 recognition sequence.

Neuronal cell lines useful in aspects of the invention include, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines.

Neuroblastoma cell lines, such as, e.g., murine, rat, primate or human neuroblastoma cell lines can be useful in aspects of the invention. Neuroblastoma cell lines useful in aspects of the invention include, without limitation, BE(2)-C (ATCC CRL-2268; ECACC 95011817), BE(2)-M17 (ATCC CRL-2267; ECACC 95011816), C1300 (ECACC 93120817), CHP-212 (ATCC CRL-2273), CHP-126 (DSMZ ACC 304), IMR 32 (ATCC CRL-127; ECACC 86041809; DSMZ ACC 165), KELLY (ECACC 92110411; DSMZ ACC 355), LA-N-2, see, e.g., Robert C. Seeger et al., Morphology, growth, chromosomal pattern and fibrinolytic activity of two new human neuroblastoma cell lines, 37(5) Cancer Res. 1364-1371 (1977); and G. J. West et al., Adrenergic, cholinergic, and inactive human neuroblastoma cell lines with the action-potential Na+ ionophore, 37(5) Cancer Res. 1372-1376 (1977), MC-IXC (ATCC CRL-2270), MHH-NB-11 (DSMZ ACC 157), N18Tg2 (DSMZ ACC 103), N1E-115 (ATCC CCL-2263; ECACC 88112303), N4TG3 (DSMZ ACC 101), Neuro-2A (ATCC CCL-131; ECACC 89121404; DSMZ ACC 148), NB41A3 (ATCC CCL-147; ECACC 89121405), NS20Y (DSMZ ACC 94), SH-SY5Y (ATCC CRL-2266; ECACC 94030304; DSMZ ACC 209), SIMA (DSMZ ACC 164), SK-N-DZ (ATCC CRL-2149; ECACC 94092305), SK-N-F1 (ATCC CRL-2142, ECACC 94092304), SK-N-MC (ATCC HTB-10, DSMZ ACC 203) and SK-N-SH (ATCC HTB-11, ECACC 86012802). Thus, in an embodiment, a cell capable of Clostridial toxin intoxication can be a neuroblastoma cell. In aspects of this embodiment, a neuroblastoma cell can be, e.g., BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH. As non-limiting examples, cells useful for determining Clostridial toxin activity according to a method disclosed in the present specification can include, a neuroblastoma cell, such as, e.g., SH-SY5Y cells, that include a Clostridial toxin substrate comprising a SNAP-25 recognition sequence; such as, e.g., a BoNT/A recognition sequence or a BoNT/E recognition sequence; Neuro-2a cells, that include a Clostridial toxin substrate comprising a SNAP-25 recognition sequence; such as, e.g., a BoNT/A recognition sequence; and N1E-115 cells or SK-N-DZ cells, that include a Clostridial toxin substrate comprising a SNAP-25 recognition sequence; such as, e.g., a BoNT/E recognition sequence.

Neuronal hybrid cell lines, such as, e.g., murine, rat, primate and human hybrid neuronal cell lines can be useful in aspects of the invention. Such hybrid cell lines include neuroblastoma/glioma hybrids, such as, e.g., N18 (ECACC 88112301), NG108-15 (ATCC HB-12317, ECACC 88112302) and NG115-401L (ECACC 87032003); neuroblastoma/motor neuron hybrids, such as, e.g., NSC-19 and NSC-34, which express motor neuron characteristics, display a multipolar neuron-like phenotype, express high levels of choline acetyltransferase (CHAT), generate action potentials, express neurofilament triplet proteins and synthesize, store and release acetylcholine., see, e.g., N. R. Cashman et al., Neuroblastoma x spinal cord (NSC) hybrid cell lines resemble developing motor neurons, 194(3) Dev. Dyn. 209-221 (1992); and Christopher J. Eggett et al., Development and characterisation of a glutamate-sensitive motor neuronal cell line, 74(5) J. Neurochem. 1895-1902 (2000); neuroblastoma/dorsal root ganglion neuron hybrids, such as, e.g., F11, see, e.g., Doros Platika et al., Neuronal traits of clonal cell lines derived by fusion of dorsal root ganglia neurons with neuroblastoma cells, 82(10) Proc. Natl. Acad. Sci. U.S.A. 3499-3503 (1985), ND-C (ECACC 92090913), ND-E (ECACC 92090915), ND-U1 (ECACC 92090916), ND3 (ECACC 92090901), ND7/23 (ECACC 92090903), ND8/34 (ECACC 92090904), ND8/47, ND15 (ECACC 92090907), ND27 (ECACC 92090912); neuroblastoma/hippocampal neuron hybrids, such as, e.g., HN-33, see, e.g., Henry J. Lee et al., Neuronal properties and trophic activities of immortalized hippocampal cells from embryonic and young adult mice. 10(6) J. Neurosci. 1779-1787 (1990). Thus, in an embodiment, a cell capable of Clostridial toxin intoxication can be a hybrid neuron. In aspects of this embodiment, a hybrid neuron can be, e.g., a neuroblastoma/glioma hybrid, a neuroblastoma/motor neuron hybrid, a neuroblastoma/root ganglion neuron hybrid and a neuroblastoma/hippocampal neuron hybrid. In further aspects of this embodiment, a neuroblastoma/glioma hybrid can be, e.g., N18, NG108-15 and NG115-401 L. In further aspects of this embodiment, a neuroblastoma/motor neuron hybrid can be, e.g., NSC-19 and NSC-32. In further aspects of this embodiment, a neuroblastoma/dorsal root ganglion neuron hybrid can be, e.g., ND8-47. In further aspects of this embodiment, a neuroblastoma/root ganglion neuron hybrid can be, e.g., F11, ND-C, ND-E, ND-U1, ND3, ND7/23, ND8/34, ND8/47, ND15 and ND27. In further aspects of this embodiment, a neuroblastoma/hippocampal neuron hybrid can be, e.g., HN-33.

The NG108-15 cell line is a hybrid of mouse neuroblastoma and rat glioma cells that binds BoNT/C1 at subnanomolar concentrations with an $IC_{50}$ of 0.2 nM (0.18 ng of complex per microliter), reaching saturation at 6 nM, see, e.g., Noriko Yokosawa et al., Binding of *Clostridium botulinum* type C neurotoxin to different neuroblastoma cell lines, 57(1) Infect. Immun. 272-277 (1989); and Noriko Yokosawa et al., Binding of botulinum type Cl, D and E neurotoxins to neuronal cell lines and synaptosomes, 29(2) Toxicon 261-264 (1991). Based on binding data, the NG108-15 cell line may contain both low and high affinity receptors for BoNT/C1. As non-limiting examples, cells useful for determining Clostridial toxin activity according to a method disclosed in the present specification can include, a neuronal hybrid cell, such as, e.g., NG108-15 cells, that include a Clostridial toxin substrate comprising a SNAP-25 recognition sequence; such as, e.g., a BoNT/A recognition sequence, a BoNT/C1 recognition sequence or a BoNT/E recognition sequence; and NG108-15 cells, that include a Clostridial toxin substrate comprising a Syntaxin recognition sequence; such as, e.g., a BoNT/C1 recognition sequence.

Spinal cord cell lines, such as, e.g., murine, rat, primate or human spinal cord cell lines can be useful in aspects of the invention and include, without limitation, TE 189.T (ATCC CRL-7947) and M4b, see, e.g., Ana M. Cardenas et al., Establishment and characterization of immortalized neuronal cell lines derived from the spinal cord of normal and trisomy 16 fetal mice, an animal model of Down syndrome, 68(1) J. Neurosci. Res. 46-58 (2002). As an example, a human spinal cord cell line can be generated from precursors of human embryonic spinal cord cells (first trimester embryos) that are immortalized with a tetracycline repressible v-myc oncogene as described in Ronghao Li et al., Motoneuron differentiation of immortalized human spinal cord cell lines, 59(3) J. Neurosci. Res. 342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP 2 and choline acetyltransferase, and can release acetylcholine upon appropriate stimulation, see, e.g., Cardenas et al., supra, (2002). Thus, in an embodiment, a cell capable of Clostridial toxin intoxication can be a spinal cord cell. In aspects of this embodiment, a spinal cord cell can be, e.g., TE 189.T and M4b.

Central nervous system (CNS) cell lines, such as, e.g., murine, rat, primate and human CNS cell lines, can be useful in aspects of the invention. A useful CNS cell line can be, for example, a human CNS cell line immortalized with a tetracycline repressible v-myc oncogene as described in Dinah W. Sah et al., Bipotent progenitor cell lines from the human CNS, 15(6) Nat. Biotechnol. 574-580 (1997). Upon repression of the oncogene, the cells differentiate into neurons. Thus, in an embodiment, a cell capable of Clostridial toxin intoxication can be a CNS cell.

Cerebral cortex cell lines, such as, e.g., murine, rat, primate and human cerebral cortex cell lines, can be useful in aspects of the invention and include, without limitation, CNh, see, e.g., Ana M. Cardenas et al., Calcium signals in cell lines derived from the cerebral cortex of normal and trisomy 16 mice, 10(2) Neuroreport 363-369 (1999), HCN-1a (ATCC CRL-10442) and HCN-2 (ATCC CRL-10742). As an example, murine cortex primary cultures from 12-16 days embryos can be immortalized, for example, by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation, see, e.g., David D. Allen et al., Impaired cholinergic function in cell lines derived from the cerebral cortex of normal and trisomy 16 mice, 12(9) Eur. J. Neurosci. 3259-3264 (2000). Thus, in an embodiment, a cell capable of Clostridial toxin intoxication can be a cerebral cortex cell. In aspects of this embodiment, a cerebral cortex cell can be, e.g., CNh, HCN-1a and HCN-2.

Dorsal root ganglia cell lines, such as, e.g., murine, rat, primate and human dorsal root ganglia cell lines, can be useful in aspects of the invention and include, without limitation, G4b, see, e.g., David D. Allen et al., A dorsal root ganglia cell line derived from trisomy 16 fetal mice, a model for Down syndrome, 13(4) Neuroreport 491-496 (2002). Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine, see, e.g., Allen et al., supra, (2002). Thus, in an embodiment, a cell capable of Clostridial toxin intoxication can be a dorsal root ganglia cell. In aspects of this embodiment, a dorsal root ganglia cell can be, e.g., G4b.

Hippocampal cell lines, such as, e.g., murine, rat, primate and human hippocampal lines can be useful in aspects of the invention and include, without limitation, HT-4, see, e.g., K. Frederiksen et al., Immortalization of precursor cells from the mammalian CNS, 1(6) Neuron 439-448 (1988) and HT-22, see, e.g., John B. Davis and Pamela Maher, Protein kinase C activation inhibits glutamate-induced cytotoxicity in a neuronal cell line, 652(1) Brain Res. 169-173 (1994). As a non-limiting example, the murine hippocampal cell line HT-22 can be useful in the invention. As a further non-limiting example, the immortalized HN33 hippocampal cell line can be useful in the invention. This hippocampal cell line was derived from the fusion of primary neurons from the hippocampus of postnatal day 21 mice with the N18TG2 neuroblastoma cell line, and, when differentiated, shares membrane properties with adult hippocampal neurons in primary culture, see, e.g., Henry J. Lee et al., Neuronal Properties and Trophic Activities of Immortalized Hippocampal Cells from Embryonic and Young Adult Mice, 19(6) J. Neurosci. 1779-1787 (1990); and Henry J. Lee et al., Immortalized young adult neurons from the septal region: generation and characterization, 52(1-2) Brain Res. Dev Brain Res. 219-228 (1990). Thus, in an embodiment, a cell capable of Clostridial toxin intoxication can be a hippocampal cell. In aspects of this embodiment, a hippocampal cell can be, e.g., HT-4, HT-22 and HN33.

A variety of non-neuronal cells are useful in aspects of the invention. Non-neuronal cells useful in aspects of the invention include, without limitation, primary non-neuronal cells; immortalized or established non-neuronal cells; transformed non-neuronal cells; non-neuronal tumor cells; stably and transiently transfected non-neuronal cells and further include, yet are not limited to, mammalian, murine, rat, primate and human non-neuronal cells. Non-neuronal cells useful in aspects of the invention further include, without limitation, any of the following primary or established cells: anterior pituitary cells; adrenal cells, such as. e.g., chromaffin cells of the adrenal medulla; pancreatic cells, such as. e.g., pancreatic acinar cells, pancreatic islet β cells and insulinoma HIT or INS-1 cells; ovarian cells, such as. e.g., steroid-producing ovarian cells; kidney cells, such as. e.g., HEK-293 cells (ATCC CRL 1573) and inner medullary collecting duct (IMCD) cells; stomach cells, such as, e.g., enterochromaffin cells; blood cells, such as. e.g., eurythrocytes, leucocytes, platelets, neutrophils, eosinophils, mast cells; epithelial cells, such as. e.g., those of the apical plasma membrane; fibroblasts; thyroid cells; chondrocytes; muscle cells; hepatocytes; glandular cells such as, e.g., pituitary cells, adrenal cells, chromaffin cells; and cells involved in glucose transporter (GLUT4) translocation. Thus, in an embodiment, a cell capable of Clostridial toxin intoxication can be a non-neuronal cell. In aspects of this embodiment, a non-neuronal cell can be from a primary or established non-neuronal cell line from the, e.g., anterior pituitary cells, adrenal cells, pancreatic cells, ovarian cells, kidney cells, stomach cells, blood cells, epithelial cells, fibroblasts, thyroid cells, chondrocytes, muscle cells, hepatocytes and glandular cells. In an aspects of this embodiment, a kidney cell line can be, e.g., HEK-293.

As non-limiting examples, cells useful for determining Clostridial toxin activity according to a method disclosed in the present specification can include, a primary or established non-neuronal cell, such as, e.g., chromaffin cells or pancreatic acinar cells, that include a Clostridial toxin substrate comprising a SNAP-25 recognition sequence; such as, e.g., a BoNT/A recognition sequence or a BoNT/E recognition sequence; a primary neuronal cell, such as, e.g., chromaffin cells or pancreatic acinar cells, that include a Clostridial toxin substrate comprising a VAMP recognition sequence; such as, e.g., a BoNT/B recognition sequence or a TeNT recognition sequence; and a primary neuronal cell, such as, e.g., chromaffin cells or pancreatic acinar cells, that include a Clostridial toxin substrate comprising a Syntaxin recognition sequence; such as, e.g., a BoNT/C1 recognition sequence.

As discussed above, cells useful in the invention include neuronal and non-neuronal cells that express low or undetectable levels of endogenous receptor but which have been transfected with, or otherwise engineered to express, one or more exogenous polynucleotide molecules encoding one or more Clostridial toxin receptors. The selection of the Clostridial toxin receptor depends on which Clostridial toxin is to be assayed. As a non-limiting example, a neuronal or non-neuronal cell can be transiently or stably engineered to express an exogenous polynucleotide molecule encoding the fibroblast growth factor 3 receptor (FGFR3), which serves as a BoNT/A receptor, see, e.g., PCT Patent Application No. 2005/006421. As another non-limiting example, a neuronal or non-neuronal cell can be transiently or stably engineered to express an exogenous polynucleotide molecule encoding a synaptic vesicle glycoprotein 2 (SV2) isoform, which serves as a BoNT/A receptor, see, e.g., Min Dong et al., *SV2 Is the Protein Receptor for Botulinum Neurotoxin A*, Science (2006); S. Mahrhold et al, *The Synaptic Vesicle Protein 2C Mediates the Uptake of Botulinum Neurotoxin A into Phrenic Nerves*, 580(8) FEBS Lett. 2011-2014 (2006). Additionally, a neuronal or non-neuronal cell can be transiently or stably engineered to express multiple exogenous polynucleotide molecules encoding FGFR3 isoform and an SV2 isoform. As another non-limiting example, a neuronal or non-neuronal cell can be transiently or stably engineered to express an exogenous polynucleotide molecule encoding the Synaptotagmin I, which serves as a BoNT/B receptor and as a BoNT/G receptor, see, e.g., Min Dong et al., Synaptotagmins I and II mediate entry of botulinum neurotoxin B into cells, 162(7) J. Cell Biol. 1293-1303 (2003); and Andreas Rummel et al., Synaptotagmins I and II act as nerve cell receptors for botulinum neurotoxin G, 279(29) J. Biol. Chem. 30865-30870 (2004). As another non-limiting example, a neuronal or non-neuronal cell can be transiently or stably engineered to express an exogenous polynucleotide molecule encoding the Synaptotagmin II, which serves as a BoNT/B receptor and as a BoNT/G receptor, see, e.g., Min Dong et al., supra, (2003); and Andreas Rummel et al., supra, (2004).

Thus in an embodiment, a neuronal or non-neuronal cell is transiently or stably engineered to express an exogenous polynucleotide molecule encoding a FGFR3. In aspects of this embodiment, a neuronal or non-neuronal cell is transiently or stably engineered to express an exogenous polynucleotide molecule encoding the FGFR3 of SEQ ID NO: 164, the FGFR3 of SEQ ID NO: 165 or the FGFR3 of SEQ ID NO: 166.

In another embodiment, a neuronal or non-neuronal cell is transiently or stably engineered to express an exogenous polynucleotide molecule encoding a SV2. In aspects of this embodiment, a neuronal or non-neuronal cell is transiently or stably engineered to express an exogenous polynucleotide molecule encoding the SV2 of SEQ ID NO: 167, the SV2 of SEQ ID NO: 168, the SV2 of SEQ ID NO: 169 or the SV2 of SEQ ID NO: 170.

In another embodiment, a neuronal or non-neuronal cell is transiently or stably engineered to express an exogenous polynucleotide molecule encoding a FGFR3 and an exogenous polynucleotide molecule encoding a SV2. In aspects of this embodiment, a neuronal or non-neuronal cell is transiently or stably engineered to express an exogenous polynucleotide molecule encoding the FGFR3 of SEQ ID NO: 164, the FGFR3 of SEQ ID NO: 165 or the FGFR3 of SEQ ID NO: 166 and an exogenous polynucleotide molecule encoding the SV2 of SEQ ID NO: 167, the SV2 of SEQ ID NO: 168, the SV2 of SEQ ID NO: 169 or the SV2 of SEQ ID NO: 170.

In another embodiment, a neuronal or non-neuronal cell is transiently or stably engineered to express an exogenous polynucleotide molecule encoding a Synaptotagmin I. In aspects of this embodiment, a neuronal or non-neuronal cell is transiently or stably engineered to express an exogenous polynucleotide molecule encoding the Synaptotagmin of SEQ ID NO: 171.

In another embodiment, a neuronal or non-neuronal cell is transiently or stably engineered to express an exogenous polynucleotide molecule encoding a Synaptotagmin II. In aspects of this embodiment, a neuronal or non-neuronal cell is transiently or stably engineered to express an exogenous polynucleotide molecule encoding the Synaptotagmin of SEQ ID NO: 172.

Cells useful in aspects of the present invention further include, without limitation, transformed, tumor or other cells which over-express one or more endogenous Clostridial toxin receptors or which express one or more endogenous Clostridial toxin receptors. It is understood that the over-expressed receptor can be a wild type form of the receptor or can include one or more amino acid modifications as compared to the wild type receptor, with the proviso that the process of Clostridial toxin intoxication can still occur. As a non-limiting example, cells useful for determining BoNT/A activity encompass those which express or over-express a form of the fibroblast growth factor 3 receptor (FGFR3). As another non-limiting example, cells useful for determining BoNT/B activity encompass those which express or over-express a form of synaptotagmin I. As another non-limiting example, cells useful for determining BoNT/B activity encompass those which express or over-express a form of synaptotagmin II. As another non-limiting example, cells useful for determining BoNT/G activity encompass those which express or over-express a form of synaptotagmin I. As another non-limiting example, cells useful for determining BoNT/G activity encompass those which express or over-express a form of synaptotagmin II.

Cells which express or over-express a form of the fibroblast growth factor 3 receptor include, yet are not limited to, naturally occurring and genetically modified as well as primary and established myeloma cells, bladder carcinoma cells, prostate carcinoma cells, thyroid carcinoma cells and cervical carcinoma cells. Such cells useful in aspects of the invention further encompass, without limitation, human myeloma cell lines including H929 (ATCC CRL-9068; ECACC 95050415; DSMZ ACC 163), JIM-3, see, e.g., H. Barker et al., pp. 155-158 (J. Radl & B. van Camp eds., EURAGE Monoclonal Gammopathies III: Clinical Significance and Basic Mechanisms, 1991), KMS-11, see, e.g., Masayoshi Namba et al., Establishment of five human myeloma cell lines, 25(8) In Vitro Cell Dev. Biol. 723-729 (1989), KMS-18, see, e.g., Naozo Nakazawa et al., Interphase detection of t(4; 14) (p16.3;q32.3) by in situ hybridization and FGFR3 over-expression in plasma cell malignancies, 117(2) Cancer Genet. Cytogenet. 89-96 (2000), LB278, see, e.g., D. Ronchetti et al., Characterization of the t(4; 14)(p16.3;q32) in the KMS-18 multiple myeloma cell line, 15(5) Leukemia 864-865 (2001), LB375, see, e.g., Ronchetti et al., supra, (2001), LB1017, see, e.g., Ronchetti et al., supra, (2001), LB2100, see, e.g., Ronchetti et al., supra, (2001), LP-1 (DSMZ ACC 41), OPM-2 (DSMZ ACC 50), PCL1, see, e.g., Ronchetti et al., supra, (2001), UTMC-2, see, e.g., Shuji Ozaki et al., Characterization of a novel interleukin-6 autocrine-dependent human plasma cell line, 8(12) Leukemia 2207-2213 (1994), which over-express FGFR3 due to chromosomal translocation t(4; 14)(q16.3; q32.3) and other multiple myeloma cells with a t(4:14) translocation; leukemia cells including chronic myeloid leukemia (CML) cells such as CD34+ BCR-ABL+ cells; and bladder carcinoma cells including primary and other urothelial carcinoma cells. One skilled in the art understands that these and other cells which over-express or express a form of the fibroblast growth factor 3 receptor can be useful in determining BoNT/A activity according to a method of the invention.

Thus, in an embodiment, a cell capable of Clostridial toxin intoxication can be a cell expressing an endogenous Clostridial toxin receptor. In aspects of this embodiment, an endogenous Clostridial toxin receptor expressed by a cell is a Clostridial toxin receptor for, e.g., BoNT/A, BoNT/B, BoNT/C1, BoNT/D, BoNT/E, BoNT/F, BoNT/G and TeNT. In further aspects of this embodiment, an endogenous Clostridial toxin receptor is, e.g., FGFR3, synaptotagmin I or synaptotagmin II. In another aspect of this embodiment, a cell expressing an endogenous Clostridial toxin receptor can be from, e.g., a primary myeloma cell line, an established myeloma cell line, a primary bladder carcinoma cell line, an established bladder carcinoma cell line, a primary cervical carcinoma cell line and an established cervical carcinoma cell line. In another embodiment, an FGFR3 expressing cell can be, e.g., a cell containing a t(4; 14)(q16.3; q32.3) chromosomal translocation. In further aspects of this embodiment, an FGFR3 expressing cell can be, e.g., H929, JIM-3, KMS-11, KMS-18, LB278, LB375, LB1017, LB2100, LP-1, OPM-2, PCL1 and UTMC-2.1n further aspects of this embodiment, an FGFR3 expressing cell can be, e.g., H929, JIM-3, KMS-11, KMS-18, LB278, LB375, LB1017, LB2100, LP-1, OPM-2, PCL1 and UTMC-2. As non-limiting examples, cells useful for determining Clostridial toxin activity according to a method disclosed in the present specification can include, an established myeloma cell, such as, e.g., KMS-11 or H929, that include a Clostridial toxin substrate comprising a SNAP-25 recognition sequence; such as, e.g., a BoNT/A recognition sequence; a primary or established bladder carcinoma cell that includes a Clostridial toxin substrate comprising a SNAP-25 recognition sequence; such as, e.g., a BoNT/A recognition sequence; and a primary or established cervical carcinoma cell that includes a Clostridial toxin substrate comprising a SNAP-25 recognition sequence; such as, e.g., a BoNT/A recognition sequence.

Further such cells useful in aspects of the invention further encompass, without limitation, stably transfected cell lines expressing a Clostridial toxin receptor. including, e.g., B9, see, e.g., Elizabeth E. Plowright et al., Ectopic expression of fibroblast growth factor receptor 3 promotes myeloma cell proliferation and prevents apoptosis, 95(3) Blood 992-998 (2000); TC, see, e.g., Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999); L6, see, e.g., M. Kana et al., Signal transduction pathway of human fibroblast growth factor receptor 3. Identification of a novel 66-kDa phosphoprotein, 272(10) J. Biol. Chem. 6621-6628 (1997); and CFK2, see, e.g., Janet E. Henderson et al., Expression of FGFR3 with the G380R achondroplasia mutation inhibits proliferation and maturation of CFK2 chondrocytic cells, 15(1) J. Bone Miner. Res. 155-165 (2000). One skilled in the art understands that these and other cells which over-express or express an activated form of the fibroblast growth factor 3 receptor can be useful in determining BoNT/A activity according to a method of the invention. Thus, in an embodiment, a cell capable of Clostridial toxin intoxication can be a cell stably expressing an exogenous Clostridial toxin receptor. In aspects of this embodiment, an exogenous Clostridial toxin receptor expressed by a cell is a receptor for, e.g., BoNT/A, BoNT/B, BoNT/C1, BoNT/D, BoNT/E, BoNT/F, BoNT/G and TeNT. In further aspects of this embodiment, an exogenous Clostridial toxin receptor is, e.g., FGFR3. In further aspects of this embodiment, an FGFR3 expressing cell can be, e.g., B9, TC, L6 and CFK2. As non-limiting examples, cells useful for determining Clostridial toxin activity according to a method disclosed in the present specification can include a B9 cell which stably express a polynucleotide molecule encoding a Clostridial toxin substrate, such as, e.g., a BoNT/A substrate; a B9 cell which stably contains a Clostridial toxin substrate, such as, e.g., a BoNT/A substrate; a TC cell which stably express a polynucleotide molecule encoding a Clostridial toxin substrate, such as, e.g., a BoNT/A substrate; a TC cell which stably contains a Clostridial toxin substrate, such as, e.g., a BoNT/A substrate; a L6 cell which stably express a polynucleotide molecule encoding a Clostridial toxin substrate, such as, e.g., a BoNT/A substrate; a L6 cell which stably contains a Clostridial toxin substrate, such as, e.g., a BoNT/A substrate; a CFK2 cell which stably express a polynucleotide molecule encoding a Clostridial toxin substrate, such as, e.g., a BoNT/A substrate; and a CFK2 cell which stably contains a Clostridial toxin substrate, such as, e.g., a BoNT/A substrate.

The cell compositions disclosed in the present specification include, in part, a cell that transiently contains a Clostridial toxin substrate and/or a Clostridial toxin receptor. As used herein, the term "transiently containing" means a Clostridial toxin substrate and/or a Clostridial toxin receptor that is temporarily introduced into a cell in order to perform the assays disclosed in the present specification. By definition, in order to perform the assays disclosed in the present specification at least 50% of the cells comprising a cell population must contain a Clostridial toxin substrate. As used herein, the term "cell population" means the total number of cells used in a method that transiently introduces a Clostridial toxin substrate for a given assay. As a non-limiting example, given a cell population comprising $1.5 \times 10^5$ cells, at least $7.5 \times 10^4$ cells must contain a non-naturally occurring Clostridial toxin substrate after transduction using, e.g., an adenoviral method or a lentiviral method. As another non-limiting example, given a cell population comprising $1.5 \times 10^5$ cells, at least $7.5 \times 10^4$ cells must contain a Clostridial toxin substrate after transfection using, e.g., a protein transfection method. Thus, aspects of a cell transiently containing a Clostridial toxin substrate disclosed in the specification may include a cell that contains a substrate for, e.g., at most about one day, at most about two days, at most about three days, at most about four days, at most about five days, and at most about six days, at most about seven days, at most about eight days, at most about nine days and at most about ten days and wherein the cell population containing a Clostridial toxin substrate comprises, e.g., at least 50% of the cells within the cell population, at least 60% of the cells within the cell population, at least 70% of the cells within the cell population, at least 80% of the cells within the cell population, and at least 90% of the cells within the cell population.

Thus, in an embodiment, a cell transiently contains a polynucleotide molecule that encodes a membrane-associated Clostridial toxin substrate. In aspects of this embodiment, the membrane-associated Clostridial toxin substrate encoded by the polynucleotide molecule can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which transiently express a polynucleotide molecule encoding a Clostridial toxin substrate, such as, e.g., a BoNT/A substrate or a BoNT/E substrate; NG108-15 cells such as, e.g., differentiated NG108-15 cells and NG108-15 cells which transiently express a polynucleotide molecule encoding a Clostridial toxin substrate, such as, e.g., a BoNT/A substrate or a BoNT/E substrate; Neuro-2A cells such as, e.g., differentiated Neuro-2A cells and Neuro-2A cells which transiently express a polynucleotide molecule encoding a Clostridial toxin substrate, such as, e.g., a BoNT/A substrate; N1E-115 cells such as, e.g., differentiated N1E-115 cells and N1E-115 cells which transiently express a polynucleotide molecule encoding a Clostridial toxin substrate, such as, e.g., a BoNT/E substrate; and SK-N-DZ cells such as, e.g., differentiated SK-N-DZ cells and SK-N-DZ cells which transiently express a polynucleotide molecule encoding a Clostridial toxin substrate, such as, e.g., a BoNT/E substrate.

In another embodiment, a cell transiently contains a polynucleotide molecule that encodes a Clostridial toxin receptor. In aspects of this embodiment, the transiently-maintained Clostridial toxin receptor encoded by the polynucleotide molecule can be, e.g., a BoNT/A receptor, a BoNT/B receptor, a BoNT/C1 receptor, a BoNT/D receptor, a BoNT/E receptor, a BoNT/F receptor, a BoNT/G receptor, or a TeNT receptor. In other aspects of this embodiment, the transiently-maintained Clostridial toxin receptor encoded by the polynucleotide molecule can be, e.g., a FGFR3, a SV2, a Synaptotagmin I, and a Synaptotagmin II. In yet other aspects of this embodiment, the transiently-maintained Clostridial toxin receptor encoded by the polynucleotide molecule can be, e.g., the FGFR3 of SEQ ID NO: 164, the FGFR3 of SEQ ID NO: 165, the FGFR3 of SEQ ID NO: 166, the SV2 of SEQ ID NO: 167, the SV2 of SEQ ID NO: 168, the SV2 of SEQ ID NO: 169, the SV2 of SEQ ID NO: 170, the Synaptotagmin of SEQ ID NO: 171 or the Synaptotagmin of SEQ ID NO: 172.

In another embodiment, a cell transiently contains a membrane-associated Clostridial toxin substrate. In aspects of this embodiment, the Clostridial toxin substrate capable of being localized to the plasma membrane can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which transiently contain a Clostridial toxin substrate, such as, e.g., a BoNT/A substrate or a BoNT/E substrate; NG108-15 cells such as, e.g., differentiated NG108-15 cells and NG108-15 cells which transiently contain a Clostridial toxin substrate, such as, e.g., a BoNT/A substrate or a BoNT/E substrate; Neuro-2A cells such as, e.g., differentiated Neuro-2A cells and Neuro-2A cells which transiently contain a Clostridial toxin substrate, such as, e.g., a BoNT/A substrate; N1E-115 cells such as, e.g., differentiated N1E-115 cells and N1E-115 cells which transiently contain a Clostridial toxin substrate, such as, e.g., a BoNT/E substrate; and SK-N-DZ cells such as, e.g., differentiated SK-N-DZ cells and SK-N-DZ cells which transiently contain a Clostridial toxin substrate, such as, e.g., a BoNT/E substrate.

In another embodiment, a cell transiently contains a Clostridial toxin receptor. In aspects of this embodiment, the transiently-maintained Clostridial toxin receptor can be, e.g., a BoNT/A receptor, a BoNT/B receptor, a BoNT/C1 receptor, a BoNT/D receptor, a BoNT/E receptor, a BoNT/F receptor, a BoNT/G receptor, or a TeNT receptor. In other aspects of this embodiment, the transiently-maintained Clostridial toxin receptor can be, e.g., a FGFR3, a SV2, a Synaptotagmin I, and a Synaptotagmin II. In yet other aspects of this embodiment, the transiently-maintained Clostridial toxin receptor can be, e.g., the FGFR3 of SEQ ID NO: 164, the FGFR3 of SEQ ID NO: 165, the FGFR3 of SEQ ID NO: 166, the SV2 of SEQ ID NO: 167, the SV2 of SEQ ID NO: 168, the SV2 of SEQ ID NO: 169, the SV2 of SEQ ID NO: 170, the Synaptotagmin of SEQ ID NO: 171 or the Synaptotagmin of SEQ ID NO: 172.

The cell compositions disclosed in the present specification include, in part, a cell that stably contains a Clostridial toxin substrate and/or a Clostridial toxin receptor. As used herein, the term "stably containing" means a Clostridial toxin substrate and/or a Clostridial toxin receptor that is introduced into a cell and maintained for long periods of time in order to perform the assays of the present invention. Stably-maintained polynucleotide molecules encompass stably-maintained polynucleotide molecules that are extra-chromosomal and replicate autonomously and stably-maintained polynucleotide molecules that are integrated into the chromosomal material of the cell and replicate non-autonomously. Thus aspects of a cell stably containing a Clostridial toxin substrate disclosed in the specification may include a cell that contains a substrate for, e.g., at least ten days, at least 20 two days, at least 30 days, at least forty days, at least 50 days, and at least 60 days, at least 70 days, at least 80 days, at least 90 days and at least 100 days. Other aspects of a cell stably containing a Clostridial toxin substrate disclosed in the specification may include a cell that contains a substrate for, e.g., at least 100 days, at least 200 days, at least 300 days, at least 400 days, and at least 500 days. Still other aspects of a cell stably containing a Clostridial toxin substrate disclosed in the specification may include a cell that permanently contains a Clostridial toxin substrate.

In another embodiment, a cell stably contains a polynucleotide molecule that encodes a Clostridial toxin receptor. In aspects of this embodiment, the stably-maintained Clostridial toxin receptor encoded by the polynucleotide molecule can be, e.g., a BoNT/A receptor, a BoNT/B receptor, a BoNT/C1 receptor, a BoNT/D receptor, a BoNT/E receptor, a BoNT/F receptor, a BoNT/G receptor, or a TeNT receptor. In other aspects of this embodiment, the stably-maintained Clostridial toxin receptor encoded by the polynucleotide molecule can be, e.g., a FGFR3, a SV2, a Synaptotagmin I, and a Synaptotagmin II. In yet other aspects of this embodiment, the stably-maintained Clostridial toxin receptor encoded by the polynucleotide molecule can be, e.g., the FGFR3 of SEQ ID NO: 164, the FGFR3 of SEQ ID NO: 165, the FGFR3 of SEQ ID NO: 166, the SV2 of SEQ ID NO: 167, the SV2 of SEQ ID NO: 168, the SV2 of SEQ ID NO: 169, the SV2 of SEQ ID NO: 170, the Synaptotagmin of SEQ ID NO: 171 or the Synaptotagmin of SEQ ID NO: 172.

Thus, in an embodiment, a cell stably contains a polynucleotide molecule that encodes a membrane-associated Clostridial toxin substrate. In aspects of this embodiment, the membrane-associated Clostridial toxin substrate encoded by the polynucleotide molecule can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which stably express a polynucleotide molecule encoding a Clostridial toxin substrate, such as, e.g., a BoNT/A substrate or a BoNT/E substrate; NG108-15 cells such as, e.g., differentiated NG108-15 cells and NG108-15 cells which stably express a polynucleotide molecule encoding a Clostridial toxin substrate, such as, e.g., a BoNT/A substrate or a BoNT/E substrate; Neuro-2A cells such as, e.g., differentiated Neuro-2A cells and Neuro- 2A cells which stably express a polynucleotide molecule encoding a Clostridial toxin substrate, such as, e.g., a BoNT/A substrate; KMS-11 cells such as, e.g., differentiated KMS-11 cells and KMS-11 cells which stably express a polynucleotide molecule encoding a Clostridial toxin substrate, such as, e.g., a BoNT/A substrate; N1E-115 cells such as, e.g., differentiated N1E-115 cells and N1E-115 cells which stably express a polynucleotide molecule encoding a Clostridial toxin substrate, such as, e.g., a BoNT/E substrate; and SK-N-DZ cells such as, e.g., differentiated SK-N-DZ cells and SK-N-DZ cells which stably express a polynucleotide molecule encoding a Clostridial toxin substrate, such as, e.g., a BoNT/E substrate.

In another embodiment, a cell stably contains a Clostridial toxin receptor. In aspects of this embodiment, the stably-maintained Clostridial toxin receptor can be, e.g., a BoNT/A receptor, a BoNT/B receptor, a BoNT/C1 receptor, a BoNT/D receptor, a BoNT/E receptor, a BoNT/F receptor, a BoNT/G receptor, or a TeNT receptor. In other aspects of this embodiment, the stably-maintained Clostridial toxin receptor can be, e.g., a FGFR3, a SV2, a Synaptotagmin I, and a Synaptotagmin II. In yet other aspects of this embodiment, the stably-maintained Clostridial toxin receptor can be, e.g., the FGFR3 of SEQ ID NO: 164, the FGFR3 of SEQ ID NO: 165, the FGFR3 of SEQ ID NO: 166, the SV2 of SEQ ID NO: 167, the SV2 of SEQ ID NO: 168, the SV2 of SEQ ID NO: 169, the SV2 of SEQ ID NO: 170, the Synaptotagmin of SEQ ID NO: 171 or the Synaptotagmin of SEQ ID NO: 172.

In another embodiment, a cell stably contains a membrane-associated Clostridial toxin substrate. In aspects of this embodiment, the membrane-associated Clostridial toxin substrate can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which stably contain a Clostridial toxin substrate, such as, e.g., a BoNT/A substrate or a BoNT/E substrate; NG108-15 cells such as, e.g., differentiated NG108-15 cells and NG108-15 cells which stably contain a Clostridial toxin substrate, such as, e.g., a BoNT/A substrate or a BoNT/E substrate; Neuro-2A cells such as, e.g., differentiated Neuro-2A cells and Neuro-2A cells which stably contain a Clostridial toxin substrate, such as, e.g., a BoNT/A substrate; KMS-11 cells such as, e.g., differentiated KMS-11 cells and KMS-11 cells which stably contain a Clostridial toxin substrate, such as, e.g., a BoNT/A substrate; N1E-115 cells such as, e.g., differentiated N1E-115 cells and N1E-115 cells which stably contain a Clostridial toxin substrate, such as, e.g., a BoNT/E substrate; and SK-N-DZ cells such as, e.g., differentiated SK-N-DZ cells and SK-N-DZ cells which stably contain a Clostridial toxin substrate, such as, e.g., a BoNT/E substrate.

As mentioned above, a polynucleotide molecule can be used to express a Clostridial toxin substrate and/or a Clostridial toxin receptor disclosed in the present specification. It is envisioned that any and all methods for introducing a polynucleotide molecule into a cell can be used. Methods useful for introducing a polynucleotide molecule into a cell including, without limitation, calcium phosphate-mediated, DEAE dextran-mediated, lipid-mediated, polybrene-mediated, polylysine-mediated, viral-mediated, microinjection, protoplast fusion, biolistic, electroporation and conjugation to an antibody, gramacidin S, artificial viral envelope or other intracellular carrier such as TAT., see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001); Alessia Colosimo et al., Transfer and expression of foreign genes in mammalian cells, 29(2) Biotechniques 314-318, 320-322, 324 (2000); Philip Washbourne & A. Kimberley McAllister, Techniques for gene transfer into neurons, 12(5) Curr. Opin. Neurobiol. 566-573 (2002); and Current Protocols in Molecular Biology, John Wiley and Sons, pp 9.16.4-9.16.11 (2000). One skilled in the art understands that selection of a specific method to introduce a polynucleotide molecule into a cell will depend, in part, on whether the cell will transiently contain the Clostridial toxin substrate or whether the cell will stably contain the Clostridial toxin substrate.

In an aspect of this embodiment, a chemical-mediated method, termed transfection, is used to introduce a polynucleotide molecule encoding a Clostridial toxin substrate into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethyl-laminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a Clostridial toxin substrate into a cell. Physical reagents include, without limitation, electroporation, biolistic and microinjection. Biolistics and microinjection techniques perforate the cell wall in order to introduce the polynucleotide molecule into the cell, see, e.g., Jeike E. Biewenga et al., Plasmid-mediated gene transfer in neurons using the biolistics technique, 71(1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the polynucleotide molecules enter and be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Gresch et al., New non-viral method for gene transfer into primary cells, 33(2) Methods 151-163 (2004).

In another aspect of this embodiment, a viral-mediated method, termed transduction, is used to introduce a polynucleotide molecule encoding a Clostridial toxin substrate into a cell. In viral-mediated methods of transient transduction, the process by which viral particles infect and replicate in a host cell has been manipulated in order to use this mechanism to introduce a polynucleotide molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirus-based expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kd, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71 (1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the polynucleotide molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEaSy™ Adenoviral Vector System (Stratagene, Inc., La Jolla, Calif.) and AdEaSy™ Adenoviral Vector System Instruction Manual 064004f, Stratagene, Inc.

Polynucleotide molecule delivery can also use single-stranded RNA retroviruses viruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Félix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persist expression since the polynucleotide molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272(5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vector systems and specific protocols for how to use such vectors are disclosed in, e.g., U.S. Patent Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

As mentioned above, a Clostridial toxin receptor and a Clostridial toxin substrate disclosed in the present specification can be introduced into a cell. As used herein, the term "delivery agent" means any molecule that enables or enhances internalization of a covalently-linked, non-covalently-linked or in any other manner associated with a polypeptide into a cell. Thus, the term "delivery agent" encompasses, without limitation, proteins, peptides, peptidomimetics, small molecules, polynucleotide molecules, liposomes, lipids, viruses, retroviruses and cells that, without limitation, transport a covalently or non-covalently linked substrate to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

It is envisioned that any and all methods useful for introducing a Clostridial toxin receptor or a Clostridial toxin substrate disclosed in the present specification linked to a delivery agent can be useful, including methods that covalently link the delivery agent to the substrate and methods that non-covalently link the delivery agent to the substrate. Covalent linking methods that attach a delivery agent to a Clostridial toxin substrate can include chemical conjugation and genetically produced fusion proteins. In one non-limiting method, a polynucleotide molecule, such as, e.g., a plasmid or oligonucleotide, is attached to a Clostridial toxin receptor or a Clostridial toxin substrate by conjugation chemistry and introduced into the cell using a method useful for introducing a polynucleotide molecule into a cell as described in the present specification. In another non-limiting method, a lipid, such as, e.g., a cationic liposome, is attached to a Clostridial toxin receptor or a Clostridial toxin substrate by conjugation chemistry and introduced into the cell using a method useful for introducing a polynucleotide molecule into a cell as described in the present specification. In yet another non-limiting method, a peptide, is attached to a Clostridial toxin receptor or a Clostridial toxin substrate by conjugation chemistry and introduced into the cell using a protein delivery method described below. In yet another non-limiting method, a peptide is attached to a Clostridial toxin receptor or a Clostridial toxin substrate by producing a polynucleotide molecule that encodes the peptide delivery agent and substrate as an operably-linked fusion protein and this fusion protein is introduced into the cell using a protein delivery method described below.

A delivery agent useful in the invention can be an agent that enables or enhances cellular uptake when covalently linked to a Clostridial toxin receptor, such as, e.g., by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308 (Jun. 15, 2000); Gérard Chassaing & Alain Prochiantz, Peptides which can be Used as Vectors for the Intracellular Addressing of Active Molecules, U.S. Pat. No. 6,080,724 (Jun. 27, 2000); Alan Frankel et al., Fusion Protein Comprising TAT-derived Transport Moiert, U.S. Pat. No. 5,674,980 (Oct. 7, 1995); Alan Frankel et al., TAT-derived Transport Polypeptide Conjugates, U.S. Pat. No. 5,747,641 (May 5, 1998); Alan Frankel et al., TAT-derived Transport Polypeptides and Fusion Proteins, U.S. Pat. No. 5,804,604 (Sep. 8, 1998); Peter F. J. O'Hare et al., Use of Transport Proteins, U.S. Pat. No. 6,734,167 (May 11, 2004); Yao-Zhong Lin & Jack J. Hawiger, Method for Importing Biologically Active Molecules into Cells, U.S. Pat. No. 5,807,746 (Sep. 15, 1998); Yao-Zhong Lin & Jack J. Hawiger, Method for Importing Biologically Active Molecules into Cells, U.S. Pat. No. 6,043,339 (Mar. 28, 2000); Yao-Zhong Lin et al., Sequence and Method for Genetic Engineering of Proteins with Cell Membrane Translocating Activity, U.S. Pat. No. 6,248,558 (Jun. 19, 2001); Yao-Zhong Lin et al., Sequence and Method for Genetic Engineering of Proteins with Cell Membrane Translocating Activity, U.S. Pat. No. 6,432,680 (Aug. 13, 2002); Jack J. Hawiger et al., Method for Importing Biologically Active Molecules into Cells, U.S. Pat. No. 6,495,518 (Dec. 17, 2002); Yao-Zhong Lin et al., Sequence and Method for Genetic Engineering of Proteins with Cell Membrane Translocating Activity, U.S. Pat. No. 6,780,843 (Aug. 24, 2004); Jonathan B. Rothbard & Paul A Wender, Method and Composition for Enhancing Transport Across Biological Membranes, U.S. Pat. No. 6,306,993 (Oct. 23, 2001); Jonathan B. Rothbard & Paul A Wender, Method and Composition for Enhancing Transport Across Biological Membranes, U.S. Pat. No. 6,495,663 (Dec. 17, 2002); and Pamela B. Davis et al., Fusion Proteins for Protein Delivery, U.S. Pat. No. 6,287,817 (Sep. 11, 2001).

A delivery agent useful in the invention also can be an agent that enables or enhances cellular uptake when non-covalently associated with a Clostridial toxin receptor. Methods that function in the absence of covalent linkage and methods of using such agents are described in, e.g., Gilles Divita et al, Peptide-Mediated Transfection Agents and Methods of Use, U.S. Pat. No. 6,841,535 (Jan. 11, 2005); Philip L Felgner and Olivier Zelphati, Intracellular Protein Delivery Compositions and Methods of Use, U.S. Patent Publication No. 2003/0008813); and Michael Karas, Intracellular Delivery of Small Molecules, Proteins and Nucleic Acids, U.S. Patent Publication 2004/0209797 (Oct. 21, 2004). Such peptide delivery agents can be prepared and used by standard methods and are commercially available, see, e.g. the Chariot™ Reagent (Active Motif, Carlsbad, Calif.); BioPORTER® Reagent (Gene Therapy Systems, Inc., San Diego, Calif.), BioTrek™ Protein Delivery Reagent (Stratagene, La Jolla, Calif.), and Pro-Ject™ Protein Transfection Reagent (Pierce Biotechnology Inc., Rockford, Ill.).

Another aspect of the present invention provides expression constructs that allow for expression of a polynucleotide molecule encoding a Clostridial toxin substrate or a Clostridial toxin receptor disclosed in the present specification disclosed in the present specification. These expression constructs comprise an open reading frame encoding a Clostridial toxin substrate or a Clostridial toxin receptor, operably-linked to control sequences from an expression vector useful for expressing such a Clostridial toxin receptor or substrate in a cell. The term "operably linked" as used herein, refers to any of a variety of cloning methods that can ligate a polynucleotide molecule disclosed in the present specification into an expression vector such that a peptide encoded by the composition is expressed when introduced into a cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, polynucleotide ligation, bacterial transformation, polynucleotide purification, polynucleotide sequencing are routine procedures well within the scope of one skilled in the art and from the teaching herein. Non-limiting examples of specific protocols necessary to make an expression construct are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004), which are hereby incorporated by reference. These protocols are routine procedures well within the scope of one skilled in the art and from the teaching herein.

A wide variety of expression vectors can be employed for expressing an open reading frame encoding a Clostridial toxin substrate or a Clostridial toxin receptor and include without limitation, viral expression vectors, prokaryotic expression vectors and eukaryotic expression vectors including yeast, insect and mammalian expression vectors and generally are equivalent to the expression vectors disclosed herein in Examples 4-6 and 8-14. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing construct compositions disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001), which are hereby incorporated by reference. These protocols are routine procedures well within the scope of one skilled in the art and from the teaching herein.

An expression construct comprising a polynucleotide molecule encoding a Clostridial toxin substrate or a Clostridial toxin receptor disclosed in the present specification can be operationally-linked to a variety of regulatory elements that can positively or negatively modulate, either directly or indirectly, the expression of a polynucleotide molecule, such as, e.g., constitutive, tissue-specific, inducible or synthetic promoters and enhancers. Non-limiting examples of constitutive regulatory elements include, e.g., the cytomegalovirus (CMV), herpes simplex virus thymidine kinase (HSV TK), simian virus 40 (SV40) early, 5' long terminal repeat (LTR), elongation factor-1α (EF-1α) and polybiquitin (UbC) regulatory elements. Non-limiting examples of inducible regulatory elements useful in aspects of the present invention include, e.g., chemical-inducible regulatory elements such as, without limitation, alcohol-regulated, tetracycline-regulated, steroid-regulated, metal-regulated and pathogenesis-related; and physical-inducible regulatory elements such as, without limitation, temperature-regulated and light-regulated. Such inducible regulatory elements can be prepared and used by standard methods and are commercially available, including, without limitation, tetracycline-inducible and tetracycline-repressible elements such as, e.g., Tet-On™ and Tet-Off™ (BD Biosciences-Clontech, Palo Alto, Calif.) and the T-REx™ (Tetracycline-Regulated Expression) and Flp-In™ T-REx™ systems (Invitrogen, Inc., Carlsbad, Calif.); ecdysone-inducible regulatory elements such as, e.g., the Complete Control® Inducible Mammalian Expression System (Stratagene, Inc., La Jolla, Calif.); isopropyl β-D-galactopyranoside (IPTG)-inducible regulatory elements such as, e.g., the LacSwitch™$^{II}$ Inducible Mammalian Expression System (Stratagene, Inc., La Jolla, Calif.); and steroid-inducible regulatory elements such as, e.g., the chimeric progesterone receptor inducible system, GeneSwitch™ (Invitrogen, Inc., Carlsbad, Calif.). The skilled person understands that these and a variety of other constitutive and inducible regulatory systems are commercially available or well known in the art and can be useful in the invention for controlling expression of a polynucleotide molecule which encodes a Clostridial toxin substrate or a Clostridial toxin receptor.

In an embodiment, a polynucleotide molecule encoding a Clostridial toxin receptor can optionally be linked to a regulatory element such as a constitutive regulatory element. In another embodiment, a polynucleotide molecule encoding a Clostridial toxin substrate can optionally be linked to a regulatory element such as a constitutive regulatory element.

In another embodiment, a polynucleotide molecule encoding a Clostridial toxin receptor can optionally be linked to a regulatory element such as an inducible regulatory element. In an aspect of this embodiment, expression of the polynucleotide molecule is induced using, e.g., tetracycline-inducible, ecdysone-inducible or steroid-inducible. In another embodiment, a polynucleotide molecule encoding a Clostridial toxin substrate can optionally be linked to a regulatory element such as an inducible regulatory element. In an aspect of this embodiment, expression of the polynucleotide molecule is induced using, e.g., tetracycline-inducible, ecdysone-inducible or steroid-inducible.

The methods disclosed in the present specification include, in part, a test sample. As used herein, the term "test sample" means any biological matter that contains or potentially contains an active Clostridial toxin. A variety of test samples can be assayed according to a method disclosed in the present specification including, without limitation, purified, partially purified, or unpurified Clostridial toxin; recombinant single chain or di-chain toxin with a naturally or non-naturally occurring sequence; recombinant Clostridial toxin with a modified protease specificity; chimeric toxin containing structural elements from multiple Clostridial toxin species or subtypes; bulk Clostridial toxin; formulated Clostridial toxin product, including, e.g., a formulated BoNT/A product, a formulated BoNT/B product, a formulated BoNT/C1 product, a formulated BoNT/D product, a formulated BoNT/E product, a formulated BoNT/F product, a formulated BoNT/G product, or a formulated TeNT product; and foods; cells or crude, fractionated or partially purified cell lysates, for example, engineered to include a recombinant polynucleotide encoding a Clostridial toxin; bacterial, baculoviral and yeast lysates; raw, cooked, partially cooked or processed foods; beverages; animal feed; soil samples; water samples; pond sediments; lotions; cosmetics; and clinical formulations. It is understood that the term test sample encompasses tissue samples, including, without limitation, mammalian tissue samples, livestock tissue samples, such as, e.g., sheep, cow and pig tissue samples; primate tissue samples; and human tissue samples. Such test samples encompass, without limitation, intestinal samples such as infant intestinal samples, and tissue samples obtained from a wound. As non-limiting examples, a method of the invention can be useful for determining the presence or activity of a Clostridial toxin in a food or beverage sample; to assay a test sample from a human or animal, for example, exposed to a Clostridial toxin or having one or more symptoms of a Clostridial toxin; to follow activity during production and purification of Clostridial toxin; or to assay formulated Clostridial toxin products such as pharmaceuticals or cosmetics.

In several methods of the invention, resonance energy transfer of the test sample is compared relative to a control sample. As used herein, the term "control sample" means a sample of the same or similar type as a test sample, but which the amount of Clostridial toxin is known. One skilled in the art understands that a variety of control samples are useful in the methods of the invention and that a control sample can be a positive control sample or a negative control sample. A positive control sample is a sample comprising a defined amount of a Clostridial toxin that is the same or similar to the Clostridial toxin suspected to be in the test sample. A negative control sample is a sample that is the same or similar to test sample, except that the negative control sample lacks the presence of any Clostridial toxin.

The methods disclosed in the present specification include, in part, detecting activity of a Clostridial toxin from a test sample by comparing the resonance energy transfer of a test sample relative to a control sample. A variety of means can be useful in the methods of the invention for comparing resonance energy transfer of a test sample relative to a control sample. In one embodiment, resonance energy transfer is determined by detecting acceptor fluorescence intensity of the test sample, where decreased acceptor fluorescence intensity of the test sample as compared to the control sample is indicative of clostridial toxin activity. In another embodiment, resonance energy transfer is determined by detecting donor fluorescence/luminescence intensity of the test sample, where increased donor fluorescence/luminescence intensity of the test sample as compared to the control sample is indicative of clostridial toxin activity. In still another embodiment, resonance energy transfer is determined by detecting an acceptor emission maximum and a donor fluorophore emission maximum of the test sample, where a shift in emission maxima from near the acceptor emission maximum to near the donor fluorophore emission maximum is indicative of clostridial toxin activity. In yet another embodiment, resonance energy transfer is determined by detecting the ratio of fluorescence amplitudes near an acceptor emission maximum to the fluorescence amplitudes near a donor fluorophore emission maximum, where a decreased ratio in the test sample as compared to the control sample is indicative of clostridial toxin activity. In a further embodiment, resonance energy transfer is determined by detecting the excited state lifetime of the donor fluorophore in the test sample, where an increased donor fluorophore excited state lifetime in the test sample as compared to the control sample is indicative of clostridial toxin activity.

Resonance energy transfer and, hence, clostridial toxin activity, can be detected by a variety of means, for example, by detecting increased donor fluorescence/luminescence intensity; decreased acceptor fluorescence intensity; a shift in emission maxima from near the acceptor emission maximum to near the donor fluorophore emission maximum; a increased ratio of fluorescence amplitudes near the donor emission maximum to the fluorescence amplitudes near the acceptor fluorophore emission maximum; a decreased ratio of fluorescence amplitudes near the acceptor emission maximum to the fluorescence amplitudes near the donor fluorophore emission maximum; an increased donor fluorophore excited state lifetime; or a decrease acceptor fluorophore excited state lifetime. In aspects of this embodiment, an increased donor fluorescence/luminescence intensity can be, e.g., at least two-fold, at least three-fold, at least four-fold, at least five-fold, at least ten-fold, at least twenty-fold or more relative to fluorescence/luminescence intensity at the same wavelength of the same test sample detected at a different time point, or relative to fluorescence/luminescence intensity at the same wavelength of a similar sample not contacted with a test sample, such as, e.g., a control sample. In other aspects of this embodiment, an increased donor fluorescence/luminescence intensity can be, e.g., at most two-fold, at most three-fold, at most four-fold, at most five-fold, at most ten-fold, at most twenty-fold relative to fluorescence/luminescence intensity at the same wavelength of the same test sample detected at a different time point, or relative to fluorescence/luminescence intensity at the same wavelength of a similar sample not contacted with a test sample, such as, e.g., a control sample. In yet other aspects of this embodiment, a decreased acceptor fluorescence intensity can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control cell. In yet other aspects of this embodiment, a decreased acceptor fluorescence intensity can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample.

In additional aspects of this embodiment, a shift in emission maxima from near the acceptor emission maximum to near the donor fluorophore emission maximum can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control sample. In yet additional aspects of this embodiment, a shift in emission maxima from near the acceptor emission maximum to near the donor fluorophore emission maximum can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample.

In still other aspects of this embodiment, a decreased ratio of fluorescence amplitudes near the acceptor emission maximum to the fluorescence amplitudes near the donor fluorophore emission maximum can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control sample. In still other aspects of this embodiment, a decreased ratio of fluorescence amplitudes near the acceptor emission maximum to the fluorescence amplitudes near the donor fluorophore emission maximum can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample. In still other aspects of this embodiment, an increased ratio of fluorescence amplitudes near the donor emission maximum to the fluorescence amplitudes near the acceptor fluorophore emission maximum can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control sample. In still other aspects of this embodiment, an increased ratio of fluorescence amplitudes near the donor emission maximum to the fluorescence amplitudes near the acceptor fluorophore emission maximum can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample.

In further aspects of this embodiment, an increased donor fluorophore excited state lifetime can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control sample. In still further aspects of this embodiment, an increased donor fluorophore excited state lifetime can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample. In still further aspects of this embodiment, a decrease acceptor fluorophore excited state lifetime can be, e.g., at least two-fold, at least three-fold, at least four-fold, at least five-fold, at least ten-fold, at least twenty-fold or more relative to fluorescence intensity at the same wavelength of the same test sample detected at a different time point, or relative to fluorescence intensity at the same wavelength of a similar sample not contacted with a test sample, such as, e.g., a control sample. In still further aspects of this embodiment, a decrease acceptor fluorophore excited state lifetime can be, e.g., at most two-fold, at most three-fold, at most four-fold, at most five-fold, at most ten-fold, at most twenty-fold relative to fluorescence intensity at the same wavelength of the same test sample detected at a different time point, or relative to fluorescence intensity at the same wavelength of a similar sample not contacted with a test sample, such as, e.g., a control sample.

It is recognized that changes in the absolute amount of clostridial toxin substrate in the cell, excitation intensity, and turbidity or other background absorbance at the excitation wavelength effects the fluorescence intensities of donor and acceptor fluorophores roughly in parallel. Thus, it is understood that a ratio of emission intensities is independent of the absolute amount of substrate, excitation intensity, and turbidity or other background absorbance, and can be a useful indicator of clostridial toxin activity. Similarly, one skilled in the art understands that the excitation state lifetime of a donor fluorophore is independent of the absolute amount of substrate, excitation intensity, and turbidity or other background absorbance and can be useful in a method of the invention. It is understood that the relevant fluorescence intensities or excited state lifetimes are detected at the appropriate wavelength or range of wavelengths. As an example, where donor fluorescence intensity is detected, the appropriate wavelength is at or near the emission maxima of the donor fluorophore, or is a range of wavelengths encompassing or near to the emission maxima of the donor fluorophore.

In one embodiment, Clostridial toxin activity from a sample is determined by detecting the fluorescence/luminescence intensity. Detection of fluorescence/luminescence intensity can be practiced as "fixed-time" assays or as continuous-time assays and comparisons can be made using different time points taken from the same contacted cell or relative to a control cell. Thus, aspect of this embodiment include detecting the fluorescence/luminescence intensity in, e.g., at least two different time points, at least three different time points, at least four different time points, at least five different time points, at least ten different time points and at least 20 different time points. Other aspects of this embodiment include detecting the fluorescence/luminescence intensity over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the fluorescence/luminescence intensity over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the fluorescence/luminescence intensity continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the fluorescence/luminescence intensity continuously over time for, e.g., at least about 15 minutes, at least about 30 minutes, at least about 45 minutes, at least about 60 minutes, at least about 90 minutes and at least about 120 minutes.

It is understood that fluorescence/luminescence intensity can be detected from a single time point or a plurality of time points. It is envisioned that comparison of the fluorescence/luminescence intensity detected from the test sample to the fluorescence/luminescence intensity detected from the control sample can be made using the values obtained from the same or similar time point or from different time points. Thus, aspect of this embodiment include detecting the fluorescence/luminescence intensity from the test sample and control sample in, e.g., at least one different time point, at least two different time points, at least three different time points, at least four different time points, at least five different time points, at least ten different time points and at least 20 different time points. Other aspects of this embodiment can include comparison of the fluorescence/luminescence intensity detected from the test sample obtained from a single time point to the fluorescence/luminescence intensity detected from the control sample obtained, e.g., at the same time point, at a similar time point, at a time point later than the time point obtained from the test sample, at a time point earlier than the time point obtained from the test sample, at a plurality time points later than the time point obtained from the test sample, at a plurality time points earlier than the time point obtained from the test sample and at a plurality time point both later than and earlier than the time point obtained from the test sample, Other aspects of this embodiment can include comparison of the fluorescence/luminescence intensity detected from the test sample obtained from a plurality of time points to the fluorescence/luminescence intensity detected from the control sample obtained, e.g., from a single time point, at the same time points, at a similar time points, at a time point later than the time points obtained from the test sample, at a time point earlier than the time points obtained from the test sample, at a plurality time points later than the time points obtained from the test sample, at a plurality time points earlier than the time points obtained from the test sample and at a plurality time point both later than and earlier than the time points obtained from the test sample.

In another embodiment, Clostridial toxin activity from a sample is determined by detecting the shift in emission maxima. Detection the shift in emission maxima can be practiced as a "fixed-time" assay or as a continuous-time assay and comparisons can be made using different time points taken from the same test sample or relative to a control sample. Thus, aspect of this embodiment include detecting the shift in emission maxima in, e.g., at least two different time points, at least three different time points, at least four different time points, at least five different time points, at least ten different time points and at least 20 different time points. Other aspects of this embodiment include detecting the shift in emission maxima over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the shift in emission maxima over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the shift in emission maxima continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the shift in emission maxima continuously over time for, e.g., at least about 15 minutes, at least about 30 minutes, at least about 45 minutes, at least about 60 minutes, at least about 90 minutes and at least about 120 minutes. It is understood that the observed shift in emission maxima generally will not be a complete shift but that only part of the emission intensity will be shifted to near the donor fluorophore emission maximum.

It is understood that the shift in emission maxima can be detected from a single time point or a plurality of time points. It is envisioned that comparison of the shift in emission maxima detected from the test sample to the shift in emission maxima detected from the control sample can be made using the values obtained from the same or similar time point or from different time points. Thus, aspect of this embodiment include detecting the shift in emission maxima from the test sample and control sample in, e.g., at least one different time point, at least two different time points, at least three different time points, at least four different time points, at least five different time points, at least ten different time points and at least 20 different time points. Other aspects of this embodiment can include comparison of the shift in emission maxima detected from the test sample obtained from a single time point to the shift in emission maxima detected from the control sample obtained, e.g., at the same time point, at a similar time point, at a time point later than the time point obtained from the test sample, at a time point earlier than the time point obtained from the test sample, at a plurality time points later than the time point obtained from the test sample, at a plurality time points earlier than the time point obtained from the test sample and at a plurality time point both later than and earlier than the time point obtained from the test sample, Other aspects of this embodiment can include comparison of the shift in emission maxima detected from the test sample obtained from a plurality of time points to the shift in emission maxima detected from the test sample obtained, e.g., from a single time point, at the same time points, at a similar time points, at a time point later than the time points obtained from the test sample, at a time point earlier than the time points obtained from the test sample, at a plurality time points later than the time points obtained from the test sample, at a plurality time points earlier than the time points obtained from the test sample and at a plurality time point both later than and earlier than the time points obtained from the test sample.

In another embodiment, Clostridial toxin activity from a sample is determined by detecting the ratio of fluorescent amplitudes. Detection the ratio of fluorescent amplitudes can be practiced as a "fixed-time" assay or as a continuous-time assay and comparisons can be made using different time points taken from the same test sample or relative to a control sample. Thus, aspect of this embodiment include detecting the ratio of fluorescent amplitudes in, e.g., at least two different time points, at least three different time points, at least four different time points, at least five different time points, at least ten different time points and at least 20 different time points. Other aspects of this embodiment include detecting the ratio of fluorescent amplitudes over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the ratio of fluorescent amplitudes over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the ratio of fluorescent amplitudes continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the ratio of fluorescent amplitudes continuously over time for, e.g., at least about 15 minutes, at least about 30 minutes, at least about 45 minutes, at least about 60 minutes, at least about 90 minutes and at least about 120 minutes.

It is understood that the ratio of fluorescent amplitudes can be detected from a single time point or a plurality of time points. It is envisioned that comparison of the ratio of fluorescent amplitudes detected from the contacted cell to the ratio of fluorescent amplitudes detected from the control cell can be made using the values obtained from the same or similar time point or from different time points. Thus, aspect of this embodiment include detecting the ratio of fluorescent amplitudes from the contacted cell and control cell in, e.g., at least one different time point, at least two different time points, at least three different time points, at least four different time points, at least five different time points, at least ten different time points and at least 20 different time points. Other aspects of this embodiment can include comparison of the ratio of fluorescent amplitudes detected from the contacted cell obtained from a single time point to the ratio of fluorescent amplitudes detected from the control cell obtained, e.g., at the same time point, at a similar time point, at a time point later than the time point obtained from the contact cell, at a time point earlier than the time point obtained from the contact cell, at a plurality time points later than the time point obtained from the contact cell, at a plurality time points earlier than the time point obtained from the contact cell and at a plurality time point both later than and earlier than the time point obtained from the contact cell, Other aspects of this embodiment can include comparison of the ratio of fluorescent amplitudes detected from the contacted cell obtained from a plurality of time points to the ratio of fluorescent amplitudes detected from the control cell obtained, e.g., from a single time point, at the same time points, at a similar time points, at a time point later than the time points obtained from the contact cell, at a time point earlier than the time points obtained from the contact cell, at a plurality time points later than the time points obtained from the contact cell, at a plurality time points earlier than the time points obtained from the contact cell and at a plurality time point both later than and earlier than the time points obtained from the contact cell.

In another embodiment, Clostridial toxin activity from a sample is determined by detecting the fluorophore excited state lifetime. Detection the fluorophore excited state lifetime can be practiced as a "fixed-time" assay or as a continuous-time assay and comparisons can be made using different time points taken from the same contacted cell or relative to a control cell. Thus, aspect of this embodiment include detecting the fluorophore excited state lifetime in, e.g., at least two different time points, at least three different time points, at least four different time points, at least five different time points, at least ten different time points and at least 20 different time points. Other aspects of this embodiment include detecting the fluorophore excited state lifetime over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the fluorophore excited state lifetime over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the fluorophore excited state lifetime continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the fluorophore excited state lifetime continuously over time for, e.g., at least about 15 minutes, at least about 30 minutes, at least about 45 minutes, at least about 60 minutes, at least about 90 minutes and at least about 120 minutes.

It is understood that the fluorophore excited state lifetime can be detected from a single time point or a plurality of time points. It is envisioned that comparison of the fluorophore excited state lifetime detected from the test sample to the fluorophore excited state lifetime detected from the control sample can be made using the values obtained from the same or similar time point or from different time points. Thus, aspect of this embodiment include detecting the fluorophore excited state lifetime from the test sample and control sample in, e.g., at least one different time point, at least two different time points, at least three different time points, at least four different time points, at least five different time points, at least ten different time points and at least 20 different time points. Other aspects of this embodiment can include comparison of the fluorophore excited state lifetime detected from the test sample obtained from a single time point to the fluorophore excited state lifetime detected from the test sample obtained, e.g., at the same time point, at a similar time point, at a time point later than the time point obtained from the test sample, at a time point earlier than the time point obtained from the test sample, at a plurality time points later than the time point obtained from the test sample, at a plurality time points earlier than the time point obtained from the test sample and at a plurality time point both later than and earlier than the time point obtained from the test sample, Other aspects of this embodiment can include comparison of the fluorophore excited state lifetime detected from the test sample obtained from a plurality of time points to the fluorophore excited state lifetime detected from the test sample obtained, e.g., from a single time point, at the same time points, at a similar time points, at a time point later than the time points obtained from the test sample, at a time point earlier than the time points obtained from the test sample, at a plurality time points later than the time points obtained from the test sample, at a plurality time points earlier than the time points obtained from the test sample and at a plurality time point both later than and earlier than the time points obtained from the test sample.

Fluorescence is typically determined using a fluorimeter, whereas luminescence is typically determined using a luminometer. In general, exciting light from an optical light source having a first wavelength passes through excitation optics. The excitation optics causes the excitation radiation to excite the donor fluorophore of substrate. In response, donor fluorophore in the substrate emits radiation which has a wavelength that is longer from the excitation wavelength. Emission optics then collect the emitted light; if desired, the device may include a temperature controller to maintain the cells at a specific temperature while being scanned. If desired, a multi axis translation stage moves a microtiter plate containing a plurality of samples in order to position different wells to be exposed to the exciting light. It is understood that the multi-axis translation stage, temperature controller, auto-focusing feature, and electronics associated with imaging and data collection can be managed by the appropriate digital computer. The aspects of the invention involve exciting a donor fluorophore. One skilled in the art understands that a donor fluorophore generally is excited at or near the optimal absorption wavelength (excitation wavelength) of the donor fluorophore.

For detection of donor fluorescence/luminescence intensity, excitation is set at the wavelength of donor fluorophore absorption, and the emission of the donor fluorophore is monitored. The emission wavelength of the donor fluorophore generally is selected such that little or no contribution from acceptor fluorescence is observed. The presence of acceptor quenches donor fluorescence. Energy transfer efficiency, E, is calculated from $E=1-I_{DA}/I_D$, where $I_{DA}$ and $I_D$ are donor intensities in the presence and absence of acceptor. Both are normalized to the same donor fluorophore concentration. If desired, time resolved measurements, for which donor fluorophore concentration is not required, can be performed using $E=1-\{T_{DA}\}/T_D$, where $\{T_{DA}\}$ and $\{T_D\}$ are amplitude averaged lifetimes of donor fluorophore in the presence and absence of acceptor.

For detection of acceptor fluorescence intensity, excitation is set at the wavelength of donor fluorophore absorption, and the emission of the acceptor fluorophore is monitored. The emission wavelength of the acceptor fluorophore generally is selected such that little or no contribution from donor fluorescence is observed. The presence of acceptor quenches donor fluorescence. Energy transfer efficiency, E, is calculated from $E=1-I_{AD}/I_A$, where $I_{AD}$ and $I_A$ are acceptor intensities in the presence and absence of donor. Both are normalized to the same acceptor fluorophore concentration. If desired, time resolved measurements, for which acceptor fluorophore concentration is not required, can be performed using $E=1-\{T_{AD}\}/T_A$, where $\{T_{AD}\}$ and $\{T_A\}$ are amplitude averaged lifetimes of acceptor fluorophore in the presence and absence of acceptor.

It is further understood that the methods of the invention can be automated and can be configured in a high throughput or ultra high-throughput format using, without limitation, 96-well, 384-well or 1536-well plates. As one non-limiting example, fluorescence emission can be detected using the SpectraMax M5 microplate reader (Molecular Devices, Sunnyvale, Calif.), a dual-monochromator, multi-detection microplate reader with a wavelength range of 250-850 nm and a 6-384 microplate reading capability. As another non-limiting example, fluorescence emission can be detected using the Typhoon™ 9410 system (Amersham Biosciences, Piscataway, N.J.). Designed for microplate assays, this system utilizes exciting light at 337 nm, 488 nm, 532 nm or 633 nm and has a semiconfocal optimal system with a charge coupled device (CCD) camera to illuminate and image the entire plate. The FPM-2 96-well plate reader (Folley Consulting and Research, Round Lake, Ill.) also can be useful in detecting fluorescence emission in the methods of the invention. One skilled in the art understands that these and other automated systems with the appropriate spectroscopic compatibility such as the ECLIPSE spectroflurimeter system (Varian-Cary; Walnut Creek, Calif.) and the FLIPR® and Gemini XPS spectrofluorometer system (Molecular Devices, Sunnyvale, Calif.).

It is envisioned that a variety of conditions suitable for determining activity of a Clostridial toxin in a sample can be useful according to the methods disclosed in the present specification. In aspects of this embodiment, conditions suitable for determining activity of a Clostridial toxin can be provided such that, e.g., at least 10% of the substrate is cleaved, at least 20% of the substrate is cleaved, at least 30% of the substrate is cleaved, at least 40% of the substrate is cleaved, at least 50% of the substrate is cleaved, at least 60% of the substrate is cleaved, at least 70% of the substrate is cleaved, at least 80% of the substrate is cleaved or at least 90% of the substrate is cleaved. In other aspects of this embodiment, conditions suitable for determining activity of a Clostridial toxin can be provided such that, e.g., at most 10% of the substrate is cleaved, at most 20% of the substrate is cleaved, at most 30% of the substrate is cleaved, at most 40% of the substrate is cleaved, at most 50% of the substrate is cleaved, at most 60% of the substrate is cleaved, at most 70% of the substrate is cleaved, at most 80% of the substrate is cleaved or at most 90% of the substrate is cleaved. In another aspect of this embodiment, conditions suitable for determining activity of a Clostridial toxin can be provided such that 100% of the substrate is cleaved. In another aspect of this embodiment, the conditions suitable for determining activity of a Clostridial toxin are provided such that the assay is linear. In another aspect of this embodiment, the conditions suitable for determining activity of a Clostridial toxin are provided such that the assay is non-linear.

Clostridial toxins are zinc metalloproteases, and a source of zinc, such as zinc chloride or zinc acetate, typically in the range of 1 to 500 µM, for example, 5 to 10 µM can be included, if desired, as part of the conditions suitable for determining Clostridial toxin activity. One skilled in the art understands that zinc chelators such as EDTA generally are excluded from a buffer for determining the presence or activity of a Clostridial toxin.

The concentration of purified or partially purified Clostridial toxin to be assayed in a method of the invention generally is in the range of about 0.0001 ng/ml to 500 µg/ml toxin, for example, about 0.0001 ng/ml to 50 µg/ml toxin, 0.001 ng/ml to 500 µg/ml toxin, 0.001 ng/ml to 50 µg/ml toxin, 0.0001 to 5000 ng/ml toxin, 0.001 ng/ml to 5000 ng/ml, 0.01 ng/ml to 5000 ng/ml, 0.1 ng/ml to 5000 ng/ml, 0.1 ng/ml to 500 ng/ml, 0.1 ng/ml to 50 ng/ml, 1 ng/ml to 5000 ng/ml, 1 ng/ml to 500 ng/ml, 1 ng/ml to 50 ng/ml, 10 ng/ml to 5000 ng/ml, 10 ng/ml to 500 ng/ml, 50 ng/ml to 5000 ng/ml, 50 ng/ml to 500 ng/ml or 100 ng/ml to 5000 ng/ml toxin, which can be, for example, purified recombinant di-chain or single chain toxin or formulated Clostridial toxin product containing human serum albumin and excipients. In aspects of this embodiment, the concentration of purified or partially purified Clostridial toxin assayed results in cleavage of, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the concentration of purified or partially purified Clostridial toxin assayed results in cleavage of, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the concentration of purified or partially purified Clostridial toxin assayed results in cleavage of 100% of the total substrate present.

The concentration of purified or partially purified Clostridial toxin assayed in a method of the invention can be, for example, in the range of about 0.1 pM to 500 µM, 0.1 pM to 100 µM, 0.1 pM to 10 µM, 0.1 pM to 1 µM, 0.1 pM to 500 nM, 0.1 pM to 100 nM, 0.1 pM to 10 nM, 0.1 pM to 1 nM, 0.1 pM to 500 pM, 0.1 pM to 100 pM, 0.1 pM to 50 pM, 0.1 pM to 10 pM, 1 pM to 500 µM, 1 pM to 100 µM, 1 pM to 10 µM, 1 pM to 1 µM, 1 pM to 500 nM, 1 pM to 100 nM, 1 pM to 10 nM, 1 pM to 1 nM, 1 pM to 500 pM, 1 pM to 100 pM, 1 pM to 50 pM, 1 pM to 10 pM, 10 pM to 500 µM, 10 pM to 100 µM, 10 pM to 10 µM, 10 pM to 10 µM, 10 pM to 500 nM, 10 pM to 100 nM, 10 pM to 10 nM, 10 pM to 1 nM, 10 pM to 500 pM, 10 pM to 100 pM, 10 pM to 50 pM, 100 pM to 500 µM, 100 pM to 100 µM, 100 pM to 10 µM, 100 pM to 1 µM, 100 pM to 500 nM, 100 pM to 100 nM, 100 pM to 10 nM, 100 pM to 1 nM, 100 pM to 500 pM 1 nM to 500 µM, 1 nM to 100 µM, 1 nM to 10 µM, 1 nM to 1 µM, 1 nM to 500 nM, 1 nM to 100 nM, 1 nM to 50 nM, 1 nM to 10 nM, 3 nM to 100 nM toxin, which can be, for example, purified native or recombinant light chain or di-chain toxin or formulated Clostridial toxin product containing human serum albumin and excipients. One skilled in the art understands that the concentration of purified or partially purified Clostridial toxin will depend on the serotype of the toxin assayed, as well as the purity or recombinant sequence of the toxin, the presence of inhibitory components, and the assay conditions. It is additionally understood that purified, partially purified or crude samples can be diluted to within a convenient range for assaying for Clostridial toxin activity against a standard curve. Similarly, it is understood that a sample can be diluted, if desired, such that the assay is linear. In aspects of this embodiment, the concentration of purified or partially purified Clostridial toxin assayed results in cleavage of, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present at least 90% of the total substrate present. In further aspects of this embodiment, the concentration of purified or partially purified Clostridial toxin assayed results in cleavage of, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present at most 90% of the total substrate present. In another aspect of this embodiment, the concentration of purified or partially purified Clostridial toxin assayed results in cleavage of 100% of the total substrate present.

In still another embodiment, it is envisioned that any and all temperatures that allow the function of a Clostridial activity assay can be used in methods disclosed in the present specification. Assay temperatures can be varied as appropriate by one skilled in the art and generally depend, in part, on the concentration, purity and activity of the Clostridial toxin, the sample to be assayed, the assay time or the convenience of the artisan. Thus, an assay temperature should not be as low as to cause the solution to freeze and should not be as high as to denature the Clostridial toxin, the Clostridial toxin substrate disclosed in the present specification. In an aspect of this embodiment, the assay is performed within a temperature range above 0° C., but below 40° C. In another aspect of this embodiment, the assay is performed within a temperature range of about 4° C. to about 37° C. In yet another aspect of this embodiment, the assay is performed within a temperature range of about 2° C. to 10° C. In yet another aspect of this embodiment, the assay is performed at about 4° C. In still another aspect of this embodiment, the assay is performed within a temperature range of about 10° C. to about 18° C. In still another aspect of this embodiment, the assay is performed at about 16° C. In yet another aspect of this embodiment, the assay is performed within a temperature range of about 18° C. to about 32° C. In yet another aspect of this embodiment, the assay is performed at about 20° C. In another aspect of this embodiment, the assay is performed within a temperature range of about 32° C. to about 40° C. In another aspect of this embodiment, the assay is performed at about 37° C. In aspects of this embodiment, the amount of Clostridial toxin substrate cleaved within a temperature range is, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the amount of Clostridial toxin substrate cleaved within a temperature range is, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the amount of Clostridial toxin substrate cleaved within a temperature range is 100%.

In still another embodiment, it is foreseen that any and all times sufficient for the detection of the presence of Clostridial toxin substrate cleavage products can be used in methods disclosed in the present specification. Assay times can be varied as appropriate by the skilled artisan and generally depend, in part, on the concentration, purity and activity of the Clostridial toxin, the sample to be assayed, incubation temperature or the convenience of the artisan. Assay times generally vary, without limitation, in the range of about 15 minutes to about 4 hours, 30 minutes to 8 hours, 1 hour to 12 hours, 2 hours to 24 hours, 4 hours to 48 hours, 6 hours to 72 hours. In aspects of this embodiment, the amount of Clostridial toxin substrate cleaved during an assay time is, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the amount of Clostridial toxin substrate cleaved during an assay time is, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the amount of Clostridial toxin substrate cleaved during an assay time is 100%. It is understood that assays can be terminated, if desired, prior to exciting the fluorescent protein.

Aspects of the present invention can also be described as follows:

1. A Clostridial toxin substrate comprising:
   a. a lanthanide donor complex comprising a lanthanide binding site and a lanthanide ion;
   b. an acceptor; and
   c. a Clostridial toxin recognition sequence including a $P_1$-$P_1'$ cleavage site that intervenes between the lanthanide donor complex and the acceptor;
   wherein the acceptor has an absorbance spectrum overlapping the emission spectrum of the lanthanide donor complex; and
   wherein, under the appropriate conditions, resonance energy transfer is exhibited between the lanthanide donor complex and the acceptor.
2. The substrate of 1, wherein the lanthanide binding site has a Kd for a lanthanide ion of less than 1 μM.
3. The substrate of 1, wherein the lanthanide binding site is selected from the group consisting of a chelate, a cryptate and a EF-hand motif.
4. The substrate of 3, wherein the chelate is a thiol-reactive chelator.
5. The substrate of 3, wherein the chelate is selected from the group consisting of a polyphenol chelate, a β-diketone chelate, a polyaminopolycarboxylic acid chelate, a pyridine chelate, a polypyridine chelate, a porphyrin chelate, and a calixarene chelate.
6. The substrate of 3, wherein the chelate is selected from the group consisting of a BPTA chelate, a BCPDA chelate, a BHHCT chelate, a CDPP chelate, a Cyclen chelate, a DOTA chelate, a DOTMA chelate, a DOTP chelate, a DO2A chelate, a DO3A chelate, a DTPA chelate, a TETA chelate, and a TTHA chelate.

7. The substrate of 3, wherein the cryptate is selected from the group consisting of a trisbipyridine cryptate, a trisbipyridine tetracarboxylate cryptate, a trisbipyridine pentacarboxylate cryptate and a pyridine bipyridine tetracarboxylate cryptate.

8. The substrate of 3, wherein the EF-hand motif is derived from a S100 subfamily protein, a Calmodulin subfamily protein, a Myosin light chain subfamily protein, a Parvalbumin subfamily protein, a Spectrin α-chain subfamily protein, a Calcineurin subfamily protein, a Calbindin D28k subfamily protein, a Neuronal calcium sensor subfamily protein, a Calpain subfamily protein, a Sarcoplasmic calcium-binding protein subfamily protein, or a SPARC/BM-40 subfamily protein.

9. The substrate of 8, wherein the S100 subfamily protein is selected from the group consisting of a S100A1, a S100A10/p11, a S100A12/calgranulin C, a S100A2/S100L, a S100A3/S100E, a S100A4/placental calcium-binding protein, a S100A5/S100D, a S100A6/calcyclin, a S100A7/psoriasin, a S100A8/MRP-8, a S100A9/MRP-14, a S100B, a S100C, a SLOOP and a calbindin D9k.

10. The substrate of 8, wherein the S100 subfamily protein is selected from the group consisting of SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, and SEQ ID NO: 213.

11. The substrate of 8, wherein the Calmodulin-like subfamily protein is selected from the group consisting of a calcium-dependent protein kinase, a calmodulin, a calmodulin-like protein, a caltractin, a squidulin, a troponin C, and a nonvertebrate troponin.

12. The substrate of 8, wherein the Calmodulin-like subfamily protein is selected from the group consisting of SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, and SEQ ID NO: 237.

13. The substrate of 8, wherein the Myosin light chain subfamily protein is selected from the group consisting of a myosin essential light chain, and a myosin regulatory light chain.

14. The substrate of 8, wherein the Myosin light chain subfamily protein is selected from the group consisting of SEQ ID NO: 238, SEQ ID NO: 239, SEQ ID NO: 240, SEQ ID NO: 241, SEQ ID NO: 242, SEQ ID NO: 243, SEQ ID NO: 244, and SEQ ID NO: 245.

15. The substrate of 8, wherein the Parvalbumin subfamily protein is a parvalbumin.

16. The substrate of 8, wherein the Parvalbumin subfamily protein is SEQ ID NO: 246 or SEQ ID NO: 247.

17. The substrate of 8, wherein the Spectrin subfamily protein is a spectrin.

18. The substrate of 8, wherein the Spectrin subfamily protein is SEQ ID NO: 248 or SEQ ID NO: 249.

19. The substrate of 8, wherein the Calcineurin B subfamily protein is a calcineurin B.

20. The substrate of 8, wherein the Calcineurin B subfamily protein is SEQ ID NO: 250, SEQ ID NO: 251, SEQ ID NO: 252 or SEQ ID NO: 253.

21. The substrate of 8, wherein the Calbindin D28k subfamily protein is a calbindin D28k or a calretinin.

22. The substrate of 8, wherein the Calbindin D28k subfamily protein is selected from the group consisting of SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, and SEQ ID NO: 265.

23. The substrate of 8, wherein the Neuron specific calcium sensor protein is selected from the group consisting of a neuronal calcium sensor-1 (NCS-1), a hippocalcin and a recoverin (visinin).

24. The substrate of 8, wherein the Neuron specific calcium sensor protein is selected from the group consisting of SEQ ID NO: 266, SEQ ID NO: 267, SEQ ID NO: 268, SEQ ID NO: 269, SEQ ID NO: 270, SEQ ID NO: 271, SEQ ID NO: 272, and SEQ ID NO: 273.

25. The substrate of 8, wherein the Calpain subfamily protein is selected from the group consisting of a ALG-2, a calpain, a grancalcin and a sorcin.

26. The substrate of 8, wherein the Calpain subfamily protein is selected from the group consisting of SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, and SEQ ID NO: 293.

27. The substrate of 8, wherein the Sarcoplasmic calcium-binding protein subfamily protein is a sarcoplasmic calcium-binding protein.

28. The substrate of 8, wherein the Sarcoplasmic calcium-binding protein subfamily protein is selected from the group consisting of SEQ ID NO: 294, SEQ ID NO: 295, SEQ ID NO: 296, SEQ ID NO: 297, SEQ ID NO: 298, SEQ ID NO: 299, SEQ ID NO: 300, and SEQ ID NO: 301.

29. The substrate of 8, wherein the BM-40 subfamily protein is a BM-40.

30. The substrate of 8, wherein the BM-40 subfamily protein is SEQ ID NO: 302 or SEQ ID NO: 303.

31. The substrate of 3, wherein the EF-hand motif is derived from a LAV1, a EHF5, p24 thyroid protein, a diacylglycerol kinase (DGK), an α-actinin, a SPEC, a SPEC resembling protein (LPS), an Aequorin binding protein, a luciferin binding protein, a calcium vector protein (CVP), a 1F8, or a TB17.

32. The substrate of 1, wherein the lanthanide ion is selected from the group consisting of terbium (Tb), europium (Eu), dysprosium (Dy) and samarium (Sm).

33. The substrate of 1, wherein the acceptor is an acceptor fluorophore comprising a fluorescent protein.

34. The substrate of 3, wherein the fluorescent protein is selected from the group consisting of blue fluorescent protein, cyan fluorescent protein, green fluorescent protein, yellow fluorescent protein and red fluorescent protein.

35. The substrate of 1, wherein the acceptor is an acceptor fluorophore comprising a fluorophore binding protein.

36. The substrate of 35, wherein the fluorophore binding protein is selected from the group consisting of a tetracysteine peptide, an AGT and a dehalogenase.

37. The substrate of 36, wherein the tetracysteine peptide binds to a fluorophore selected from the group consisting of a nonfluorescent biarsenical derivative of fluorescein and a nonfluorescent biarsenical derivative of resorufin.

38. The substrate of 36, wherein the AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

39. The substrate of 36, wherein the dehalogenase binds to a fluorophore selected from the group consisting of a Coumarian derivative, a diAcFAM derivative and a TMR derivative.

40. The substrate of 1, wherein the acceptor is a non fluorescent acceptor protein 41. The substrate of 40, wherein the non fluorescent acceptor protein is a heme-containing protein.

42. The substrate of 1, wherein the lanthanide donor complex further comprises an antennae.

43. The substrate of 42, wherein the antennae is distinct from the lanthanide-binding site.

44. The substrate of 42, wherein the antennae is incorporated within lanthanide biding site.

45. The substrate of 42, wherein the antennae is selected from the group consisting of carbostyril 124 a tryptophan, and a 2-hydroxyisophthalamide.

46. The substrate of 1, wherein the Clostridial toxin recognition sequence is a botulinum toxin recognition sequence.

47. The substrate of 1, wherein the botulinum toxin recognition sequence is selected from the group consisting of a BoNT/A recognition sequence, a BoNT/B recognition sequence, a BoNT/C1 recognition sequence, a BoNT/D recognition sequence, a BoNT/E recognition sequence, a BoNT/F recognition sequence, and a BoNT/G recognition sequence.

48. The substrate of 46, wherein the BoNT/A recognition sequence comprises at least six consecutive residues of a SNAP-25 or a peptidomimetic thereof, the six consecutive residues comprising Gln-Arg, or a peptidomimetic thereof.

49. The substrate of 48, wherein the BoNT/A recognition sequence comprises SEQ ID NO: 96, or a peptidomimetic thereof.

50. The substrate of 46, wherein the BoNT/B recognition sequence comprises at least six consecutive residues of a VAMP or a peptidomimetic thereof, the six consecutive residues comprising Gln-Phe, or a peptidomimetic thereof.

51. The substrate of 50, wherein the BoNT/B recognition sequence comprises SEQ ID NO: 97, or a peptidomimetic thereof.

52. The substrate of 46, wherein the BoNT/C1 recognition sequence comprises at least six consecutive residues of VAMP or a peptidomimetic thereof, the six consecutive residues comprising Lys-Ala, or a peptidomimetic thereof.

53. The substrate of 52, wherein the BoNT/C1 recognition sequence comprises SEQ ID NO: 98, or a peptidomimetic thereof.

54. The substrate of 46, wherein the BoNT/C1 recognition sequence comprises at least six consecutive residues of VAMP or a peptidomimetic thereof, the six consecutive residues comprising Arg-Ala, or a peptidomimetic thereof.

55. The substrate of 54, wherein the BoNT/C1 recognition sequence comprises SEQ ID NO: 99, or a peptidomimetic thereof.

56. The substrate of 46, wherein the BoNT/D recognition sequence comprises at least six consecutive residues of VAMP or a peptidomimetic thereof, the six consecutive residues comprising Lys-Leu, or a peptidomimetic thereof.

57. The substrate of 56, wherein the BoNT/D recognition sequence comprises SEQ ID NO: 100, or a peptidomimetic thereof.

58. The substrate of 46, wherein the BoNT/E recognition sequence comprises at least six consecutive residues of VAMP or a peptidomimetic thereof, the six consecutive residues comprising Arg-Ile, or a peptidomimetic thereof.

59. The substrate of 58, wherein the BoNT/E recognition sequence comprises SEQ ID NO: 101, or a peptidomimetic thereof.

60. The substrate of 46, wherein the BoNT/F recognition sequence comprises at least six consecutive residues of VAMP or a peptidomimetic thereof, the six consecutive residues comprising Gln-Lys, or a peptidomimetic thereof.

61. The substrate of 60, wherein the BoNT/F recognition sequence comprises SEQ ID NO: 102, or a peptidomimetic thereof.

62. The substrate of 46, wherein the BoNT/G recognition sequence comprises at least six consecutive residues of VAMP or a peptidomimetic thereof, the six consecutive residues comprising Ala-Ala, or a peptidomimetic thereof.

63. The substrate of 62, wherein the BoNT/G recognition sequence comprises SEQ ID NO: 103, or a peptidomimetic thereof.

64. The substrate of 1, wherein the Clostridial toxin recognition sequence is a TeNT recognition sequence.

65. The substrate of 64, wherein the TeNT recognition sequence comprises at least six consecutive residues of VAMP or a peptidomimetic thereof, the six consecutive residues comprising Gln-Phe, or a peptidomimetic thereof.

66. The substrate of 65, wherein the TeNT recognition sequence comprises SEQ ID NO: 104, or a peptidomimetic thereof.

67. The substrate of 1, wherein the substrate is a peptide or peptidomimetic having a length of at most 20 residues, at most 50 residues, at most 100 residues, or at most 150 residues.

68. The substrate of 1, wherein the substrate is a peptide or peptidomimetic having a length of at least 100 residues, at least 300 residues, at least 500 residues, or at least 700 residues.

69. The substrate of 1, wherein the Clostridial toxin recognition sequence is a peptide or peptidomimetic having a length of at most 20 residues, at most 30 residues, or at most 40 residues.

70. The substrate of 1, wherein the Clostridial toxin recognition sequence is a peptide or peptidomimetic having a length of at least 20 residues, at least 50 residues, at least 100 residues, or at least 200 residues.

71. The substrate of 1, wherein the acceptor is an acceptor fluorophore comprising a fluorescent dye.

72. The substrate of 71, wherein the fluorescent dye is selected from the group consisting of a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye and an infrared fluorescent dye.

73. The substrate of 1, wherein the acceptor is a non-fluorescent acceptor molecule.

74. The substrate of 73, wherein the non-fluorescent acceptor molecule is selected from the group consisting of DNP, DABCYL, DABSYL and DABMI.

75. The substrate of 1, wherein the substrate can be cleaved with an activity of at least 1 nanomole/minute/milligram toxin, at least 20 nanomoles/minute/milligram toxin or at least 100 nanomoles/minute/milligram toxin.

76. A polynucleotide molecule encoding a Clostridial toxin substrate according to any one of Claims 1-70.

77. The polynucleotide molecule according to 76, wherein the polynucleotide molecule comprises an expression vector.

78. A method of detecting activity of a Clostridial toxin, the method comprising the steps of
   a. treating with a test sample, under conditions suitable for Clostridial toxin protease activity, a Clostridial toxin substrate according to any one of Claims 1-75.
   b. exciting the lanthanide donor complex; and
   c. detecting resonance energy transfer of the treated substrate from the test sample.
   d. comparing the resonance energy transfer detected from the test sample with the resonance energy transfer detected from a control sample subjected to steps (a)-(c); wherein a difference in fluorescence resonance energy transfer of the test sample as compared to a control sample is indicative of activity from a Clostridial toxin.

79. The method of 78, wherein the sample is selected from the group consisting of a crude cell lysate, a bulk Clostridial toxin, a partially purified Clostridial toxin, a purified Clostridial toxin, an isolated Clostridial toxin light chain, and a formulated Clostridial toxin product.

80. The method of 79, wherein the sample comprises a formulated Clostridial toxin product.

81. The method of 78, wherein the sample is selected from the group consisting of a raw food, a partially cooked or processed food, a cooked or processed food, a beverage, an animal feed, a soil sample, a water sample, and a pond sediments.

82. The method of 78, wherein the acceptor is a fluorophore and step (c) comprises detecting donor fluorescence intensity of the test sample, wherein an increase in substrate cleavage results in an increase in donor fluorescence intensity of the test sample as compared to the control sample, the increased donor fluorescence intensity being indicative of Clostridial toxin protease activity.

83. The method of 78, wherein the acceptor is a fluorophore and step (c) comprises detecting acceptor fluorescence intensity of the test sample, wherein an increase in substrate cleavage results in a decrease in acceptor fluorescence intensity of the test sample as compared to the control sample, the decreased acceptor fluorescence intensity being indicative of Clostridial toxin protease activity.

84. The method of 78, wherein the acceptor is a fluorophore and step (c) comprises detecting an acceptor emission maximum and a donor fluorophore emission maximum in the test sample, wherein an increase in substrate cleavage results in a shift in emission maxima from near the acceptor emission maximum to near the donor fluorophore emission maximum, the shift in emission maxima being indicative of Clostridial toxin protease activity.

85. The method of 78, wherein the acceptor is a fluorophore and step (c) comprises detecting the ratio of fluorescence amplitudes near an acceptor emission maximum over the fluorescence amplitudes near a donor fluorophore emission maximum in the test sample, wherein an increase in substrate cleavage results in a decreased ratio of the test sample as compared to the control sample, the decreased ratio being indicative of Clostridial toxin protease activity.

86. The method of 78, wherein the acceptor is a fluorophore and step (c) comprises detecting the ratio of fluorescence amplitudes near an donor emission maximum over the fluorescence amplitudes near a acceptor fluorophore emission maximum, wherein an increase in substrate cleavage results in an increased ratio in the test sample as compared to the control sample, the increased ratio being indicative of Clostridial toxin protease activity.

87. The method of 78, wherein the acceptor is a fluorophore and step (c) comprises detecting the excited state lifetime of the donor fluorophore of the test sample, wherein an increase in substrate cleavage results in an increase in donor fluorophore excited state lifetime of the test sample as compared to the control sample, the increased excited state lifetime being indicative of Clostridial toxin protease activity.

88. The method of 78, wherein the acceptor is a non-fluorescent acceptor and step (c) comprises detecting donor fluorescence intensity of the test sample, wherein an increase in substrate cleavage results in an increase in donor fluorescence intensity of the test sample as compared to the control sample, the increased donor fluorescence intensity being indicative of Clostridial toxin protease activity.

89. The method of 78, further comprising repeating step (c) at one or more later time intervals.

90. The method of 78, wherein at least 90% of the Clostridial toxin substrate is cleaved.

91. The method of 78, wherein at most 5% of the Clostridial toxin substrate is cleaved, at most 15% of the Clostridial toxin substrate is cleaved, or at most 25% of the Clostridial toxin substrate is cleaved.

92. The method of 78, wherein the conditions suitable for Clostridial toxin protease activity are selected such that the assay is linear.

93. A Clostridial toxin substrate comprising:
   a. a lanthanide donor complex comprising a lanthanide binding site and a lanthanide ion;
   b. an acceptor; and
   c. a Clostridial toxin recognition sequence including a $P_1$-$P_1$' cleavage site that intervenes between the lanthanide donor complex and the acceptor;
   d. a MTD;
   wherein the acceptor has an absorbance spectrum overlapping the emission spectrum of the lanthanide donor complex; and
   wherein, under the appropriate conditions, resonance energy transfer is exhibited between the lanthanide donor complex and the acceptor.

94. The substrate of 93, wherein the Clostridial toxin substrate comprises an amino to carboxyl single polypeptide linear order comprising a MTD, a lanthanide donor complex, Clostridial toxin recognition sequence including a Clostridial toxin cleavage site, and an acceptor.

95. The substrate of 93, wherein the Clostridial toxin substrate comprises an amino to carboxyl single polypeptide linear order comprising a lanthanide donor complex, a MTD, Clostridial toxin recognition sequence including a Clostridial toxin cleavage site, and an acceptor.

96. The substrate of 93, wherein the Clostridial toxin substrate comprises an amino to carboxyl single polypeptide linear order comprising a lanthanide donor complex, Clostridial toxin recognition sequence including a Clostridial toxin cleavage site, a MTD, and an acceptor.

97. The substrate of 93, wherein the Clostridial toxin substrate comprises an amino to carboxyl single polypeptide linear order comprising a lanthanide donor complex, Clostridial toxin recognition sequence including a Clostridial toxin cleavage site, an acceptor and a MTD.

98. The substrate of 93, wherein the Clostridial toxin substrate comprises an amino to carboxyl single polypeptide linear order comprising a MTD, an acceptor, Clostridial toxin recognition sequence including a Clostridial toxin cleavage site, and a lanthanide donor complex.

99. The substrate of 93, wherein the Clostridial toxin substrate comprises an amino to carboxyl single polypeptide linear order comprising an acceptor, a MTD, Clostridial toxin recognition sequence including a Clostridial toxin cleavage site, and a lanthanide donor complex.

100. The substrate of 93, wherein the Clostridial toxin substrate comprises an amino to carboxyl single polypeptide linear order comprising an acceptor, Clostridial toxin recognition sequence including a Clostridial toxin cleavage site, a MTD, and a lanthanide donor complex.

101. The substrate of 93, wherein the Clostridial toxin substrate comprises an amino to carboxyl single polypeptide linear order comprising an acceptor, Clostridial toxin recognition sequence including a Clostridial toxin cleavage site, a lanthanide donor complex and a MTD.

102. The substrate of 93, wherein the lanthanide binding site has a Kd for a lanthanide ion of less than 1 μM.

103. The substrate of 93, wherein the lanthanide binding site is selected from the group consisting of a chelate, a cryptate and an EF-hand motif.

104. The substrate of 103, wherein the chelate is a thiol-reactive chelator.

105. The substrate of 103, wherein the chelate is selected from the group consisting of a polyphenol chelate, a β-diketone chelate, a polyaminopolycarboxylic acid chelate, a pyridine chelate, a polypyridine chelate, a porphyrin chelate, and a calixarene chelate.

106. The substrate of 103, wherein the chelate is selected from the group consisting of a BPTA chelate, a BCPDA chelate, a BHHCT chelate, a CDPP chelate, a Cyclen chelate, a DOTA chelate, a DOTMA chelate, a DOTP chelate, a DO2A chelate, a DO3A chelate, a DTPA chelate, a TETA chelate, and a TTHA chelate.

107. The substrate of 103, wherein the cryptate is selected from the group consisting of a trisbipyridine cryptate, a trisbipyridine tetracarboxylate cryptate, a trisbipyridine pentacarboxylate cryptate and a pyridine bipyridine tetracarboxylate cryptate.

108. The substrate of 103, wherein the EF-hand motif is derived from a S100 subfamily protein, a Calmodulin subfamily protein, a Myosin light chain subfamily protein, a Parvalbumin subfamily protein, a Spectrin α-chain subfamily protein, a Calcineurin subfamily protein, a Calbindin D28k subfamily protein, a Neuronal calcium sensor subfamily protein, a Calpain subfamily protein, a Sarcoplasmic calcium-binding protein subfamily protein, or a SPARC/BM-40 subfamily protein.

109. The substrate of 108, wherein the S100 subfamily protein is selected from the group consisting of a S100A1, a S100A10/p11, a S100A12/calgranulin C, a S100A2/S100L, a S100A3/S100E, a S100A4/placental calcium-binding protein, a S100A5/S100D, a S100A6/calcyclin, a S100A7/psoriasin, a S100A8/MRP-8, a S100A9/MRP-14, a S100B, a S100C, a S100P and a calbindin D9k.

110. The substrate of 108, wherein the S100 subfamily protein is selected from the group consisting of SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, and SEQ ID NO: 213.

111. The substrate of 108, wherein the Calmodulin-like subfamily protein is selected from the group consisting of a calcium-dependent protein kinase, a calmodulin, a calmodulin-like protein, a caltractin, a squidulin, a troponin C, and a nonvertebrate troponin.

112. The substrate of 108, wherein the Calmodulin-like subfamily protein is selected from the group consisting of SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, and SEQ ID NO: 237.

113. The substrate of 108, wherein the Myosin light chain subfamily protein is selected from the group consisting of a myosin essential light chain, and a myosin regulatory light chain.

114. The substrate of 108, wherein the Myosin light chain subfamily protein is selected from the group consisting of SEQ ID NO: 238, SEQ ID NO: 239, SEQ ID NO: 240, SEQ ID NO: 241, SEQ ID NO: 242, SEQ ID NO: 243, SEQ ID NO: 244, and SEQ ID NO: 245.

115. The substrate of 108, wherein the Parvalbumin subfamily protein is a parvalbumin.

116. The substrate of 108, wherein the Parvalbumin subfamily protein is SEQ ID NO: 246 or SEQ ID NO: 247.

117. The substrate of 108, wherein the Spectrin subfamily protein is a spectrin.

118. The substrate of 108, wherein the Spectrin subfamily protein is SEQ ID NO: 248 or SEQ ID NO: 249.

119. The substrate of 108, wherein the Calcineurin B subfamily protein is a calcineurin B.

120. The substrate of 108, wherein the Calcineurin B subfamily protein is SEQ ID NO: 250, SEQ ID NO: 251, SEQ ID NO: 252 or SEQ ID NO: 253.

121. The substrate of 108, wherein the Calbindin D28k subfamily protein is a calbindin D28k or a calretinin.

122. The substrate of 108, wherein the Calbindin D28k subfamily protein is selected from the group consisting of SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, and SEQ ID NO: 265.

123. The substrate of 101, wherein the Neuron specific calcium sensor protein is selected from the group consisting of a neuronal calcium sensor-1 (NCS-1), a hippocalcin and a recoverin (visinin).

124. The substrate of 108, wherein the Neuron specific calcium sensor protein is selected from the group consisting of SEQ ID NO: 266, SEQ ID NO: 267, SEQ ID NO: 268, SEQ ID NO: 269, SEQ ID NO: 270, SEQ ID NO: 271, SEQ ID NO: 272, and SEQ ID NO: 273.

125. The substrate of 108, wherein the Calpain subfamily protein is selected from the group consisting of a ALG-2, a calpain, a grancalcin and a sorcin.

126. The substrate of 108, wherein the Calpain subfamily protein is selected from the group consisting of SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, and SEQ ID NO: 293.

127. The substrate of 108, wherein the Sarcoplasmic calcium-binding protein subfamily protein is a sarcoplasmic calcium-binding protein.

128. The substrate of 108, wherein the Sarcoplasmic calcium-binding protein subfamily protein is selected from the group consisting of SEQ ID NO: 294, SEQ ID NO: 295, SEQ ID NO: 296, SEQ ID NO: 297, SEQ ID NO: 298, SEQ ID NO: 299, SEQ ID NO: 300, and SEQ ID NO: 301.

129. The substrate of 108, wherein the BM-40 subfamily protein is a BM-40.

130. The substrate of 108, wherein the BM-40 subfamily protein is SEQ ID NO: 302 or SEQ ID NO: 303.

131. The substrate of 103, wherein the EF-hand motif is derived from a LAV1, a EHF5, p24 thyroid protein, a diacylglycerol kinase (DGK), an α-actinin, a SPEC, a SPEC resembling protein (LPS), an Aequorin binding protein, a luciferin binding protein, a calcium vector protein (CVP), a 1F8, or a TB17.

132. The substrate of 93, wherein the lanthanide ion is selected from the group consisting of terbium (Tb), europium (Eu), dysprosium (Dy) and samarium (Sm).

133. The substrate of 93, wherein the acceptor is an acceptor fluorophore comprising a fluorescent protein.

134. The substrate of 96, wherein the fluorescent protein is selected from the group consisting of blue fluorescent protein, cyan fluorescent protein, green fluorescent protein, yellow fluorescent protein and red fluorescent protein.

135. The substrate of 93, wherein the acceptor is an acceptor fluorophore comprising a fluorophore binding protein.

136. The substrate of 135, wherein the fluorophore binding protein is selected from the group consisting of a tetracysteine peptide, an AGT and a dehalogenase.

137. The substrate of 136, wherein the tetracysteine peptide binds to a fluorophore selected from the group consisting of a nonfluorescent biarsenical derivative of fluorescein and a nonfluorescent biarsenical derivative of resorufin.

138. The substrate of 136, wherein the AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

139. The substrate of 136, wherein the dehalogenase binds to a fluorophore selected from the group consisting of a Coumarian derivative, a diAcFAM derivative and a TMR derivative.

140. The substrate of 93, wherein the acceptor is a non fluorescent acceptor protein 141. The substrate of 140, wherein the non fluorescent acceptor protein is a heme-containing protein.

142. The substrate of 93, wherein the lanthanide donor complex further comprises an antennae.

143. The substrate of 142, wherein the antennae is distinct from the lanthanide-binding site.

144. The substrate of 142, wherein the antennae is incorporated within lanthanide biding site.

145. The substrate of 142, wherein the antennae is selected from the group consisting of carbostyril 124 a tryptophan, and a 2-hydroxyisophthalamide.

146. The substrate of 93, wherein the Clostridial toxin recognition sequence is a botulinum toxin recognition sequence.

147. The substrate of 93, wherein the botulinum toxin recognition sequence is selected from the group consisting of a BoNT/A recognition sequence, a BoNT/B recognition sequence, a BoNT/C1 recognition sequence, a BoNT/D recognition sequence, a BoNT/E recognition sequence, a BoNT/F recognition sequence, and a BoNT/G recognition sequence.

148. The substrate of 146, wherein the BoNT/A recognition sequence comprises at least six consecutive residues of a SNAP-25 or a peptidomimetic thereof, the six consecutive residues comprising Gln-Arg, or a peptidomimetic thereof.

149. The substrate of 148, wherein the BoNT/A recognition sequence comprises SEQ ID NO: 96, or a peptidomimetic thereof.

150. The substrate of 146, wherein the BoNT/B recognition sequence comprises at least six consecutive residues of a VAMP or a peptidomimetic thereof, the six consecutive residues comprising Gln-Phe, or a peptidomimetic thereof.

151. The substrate of 150, wherein the BoNT/B recognition sequence comprises SEQ ID NO: 97, or a peptidomimetic thereof.

152. The substrate of 146, wherein the BoNT/C1 recognition sequence comprises at least six consecutive residues of VAMP or a peptidomimetic thereof, the six consecutive residues comprising Lys-Ala, or a peptidomimetic thereof.

153. The substrate of 152, wherein the BoNT/C1 recognition sequence comprises SEQ ID NO: 98, or a peptidomimetic thereof.

154. The substrate of 146, wherein the BoNT/C1 recognition sequence comprises at least six consecutive residues of VAMP or a peptidomimetic thereof, the six consecutive residues comprising Arg-Ala, or a peptidomimetic thereof.

155. The substrate of 154, wherein the BoNT/C1 recognition sequence comprises SEQ ID NO: 99, or a peptidomimetic thereof.

156. The substrate of 146, wherein the BoNT/D recognition sequence comprises at least six consecutive residues of VAMP or a peptidomimetic thereof, the six consecutive residues comprising Lys-Leu, or a peptidomimetic thereof.

157. The substrate of 156, wherein the BoNT/D recognition sequence comprises SEQ ID NO: 100, or a peptidomimetic thereof.

158. The substrate of 146, wherein the BoNT/E recognition sequence comprises at least six consecutive residues of VAMP or a peptidomimetic thereof, the six consecutive residues comprising Arg-Ile, or a peptidomimetic thereof.

159. The substrate of 158, wherein the BoNT/E recognition sequence comprises SEQ ID NO: 101, or a peptidomimetic thereof.

160. The substrate of 146, wherein the BoNT/F recognition sequence comprises at least six consecutive residues of VAMP or a peptidomimetic thereof, the six consecutive residues comprising Gln-Lys, or a peptidomimetic thereof.

161. The substrate of 160, wherein the BoNT/F recognition sequence comprises SEQ ID NO: 102, or a peptidomimetic thereof.

162. The substrate of 146, wherein the BoNT/G recognition sequence comprises at least six consecutive residues of VAMP or a peptidomimetic thereof, the six consecutive residues comprising Ala-Ala, or a peptidomimetic thereof.

163. The substrate of 162, wherein the BoNT/G recognition sequence comprises SEQ ID NO: 103, or a peptidomimetic thereof.

164. The substrate of 93, wherein the Clostridial toxin recognition sequence is a TeNT recognition sequence.

165. The substrate of 164, wherein the TeNT recognition sequence comprises at least six consecutive residues of VAMP or a peptidomimetic thereof, the six consecutive residues comprising Gln-Phe, or a peptidomimetic thereof.

166. The substrate of 165, wherein the TeNT recognition sequence comprises SEQ ID NO: 104, or a peptidomimetic thereof.

167. The substrate of 93, wherein the MTD comprises a SNAP-25 or a Syntaxin peptide which directs a Clostridial toxin substrate to the cell membrane.

168. The substrate of 167, wherein the MTD comprises a region from the interhelical region of SNAP-25 sufficient to target a toxin substrate disclosed in the present specification to the cell membrane.

168. The substrate of 168, wherein the MTD comprises amino acids 85-120 of SEQ ID NO: 1.

170. The substrate of 168, wherein the MTD comprises an amino acid sequence selected from the group consisting of SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, and SEQ ID NO: 142.

171. The substrate of 167, wherein the MTD comprises a region from the membrane anchoring domain of Syntaxin sufficient to target a toxin substrate disclosed in the present specification to the cell membrane.

171. The substrate of 171, wherein the MTD comprises an amino acid sequence selected from the group consisting of residues 266-288 of SEQ ID NO: 66, 265-288 of SEQ ID NO: 67, residues 265-288 of SEQ ID NO: 68, residues 264-287 of SEQ ID NO: 69, residues 264-288 of SEQ ID NO: 70, residues 264-288 of SEQ ID NO: 71, residues 264-289 of SEQ ID NO: 72, residues 266-288 of SEQ ID NO: 73, residues 266-288 of SEQ ID NO: 75, residues 265-288 of SEQ ID NO: 76, residues 267-290 of SEQ ID NO: 80, residues 266-289 of SEQ ID NO: 81, residues 264-289 of SEQ ID NO: 82, residues 264-289 of SEQ ID NO: 83, residues 265-283 of SEQ ID NO: 84, residues 247-269 of SEQ ID NO: 85, residues 259-282 of SEQ ID NO: 86, residues 263-288 of SEQ ID NO: 87, residues 265-288 of SEQ ID NO: 88, residues 262-288 of SEQ ID NO: 89, residues 264-286 of SEQ ID NO: 90, residues 269-291 of SEQ ID NO: 91, residues 272-295 of SEQ ID NO: 92, residues 269-292 of SEQ ID NO: 93, residues 268-290 of SEQ ID NO: 94, and residues 268-290 of SEQ ID NO: 95.

172. The substrate of 93, wherein the substrate is a peptide or peptidomimetic having a length of at most 20 residues, at most 50 residues, at most 100 residues, or at most 150 residues.

173. The substrate of 93, wherein the substrate is a peptide or peptidomimetic having a length of at least 100 residues, at least 300 residues, at least 500 residues, or at least 700 residues.

174. The substrate of 93, wherein the Clostridial toxin recognition sequence is a peptide or peptidomimetic having a length of at most 20 residues, at most 30 residues, or at most 40 residues.

175. The substrate of 93, wherein the Clostridial toxin recognition sequence is a peptide or peptidomimetic having a length of at least 20 residues, at least 50 residues, at least 100 residues, or at least 200 residues.

176. The substrate of 93, wherein the acceptor is an acceptor fluorophore comprising a fluorescent dye.

177. The substrate of 176, wherein the fluorescent dye is selected from the group consisting of a violet fluorescent dye, a blue fluorescent dye, a cyan fluorescent dye, a green fluorescent dye, a yellow-green fluorescent dye, a yellow fluorescent dye, an orange fluorescent dye, a red-orange fluorescent dye, a red fluorescent dye, a far-red fluorescent dye and an infrared fluorescent dye.

178. The substrate of 93, wherein the acceptor is a non-fluorescent acceptor molecule.

179. The substrate of 178, wherein the non-fluorescent acceptor molecule is selected from the group consisting of DNP, DABCYL, DABSYL and DABMI.

180. The substrate of 93, wherein the substrate can be cleaved with an activity of at least 1 nanomole/minute/milligram toxin, at least 20 nanomoles/minute/milligram toxin or at least 100 nanomoles/minute/milligram toxin.

181. A polynucleotide molecule encoding a Clostridial toxin substrate according to any one of Claims 93-175.

182. The polynucleotide molecule according to 181, wherein the polynucleotide molecule comprises an expression vector.

183. A cell composition comprising:
   a. a Clostridial toxin substrate according to any one of Claims 93-182.
   b. a Clostridial toxin receptor capable of initiating the intoxication process by selectively binding a Clostridial toxin.

184. The composition according to 183, wherein the Clostridial toxin receptor comprises an endogenous Clostridial toxin receptor.

185. The composition according to 184, wherein the cell transiently contains the Clostridial toxin substrate.

186. The composition according to 184, wherein the cell stably contains the Clostridial toxin substrate.

187. The composition according to 183, wherein the Clostridial toxin receptor comprises an exogenous Clostridial toxin receptor.

188. The composition according to 187, wherein the cell transiently contains the Clostridial toxin substrate, the Clostridial toxin receptor or both the Clostridial toxin substrate and the exogenous Clostridial toxin receptor.

189. The composition according to 187, wherein the cell stably contains the Clostridial toxin substrate, the exogenous Clostridial toxin receptor or both the Clostridial toxin substrate and the exogenous Clostridial toxin receptor.

200. The composition according to 183, wherein the cell is a neuronal cell.

201. The composition according to 200, wherein the neuronal cell is selected from the group consisting of a primary neuronal cell, an immortalized neuronal cell and a transformed neuronal cell.

202. The composition according to 200, wherein the neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

203. The composition according to 202, wherein the neuroblastoma cell is selected from the group consisting of Neuro-2a, SiMa, SH-SY5Y, NG108-C15, N1E-115, ND8/34 and SK-N-DZ.

204. The composition according to 183, wherein the cell is a non-neuronal cell.
205. The composition according to 204, wherein the non-neuronal cell is selected from the group consisting of a primary non-neuronal cell, an immortalized non-neuronal cell and a transformed non-neuronal cell.
206. The composition according to 204, wherein the non-neuronal cell is selected from the group consisting of an anterior pituitary cell, an adrenal cell, a pancreatic cell, an ovarian cell, a kidney cell, a stomach cell, a blood cell, an epithelial cell, a fibroblast, a thyroid cell, a chondrocyte, a muscle cell, a hepatocyte, a glandular cell.
207. The composition according to 206, wherein the kidney cell is HEK-293.
208. The composition according to 183, wherein the Clostridial toxin receptor is a BoNT/A receptor, a BoNT/B receptor, a BoNT/C1 receptor, a BoNT/D receptor, a BoNT/E receptor, a BoNT/F receptor, a BoNT/G receptor, and a TeNT receptor.
209. The composition according to 208, wherein the BoNT/A receptor is selected from the group consisting of a FGFR3 and a SV2.
210. The composition according to 209, wherein the FGFR3 is SEQ ID NO: 164, SEQ ID NO: 165, or SEQ ID NO: 166.
211. The composition according to 209, wherein the SV2 is SEQ ID NO: 167, SEQ ID NO: 168, SEQ ID NO: 169, or SEQ ID NO: 170.
212. The composition according to 208, wherein the BoNT/B receptor is selected from the group consisting of a Synaptotagmin I and a Synaptotagmin II.
213. The composition according to 209, wherein the Synaptotagmin I is SEQ ID NO: 171.
214. The composition according to 209, wherein the Synaptotagmin II is SEQ ID NO: 172.
215. A method of determining activity of a Clostridial toxin, the method comprising the steps of:
   a. contacting with a test sample a cell according to any one of the Claims 183-214
   b. exciting the lanthanide donor complex; and
   c. detecting resonance energy transfer of the treated substrate from the test sample.
   d. comparing the resonance energy transfer detected from the test sample with the resonance energy transfer detected from a control sample subjected to steps (a)-(c); wherein a difference in resonance energy transfer of the test sample as compared to a control sample is indicative of activity from a Clostridial toxin.
216. The method of 215, wherein the sample is selected from the group consisting of a crude cell lysate, a bulk Clostridial toxin, a partially purified Clostridial toxin, a purified Clostridial toxin, an isolated Clostridial toxin light chain, and a formulated Clostridial toxin product.
217. The method of 216, wherein the sample comprises a formulated Clostridial toxin product.
218. The method of 215, wherein the sample is selected from the group consisting of a raw food, a partially cooked or processed food, a cooked or processed food, a beverage, an animal feed, a soil sample, a water sample, and a pond sediments.
219. The method of 215, wherein the acceptor is a fluorophore and step (c) comprises detecting donor fluorescence intensity of the test sample, wherein an increase in substrate cleavage results in an increase in donor fluorescence intensity of the test sample as compared to the control sample, the increased donor fluorescence intensity being indicative of Clostridial toxin protease activity.
220. The method of 215, wherein the acceptor is a fluorophore and step (c) comprises detecting acceptor fluorescence intensity of the test sample, wherein an increase in substrate cleavage results in a decrease in acceptor fluorescence intensity of the test sample as compared to the control sample, the decreased acceptor fluorescence intensity being indicative of Clostridial toxin protease activity.
221. The method of 215, wherein the acceptor is a fluorophore and step (c) comprises detecting an acceptor emission maximum and a donor fluorophore emission maximum in the test sample, wherein an increase in substrate cleavage results in a shift in emission maxima from near the acceptor emission maximum to near the donor fluorophore emission maximum, the shift in emission maxima being indicative of Clostridial toxin protease activity.
222. The method of 215, wherein the acceptor is a fluorophore and step (c) comprises detecting the ratio of fluorescence amplitudes near an acceptor emission maximum over the fluorescence amplitudes near a donor fluorophore emission maximum in the test sample, wherein an increase in substrate cleavage results in a decreased ratio of the test sample as compared to the control sample, the decreased ratio being indicative of Clostridial toxin protease activity.
223. The method of 215, wherein the acceptor is a fluorophore and step (c) comprises detecting the ratio of fluorescence amplitudes near an donor emission maximum over the fluorescence amplitudes near a acceptor fluorophore emission maximum, wherein an increase in substrate cleavage results in an increased ratio in the test sample as compared to the control sample, the increased ratio being indicative of Clostridial toxin protease activity.
224. The method of 215, wherein the acceptor is a fluorophore and step (c) comprises detecting the excited state lifetime of the donor fluorophore of the test sample, wherein an increase in substrate cleavage results in an increase in donor fluorophore excited state lifetime of the test sample as compared to the control sample, the increased excited state lifetime being indicative of Clostridial toxin protease activity.
225. The method of 215, wherein the acceptor is a non-fluorescent acceptor and step (c) comprises detecting donor fluorescence intensity of the test sample, wherein an increase in substrate cleavage results in an increase in donor fluorescence intensity of the test sample as compared to the control sample, the increased donor fluorescence intensity being indicative of Clostridial toxin protease activity.
226. The method of 215, further comprising repeating step (c) at one or more later time intervals.
227. The method of 215, wherein at least 90% of the Clostridial toxin substrate is cleaved.
228. The method of 215, wherein at most 5% of the Clostridial toxin substrate is cleaved, at most 15% of the Clostridial toxin substrate is cleaved, or at most 25% of the Clostridial toxin substrate is cleaved.
229. The method of 215, wherein the conditions suitable for Clostridial toxin protease activity are selected such that the assay is linear.

EXAMPLES

The following non-limiting examples are provided for illustrative purposes only in order to facilitate a more complete understanding of disclosed embodiments and are in no way intended to limit any of the embodiments disclosed in the present invention.

Example I

Construction of a Construct Encoding a Clostridial Toxin Recognition Sequence This example illustrates how to make a Clostridial toxin recognition sequence disclosed in the present specification.

A polynucleotide molecule encoding SNAP-25$_{1-206}$ (SEQ ID NO: 2) and containing restriction endonuclease sites suitable for subsequent cloning steps is synthesized using standard procedures (BlueHeron® Biotechnology, Bothell, Wash.). Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/SNAP-25$_{1-206}$. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule encoding SNAP-25$_{1-206}$ (SEQ ID NO: 2) can be synthesized in order to improve expression in an *Escherichia coli* strain. The polynucleotide molecule encoding the SNAP-25$_{1-206}$ can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, PCT Patent Serial No. 2005/020578 (Jun. 9, 2005); Lance E. Steward et al. Optimizing Expression of Active Botulinum Toxin Type A, PCT Patent Serial No. 2005/027917 (Aug. 3, 2005). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/SNAP-25$_{1-206}$. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). Is so desired, optimization to a different organism, such as, e.g., a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005).

A similar cloning strategy is used to make pUCBHB1 cloning constructs comprising a polynucleotide molecule encoding any Clostridial toxin substrate disclosed in the present specification, such as, e.g., a polynucleotide molecule encoding a Clostridial toxin substrate comprising a BoNT/A recognition sequence; a polynucleotide molecule encoding a Clostridial toxin substrate comprising a BoNT/B recognition sequence; a polynucleotide molecule encoding a Clostridial toxin substrate comprising a BoNT/C1 recognition sequence; a polynucleotide molecule encoding a Clostridial toxin substrate comprising a BoNT/D recognition sequence; a polynucleotide molecule encoding a Clostridial toxin substrate comprising a BoNT/E recognition sequence; a polynucleotide molecule encoding a Clostridial toxin substrate comprising a BoNT/F recognition sequence; a polynucleotide molecule encoding a Clostridial toxin substrate comprising a BoNT/G recognition sequence; and a polynucleotide molecule encoding a Clostridial toxin substrate comprising a TeNT recognition sequence. As non-limiting examples, a similar cloning strategy is used to make pUCBHB1 cloning constructs comprising a polynucleotide molecule encoding a BoNT/A, BoNT/C1 and BoNT/E SNAP-25 substrate comprising amino acids 80-206 of SNAP-25 (SEQ ID NO: 2), amino acids 134-206 of SNAP-25 (SEQ ID NO: 2), amino acids 137-206 of SNAP-25 (SEQ ID NO: 2) or amino acids 141-206 of SNAP-25 (SEQ ID NO: 2); a polynucleotide molecule encoding a BoNT/B, BoNT/D, BoNT/F, BoNT/G and TeNT VAMP substrate comprising amino acids 49-92 of VAMP-1 (SEQ ID NO: 28), amino acids 33-94 of VAMP-2 (SEQ ID NO: 31), amino acids 47-90 of VAMP-2 (SEQ ID NO: 31) or amino acids 34-77 of VAMP-3 (SEQ ID NO: 33); and a polynucleotide molecule encoding a BoNT/C1 Synataxin-1 substrate comprising amino acids 1-288 of Syntaxin-1 (SEQ ID NO: 66).

Example II

Construction of Clostridial Toxin Substrates

This example illustrates how to make a Clostridial toxin substrate disclosed in the present specification.

1. Construction of BoNT/A, BoNT/C1 and BoNT/E SNAP-25 Substrates

1a. Construction of pQBI25/BFP-SNAP-25$_{1-206}$-GFP

This example illustrates how to make a Clostridial toxin substrate comprising a donor fluorophore that is a fluorescent protein, an acceptor fluorophore that is a fluorescent protein and a Clostridial toxin recognition sequence that contains a BoNT/A recognition sequence, a BoNT/C1 recognition sequence and a BoNT/E recognition sequence.

1a1. Construction of pQBI-25/SNAP-25$_{1-206}$-GFP

To construct pQBI-25/SNAP-25$_{1-206}$-GFP, a pGEX/SNAP-25$_{1-206}$ construct was digested with BamHI and EcoRI to excise a fragment containing the entire open reading frame of SNAP-25$_{1-206}$ (SEQ ID NO: 2). Alternatively, a pUCBHB1/SNAP-25$_{1-206}$ construct as described in Example I can be used. The resulting restriction fragment was purified by the QIAquick Gel Extraction Kit (QIAGEN, Inc., Valencia, Calif.), and subcloned using a T4 DNA ligase procedure into a pQBI-25A2/GFP vector (BD Biosciences-Clonetech, Palo Alto, Calif.), digested BamHI and NotI, to yield pQBI-25/SNAP-25$_{1-206}$-GFP. The ligation mixture was transformed into chemically competent *E. coli* TOP10 cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding the SNAP-25$_{1-206}$-GFP operably-linked to the expression elements of the pQBI-25 expression vector.

1a2. Construction of pCR2.1/SNAP-25$_{1-206}$-GFP

To construct pCR2.1/SNAP-25$_{1-206}$-GFP, a polynucleotide fragment encoding the amino acid region comprising SNAP-25$_{1-206}$-GFP was amplified from a pQBI-25/SNAP-25$_{1-206}$-GFP using a polymerase chain reaction method and subcloned into a pCR2.1 vector using the TOPO® TA cloning method (Invitrogen, Inc, Carlsbad, Calif.). The polymerase chain reaction (PCR) mix contained 5 µL of 10× Pfu Buffer, 1 µL of deoxyribonucleotides (containing 12.5 mM of each deoxyribonucleotide), 1 µL of Pfu Turbo DNA polymerase (2.5 units/µL), 125 ng of each primer, 50 ng of pQBI-25/SNAP-25$_{1-206}$-GFP template DNA, and nuclease-free water to a final volume of 50 µL. The thermocycler conditions were: one cycle of 95° C. for 2 minutes; 25 cycles of 95° C. for 1 minute, 50° C. for 30 seconds, and 72° C. for 18 minutes; one cycle of 72° C. for 5 minutes; and 10° C. to hold. Following thermocycling, 1 µL of DpnI restriction enzyme (Stratagene, La Jolla, Calif.) was added to the reaction and incubated for 1 hour at 37° C. to digest the template DNA. The reaction was purified by QIAquick kit (QIAGEN, Inc., Valencia, Calif.) and analysis by agarose gel electrophoresis showed that the reaction produced full-length plasmid. The amplification mixture was transformed into chemically competent E. coli TOP10 cells (Invitrogen, Inc, Carlsbad, Calif.) using a heat shock method, plated on 1.5% Luria-Bertani agar plates (pH 7.0) containing 50 µg/mL of Kanamycin, and placed in a 37° C. incubator for overnight growth. Kanamycin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 50 µg/mL of Kanamycin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a pCR2.1 construct encoding SNAP-25$_{1-206}$-GFP.

1a3. Construction of pQBI-50/BFP—SNAP-25$_{1-206}$-GFP

To construct pQBI-25/BFP—SNAP-25$_{1-206}$-GFP, the resulting pCR2.1/SNAP-25$_{1-206}$-GFP construct from 1a2 was digested with BamHI and NotI to excise a fragment containing the SNAP-25$_{1-206}$-GFP open reading frame. This BamHI and NotI restriction fragment was purified by the QIAquick Gel Extraction Kit (QIAGEN, Inc., Valencia, Calif.), and subcloned using a T4 DNA ligase procedure into a pQBI-50 C3/BFP vector (BD Biosciences-Clonetech, digested with BamHI and NotI and dephosphorylated with shrimp alkaline phosphatase, to yield pQBI-50/BFP-SNAP-25$_{1-206}$-GFP. The ligation mixture was transformed into chemically competent E. coli TOP10 cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding BFP—SNAP-25$_{1-206}$-GFP (SEQ ID NO: 173) operably-linked to the expression elements of the pQBI-50 expression vector.

A similar cloning strategy was used to construct BFP—SNAP-25$_{80-206}$-GFP (SEQ ID NO: 174) operably-linked to the expression elements of the pQBI-50 mammalian expression vector.

1b. Construction of pQBI25/GFP-SNAP-25$_{134-206}$

This example illustrates how to make a Clostridial toxin substrate comprising a donor fluorophore that is a fluorescent protein, an acceptor fluorophore that is a fluorescent protein and a Clostridial toxin recognition sequence that contains a BoNT/A recognition sequence, a BoNT/C1 recognition sequence and a BoNT/E recognition sequence.

1b1. Construction of pQBI-25/GFP

To construct pQBI-25/GFP, a pQBI-T7/GFP vector (BD Biosciences-Clonetech, Palo Alto, Calif.) was PCR-modified to remove the stop codon at the 3' terminus of the GFP-coding sequence and to insert the coding sequence for a portion of the peptide linker separating GFP from the SNAP-25$_{134-206}$ fragment.

1b2. Construction of pQBI-25/GFP-SNAP-25$_{134-206}$

To construct pQBI-25/GFP-SNAP-25$_{134-206}$, a polynucleotide fragment encoding amino acids 134-206 of SNAP-25 (SEQ ID NO: 2) was amplified from a pQE50/BirASNAP-25$_{128-206}$. Alternatively, a pUCBHB1/SNAP-25$_{134-206}$ construct as described in Example I can be used. The 5' oligonucleotide primer was designed to incorporate the coding sequence for the remainder of the peptide linker fused to the 5' end of the polynucleotide fragment encoding SNAP-25$_{134-206}$. The 3' oligonucleotide primer was designed to incorporate a 6×His affinity tag operationally-linked to the 3' end of the polynucleotide fragment encoding SNAP-25$_{134-206}$. The resultant PCR product was cloned into the pQBI-25/GFP described in 1b1 to yield pQBI-25/GFP-SNAP-25$_{134-206}$. The ligation mixture was transformed into chemically competent E. coli TOP10 cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding GFP-SNAP-25$_{134\text{-}206}$ operably-linked to the expression elements of the pQBI-25 expression vector.

1b3. Construction of pCR2.1/BFP

To construct pCR2.1/BFP, a polynucleotide fragment encoding the amino acid region comprising BFP was amplified from a pQBI-25/BFP using a polymerase chain reaction method and subcloned into a pCR2.1 vector using the TOPO® TA cloning method (Invitrogen, Inc, Carlsbad, Calif.). The polymerase chain reaction (PCR) mix contained 5 μL of 10× Pfu Buffer, 1 μL of deoxyribonucleotides (containing 12.5 mM of each deoxyribonucleotide), 1 μL of Pfu Turbo DNA polymerase (2.5 units/μL), 125 ng of each primer, 50 ng of pQBI-25/BFP template DNA, and nuclease-free water to a final volume of 50 μL. The thermocycler conditions were: one cycle of 95° C. for 2 minutes; 25 cycles of 95° C. for 1 minute, 50° C. for 30 seconds, and 72° C. for 18 minutes; one cycle of 72° C. for 5 minutes; and 10° C. to hold. Following thermocycling, 1 μL of DpnI restriction enzyme (Stratagene, La Jolla, Calif.) was added to the reaction and incubated for 1 hour at 37° C. to digest the template DNA. The reaction was purified by QIAquick kit (QIAGEN, Inc., Valencia, Calif.) and analysis by agarose gel electrophoresis showed that the reaction produced full-length plasmid. The amplification mixture was transformed into chemically competent E. coli TOP10 cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Kanamycin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 50 μg/mL of Kanamycin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a pCR2.1 construct encoding BFP.

1b4. Construction of pQBI-25/GFP-SNAP-25$_{134\text{-}206}$-BFP

To construct pQBI-25/GFP-SNAP-25$_{134\text{-}206}$-BFP, the resulting pCR2.1/BFP construct from 1b3 was digested with KpnI to excise a fragment containing the BFP open reading frame. This KpnI restriction fragment was purified by the QIAquick Gel Extraction Kit (QIAGEN, Inc., Valencia, Calif.), and subcloned using a T4 DNA ligase procedure into a pQBI-25/GFP-SNAP-25$_{134\text{-}206}$ construct described in 1b2, digested with KpnI and dephosphorylated with shrimp alkaline phosphatase, to yield pQBI-25/GFP-SNAP-25$_{134\text{-}206}$-BFP. The ligation mixture was transformed into chemically competent E. coli TOP10 cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding GFP-SNAP-25$_{134\text{-}206}$-BFP (SEQ ID NO: 175) operably-linked to the expression elements of the pQBI-25 expression vector.

1c. Construction of pQBI25/GFP-SNAP-25$_{134\text{-}206}$(Cys)-Alexa Fluor® 546

This example illustrates how to make a Clostridial toxin substrate comprising a donor fluorophore that is a fluorescent protein, an acceptor fluorophore that is a fluorescent dye and a Clostridial toxin recognition sequence that contains a BoNT/A recognition sequence, a BoNT/C1 recognition sequence and a BoNT/E recognition sequence.

1c1. Construction of pQBI-25/GFP-SNAP-25$_{134\text{-}206}$(Cys)

To construct pQBI-25/GFP-SNAP-25$_{134\text{-}206}$(Cys), a open reading frame encoding a GFP-SNAP-25$_{134\text{-}206}$ from a pQBI-25/GFP-SNAP-25$_{134\text{-}206}$, as described in 1b2, was modified by a PCR-based in vitro mutagenesis procedure to incorporate a cysteine residue at the carboxyl-terminus of the substrate. The polymerase chain reaction (PCR) mix contained 5 μL of 10× Pfu Buffer, 1 μL of deoxyribonucleotides (containing 12.5 mM of each deoxyribonucleotide), 1 μL of Pfu Turbo DNA polymerase (2.5 units/μL), 125 ng of each primer, 30 ng of pQBI-25/GFP-SNAP-25$_{134\text{-}206}$ template DNA, and nuclease-free water to a final volume of 50 μL. The oligonucleotide primers used to introduce the cysteine residue were as follows: 5' Primer Cys-Stop, 5'-GTTATTGCTCAGCTTTAGCAGTGATGGTGATGGTG-3' and 3' Primer Cys-Stop, 5'-CACCATCACATCACTGCTAAAGCTGAGCAATAAC-'3. Amplify the GFP-SNAP-25$_{134\text{-}206}$ coding region introduced a cysteine residue followed by the termination codon. The thermocycler conditions were: one cycle of 95° C. for 2 minutes; 25 cycles of 95° C. for 1 minute, 50° C. for 30 seconds, and 72° C. for 12 minutes; one cycle of 72° C. for 5 minutes; and 10° C. to hold. Following thermocycling, 1 μL of DpnI restriction enzyme (Stratagene, La Jolla, Calif.) was added to the reaction and incubated for 1 hour at 37° C. to digest the template DNA. The reaction was purified by QIAquick kit (QIAGEN, Inc., Valencia, Calif.) and analysis by agarose gel electrophoresis showed that the reaction produced full-length plasmid. The amplification mixture was transformed into chemically competent E. coli TOP10 cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Kanamycin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 50 μg/mL of Kanamycin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding GFP-SNAP-25$_{134-206}$(Cys) (SEQ ID NO: 176) operably-linked to the expression elements of the pQBI-25 expression vector.

1c2. Expression and purification of pQBI-25/GFP-SNAP-25$_{134-206}$(Cys)

To express GFP-SNAP-25$_{134-206}$(Cys), pQBI-25/GFP-SNAP-25$_{134-206}$(Cys) was transformed into *E. coli* BL21-CodonPluse (DE2)-RIL cells (Stratagene, La Jolla, Calif.) containing the T7 RNA polymerase gene using a heat shock method, plated on 1.5% Luria-Bertani agar plates (pH 7.0) containing 100 µg/mL of Ampicillin, and placed in a 37° C. incubator for overnight growth. Ampicillin-resistant colonies were used to inoculate 5 L baffled flasks containing 500 mL of Luria-Bertani media containing 100 µg/mL of Ampicillin and placed in a 37° C. incubator, shaking at 250 rpm, for overnight growth. Cells were harvested by centrifugation (6,000×g at 4° C. for 15 minutes) and used immediately, or stored dry at –80° C. until needed.

To purify GFP-SNAP-25$_{134-206}$(Cys), the cell pellet from above was resuspended in 10 mL Fusion Protein Column Binding Buffer (25 mM HEPES, pH 8.0; 500 mM NaCl; 1 mM β-mercaptoethanol; 10 mM imidazole) to which had been added 100 µL (10 µL/mL) Protease Inhibitor Cocktail Set III (EMD Biosciences-Calbiochem, San Diego Calif.). The cell suspension was sonicated on ice (1 min 40 sec in 10-sec pulses at 38% amplitude on a Branson Digital Sonifier) in order to lyse the cells and release the GFP-SNAP-25$_{134-206}$(Cys), and then centrifuged (16,000 rpm at 4° C. for 45 minutes) to clarify the lysate. An immobilized metal affinity chromatography column was prepared using a 20 mL Econo-Pac column support (Bio-Rad Laboratories, Hercules, Calif.) packed with 8.0 mL of TALON™ SuperFlow Co$^{2+}$ affinity resin (BD Biosciences-Clontech, Palo Alto, Calif.), which was then equilibrated by rinsing with 8 column volumes of deionized, distilled water, followed by 8 column volumes of Column Binding Buffer. The clarified lysates were added to the resin and batch bound by horizontal incubation for 1 to 1.5 hour with gentle rocking. Following batch binding, the columns were righted and the solutions drained, collected, and batch bound over the resin beds again by horizontal incubation for 1 to 1.5 hour with gentle rocking. The columns were then washed with 8 column volumes of Column Wash Buffer ((25 mM HEPES, pH 8.0; 500 mM sodium chloride; 0.1% (v/v) Triton-X® 1004-octylphenol polyethoxylate; 10% (v/v) glycerol; 1 mM β-mercaptoethanol; 20 mM imidazole) and GFP-SNAP-25$_{134-206}$(Cys) eluted with 15 mL Column Elution Buffer (25 mM HEPES, pH 8.0; 500 mM NaCl; 1 mM β-mercaptoethanol; 500 mM imidazole), which was collected in fractions of approximately 1.4 mL. The green fractions were combined and concentrated to a total volume less than 5 mL in an Apollo 20-mL concentrator (QMWL 25 kDa, Orbital Biosciences). The green fractions were then desalted using a FPLC desalting column. A HiPrep™ 26/10 size exclusion column (Amersham Biosciences, Piscataway, N.J.) was pre-equilibrated with 80 mL of 4° C. Column Buffer (50 mM sodium phosphate, pH 6.5). After the column was equilibrated, a GFP-SNAP-25$_{134-206}$(Cys) sample was applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted GFP-SNAP-25$_{134-206}$(Cys) sample was collected as a single fraction and the protein concentration determined by BioRad Protein Assay (Bio-Rad Laboratories, Hercules, Calif.). The protein solutions were divided into 500 µL aliquots, flash-frozen with N$_2$ (I) and stored at –80° C. Once defrosted, working aliquots are stored at 4° C., protected from light.

1c3. Covalent Attachment of Alexa 546 C$_5$ Maleimide to GFP-SNAP-25$_{134-206}$(Cys)

To chemically conjugate GFP-SNAP-25$_{134-206}$(Cys) to a fluorescent dye, 4 µL of 10 mM Alexa Fluor® 546 C$_5$ maleimide (Invitrogen, Inc., Carlsbad, Calif.) were added to 200 µL of solution containing 135 mM GFP-SNAP-25$_{134-206}$(Cys) in 25 mM HEPES, pH 7.2) and incubated overnight at 4° C. The reactions were transferred to Biomax Ultrafree centrifugal filters (30 KDa NMWL, Millipore), concentrated, and then reconcentrated two times from 25 mM HEPES, pH 7.2, to remove most of the excess Alexa Fluor® 546. To remove the remaining unreacted Alexa Fluor® 546, the concentrated solutions were transferred to Spin Microdialyzers (Harvard Apparatus) and each was dialyzed against 500 mL 20 mM HEPES, pH 6.9, for 1 hour, and against 3×250 mL of that buffer for approximately 1.5 hour each. This labeling strategy yielded a GFP-SNAP-25$_{134-206}$(Cys)-Alexa Fluor® 546 substrate. Small aliquots were removed for fluorescence measurements and the balance of the reactions were flash-frozen in N$_2$(1) and stored at –80° C.

1d. Construction of pQBI25/GFP-SNAP-25$_{134-206}$(Cys)-CS124-DTPA-EMCH-Tb

This example illustrates how to make a Clostridial toxin substrate comprising a lanthanide donor complex, an acceptor fluorophore that is a fluorescent protein and a Clostridial toxin recognition sequence that contains a BoNT/A recognition sequence, a BoNT/C1 recognition sequence and a BoNT/E recognition sequence.

1d1. Covalent Attachment of CS124-DTPA-EMCH-Tb Maleimide to GFP-SNAP-25$_{134-206}$(Cys)

To produce a Clostridial toxin substrate comprising a lanthanide donor complex, the lumiphore CS124-DTPA-EMCH-Tb (Invitrogen, Inc., Carlsbad, Calif.) was derivatized to the carboxy-terminal cysteine of GFP-SNAP-25$_{134-206}$(Cys) using maleimide chemistry at pH 6.9 in HEPES buffer. Unreacted probe was removed by extensive dialysis in 20 mM HEPES buffer pH 6.9 using a 25 kDa membrane.

1e1. Construction of pQBI-25/CALMOD-SNAP-25$_{134-206}$-GFP

This example illustrates how to make a Clostridial toxin substrate comprising a lanthanide donor complex comprising an EF-hand, an acceptor fluorophore that is a fluorescent protein and a Clostridial toxin recognition sequence that contains a BoNT/A recognition sequence, a BoNT/C1 recognition sequence and a BoNT/E recognition sequence.

To construct pQBI-25/CALMOD-SNAP-25$_{134-206}$, a polynucleotide molecule encoding CALMOD-SNAP-25$_{134-206}$-GFP and containing restriction endonuclease sites suitable for subsequent cloning steps is synthesized as described in Example I. The resulting construct, pUCBHB1/CALMOD-SNAP-25$_{1-206}$, includes the EF1-hand derived from Calmodulin-I (SEQ ID NO: 214) and the BoNT/A, /C1, and /E recognition sequence (amino acids 134-206 of SEQ ID NO: 2). pUCBHB1/CALMOD-SNAP-25$_{1-206}$ will be digested with BamHI and EcoRI to excise a fragment containing the entire open reading frame of CALMOD-SNAP-25$_{1-206}$. The resulting restriction fragment was purified by the QIAquick Gel Extraction Kit (QIAGEN, Inc., Valencia, Calif.), and subcloned using a T4 DNA ligase procedure into a pQBI-25A2/GFP vector (BD Biosciences-Clonetech, Palo Alto, Calif.), digested BamHI and NotI, to yield pQBI-25/SNAP-25$_{1-206}$-GFP. The ligation mixture was transformed into chemically competent *E. coli* TOP10 cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yields a mammalian expression construct encoding the CALMOD-SNAP-25$_{1-206}$-GFP operably-linked to the expression elements of the pQBI-25 expression vector.

A similar cloning strategy can be used to construct a Clostridial toxin substrate where the lanthanide donor complex comprises an EF-hand of SEQ ID NO: 181 through SEQ ID NO: 213 and SEQ ID NO: 215 through SEQ ID NO: 303. Likewise, a similar strategy can be used to construct a Clostridial toxin substrate comprising a BoNT/B, /D, /F, /G and/or TeNT recognition sequence as disclosed in the present specification.

2. Construction of BoNT/B, BoNT/D, BoNT/F, BoNT/G and TeNT VAMP Substrates

2a. Construction of pQBI25/GFP-VAMP-1$_{49-92}$-BFP

This example illustrates how to make a Clostridial toxin substrate comprising a donor fluorophore that is a fluorescent protein, an acceptor fluorophore that is a fluorescent protein and a Clostridial toxin recognition sequence that contains a BoNT/B recognition sequence, a BoNT/D recognition sequence, a BoNT/F recognition sequence, a BoNT/G recognition sequence and a TeNT recognition sequence.

2a1. Construction of pQBI25/GFP-VAMP-1$_{49-92}$

To construct pQBI-25/GFP-VAMP-1$_{49-92}$, a pUCBHB1/VAMP-1$_{49-92}$ construct, as described in Example I, will be digested with the appropriate restriction endonucleases to excise a fragment containing the VAMP-1$_{49-92}$ open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pQBI-25C3 vector (BD Biosciences-Clonetech, Palo Alto, Calif.), to yield pQBI-25/GFP-VAMP-1$_{49-92}$. The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-1$_{49-92}$ operably-linked to the expression elements of the pQBI-25 expression vector.

2a2. Construction of pQBI-25/GFP-VAMP-1$_{49-92}$-BFP

To construct pQBI-25/GFP-VAMP-1$_{49-92}$-BFP, the resulting pCR2.1/BFP construct from 1a2 will be digested with KpnI to excise a fragment containing the BFP open reading frame. This KpnI restriction fragment will be purified by the QIAquick Gel Extraction Kit (QIAGEN, Inc., Valencia, Calif.), and will be subcloned using a T4 DNA ligase procedure into a pQBI-25/GFP-VAMP-1$_{49-92}$ construct described in 2a2, digested with KpnI and dephosphorylated with shrimp alkaline phosphatase, to yield pQBI-25/GFP-VAMP-1$_{49-92}$-BFP. The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 μg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding GFP-VAMP-1$_{49-92}$-BFP (SEQ ID NO: 177) operably-linked to the expression elements of the pQBI-25 expression vector.

2b. Construction of pQBI25/GFP-VAMP-2$_{33-94}$-BFP

This example illustrates how to make a Clostridial toxin substrate comprising a donor fluorophore that is a fluorescent protein, an acceptor fluorophore that is a fluorescent protein and a Clostridial toxin recognition sequence that contains a BoNT/B recognition sequence, a BoNT/D recognition sequence, a BoNT/F recognition sequence, a BoNT/G recognition sequence and a TeNT recognition sequence.

2b1. Construction of pQBI25/GFP-VAMP-2$_{33-94}$

To construct pQBI-25/GFP-VAMP-2$_{33-94}$, a pUCBHB1/VAMP-2$_{33-94}$ construct, as described in Example I, will be digested with the appropriate restriction endonucleases to excise a fragment containing the VAMP-2$_{33-94}$ open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pQBI-25C3 vector (BD Biosciences-Clonetech, Palo Alto, Calif.), to yield pQBI-25/GFP-VAMP-2$_{33-94}$. The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-$2_{33-94}$ operably-linked to the expression elements of the pQBI-25 expression vector.

2b2. Construction of pQBI-25/GFP-VAMP-$2_{33-94}$-BFP

To construct pQBI-25/GFP-VAMP-$2_{33-94}$-BFP, the resulting pCR2.1/BFP construct from 1a2 will be digested with KpnI to excise a fragment containing the BFP open reading frame. This KpnI restriction fragment will be purified by the QIAquick Gel Extraction Kit (QIAGEN, Inc., Valencia, Calif.), and will be subcloned using a T4 DNA ligase procedure into a pQBI-25/GFP-VAMP-$2_{33-94}$ construct described in 2b2, digested with KpnI and dephosphorylated with shrimp alkaline phosphatase, to yield pQBI-25/GFP-VAMP-$2_{33-94}$-BFP. The ligation mixture will be transformed into chemically competent E. coli TOP10 cells (Invitrogen, Inc, Carlsbad, Calif.) using a heat shock method, will be plated on 1.5% Luria-Bertani agar plates (pH 7.0) containing 100 µg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-$2_{33-94}$-BFP (SEQ ID NO: 178) operably-linked to the expression elements of the pQBI-25 expression vector.

2c. Construction of pQBI25/GFP-VAMP-$3_{34-77}$-BFP

This example illustrates how to make a Clostridial toxin substrate comprising a donor fluorophore that is a fluorescent protein, an acceptor fluorophore that is a fluorescent protein and a Clostridial toxin recognition sequence that contains a BoNT/B recognition sequence, a BoNT/D recognition sequence, a BoNT/F recognition sequence, a BoNT/G recognition sequence and a TeNT recognition sequence.

2c1. Construction of pQBI25/GFP-VAMP-$3_{34-77}$

To construct pQBI-25/GFP-VAMP-$3_{34-77}$, a pUCBHB1/VAMP-$3_{34-77}$ construct, as described in Example I, will be digested with the appropriate restriction endonucleases to excise a fragment containing the VAMP-$3_{34-77}$ open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pQBI-25C3 vector (BD Biosciences-Clonetech, Palo Alto, Calif.), to yield pQBI-25/GFP-VAMP-$3_{34-77}$. The ligation mixture will be transformed into chemically competent E. coli TOP10 cells (Invitrogen, Inc, Carlsbad, Calif.) using a heat shock method, will be plated on 1.5% Luria-Bertani agar plates (pH 7.0) containing 100 µg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-$3_{34-77}$ operably-linked to the expression elements of the pQBI-25 expression vector.

2c2. Construction of pQBI-25/GFP-VAMP-$3_{34-77}$-BFP

To construct pQBI-25/GFP-VAMP-$3_{34-77}$-BFP, the resulting pCR2.1/BFP construct from 1a2 will be digested with KpnI to excise a fragment containing the BFP open reading frame. This KpnI restriction fragment will be purified by the QIAquick Gel Extraction Kit (QIAGEN, Inc., Valencia, Calif.), and will be subcloned using a T4 DNA ligase procedure into a pQBI-25/GFP-VAMP-$3_{34-77}$ construct described in 2b2, digested with KpnI and dephosphorylated with shrimp alkaline phosphatase, to yield pQBI-25/GFP-VAMP-$3_{34-77}$-BFP. The ligation mixture will be transformed into chemically competent E. coli TOP10 cells (Invitrogen, Inc, Carlsbad, Calif.) using a heat shock method, will be plated on 1.5% Luria-Bertani agar plates (pH 7.0) containing 100 µg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-$3_{34-77}$-BFP (SEQ ID NO: 179) operably-linked to the expression elements of the pQBI-25 expression vector.

3. Construction of BoNT/C1 Syntaxin Substrate

3a. Construction of pQBI25/GFP-Syntaxin-$1_{1-288}$-BFP

This example illustrates how to make a Clostridial toxin substrate comprising a donor fluorophore that is a fluorescent protein, an acceptor fluorophore that is a fluorescent protein and a Clostridial toxin recognition sequence that contains a BoNT/C1 recognition sequence.

3a1. Construction of pQBI25/GFP-Syntaxin-1$_{1-288}$

To construct pQBI-25/GFP-Syntaxin-1$_{1-288}$, a pUCBHB1/Syntaxin-1$_{1-288}$ construct, as described in Example I, will be digested with the appropriate restriction endonucleases to excise a fragment containing the Syntaxin-1$_{1-288}$ open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pQBI-25C3 vector (BD Biosciences-Clonetech, Palo Alto, Calif.), to yield pQBI-25/GFP-Syntaxin-1$_{1-288}$. The ligation mixture will be transformed into chemically competent E. coli TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-Syntaxin-1'-288 operably-linked to the expression elements of the pQBI-25 expression vector.

3a2. Construction of pQBI-25/GFP-Syntaxin-1$_{1-288}$-BFP

To construct pQBI-25/GFP-Syntaxin-1$_{1-288}$-BFP, the resulting pCR2.1/BFP construct from 1a2 will be digested with KpnI to excise a fragment containing the BFP open reading frame. This KpnI restriction fragment will be purified by the QIAquick Gel Extraction Kit (QIAGEN, Inc., Valencia, Calif.), and will be subcloned using a T4 DNA ligase procedure into a pQBI-25/GFP-Syntaxin-1$_{1-288}$ construct described in 3a2, digested with KpnI and dephosphorylated with shrimp alkaline phosphatase, to yield pQBI-25/GFP-Syntaxin-1$_{1-288}$-BFP. The ligation mixture will be transformed into chemically competent E. coli TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 μg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-Syntaxin-1$_{1-288}$-BFP (SEQ ID NO: 180) operably-linked to the expression elements of the pQBI-25 expression vector.

Example III

Identification of Cell Lines with High Affinity Uptake for a Clostridial Toxin

Distinct sensitivities to each of the Clostridial toxin might be expected based on the individual receptor systems for each different toxin and toxin serotype and their differing expression in different cell lines. The presence of a high affinity receptor system in a cell for Clostridial toxin can be characterized by two attributes: a rapid uptake of the neurotoxin by the cell, and a low neurotoxin concentration needed for cell intoxication. To identify a cell line having a high affinity receptor system for a Clostridial toxin, we tested cell lines using one of two different in vitro cleavage assay, one to determine the amount of toxin required for intoxication, the other to determine the length of time necessary for the cell to uptake the neurotoxin.

1. Identification of Cell Lines with High Affinity Uptake for BoNT/A

1a. Assay to Determine the BoNT/A Concentration Necessary for Cell Intoxication

In order to assess the amount of BoNT/A needed to intoxicate a cell, a panel of mammalian cell lines of neuronal origin was screened to determine the concentration of toxin necessary to cleave endogenously expressed SNAP-25 (see Table 14). A suitable seed density of cells from each line was plated into individual wells of 6-well, poly-D-lysine/Laminin coated, tissue culture plates containing 3 mL of a suitable medium (see Table 14), and grown in a 37° C. incubator under 5% carbon dioxide for approximately 24 hours. BoNT/A (Metabiologics, Inc., Madison, Wis.) was added at different concentrations (0 nM, 1 nM, 5 nM, 12.5 nM, 25 nM, 50 nM) in the culture medium containing the cells for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 6A:
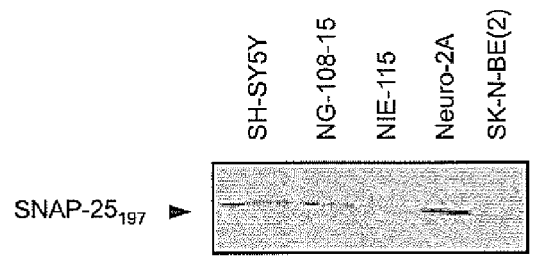
FIG. 6a shows a Western blot analysis used to identify cells capable of BoNT/A uptake. The blot shows five cell lines treated with 1 nM of Pure BoNT/A overnight, with equal amounts of protein loaded per lane and probed with an antibody that detects the BoNT/A SNAP-25$_{197}$ cleavage product.

To detect for the presence of a cleaved BoNT/A substrate, samples were boiled for 5 min, and 40 μl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-200 (25 mM Tris-Buffered Saline, 0.1% TWEEN-20®, polyoxyethylene (20) sorbitan monolaureate) containing a 1:5,000 dilution of rabbit polyclonal anti-SNAP25 antiserum pAb anti-SNAP25197 #1, a polyclonal antibody which is specific for the SNAP25$_{197}$-cleavage product and does not cross-react with full-length SNAP25$_{206}$, (Allergan, Inc., generated under contract with Zymed Laboratories Inc., South San Francisco, Calif.). Primary antibody probed blots were washed three times for 15 minutes each time in Tris-Buffered Saline TWEEN-20®. Washed membranes were incubated at room temperature for 2 hours in Tris-Buffered Saline TWEEN-20® containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of the labeled BoNT/A SNAP25$_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A BoNT/A SNAP25$_{197}$-cleavage product was detected in the cell lines SH-SY5Y, NG108-15, N1E-115, Neuro-2A and SK-N-BE(2) after at least an 8 hour incubation with at least 5 nM BoNT/A, thereby indicating the ability of BoNT/A to intoxicate these cell lines (see FIG. 6a).

Figure 6B:
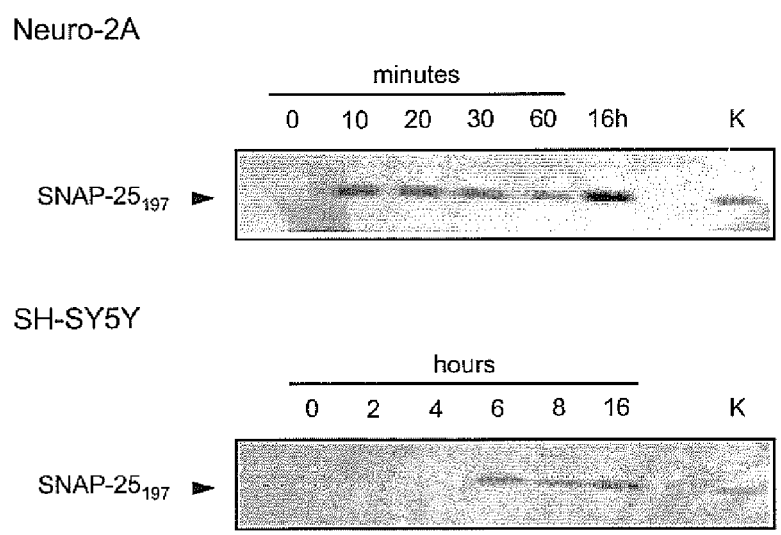
FIG. 6b shows Western blot analysis used to evaluate the time necessary for BoNT/A uptake. The blots show either Neuro-2A cells or SH-SY5Y cells treated with 1 nM of Pure BoNT/A for various lengths of time, with equal amounts of protein loaded per lane and probed with an antibody that detects the BoNT/A SNAP-25$_{197}$ cleavage product.
Figure 6C:
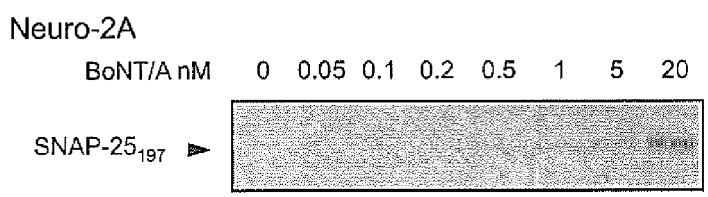
FIG. 6c shows a Western blot analysis used to evaluate the concentration range necessary of BoNT/A uptake. The blots show Neuro-2A cells treated with a range of Pure BoNT/A concentrations overnight, with equal amounts of protein loaded per lane and probed with an antibody that detects the BoNT/A SNAP-25$_{197}$ cleavage product.

0.1 nM, 0.2 nM, 0.5 nM, 1 nM, 5 nM and 20 nM) in the culture medium containing cells for either approximately 8 or approximately 16 hours. Toxin treated cells were harvested and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell line Neuro-2A after at least a 8 hour incubation with at least 0.5 nM BoNT/A, thereby indicating the ability of BoNT/A to intoxicate these cell lines (see FIG. 6c).

1b. Assay to Determine the Time Required by a Cell to Uptake BoNT/A

In order to assess the amount of time needed by a cell line to uptake BoNT/A, a panel of mammalian cell lines of neuronal origin was screened to determine the length of toxin exposure necessary to cleave endogenously expressed SNAP-25. Cells from each line were grown in poly-D-lysine/Laminin coated 6-well plates as described above in Example II, 1a. Approximately 1 nM BoNT/A (Metabiologics, Inc., Madison, Wis.) was added to the culture medium for 10 min, 20 min, 30 min, 60 min 2 hours, 4 hours, 6 hours, 8 hours or 16 hours. Toxin treated cells were collected and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell lines Neuro-2A, SH-SY5Y, and NG108-15 after at least an 8 hour incubation with 1 nM BoNT/A, thereby indicating the ability of these cell lines to rapidly uptake BoNT/A (see FIG. 6b).

TABLE 14

Culture Conditions for Cell Lines

| Cell Line | Complete Culture Media | Passage Conditions | Seed Density (cells/mm$^2$) |
| --- | --- | --- | --- |
| SK-N-DZ | 90% DMEM, A | Trypsin/EDTA treatment, 1:4 dilution split every 2-3 day | $4.25 \times 10^3$ |
| SK-N-F1 | 90% DMEM, A | Trypsin/EDTA treatment, 1:4 dilution spilt twice a week | $4.25 \times 10^3$ |
| SK-N-SH | Ham's F12, DMEM or EMEM, B | Trypsin/EDTA treatment, 1:20 dilution split every 4-7 day | $4.25 \times 10^3$ |
| SH-SY5Y | EMEM and Ham's F12 1:1, C | Trypsin/EDTA treatment, 1:6 dilution split every 2-3 day | $4.25 \times 10^3$ |
| SK-N-BE(2) | EMEM and Ham's F12 1:1, D | Trypsin/EDTA treatment, 1:6 dilution split every 3 day | $4.25 \times 10^3$ |
| BE(2)-C | EMEM and Ham's F12 1:1, D | Trypsin/EDTA treatment, 1:4 dilution split every 2-3 day | $4.25 \times 10^3$ |
| BE(2)-M17 | EMEM and Ham's F12 1:1, D | Trypsin/EDTA treatment, 1:20 dilution split every 4-7 day | $4.25 \times 10^3$ |
| Neuro 2a | EMEM, E | Trypsin/EDTA treatment, 1:3 dilution split every 3 day | $4.25 \times 10^3$ |
| C1300 | RPMI 1640, B | Trypsin/EDTA treatment, 1:3 dilution split every 3 day | $4.25 \times 10^3$ |
| NB4 1A3 | Ham's F10, F | Trypsin/EDTA treatment, 1:3 dilution split every 3 day | $4.25 \times 10^3$ |
| N1E-115 | DMEM, G | Trypsin/EDTA treatment, 1:3 dilution split every 3 day | $4.25 \times 10^3$ |
| NG108-15 | DMEM, B | 1:4 dilution split every 1-2 days | $4.25 \times 10^3$ |
| HCN-1A | DMEM, H | Trypsin/EDTA treatment, 1:3 dilution split every 3 day | $4.25 \times 10^3$ |
| HCN-2 | DMEM, H | Trypsin/EDTA treatment, 1:3 dilution split every 3 day | $4.25 \times 10^3$ |
| TE 189.T | DMEM, H | Trypsin/EDTA treatment, 1:3 dilution split every 3 day | $4.25 \times 10^3$ |
| ND8/34 | DMEM, B | Trypsin/EDTA treatment, 1:3 dilution split every 3 day | $4.25 \times 10^3$ |

A contains 1.5 g/L sodium bicarbonate, 0.1 mM Non-essential amino acids (NEAA), 4 mM Glutamine & 10% Fetal Calf serum (FCS)
B contains 2 mM Glutamine & 10% FCS
C contains 1.5 g/L sodium bicarbonate, 0.1 mM NEAA, 4 mM Glutamine, 1% sodium pyruvate, 1% penicillin/streptomycin (P/S) & 10% FCS
D contains 0.1 mM NEAA, 4 mM Glutamine, & 10% FCS
E contains 1.5 g/L sodium bicarbonate, 0.1 mM NEAA, 2 mM Glutamine, 1 mM sodium pyruvate & 10% FCS
F contains 2 mM Glutamine, 15% Horse Serum & 2.5% FCS
G contains 4.5 g/L glucose & 10% FCS
H contains 4 mM glucose & 10% FCS
Freeze medium comprises 95% culture medium and 5% DMSO The mouse neuroblastoma cell line Neuro-2A was further analyzed with lower concentrations of BoNT/A to determine the concentration of neurotoxin necessary to cleave endogenously expressed SNAP-25. Cells were grown in poly-D-lysine/Laminin coated 6-well plates as described above in Example II, 1a. BoNT/A (Metabiologics, Inc., Madison, Wis.) was added at different concentrations (0 nM, 0.05 nM, 2. Identification of Cell Lines with High Affinity Uptake for BoNT/B 2a. Assay to Determine the BoNT/B Concentration Necessary for Cell Intoxication In order to assess the amount of BoNT/B needed to intoxicate a cell line, a panel of mammalian cell lines of neuronal origin will be screened to determine the concentration of neurotoxin necessary to cleave endogenously expressed VAMP (see Table 14). Cells will be grown in poly-D-lysine/Laminin coated 6-well plates as described above in Example II, 1a. BoNT/B (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/B substrate, western blot analysis will be conducted as described above in Example II, 1a, with the exception that blocked PVDF membranes will be incubated in a primary antibody solution containing one of the following antibodies in order to detect a BoNT/B VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/B VAMP-cleavage product in a cell line after at least an 8 hours incubation with at least 20 nM BoNT/B will indicate the ability of BoNT/B to intoxicate these cell lines.

2b. Assay to Determine the Time Required by a Cell to Uptake BoNT/B

In order to assess the amount of time needed by a cell line to uptake BoNT/B, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 2a. Approximately 1 nM BoNT/B (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 2a. The presence of a BoNT/B VAMP-cleavage product will be determined by Western blot analysis as described above in Example II, 2a. Detection of a BoNT/B VAMP-cleavage product in a cell line after at least an 8 hour incubation with 1 nM BoNT/B will indicate a cell line that can rapidly uptake BoNT/B.

3. Identification of Cell Lines with High Affinity Uptake for BoNT/C1

3a. Assay to Determine the BoNT/C1 Concentration Necessary for Cell Intoxication In order to assess the amount of BoNT/C1 needed to intoxicate a cell line, a panel of mammalian cell lines of neuronal origin will be screened to determine the concentration of neurotoxin necessary to cleave endogenously expressed SNAP-25 or endogenously expressed Syntaxin (see Table 14). Cells will be grown in poly-D-lysine/Laminin coated 6-well plates as described above in Example II, 1a. BoNT/C1 (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/C1 substrate, western blot analysis will be conducted as described above in Example II, 1a, with the exception: 1) blocked PVDF membranes will be incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 SNAP25$_{198}$-cleavage product; 2) blocked PVDF membranes will be incubated in a primary antibody solution containing a 1:5000 dilution of mouse monoclonal anti-Syntaxin-1 antibody clone Cl 78.2 (Synaptic Systems, Goettingen, Germany) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 Syntaxin-cleavage product. Detection of a SNAP25$_{198}$-cleavage product in a cell line after at least an 8 hours incubation with at least 20 nM BoNT/C1 will indicate the ability of BoNT/C1 to intoxicate these cell lines. Detection of a Syntaxin-cleavage product in a cell line after at least an 8 hours incubation with at least 20 nM BoNT/C1 will indicate the ability of BoNT/C1 to intoxicate these cell lines.

3b. Assay to Determine the Time Required by a Cell to Uptake BoNT/C1

In order to assess the amount of time needed by a cell line to uptake BoNT/C1, a panel of mammalian cell lines of neuronal origin will be screened to determine the length of toxin exposure necessary to cleave endogenously expressed SNAP-25 or endogenously expressed Syntaxin. Cells will be grown in poly-D-lysine/Laminin coated 6-well plates as described above in Example II, 3a. Approximately 1 nM BoNT/C1 (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 3a. The presence of a BoNT/C1 SNAP25$_{198}$-cleavage product and BoNT/C1 Syntaxin-cleavage product will be determined by Western blot analysis as described above in Example II, 3a. Detection of a BoNT/C1 SNAP25$_{198}$-cleavage product in a cell line after at least an 8 hour incubation with 1 nM BoNT/C1 will indicate a cell line that can rapidly uptake BoNT/C1. Detection of a BoNT/C1 Syntaxin-cleavage product in a cell line after at least an 8 hour incubation with 1 nM BoNT/C1 will indicate a cell line that can rapidly uptake BoNT/C1.

4. Identification of Cell Lines with High Affinity Uptake for BoNT/D

4a. Assay to Determine the BoNT/D Concentration Necessary for Cell Intoxication

In order to assess the amount of BoNT/D needed to intoxicate a cell line, a panel of mammalian cell lines of neuronal origin will be screened to determine the concentration of neurotoxin necessary to cleave endogenously expressed VAMP (see Table 14). Cells will be grown in poly-D-lysine/

Laminin coated 6-well plates as described above in Example II, 1a. BoNT/D (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/D substrate, western blot analysis will be conducted as described above in Example II, 1a, with the exception that blocked PVDF membranes will be incubated in a primary antibody solution containing one of the following antibodies in order to detect a BoNT/D VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/D VAMP-cleavage product in a cell line after at least an 8 hours incubation with at least 20 nM BoNT/D will indicate the ability of BoNT/D to intoxicate these cell lines.

4b. Assay to Determine the Time Required by a Cell to Uptake BoNT/D

In order to assess the amount of time needed by a cell line to uptake BoNT/D, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 4a. Approximately 1 nM BoNT/D (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 4a. The presence of a BoNT/D VAMP-cleavage product will be determined by Western blot analysis as described above in Example II, 4a. Detection of a BoNT/D VAMP-cleavage product in a cell line after at least an 8 hour incubation with 1 nM BoNT/D will indicate a cell line that can rapidly uptake BoNT/D.

5. Identification of Cell Lines with High Affinity Uptake for BoNT/E

5a. Assay to Determine the BoNT/E Concentration Necessary for Cell Intoxication

In order to assess the amount of BoNT/E needed to intoxicate a cell line, a panel of mammalian cell lines of neuronal origin was screened to determine the concentration of neurotoxin necessary to cleave endogenously expressed SNAP-25 (see Table 14). A suitable density of cells from each line was plated into individual wells of 6-well, poly-D-lysine/Laminin coated, tissue culture plates containing 3 mL of a suitable medium (see Table 14), and grown in a 37° C. incubator under 5% carbon dioxide for approximately 24 hours. BoNT/E (Metabiologics, Inc., Madison, Wis.) was added at different concentrations (0 nM, 2 nM or 20 nM) in the culture medium containing cells for either approximately 6 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N, N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 7A:
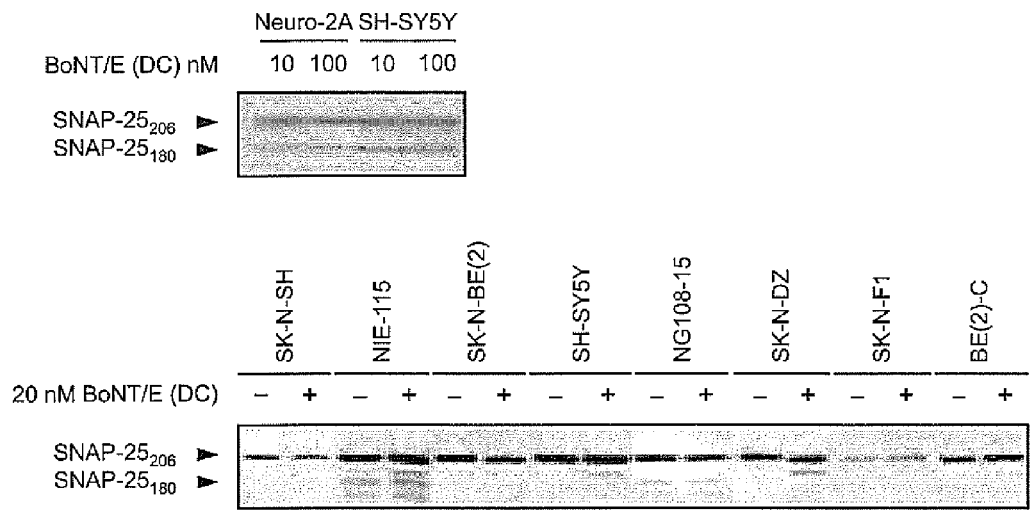
FIG. 7a shows a Western blot analysis used to identify cells capable of BoNT/E uptake. The top blot show Neuro-2A cells and SH-SY5Y cells treated with either 10 nM or 100 nM of BoNT/E di-chain overnight, with equal amounts of protein loaded per lane and probed with an antibody (SMI-81; Sternberger Monoclonals, Lutherville, Md.) that detects the uncleaved SNAP-25$_{206}$ substrate and the BoNT/E SNAP-25$_{180}$ cleavage product. The bottom blot show various cells treated with 20 nM of BoNT/E di-chain, with equal amounts of protein loaded per lane and probed with an antibody for the uncleaved SNAP-25$_{206}$ substrate and the BoNT/E SNAP-25$_{180}$ cleavage product.

To detect for the presence of a cleaved BoNT/E substrate, western blot analysis was conducted as described above in Example II, 1a, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/E SNAP25$_{180}$-cleavage product. A BoNT/E SNAP25$_{180}$-cleavage product was detected in the cell lines Neuro-2A, SH-SY5Y, N1E-115, SK-N-BE(2), NG108-15, SK-N-DZ and BE(2)-C after at least a 6 hour incubation with at least 20 nM BoNT/E, thereby indicating the ability of BoNT/E to intoxicate these cell lines (see FIG. 7a).

Figure 7B:
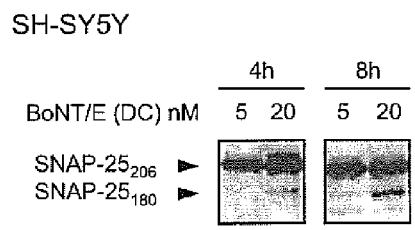
FIG. 7b shows Western blot analysis used to determine a time course for BoNT/E uptake. The blots show SH-SY5Y cells treated with either 5 nM or 20 nM of BoNT/E di-chain for either 4 hours or 8 hours, with equal amounts of protein loaded per lane or probed with an antibody (SMI-81; Sternberger Monoclonals, Lutherville, Md.) that detects the uncleaved SNAP-25$_{206}$ substrate and the BoNT/E SNAP-25$_{180}$ cleavage product.
Figure 7C:
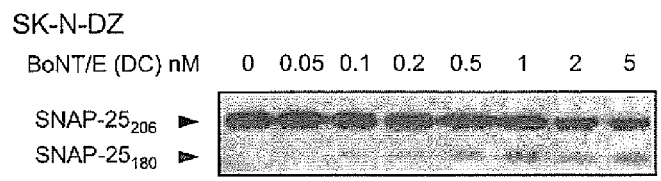
FIG. 7c shows a Western blot analysis used to evaluate the concentration range necessary of BoNT/E uptake. The blots show SK-N-DZ cells treated with a range of BoNT/E di-chain concentrations for approximately 6 hours, with equal amounts of protein loaded per lane and probed with an antibody (SMI-81; Sternberger Monoclonals, Lutherville, Md.) that detects the uncleaved SNAP-25$_{206}$ substrate and the BoNT/E SNAP-25$_{180}$ cleavage product.

The human neuroblastoma cell line SK-N-DZ was further analyzed with lower concentrations of BoNT/E to determine the concentration of neurotoxin necessary to cleave endogenously expressed SNAP-25. Cells were grown in poly-D-lysine/Laminin coated 6-well plates as described above in Example II, 5a. BoNT/E (Metabiologics, Inc., Madison, Wis.) was added at different concentrations (0 nM, 0.05 nM, 0.1 nM, 0.2 nM, 0.5 nM, 1 nM, 2 nM and 5 nM) in the culture medium containing cells for approximately 6 hours. Toxin treated cells were harvested and lysed as described above in Example II, 5a. The presence of a BoNT/E SNAP25$_{180}$-cleavage product was determined by Western blot analysis as described above in Example II, 5a. A BoNT/E SNAP25$_{180}$-cleavage product was detected in the cell line SK-N-DZ after at least a 6 hour incubation with at least 0.1 nM BoNT/E, thereby indicating the ability of BoNT/E to intoxicate these cell lines (see FIG. 7c).

5b. Assay to Determine the Time Required by a Cell to Uptake BoNT/E

In order to assess the amount of time needed by a cell line to uptake BoNT/E, a panel of mammalian cell lines of neuronal origin was screened to determine the length of toxin exposure necessary to cleave endogenously expressed SNAP-25 (see Table 14). Cells were grown in poly-D-lysine/Laminin coated 6-well plates as described above in Example II, 5a. Approximately 1 nM BoNT/E (Metabiologics, Inc., Madison, Wis.) was added to the culture medium for 10 min, 20 min, 30 min, 60 min 2 hours, 4 hours, 6 hours, 8 hours or 16 hours. Toxin treated cells were harvested and lysed as described above in Example II, 5a. The presence of a BoNT/E SNAP25$_{180}$-cleavage product was determined by Western blot analysis as described above in Example II, 5a. A BoNT/E SNAP25$_{180}$-cleavage product was detected in the cell lines Neuro-2A, SH-SY5Y, and NG108-15 after at least an 6 hour incubation with 1 nM BoNT/E, thereby indicating the ability of these cell lines to rapidly uptake BoNT/E (see FIG. 7b).

6. Identification of Cell Lines with High Affinity Uptake for BoNT/F

6a. Assay to determine the BoNT/F concentration necessary for cell intoxication

In order to assess the amount of BoNT/F needed to intoxicate a cell line, a panel of mammalian cell lines of neuronal origin will be screened to determine the concentration of neurotoxin necessary to cleave endogenously expressed VAMP (see Table 14). Cells will be grown in poly-D-lysine/Laminin coated 6-well plates as described above in Example II, 1a. BoNT/F (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/F substrate, western blot analysis will be conducted as described above in Example II, 1a, with the exception that blocked PVDF membranes will be incubated in a primary antibody solution containing one of the following antibodies in order to detect a BoNT/F VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/F VAMP-cleavage product in a cell line after at least an 8 hours incubation with at least 20 nM BoNT/F will indicate the ability of BoNT/F to intoxicate these cell lines.

6b. Assay to Determine the Time Required by a Cell to Uptake BoNT/F

In order to assess the amount of time needed by a cell line to uptake BoNT/F, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 6a. Approximately 1 nM BoNT/F (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 6a. The presence of a BoNT/F VAMP-cleavage product will be determined by Western blot analysis as described above in Example II, 6a. Detection of a BoNT/F VAMP-cleavage product in a cell line after at least an 8 hour incubation with 1 nM BoNT/F will indicate a cell line that can rapidly uptake BoNT/F.

7. Identification of Cell Lines with High Affinity Uptake for BoNT/G

7a. Assay to Determine the BoNT/G Concentration Necessary for Cell Intoxication

In order to assess the amount of BoNT/G needed to intoxicate a cell line, a panel of mammalian cell lines of neuronal origin will be screened to determine the concentration of neurotoxin necessary to cleave endogenously expressed VAMP (see Table 14). Cells will be grown in poly-D-lysine/Laminin coated 6-well plates as described above in Example II, 1a. BoNT/G (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/G substrate, western blot analysis will be conducted as described above in Example II, 1a, with the exception that blocked PVDF membranes will be incubated in a primary antibody solution containing one of the following antibodies in order to detect a BoNT/G VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/G VAMP-cleavage product in a cell line after at least an 8 hours incubation with at least 20 nM BoNT/G will indicate the ability of BoNT/G to intoxicate these cell lines.

7b. Assay to Determine the Time Required by a Cell to Uptake BoNT/G

In order to assess the amount of time needed by a cell line to uptake BoNT/G, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 7a. Approximately 1 nM BoNT/G (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 7a. The presence of a BoNT/G VAMP-cleavage product will be determined by Western blot analysis as described above in Example II, 7a. Detection of a BoNT/G VAMP-cleavage product in a cell line after at least an 8 hour incubation with 1 nM BoNT/G will indicate a cell line that can rapidly uptake BoNT/G.

8. Identification of Cell Lines with High Affinity Uptake for TeNT

8a. Assay to Determine the TeNT Concentration Necessary for Cell Intoxication

In order to assess the amount of TeNT needed to intoxicate a cell line, a panel of mammalian cell lines of neuronal origin will be screened to determine the concentration of neurotoxin necessary to cleave endogenously expressed VAMP (see Table 14). Cells will be grown in poly-D-lysine/Laminin coated 6-well plates as described above in Example II, 1a. TeNT (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved TeNT substrate, western blot analysis will be conducted as described above in Example II, 1a, with the exception that blocked PVDF membranes will be incubated in a primary antibody solution containing one of the following antibodies in order to detect a TeNT VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a TeNT VAMP-cleavage product in a cell line after at least an 8 hours incubation with at least 20 nM TeNT will indicate the ability of TeNT to intoxicate these cell lines.

8b. Assay to Determine the Time Required by a Cell to Uptake TeNT

In order to assess the amount of time needed by a cell line to uptake TeNT, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 8a. Approximately 1 nM TeNT (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 8a. The presence of a TeNT VAMP-cleavage product will be determined by Western blot analysis as described above in Example II, 8a. Detection of a TeNT VAMP-cleavage product in a cell line after at least an 8 hour incubation with 1 nM TeNT will indicate a cell line that can rapidly uptake TeNT.

Example IV

Treatments to Increase Uptake of a Cell for a Clostridial Toxin

Cell surface gangliosides are part of the receptor system for Clostridial toxins and appear to participate in binding of a toxin to its receptor system. Although toxin binding is not strictly dependent on the presence of gangliosides, the presence of specific gangliosides appears to enhance the binding affinity of the Clostridial toxin for its receptor. In particular, CoNTs have been observed to interact in vitro and in vivo with polysialogangliosides, especially those of the G1b series (GD1a, GD1b, GD3, GQ1b, or GT1b), see, e.g., Jane L. Halpern & Elaine A. Neale, Neurospecific binding, internalization, and retrograde axonal transport, 195 Curr. Top. Microbiol. Immunol. 221-241 (1995). Likewise, the differentiated state of a cell could influence the expression, or level of expression of important components of a Clostridial toxin receptor system, such as, e.g., a cell-surface receptor. For example, Neuro-2A and SH-SY5Y cells can be differentiated to acquire a neuronal-like phenotype that may facilitate toxin uptake. To determine whether we could increase the uptake of a Clostridial toxin by a particular cell, we tested 1) whether a treatment that increased the ganglioside content of the cell membrane increased uptake of a Clostridial toxin by a cell; and 2) whether changing the state of differentiation of a cell could increase uptake of a Clostridial toxin by a cell.

1. Identification of Treatments that Increased Uptake of BoNT/A by a Cell

1a. Ganglioside Treatment to Increase High Affinity Uptake of BoNT/A by a Cell

Figure 8A:
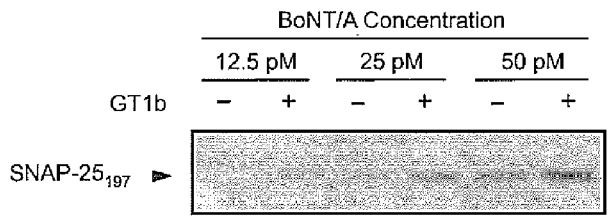
FIG. 8a shows a Western blot analysis evaluating the effects of ganglioside treatment on the uptake of BoNT/A. The blot shows Neuro-2A cells treated without or with 25 μg/mL of GT1b (− or +) and exposed overnight to three different concentrations of BoNT/A (12.5 pM, 25 pM or 50 pM), with equal amounts of protein loaded per lane and probed with an antibody that detects the BoNT/A SNAP-25$_{197}$ cleavage product.

In order to assess the effect of ganglioside treatment on the ability of BoNT/A to intoxicate a cell, a Neuro-2A cell line was pre-treated with different gangliosides to determine whether these sugar moieties could increase the uptake of BoNT/A by these cells. Neuro-2A cells were plated at a suitable density into individual wells of 6-well, poly-D-lysine/Laminin coated, tissue culture plates containing 3 mL of a suitable medium (see Table 14), and grown in a 37° C. incubator under 5% carbon dioxide. After approximately 24 hours, the medium was replaced by a serum-free media and 25 µg/mL of one of the following gangliosides was added to individual wells: GD1a, GD1b, GD3, GQ1b, or GT1b (AXXORA, LLC, San Diego, Calif.). After an overnight 37° C. incubation period, the ganglioside-treated cells were washed three times with 1 ml of phosphate-buffered saline, pH 7.4 and then incubated at 37° C. with 1% serum media containing different concentrations (0 nM, 12.5 nM, 25 nM, 50 nM) of BoNT/A (Metabiologics, Inc., Madison, Wis.) for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration. The presence of a BoNT/A SNAP25$_{197}$-cleavage product was determined by Western blot analysis as described above in Example II, 1a. An increase in BoNT/A SNAP25$_{197}$-cleavage product was detected in the Neuro-2A cell line treated with the ganglioside GT1b, thereby indicating that GT1b-treatment can increase the uptake of BoNT/A by Neuro-2A cells (see FIG. 8a).

1b. Differentiation Reagent Treatment to Increase High Affinity Uptake of BoNT/A by a Cell In order to assess the effect of cellular differentiation on the ability of BoNT/A to intoxicate a cell, Neuro-2A and SH-SY5Y cells were treated with different growth conditions or differentiation reagents to determine whether differentiation of these cells could result in an increased uptake of BoNT/A by these cells. Cells were plated at a suitable density into individual wells of 6-well, poly-D-lysine/Laminin coated, tissue culture plates containing 3 mL of a suitable medium (see Table 14), and grown in a 37° C. incubator under 5% carbon dioxide. After approximately 24 hours, the medium was replaced with either a serum-free culture media or a 10% serum media and one of the following differentiating reagents was added to individual wells: 0.2 units Neuraminidase Type V (Sigma-Aldrich, St. Louis, Mo.), in water containing 0.2% ALBUMAX II (Invitrogen, Inc., Carlsbad, Calif.); 20 µM All Trans-Retinoic acid (Sigma-Aldrich, St. Louis, Mo.) in DMSO (Sigma-Aldrich, St. Louis, Mo.); 1 mM N6,2'-0-Dibutyryladenosine 3':5'-cyclic monophosphate sodium salt (db-cAMP) (Sigma-Aldrich, St. Louis, Mo.); 1 µM Ionomycin, calcium salt (Molecular Probes, Eugene, Oreg.) in DMSO (Sigma-Aldrich, St. Louis, Mo.); or 1× N-2 Supplement (Invitrogen, Inc., 17502-048, Carlsbad, Calif.). After a three day 37° C. incubation period, the serum-free media cells and the reagent-treated cells were washed three times with 1 ml of phosphate-buffered saline, pH 7.4 and then incubated at 37° C. with either serum-free media containing 2 nM Pure A (BTX-540) toxin (Metabiologics, Inc., Madison, Wis.) for approximately 18 hours (the growth condition experiments), or 10% serum media containing 2 nM Pure A (BTX-540) toxin (Metabiologics, Inc., Madison, Wis.) for approximately 18 hours (the differentiation reagent experiments). Cells were harvested by trypsin treatment, collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X®100 (4-octylphenol polyethoxylate), with rotation for 1 to 2 hours at 4° C. Lysed cells were centrifuged at 5000 rpm for 10 min at 4° C. to eliminate debris and the supernatants were transferred to fresh 1.5 mL siliconized tubes. Protein concentrations were measured by Bradford's method and resuspended in 1×SDS sample buffer at 1 mg/ml or higher concentration. The presence of a BoNT/A SNAP25$_{197}$-cleavage product was determined by Western blot analysis as described above in Example II, 1a, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect both the uncleaved SNAP-25 and the BoNT/A SNAP25$_{197}$-cleavage product. An increase in BoNT/A SNAP25$_{197}$-cleavage product was detected in Neuro-2A and SH-SY5Y cells differentiated in serum-free conditions as compared to 10% serum media, thereby indicating that serum-free media conditions can increase the uptake of BoNT/A by Neuro-2A and SH-SY5Y cells (see FIG. 8b). Likewise, an increase in BoNT/A SNAP25$_{197}$-cleavage product was detected in Neuro-2A cells treated with all trans retinoic acid, thereby indicating that retinoic-induced differentiation of Neuro-2A can increase the uptake of BoNT/A by these cells (see FIG. 8b).

2. Identification of Treatments that Increased Uptake of BoNT/B by a Cell

2a. Ganglioside Treatment to Increase High Affinity Uptake of BoNT/B by a Cell

In order to assess the effect of ganglioside treatment on the ability of BoNT/B to intoxicate a cell, suitable mammalian cells will be pre-treated with different gangliosides to determine whether these sugar moieties can increase the uptake of BoNT/B by these cells. Cells will be grown in poly-D-lysine/ Laminin coated 6-well plates and treated with gangliosides as described above in Example III, 1a. The ganglioside-treated cells will be incubated with BoNT/B (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/B VAMP-cleavage product will be determined by Western blot analysis as described above in Example II, 2a. An increase in BoNT/B VAMP-cleavage product detected in the cell line treated with a ganglioside will indicate that treatment with that ganglioside can increase the uptake of BoNT/B by these cells.

2b. Differentiation Reagent Treatment to Increase High Affinity Uptake of BoNT/B by a Cell In order to assess the effect of cellular differentiation on the ability of BoNT/B to intoxicate a cell, suitable mammalian cells will be treated with different growth conditions or differentiation reagents to determine whether differentiation of these cells can result in an increased uptake of BoNT/B by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/B (Metabiologics, Inc., Madison, Wis.) for approximately 18 hours (the growth condition experiments), or 10% serum media containing BoNT/B (Metabiologics, Inc., Madison, Wis.) for approximately 18 hours (the differentiation reagent experiments). Cells were harvested, collected and lysed as described above in Example III, 1a. The presence of a BoNT/B VAMP-cleavage product will be determined by Western blot analysis as described above in Example II, 2a. An increase in a BoNT/B VAMP-cleavage product detected in cells grown in serum-free media will indicate that treatment with that reagent can increase the uptake of BoNT/B by these cells. An increase in a BoNT/B VAMP-cleavage product detected in cells treated with a differentiation reagent will indicate that treatment with that reagent can increase the uptake of BoNT/B by these cells.

3. Identification of Treatments that Increased Uptake of BoNT/C1 by a Cell

3a. Ganglioside Treatment to Increase High Affinity Uptake of BoNT/C1 by a Cell

In order to assess the effect of ganglioside treatment on the ability of BoNT/C1 to intoxicate a cell, suitable mammalian cells will be pre-treated with different gangliosides to determine whether these sugar moieties can increase the uptake of BoNT/C1 by these cells. Cells will be grown in poly-D-lysine/Laminin coated 6-well plates and treated with gangliosides as described above in Example III, 1a. The ganglioside-treated cells will be incubated with BoNT/C1 (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/C1 SNAP25$_{180}$-cleavage product will be determined by Western blot analysis as described above in Example II, 3a. The presence of a BoNT/C1 Syntaxin-cleavage product will be determined by Western blot analysis as described above in Example II, 3a. An increase in BoNT/C1 SNAP25$_{180}$-cleavage product detected in the cell line treated with a ganglioside will indicate that treatment with that ganglioside can increase the uptake of BoNT/C1 by these cells. An increase in BoNT/C1 Syntaxin-cleavage product detected in the cell line treated with a ganglioside will indicate that treatment with that ganglioside can increase the uptake of BoNT/C1 by these cells.

3b. Differentiation Reagent Treatment to Increase High Affinity Uptake of BoNT/C1 by a Cell In order to assess the effect of cellular differentiation on the ability of BoNT/C1 to intoxicate a cell, suitable mammalian cells will be treated with different growth conditions or differentiation reagents to determine whether differentiation of these cells can result in an increased uptake of BoNT/C1 by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/C1 (Metabiologics, Inc., Madison, Wis.) for approximately 18 hours (the growth condition experiments), or 10% serum media containing BoNT/C1 (Metabiologics, Inc., Madison, Wis.) for approximately 18 hours (the differentiation reagent experiments). Cells were harvested, collected and lysed as described above in Example III, 1a. The presence of a BoNT/C1 SNAP25$_{180}$-cleavage product will be determined by Western blot analysis as described above in Example II, 3a. The presence of a BoNT/C1 Syntaxin-cleavage product will be determined by Western blot analysis as described above in Example II, 3a. An increase in a BoNT/C1 SNAP25$_{180}$-cleavage product detected in cells grown in serum-free media will indicate that treatment with that reagent can increase the uptake of BoNT/C1 by these cells. An increase in a BoNT/C1 SNAP25$_{180}$-cleavage product detected in cells treated with a differentiation reagent will indicate that treatment with that reagent can increase the uptake of BoNT/C1 by these cells. An increase in a BoNT/C1 Syntaxin-cleavage product detected in cells grown in serum-free media will indicate that treatment with that reagent can increase the uptake of BoNT/C1 by these cells. An increase in a BoNT/C1 Syntaxin-cleavage product detected in cells treated with a differentiation reagent will indicate that treatment with that reagent can increase the uptake of BoNT/C1 by these cells.

4. Identification of Treatments that Increased Uptake of BoNT/D by a Cell

4a. Ganglioside Treatment to Increase High Affinity Uptake of BoNT/D

In order to assess the effect of ganglioside treatment on the ability of BoNT/D to intoxicate a cell, suitable mammalian cells will be pre-treated with different gangliosides to determine whether these sugar moieties can increase the uptake of BoNT/D by these cells. Cells will be grown in poly-D-lysine/Laminin coated 6-well plates and treated with gangliosides as described above in Example III, 1a. The ganglioside-treated cells will be incubated with BoNT/D (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/D VAMP-cleavage product will be determined by Western blot analysis as described above in Example II, 4a. An increase in BoNT/D VAMP-cleavage product detected in the cell line treated with a ganglioside will indicate that treatment with that ganglioside can increase the uptake of BoNT/D by these cells.

4b. Differentiation Reagent Treatment to Increase High Affinity Uptake of BoNT/D by a Cell In order to assess the effect of cellular differentiation on the ability of BoNT/D to intoxicate a cell, suitable mammalian cells will be treated with different growth conditions or differentiation reagents to determine whether differentiation of these cells can result in an increased uptake of BoNT/D by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/D (Metabiologics, Inc., Madison, Wis.) for approximately 18 hours (the growth condition experiments), or 10% serum media containing BoNT/D (Metabiologics, Inc., Madison, Wis.) for approximately 18 hours (the differentiation reagent experiments). Cells were harvested, collected and lysed as described above in Example III, 1a. The presence of a BoNT/D VAMP-cleavage product will be determined by Western blot analysis as described above in Example II, 4a. An increase in a BoNT/D VAMP-cleavage product detected in cells grown in serum-free media will indicate that treatment with that reagent can increase the uptake of BoNT/D by these cells. An increase in a BoNT/D VAMP-cleavage product detected in cells treated with a differentiation reagent will indicate that treatment with that reagent can increase the uptake of BoNT/D by these cells.

5. Identification of Treatments that Increased Uptake of BoNT/E by a Cell

5a. Ganglioside Treatment to Increase High Affinity Uptake of BoNT/E by a Cell

Figure 9A:
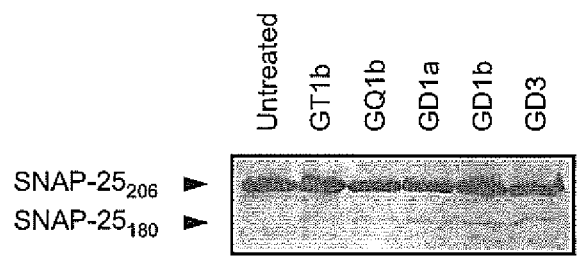
FIG. 9a shows a Western blot analysis evaluating the effects of ganglioside treatment on the uptake of BoNT/E. The blot shows Neuro-2A cells treated with either 25 μg/mL of GT1b, GQ1b, GD1a, GD1b or GD3 and exposed for approximately 5 hours to 14 nM of BoNT/E di-chain, with equal amounts of protein loaded per lane and probed with an antibody (SMI-81; Sternberger Monoclonals, Lutherville, Md.) that detects the uncleaved SNAP-25$_{206}$ substrate and the BoNT/E SNAP-25$_{180}$ cleavage product.

In order to assess the effect of ganglioside treatment on the ability of BoNT/E to intoxicate a cell, a Neuro-2A cell line was pre-treated with different gangliosides to determine whether these sugar moieties could increase the uptake of BoNT/E by these cells. Neuro-2A cells were grown in poly-D-lysine/Laminin coated 6-well plates and treated with gangliosides as described above in Example III, 1a. The ganglioside-treated cells were incubated with BoNT/E (Metabiologics, Inc., Madison, Wis.) at different concentrations (0 nM, 12.5 nM, 25 nM, 50 nM) in 1% serum media for either approximately 6 or approximately 16 hours. Toxin treated cells were harvested and lysed as described above in Example II, 5a. The presence of a BoNT/E SNAP25$_{180}$-cleavage product was determined by Western blot analysis as described above in Example II, 5a. An increase in BoNT/E SNAP25$_{180}$-cleavage product was detected in the Neuro-2A cell lines treated with the gangliosides GD3, GD1b and GD1a, thereby indicating that GD3-treatment, GD1b-treatment or GD1a-treatment can increase the uptake of BoNT/E by Neuro-2A cells (see FIG. 9a).

Figure 9B:
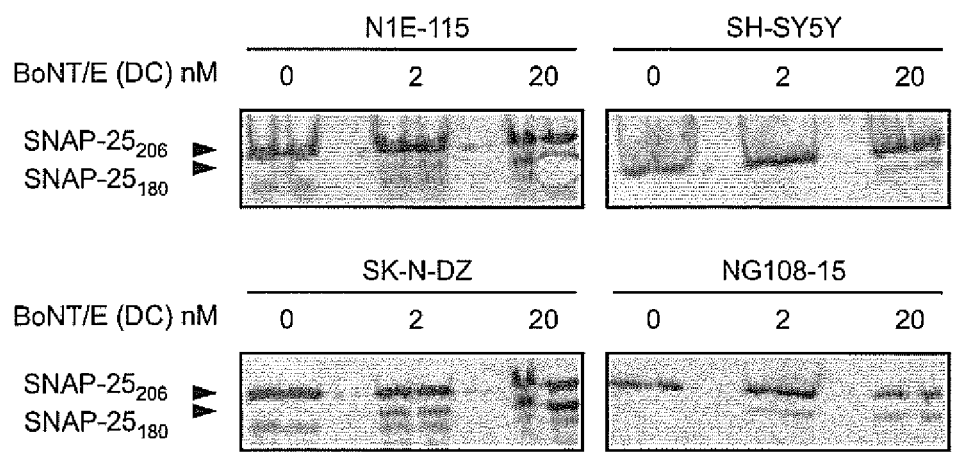
FIG. 9b shows Western blot analysis evaluating the effects of cell differentiation on the uptake of BoNT/E. The blots show either N1E-115 cells, SH-SY5Y cells, SK-N-DZ cells or NG108-15 cells treated with either 0 nM, 2 nM or 20 nM of BoNT/E di-chain for approximately 6 hours that where grown in serum-free media, with equal amounts of protein loaded per lane and probed with an antibody (SMI-81; Sternberger Monoclonals, Lutherville, Md.) that detects the uncleaved SNAP-25$_{206}$ substrate and the BoNT/E SNAP-25$_{180}$ cleavage product.

5b. Differentiation Reagent Treatment to Increase High Affinity Uptake of BoNT/E by a Cell In order to assess the effect of cellular differentiation on the ability of BoNT/E to intoxicate a cell, SH-SY5Y cells were treated with different growth conditions to determine whether differentiation of these cells could result in an increased uptake of BoNT/E by these cells. SH-SY5Y cells were grown in poly-D-lysine/Laminin coated 6-well plates using serum-free as described above in Example III, 1b. The serum-free media cells were incubated with BoNT/E (Metabiologics, Inc., Madison, Wis.) at concentrations of 5 nM and 20 nM for approximately 30 minutes, approximately 1 hour, approximately 2 hours, approximately 4 hours, approximately 8 hours and approximately 16 hours. Toxin treated cells were harvested, collected and lysed as described above in Example III, 1b. The presence of a BoNT/E SNAP25$_{180}$-cleavage product was determined by Western blot analysis as described above in Example II, 5a. An increase in BoNT/E SNAP25$_{180}$-cleavage product was detected in SH-SY5Y cells differentiated in serum-free conditions as early as 4 hours following exposure to toxin, with a maximal signal evident at least at 8 hours after BoNT/E-treatment, as compared to 10% serum media, thereby indicating that serum-free media conditions can increase the uptake of BoNT/E by SH-SY5Y cells (see FIG. 9b).

6. Identification of Treatments that Increased Uptake of BoNT/F by a Cell

6a. Ganglioside Treatment to Increase High Affinity Uptake of BoNT/F by a Cell

In order to assess the effect of ganglioside treatment on the ability of BoNT/F to intoxicate a cell, suitable mammalian cells will be pre-treated with different gangliosides to determine whether these sugar moieties can increase the uptake of BoNT/F by these cells. Cells will be grown in poly-D-lysine/Laminin coated 6-well plates and treated with gangliosides as described above in Example III, 1a. The ganglioside-treated cells will be incubated with BoNT/F (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/F VAMP-cleavage product will be determined by Western blot analysis as described above in Example II, 6a. An increase in BoNT/F VAMP-cleavage product detected in the cell line treated with a ganglioside will indicate that treatment with that ganglioside can increase the uptake of BoNT/F by these cells.

6b. Differentiation Reagent Treatment to Increase High Affinity Uptake of BoNT/F by a Cell In order to assess the effect of cellular differentiation on the ability of BoNT/F to intoxicate a cell, suitable mammalian cells will be treated with different growth conditions or differentiation reagents to determine whether differentiation of these cells can result in an increased uptake of BoNT/F by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/F (Metabiologics, Inc., Madison, Wis.) for approximately 18 hours (the growth condition experiments), or 10% serum media containing BoNT/F (Metabiologics, Inc., Madison, Wis.) for approximately 18 hours (the differentiation reagent experiments). Cells were harvested, collected and lysed as described above in Example III, 1a. The presence of a BoNT/F VAMP-cleavage product will be determined by Western blot analysis as described above in Example II, 6a. An increase in a BoNT/F VAMP-cleavage product detected in cells grown in serum-free media will indicate that treatment with that reagent can increase the uptake of BoNT/F by these cells. An increase in a BoNT/F VAMP-cleavage product detected in cells treated with a differentiation reagent will indicate that treatment with that reagent can increase the uptake of BoNT/F by these cells.

7. Identification of Treatments that Increased Uptake of BoNT/G by a Cell

7a. Ganglioside Treatment to Increase High Affinity Uptake of BoNT/G by a Cell

In order to assess the effect of ganglioside treatment on the ability of BoNT/G to intoxicate a cell, suitable mammalian cells will be pre-treated with different gangliosides to determine whether these sugar moieties can increase the uptake of BoNT/G by these cells. Cells will be grown in poly-D-lysine/Laminin coated 6-well plates and treated with gangliosides as described above in Example III, 1a. The ganglioside-treated cells will be incubated with BoNT/G (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/G VAMP-cleavage product will be determined by Western blot analysis as described above in Example II, 7a. An increase in BoNT/G VAMP-cleavage product detected in the cell line treated with a ganglioside will indicate that treatment with that ganglioside can increase the uptake of BoNT/G by these cells.

7b. Differentiation Reagent Treatment to Increase High Affinity Uptake of BoNT/G by a Cell In order to assess the effect of cellular differentiation on the ability of BoNT/G to intoxicate a cell, suitable mammalian cells will be treated with different growth conditions or differentiation reagents to determine whether differentiation of these cells can result in an increased uptake of BoNT/G by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/G (Metabiologics, Inc., Madison, Wis.) for approximately 18 hours (the growth condition experiments), or 10% serum media containing BoNT/G (Metabiologics, Inc., Madison, Wis.) for approximately 18 hours (the differentiation reagent experiments). Cells were harvested, collected and lysed as described above in Example III, 1a. The presence of a BoNT/G VAMP-cleavage product will be determined by Western blot analysis as described above in Example II, 7a. An increase in a BoNT/G VAMP-cleavage product detected in cells grown in serum-free media will indicate that treatment with that reagent can increase the uptake of BoNT/G by these cells. An increase in a BoNT/G VAMP-cleavage product detected in cells treated with a differentiation reagent will indicate that treatment with that reagent can increase the uptake of BoNT/G by these cells.

8. Identification of Treatments that Increased Uptake of TeNT by a Cell

8a. Ganglioside Treatment to Increase High Affinity Uptake of TeNT by a Cell

In order to assess the effect of ganglioside treatment on the ability of TeNT to intoxicate a cell, suitable mammalian cells will be pre-treated with different gangliosides to determine whether these sugar moieties can increase the uptake of TeNT by these cells. Cells will be grown in poly-D-lysine/Laminin coated 6-well plates and treated with gangliosides as described above in Example III, 1a. The ganglioside-treated cells will be incubated with TeNT (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a TeNT VAMP-cleavage product will be determined by Western blot analysis as described above in Example II, 8a. An increase in TeNT VAMP-cleavage product detected in the cell line treated with a ganglioside will indicate that treatment with that ganglioside can increase the uptake of TeNT by these cells.

8b. Differentiation Reagent Treatment to Increase High Affinity Uptake of TeNT by a Cell In order to assess the effect of cellular differentiation on the ability of TeNT to intoxicate a cell, suitable mammalian cells will be treated with different growth conditions or differentiation reagents to determine whether differentiation of these cells can result in an increased uptake of TeNT by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing TeNT (Metabiologics, Inc., Madison, Wis.) for approximately 18 hours (the growth condition experiments), or 10% serum media containing TeNT (Metabiologics, Inc., Madison, Wis.) for approximately 18 hours (the differentiation reagent experiments). Cells were harvested, collected and lysed as described above in Example III, 1a. The presence of a TeNT VAMP-cleavage product will be determined by Western blot analysis as described above in Example II, 8a. An increase in a TeNT VAMP-cleavage product detected in cells grown in serum-free media will indicate that treatment with that reagent can increase the uptake of TeNT by these cells. An increase in a TeNT VAMP-cleavage product detected in cells treated with a differentiation reagent will indicate that treatment with that reagent can increase the uptake of TeNT by these cells.

Example V

Construction of Cell Line Transiently Expressing a Clostridial Toxin Substrate

This example illustrates how to make a cell line that transiently expresses a Clostridial toxin substrate disclosed in the present specification.

1. Generation of Cells Containing a BoNT/A, BoNT/C1 or BoNT/E SNAP-25 Substrate by Adenoviral Transduction 1a. Construction of pAd-DEST/GFP-SNAP-$25_{1-206}$-BFP To make a pAd-DEST/GFP-SNAP-$25_{1-206}$-BFP construct, a polynucleotide fragment encoding the amino acid region comprising GFP-SNAP-$25_{1-206}$-BFP is amplified from pQBI-25/GFP-SNAP25$_{1-206}$-BFP DNA (see Example II, 1a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-SNAP-$25_{1-206}$-BFP construct is digested with restriction enzymes that 1) excise the insert containing the entire open reading frame encoding GFP-SNAP-$25_{1-206}$-BFP; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/GFP-SNAP-$25_{1-206}$-BFP. The ligation mixture is transformed into chemically competent E. coli BL21 (DE3) cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-SNAP-$25_{1-206}$-BFP operably-linked to the expression elements of the pAd-DEST vector.

This cloning strategy can be used to make a pAd-DEST mammalian expression construct encoding any of the BoNT/A substrates, BoNT/C1 substrates or BoNT/E substrates disclosed in the present specification.

1b. Production of an Adenoviral Stock Containing pAd-DEST/GFP-SNAP-$25_{1-206}$-BFP To produce an adenoviral stock containing an expression construct encoding a BoNT/A, BoNT/C1 or BoNT/E substrate, such as, e.g., pAd-DEST/GFP-SNAP-$25_{1-206}$-BFP, about $5 \times 10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5 \times 10^5$ cells/ml (6-16 hours). One the day of transfection, replace complete, supplemented DMEM media with 2 mL of OPTI-MEM Reduced Serum Medium. A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of the linearized expression construct encoding a BoNT/A, BoNT/C1 or BoNT/E GFP-SNAP-$25_{1-206}$-BFP substrate, such as, e.g., pAd-DEST/GFP-SNAP-$25_{1-206}$-BFP. To linearize a pAd-DEST/GFP-SNAP-$25_{1-206}$-BFP construct, 5 µg of a pAd-DEST/GFP-SNAP-$25_{1-206}$-BFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 µL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1 \times 10^7$ to $10^8$ pfu of adenoviral particles. Aliquots can be stored at −80° C. until needed.

1c. Amplification of an Adenoviral Stock Containing pAd-DEST/GFP-SNAP-25$_{1-206}$-BFP To amplified to the adenoviral stock containing an expression construct encoding a BoNT/A, BoNT/C1 or BoNT/E substrate, such as, e.g., pAd-DEST/GFP-SNAP-25$_{1-206}$-BFP, about $3 \times 10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 µL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1 \times 10^8$ to $10^9$ pfu of adenoviral particles. Aliquots can be stored at −80° C. until needed.

1d. Transduction of Cells with an Adenoviral Stock Containing pAd-DEST/GFP-SNAP-25$_{1-206}$-BFP To transduce cells with the adenoviral stock containing an expression construct encoding a BoNT/A, BoNT/C1 or BoNT/E substrate, such as, e.g., pAd-DEST/GFP-SNAP-25$_{1-206}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with approximately 4 µL of the adenoviral stock (approximately $5 \times 10^8$ pfu/ml) and are incubated for approximately 24 hours in a 37° C. incubator under 5% carbon dioxide. The transduction media is replaced with 3 mL of fresh complete, supplemented media and the cells are incubated in a 37° C. incubator under 5% carbon dioxide for approximately 24 hours. The transduced cells can be used to conduct a BoNT/A, BoNT/C1 or BoNT/E activity assay using a GFP-SNAP-25$_{1-206}$-BFP substrate (Example X).

2. Generation of Cells Containing a BoNT/A, BoNT/C1 or BoNT/E SNAP-25 Substrate by Lentiviral Transduction 2a. Construction of pLenti6Ubc/V5-GFP-SNAP-25$_{1-206}$-BFP To make a pLenti6Ubc/V5-GFP-SNAP-25$_{1-206}$-BFP construct, a polynucleotide fragment encoding the amino acid region comprising a BoNT/A, BoNT/C1 or BoNT/E GFP-SNAP-25$_{1-206}$-BFP substrate is amplified from, e.g., pQBI-25/GFP-SNAP-25$_{1-206}$-BFP DNA (see Example II, 1a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-SNAP-25$_{1-206}$-BFP construct is digested with restriction enzymes that 1) excise the insert containing the entire open reading frame encoding GFP-SNAP-25$_{1-206}$-BFP; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-GFP-SNAP-25$_{1-206}$-BFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding GFP-SNAP-25$_{1-206}$-BFP operably-linked to the expression elements of the pLenti6Ubc/V5 vector an amino-terminal V5 peptide.

This cloning strategy can be used to make a pLenti6Ubc/V5 mammalian expression construct encoding any of the BoNT/A substrates, BoNT/C1 substrates or BoNT/E substrates disclosed in the present specification.

2b. Production of a Lentiviral Stock Containing pLenti6Ubc/V5-GFP-SNAP-25$_{1-206}$-BFP To produce a lentiviral stock containing an expression construct encoding a BoNT/A, BoNT/C1 or BoNT/E substrate, such as, e.g., pLenti6Ubc/V5-GFP-SNAP-25$_{1-206}$-BFP, a 3.0 mL transfection solution is prepared by adding 1.5 mL of OPTI-MEM Reduced Serum Medium containing 36 µL of LipofectAmine 2000 (Invitrogen, Carlsbad, Calif.) incubated at room temperature for 5 minutes to 1.5 mL of OPTI-MEM Reduced Serum Medium containing 3 µg of an expression construct encoding a BoNT/A, BoNT/C1 or BoNT/E GFP-SNAP-25$_{1-206}$-BFP substrate, such as, e.g., pLenti6Ubc/V5-GFP-SNAP-25$_{1-206}$-BFP and 9 µg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6 \times 10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentiovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5\times10^5$ to $2\times10^7$ pfu/mL of lentiviral particles. Aliquots can be stored at −80° C. until needed.

2c. Transduction of Cells with an Lentiviral Stock Containing a pLenti6Ubc/V5-GFP-SNAP-25$_{1-206}$-BFP To transduce cells with a lentiviral stock containing an expression construct encoding a BoNT/A, BoNT/C1 or BoNT/E substrate, such as, e.g., pLenti6Ubc/V5-GFP-SNAP-$25_{1-206}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with the lentiviral stock containing an expression construct encoding a BoNT/A, BoNT/C1 or BoNT/E GFP-SNAP-$25_{1-206}$-BFP substrate, such as, e.g., pLenti6Ubc/V5-GFP-SNAP-$25_{1-206}$-BFP, using a suitable multiplicity of infection and are incubated for approximately 16-24 hours in a 37° C. incubator under 5% carbon dioxide. The transduction media is replaced with 3 mL of fresh complete, supplemented cell culture media and the cells are incubated in a 37° C. incubator under 5% carbon dioxide for approximately 24-48 hours. The transduced cells can be used to conduct a BoNT/A, BoNT/C1 or BoNT/E activity assay using a GFP-SNAP-$25_{1-206}$-BFP substrate (Example X).

3. Generation of Cells Containing a BoNT/A, BoNT/C1 or BoNT/E SNAP-25 Substrate by Protein Transformation 3a. Protein Transformation of a GFP-SNAP-$25_{134-206}$(Cys)-Alexa Fluor® 546 Substrate To transform a BoNT/A, BoNT/C1 or BoNT/E SNAP-25 substrate, such as, e.g., GFP-SNAP-$25_{134-206}$(Cys)-Alexa Fluor® 546 (see Example 111c3), into a mammalian cell line, cells suitable to conduct the activity assay, as identified in Example III, are plated in a 6-well tissue culture dish containing 3 mL of an appropriate supplemented cell culture media, and are grown in a 37° C. incubator under 5% carbon dioxide until the cells reach the required density. A 200 μL protein transfection solution is prepared by adding 100 μL of distilled water containing 6 μL of Chariot™ protein delivery agent (Active Motif, Carlsbad, Calif.) to 100 μL of 100 mM phosphate-buffered saline, pH 7.4 containing 1 μg of a GFP-SNAP25-BFP substrate, such as, e.g., GFP-SNAP-$25_{134-206}$ (Cys)-Alexa Fluor® 546, and this solution is incubated at room temperature for approximately 30 minutes. After incubation, the cells are washed once by rinsing cells with 3.0 mL of 100 mM phosphate-buffered saline, pH 7.4. The 200 μL protein transfection solution is added to the washed cells, followed by 400 μL of OPTI-MEM Reduced Serum Medium and the cells are incubated in a 37° C. incubator under 5% carbon dioxide for approximately 1 hour. Add 1 mL of fresh complete, supplemented cell culture media to the cells and incubate in a 37° C. incubator under 5% carbon dioxide. After 1-2 hours, the transformed cells can be used to conduct a BoNT/A, BoNT/C1 or BoNT/E activity assay (Example X).

4. Generation of Cells Containing a BoNT/B, BoNT/D, BoNT/F, BoNT/G or TeNT VAMP Substrate by Adenoviral Transduction 4a. Construction of pAd-DEST/GFP-VAMP-$1_{49-92}$-BFP To make a pAd-DEST/GFP-VAMP-$1_{49-92}$-BFP construct, a polynucleotide fragment encoding the amino acid region comprising GFP-VAMP-$1_{49-92}$-BFP is amplified from pQBI-25/GFP-VAMP-$1_{49-92}$-BFP DNA (see Example II, 2a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-VAMP-$1_{49-92}$-BFP construct is digested with restriction enzymes that 1) excise the insert containing the entire open reading frame encoding GFP-VAMP-$1_{49-92}$-BFP; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/GFP-VAMP-$1_{49-92}$-BFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-VAMP-$1_{49-92}$-BFP operably-linked to the expression elements of the pAd-DEST vector.

This cloning strategy can be used to make a pAd-DEST mammalian expression construct encoding any of the BoNT/B substrates, BoNT/D substrates, BoNT/F substrates, BoNT/G substrates or TeNT substrates disclosed in the present specification.

4b. Production of an Adenoviral Stock Containing pAd-DEST/GFP-VAMP-$1_{49-92}$-BFP To produce an adenoviral stock containing an expression construct encoding a BoNT/B, BoNT/D, BoNT/F, BoNT/G or TeNT substrate, such as, e.g., pAd-DEST/GFP-VAMP-$1_{49-92}$-BFP, about $5\times10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). One the day of transfection, replace complete, supplemented DMEM media with 2 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of the linearized expression construct encoding a BoNT/B, BoNT/D, BoNT/F, BoNT/G or TeNT GFP-VAMP-1$_{49-92}$-BFP substrate, such as, e.g., pAd-DEST/GFP-VAMP-1$_{49-92}$-BFP. To linearize a pAd-DEST/GFP-SNAP-25$_{1-206}$-BFP construct, 5 µg of a pAd-DESTNAMP-1$_{49-92}$-BFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 µL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of –80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately 1×10$^7$ to 10$^8$ pfu of adenoviral particles. Aliquots can be stored at –80° C. until needed.

4c. Amplification of an Adenoviral Stock Containing pAd-DEST/GFP-VAMP-1$_{49-92}$-BFP To amplified to the adenoviral stock containing an expression construct encoding a BoNT/B, BoNT/D, BoNT/F, BoNT/G or TeNT substrate, such as, e.g., pAd-DEST/GFP-VAMP-1$_{49-92}$-BFP, about 3×10$^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 µL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of –80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately 1×10$^8$ to 10$^9$ pfu of adenoviral particles. Aliquots can be stored at –80° C. until needed.

4d. Transduction of Cells with an Adenoviral Stock Containing pAd-DEST/GFP-VAMP-1$_{49-92}$-BFP To transduce cells with the adenoviral stock containing an expression construct encoding a BoNT/B, BoNT/D, BoNT/F, BoNT/G or TeNT substrate, such as, e.g., pAd-DEST/GFP-VAMP-1$_{49-92}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with approximately 4 µL of the adenoviral stock (approximately 5×10$^8$ pfu/ml) and are incubated for approximately 24 hours in a 37° C. incubator under 5% carbon dioxide. The transduction media is replaced with 3 mL of fresh complete, supplemented media and the cells are incubated in a 37° C. incubator under 5% carbon dioxide for approximately 24 hours. The transduced cells can be used to conduct a BoNT/B, BoNT/D, BoNT/F, BoNT/G or TeNT activity assay using a GFP-VAMP-1$_{49-92}$-BFP substrate (Example X).

5. Generation of Cells Containing a BoNT/B, BoNT/D, BoNT/F, BoNT/G or TeNT VAMP Substrate by Lentiviral Transduction 5a. Construction of pLenti6Ubc/V5-GFP-VAMP-1$_{49-92}$-BFP To make a pLenti6Ubc/V5-GFP-VAMP-1$_{49-92}$-BFP construct, a polynucleotide fragment encoding the amino acid region comprising a BoNT/B, BoNT/D, BoNT/F, BoNT/G or TeNT GFP-VAMP-1$_{49-92}$-BFP substrate is amplified from, e.g., pQBI-25/GFP-VAMP-1$_{49-92}$-BFP DNA (see Example II, 2a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-VAMP-1$_{49-92}$-BFP construct is digested with restriction enzymes that 1) excise the insert containing the entire open reading frame encoding GFP-VAMP-1$_{49-92}$-BFP; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-GFP-VAMP-1$_{49-92}$-BFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding GFP-VAMP-1$_{49-92}$-BFP operably-linked to the expression elements of the pLenti6Ubc/V5 vector an amino-terminal V5 peptide.

This cloning strategy can be used to make a pLenti6Ubc/V5 mammalian expression construct encoding any of the BoNT/B substrates, BoNT/D substrates, BoNT/F substrates, BoNT/G substrates or TeNT substrates disclosed in the present specification.

5b. Production of a Lentiviral Stock Containing pLenti6Ubc/V5-GFP-VAMP-$1_{49-92}$-BFP To produce a lentiviral stock containing an expression construct encoding a BoNT/B, BoNT/D, BoNT/F, BoNT/G or TeNT substrate, such as, e.g., pLenti6Ubc/V5-GFP-VAMP-$1_{49-92}$-BFP, a 3.0 mL transfection solution is prepared by adding 1.5 mL of OPTI-MEM Reduced Serum Medium containing 36 μL of LipofectAmine 2000 (Invitrogen, Carlsbad, Calif.) incubated at room temperature for 5 minutes to 1.5 mL of OPTI-MEM Reduced Serum Medium containing 3 μg of an expression construct encoding a BoNT/B, BoNT/D, BoNT/F, BoNT/G or TeNT GFP-VAMP-$1_{49-92}$-BFP substrate, such as, e.g., pLenti6Ubc/V5-GFP-VAMP-$1_{49-92}$-BFP and 9 μg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6\times10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentiovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5\times10^5$ to $2\times10^7$ pfu/mL of lentiviral particles. Aliquots can be stored at −80° C. until needed.

5c. Transduction of Cells with an Lentiviral Stock Containing a pLenti6Ubc/V5-GFP-VAMP-$1_{49-92}$-BFP To transduce cells with a lentiviral stock containing an expression construct encoding a BoNT/B, BoNT/D, BoNT/F, BoNT/G or TeNT substrate, such as, e.g., pLenti6Ubc/V5-GFP-VAMP-$1_{49-92}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with the lentiviral stock containing an expression construct encoding a BoNT/B, BoNT/D, BoNT/F, BoNT/G or TeNT GFP-VAMP-$1_{49-92}$-BFP substrate, such as, e.g., pLenti6Ubc/V5-GFP-VAMP-$1_{49-92}$-BFP, using a suitable multiplicity of infection and are incubated for approximately 16-24 hours in a 37° C. incubator under 5% carbon dioxide. The transduction media is replaced with 3 mL of fresh complete, supplemented cell culture media and the cells are incubated in a 37° C. incubator under 5% carbon dioxide for approximately 24-48 hours. The transduced cells can be used to conduct a BoNT/B, BoNT/D, BoNT/F, BoNT/G or TeNT activity assay using a GFP-VAMP-$1_{49-92}$-BFP substrate (Example X).

6. Generation of Cells Containing a BoNT/C1 Syntaxin Substrate by Adenoviral Transduction 6a. Construction of pAd-DEST/GFP-Syntaxin-$1_{1-288}$-BFP To make a pAd-DEST/GFP-Syntaxin-$1_{1-288}$-BFP construct, a polynucleotide fragment encoding the amino acid region comprising GFP-Syntaxin-$1_{1-288}$-BFP is amplified from pQBI-25/GFP-Syntaxin-$1_{1-288}$-BFP DNA (see Example II, 3a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-Syntaxin-$1_{1-288}$-BFP construct is digested with restriction enzymes that 1) excise the insert containing the entire open reading frame encoding GFP-Syntaxin-$1_{1-288}$-BFP; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/GFP-Syntaxin-$1_{1-288}$-BFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the GFP-Syntaxin-$1_{1-288}$-BFP operably-linked to the expression elements of the pAd-DEST vector.

This cloning strategy can be used to make a pAd-DEST mammalian expression construct encoding any of the BoNT/C1 substrates disclosed in the present specification.

6b. Production of an Adenoviral Stock Containing pAd-DEST/GFP-Syntaxin-$1_{1-288}$-BFP To produce an adenoviral stock containing an expression construct encoding a BoNT/C1 substrate, such as, e.g., pAd-DEST/GFP-Syntaxin-$1_{1-288}$-BFP, about $5\times10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). One the day of transfection, replace complete, supplemented DMEM media with 2 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of the linearized expression construct encoding a BoNT/C1 GFP-Syntaxin-$1_{1-288}$-BFP substrate, such as, e.g., pAd-DEST/GFP-Syntaxin-$1_{1-288}$-BFP. To linearize a pAd-DEST/GFP-Syntaxin-$1_{1-288}$-BFP construct, 5 μg of a pAd-DEST/GFP-Syntaxin- $1_{1-288}$-BFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 µL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1 \times 10^7$ to $10^8$ pfu of adenoviral particles. Aliquots can be stored at −80° C. until needed.

6c. Amplification of an Adenoviral Stock Containing pAd-DEST/GFP-Syntaxin-$1_{1-288}$-BFP To amplified to the adenoviral stock containing an expression construct encoding a BoNT/C1 substrate, such as, e.g., pAd-DEST/GFP-Syntaxin-$1_{1-288}$-BFP, about $3 \times 10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 μL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^8$ to $10^9$ pfu of adenoviral particles. Aliquots can be stored at −80° C. until needed.

6d. Transduction of Cells with an Adenoviral Stock Containing pAd-DEST/GFP-Syntaxin-$1_{1\text{-}288}$-BFP To transduce cells with the adenoviral stock containing an expression construct encoding a BoNT/C1 substrate, such as, e.g., pAd-DEST/GFP-Syntaxin-$1_{1\text{-}288}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with approximately 4 μL of the adenoviral stock (approximately $5\times10^8$ pfu/ml) and are incubated for approximately 24 hours in a 37° C. incubator under 5% carbon dioxide. The transduction media is replaced with 3 mL of fresh complete, supplemented media and the cells are incubated in a 37° C. incubator under 5% carbon dioxide for approximately 24 hours. The transduced cells can be used to conduct a BoNT/C1 activity assay using a GFP-Syntaxin-$1_{1\text{-}288}$-BFP substrate (Example X).

7. Generation of Cells Containing a BoNT/C1 Syntaxin Substrate by Lentiviral Transduction 7a. Construction of pLenti6Ubc/V5-GFP-Syntaxin-$1_{1\text{-}288}$-BFP To make a pLenti6Ubc/V5-GFP-Syntaxin-$1_{1\text{-}288}$-BFP construct, a polynucleotide fragment encoding the amino acid region comprising a BoNT/C1 GFP-Syntaxin-$1_{1\text{-}288}$-BFP substrate is amplified from, e.g., pQBI-25/GFP-Syntaxin-$1_{1\text{-}288}$-BFP DNA (see Example II, 3a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/GFP-Syntaxin-$1_{1\text{-}288}$-BFP construct is digested with restriction enzymes that 1) excise the insert containing the entire open reading frame encoding GFP-Syntaxin-$1_{1\text{-}288}$-BFP; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-GFP-Syntaxin-$1_{1\text{-}288}$-BFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding GFP-Syntaxin-$1_{1\text{-}288}$-BFP operably-linked to the expression elements of the pLenti6Ubc/V5 vector an amino-terminal V5 peptide.

This cloning strategy can be used to make a pLenti6Ubc/V5 mammalian expression construct encoding any of the BoNT/C1 substrates disclosed in the present specification.

7b. Production of a Lentiviral Stock Containing pLenti6Ubc/V5-GFP-Syntaxin-$1_{1\text{-}288}$-BFP To produce a lentiviral stock containing an expression construct encoding a BoNT/C1 substrate, such as, e.g., pLenti6Ubc/V5-GFP-Syntaxin-$1_{1\text{-}288}$-BFP, a 3.0 mL transfection solution is prepared by adding 1.5 mL of OPTI-MEM Reduced Serum Medium containing 36 μL of LipofectAmine 2000 (Invitrogen, Carlsbad, Calif.) incubated at room temperature for 5 minutes to 1.5 mL of OPTI-MEM Reduced Serum Medium containing 3 μg of an expression construct encoding a BoNT/C1 GFP-Syntaxin-$1_{1-288}$-BFP substrate, such as, e.g., pLenti6Ubc/V5-GFP-Syntaxin-$1_{1-288}$-BFP and 9 μg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately 6×10$^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentivirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately 5×10$^5$ to 2×10$^7$ pfu/mL of lentiviral particles. Aliquots can be stored at −80° C. until needed.

7c. Transduction of Cells with an Lentiviral Stock Containing a pLenti6Ubc/V5-GFP-Syntaxin-$1_{1-288}$-BFP To transduce cells with a lentiviral stock containing an expression construct encoding a BoNT/C1 substrate, such as, e.g., pLenti6Ubc/V5-GFP-Syntaxin-$1_{1-288}$-BFP, cells suitable to conduct the activity assay, as identified in Example III, are plated in a 6-well tissue culture dish containing 3 mL of an appropriate complete supplemented cell culture media, and are grown in a 37° C. incubator under 5% carbon dioxide until the cells reach the required density. Cells are inoculated with the lentiviral stock containing an expression construct encoding a BoNT/C1 GFP-Syntaxin-$1_{1-288}$-BFP substrate, such as, e.g., pLenti6Ubc/V5-GFP-Syntaxin-$1_{1-288}$-BFP, using a suitable multiplicity of infection and are incubated for approximately 16-24 hours in a 37° C. incubator under 5% carbon dioxide. The transduction media is replaced with 3 mL of fresh complete, supplemented cell culture media and the cells are incubated in a 37° C. incubator under 5% carbon dioxide for approximately 24-48 hours. The transduced cells can be used to conduct a BoNT/A, a BoNT/C1 or a BoNT/E activity assay using a GFP-Syntaxin-$1_{1-288}$-BFP substrate (Example X).

Example VI

Construction of Cell Line Stably Expressing a Clostridial Toxin Substrate

This example illustrates how to make a cell line that stably expresses a Clostridial toxin substrate disclosed in the present specification.

1. Generation of Cells Stably Containing a BoNT/A, BoNT/C1 or BoNT/E SNAP-25 Substrate 1a. Stably Transformed Cells Using a Recombinant Crossing-Over Procedure To generate a stably-integrated cell line expressing a BoNT/A, BoNT/C1 or BoNT/E substrate using a crossing over procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. A 500 μL transfection solution was prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/A, BoNT/C1 or BoNT/E, substrate, such as, e.g., pQBI-25/GFP-SNAP-$25_{1-206}$-BFP or pQBI-25/GFP-SNAP-$25_{134-206}$-BFP (see Example II, 1a and 1b). This transfection was incubated at room temperature for approximately 20 minutes. The complete, supplemented cell culture media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented cell culture media and the cells are incubated in a 37° C. incubator under 5% carbon dioxide for approximately 48 hours. Media is replaced with 3 mL of fresh complete cell culture media containing approximately 5 μg/mL of G418. Cells are incubated in a 37° C. incubator under 5% carbon dioxide for approximately 4 weeks, with old media being replaced with fresh G418-selective, complete, supplemented cell culture media every 4 to 5 days. Once G418-resistant cell colonies are established, resistant clones are replated to new 35 mm culture plates containing fresh G418-selective, complete, supplemented cell culture media, until these cells reached a density of 6 to 20×10$^5$ cells/mL.

To test for expression of a BoNT/A, BoNT/C1 or BoNT/E substrate from isolated cell lines that stably-integrated an expression construct encoding a BoNT/A, BoNT/C1 or BoNT/E, substrate, such as, e.g., pQBI-25/GFP-SNAP$25_{1-206}$-BFP or pQBI-25/GFP-SNAP$25_{134-206}$-BFP, approximately 1.5×10$^5$ cells from each cell line are plated in a 35 mm tissue culture dish containing 3 mL of G418-selective, complete, supplemented cell culture media and are grown in a 37° C. incubator under 5% carbon dioxide until cells reached a density of about 5×10$^5$ cells/ml (6-16 hours). Media is replaced with 3 mL of fresh G418-selective, complete, supplemented cell culture media and the cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and resuspended in 1×SDS sample buffer at 1 mg/ml or higher concentration.

To detect for the presence of a BoNT/A, BoNT/C1 or BoNT/E substrate, samples are boiled for 5 min, and 40 μl aliquots are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM Tris-HCl (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing a 1:50,000 dilution of mouse monoclonal anti-SNAP-25 antibody (SMI-81; Sternberger Monoclonals, Lutherville, Md.). Primary antibody probed blots are washed three times for 15 minutes each time in Tris-Buffered Saline TWEEN-20®. Washed membranes are incubated at room temperature for 2 hours in Tris-Buffered Saline TWEEN-20® containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots are washed three times for 15 minutes each time in Tris-Buffered Saline TWEEN-20®. Signal detection of the labeled SNAP-$25_{206}$-GFP substrate is visualized using the ECL Plus™ Western Blot Detection System (Amersham Biosciences, Piscataway, N.J.) and the membrane are imaged and substrate quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. Detection of the GFP-SNAP-25-BFP substrate identifies isolated cell lines that have stably integrated and express the GFP-SNAP-25-BFP substrate.

To determine the subcellular localization of a BoNT/A, BoNT/C1 or BoNT/E substrate from isolated cell lines that stably-integrated an expression construct encoding a BoNT/A, BoNT/C1 or BoNT/E SNAP-25 substrate, such as, e.g., pQBI-25/GFP-SNAP-$25_{1-206}$-BFP or pQBI-25/GFP-SNAP-$25_{134-206}$-BFP, isolated cell lines expressing GFP-SNAP-$25_{1-206}$-BFP are plated in a 35 mm tissue culture dish containing 3 mL of G418-selective, complete, supplemented cell culture media and are grown in a 37° C. incubator under 5% carbon dioxide until cells reached a density of about $5 \times 10^5$ cells/ml (6-16 hours). Media is replaced with 3 mL of fresh G418-selective, complete, supplemented cell culture media and the cells are incubated in a 37° C. incubator under 5% carbon dioxide. After 24-48 hours, living cells were observation using a fluorescence inverted microscope. Detection of GFP fluorescence in the cell membrane indicate that the expression of GFP-SNAP-$25_{1-206}$-BFP in these isolated cell lines are correctly targeted to the cell membrane. Stably transduced cells can be used to conduct a BoNT/A, a BoNT/C1 or a BoNT/E activity assay using a GFP-SNAP-25-BFP substrate (Example X).

1b. Stably Transduced Cells Using a Lentiviral Procedure

To generate a stably-integrated cell line expressing a BoNT/A, BoNT/C1 or BoNT/E substrate using a lentiviral procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. Cells are inoculated with the lentiviral stock containing an expression construct encoding a BoNT/A, BoNT/C1 or BoNT/E substrate, such as, e.g., pLenti6Ubc/V5-GFP-SNAP-$25_{1-206}$-BFP, as described above in Example V, 2b, using a suitable multiplicity of infection and are incubated for approximately 16-24 hours in a 37° C. incubator under 5% carbon dioxide. The transduction media is replaced with 3 mL of fresh complete, supplemented cell culture media containing an appropriate amount of Blasticidin. Cells are incubated in a 37° C. incubator under 5% carbon dioxide for approximately 2 weeks, with old media being replaced with fresh Blasticidin-selective, complete, supplemented cell culture media every 3 to 4 days. Once Blasticidin-resistant colonies are established, resistant clones are replated to new 35 mm culture plates containing fresh Blasticidin-selective, complete, supplemented cell culture media, until these cells reached a density of 6 to $20 \times 10^5$ cells/mL.

The presence of a BoNT/A, BoNT/C1 or BoNT/E substrate in isolated cell lines will be determined by Western blot analysis as describes above in Example V, 1a. The subcellular localization of a BoNT/A, BoNT/C1 or BoNT/E substrate in isolated cell lines will be determined by fluorescence microscopy as describes above in Example V, 1a. Stably transduced cells can be used to conduct a BoNT/A, a BoNT/C1 or a BoNT/E activity assay using a BoNT/A, a BoNT/C1 or a BoNT/E substrate (Example X).

2. Generation of Cells Stably Containing a BoNT/B, BoNT/D, BoNT/F, BoNT/G or TeNT VAMP Substrate 2a. Stably Transformed Cells Using a Recombinant Crossing-Over Procedure To generate a stably-integrated cell line expressing a BoNT/B, a BoNT/D, a BoNT/F, a BoNT/G or a TeNT substrate using a crossing over procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of expression construct encoding a BoNT/B, BoNT/D, BoNT/F, BoNT/G or TeNT VAMP substrate, such as, e.g., pQBI-25/GFP-VAMP-$1_{49-92}$-BFP, pQBI-25/GFP-VAMP-$2_{33-94}$-BFP or pQBI-25/GFP-VAMP-$3_{33-77}$-BFP (see Examples II, 2a; II, 2b; or II, 2c). This transfection is incubated at room temperature for approximately 20 minutes. The complete, supplemented media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 μg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 μg/mL of G418 until these cells reached a density of 6 to $20 \times 10^5$ cells/mL.

To test for expression of a BoNT/B, BoNT/D, BoNT/F, BoNT/G or TeNT substrate from isolated cell lines that stably-integrated an expression construct encoding a BoNT/B, BoNT/D, BoNT/F, BoNT/G or TeNT substrate, such as, e.g., pQBI-25/GFP-VAMP-$1_{49-92}$-BFP, pQBI-25/GFP-VAMP- $2_{33-94}$-BFP or pQBI-25/GFP-VAMP-$3_{33-77}$-BFP, approximately $1.5 \times 10^5$ cells from each cell line are plated in a 35 mm tissue culture dish containing 3 mL of G418-selective, complete, supplemented cell culture media and are grown in a 37° C. incubator under 5% carbon dioxide until cells reached a density of about $5 \times 10^5$ cells/ml (6-16 hours). Media is replaced with 3 mL of fresh G418-selective, complete, supplemented cell culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM Tris-HCl (pH 6.8) and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of a BoNT/B, BoNT/D, BoNT/F, BoNT/G or TeNT substrate, western blot analysis will be conducted as described above (Example VI, 1a), with the exception that blocked PVDF membranes will be incubated in a primary antibody solution containing one of the following antibodies in order to detect a BoNT/B VAMP-cleavage product rather than the rabbit polyclonal anti-SNAP25 antiserum pAb anti-SNAP25197 #1:1) 1:1000 dilution of mouse monoclonal anti-VAMP-1 antibody clone Cl 10.1 (Synaptic Systems, Goettingen, Germany); 2) 1:20,000 dilution of mouse monoclonal anti-VAMP-2 antibody clone Cl 69.1 (Synaptic Systems, Goettingen, Germany); or 3) 1:1000 dilution of mouse monoclonal anti-VAMP-3 antibody clone Cl 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of the GFP-VAMP-BFP substrate identifies isolated cell lines that have stably integrated and express the GFP-VAMP-BFP substrate.

To determine the subcellular localization of a BoNT/B, BoNT/D, BoNT/F, BoNT/G or TeNT substrate from isolated cell lines that stably-integrated an expression construct encoding a BoNT/B, BoNT/D, BoNT/F, BoNT/G or TeNT substrate, such as, e.g., pQBI-25/GFP-VAMP-$1_{49-92}$-BFP, pQBI-25/GFP-VAMP-$2_{33-94}$-BFP or pQBI-25/GFP-VAMP-$3_{33-77}$-BFP, isolated cell lines expressing a GFP-VAMP-BFP are plated in a 35 mm tissue culture dish containing 3 mL of G418-selective, complete, supplemented cell culture media and are grown in a 37° C. incubator under 5% carbon dioxide until cells reach a density of about $5 \times 10^5$ cells/ml (6-16 hours). Media is replaced with 3 mL of fresh G418-selective, complete, supplemented cell culture media and the cells are incubated in a 37° C. incubator under 5% carbon dioxide. After 24-48 hours, living cells were observation using a fluorescence inverted microscope. Detection of GFP fluorescence in the cell membrane indicates that the expression of GFP-VAMP-BFP in these isolated cell lines are correctly targeted to the cell membrane. Stably transduced cells can be used to conduct a BoNT/B, a BoNT/D, a BoNT/F, a BoNT/G or a TeNT activity assay using a GFP-VAMP-BFP (Example X).

2b. Stably Transduced Cells Using a Lentiviral Procedure

To generate a stably-integrated cell line expressing a BoNT/B, a BoNT/D, a BoNT/F, a BoNT/G or a TeNT substrate using a lentiviral procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. Cells are inoculated with the lentiviral stock containing an expression construct encoding a BoNT/B, BoNT/D, BoNT/F, BoNT/G or TeNT VAMP substrate, such as, e.g., pLenti6Ubc/V5-GFP-VAMP-$1_{49-92}$-BFP, as described above in Example V, 4b, using a suitable multiplicity of infection and are incubated for approximately 16-24 hours in a 37° C. incubator under 5% carbon dioxide. The transduction media is replaced with 3 mL of fresh complete, supplemented cell culture media containing an appropriate amount of Blasticidin. Cells are incubated in a 37° C. incubator under 5% carbon dioxide for approximately 2 weeks, with old media being replaced with fresh Blasticidin-selective, complete, supplemented cell culture media every 3 to 4 days. Once Blasticidin-resistant colonies are established, resistant clones are replated to new 35 mm culture plates containing fresh Blasticidin-selective, complete, supplemented cell culture media, until these cells reached a density of 6 to $20 \times 10^5$ cells/mL.

The presence of a BoNT/B, BoNT/D, BoNT/F, BoNT/G or TeNT substrate in isolated cell lines will be determined by Western blot analysis as describes above in Example V, 1a. The subcellular localization of a BoNT/B, a BoNT/D, a BoNT/F, a BoNT/G or a TeNT substrate in isolated cell lines will be determined by fluorescence microscopy as describes above in Example V, 1a. Stably transduced cells can be used to conduct a BoNT/B, a BoNT/D, a BoNT/F, a BoNT/G or a TeNT activity assay using a BoNT/B, a BoNT/D, a BoNT/F, a BoNT/G or a TeNT substrate (Example X).

3. Generation of Cells Stably Containing a BoNT/C1 Syntaxin Substrate

3a. Stably Transformed Cells Using a Recombinant Crossing-Over Procedure

To generate a stably-integrated cell line expressing a BoNT/C1 Syntaxin substrate using a crossing over procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of expression construct encoding a BoNT/C1 Syntaxin substrate, such as, e.g., pQBI-25/GFP-Syntaxin-$1_{1-288}$-BFP (see Examples II, 3a). This transfection is incubated at room temperature for approximately 20 minutes. The complete, supplemented media is replaced with 2 mL of OPTI-MEM Reduced Serum Medium and the 500 µL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 µg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 μg/mL of G418 until these cells reached a density of 6 to $20 \times 10^5$ cells/mL.

To test for expression of a BoNT/C1 Syntaxin substrate from isolated cell lines that stably-integrated an expression construct encoding a BoNT/C1 VAMP substrate, such as, e.g., pQBI-25/GFP-Syntaxin-$1_{1-288}$-BFP, approximately $1.5 \times 10^5$ cells from each cell line are plated in a 35 mm tissue culture dish containing 3 mL of G418-selective, complete, supplemented cell culture media and are grown in a 37° C. incubator under 5% carbon dioxide until cells reached a density of about $5 \times 10^5$ cells/ml (6-16 hours). Media is replaced with 3 mL of fresh G418-selective, complete, supplemented cell culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM Tris-HCl (pH 6.8) and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of a BoNT/C1 Syntaxin substrate, western blot analysis will be conducted as described above (Example V, 1a), with the exception: 1) blocked PVDF membranes will be incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 SNAP25$_{198}$-cleavage product; 2) blocked PVDF membranes will be incubated in a primary antibody solution containing a 1:5000 dilution of mouse monoclonal anti-Syntaxin-1 antibody clone Cl 78.2 (Synaptic Systems, Goettingen, Germany) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 Syntaxin-cleavage product. Detection of the GFP-Syntaxin-BFP substrate identifies isolated cell lines that have stably integrated and express the GFP-Syntaxin-BFP substrate.

To determine the subcellular localization of a BoNT/C1 Syntaxin substrate from isolated cell lines that stably-integrated an expression construct encoding a BoNT/C1 Syntaxin substrate, such as, e.g., pQBI-25/GFP-Syntaxin-$1_{1-288}$-BFP, isolated cell lines expressing a GFP-Syntaxin-BFP are plated in a 35 mm tissue culture dish containing 3 mL of G418-selective, complete, supplemented cell culture media and are grown in a 37° C. incubator under 5% carbon dioxide until cells reach a density of about $5 \times 10^5$ cells/ml (6-16 hours). Media is replaced with 3 mL of fresh G418-selective, complete, supplemented cell culture media and the cells are incubated in a 37° C. incubator under 5% carbon dioxide. After 24-48 hours, living cells were observation using a fluorescence inverted microscope. Detection of GFP fluorescence in the cell membrane indicates that the expression of GFP-Syntaxin-BFP in these isolated cell lines are correctly targeted to the cell membrane. Stably transduced cells can be used to conduct a BoNT/C1 activity assay using a GFP-Syntaxin-BFP (Example X).

3b. Stably Transduced Cells Using a Lentiviral Procedure

To generate a stably-integrated cell line expressing a BoNT/C1 Syntaxin substrate using a lentiviral procedure, cells suitable to conduct a Clostridial toxin activity assay, as identified in Example III, are plated in a 35 mm culture dish containing 3 mL of an appropriate complete supplemented cell culture media, and are grown in a 37° C. incubator under 5% carbon dioxide until the cells reach an appropriate density for transfection. Cells are inoculated with the lentiviral stock containing an expression construct encoding a BoNT/C1 Syntaxin substrate, such as, e.g., pLenti6Ubc/V5-GFP-Syntaxin-$1_{1-288}$-BFP, as described above in Example V, 4b, using a suitable multiplicity of infection and are incubated for approximately 16-24 hours in a 37° C. incubator under 5% carbon dioxide. The transduction media is replaced with 3 mL of fresh complete, supplemented cell culture media containing an appropriate amount of Blasticidin. Cells are incubated in a 37° C. incubator under 5% carbon dioxide for approximately 2 weeks, with old media being replaced with fresh Blasticidin-selective, complete, supplemented cell culture media every 3 to 4 days. Once Blasticidin-resistant colonies are established, resistant clones are replated to new 35 mm culture plates containing fresh Blasticidin-selective, complete, supplemented cell culture media, until these cells reached a density of 6 to $20 \times 10^5$ cells/mL.

The presence of a BoNT/C1 Syntaxin substrate in isolated cell lines will be determined by Western blot analysis as describes above in Example V, 1a. The subcellular localization of a BoNT/C1 Syntaxin substrate in isolated cell lines will be determined by fluorescence microscopy as describes above in Example V, 1a. Stably transduced cells can be used to conduct a BoNT/C1 activity assay using a BoNT/C1 Syntaxin substrate (Example X).

Example VII

Construction of a Clostridial Toxin Receptor Construct

This example illustrates how to make a Clostridial toxin receptor construct disclosed in the present specification.

1. Construction of a pUCBHB1/FGFR3 Cloning Construct

A polynucleotide molecule encoding FGFR3 (SEQ ID NO: 164) and containing restriction endonuclease sites suitable for subsequent cloning steps is synthesized using standard procedures (BlueHeron® Biotechnology, Bothell, Wash.). Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/ORL-1. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule encoding FGFR3 (SEQ ID NO: 164) can be synthesized in order to improve expression in an *Escherichia coli* strain. The polynucleotide molecule encoding the FGFR3 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, PCT Patent Serial No. 2005/020578 (Jun. 9, 2005); Lance E. Steward et al. Optimizing Expression of Active Botulinum Toxin Type A, PCT Patent Serial No. 2005/027917 (Aug. 3, 2005). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/ORL-1. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). Is so desired, optimization to a different organism, such as, e.g., a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005).

A similar cloning strategy is used to make pUCBHB1 cloning constructs comprising a polynucleotide molecule encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

Example VIII

Construction of Cell Line Transiently Expressing a Clostridial Toxin Receptor and Clostridial Toxin Substrate This example illustrates how to make a cell line that transiently expresses a Clostridial toxin receptor and a Clostridial toxin substrate disclosed in the present specification.

1. Generation of Cells Containing a FGFR3 by Adenoviral Transduction

1a. Construction of pAd-DEST/FGFR3 Expression Construct

To construct pAd-DEST/FGFR3, a pUCBHB1/FGFR3 construct will be digested with the appropriate restriction endonucleases to excise a fragment containing the FGFR3 open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pAd-DEST vector (Invitrogen, Inc, Carlsbad, Calif.), to yield pAd-DEST/FGFR3. The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 µg/mL of Ampicillin, and will be placed in a 37° C. incubator for overnight growth. Ampicillin-resistant colonies will be analyzed using an alkaline lysis plasmid mini-preparation procedure and candidate expression constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the FGFR3 operably-linked to the expression elements of the pAd-DEST vector expression vector.

A similar cloning strategy can be used to make pAd-DEST expression constructs comprising a polynucleotide molecule encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

1b. Production of an Adenoviral Stock Containing pAd-DEST/FGFR3

To produce an adenoviral stock containing an expression construct encoding a Clostridial toxin receptor, such as, e.g., pAd-DEST/FGFR3, about $5 \times 10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and are grown in a 37° C. incubator under 5% carbon dioxide until the cells reach a density of about $5 \times 10^5$ cells/ml (6-16 hours). One the day of transfection, replace complete, supplemented DMEM media with 2 mL of OPTI-MEM Reduced Serum Medium. A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of the linearized expression construct encoding an FGFR3Clostridial toxin receptor, such as, e.g., pAd-DEST/FGFR3. To linearize a pAd-DEST/FGFR3 construct, 5 µg of a pAd-DEST/FGFR31 construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 µL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection).

The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1 \times 10^7$ to $10^8$ pfu of adenoviral particles. Aliquots can be stored at −80° C. until needed.

A similar strategy can be used to produce an adenoviral stock containing an expression construct encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

1c. Amplification of an Adenoviral Stock Containing pAd-DEST/FGFR3

To amplify to the adenoviral stock containing an expression construct encoding a Clostridial toxin receptor, such as, e.g., pAd-DEST/FGFR3, about $3 \times 10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 μL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1 \times 10^8$ to $10^9$ pfu of adenoviral particles. Aliquots can be stored at −80° C. until needed.

A similar strategy can be used to amplify an adenoviral stock containing an expression construct encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

1d. Transduction of Cells with an Adenoviral Stock Containing pAd-DEST/FGFR3

To co-transduce cells with an adenoviral stock containing an expression construct encoding a Clostridial toxin receptor, such as, e.g., pAd-DEST/FGFR3 and an adenoviral stock containing an expression construct encoding a Clostridial toxin substrate (see Example V), cells suitable to conduct the activity assay are plated in a 6-well tissue culture dish containing 3 mL of an appropriate complete supplemented cell culture media, and are grown in a 37° C. incubator under 5% carbon dioxide until the cells reach the required density. Cells are inoculated with approximately 4 μL of each adenoviral stock (approximately $5 \times 10^8$ pfu/ml) and are incubated for approximately 24 hours in a 37° C. incubator under 5% carbon dioxide. The transduction media is replaced with 3 mL of fresh complete, supplemented media and the cells are incubated in a 37° C. incubator under 5% carbon dioxide for approximately 24 hours. The transduced cells can be used to conduct an activity assay for a Clostridial toxin, such as, e.g., BoNT/A.

A similar strategy can be used to co-transduce an adenoviral stock containing an expression construct encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172 and an adenoviral stock containing an expression construct encoding a Clostridial toxin substrate (see Example V).

2. Generation of Cells Containing a FGFR3 by Lentiviral Transduction

2a. Construction of pLenti6Ubc/V5-FGFR3

To make a pLenti6Ubc/V5-FGFR3 construct, a pUCBHB1/FGFR3 construct will be digested with the appropriate restriction endonucleases to excise a fragment containing the FGFR3 open reading frame. The resulting restriction fragment will be purified by the QIAquick Gel Extraction Kit (QIAGEN, Inc., Valencia, Calif.), and will be subcloned using a T4 DNA ligase procedure into a restriction endonuclease digested pLenti6Ubc vector (Invitrogen, Inc, Carlsbad, Calif.), to yield pLenti6Ubc/FGFR3. The ligation mixture is transformed into chemically competent E. coli BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy yields a mammalian expression construct encoding the FGFR3 operably-linked to the expression elements of the pLenti6Ubc/V5 vector an amino-terminal V5 peptide.

A similar cloning strategy can be used to make pLenti6Ubc/V5 expression constructs comprising a polynucleotide molecule encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

2b. Production of a Lentiviral Stock Containing pLenti6Ubc/V5-FGFR3

To produce a lentiviral stock containing an expression construct encoding a Clostridial toxin receptor, such as, e.g., pLenti6Ubc/V5-FGFR3, a 3.0 mL transfection solution is prepared by adding 1.5 mL of OPTI-MEM Reduced Serum Medium containing 36 µL of LipofectAmine 2000 (Invitrogen, Carlsbad, Calif.) incubated at room temperature for 5 minutes to 1.5 mL of OPTI-MEM Reduced Serum Medium containing 3 µg of an expression construct encoding an FGFR3, such as, e.g., pLenti6Ubc/V5-FGFR3 and 9 µg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6 \times 10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentiovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5 \times 10^5$ to $2 \times 10^7$ pfu/mL of lentiviral particles. Aliquots can be stored at −80° C. until needed.

A similar strategy can be used to produce a lentiviral stock containing an expression construct encoding a Clostridial toxin receptor, such as, e.g., pLenti6Ubc/V5 expression construct encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172.

2c. Transduction of Cells with an Lentiviral Stock Containing a pLenti6Ubc/V5-FGFR3

To co-transduce cells with a lentiviral stock containing an expression construct encoding a Clostridial toxin receptor, such as, e.g., pLenti6Ubc/V5-FGFR3 and a lentiviral stock containing an expression construct encoding a BoNT/A substrate (see Example V), cells suitable to conduct the activity assay are plated in a 6-well tissue culture dish containing 3 mL of an appropriate complete supplemented cell culture media, and are grown in a 37° C. incubator under 5% carbon dioxide until the cells reach the required density. Cells are inoculated with each lentiviral stock using a suitable multiplicity of infection and are incubated for approximately 16-24 hours in a 37° C. incubator under 5% carbon dioxide. The transduction media is replaced with 3 mL of fresh complete, supplemented cell culture media and the cells are incubated in a 37° C. incubator under 5% carbon dioxide for approximately 24-48 hours. The transduced cells can be used to conduct an activity assay for a Clostridial toxin, such as, e.g., BoNT/A.

A similar strategy can be used to co-transduce a lentiviral stock containing an expression construct encoding any Clostridial toxin receptor disclosed in the present specification, such as, e.g., a polynucleotide molecule encoding a SV2 receptor, such as, e.g., SEQ ID NO: 167, SEQ ID NO: 168, SEQ ID NO: 169, and SEQ ID NO: 170; a polynucleotide molecule encoding a Synaptotagmin I, such as, e.g., SEQ ID NO: 171; or a polynucleotide molecule encoding a Synaptotagmin II, such as, e.g., SEQ ID NO: 172 and a lentiviral stock containing an expression construct encoding a Clostridial toxin substrate (see Example V).

Example IX

Construction of Cell Line Stably Expressing a Clostridial Toxin Receptor and Clostridial Toxin Substrate This example illustrates how to make a cell line that stably expresses a Clostridial toxin receptor and a Clostridial toxin substrate disclosed in the present specification.

1. Stably Transduced Cells Using a Lentiviral Procedure

To generate a stably-integrated cell line expressing a Clostridial toxin receptor and a Clostridial toxin substrate using a lentiviral procedure, a suitable density of appropriate cells are plated in a 6-well tissue culture dish containing 3 mL of complete, supplemented culture media and are grown in a 37° C. incubator under 5% carbon dioxide until the cells reach a density appropriate for transduction. Cells are inoculated with each lentiviral stock, as described above in Example VII, 2c, using a suitable multiplicity of infection and are incubated for approximately 16-24 hours in a 37° C. incubator under 5% carbon dioxide. The transduction media is replaced with 3 mL of fresh complete, supplemented media containing an appropriate amount of Blasticidin. Cells are incubated in a 37° C. incubator under 5% carbon dioxide for approximately 2 weeks, with old media being replaced with fresh Blasticidin-selective, complete, supplemented media every 3 to 4 days. Once Blasticidin-resistant colonies are established, resistant clones are replated to new 35 mm culture plates containing fresh Blasticidin-selective, complete, supplemented media, until these cells reached a density of 6 to $20 \times 10^5$ cells/mL.

The presence of the Clostridial toxin substrate in isolated cell lines will be determined by Western blot analysis as describes above in Example V. The presence of the FGFR3 in isolated cell lines will be determined by Western blot analysis as describes above in Example VI, except a 1:50,000 dilution of mouse monoclonal anti-V5 antibody (Invitrogen, Inc, Carlsbad, Calif.) will be used as the primary antibody. The subcellular localization of Clostridial toxin substrate in isolated cell lines will be determined by fluorescence microscopy as describes above in Example V. Stably transduced cells can be used to conduct an activity assay for a Clostridial toxin, such as, e.g., BoNT/A (Example X).

This strategy is suitable to establish a stably-integrated cell line expressing any of the Clostridial toxin substrates and any Clostridial toxin receptor disclosed in the present specification.

Example X

Cell-based Assays for Clostridial Toxin Activity

This example illustrates how to conduct a cell-based FRET Clostridial toxin activity assay.

1. Cell-Based FRET Activity Assay for a BoNT/A

To conduct a cell-based FRET activity assay using a BoNT/A, cells expressing a Clostridial toxin receptor and a BoNT/A SNAP-25 substrate cleavable by the BoNT/A will be generated by either 1) identifying cells expressing an endogenous BoNT/A receptor, like FGFR3 identified (Example IV) and transiently expressing a GFP-SNAP-25-BFP substrate (Example V); 2) identifying cells expressing an endogenous BoNT/A receptor, like FGFR3 identified (Example IV) and stably expressing a GFP-SNAP-25-BFP substrate (Example VI); 3) generating cells that transiently express a BoNT/A receptor and a GFP-SNAP-25-BFP substrate (Example VII); or 4) generating cells that stably express a BoNT/A receptor and GFP-SNAP-25-BFP substrate (Example VIII). These cells are plated in a 35 mm culture dish containing 3 mL of an appropriate complete supplemented cell culture media, and are grown in a 37° C. incubator under 5% carbon dioxide until the cells reach an appropriate density. A standard curve will be obtained by treating the cells with 0.001 nM, 0.002 nM, 0.005 nM, 0.01 nM, 0.02 nM or 0.05 nM of a BoNT/A, with each of the concentrations run in triplicates. FRET will be determined using the Typhoon 9140 software with excitation at 380 nm and emission collection at 510 nm±30 nm. The emissions at each concentration of a BoNT/A will be calculated as a percentage of the untreated control (fluorescence measured at 510 nm±30 nm of cells not treated with the modified toxin). Increased detection of emissions collection at 510 nm±30 nm from the test sample as compared to the control sample will indicate the presence of activity from the BoNT/A.

A similar design will be used to assay for activity from 1) a BoNT/C1; and 2) a BoNT/E, except that the GFP-SNAP-25-BFP substrate introduced into the appropriate cell line will be cleavable by a BoNT/C1 and/or a BoNT/E and either a cell line expressing an endogenous BoNT/C1 receptor and/or an endogenous BoNT/E receptor will be isolated, or an exogenous BoNT/C1 receptor and/or an exogenous BoNT/E receptor will be transfected into an appropriate cell line.

2. Cell-Based FRET Activity Assay for a BoNT/B

To conduct a cell-based FRET activity assay using a BoNT/B, cells expressing a BoNT/B receptor and a BoNT/B VAMP substrate cleavable by the BoNT/B will be generated by either 1) identifying cells expressing an endogenous BoNT/B receptor, like Synaptobrevin I identified (Example III) and transiently expressing a GFP-VAMP-BFP substrate (Example V); 2) identifying cells expressing an endogenous BoNT/B receptor, like Synaptobrevin I identified (Example III) and stably expressing a GFP-VAMP-BFP substrate (Example VI); 3) generating cells that transiently express a BoNT/B receptor and a GFP-VAMP-BFP substrate (Example VII); or 4) generating cells that stably express a BoNT/B receptor and GFP-VAMP-BFP substrate (Example VII). These cells are plated in a 35 mm culture dish containing 3 mL of an appropriate complete supplemented cell culture media, and are grown in a 37° C. incubator under 5% carbon dioxide until the cells reach an appropriate density. A standard curve will be obtained by treating the cells with 0.001 nM, 0.002 nM, 0.005 nM, 0.01 nM, 0.02 nM or 0.05 nM of a BoNT/B, with each of the concentrations run in triplicates. FRET will be determined using the Typhoon 9140 software with excitation at 380 nm and emission collection at 510 nm±30 nm. The emissions at each concentration of a BoNT/B will be calculated as a percentage of the untreated control (fluorescence measured at 510 nm±30 nm of cells not treated with the modified toxin). Increased detection of emissions collection at 510 nm±30 nm from the test sample as compared to the control sample will indicate the presence of activity from the BoNT/B.

A similar assay design will be used to assay for activity from 1) a BoNT/D; 2) a BoNT/F; 3) a BoNT/G; and 2) a TeNT, except that the GFP-VAMP-BFP substrate introduced into the appropriate cell line will be cleavable by a BoNT/D, a BoNT/F, a BoNT/G and/or a TeNT and either a cell line expressing an endogenous BoNT/D receptor, an endogenous BoNT/F receptor, an endogenous BoNT/G receptor and/or an endogenous TeNT receptor will be isolated, or an exogenous BoNT/D receptor, an exogenous BoNT/F receptor, an exogenous BoNT/G receptor and/or an exogenous TeNT receptor will be transfected into an appropriate cell line.

3. Cell-Based FRET Activity Assay for a BoNT/C1

To conduct a cell-based FRET activity assay using a BoNT/C1, cells expressing a Clostridial toxin receptor and a BoNT/C1 Syntaxin substrate cleavable by the BoNT/C1 will be generated by either 1) identifying cells expressing an endogenous BoNT/C1 receptor identified (Example III) and transiently expressing a GFP-Syntaxin-BFP substrate (Example IV); 2) identifying cells expressing an endogenous BoNT/C1 receptor identified (Example III) and stably expressing a GFP-Syntaxin-BFP substrate (Example V); 3) generating cells that transiently express a BoNT/C1 receptor and a GFP-Syntaxin-BFP substrate (Example VII); or 4) generating cells that stably express a BoNT/C1 receptor and GFP-Syntaxin-BFP substrate (Example VIII). These cells are plated in a 35 mm culture dish containing 3 mL of an appropriate complete supplemented cell culture media, and are grown in a 37° C. incubator under 5% carbon dioxide until the cells reach an appropriate density. A standard curve will be obtained by treating the cells with 0.001 nM, 0.002 nM, 0.005 nM, 0.01 nM, 0.02 nM or 0.05 nM of a BoNT/C1, with each of the concentrations run in triplicates. FRET will be determined using the Typhoon 9140 software with excitation at 380 nm and emission collection at 510 nm±30 nm. The emissions at each concentration of a BoNT/C1 will be calculated as a percentage of the untreated control (fluorescence measured at 510 nm±30 nm of cells not treated with the modified toxin). Increased detection of emissions collection at 510 nm±30 nm from the test sample as compared to the control sample will indicate the presence of activity from the BoNT/C1.

Example XI

In Vitro Assays for Clostridial Toxin Activity

This example illustrates how to conduct an in vitro Clostridial toxin activity assay.

1. In Vitro Activity Assay for a BoNT/A

To conduct a FRET-based in vitro activity assay using a BoNT/A, a BoNT/A substrate, such as, e.g., GFP-SNAP-$25_{134-206}$(Cys)-Alexa Fluor® 546 is mixed with a test sample, such as, e.g., a reconstituted formulated BoNT/A product. FRET will be determined using the Typhoon 9140 software with excitation at 380 nm and emission collection at 510 nm±30 nm. The emissions of the sample will be calculated as a percentage of the untreated control (fluorescence measured at 510 nm±30 nm of cells not treated with the toxin). Increased detection of emissions collection at 510 nm±30 nm from the test sample as compared to the control sample will indicate the presence of BoNT/A activity.

To conduct a LRET-based in vitro activity assay using a BoNT/A, a BoNT/A substrate, such as, e.g., GFP-SNAP-$25_{134-206}$(Cys)-CS124-DTPA-EMCH-Tb is mixed with a test sample, such as, e.g., a reconstituted formulated BoNT/A product. LRET will be determined using the Typhoon 9140 software with excitation at 330 nm and emission collection at 586 nm±30 nm. The emissions of the sample will be calculated as a percentage of the untreated control (fluorescence measured at 586 nm±30 nm of cells not treated with the toxin). Increased detection of emissions collection at 586 nm±30 nm from the test sample as compared to the control sample will indicate the presence of BoNT/A activity.

Although the invention has been described with reference to the examples provided above, it should be understood that various modifications can be made without departing from the spirit of the invention. Accordingly, the invention is limited only by the following claims.

What is claimed:

1. A cell composition comprising:
   a. a Clostridial toxin substrate comprising
      i. a lanthanide donor complex comprising a lanthanide binding site and a lanthanide ion;
      ii. an acceptor;
      iii. a Clostridial toxin recognition sequence including a $P_1$-$P_1'$ cleavage site that intervenes between the lanthanide donor complex and the acceptor; and
      iv. a membrane targeting domain;
         wherein the acceptor has an absorbance spectrum overlapping the emission spectrum of the lanthanide donor complex; and
         wherein, under the appropriate conditions, resonance energy transfer is exhibited between the lanthanide donor complex and the acceptor; and
   b. a Clostridial toxin receptor capable of initiating the intoxication process by selectively binding a Clostridial toxin.

2. The composition according to 1, wherein the Clostridial toxin receptor comprises an endogenous Clostridial toxin receptor.

3. The composition according to 1, wherein the Clostridial toxin receptor comprises an exogenous Clostridial toxin receptor.

4. The composition according to 1, wherein the cell is a neuronal cell.

5. The composition according to 1, wherein the cell is a non-neuronal cell.

6. The substrate according to claim 1, wherein the lanthanide binding site has a Kd for a lanthanide ion of less than 1 μM.

7. The composition according to claim 1, wherein the lanthanide binding site comprises a chelate, a cryptate, or an EF-hand motif.

8. The composition according to claim 1, wherein the acceptor is an acceptor fluorophore.

9. The composition according to claim 8, wherein the acceptor fluorophore comprises a fluorescent protein, a fluorophore binding protein, or a fluorescent dye.

10. The composition according to claim 1, wherein the acceptor is a non fluorescent acceptor.

11. The composition according to claim 1, wherein the lanthanide donor complex further comprises an antenna.

12. The composition according to claim 11, wherein the antenna is distinct from the lanthanide-binding site.

13. The composition according to claim 11, wherein the antenna is incorporated with lanthanide biding site.

14. The composition according to claim 1, wherein the substrate is a peptide having a length of at most 20 residues, at most 50 residues, at most 100 residues, or at most 150 residues.

15. The composition according to claim 1, wherein the substrate is a peptide having a length of at least 100 residues, at least 300 residues, at least 500 residues, or at least 700 residues.

16. The composition according to claim 1, wherein the Clostridial toxin recognition sequence is a peptide having a length of at most 20 residues, at most 30 residues, at most 40 residues or at most 50 residues.

17. The composition according to claim 1, wherein the Clostridial toxin recognition sequence is a peptide having a length of at least 20 residues, at least 50 residues, at least 100 residues, or at least 200 residues.

18. The composition according to claim 1, wherein the substrate can be cleaved with an activity of at least 1 nanomole/minute/milligram toxin, at least 20 nanomoles/minute/milligram toxin or at least 100 nanomoles/minute/milligram toxin.

* * * * *

UNITED STATES PATENT AND TRADEMARK OFFICE
CERTIFICATE OF CORRECTION

PATENT NO. : 7,846,722 B2
APPLICATION NO. : 11/754046
DATED : December 7, 2010
INVENTOR(S) : Dudley J. Williams et al.

It is certified that error appears in the above-identified patent and that said Letters Patent is hereby corrected as shown below:

On page 2, in column 2, under "Other Publications", line 24, delete "affmity" and insert -- affinity --, therefor.

On page 2, in column 2, under "Other Publications", line 47, delete "fmal" and insert -- final --, therefor.

On page 2, in column 2, under "Other Publications", line 57, delete "affmity" and insert -- affinity --, therefor.

On page 4, in column 1, under "Other Publications", line 63, delete "gluthation" and insert -- glutathione --, therefor.

On page 4, in column 2, under "Other Publications", line 52, delete "flourescent" and insert -- fluorescent --, therefor.

Figure 8B:
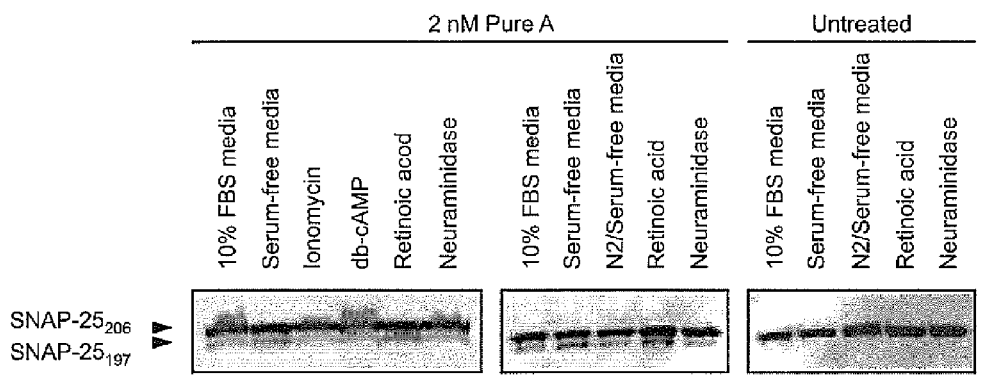
FIG. 8b shows Western blot analysis evaluating the effects of cell differentiation on the uptake of BoNT/A. The blots show either Neuro-2A cells or SH-SY5Y cells treated 2 nM of Pure BoNT/A overnight that where either grown in serum-free media or with various differentiation reagents (Ionomycin, db-cAMP, Retinoic acid, Neuraminidase or N2), with equal amounts of protein loaded per lane and probed with an antibody (SMI-81; Sternberger Monoclonals, Lutherville, Md.) that detects the uncleaved SNAP-25$_{206}$ substrate and the BoNT/A SNAP-25$_{197}$ cleavage product.
Figure 8B:
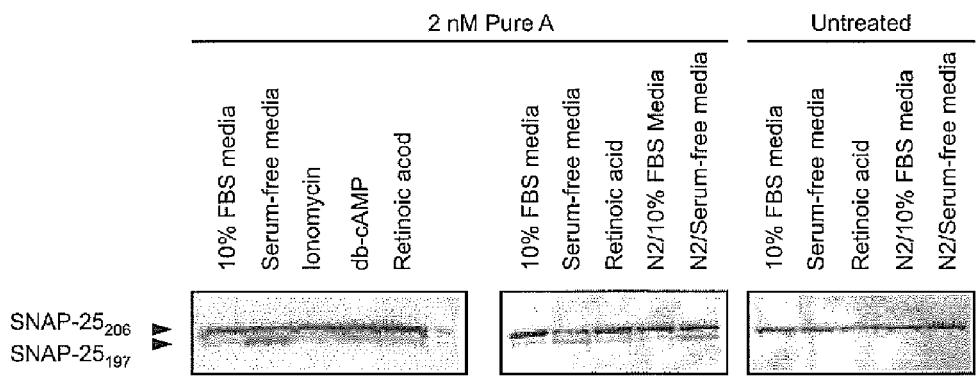

On sheet 9 of 10, in Figure 8b, below db-cAMP, line 5, delete "acod" and insert -- acid --, therefor.

On sheet 9 of 10, in Figure 8b, below db-cAMP, line 5, delete "acod" and insert -- acid --, therefor.

In column 62, line 25, delete "obelin;" and insert -- oberlin; --, therefor.

In column 62, line 44, delete "Greene®" and insert -- Green® --, therefor.

In column 62, line 62, delete "Color S™" and insert -- Colors™ --, therefor.

In column 63, line 44, delete "muleri" and insert -- mulleri --, therefor.

Signed and Sealed this
Seventeenth Day of May, 2011

David J. Kappos
*Director of the United States Patent and Trademark Office*

CERTIFICATE OF CORRECTION (continued)
U.S. Pat. No. 7,846,722 B2

In column 67, line 22, delete "striate" and insert -- striata --, therefor.

In column 67, line 44, delete "Anthozoa," and insert -- (Anthozoa, --, therefor.

In column 67, line 45, delete "Actinaria)," and insert -- Actiniaria), --, therefor.

In column 72, line 64, delete "Clostridila" and insert -- Clostridial --, therefor.

In column 73, line 10, delete "Clostridila" and insert -- Clostridial --, therefor.

In column 73, line 17, delete "Clostridila" and insert -- Clostridial --, therefor.

In column 78, line 25, delete "e.g.," and insert -- e.g., --, therefor.

In column 82, line 6, after "nine, or" insert -- 10 --.

In column 85, line 57, delete "subtilus" and insert -- subtilis --, therefor.

In column 89, line 45, delete "Electostatic" and insert -- Electrostatic --, therefor.

In column 93, line 12, delete "Vitalitye" and insert -- Vitality® --, therefor.

In column 93, line 19, delete "Vitalitye" and insert -- Vitality® --, therefor.

In column 95, line 17, delete "hemagluttinin" and insert -- hemagglutinin --, therefor.

In column 96, line 45, delete "laminoethyl" and insert -- aminoethyl --, therefor.

In column 96, line 47, delete "tranfection" and insert -- transfection --, therefor.

In column 98, line 6, delete "[125I]" and insert -- [125I] --, therefor.

In column 106, line 33, delete "eurythrocytes," and insert -- erythrocytes, --, therefor.

In column 109, line 23, delete "2.1n" and insert -- 2. In --, therefor.

In column 113, line 65, delete "gramacidin" and insert -- gramicidin --, therefor.

In column 115, line 47, delete "AdEaSy™" and insert -- AdEasy™ --, therefor.

In column 115, line 49, delete "AdEaSy™" and insert -- AdEasy™ --, therefor.

In column 116, line 46, delete "Clonetech," and insert -- Clontech, --, therefor.

In column 116, line 48, delete "Clonetech," and insert -- Clontech, --, therefor.

In column 133, line 25, delete "SLOOP" and insert -- S100P --, therefor.

In column 148, line 50, delete "Clonetech," and insert -- Clontech, --, therefor.

In column 149, line 58, delete "Clonetech," and insert -- Clontech, --, therefor.

In column 150, line 30, delete "Clonetech," and insert -- Clontech, --, therefor.

In column 154, line 65, delete "Clonetech," and insert -- Clontech, --, therefor.

In column 155, line 51, delete "Clonetech," and insert -- Clontech, --, therefor.

In column 156, line 60, delete "Clonetech," and insert -- Clontech, --, therefor.

In column 158, line 2, delete "Clonetech," and insert -- Clontech, --, therefor.

In column 159, line 10, delete "Clonetech," and insert -- Clontech, --, therefor.

In column 159, line 31-32, delete "Syntaxin-1'-288" and insert -- Syntaxin-$1_{1-288}$ --, therefor.

In column 181, line 2-3, delete "lentiovirus" and insert -- lentivirus --, therefor.

In column 185, line 34, delete "lentiovirus" and insert -- lentivirus --, therefor.

In column 189, line 20, delete "lentiovirus" and insert -- lentivirus --, therefor.

In column 201, line 23, delete "lentiovirus" and insert -- lentivirus --, therefor.

In column 202, line 25, delete "Example VII," and insert -- Example VIII, --, therefor.

SEQUENCE LISTING

<160> NUMBER OF SEQ ID NOS: 303

<210> SEQ ID NO 1
<211> LENGTH: 206
<212> TYPE: PRT
<213> ORGANISM: Homo sapiens

<400> SEQUENCE: 1

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
                35                  40                  45

Met Leu Asp Glu Gln Gly Glu Gln Leu Asp Arg Val Glu Glu Gly Met
        50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
            195                 200                 205
```

<210> SEQ ID NO 2
<211> LENGTH: 206
<212> TYPE: PRT
<213> ORGANISM: Homo sapiens

<400> SEQUENCE: 2

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
                35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
```

```
                65                  70                  75                  80
Leu Gly Lys Phe Cys Gly Leu Cys Val Cys Pro Cys Asn Lys Leu Lys
                    85                  90                  95

Ser Ser Asp Ala Tyr Lys Lys Ala Trp Gly Asn Asn Gln Asp Gly Val
                100                 105                 110

Val Ala Ser Gln Pro Ala Arg Val Asp Glu Arg Gln Met Ala
                115                 120                 125

Ile Ser Gly Gly Phe Ile Arg Arg Val Thr Asn Asp Ala Arg Glu Asn
            130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
                195                 200                 205

<210> SEQ ID NO 3
<211> LENGTH: 211
<212> TYPE: PRT
<213> ORGANISM: Homo sapiens

<400> SEQUENCE: 3

Met Asp Asn Leu Ser Ser Glu Glu Ile Gln Gln Arg Ala His Gln Ile
  1               5                  10                  15

Thr Asp Glu Ser Leu Glu Ser Thr Arg Arg Ile Leu Gly Leu Ala Ile
                 20                  25                  30

Glu Ser Gln Asp Ala Gly Ile Lys Thr Ile Thr Met Leu Asp Glu Gln
             35                  40                  45

Lys Glu Gln Leu Asn Arg Ile Glu Glu Gly Leu Asp Gln Ile Asn Lys
         50                  55                  60

Asp Met Arg Glu Thr Glu Lys Thr Leu Thr Glu Leu Asn Lys Cys Cys
 65                  70                  75                  80

Gly Leu Cys Val Cys Pro Cys Asn Arg Thr Lys Asn Phe Glu Ser Gly
                 85                  90                  95

Lys Ala Tyr Lys Thr Thr Trp Gly Asp Gly Glu Asn Ser Pro Cys
                100                 105                 110

Asn Val Val Ser Lys Gln Pro Gly Pro Val Thr Asn Gly Gln Leu Gln
                115                 120                 125

Gln Pro Thr Thr Gly Ala Ala Ser Gly Gly Tyr Ile Lys Arg Ile Thr
            130                 135                 140

Asn Asp Ala Arg Glu Asp Glu Met Glu Glu Asn Leu Thr Gln Val Gly
145                 150                 155                 160

Ser Ile Leu Gly Asn Leu Lys Asp Met Ala Leu Asn Ile Gly Asn Glu
                165                 170                 175

Ile Asp Ala Gln Asn Pro Gln Ile Lys Arg Ile Thr Asp Lys Ala Asp
                180                 185                 190

Thr Asn Arg Asp Arg Ile Asp Ile Ala Asn Ala Arg Ala Lys Lys Leu
            195                 200                 205

Ile Asp Ser
    210

<210> SEQ ID NO 4
<211> LENGTH: 158
```

```
<212> TYPE: PRT
<213> ORGANISM: Homo sapiens

<400> SEQUENCE: 4

Met Asp Asn Leu Ser Ser Glu Glu Ile Gln Gln Arg Ala His Gln Ile
 1               5                  10                  15

Thr Asp Glu Ser Leu Glu Ser Thr Arg Arg Ile Leu Gly Leu Ala Ile
                20                  25                  30

Glu Ser Gln Asp Ala Gly Ile Lys Thr Ile Thr Met Leu Asp Glu Gln
                35                  40                  45

Lys Glu Gln Leu Asn Arg Ile Glu Glu Gly Leu Asp Gln Ile Asn Lys
 50                  55                  60

Asp Met Arg Glu Thr Glu Lys Thr Leu Thr Glu Leu Asn Lys Cys Cys
65                   70                  75                  80

Gly Leu Cys Val Cys Pro Cys Asn Ser Ile Thr Asn Asp Ala Arg Glu
                85                  90                  95

Asp Glu Met Glu Glu Asn Leu Thr Gln Val Gly Ser Ile Leu Gly Asn
                100                 105                 110

Leu Lys Asp Met Ala Leu Asn Ile Gly Asn Glu Ile Asp Ala Gln Asn
                115                 120                 125

Pro Gln Ile Lys Arg Ile Thr Asp Lys Ala Asp Thr Asn Arg Asp Arg
130                 135                 140

Ile Asp Ile Ala Asn Ala Arg Ala Lys Lys Leu Ile Asp Ser
145                 150                 155

<210> SEQ ID NO 5
<211> LENGTH: 206
<212> TYPE: PRT
<213> ORGANISM: Macaca mulatta

<400> SEQUENCE: 5

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
                35                  40                  45

Met Leu Asp Glu Gln Gly Glu Gln Leu Glu Arg Ile Glu Glu Gly Met
 50                  55                  60

Asp Gln Ile Asn Lys Asp Met Lys Glu Ala Glu Lys Asn Leu Thr Asp
65                   70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
                115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190
```

```
Asp Glu Ala Asn Gln Arg Ala Thr Lys Met Leu Gly Ser Gly
        195                 200                 205
```

<210> SEQ ID NO 6
<211> LENGTH: 206
<212> TYPE: PRT
<213> ORGANISM: Rattus norvegicus

<400> SEQUENCE: 6

```
Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
             20                  25                  30

Leu Gln Leu Val Glu Glu Ser Lys Asp Ala Gly Ile Arg Thr Leu Val
         35                  40                  45

Met Leu Asp Glu Gln Gly Glu Gln Leu Asp Arg Val Glu Glu Gly Met
     50                  55                  60

Asn His Ile Asn Gln Asp Met Lys Glu Ala Lys Asn Leu Lys Asp
 65                  70                  75                  80

Leu Gly Lys Cys Cys Gly Leu Phe Ile Cys Pro Cys Asn Lys Leu Lys
                 85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 7
<211> LENGTH: 206
<212> TYPE: PRT
<213> ORGANISM: Rattus norvegicus

<400> SEQUENCE: 7

```
Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
             20                  25                  30

Leu Gln Leu Val Glu Glu Ser Lys Asp Ala Gly Ile Arg Thr Leu Val
         35                  40                  45

Met Leu Asp Glu Gln Gly Glu Gln Leu Glu Arg Ile Glu Glu Gly Met
     50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
                100                 105                 110
```

```
Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205
```

<210> SEQ ID NO 8
<211> LENGTH: 206
<212> TYPE: PRT
<213> ORGANISM: Mus musculus

<400> SEQUENCE: 8

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205
```

<210> SEQ ID NO 9
<211> LENGTH: 210
<212> TYPE: PRT
<213> ORGANISM: Rattus norvegicus

<400> SEQUENCE: 9

```
Met Asp Asp Leu Ser Pro Glu Glu Ile Gln Leu Arg Ala His Gln Val
1               5                   10                  15

Thr Asp Glu Ser Leu Glu Ser Thr Arg Arg Ile Leu Gly Leu Ala Ile
            20                  25                  30
```

```
Glu Ser Gln Asp Ala Gly Ile Lys Thr Ile Thr Met Leu Asp Glu Gln
            35                  40                  45

Gly Glu Gln Leu Asn Arg Ile Glu Glu Gly Met Asp Gln Ile Asn Lys
        50                  55                  60

Asp Met Arg Glu Ala Glu Lys Thr Leu Thr Glu Leu Asn Lys Cys Cys
 65                  70                  75                  80

Gly Leu Cys Val Cys Pro Cys Asn Arg Thr Lys Asn Phe Glu Ser Gly
                85                  90                  95

Lys Asn Tyr Lys Ala Thr Trp Gly Asp Gly Gly Asp Ser Ser Pro Ser
            100                 105                 110

Asn Val Val Ser Lys Gln Pro Ser Arg Ile Thr Asn Gly Gln Pro Gln
        115                 120                 125

Gln Thr Thr Gly Ala Ala Ser Gly Gly Tyr Ile Lys Arg Ile Thr Asn
    130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190

Asn Lys Asn Arg Ile Asp Ile Ala Asn Thr Arg Ala Lys Lys Leu Ile
        195                 200                 205

Asp Ser
   210

<210> SEQ ID NO 10
<211> LENGTH: 210
<212> TYPE: PRT
<213> ORGANISM: Mus musculus

<400> SEQUENCE: 10

Met Asp Asn Leu Ser Pro Glu Glu Val Gln Leu Arg Ala His Gln Val
  1               5                  10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
            35                  40                  45

Gly Glu Gln Leu Asn Arg Ile Glu Glu Gly Met Asp Gln Ile Asn Lys
        50                  55                  60

Asp Met Arg Glu Ala Glu Lys Thr Leu Thr Glu Leu Asn Lys Cys Cys
 65                  70                  75                  80

Gly Leu Cys Ile Cys Pro Cys Asn Arg Thr Lys Asn Phe Glu Ser Gly
                85                  90                  95

Lys Asn Tyr Lys Ala Thr Trp Gly Asp Gly Gly Asp Asn Ser Pro Ser
            100                 105                 110

Asn Val Val Ser Lys Gln Pro Ser Arg Ile Thr Asn Gly Gln Pro Gln
        115                 120                 125

Gln Thr Thr Gly Ala Ala Ser Gly Gly Tyr Ile Lys Arg Ile Thr Asn
    130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190
```

-continued

Asn Lys Asn Arg Ile Asp Ile Ala Asn Thr Arg Ala Lys Lys Leu Ile
        195                 200                 205

Asp Ser
    210

<210> SEQ ID NO 11
<211> LENGTH: 206
<212> TYPE: PRT
<213> ORGANISM: Gallus gallus

<400> SEQUENCE: 11

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 12
<211> LENGTH: 204
<212> TYPE: PRT
<213> ORGANISM: Carassius auratus

<400> SEQUENCE: 12

Met Ala Glu Asp Ala Asp Met Arg Asn Glu Leu Ser Asp Met Gln Gln
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

```
Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200
```

<210> SEQ ID NO 13
<211> LENGTH: 203
<212> TYPE: PRT
<213> ORGANISM: Carassius auratus

<400> SEQUENCE: 13

```
Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200
```

<210> SEQ ID NO 14
<211> LENGTH: 204
<212> TYPE: PRT
<213> ORGANISM: Danio rerio

<400> SEQUENCE: 14

```
Met Ala Glu Asp Ser Asp Met Arg Asn Glu Leu Ala Asp Met Gln Gln
1               5                   10                  15
```

```
Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Ala Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200

<210> SEQ ID NO 15
<211> LENGTH: 203
<212> TYPE: PRT
<213> ORGANISM: Danio rerio

<400> SEQUENCE: 15

Met Ala Asp Glu Ser Asp Met Arg Asn Glu Leu Asn Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190
```

```
                   180                 185                 190
Asn Gln Arg Ala Thr Lys Met Leu Gly Ser Gly
        195                 200

<210> SEQ ID NO 16
<211> LENGTH: 214
<212> TYPE: PRT
<213> ORGANISM: Danio rerio

<400> SEQUENCE: 16

Met Ala Asp Met Thr Val Glu Asp Ile Thr Met Arg Ala Asn Gln Val
 1               5                  10                  15

Thr Asp Glu Ser Leu Glu Ser Thr Arg Arg Met Leu Gln Met Ala Glu
            20                  25                  30

Glu Ser Arg Glu Thr Gly Val Lys Thr Met Thr Met Leu Asp Glu Gln
        35                  40                  45

Gly Glu Gln Leu Arg Arg Val Asp Gln Gly Met Asp Gln Ile Asn Gln
    50                  55                  60

Asp Met Arg Gln Ala Glu Lys Asn Leu Thr Asp Leu Ser Lys Cys Cys
65                  70                  75                  80

Gly Leu Cys Val Cys Pro Cys Glu Arg Val Thr Ser Ile Glu His Asp
                85                  90                  95

Gly Arg Tyr Lys Arg Thr Trp Gly Thr Gly Ser Asp Asn Ser Ser Thr
            100                 105                 110

Glu Gly Lys Glu Gly Gly Val Val Ser Ser Gln Pro Thr Ala Val Arg
        115                 120                 125

Asn Gly Gln Ala Val Ser Gly Gly Ser Ser Gly Ala Ser Gly Pro Tyr
    130                 135                 140

Ile Lys Arg Ile Thr Asn Asp Ala Arg Glu Asp Glu Met Glu Glu Asn
145                 150                 155                 160

Leu Asp Gln Val Gly Ser Ile Ile Gly Asn Leu Lys Asn Leu Ala Leu
                165                 170                 175

Asp Met Gly Asn Glu Ile Asp Lys Gln Asn Lys Thr Ile Asp Arg Ile
            180                 185                 190

Thr Asp Lys Ala Asp Met Asn Lys Ala Arg Ile Asp Glu Ala Asn Gln
        195                 200                 205

Arg Ala Asn Lys Leu Leu
    210

<210> SEQ ID NO 17
<211> LENGTH: 210
<212> TYPE: PRT
<213> ORGANISM: Torpedo marmorata

<400> SEQUENCE: 17

Met Glu Asn Ser Val Glu Asn Ser Met Asp Pro Arg Ser Glu Gln Glu
 1               5                  10                  15

Glu Met Gln Arg Cys Ala Asp Gln Ile Thr Asp Glu Ser Leu Glu Ser
            20                  25                  30

Thr Arg Arg Met Leu Gln Leu Val Glu Glu Ser Lys Asp Ala Gly Ile
        35                  40                  45

Arg Thr Leu Val Met Leu Asp Glu Gln Gly Glu Gln Leu Glu Arg Ile
    50                  55                  60

Glu Glu Gly Met Asp Gln Ile Asn Lys Asp Met Lys Glu Ala Glu Lys
65                  70                  75                  80

Asn Leu Ser Asp Leu Gly Lys Cys Cys Gly Leu Cys Ser Cys Pro Cys
```

```
                    85                  90                  95
Asn Lys Leu Lys Asn Phe Glu Ala Gly Gly Ala Tyr Lys Lys Val Trp
                100                 105                 110
Gly Asn Asn Gln Asp Gly Val Val Ala Ser Gln Pro Ala Arg Val Met
                115                 120                 125
Asp Asp Arg Glu Gln Met Ala Met Ser Gly Gly Tyr Ile Arg Arg Ile
                130                 135                 140
Thr Asp Asp Ala Arg Glu Asn Glu Met Glu Glu Asn Leu Asp Gln Val
145                 150                 155                 160
Gly Ser Ile Ile Gly Asn Leu Arg His Met Ala Leu Asp Met Ser Asn
                165                 170                 175
Glu Ile Gly Ser Gln Asn Ala Gln Ile Asp Arg Ile Val Val Lys Gly
                180                 185                 190
Asp Met Asn Lys Ala Arg Ile Asp Glu Ala Asn Lys His Ala Thr Lys
                195                 200                 205
Met Leu
    210

<210> SEQ ID NO 18
<211> LENGTH: 206
<212> TYPE: PRT
<213> ORGANISM: Xenopus laevis

<400> SEQUENCE: 18

Met Ala Asp Asp Ala Asp Met Arg Asn Glu Leu Glu Glu Met Gln Arg
1               5                   10                  15
Arg Ala Asp Gln Leu Ala Asp Glu Ser Leu Glu Ser Thr Arg Arg Met
                20                  25                  30
Leu Gln Tyr Val Glu Gly Ser Lys Asp Ala Gly Ile Arg Thr Leu Val
                35                  40                  45
Met Leu Asp Glu Gln Gly Glu Gln Leu Asp Arg Val Glu Glu Gly Met
            50                  55                  60
Asn His Ile Asn Gln Asp Met Lys Glu Ala Glu Lys Asn Leu Lys Asp
65                  70                  75                  80
Leu Gly Lys Cys Cys Gly Leu Phe Ile Cys Pro Cys Asn Lys Leu Lys
                85                  90                  95
Ser Ser Gly Ala Tyr Asn Lys Ala Trp Gly Asn Asn Gln Asp Gly Val
                100                 105                 110
Val Ala Ser Gln Pro Ala Arg Val Val Asp Glu Arg Glu Gln Met Ala
                115                 120                 125
Ile Ser Gly Gly Phe Val Arg Arg Val Thr Asn Asp Ala Arg Glu Thr
            130                 135                 140
Glu Met Asp Glu Asn Leu Glu Gln Val Gly Gly Ile Ile Gly Asn Leu
145                 150                 155                 160
Arg His Met Ala Leu Asp Met Gly Asn Glu Ile Asp Thr Gln Asn Arg
                165                 170                 175
Gln Ile Asp Arg Ile Met Glu Lys Ala Asp Ser Asn Lys Ala Arg Ile
                180                 185                 190
Asp Glu Ala Asn Lys His Ala Thr Lys Met Leu Gly Ser Gly
                195                 200                 205

<210> SEQ ID NO 19
<211> LENGTH: 206
<212> TYPE: PRT
<213> ORGANISM: Xenopus laevis
```

<400> SEQUENCE: 19

Met Ala Asp Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205

<210> SEQ ID NO 20
<211> LENGTH: 204
<212> TYPE: PRT
<213> ORGANISM: Xenopus laevis

<400> SEQUENCE: 20

Met Asp Asp Met Thr Ala Glu Glu Ile Gln Leu Lys Ala Asn Gln Val
1               5                   10                  15

Ala Asp Glu Ser Leu Glu Ser Thr Arg Arg Met Leu Asn Leu Ala Leu
            20                  25                  30

Glu Ser Gln Asp Ala Gly Ile Lys Thr Ile Thr Met Leu Asp Glu Gln
        35                  40                  45

Gly Glu Gln Leu Asp Arg Ile Glu Glu Gly Met Asp Gln Ile Asn Lys
    50                  55                  60

Asp Met Arg Glu Ala Glu Lys Asn Leu Thr Glu Leu Asn Lys Cys Cys
65                  70                  75                  80

Gly Leu Cys Val Cys Pro Gly Leu Arg Ser Lys Asp Phe Glu Thr Gly
                85                  90                  95

Glu Asn Tyr Lys Lys Ala Trp Gly Ser Lys Asp Asn Ser Asp Val
            100                 105                 110

Val Ser Lys Gln Pro Gly Gln Thr Asn Gly Gln Leu Ser Gly Ala Gly
        115                 120                 125

Gln Ser Gly Pro Tyr Ile Lys Arg Ile Thr Asn Asp Asp Arg Glu Asp
    130                 135                 140

Glu Met Asp Glu Asn Leu Val Gln Val Gly Ser Ile Leu Gly Asn Leu
145                 150                 155                 160

```
Lys Asn Met Ala Ile Asp Met Gly Asn Glu Leu Glu Ser His Asn Gln
                165                 170                 175

Gln Ile Gly Arg Ile Asn Glu Lys Ala Glu Thr Asn Lys Thr Arg Ile
            180                 185                 190

Asp Glu Ala Asn Thr Lys Ala Lys Lys Leu Ile Glu
        195                 200

<210> SEQ ID NO 21
<211> LENGTH: 212
<212> TYPE: PRT
<213> ORGANISM: Strongylocentrotus purpuratus

<400> SEQUENCE: 21

Met Glu Asp Gln Asn Asp Met Asn Met Arg Ser Glu Leu Glu Ile
1               5                   10                  15

Gln Met Gln Ser Asn Met Gln Thr Asp Glu Ser Leu Glu Ser Thr Arg
            20                  25                  30

Arg Met Leu Gln Met Ala Glu Ser Gln Asp Met Gly Ile Lys Thr
        35                  40                  45

Leu Val Met Leu Asp Glu Gln Gly Glu Gln Leu Asp Arg Ile Glu Glu
50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Tyr Lys Lys Thr Trp Lys Gly
            100                 105                 110

Asn Asp Asp Gly Lys Val Asn Ser His Gln Pro Met Arg Met Glu Asp
            115                 120                 125

Asp Arg Asp Gly Cys Gly Gly Asn Ala Ser Met Ile Thr Arg Ile Thr
130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210

<210> SEQ ID NO 22
<211> LENGTH: 212
<212> TYPE: PRT
<213> ORGANISM: Drosophila melanogaster

<400> SEQUENCE: 22

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Ser Lys Glu
        35                  40                  45

Ala Gly Ile Arg Thr Leu Val Ala Leu Asp Asp Gln Gly Glu Gln Leu
50                  55                  60
```

-continued

```
Asp Arg Ile Glu Glu Gly Met Asp Gln Ile Asn Ala Asp Met Arg Glu
 65                  70                  75                  80

Ala Glu Lys Asn Leu Ser Gly Met Glu Lys Cys Cys Gly Ile Cys Val
                 85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210
```

<210> SEQ ID NO 23
<211> LENGTH: 212
<212> TYPE: PRT
<213> ORGANISM: Drosophila melanogaster

<400> SEQUENCE: 23

```
Met Ala Ala Val Glu Asn Ala Glu Pro Arg Thr Glu Leu Gln Glu Leu
 1                   5                  10                  15

Gln Phe Lys Ser Gly Gln Val Ala Asp Glu Ser Leu Glu Ser Thr Arg
                 20                  25                  30

Arg Met Leu Ala Leu Met Asp Glu Ser Lys Glu Ala Gly Ile Arg Thr
             35                  40                  45

Leu Val Ala Leu Asp Asp Gln Gly Glu Gln Leu Asp Arg Ile Glu Glu
         50                  55                  60

Gly Met Asp Arg Ile Asn Ala Asp Met Arg Glu Ala Glu Lys Asn Leu
 65                  70                  75                  80

Ser Gly Met Glu Lys Cys Cys Gly Ile Cys Val Leu Pro Trp Lys Lys
                 85                  90                  95

Val Asn Ile Lys Asp Asp Gly Ser Ala Trp Lys Ala Asn Asp Asp
            100                 105                 110

Gly Lys Ile Val Ala Ser Gln Pro Gln Arg Val Ile Asp Glu Arg Glu
        115                 120                 125

Arg Gly Gly Met Gly Ala Pro Pro Gln Ser Gly Tyr Val Ala Arg Ile
    130                 135                 140

Thr Asn Asp Ala Arg Glu Asp Glu Met Asp Glu Asn Leu Gly Gln Val
145                 150                 155                 160

Asn Ser Met Leu Gly Asn Leu Arg Asn Met Ala Leu Asp Met Gly Ser
                165                 170                 175

Glu Leu Glu Asn Gln Asn Lys Gln Val Asp Arg Ile Asn Ala Lys Gly
            180                 185                 190

Asp Ala Asn Asn Ile Arg Met Asp Gly Val Asn Lys Arg Ala Asn Asn
        195                 200                 205

Leu Leu Lys Ser
    210
```

<210> SEQ ID NO 24
<211> LENGTH: 212
<212> TYPE: PRT
<213> ORGANISM: Hirudo medicinalis

<400> SEQUENCE: 24

Met Ala Lys Asp Ile Lys Pro Lys Pro Ala Asn Gly Arg Asp Ser Pro
1               5                   10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210

<210> SEQ ID NO 25
<211> LENGTH: 212
<212> TYPE: PRT
<213> ORGANISM: Loligo pealei

<400> SEQUENCE: 25

Met Ser Ala Asn Gly Glu Val Glu Val Pro Lys Thr Glu Leu Glu Glu
1               5                   10                  15

Ile Gln Gln Gln Cys Asn Gln Val Thr Asp Asp Ser Leu Glu Ser Thr
            20                  25                  30

Arg Arg Met Leu Asn Met Cys Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Asp Gly Pro Thr Asn Thr Asn Gly Pro Arg Val Thr Val
            115                 120                 125

Gly Asp Gln Asn Gly Met Gly Pro Ser Ser Gly Tyr Val Thr Arg Ile
            130                 135                 140

Thr Asn Asp Ala Arg Glu Asp Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
            195                 200                 205

Leu Leu Lys Asn
    210

<210> SEQ ID NO 26
<211> LENGTH: 220
<212> TYPE: PRT
<213> ORGANISM: Lymnaea stagnalis

<400> SEQUENCE: 26

Met Thr Thr Asn Gly Glu Ile Leu Pro Val Gly Glu Glu Glu Glu Glu
1               5                   10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110

Asp Tyr Asn Lys Thr Trp Lys Ala Ser Glu Asp Gly Lys Ile Asn Thr
            115                 120                 125

Asn Gly Pro Arg Leu Val Val Asp Gln Gly Asn Gly Ser Gly Pro Thr
        130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175

Met Ala Val Asp Met Gly Asn Glu Ile Glu Ser Gln Asn Lys Gln Leu
            180                 185                 190

Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220

<210> SEQ ID NO 27
<211> LENGTH: 207
<212> TYPE: PRT
<213> ORGANISM: Caenorhabditis elegans

<400> SEQUENCE: 27

```
Met Ser Gly Asp Asp Asp Ile Pro Glu Gly Leu Glu Ala Ile Asn Leu
1               5                   10                  15

Lys Met Asn Ala Thr Thr Asp Asp Ser Leu Glu Ser Thr Arg Arg Met
            20                  25                  30

Leu Ala Leu Cys Glu Glu Ser Lys Glu Ala Gly Ile Lys Thr Leu Val
            35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
            115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
            165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205

<210> SEQ ID NO 28
<211> LENGTH: 118
<212> TYPE: PRT
<213> ORGANISM: Homo sapiens

<400> SEQUENCE: 28

Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
            115

<210> SEQ ID NO 29
<211> LENGTH: 117
<212> TYPE: PRT
<213> ORGANISM: Homo sapiens

<400> SEQUENCE: 29
```

-continued

Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ser Lys Tyr Arg
        115

<210> SEQ ID NO 30
<211> LENGTH: 116
<212> TYPE: PRT
<213> ORGANISM: Homo sapiens

<400> SEQUENCE: 30

Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Arg Arg Asp
        115

<210> SEQ ID NO 31
<211> LENGTH: 116
<212> TYPE: PRT
<213> ORGANISM: Homo sapiens

<400> SEQUENCE: 31

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

```
Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 32
<211> LENGTH: 116
<212> TYPE: PRT
<213> ORGANISM: Macaca mulatta

<400> SEQUENCE: 32

Met Ser Ala Thr Ala Ala Thr Ala Pro Pro Ala Ala Pro Ala Gly Glu
  1               5                  10                  15

Gly Gly Pro Pro Ala Pro Pro Asn Leu Thr Ser Asn Arg Arg Leu
                20                  25                  30

Gln Gln Thr Gln Ala Gln Val Asp Glu Val Val Asp Ile Met Arg Val
                35                  40                  45

Asn Val Asp Lys Val Leu Glu Arg Asp Gln Lys Leu Ser Glu Leu Asp
             50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 33
<211> LENGTH: 100
<212> TYPE: PRT
<213> ORGANISM: Homo sapiens

<400> SEQUENCE: 33

Met Ser Thr Gly Pro Thr Ala Ala Thr Gly Ser Asn Arg Arg Leu Gln
  1               5                  10                  15

Gln Thr Gln Asn Gln Val Asp Glu Val Val Asp Ile Met Arg Val Asn
                20                  25                  30

Val Asp Lys Val Leu Glu Arg Asp Gln Lys Leu Ser Glu Leu Asp Asp
                35                  40                  45

Arg Ala Asp Ala Leu Gln Ala Gly Ala Ser Gln Phe Glu Thr Ser Ala
             50                  55                  60

Ala Lys Leu Lys Arg Lys Tyr Trp Trp Lys Asn Cys Lys Met Trp Ala
 65                  70                  75                  80

Ile Gly Ile Thr Val Leu Val Ile Phe Ile Ile Ile Ile Val Trp
                85                  90                  95

Val Val Ser Ser
            100

<210> SEQ ID NO 34
<211> LENGTH: 116
<212> TYPE: PRT
<213> ORGANISM: Bos taurus

<400> SEQUENCE: 34
```

```
Met Ser Ala Thr Ala Ala Thr Ala Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Ser
        115

<210> SEQ ID NO 35
<211> LENGTH: 118
<212> TYPE: PRT
<213> ORGANISM: Rattus norvegicus

<400> SEQUENCE: 35

Met Ser Ala Pro Ala Gln Pro Pro Ala Glu Gly Thr Glu Gly Ala Ala
1               5                   10                  15

Pro Gly Gly Gly Pro Pro Gly Pro Pro Asn Thr Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Val Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Ile Phe Thr
        115

<210> SEQ ID NO 36
<211> LENGTH: 117
<212> TYPE: PRT
<213> ORGANISM: Rattus norvegicus

<400> SEQUENCE: 36

Met Ser Ala Pro Ala Gln Pro Pro Ala Glu Gly Thr Glu Gly Ala Ala
1               5                   10                  15

Pro Gly Gly Gly Pro Pro Gly Pro Pro Asn Thr Thr Ser Asn Arg
            20                  25                  30

Arg Leu Gln Gln Thr Gln Ala Gln Val Glu Glu Val Val Asp Ile Met
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Val Phe Glu
65                  70                  75                  80
```

```
Ser Ser Ala Ala Lys Leu Lys Arg Lys Tyr Trp Trp Lys Asn Cys Lys
             85                  90                  95

Met Met Ile Met Leu Gly Ala Ile Cys Ala Ile Ile Val Val Val Ile
            100                 105                 110

Val Ser Lys Tyr Arg
        115

<210> SEQ ID NO 37
<211> LENGTH: 118
<212> TYPE: PRT
<213> ORGANISM: Mus musculus

<400> SEQUENCE: 37

Met Ser Ala Pro Ala Gln Pro Pro Ala Glu Gly Thr Glu Gly Ala Ala
  1               5                  10                  15

Pro Gly Gly Gly Pro Gly Pro Pro Asn Met Thr Ser Asn Arg
             20                  25                  30

Arg Leu Gln Gln Thr Gln Ala Gln Val Glu Val Val Asp Ile Met
             35                  40                  45

Arg Val Asn Val Asp Lys Val Leu Glu Arg Asp Gln Lys Leu Ser Glu
         50                  55                  60

Leu Asp Asp Arg Ala Asp Ala Leu Gln Ala Gly Ala Ser Gln Phe Glu
 65                  70                  75                  80

Ser Ser Ala Ala Lys Leu Lys Arg Lys Tyr Trp Trp Lys Asn Cys Lys
             85                  90                  95

Met Met Ile Met Leu Gly Ala Ile Cys Ala Ile Ile Val Val Val Ile
            100                 105                 110

Val Ile Tyr Phe Phe Thr
        115

<210> SEQ ID NO 38
<211> LENGTH: 116
<212> TYPE: PRT
<213> ORGANISM: Rattus norvegicus

<400> SEQUENCE: 38

Met Ser Ala Thr Ala Ala Thr Val Pro Pro Ala Ala Pro Ala Gly Glu
  1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
             35                  40                  45

Asn Val Asp Lys Val Leu Glu Arg Asp Gln Lys Leu Ser Glu Leu Asp
         50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
             85                  90                  95

Ile Ile Leu Gly Val Ile Cys Ala Ile Ile Leu Ile Ile Ile Val
            100                 105                 110

Tyr Phe Ser Thr
        115

<210> SEQ ID NO 39
<211> LENGTH: 135
<212> TYPE: PRT
<213> ORGANISM: Rattus norvegicus
```

-continued

```
<400> SEQUENCE: 39

Met Ser Ala Thr Ala Ala Thr Val Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Gly
                100                 105                 110

Glu Trp Ser Arg Ser Gly Gln Gly Pro Phe Pro Gly Glu Val Glu Gly
            115                 120                 125

Phe Pro Val Gly Ser Gly Leu
    130             135

<210> SEQ ID NO 40
<211> LENGTH: 116
<212> TYPE: PRT
<213> ORGANISM: Mus musculus

<400> SEQUENCE: 40

Met Ser Ala Thr Ala Ala Thr Val Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Thr
        115

<210> SEQ ID NO 41
<211> LENGTH: 103
<212> TYPE: PRT
<213> ORGANISM: Rattus norvegicus

<400> SEQUENCE: 41

Met Ser Thr Gly Val Pro Ser Gly Ser Ser Ala Ala Thr Gly Ser Asn
1               5                   10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
```

```
                    50                  55                  60
Glu Thr Ser Ala Ala Lys Leu Lys Arg Lys Tyr Trp Trp Lys Asn Cys
 65                  70                  75                  80

Lys Met Trp Ala Gly Ile Ser Val Leu Val Ile Val Ile Ile
                 85                  90                  95

Ile Ile Val Trp Cys Val Ser
                100

<210> SEQ ID NO 42
<211> LENGTH: 103
<212> TYPE: PRT
<213> ORGANISM: Mus musculus

<400> SEQUENCE: 42

Met Ser Thr Gly Val Pro Ser Gly Ser Ser Ala Ala Thr Gly Ser Asn
  1               5                  10                  15

Arg Arg Leu Gln Gln Thr Gln Asn Gln Val Asp Glu Val Val Asp Ile
                 20                  25                  30

Met Arg Val Asn Val Asp Lys Val Leu Glu Arg Asp Gln Lys Leu Ser
             35                  40                  45

Glu Leu Asp Asp Arg Ala Asp Ala Leu Gln Ala Gly Ala Ser Gln Phe
 50                  55                  60

Glu Thr Ser Ala Ala Lys Leu Lys Arg Lys Tyr Trp Trp Lys Asn Cys
 65                  70                  75                  80

Lys Met Trp Ala Gly Ile Ser Val Leu Val Ile Val Ile Ile
                 85                  90                  95

Ile Ile Val Trp Cys Val Ser
                100

<210> SEQ ID NO 43
<211> LENGTH: 259
<212> TYPE: PRT
<213> ORGANISM: Gallus gallus

<400> SEQUENCE: 43

Met His Gln Glu Asn Gln Thr Lys Gln Val Gln Val Ser Pro Ser
  1               5                  10                  15

Val Asn Ala Ala Trp Lys Leu Leu Val Pro Val Phe Leu Pro Gly Gly
                 20                  25                  30

Ser Thr Pro Ala Ala Pro Tyr Pro Asp Cys Cys Ser Thr Arg Ala Gln
             35                  40                  45

Arg Thr Leu Ala Ala Leu Ser Pro Ala Leu Ile Gly Arg Cys Gln Ala
 50                  55                  60

Gly Thr Gly Leu Asn Pro Gly Glu Ser Gly Gln Arg Glu Ala Gly
 65                  70                  75                  80

Leu Arg Glu Gly Ala Leu Phe Thr Gly Ala Ser Leu Arg Pro Ser Arg
                 85                  90                  95

Gly Ala Leu Ile Gly Phe Gly Glu Gly Glu Gly Ala Asp Ser Arg
            100                 105                 110

Val Ser Ala Arg Pro Ser Cys Asp Tyr Phe Ser Leu Ala Leu Gly Pro
            115                 120                 125

Cys Gly Ala Gly Leu Phe Val Cys Ala Gly Trp Gly Met Ser Glu Pro
        130                 135                 140

Ala Gln Gln Pro Ala Pro Gly Ala Pro Glu Gly Gly Ala Pro Ala Gly
145                 150                 155                 160

Gly Pro Pro Gly Pro Pro Pro Asn Leu Ser Ser Asn Arg Arg Leu Gln
```

```
                    165                 170                 175
Gln Thr Gln Ala Gln Val Glu Val Val Asp Ile Met Arg Val Asn
            180                 185                 190
Val Asp Lys Val Leu Glu Arg Asp Gln Lys Leu Ser Glu Leu Asp Asp
        195                 200                 205
Arg Ala Asp Ala Leu Gln Ala Gly Ala Ser Val Phe Glu Ser Ser Ala
    210                 215                 220
Ala Lys Leu Lys Arg Lys Tyr Trp Trp Lys Asn Cys Lys Met Met Ile
225                 230                 235                 240
Met Met Gly Val Ile Cys Ala Ile Val Val Val Ile Val Ile Tyr
                245                 250                 255
Phe Phe Thr

<210> SEQ ID NO 44
<211> LENGTH: 114
<212> TYPE: PRT
<213> ORGANISM: Gallus gallus

<400> SEQUENCE: 44

Met Ser Ala Pro Ala Pro Thr Gln Gly Pro Thr Ser Thr Gly Ala Ala
1               5                   10                  15
Gly Pro Pro Pro Ala Thr Asn Val Ser Ser Asn Lys Arg Leu Gln Gln
            20                  25                  30
Thr Gln Ala Gln Val Asp Glu Val Val Asp Ile Met Arg Met Asn Val
        35                  40                  45
Asp Lys Val Leu Glu Arg Asp Gln Lys Leu Ser Glu Leu Asp Asn Arg
    50                  55                  60
Ala Asp Ala Leu Gln Ala Gly Ala Ser Gln Phe Glu Thr Ser Ala Ala
65                  70                  75                  80
Lys Leu Lys Arg Lys Tyr Trp Trp Lys Asn Cys Lys Met Met Ile Ile
                85                  90                  95
Leu Gly Val Val Cys Thr Val Ile Leu Ile Ile Ile Ile Tyr Phe
            100                 105                 110
Ser Thr

<210> SEQ ID NO 45
<211> LENGTH: 118
<212> TYPE: PRT
<213> ORGANISM: Gallus gallus

<400> SEQUENCE: 45

Met Ser Ala Asn Val Pro Gly Asn Thr Asn Val Pro Ala Gly Ser Asn
1               5                   10                  15
Arg Arg Leu Gln Gln Thr Gln His Gln Val Asp Glu Val Val Asp Ile
            20                  25                  30
Met Arg Val Asn Val Asp Lys Val Leu Glu Arg Asp Gln Lys Leu Ser
        35                  40                  45
Glu Leu Asp Asp Arg Ala Asp Ala Leu Gln Ala Gly Ala Ser Gln Phe
    50                  55                  60
Glu Thr Ser Ala Ala Lys Leu Lys Arg Lys Tyr Trp Trp Lys Asn Cys
65                  70                  75                  80
Lys Met Trp Ala Ile Leu Ile Ala Val Val Ile Ile Ile Ile Ile
                85                  90                  95
Ile Ile Val Val Ser Val Ser Ala Ala Leu Ser Ala Arg Leu Leu Leu
            100                 105                 110
```

```
Phe Lys Ala Lys Leu Phe
        115

<210> SEQ ID NO 46
<211> LENGTH: 119
<212> TYPE: PRT
<213> ORGANISM: Danio rerio

<400> SEQUENCE: 46

Met Ser Ala Pro Asp Ala Ala Ser Pro Gly Ala Pro Gly Ala Pro
1               5                   10                  15

Glu Gly Glu Gly Gly Ala Pro Ala Gln Pro Pro Asn Leu Thr Ser Asn
            20                  25                  30

Arg Arg Leu Gln Gln Thr Gln Ala Gln Val Asp Glu Val Val Asp Ile
        35                  40                  45

Met Arg Val Asn Val Asp Lys Val Leu Glu Arg Asp Gln Lys Leu Ser
    50                  55                  60

Glu Leu Asp Asp Arg Ala Asp Ala Leu Gln Ala Gly Ala Ser Gln Phe
65                  70                  75                  80

Glu Ser Ser Ala Ala Lys Leu Lys Asn Lys Tyr Trp Trp Lys Asn Met
                85                  90                  95

Lys Met Met Ile Ile Met Gly Ile Met Gly Ile Ile Leu Leu Gly Ile
            100                 105                 110

Ala Phe Met Tyr Phe Tyr Tyr
        115

<210> SEQ ID NO 47
<211> LENGTH: 110
<212> TYPE: PRT
<213> ORGANISM: Danio rerio

<400> SEQUENCE: 47

Met Ser Ala Pro Ala Gly Ala Pro Ala Pro Glu Gly Gly Asn Gln Ala
1               5                   10                  15

Pro Pro Asn Leu Thr Ser Asn Arg Arg Leu Gln Gln Thr Gln Ala Gln
            20                  25                  30

Val Asp Glu Val Val Asp Ile Met Arg Val Asn Val Asp Lys Val Leu
        35                  40                  45

Glu Arg Asp Gln Lys Leu Ser Glu Leu Asp Asp Arg Ala Asp Ala Leu
    50                  55                  60

Gln Ala Gly Ala Ser Gln Phe Glu Thr Ser Ala Ala Lys Leu Lys Asn
65                  70                  75                  80

Lys Tyr Trp Trp Lys Asn Ala Lys Met Met Ile Ile Leu Gly Val Ile
                85                  90                  95

Cys Val Ile Val Leu Ile Ile Ile Val Tyr Phe Ser Thr
            100                 105                 110

<210> SEQ ID NO 48
<211> LENGTH: 102
<212> TYPE: PRT
<213> ORGANISM: Danio rerio

<400> SEQUENCE: 48

Met Ser Ala Pro Gly Ala Asp Ala Ser Gly Ser Ser Gly Ser Asn Arg
1               5                   10                  15

Arg Leu Gln Gln Thr Gln Ala Gln Val Asp Glu Val Val Asp Ile Met
            20                  25                  30

Arg Val Asn Val Asp Lys Val Leu Glu Arg Asp Gln Lys Leu Ser Glu
```

```
                   35                  40                  45
Leu Asp Asp Arg Ala Asp Ala Leu Gln Ala Gly Ala Ser Gln Phe Glu
         50                  55                  60

Thr Ser Ala Ala Lys Leu Lys Arg Lys Phe Trp Trp Lys Asn Val Lys
 65                  70                  75                  80

Met Trp Ala Ile Leu Ile Ala Val Val Ile Ile Ile Ile Ile Ile
                 85                  90                  95

Val Ile Trp Ser Gln Ser
            100
```

<210> SEQ ID NO 49
<211> LENGTH: 120
<212> TYPE: PRT
<213> ORGANISM: Torpedo marmorata

<400> SEQUENCE: 49

```
Met Ser Ala Pro Pro Ser Gly Pro Ala Pro Asp Ala Gln Gly Gly Ala
 1               5                  10                  15

Pro Gly Gln Pro Thr Gly Pro Pro Gly Ala Pro Pro Asn Thr Thr Ser
                20                  25                  30

Asn Arg Arg Leu Gln Gln Thr Gln Ala Gln Val Glu Glu Val Val Asp
             35                  40                  45

Ile Ile Arg Val Asn Val Asp Lys Val Leu Glu Arg Asp Gln Lys Leu
         50                  55                  60

Ser Glu Leu Asp Asp Arg Ala Asp Ala Leu Gln Ala Gly Ala Ser Gln
 65                  70                  75                  80

Phe Glu Ser Ser Ala Ala Lys Leu Lys Arg Lys Tyr Trp Trp Lys Asn
                 85                  90                  95

Cys Lys Met Met Ile Met Leu Gly Ile Gly Ala Ile Ile Val Ile
                100                 105                 110

Val Ile Ile Ile Tyr Phe Phe Thr
            115                 120
```

<210> SEQ ID NO 50
<211> LENGTH: 114
<212> TYPE: PRT
<213> ORGANISM: Xenopus laevis

<400> SEQUENCE: 50

```
Met Ser Ala Pro Ala Ala Gly Pro Pro Ala Ala Ala Pro Gly Asp Gly
 1               5                  10                  15

Ala Pro Gln Gly Pro Pro Asn Leu Thr Ser Asn Arg Arg Leu Gln Gln
                20                  25                  30

Thr Gln Ala Gln Val Asp Glu Val Val Asp Ile Met Arg Val Asn Val
             35                  40                  45

Asp Lys Val Leu Glu Arg Asp Thr Lys Leu Ser Glu Leu Asp Asp Arg
         50                  55                  60

Ala Asp Ala Leu Gln Ala Gly Ala Ser Gln Phe Glu Thr Ser Ala Ala
 65                  70                  75                  80

Lys Leu Lys Arg Lys Tyr Trp Trp Lys Asn Met Lys Met Met Ile Ile
                 85                  90                  95

Met Gly Val Ile Cys Ala Ile Ile Leu Ile Ile Ile Val Tyr Phe
                100                 105                 110

Ser Thr
```

<210> SEQ ID NO 51

```
<211> LENGTH: 101
<212> TYPE: PRT
<213> ORGANISM: Xenopus laevis

<400> SEQUENCE: 51

Met Ser Thr Pro Gly Thr Ser Ala Thr Gly Asp Pro Gly Asn Arg Arg
 1               5                  10                  15

Leu Gln Gln Thr Gln Ala Gln Val Asp Glu Val Val Asp Ile Met Arg
                20                  25                  30

Val Asn Val Asp Lys Val Leu Glu Arg Asp Gln Lys Leu Ser Glu Leu
            35                  40                  45

Asp Asp Arg Ala Asp Ala Leu Gln Ala Gly Ala Ser Gln Phe Glu Thr
        50                  55                  60

Ser Ala Ala Lys Leu Lys Arg Lys Tyr Trp Trp Lys Asn Cys Lys Met
65                  70                  75                  80

Trp Ala Ile Leu Ile Ala Val Val Leu Val Ile Ile Ile Ile Ile Ile
                85                  90                  95

Val Trp Ser Val Ser
            100

<210> SEQ ID NO 52
<211> LENGTH: 104
<212> TYPE: PRT
<213> ORGANISM: Strongylocentrotus purpuratus

<400> SEQUENCE: 52

Met Ala Ala Pro Pro Pro Gln Pro Ala Pro Ser Asn Lys Arg Leu
 1               5                  10                  15

Gln Gln Thr Gln Ala Gln Val Asp Glu Val Val Asp Ile Met Arg Val
                20                  25                  30

Asn Val Asp Lys Val Leu Glu Arg Asp Gln Ala Leu Ser Val Leu Asp
            35                  40                  45

Asp Arg Ala Asp Ala Leu Gln Gln Gly Ala Ser Gln Phe Glu Thr Asn
        50                  55                  60

Ala Gly Lys Leu Lys Arg Lys Tyr Trp Trp Lys Asn Cys Lys Met Met
65                  70                  75                  80

Ile Ile Leu Ala Ile Ile Ile Val Ile Leu Ile Ile Ile Ile Ile Val
                85                  90                  95

Ala Ile Val Gln Ser Gln Lys Lys
            100

<210> SEQ ID NO 53
<211> LENGTH: 129
<212> TYPE: PRT
<213> ORGANISM: Drosophila melanogaster

<400> SEQUENCE: 53

Met Glu Asn Asn Glu Ala Pro Ser Pro Ser Gly Ser Asn Asn Asn Glu
 1               5                  10                  15

Asn Asn Asn Ala Ala Gln Lys Lys Leu Gln Gln Thr Gln Ala Lys Val
                20                  25                  30

Asp Glu Val Val Gly Ile Met Arg Val Asn Val Glu Lys Val Leu Glu
            35                  40                  45

Arg Asp Gln Lys Leu Ser Glu Leu Gly Glu Arg Ala Asp Gln Leu Glu
        50                  55                  60

Gln Gly Ala Ser Gln Phe Glu Gln Gln Ala Gly Lys Leu Lys Arg Lys
65                  70                  75                  80
```

```
Gln Trp Trp Ala Asn Met Lys Met Met Ile Ile Leu Gly Val Ile Ala
            85                  90                  95

Val Val Leu Leu Ile Ile Val Leu Val Ser Val Trp Pro Ser Ser Ser
        100                 105                 110

Asp Ser Gly Ser Gly Gly Gly Asn Lys Ala Ile Thr Gln Ala Pro Pro
            115                 120                 125

His

<210> SEQ ID NO 54
<211> LENGTH: 152
<212> TYPE: PRT
<213> ORGANISM: Drosophila melanogaster

<400> SEQUENCE: 54

Met Glu Asn Asn Glu Ala Pro Ser Pro Ser Gly Ser Asn Asn Asn Asp
1               5                   10                  15

Phe Pro Ile Leu Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
            35                  40                  45

Gln Gln Thr Gln Ala Lys Val Asp Glu Val Val Gly Ile Met Arg Val
        50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Ser Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
            115                 120                 125

Ser Val Trp Pro Ser Ser Ser Asp Ser Gly Ser Gly Gly Gly Asn Lys
        130                 135                 140

Ala Ile Thr Gln Ala Pro Pro His
145                 150

<210> SEQ ID NO 55
<211> LENGTH: 132
<212> TYPE: PRT
<213> ORGANISM: Drosophila melanogaster

<400> SEQUENCE: 55

Met Glu Asn Asn Glu Ala Pro Ser Pro Ser Gly Ser Asn Asn Asn Asp
1               5                   10                  15

Phe Pro Ile Leu Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
            35                  40                  45

Gln Gln Thr Gln Ala Lys Val Asp Glu Val Val Gly Ile Met Arg Val
        50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Phe Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
```

```
                115                 120                 125
Ser Leu Phe Asn
    130

<210> SEQ ID NO 56
<211> LENGTH: 132
<212> TYPE: PRT
<213> ORGANISM: Drosophila melanogaster

<400> SEQUENCE: 56

Met Glu Asn Asn Glu Ala Pro Ser Pro Ser Gly Ser Asn Asn Asn Asp
  1               5                  10                  15

Phe Pro Ile Leu Pro Pro Pro Asn Ala Asn Asp Asn Tyr Asn Gln
             20                  25                  30

Phe Gly Asp His Gln Ile Arg Asn Asn Ala Ala Gln Lys Lys Leu
         35                  40                  45

Gln Gln Thr Gln Ala Lys Val Asp Glu Val Val Gly Ile Met Arg Val
 50                  55                  60

Asn Val Glu Lys Val Leu Glu Arg Asp Gln Lys Leu Ser Glu Leu Gly
 65                  70                  75                  80

Glu Arg Ala Asp Gln Leu Glu Gln Gly Ala Ser Gln Ser Glu Gln Gln
                 85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
            115                 120                 125

Ser Leu Phe Asn
    130

<210> SEQ ID NO 57
<211> LENGTH: 183
<212> TYPE: PRT
<213> ORGANISM: Drosophila melanogaster

<400> SEQUENCE: 57

Met Ala Asp Ala Ala Pro Ala Gly Asp Ala Pro Pro Asn Ala Gly Ala
  1               5                  10                  15

Pro Ala Gly Glu Gly Gly Asp Gly Glu Ile Val Gly Gly Pro His Asn
             20                  25                  30

Pro Gln Gln Ile Ala Ala Gln Lys Arg Leu Gln Gln Thr Gln Ala Gln
         35                  40                  45

Val Asp Glu Val Val Asp Ile Met Arg Thr Asn Val Glu Lys Val Leu
 50                  55                  60

Glu Arg Asp Ser Lys Leu Ser Glu Leu Asp Asp Arg Ala Asp Ala Leu
 65                  70                  75                  80

Gln Gln Gly Ala Ser Gln Phe Glu Gln Gln Ala Gly Lys Leu Lys Arg
                 85                  90                  95

Lys Phe Trp Leu Gln Asn Leu Lys Met Met Ile Ile Met Gly Val Ile
            100                 105                 110

Gly Leu Val Val Val Gly Ile Ile Ala Asn Lys Leu Gly Leu Ile Gly
            115                 120                 125

Gly Glu Gln Pro Pro Gln Tyr Gln Tyr Pro Gln Tyr Met Gln Pro
        130                 135                 140

Pro Pro Pro Pro Gln Gln Pro Ala Gly Gly Gln Ser Ser Leu Val
145                 150                 155                 160

Asp Ala Ala Gly Ala Gly Asp Gly Ala Gly Ala Gly Gly Ser Ala Gly
```

```
                         165                 170                 175

Ala Gly Asp His Gly Gly Val
        180

<210> SEQ ID NO 58
<211> LENGTH: 221
<212> TYPE: PRT
<213> ORGANISM: Drosophila melanogaster

<400> SEQUENCE: 58

Met Gly Lys Lys Asp Lys Asn Lys Glu Gln Ala Asp Ala Ala Pro Ala
1               5                   10                  15

Gly Asp Ala Pro Pro Asn Ala Gly Ala Pro Ala Gly Glu Gly Gly Asp
            20                  25                  30

Gly Glu Ile Val Gly Gly Pro His Asn Pro Gln Gln Ile Ala Ala Gln
        35                  40                  45

Lys Arg Leu Gln Gln Thr Gln Ala Gln Val Asp Glu Val Val Asp Ile
    50                  55                  60

Met Arg Thr Asn Val Glu Lys Val Leu Glu Arg Asp Ser Lys Leu Ser
65                  70                  75                  80

Glu Leu Asp Asp Arg Ala Asp Ala Leu Gln Gln Gly Ala Ser Gln Phe
                85                  90                  95

Glu Gln Gln Ala Gly Lys Leu Lys Arg Lys Phe Trp Leu Gln Asn Leu
            100                 105                 110

Lys Met Met Ile Ile Met Gly Val Ile Gly Leu Val Val Val Gly Ile
        115                 120                 125

Ile Ala Lys Arg Arg Ile Ile Thr Gln Lys Ala Ser Ala Leu Tyr
    130                 135                 140

Asn Phe Ile Asn His Lys Gln Ile Asn Leu Pro Asn Ile Thr Leu Tyr
145                 150                 155                 160

Lys Leu Gly Leu Ile Gly Gly Glu Gln Pro Gln Tyr Gln Tyr Pro
                165                 170                 175

Pro Gln Tyr Met Gln Pro Pro Pro Pro Pro Gln Gln Pro Ala Gly
            180                 185                 190

Gly Gln Ser Ser Leu Val Asp Ala Ala Gly Ala Gly Asp Gly Ala Gly
        195                 200                 205

Ala Gly Gly Ser Ala Gly Ala Gly Asp His Gly Gly Val
    210                 215                 220

<210> SEQ ID NO 59
<211> LENGTH: 192
<212> TYPE: PRT
<213> ORGANISM: Drosophila melanogaster

<400> SEQUENCE: 59

Met Gly Lys Lys Asp Lys Asn Lys Glu Gln Ala Asp Ala Ala Pro Ala
1               5                   10                  15

Gly Asp Ala Pro Pro Asn Ala Gly Ala Pro Ala Gly Glu Gly Gly Asp
            20                  25                  30

Gly Glu Ile Val Gly Gly Pro His Asn Pro Gln Gln Ile Ala Ala Gln
        35                  40                  45

Lys Arg Leu Gln Gln Thr Gln Ala Gln Val Asp Glu Val Val Asp Ile
    50                  55                  60

Met Arg Thr Asn Val Glu Lys Val Leu Glu Arg Asp Ser Lys Leu Ser
65                  70                  75                  80

Glu Leu Asp Asp Arg Ala Asp Ala Leu Gln Gln Gly Ala Ser Gln Phe
```

```
                    85                  90                  95
Glu Gln Gln Ala Gly Lys Leu Lys Arg Lys Phe Trp Leu Gln Asn Leu
            100                 105                 110
Lys Met Met Ile Ile Met Gly Val Ile Gly Leu Val Val Val Gly Ile
            115                 120                 125
Ile Ala Asn Lys Leu Gly Leu Ile Gly Gly Glu Gln Pro Pro Gln Tyr
            130                 135                 140
Gln Tyr Pro Pro Gln Tyr Met Gln Pro Pro Pro Pro Pro Gln Gln
145                 150                 155                 160
Pro Ala Gly Gly Gln Ser Ser Leu Val Asp Ala Ala Gly Ala Gly Asp
                    165                 170                 175
Gly Ala Gly Ala Gly Gly Ser Ala Gly Ala Gly Asp His Gly Gly Val
                    180                 185                 190

<210> SEQ ID NO 60
<211> LENGTH: 169
<212> TYPE: PRT
<213> ORGANISM: Hirudo medicinalis

<400> SEQUENCE: 60

Met Ala Gln Pro Pro Lys Pro Ser Thr Gly Pro Gly Gly Leu Pro
1               5                   10                  15
Ala Pro Gly Ala Pro Pro Gln Pro Ala Pro Gln Ser Lys Arg Leu Gln
                20                  25                  30
Gln Ala Gln Ala Gln Val Asp Glu Val Val Asp Met Met Arg Val Asn
                35                  40                  45
Val Asp Lys Val Leu Glu Lys Asp Gln Lys Leu Ala Glu Leu Asp Gly
            50                  55                  60
Arg Ala Asp Ala Leu Gln Ala Gly Ala Ser Gln Phe Glu Ala Ser Ala
65                  70                  75                  80
Gly Lys Leu Lys Arg Lys Phe Trp Trp Lys Asn Met Lys Met Met Leu
                    85                  90                  95
Ile Met Gly Ala Val Val Ala Val Val Val Ile Phe Gly Ala Trp
            100                 105                 110
Ile Tyr Asn Lys Phe Ser Gly Thr Ser Ser Val Pro Gln Glu Gly Thr
            115                 120                 125
Pro Val Leu Gln Ser Pro Met Ala Gln Gln Pro Gln Ser Leu Pro Glu
            130                 135                 140
Asn Ile Pro Pro Ala Ser Pro Val Gly Gly Gly Gly Gly Lys Lys
145                 150                 155                 160
Gly Lys Asn Lys Gln Pro His Ser Ser
                    165

<210> SEQ ID NO 61
<211> LENGTH: 125
<212> TYPE: PRT
<213> ORGANISM: Loligo pealei

<400> SEQUENCE: 61

Met Ser Gly Pro Gln Asn Pro Gln Ala Gly Pro Gly Gly Pro Pro Ser
1               5                   10                  15
Gly Pro Pro Gln Pro Gly Gly Pro Pro Gly Pro Pro Gln Gly Pro Pro
                20                  25                  30
Gln Pro Val Gln Gln Ser Lys Arg Leu Gln Gln Thr Gln Ala Gln Val
            35                  40                  45
Glu Glu Val Val Asp Ile Met Arg Val Asn Val Asp Lys Val Leu Glu
```

```
                    50                  55                  60
Arg Asp Ser Lys Ile Ser Glu Leu Asp Asp Arg Ala Asp Ala Leu Gln
 65                  70                  75                  80

Ala Gly Ala Ser Gln Phe Glu Ala Ser Ala Gly Lys Leu Lys Arg Lys
                 85                  90                  95

Phe Trp Trp Lys Asn Cys Lys Met Met Ile Ile Leu Gly Gly Ile Val
            100                 105                 110

Ala Val Ile Val Thr Val Ile Val Trp Ala Ala Thr
        115                 120                 125

<210> SEQ ID NO 62
<211> LENGTH: 145
<212> TYPE: PRT
<213> ORGANISM: Lymnaea stagnalis

<400> SEQUENCE: 62

Met Ala Ala Ser Gln Asn Pro Gln Ala Gly Pro Gly Gly Pro Pro Ser
 1               5                  10                  15

Ala Gly Pro Gly Gly Pro Gly Met Gln Pro Pro Arg Glu Gln Ser Lys
                20                  25                  30

Arg Leu Gln Gln Thr Gln Ala Gln Val Asp Glu Val Val Asp Ile Met
             35                  40                  45

Arg Val Asn Val Glu Lys Val Leu Asp Arg Asp Gln Lys Ile Ser Gln
 50                  55                  60

Leu Asp Asp Arg Ala Glu Ala Leu Gln Ala Gly Ala Ser Gln Phe Glu
 65                  70                  75                  80

Ala Ser Ala Gly Lys Leu Lys Arg Lys Tyr Trp Trp Lys Asn Cys Lys
                 85                  90                  95

Met Met Leu Ile Leu Gly Ala Ile Ile Gly Ile Ile Cys Ile Ile Ile
            100                 105                 110

Ile Val Trp Val Val Thr Ser Thr Lys Gly Gly Asp Asp Lys Pro Thr
        115                 120                 125

Pro Gln Pro Ala Ile Ser Ser Thr Thr Gly Thr Pro Ser Pro Lys Thr
    130                 135                 140

Thr
145

<210> SEQ ID NO 63
<211> LENGTH: 180
<212> TYPE: PRT
<213> ORGANISM: Aplysia californica

<400> SEQUENCE: 63

Met Ser Ala Gly Pro Gly Gly Pro Gln Gly Gly Met Gln Pro Pro Arg
 1               5                  10                  15

Glu Gln Ser Lys Arg Leu Gln Gln Thr Gln Ala Gln Val Asp Glu Val
                20                  25                  30

Val Asp Ile Met Arg Val Asn Val Glu Lys Val Leu Asp Arg Asp Gln
             35                  40                  45

Lys Ile Ser Gln Leu Asp Asp Arg Ala Glu Ala Leu Gln Ala Gly Ala
 50                  55                  60

Ser Gln Phe Glu Ala Ser Ala Gly Lys Leu Lys Arg Lys Tyr Trp Trp
 65                  70                  75                  80

Lys Asn Cys Lys Met Met Leu Ile Leu Gly Ala Ile Ile Gly Val Ile
                 85                  90                  95

Val Ile Ile Ile Ile Val Trp Val Val Thr Ser Gln Asp Ser Gly Gly
```

```
                100                 105                 110
Asp Asp Ser Gly Ser Lys Thr Pro Ala Thr Ala Gly Thr Ser Pro Lys
        115                 120                 125

Pro Val Glu Ser Gly Val Gln Gly Gly Gly Arg Gln Gln Arg Pro
130                 135                 140

His Ser Gln Leu Val Glu Arg Arg Asn Val Leu Arg Arg Thr Glu Asp
145                 150                 155                 160

His Ile Gly Cys Arg Pro His Ile His Ser Phe Ile His Ile Phe Met
                165                 170                 175

Ile Cys Leu Val
        180

<210> SEQ ID NO 64
<211> LENGTH: 109
<212> TYPE: PRT
<213> ORGANISM: Caenorhabditis elegans

<400> SEQUENCE: 64

Met Asp Ala Gln Gly Asp Ala Gly Ala Gln Gly Gly Ser Gln Gly Gly
1               5                   10                  15

Pro Arg Pro Ser Asn Lys Arg Leu Gln Gln Thr Gln Ala Gln Val Asp
                20                  25                  30

Glu Val Val Gly Ile Met Lys Val Asn Val Glu Lys Val Leu Glu Arg
            35                  40                  45

Asp Gln Lys Leu Ser Gln Leu Asp Asp Arg Ala Asp Ala Leu Gln Glu
        50                  55                  60

Gly Ala Ser Gln Phe Glu Lys Ser Ala Ala Thr Leu Lys Arg Lys Tyr
65                  70                  75                  80

Trp Trp Lys Asn Ile Lys Met Met Ile Ile Met Cys Ala Ile Val Val
                85                  90                  95

Ile Leu Ile Ile Ile Ile Val Leu Trp Ala Gly Gly Lys
            100                 105

<210> SEQ ID NO 65
<211> LENGTH: 118
<212> TYPE: PRT
<213> ORGANISM: Caenorhabditis elegans

<400> SEQUENCE: 65

Met Phe Ser Arg Met Ser Ala Asn Asn Glu Ala Asn Lys Asp Leu Glu
1               5                   10                  15

Ala Gly Asn Gly Glu Ala Gln Pro Pro Thr Gly Thr Tyr Asn Thr Lys
                20                  25                  30

Arg Met Gln Met Ala Gln Ala Gln Val Asn Glu Val Ile Asp Val Met
            35                  40                  45

Arg Asn Asn Val Asn Lys Val Met Glu Arg Asp Val Gln Leu Asn Ser
        50                  55                  60

Leu Asp His Arg Ala Glu Val Leu Gln Asn Gly Ala Ser Gln Phe Gln
65                  70                  75                  80

Gln Ser Ser Arg Thr Leu Arg Gln Lys Tyr Trp Trp Gln Asn Ile Arg
                85                  90                  95

Met Met Ile Ile Ile Gly Leu Ile Ala Phe Leu Val Ile Gly Ile Phe
            100                 105                 110

Leu Ile Trp Ile Phe Asn
        115
```

<210> SEQ ID NO 66
<211> LENGTH: 288
<212> TYPE: PRT
<213> ORGANISM: Homo sapiens

<400> SEQUENCE: 66

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
                20                  25                  30

Phe Phe Glu Gln Val Glu Glu Ile Arg Gly Phe Ile Asp Lys Ile Ala
            35                  40                  45

Glu Asn Val Glu Glu Val Lys Arg Lys His Ser Ala Ile Leu Ala Ser
        50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285

<210> SEQ ID NO 67
<211> LENGTH: 288
<212> TYPE: PRT
<213> ORGANISM: Homo sapiens

<400> SEQUENCE: 67

Met Lys Asp Arg Thr Gln Val Leu Arg Thr Arg Arg Asn Ser Asp Asp
1               5                   10                  15

Lys Glu Glu Val Val His Val Asp Arg Asp His Phe Met Asp Glu Phe
                20                  25                  30

Phe Glu Gln Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro

-continued

```
            50                  55                  60
Asn Pro Asp Glu Arg Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Gly Ser Thr Ala Pro Arg Pro Ile Leu
            100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Pro Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Ile Ile Ile Cys Cys Val
            260                 265                 270

Val Leu Gly Val Val Leu Ala Ser Ser Ile Gly Cys Thr Leu Gly Leu
            275                 280                 285

<210> SEQ ID NO 68
<211> LENGTH: 288
<212> TYPE: PRT
<213> ORGANISM: Homo sapiens

<400> SEQUENCE: 68

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
                 20                  25                  30

Phe Glu Gln Val Glu Glu Ile Arg Gly Cys Ile Glu Lys Leu Ser Glu
             35                  40                  45

Asp Val Glu Gln Val Lys Lys Gln His Ser Ala Ile Leu Ala Ala Pro
         50                  55                  60

Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Gly Leu Asn Arg Ser Ser Ala Asp Leu
            100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140
```

```
Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Cys Cys Val
            260                 265                 270

Val Leu Gly Val Val Leu Ala Ser Ser Ile Gly Gly Thr Leu Gly Leu
            275                 280                 285
```

<210> SEQ ID NO 69
<211> LENGTH: 287
<212> TYPE: PRT
<213> ORGANISM: Homo sapiens

<400> SEQUENCE: 69

```
Met Arg Asp Arg Leu Pro Asp Leu Thr Ala Cys Arg Lys Asn Asp Asp
  1               5                  10                  15

Gly Asp Thr Val Val Val Val Glu Lys Asp His Phe Met Asp Asp Phe
                 20                  25                  30

Phe His Gln Val Glu Glu Ile Arg Asn Ser Ile Asp Lys Ile Thr Gln
             35                  40                  45

Tyr Val Glu Glu Val Lys Lys Asn His Ser Ile Ile Leu Ser Ala Pro
 50                  55                  60

Asn Pro Glu Gly Lys Ile Lys Glu Glu Leu Glu Asp Leu Asn Lys Glu
 65                  70                  75                  80

Ile Lys Lys Thr Ala Asn Lys Ile Arg Ala Lys Leu Lys Ala Ile Glu
                 85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240
```

```
Asp Tyr Val Glu His Ala Lys Glu Thr Lys Lys Ala Ile Lys Tyr
                245                 250                 255

Gln Ser Lys Ala Arg Arg Lys Leu Met Phe Ile Ile Ile Cys Val Ile
            260                 265                 270

Val Leu Val Ile Leu Gly Ile Ile Leu Ala Thr Thr Leu Ser
        275                 280                 285
```

<210> SEQ ID NO 70
<211> LENGTH: 288
<212> TYPE: PRT
<213> ORGANISM: Homo sapiens

<400> SEQUENCE: 70

```
Met Arg Asp Arg Leu Pro Asp Leu Thr Ala Cys Arg Lys Asn Asp Asp
 1               5                  10                  15

Gly Asp Thr Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
 50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
210                 215                 220

Gln Gly Glu Met Ile Asn Asn Ile Glu Arg Asn Val Met Asn Ala Thr
225                 230                 235                 240

Asp Tyr Val Glu His Ala Lys Glu Thr Lys Lys Ala Ile Lys Tyr
                245                 250                 255

Gln Ser Lys Ala Arg Arg Lys Trp Ile Ile Ile Ala Val Ser Val
            260                 265                 270

Val Leu Val Ala Ile Ile Ala Leu Ile Ile Gly Leu Ser Val Gly Lys
        275                 280                 285
```

<210> SEQ ID NO 71
<211> LENGTH: 299
<212> TYPE: PRT
<213> ORGANISM: Homo sapiens

<400> SEQUENCE: 71

-continued

```
Met Arg Asp Arg Leu Pro Asp Leu Thr Ala Cys Arg Lys Asn Asp Asp
 1               5                  10                  15

Gly Asp Thr Val Val Val Glu Lys Asp His Phe Met Asp Asp Phe
             20                  25                  30

Phe His Gln Val Glu Glu Ile Arg Asn Ser Ile Asp Lys Ile Thr Gln
             35                  40                  45

Tyr Val Glu Glu Val Lys Lys Asn His Ser Ile Ile Leu Ser Ala Pro
 50                  55                  60

Asn Pro Glu Gly Lys Ile Lys Glu Glu Leu Glu Asp Leu Asn Lys Glu
 65                  70                  75                  80

Ile Lys Lys Thr Ala Asn Lys Ile Ala Ala Lys Leu Lys Ala Ile Glu
                 85                  90                  95

Gln Ser Phe Asp Gln Asp Glu Ser Gly Asn Arg Thr Ser Val Asp Leu
                100                 105                 110

Arg Ile Arg Arg Thr Gln His Ser Val Leu Ser Arg Lys Phe Val Glu
             115                 120                 125

Ala Met Ala Glu Tyr Asn Glu Ala Gln Thr Leu Phe Arg Glu Arg Ser
130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
                180                 185                 190

Glu Ile Glu Ser Arg His Lys Asp Ile Met Lys Leu Glu Thr Ser Ile
             195                 200                 205

Arg Glu Leu His Glu Met Phe Met Asp Met Ala Met Phe Val Glu Thr
210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Lys Trp Ile Ile Ile Ala Val Ser Val
             260                 265                 270

Val Leu Val Val Tyr Arg Leu Phe Gly Leu Ser Leu Glu Tyr Val Val
             275                 280                 285

Arg Ser Ala Ala Ser Leu Pro Gly Trp Gly Asn
             290                 295

<210> SEQ ID NO 72
<211> LENGTH: 289
<212> TYPE: PRT
<213> ORGANISM: Homo sapiens

<400> SEQUENCE: 72

Met Lys Asp Arg Leu Glu Gln Leu Lys Ala Lys Gln Leu Thr Gln Asp
 1               5                  10                  15

Asp Asp Thr Asp Ala Val Glu Ile Ala Ile Asp Asn Thr Ala Phe Met
             20                  25                  30

Asp Glu Phe Phe Ser Glu Ile Glu Glu Thr Arg Leu Asn Ile Asp Lys
             35                  40                  45

Ile Ser Glu His Val Glu Glu Ala Lys Lys Leu Tyr Ser Ile Ile Leu
 50                  55                  60

Ser Ala Pro Ile Pro Glu Pro Lys Thr Lys Asp Asp Leu Glu Gln Leu
```

```
                65                  70                  75                  80
Thr Thr Glu Ile Lys Lys Arg Ala Asn Asn Val Arg Asn Lys Leu Lys
                    85                  90                  95
Ser Met Glu Lys His Ile Glu Glu Asp Glu Val Arg Ser Ser Ala Asp
                    100                 105                 110
Leu Arg Ile Arg Lys Ser Gln His Ser Val Leu Ser Arg Lys Phe Val
                    115                 120                 125
Glu Val Met Thr Lys Tyr Asn Glu Ala Gln Val Asp Phe Arg Glu Arg
            130                 135                 140
Ser Lys Gly Arg Ile Gln Arg Gln Leu Glu Ile Thr Gly Lys Lys Thr
145                 150                 155                 160
Thr Asp Glu Glu Leu Glu Glu Met Leu Glu Ser Gly Asn Pro Ala Ile
                    165                 170                 175
Phe Thr Ser Gly Ile Ile Asp Ser Gln Ile Ser Lys Gln Ala Leu Ser
                    180                 185                 190
Glu Ile Glu Gly Arg His Lys Asp Ile Val Arg Leu Glu Ser Ser Ile
                    195                 200                 205
Lys Glu Leu His Asp Met Phe Met Asp Ile Ala Met Leu Val Glu Asn
            210                 215                 220
Gln Gly Glu Met Leu Asp Asn Ile Glu Leu Asn Val Met His Thr Val
225                 230                 235                 240
Asp His Val Glu Lys Ala Arg Asp Glu Ser Lys Lys Ala Val Lys Tyr
                    245                 250                 255
Gln Ser Gln Ala Arg Lys Lys Leu Ile Ile Ile Val Leu Val Val
                    260                 265                 270
Val Leu Leu Gly Ile Leu Ala Leu Ile Ile Gly Leu Ser Val Gly Leu
                    275                 280                 285
Asn

<210> SEQ ID NO 73
<211> LENGTH: 288
<212> TYPE: PRT
<213> ORGANISM: Bos taurus

<400> SEQUENCE: 73

Met Lys Asp Arg Thr Gln Glu Leu Arg Thr Ala Lys Asp Ser Asp Asp
 1               5                  10                  15
Asp Asp Asp Val Thr Val Thr Val Asp Arg Asp Arg Phe Met Asp Glu
                    20                  25                  30
Phe Phe Glu Gln Val Glu Glu Ile Arg Gly Phe Ile Asp Lys Ile Ser
                    35                  40                  45
Glu Asn Val Glu Glu Val Lys Arg Lys His Ser Ala Ile Leu Ala Ser
            50                  55                  60
Pro Asn Pro Asp Glu Lys Thr Lys Glu Glu Leu Glu Glu Leu Met Ser
65                  70                  75                  80
Asp Ile Lys Lys Thr Ala Asn Lys Val Arg Ser Lys Leu Lys Ser Ile
                    85                  90                  95
Glu Gln Ser Ile Glu Gln Glu Gly Leu Asn Arg Ser Ser Ala Asp
                    100                 105                 110
Leu Arg Ile Arg Lys Thr Gln His Ser Thr Leu Ser Arg Lys Phe Val
                    115                 120                 125
Glu Val Met Ser Glu Tyr Asn Ala Thr Gln Ser Asp Tyr Arg Glu Arg
            130                 135                 140
Cys Lys Gly Arg Ile Gln Arg Gln Leu Glu Ile Thr Gly Arg Thr Thr
```

```
                145                 150                 155                 160
Thr Ser Glu Glu Leu Glu Asp Met Leu Glu Ser Gly Asn Pro Ala Ile
                165                 170                 175
Phe Ala Ser Gly Ile Ile Met Asp Ser Ser Ile Ser Lys Gln Ala Leu
                180                 185                 190
Ser Glu Ile Glu Thr Arg His Ser Glu Ile Ile Lys Leu Glu Asn Ser
                195                 200                 205
Ile Arg Glu Leu His Asp Met Phe Met Asp Met Ala Met Leu Val Glu
                210                 215                 220
Ser Gln Gly Glu Met Ile Asp Arg Ile Glu Tyr Asn Val Glu His Ser
225                 230                 235                 240
Val Asp Tyr Val Glu Arg Ala Val Ser Asp Thr Lys Lys Ala Val Lys
                245                 250                 255
Tyr Gln Ser Lys Ala Arg Arg Lys Lys Ile Met Ile Val Ile Cys Cys
                260                 265                 270
Val Val Leu Gly Ile Val Ile Ala Ser Thr Phe Gly Gly Ile Phe Gly
                275                 280                 285

<210> SEQ ID NO 74
<211> LENGTH: 288
<212> TYPE: PRT
<213> ORGANISM: Bos taurus

<400> SEQUENCE: 74

Met Lys Asp Arg Thr Gln Glu Leu Arg Ser Ala Lys Asp Ser Asp Asp
  1               5                  10                  15
Glu Glu Glu Val Val His Val Asp Arg Asp His Phe Met Asp Glu Phe
                 20                  25                  30
Phe Glu Gln Val Glu Glu Ile Arg Gly Cys Ile Glu Lys Leu Ser Glu
                 35                  40                  45
Asp Val Glu Gln Val Lys Lys Gln His Ser Ala Ile Leu Ala Ala Pro
             50                  55                  60
Asn Pro Asp Glu Lys Thr Lys Gln Glu Leu Glu Asp Leu Thr Thr Asp
65                  70                  75                  80
Ile Lys Lys Thr Ala Asn Lys Val Arg Ser Lys Leu Lys Ala Ile Glu
                 85                  90                  95
Gln Ser Ile Glu Gln Glu Glu Gly Leu Asn Arg Ser Ser Ala Asp Leu
                100                 105                 110
Arg Ile Arg Lys Thr Gln His Ser Thr Leu Ser Arg Lys Phe Val Glu
                115                 120                 125
Val Met Thr Glu Tyr Asn Ala Thr Gln Ser Lys Tyr Arg Asp Arg Cys
                130                 135                 140
Lys Asp Arg Ile Gln Arg Gln Leu Glu Ile Thr Gly Arg Thr Thr Thr
145                 150                 155                 160
Asn Glu Glu Leu Glu Asp Met Leu Glu Ser Gly Lys Leu Ala Ile Phe
                165                 170                 175
Thr Asp Asp Ile Lys Met Asp Ser Gln Met Thr Lys Gln Ala Leu Asn
                180                 185                 190
Glu Ile Glu Thr Arg His Asn Glu Ile Ile Lys Leu Glu Thr Ser Ile
                195                 200                 205
Arg Glu Leu His Asp Met Phe Val Asp Met Ala Met Leu Val Glu Ser
                210                 215                 220
Gln Gly Glu Met Ile Asp Arg Ile Glu Tyr Asn Val Glu His Ser Val
225                 230                 235                 240
```

-continued

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 75
<211> LENGTH: 288
<212> TYPE: PRT
<213> ORGANISM: Rattus norvegicus

<400> SEQUENCE: 75

Met Lys Asp Arg Thr Gln Glu Leu Arg Thr Ala Lys Asp Ser Asp Asp
 1               5                  10                  15

Asp Asp Asp Val Thr Val Thr Val Asp Arg Asp Arg Phe Met Asp Glu
                20                  25                  30

Phe Phe Glu Gln Val Glu Glu Ile Arg Gly Phe Ile Asp Lys Ile Ala
            35                  40                  45

Glu Asn Val Glu Glu Val Lys Arg Lys His Ser Ala Ile Leu Ala Ser
        50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ala Ser Thr Ile Gly Gly Ile Phe Gly
        275                 280                 285

<210> SEQ ID NO 76
<211> LENGTH: 288
<212> TYPE: PRT
<213> ORGANISM: Rattus norvegicus

<400> SEQUENCE: 76

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
                20                  25                  30

Phe Glu Gln Val Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
        210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 77
<211> LENGTH: 288
<212> TYPE: PRT
<213> ORGANISM: Mus musculus

<400> SEQUENCE: 77

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
                20                  25                  30

Phe Phe Glu Gln Val Glu Glu Ile Arg Gly Phe Ile Asp Lys Ile Ala
            35                  40                  45

Glu Asn Val Glu Glu Val Lys Arg Lys His Ser Ala Ile Leu Ala Ser
        50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

```
Glu Gln Ser Ile Glu Gln Glu Gly Leu Asn Arg Ser Ser Ala Asp
                100                 105                 110

Leu Arg Ile Arg Lys Thr Gln His Ser Thr Leu Ser Arg Lys Phe Val
            115                 120                 125

Glu Val Met Ser Glu Tyr Asn Ala Thr Gln Ser Asp Tyr Arg Glu Arg
        130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Thr Ser
        195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ile Ala Ser Thr Ile Gly Gly Ile Phe Gly
        275                 280                 285

<210> SEQ ID NO 78
<211> LENGTH: 288
<212> TYPE: PRT
<213> ORGANISM: Mus musculus

<400> SEQUENCE: 78

Met Lys Glu Trp Thr Gln Glu Arg Arg Ser Ala Lys Asp Ser Asp Asp
 1               5                  10                  15

Glu Glu Glu Val Val His Val Asp Arg Ala His Phe Met Ala Glu Phe
                20                  25                  30

Phe Glu Gln Val Glu Glu Ile Arg Gly Cys Ile Glu Lys Leu Ser Glu
            35                  40                  45

Asp Val Gly Arg Val Gly Gly Gln His Ser Ala Ile Leu Ala Ala Pro
        50                  55                  60

Lys Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Gly Ile Glu Gln Glu Glu Gly Leu Asn Arg Ser Ser Ala Asp Leu
            100                 105                 110

Arg Tyr Arg Thr Thr Gln His Ser Thr Val Ser Arg Asn Phe Val Glu
        115                 120                 125

Val Met Thr Glu Tyr Asn Ala Thr Lys Ser Lys Tyr Arg Asp Arg Cys
    130                 135                 140

Lys Asp Arg Leu Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Arg Asn
```

```
                    180                 185                 190
Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
        210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Cys Cys Val
        260                 265                 270

Val Leu Gly Val Val Leu Ala Ser Ser Ile Gly Gly Thr Leu Gly Leu
            275                 280                 285

<210> SEQ ID NO 79
<211> LENGTH: 288
<212> TYPE: PRT
<213> ORGANISM: Mus musculus

<400> SEQUENCE: 79

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
             20                  25                  30

Phe Glu Gln Val Glu Glu Ile Arg Gly Cys Ile Glu Lys Leu Ser Glu
         35                  40                  45

Asp Val Glu Gln Val Lys Lys Gln His Ser Ala Ile Leu Ala Ala Pro
     50                  55                  60

Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270
```

Val Leu Gly Val Val Leu Ala Ser Ser Ile Gly Gly Thr Leu Gly Leu
        275                 280                 285

<210> SEQ ID NO 80
<211> LENGTH: 290
<212> TYPE: PRT
<213> ORGANISM: Rattus norvegicus

<400> SEQUENCE: 80

Met Arg Asp Arg Leu Pro Asp Leu Thr Ala Cys Arg Lys Ser Asp Asp
1               5                   10                  15

Gly Asp Asn Ala Val Ile Ile Thr Val Glu Lys Asp His Phe Met Asp
            20                  25                  30

Ala Phe Phe His Gln Val Glu Glu Ile Arg Ser Ser Ile Ala Arg Ile
        35                  40                  45

Ala Gln His Val Glu Asp Val Lys Lys Asn His Ser Ile Ile Leu Ser
    50                  55                  60

Ala Pro Asn Pro Glu Gly Lys Ile Lys Glu Leu Glu Asp Leu Asn
65                  70                  75                  80

Lys Glu Ile Lys Lys Thr Ala Asn Arg Ile Arg Gly Lys Leu Lys Ala
                85                  90                  95

Ile Glu Gln Ser Cys Asp Gln Asp Glu Asn Gly Asn Arg Thr Ser Val
            100                 105                 110

Asp Leu Arg Ile Arg Arg Thr Gln His Ser Val Leu Ser Arg Lys Phe
        115                 120                 125

Val Asp Val Met Thr Glu Tyr Asn Glu Ala Gln Ile Leu Phe Arg Glu
    130                 135                 140

Arg Ser Lys Gly Arg Ile Gln Arg Gln Leu Glu Ile Thr Gly Arg Thr
145                 150                 155                 160

Thr Thr Asp Glu Glu Leu Glu Glu Met Leu Glu Ser Gly Lys Pro Ser
                165                 170                 175

Ile Phe Ile Ser Asp Ile Ile Ser Asp Ser Gln Ile Thr Arg Gln Ala
            180                 185                 190

Leu Asn Glu Ile Glu Ser Arg His His Lys Asp Ile Met Lys Leu Glu Thr
        195                 200                 205

Ser Ile Arg Glu Leu His Glu Met Phe Met Asp Met Ala Met Phe Val
    210                 215                 220

Glu Thr Gln Gly Glu Met Val Asn Asn Ile Glu Arg Asn Val Val Asn
225                 230                 235                 240

Ser Val Asp Tyr Val Glu His Ala Lys Glu Glu Thr Lys Lys Ala Ile
                245                 250                 255

Lys Tyr Gln Ser Lys Ala Arg Arg Lys Lys Trp Ile Ile Ala Ala Val
            260                 265                 270

Val Val Ala Val Ile Ala Val Leu Ala Leu Ile Ile Gly Leu Ser Val
        275                 280                 285

Gly Lys
    290

<210> SEQ ID NO 81
<211> LENGTH: 289
<212> TYPE: PRT
<213> ORGANISM: Mus musculus

<400> SEQUENCE: 81

Met Arg Asp Arg Leu Pro Asp Leu Thr Ala Cys Arg Thr Asn Asp Asp
1               5                   10                  15

```
Gly Asp Thr Ala Val Val Ile Val Glu Lys Asp His Phe Met Asp Gly
            20                  25                  30

Phe Phe His Gln Val Glu Glu Ile Arg Ser Ser Ile Ala Arg Ile Ala
            35                  40                  45

Gln His Val Glu Asp Val Lys Lys Asn His Ser Ile Ile Leu Ser Ala
            50                  55                  60

Pro Asn Pro Glu Gly Lys Ile Lys Glu Leu Glu Asp Leu Asn Lys
65                  70                  75                  80

Glu Ile Lys Lys Thr Ala Asn Arg Ile Arg Gly Lys Leu Lys Ser Ile
                    85                  90                  95

Glu Gln Ser Cys Asp Gln Asp Glu Asn Gly Asn Arg Thr Ser Val Asp
                100                 105                 110

Leu Arg Ile Arg Arg Thr Gln His Ser Val Leu Ser Arg Lys Phe Val
            115                 120                 125

Asp Val Met Thr Glu Tyr Asn Glu Ala Gln Ile Leu Phe Arg Glu Arg
            130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                    165                 170                 175

Phe Ile Ser Asp Ile Ile Ser Asp Ser Gln Ile Thr Arg Gln Ala Leu
                180                 185                 190

Asn Glu Ile Glu Ser Arg His Lys Asp Ile Met Lys Leu Glu Thr Ser
                195                 200                 205

Ile Arg Glu Leu His Glu Met Phe Met Asp Met Ala Met Phe Val Glu
210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                    245                 250                 255

Tyr Gln Ser Lys Ala Arg Arg Lys Lys Trp Ile Ile Ala Ala Val Ala
                260                 265                 270

Val Ala Val Ile Ala Val Leu Ala Leu Ile Ile Gly Leu Ser Val Gly
            275                 280                 285

Lys

<210> SEQ ID NO 82
<211> LENGTH: 289
<212> TYPE: PRT
<213> ORGANISM: Rattus norvegicus

<400> SEQUENCE: 82

Met Lys Asp Arg Leu Glu Gln Leu Lys Ala Lys Gln Leu Thr Gln Asp
 1               5                  10                  15

Asp Asp Thr Asp Glu Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
            35                  40                  45

Ile Ser Glu His Val Glu Glu Ala Lys Lys Leu Tyr Ser Ile Ile Leu
            50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                    85                  90                  95
```

```
Ser Met Glu Lys His Ile Glu Asp Glu Val Arg Ser Ser Ala Asp
            100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
            130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
                180                 185                 190

Glu Ile Glu Gly Arg His Lys Asp Ile Val Arg Leu Glu Ser Ser Ile
                195                 200                 205

Lys Glu Leu His Asp Met Phe Met Asp Ile Ala Met Leu Val Glu Asn
            210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Val Ile Val Val
                260                 265                 270

Val Leu Leu Gly Ile Leu Ala Leu Ile Ile Gly Leu Ser Val Gly Leu
            275                 280                 285

Lys

<210> SEQ ID NO 83
<211> LENGTH: 289
<212> TYPE: PRT
<213> ORGANISM: Mus musculus

<400> SEQUENCE: 83

Met Lys Asp Arg Leu Glu Gln Leu Lys Ala Lys Gln Leu Thr Gln Asp
  1               5                  10                  15

Asp Asp Thr Asp Glu Val Glu Ile Ala Ile Asp Asn Thr Ala Phe Met
                 20                  25                  30

Asp Glu Phe Phe Ser Glu Ile Glu Thr Arg Leu Asn Ile Asp Lys
             35                  40                  45

Ile Ser Glu His Val Glu Ala Lys Lys Leu Tyr Ser Ile Ile Leu
 50                  55                  60

Ser Ala Pro Ile Pro Glu Pro Lys Thr Lys Asp Asp Leu Glu Gln Leu
65                   70                  75                  80

Thr Thr Glu Ile Lys Lys Arg Ala Asn Asn Val Arg Asn Lys Leu Lys
                 85                  90                  95

Ser Met Glu Lys His Ile Glu Gly Asp Glu Val Arg Ser Ser Ala Asp
            100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
            130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175
```

-continued

```
Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Val Val Val Val Val
            260                 265                 270

Val Leu Leu Gly Ile Leu Ala Leu Ile Ile Gly Leu Ser Val Gly Leu
        275                 280                 285

Lys

<210> SEQ ID NO 84
<211> LENGTH: 283
<212> TYPE: PRT
<213> ORGANISM: Mus musculus

<400> SEQUENCE: 84

Met Lys Asp Arg Leu Glu Gln Leu Lys Ala Lys Gln Leu Thr Gln Asp
  1               5                  10                  15

Asp Asp Thr Asp Glu Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Ala Met Ile Asp Arg Ile Glu Asn Asn Met Asp Gln Ser Val
225                 230                 235                 240

Gly Phe Val Glu Arg Ala Val Ala Asp Thr Lys Lys Ala Val Lys Tyr
                245                 250                 255
```

```
Gln Ser Glu Ala Arg Arg Lys Lys Ile Met Ile Met Ile Cys Cys Ile
            260                 265                 270

Ile Leu Ala Ile Ile Leu Ala Ser Thr Ile Gly
        275                 280
```

<210> SEQ ID NO 85
<211> LENGTH: 269
<212> TYPE: PRT
<213> ORGANISM: Mus musculus

<400> SEQUENCE: 85

```
Met Lys Asp Arg Leu Glu Gln Leu Lys Ala Lys Gln Leu Thr Gln Asp
  1               5                  10                  15

Asp Asp Thr Asp Glu Val Glu Ile Ala Ile Asp Asn Thr Ala Phe Met
             20                  25                  30

Asp Glu Phe Phe Ser Glu Asn Phe His Gly Ile Leu Ser Tyr Leu Leu
         35                  40                  45

Arg Leu Ser Ser His Glu Thr Lys Asp Asp Leu Glu Gln Leu Thr Thr
 50                  55                  60

Glu Ile Lys Lys Arg Ala Asn Asn Val Arg Asn Lys Leu Lys Ser Met
 65                  70                  75                  80

Glu Lys His Ile Glu Glu Asp Glu Val Arg Ser Ser Ala Asp Leu Arg
                 85                  90                  95

Ile Arg Lys Ser Gln His Ser Val Leu Ser Arg Lys Phe Val Glu Val
            100                 105                 110

Met Thr Lys Tyr Asn Glu Ala Gln Val Asp Phe Arg Glu Arg Ser Lys
        115                 120                 125

Gly Arg Ile Gln Arg Gln Leu Glu Ile Thr Gly Lys Lys Thr Thr Asp
130                 135                 140

Glu Glu Leu Glu Glu Met Leu Glu Ser Gly Asn Pro Ala Ile Phe Thr
145                 150                 155                 160

Ser Gly Ile Ile Asp Ser Gln Ile Ser Lys Gln Ala Leu Ser Glu Ile
                165                 170                 175

Glu Gly Arg His Lys Asp Ile Val Arg Leu Glu Ser Ser Ile Lys Glu
            180                 185                 190

Leu His Asp Met Phe Met Asp Ile Ala Met Leu Val Glu Asn Gln Gly
        195                 200                 205

Ala Met Ile Asp Arg Ile Glu Asn Asn Met Asp Gln Ser Val Gly Phe
210                 215                 220

Val Glu Arg Ala Val Ala Asp Thr Lys Lys Ala Val Lys Tyr Gln Ser
225                 230                 235                 240

Glu Ala Arg Arg Lys Lys Ile Met Ile Met Ile Cys Cys Ile Ile Leu
                245                 250                 255

Ala Ile Ile Leu Ala Ser Thr Ile Gly Gly Ile Phe Ala
            260                 265
```

<210> SEQ ID NO 86
<211> LENGTH: 282
<212> TYPE: PRT
<213> ORGANISM: Gallus gallus

<400> SEQUENCE: 86

```
Met Lys Asp Arg Thr Gln Glu Leu Arg His Ala Lys Asp Ser Asp Asp
  1               5                  10                  15

Glu Glu Glu Val Val His Val Asp Arg Asn His Phe Met Asp Glu Phe
             20                  25                  30
```

```
Phe Glu Gln Val Glu Glu Ile Arg Gly Cys Ile Glu Lys Leu Phe Glu
            35                  40                  45

Asp Val Glu Gln Val Lys Lys Gln His Ser Ala Ile Leu Ala Ala Pro
        50                  55                  60

Asn Pro Asp Glu Arg Thr Lys Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Ala Asp Glu Gly Leu Asn Arg Ser Ser Ala Asp Leu
            100                 105                 110

Arg Ile Arg Lys Thr His Val Arg Glu Val Met Thr Glu Tyr Asn Ala
            115                 120                 125

Thr Gln Ser Lys Tyr Arg Asp Arg Cys Lys Asp Arg Ile Gln Arg Leu
        130                 135                 140

Leu Glu Ile Thr Gly Arg Thr Thr Asn Glu Glu Leu Glu Asp Met
145                 150                 155                 160

Leu Glu Ser Gly Lys Leu Ala Val Phe Asn Asp Ile Lys Ile Asp
            165                 170                 175

Ser Gln Met Thr Lys Gln Ala Leu Asn Glu Ile Glu Thr Arg His Asn
            180                 185                 190

Glu Ile Ile Tyr Leu Glu Thr Ser Ile Arg Glu Leu His Asp Met Phe
        195                 200                 205

Val Asp Met Ala Met Leu Val Glu Ser His Gly Glu Ser Ile Arg Pro
        210                 215                 220

Ala Ser Ser Thr Thr Cys Val His Thr Val Asp Tyr Val Glu Pro Val
225                 230                 235                 240

Val Phe Val Thr Lys Ser Ala Val Met Tyr Gln Cys Lys Ser Arg Arg
            245                 250                 255

Lys Lys Ile Met Ile Ile Ile Phe Val Val Val Leu Gly Val Val Leu
            260                 265                 270

Ser Pro Val Ile Cys Gly Thr Leu Gly Leu
            275                 280

<210> SEQ ID NO 87
<211> LENGTH: 288
<212> TYPE: PRT
<213> ORGANISM: Gallus gallus

<400> SEQUENCE: 87

Met Lys Asp Arg Leu Ala Asp Leu Ala Glu Cys Lys Gly Asn Glu Asp
  1               5                  10                  15

Gly Glu Thr Val Ile Val Glu Lys Asp His Phe Met Asp Asp Phe Phe
            20                  25                  30

Gln Gln Val Glu Glu Ile Arg Asn Asn Ile Thr Lys Ile Ala Gln Asn
        35                  40                  45

Val Glu Glu Val Lys Lys Gln His Ser Ile Ile Leu Ser Ala Pro Asn
    50                  55                  60

Pro Glu Gly Arg Thr Lys Glu Glu Leu Glu Glu Leu Asn Glu Glu Ile
65                  70                  75                  80

Lys Lys Thr Ala Asn Lys Ile Arg Ala Arg Leu Lys Ala Ile Glu Gln
                85                  90                  95

Ser Val Asp Gln Ser Glu Asn Ala Asn Arg Thr Ser Val Asn Val Arg
            100                 105                 110

Ile Arg Lys Thr Gln His Ser Val Leu Ala His Lys Phe Val Glu Val
            115                 120                 125
```

```
Met Thr Glu Tyr Asn Glu Thr Gln Thr Leu Phe Arg Glu Arg Ser Lys
            130                 135                 140

Gly Arg Ile Gln Arg Gln Leu Glu Ile Thr Gly Lys Thr Thr Thr Asp
145                 150                 155                 160

Glu Glu Leu Glu Glu Met Leu Glu Ser Gly Asn Pro Ser Ile Phe Thr
                    165                 170                 175

Ser Asp Ile Ile Ser Asp Ser Gln Ile Thr Arg Gln Ala Leu Asn Glu
                180                 185                 190

Ile Glu Ser Arg His Lys Asp Ile Met Lys Leu Glu Ser Ser Ile Arg
            195                 200                 205

Glu Leu His Glu Met Phe Met Asp Met Ala Met Phe Val Glu Thr Gln
        210                 215                 220

Gly Glu Met Ile Asn Asn Ile Glu Lys Asn Val Met Asn Ala Thr Asp
225                 230                 235                 240

Tyr Val Glu His Ala Lys Glu Thr Lys Lys Ala Val Lys Tyr Gln
                245                 250                 255

Ser Lys Ala Arg Arg Lys Met Trp Ile Ile Ile Val Ser Leu Val
            260                 265                 270

Leu Ile Ala Val Ile Gly Ile Ile Gly Leu Ser Val Gly Ile Arg
            275                 280                 285

<210> SEQ ID NO 88
<211> LENGTH: 288
<212> TYPE: PRT
<213> ORGANISM: Danio rerio

<400> SEQUENCE: 88

Met Lys Asp Arg Thr Gln Glu Leu Arg Ser Ala Lys Asp Ser Asp Asp
 1               5                  10                  15

Asp Glu Glu Val Val His Val Asp Arg Asp His Phe Met Asp Glu Phe
                20                  25                  30

Phe Glu Gln Val Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Thr Thr Gln Ser Lys Tyr Arg Asp Arg Cys
130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Thr Glu Ile Ile Lys Leu Glu Asn Ser Ile
        195                 200                 205

Arg Glu Leu His Asp Met Phe Val Asp Met Ala Met Leu Val Glu Ser
```

-continued

```
                210                 215                 220
Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Gln Ala Arg Lys Lys Lys Ile Met Ile Ile Cys Cys Val
                260                 265                 270

Ile Leu Gly Val Val Leu Arg Ser Ile Gly Gly Thr Leu Gly Phe
                275                 280                 285
```

<210> SEQ ID NO 89
<211> LENGTH: 288
<212> TYPE: PRT
<213> ORGANISM: Danio rerio

<400> SEQUENCE: 89

```
Met Lys Asp Arg Leu Glu Gln Leu Lys Ala Thr Cys Asp His Asp Asp
  1               5                  10                  15

Glu Asp Val Glu Ile Ala Val Asp Asn Ala Ala Phe Met Asp Glu Phe
                 20                  25                  30

Phe Ser Gln Ile Glu Asp Ile Arg Asn Ser Ile Asp Lys Ile Asp Glu
                 35                  40                  45

Asn Val Ala Glu Val Lys Lys Leu Tyr Ser Val Ile Leu Ser Ala Pro
 50                  55                  60

Thr Ser Asp Gln Lys Thr Gln Asp Asp Leu Glu Ala Leu Thr Asn Asp
 65                  70                  75                  80

Ile Lys Lys Met Ala Asn Asn Ala Arg Asn Lys Leu Lys Thr Ile Glu
                 85                  90                  95

Arg Asn Leu Glu Thr Glu Val Glu Arg Val Ser Ala Asp Met Arg
                100                 105                 110

Ile Arg Lys Ser Gln His Ala Val Leu Ser Arg Lys Phe Val Asp Val
                115                 120                 125

Met Thr Lys Tyr Asn Glu Ala Gln Val Asp Phe Arg Glu Lys Ser Lys
130                 135                 140

Gly Arg Ile Gln Arg Gln Leu Glu Ile Thr Gly Lys Ala Thr Thr Asp
145                 150                 155                 160

Glu Glu Leu Glu Glu Met Leu Glu Gly Gly Asn Ala Ala Val Phe Thr
                165                 170                 175

Ala Gly Ile Val Asp Ser Gly Ile Ser Lys Gln Ala Leu Ser Glu Ile
                180                 185                 190

Glu Ala Arg His Lys Asp Ile Val Arg Leu Glu Ser Ser Ile Lys Glu
                195                 200                 205

Leu His Asp Met Phe Val Asp Ile Ala Met Leu Val Glu Ser Gln Gly
                210                 215                 220

Asn Met Val Asp Asn Ile Glu Val Asn Val Gly Lys Ala Val Asp His
225                 230                 235                 240

Val Glu Ala Ala Arg Asp Glu Thr Lys Lys Ala Val Arg Tyr Gln Ser
                245                 250                 255

Lys Ala Arg Lys Lys Ile Ile Ile Val Ser Val Val Leu Val Ile
                260                 265                 270

Leu Ala Ile Ile Ala Leu Ile Val Gly Leu Ser Val Gly Leu Lys Arg
                275                 280                 285
```

<210> SEQ ID NO 90
<211> LENGTH: 286

```
<212> TYPE: PRT
<213> ORGANISM: Strongylocentrotus purpuratus

<400> SEQUENCE: 90

Met Arg Asp Arg Leu Gly Ser Leu Lys Arg Asn Glu Glu Asp Val
 1               5                  10                  15

Gly Gln Ser Arg Gly His Val Glu Ser Glu Lys Phe Met Glu Phe
            20                  25                  30

Phe Glu Gln Val Glu Val Arg Asn Asn Ile Asp Lys Ile Ser Lys
        35                  40                  45

Asn Val Asp Glu Val Lys Lys His Ser Asp Ile Leu Ser Ala Pro
 50                  55                  60

Gln Ala Asp Glu Lys Val Lys Asp Glu Leu Glu Glu Leu Met Ser Asp
65                  70                  75                  80

Ile Lys Lys Thr Ala Asn Lys Val Arg Val Lys Leu Lys Met Met Tyr
                85                  90                  95

Glu Ser Ile Glu Arg Arg Arg Val Leu Arg Arg Thr Gln Thr Asp Val
            100                 105                 110

Arg Ile Arg Lys Thr Gln His Ser Thr Leu Ser Arg Lys Phe Val Glu
        115                 120                 125

Val Met Thr Asp Tyr Asn Ser Thr Gln Thr Asp Tyr Arg Glu Arg Cys
    130                 135                 140

Lys Gly Arg Ile Gln Arg Gln Leu Glu Ile Thr Gly Lys Ser Thr Thr
145                 150                 155                 160

Asp Ala Glu Leu Glu Asp Met Leu Glu Ser Gly Asn Pro Ala Ile Phe
                165                 170                 175

Thr Ser Gly Ile Ile Met Asp Thr Gln Gln Ala Lys Gln Thr Leu Arg
            180                 185                 190

Asp Ile Glu Ala Arg His Asn Asp Ile Ile Lys Leu Glu Ser Ser Ile
        195                 200                 205

Arg Glu Leu His Asp Met Phe Met Asp Met Ala Met Leu Val Glu Ser
    210                 215                 220

Gln Gly Glu Met Ile Asp Arg Ile Glu Tyr Asn Val Glu Gln Ser Val
225                 230                 235                 240

Asp Tyr Val Arg Arg Gln Asn Asp Thr Lys Lys Ala Val Lys Tyr Gln
                245                 250                 255

Ser Lys Ala Arg Arg Lys Lys Phe Tyr Ile Ala Ile Cys Cys Gly Val
            260                 265                 270

Ala Leu Gly Ile Leu Ile Leu Val Leu Ile Ile Val Leu Ala
        275                 280                 285

<210> SEQ ID NO 91
<211> LENGTH: 291
<212> TYPE: PRT
<213> ORGANISM: Drosophila melanogaster

<400> SEQUENCE: 91

Met Thr Lys Asp Arg Leu Ala Ala Leu His Ala Ala Gln Ser Asp Asp
 1               5                  10                  15

Glu Glu Glu Thr Glu Val Ala Val Asn Val Asp Gly His Asp Ser Tyr
            20                  25                  30

Met Asp Asp Phe Phe Ala Gln Val Glu Glu Ile Arg Gly Met Ile Asp
        35                  40                  45

Lys Val Gln Asp Asn Val Glu Glu Val Lys Lys His Ser Ala Ile
 50                  55                  60
```

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu
                85                  90                  95

Lys Gly Ile Glu Gln Asn Ile Glu Gln Glu Gln Gln Asn Lys Ser
            100                 105                 110

Ser Ala Asp Leu Arg Ile Arg Lys Thr Gln His Ser Thr Leu Ser Arg
            115                 120                 125

Lys Phe Val Glu Val Met Thr Glu Tyr Asn Arg Thr Gln Thr Asp Tyr
        130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Gln Ala Lys
            180                 185                 190

Gln Thr Leu Ala Asp Ile Glu Ala Arg His Gln Asp Ile Met Lys Leu
        195                 200                 205

Glu Thr Ser Ile Lys Glu Leu His Asp Met Phe Met Asp Met Ala Met
210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
            260                 265                 270

Ile Cys Leu Thr Val Leu Gly Ile Leu Ala Ala Ser Tyr Val Ser Ser
        275                 280                 285

Tyr Phe Met
    290

<210> SEQ ID NO 92
<211> LENGTH: 295
<212> TYPE: PRT
<213> ORGANISM: Hirudo medicinalis

<400> SEQUENCE: 92

Met Thr Lys Asp Arg Leu Ala Ala Leu Lys Ala Ala Gln Ser Asp Asp
1               5                   10                  15

Asp Asp Glu Pro Gly Glu His Met Pro Met Thr Met Asn Val Asp Gly
            20                  25                  30

Gly Lys Phe Met Glu Glu Phe Phe Glu Gln Val Asn Glu Ile Arg Glu
        35                  40                  45

Met Ile Asp Lys Ile Ala Val Asp Val Asp Glu Val Lys Lys Lys His
    50                  55                  60

Ser Ala Ile Leu Ser Ala Pro Gln Thr Asp Asp Lys Thr Lys Glu Glu
65                  70                  75                  80

Leu Glu Asp Leu Met Ala Glu Ile Lys Lys Thr Ala Asn Lys Val Arg
                85                  90                  95

Gly Lys Leu Lys Val Leu Glu Gln Lys Ile Glu Gln Glu Glu Glu Thr
            100                 105                 110

Asn Lys Ser Ser Ala Asp Leu Arg Ile Arg Lys Thr Gln His Ser Thr
            115                 120                 125

Ile Leu Arg Lys Phe Ile Glu Val Met Asn Gln Tyr Asn Ala Ala Gln
        130                 135                 140

```
Val Asp Tyr Arg Asp Gly Cys Lys Lys Arg Leu Gln Arg Gln Met Glu
145                 150                 155                 160

Ile Thr Gly Arg Ala Thr Thr Asn Glu Glu Leu Glu Asp Met Leu Glu
                165                 170                 175

Ser Gly Asn Pro Ala Ile Phe Thr Gln Gly Ile Ile Thr Asp Thr Gln
            180                 185                 190

Gln Ala Lys Gln Ser Leu Met Asp Ile Glu Ala Arg His Asn Asp Ile
        195                 200                 205

Met Lys Leu Glu Gln Ser Ile Lys Glu Leu His Asp Met Phe Met Asp
    210                 215                 220

Met Ala Met Leu Val Glu Ser Gln Gly Glu Met Ile Asp Arg Ile Glu
225                 230                 235                 240

His Asn Val Glu Lys Ala Val Asp Tyr Val Glu Thr Ala Ala Ala Asp
                245                 250                 255

Thr Lys Lys Ala Met Lys Tyr Gln Ser Ala Ala Arg Lys Lys Lys Ile
                260                 265                 270

Ile Ile Leu Ile Cys Val Ser Val Leu Ile Leu Ile Val Gly Gly Ser
            275                 280                 285

Leu Leu Gly Ile Phe Ile Pro
            290                 295

<210> SEQ ID NO 93
<211> LENGTH: 292
<212> TYPE: PRT
<213> ORGANISM: Loligo pealei

<400> SEQUENCE: 93

Met Thr Lys Asp Arg Leu Ala Ala Leu Lys Ala Val Ser Asp Glu
1               5                  10                  15

Glu Asp Val Glu Glu Val Ala Val Gln Val Asp Ser Gly Gly Gly Phe
                20                  25                  30

Met Glu Glu Phe Phe Glu Gln Val Glu Glu Ile Arg Ala Met Ile Asp
            35                  40                  45

Lys Ile Ser Asp Asn Val Asp Ala Val Lys Lys His Ser Asp Ile
50                  55                  60

Leu Ser Ala Pro Gln Thr Asp Asp Gln Met Lys Glu Glu Leu Glu Glu
65                  70                  75                  80

Leu Met Thr Asp Ile Lys Arg Thr Ala Asn Lys Val Arg Gly Lys Leu
                85                  90                  95

Lys Thr Ile Glu Leu Asn Ile Glu Gln Glu Glu His Ser Asn Lys Ser
            100                 105                 110

Ser Ala Asp Leu Arg Ile Arg Lys Thr Gln Tyr Ser Thr Ile Ser Arg
        115                 120                 125

Lys Phe Val Glu Val Met Ser Asp Tyr Asn Thr Thr Gln Ile Asp Tyr
    130                 135                 140

Arg Asp Arg Cys Lys Ala Arg Ile Lys Arg Gln Met Glu Ile Thr Gly
145                 150                 155                 160

Arg Thr Thr Thr Asn Glu Glu Leu Glu Asp Met Leu Glu Ser Gly Asn
                165                 170                 175

Pro Ala Ile Phe Thr Gln Gly Ile Met Glu Thr Gln Gln Ala Lys
                180                 185                 190

Gln Thr Leu Ala Asp Ile Glu Ala Arg His Ala Asp Ile Met Lys Leu
        195                 200                 205

Glu Thr Ser Ile Arg Glu Leu His Asp Met Phe Met Asp Met Ala Met
```

```
                210                 215                 220
Leu Val Glu Ser Gln Gly Glu Met Ile Asp Arg Ile Glu Tyr Asn Val
225                 230                 235                 240

Glu Ala Ala Val Asp Tyr Ile Glu Thr Ala Lys Val Asp Thr Lys Lys
                245                 250                 255

Ala Val Lys Tyr Gln Ser Lys Ala Arg Gln Lys Lys Ile Ala Ile Leu
            260                 265                 270

Val Cys Leu Val Ile Leu Val Leu Val Ile Val Ser Thr Val Gly Gly
        275                 280                 285

Val Phe Gly Gly
    290

<210> SEQ ID NO 94
<211> LENGTH: 290
<212> TYPE: PRT
<213> ORGANISM: Lymnaea stagnalis

<400> SEQUENCE: 94

Met Thr Lys Asp Arg Leu Ala Ala Leu Lys Ala Ala Gln Ser Asp Asp
1               5                   10                  15

Asp Glu Asn Asp Asp Val Ala Val Thr Val Asp Ser Ser Gly Phe Met
                20                  25                  30

Glu Glu Phe Phe Glu Gln Val Asp Glu Ile Arg Glu Met Ile Asp Lys
            35                  40                  45

Ile Ala Ser Asn Val Asp Glu Val Lys Lys Lys His Ser Ala Ile Leu
50                  55                  60

Ser Ala Pro Gln Thr Asp Asp Lys Met Lys Glu Glu Leu Glu Glu Leu
65                  70                  75                  80

Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Lys Gln
            180                 185                 190

Thr Leu Ala Asp Ile Glu Ala Arg His Asn Asp Ile Met Lys Leu Glu
        195                 200                 205

Thr Ser Ile Arg Asp Leu His Asp Met Phe Met Asp Met Ala Met Leu
    210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
                245                 250                 255

Val Lys Tyr Gln Ser Lys Ala Arg Arg Lys Lys Ile Met Ile Ile Ile
            260                 265                 270

Cys Val Cys Val Leu Ile Ile Ile Leu Val Gly Ile Leu Gly Gly Thr
        275                 280                 285
```

Phe Gly
    290

<210> SEQ ID NO 95
<211> LENGTH: 290
<212> TYPE: PRT
<213> ORGANISM: Aplysia californica

<400> SEQUENCE: 95

Met Thr Lys Asp Arg Leu Ala Ala Leu Lys Ala Ala Gln Ser Asp Asp
 1               5                  10                  15

Asp Asp Asn Asp Asp Val Ala Val Thr Val Asp Ser Ser Gly Phe Met
            20                  25                  30

Glu Glu Phe Phe Glu Gln Val Asp Glu Ile Arg Glu Met Ile Asp Lys
        35                  40                  45

Ile Ala Ser Asn Val Asp Glu Val Lys Lys His Ser Ala Ile Leu
    50                  55                  60

Ser Ala Pro Gln Thr Asp Asp Lys Met Lys Glu Leu Glu Glu Leu
65                  70                  75                  80

Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
    130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Asn Glu
            180                 185                 190

Thr Leu Ala Asp Ile Glu Ala Arg His Asn Asp Ile Met Lys Leu Glu
        195                 200                 205

Thr Ser Ile Arg Asp Leu His Asp Met Phe Met Asp Met Ala Met Leu
    210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
                245                 250                 255

Val Lys Tyr Gln Ser Lys Ala Arg Arg Lys Lys Ile Met Ile Leu Val
            260                 265                 270

Cys Leu Ala Ile Leu Ile Ile Ile Leu Val Gly Val Ile Gly Gly Thr
        275                 280                 285

Leu Gly
    290

<210> SEQ ID NO 96
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/A SNAP-25 recognition site

<400> SEQUENCE: 96

-continued

```
Glu Ala Asn Gln Arg Ala Thr Lys
 1               5

<210> SEQ ID NO 97
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/B VAMP2 recognition site

<400> SEQUENCE: 97

Gly Ala Ser Gln Phe Glu Thr Ser
 1               5

<210> SEQ ID NO 98
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/C1 Syntaxin recognition sequence

<400> SEQUENCE: 98

Asp Thr Lys Lys Ala Val Lys Tyr
 1               5

<210> SEQ ID NO 99
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/C1 SNAP-25 recognition sequence

<400> SEQUENCE: 99

Ala Asn Gln Arg Ala Thr Lys Met
 1               5

<210> SEQ ID NO 100
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/D VAMP2 recognition site

<400> SEQUENCE: 100

Arg Asp Gln Lys Leu Ser Glu Leu
 1               5

<210> SEQ ID NO 101
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/E SNAP-25 recognition site

<400> SEQUENCE: 101

Gln Ile Asp Arg Ile Met Glu Lys
 1               5
```

-continued

<210> SEQ ID NO 102
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/F VAMP2 recognition site

<400> SEQUENCE: 102

Glu Arg Asp Gln Lys Leu Ser Glu
1               5

<210> SEQ ID NO 103
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a BoNT/G VAMP2 recognition site

<400> SEQUENCE: 103

Glu Thr Ser Ala Ala Lys Leu Lys
1               5

<210> SEQ ID NO 104
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: a TeNT VAMP2 recognition site

<400> SEQUENCE: 104

Gly Ala Ser Gln Phe Glu Thr Ser
1               5

<210> SEQ ID NO 105
<211> LENGTH: 13
<212> TYPE: PRT
<213> ORGANISM: Artificial Sequence
<220> FEATURE:
<221> NAME/KEY: SITE
<222> LOCATION: (1)...(13)
<223> OTHER INFORMATION: a BoNT/A SNAP-25 recognition site

<400> SEQUENCE: 105

Thr Arg Ile Asp Glu Ala Asn Gln Arg Ala Thr Lys Met
1               5                   10

<210> SEQ ID NO 106
<211> LENGTH: 15
<212> TYPE: PRT
<213> ORGANISM: Artificial Sequence
<220> FEATURE:
<221> NAME/KEY: SITE
<222> LOCATION: (1)...(15)
<223> OTHER INFORMATION: a BoNT/A SNAP-25 recognition site

<400> SEQUENCE: 106

Ser Asn Lys Thr Arg Ile Asp Glu Ala Asn Gln Arg Ala Thr Lys
1               5                   10                  15

<210> SEQ ID NO 107
<211> LENGTH: 16
<212> TYPE: PRT

-continued

<213> ORGANISM: Artificial Sequence
<220> FEATURE:
<221> NAME/KEY: SITE
<222> LOCATION: (1)...(16)
<223> OTHER INFORMATION: a BoNT/A SNAP-25 recognition site

<400> SEQUENCE: 107

Ser Asn Lys Thr Arg Ile Asp Glu Ala Asn Gln Arg Ala Thr Lys Met
1 5 10 15

<210> SEQ ID NO 108
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 108

Ser Asn Lys Thr Arg Ile Asp Glu Ala Asn Gln Arg Ala Thr Lys Met
1 5 10 15

Leu

<210> SEQ ID NO 109
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 109

Asp Ser Asn Lys Thr Arg Ile Asp Glu Ala Asn Gln Arg Ala Thr Lys
1 5 10 15

Met

<210> SEQ ID NO 110
<211> LENGTH: 18
<212> TYPE: PRT
<213> ORGANISM: Artificial Sequence
<220> FEATURE:
<221> NAME/KEY: SITE
<222> LOCATION: (1)...(18)
<223> OTHER INFORMATION: a BoNT/A SNAP-25 recognition site

<400> SEQUENCE: 110

Asp Ser Asn Lys Thr Arg Ile Asp Glu Ala Asn Gln Arg Ala Thr Lys
1 5 10 15

Met Leu

<210> SEQ ID NO 111
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 111

Ser Asn Lys Thr Arg Ile Asp Glu Ala Asn Gln Arg Ala Thr Lys Ala
1 5 10 15

Leu

-continued

<210> SEQ ID NO 112
<211> LENGTH: 17
<212> TYPE: PRT
<213> ORGANISM: Artificial Sequence
<220> FEATURE:
<221> NAME/KEY: SITE
<222> LOCATION: (1)...(16)
<223> OTHER INFORMATION: a BoNT/A SNAP-25 recognition site
<220> FEATURE:
<221> NAME/KEY: VARIANT
<222> LOCATION: (16)...(16)
<223> OTHER INFORMATION: Xaa=2-aminohexanoic acid (norleucine)

<400> SEQUENCE: 112

Ser Asn Lys Thr Arg Ile Asp Glu Ala Asn Gln Arg Ala Thr Lys Xaa
1 5 10 15

Leu

<210> SEQ ID NO 113
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 113

Ser Asn Lys Thr Arg Ile Asp Glu Ala Asn Gln Arg Ala Thr Ala Met
1 5 10 15

Leu

<210> SEQ ID NO 114
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 114

Ser Asn Lys Thr Arg Ile Asp Glu Ala Asn Gln Arg Ala Ser Lys Met
1 5 10 15

Leu

<210> SEQ ID NO 115
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site
<220> FEATURE:
<221> NAME/KEY: VARIANT
<222> LOCATION: (14)...(14)
<223> OTHER INFORMATION: Xaa=2-aminobutyric acid

<400> SEQUENCE: 115

Ser Asn Lys Thr Arg Ile Asp Glu Ala Asn Gln Arg Ala Xaa Lys Met
1 5 10 15

Leu

<210> SEQ ID NO 116
<211> LENGTH: 17

-continued

<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site
<220> FEATURE:
<221> NAME/KEY: VARIANT
<222> LOCATION: (13)...(13)
<223> OTHER INFORMATION: Xaa=2-aminobutyric acid

<400> SEQUENCE: 116

Ser Asn Lys Thr Arg Ile Asp Glu Ala Asn Gln Arg Xaa Thr Lys Met
1 5 10 15

Leu

<210> SEQ ID NO 117
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 117

Ser Asn Lys Thr Arg Ile Asp Glu Ala Asn Ala Arg Ala Thr Lys Met
1 5 10 15

Leu

<210> SEQ ID NO 118
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site
<220> FEATURE:
<221> NAME/KEY: VARIANT
<222> LOCATION: (11)...(11)
<223> OTHER INFORMATION: Xaa=2-aminobutyric acid

<400> SEQUENCE: 118

Ser Asn Lys Thr Arg Ile Asp Glu Ala Asn Xaa Arg Ala Thr Lys Met
1 5 10 15

Leu

<210> SEQ ID NO 119
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 119

Ser Asn Lys Thr Arg Ile Asp Glu Ala Asn Asn Arg Ala Thr Lys Met
1 5 10 15

Leu

<210> SEQ ID NO 120
<211> LENGTH: 17
<212> TYPE: PRT
<213> ORGANISM: Artificial Sequence
<220> FEATURE:

-continued

```
<221> NAME/KEY: SITE
<222> LOCATION: (1)...(17)
<223> OTHER INFORMATION: a BoNT/A SNAP-25 recognition site

<400> SEQUENCE: 120

Ser Asn Lys Thr Arg Ile Asp Glu Ala Ala Gln Arg Ala Thr Lys Met
 1               5                   10                  15

Leu

<210> SEQ ID NO 121
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site
<220> FEATURE:
<221> NAME/KEY: VARIANT
<222> LOCATION: (9)...(9)
<223> OTHER INFORMATION: Xaa=2-aminobutyric acid

<400> SEQUENCE: 121

Ser Asn Lys Thr Arg Ile Asp Glu Xaa Asn Gln Arg Ala Thr Lys Met
 1               5                   10                  15

Leu

<210> SEQ ID NO 122
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 122

Ser Asn Lys Thr Arg Ile Asp Gln Ala Asn Gln Arg Ala Thr Lys Met
 1               5                   10                  15

Leu

<210> SEQ ID NO 123
<211> LENGTH: 17
<212> TYPE: PRT
<213> ORGANISM: Artificial Sequence
<220> FEATURE:
<221> NAME/KEY: SITE
<222> LOCATION: (1)...(17)
<223> OTHER INFORMATION: a BoNT/A SNAP-25 recognition site

<400> SEQUENCE: 123

Ser Asn Lys Thr Arg Ile Asn Glu Ala Asn Gln Arg Ala Thr Lys Met
 1               5                   10                  15

Leu

<210> SEQ ID NO 124
<211> LENGTH: 35
<212> TYPE: PRT
<213> ORGANISM: Artificial Sequence
<220> FEATURE:
<221> NAME/KEY: SITE
<222> LOCATION: (1)...(35)
<223> OTHER INFORMATION: a BoNT/B VAMP2 recognition site

<400> SEQUENCE: 124

Leu Ser Glu Leu Asp Asp Arg Ala Asp Ala Leu Gln Ala Gly Ala Ser
```

```
                1               5                  10                 15
Gln Phe Glu Thr Ser Ala Ala Lys Leu Lys Arg Lys Tyr Trp Trp Lys
                20                 25                 30

Asn Leu Lys
        35

<210> SEQ ID NO 125
<211> LENGTH: 35
<212> TYPE: PRT
<213> ORGANISM: Artificial Sequence
<220> FEATURE:
<221> NAME/KEY: SITE
<222> LOCATION: (1)...(35)
<223> OTHER INFORMATION: a BoNT/B VAMP1 recognition site

<400> SEQUENCE: 125

Leu Ser Glu Leu Asp Asp Arg Ala Asp Ala Leu Gln Ala Gly Ala Ser
 1               5                 10                 15

Gln Phe Glu Ser Ser Ala Ala Lys Leu Lys Arg Lys Tyr Trp Trp Lys
                20                 25                 30

Asn Cys Lys
        35

<210> SEQ ID NO 126
<211> LENGTH: 39
<212> TYPE: PRT
<213> ORGANISM: Artificial Sequence
<220> FEATURE:
<223> OTHER INFORMATION: a BoNT/D and BoNT/F VAMP2 recognition site

<400> SEQUENCE: 126

Ala Gln Val Asp Glu Val Val Asp Ile Met Arg Val Asn Val Asp Lys
 1               5                 10                 15

Val Leu Glu Arg Asp Gln Lys Leu Ser Glu Leu Asp Asp Arg Ala Asp
                20                 25                 30

Ala Leu Gln Ala Gly Ala Ser
        35

<210> SEQ ID NO 127
<211> LENGTH: 39
<212> TYPE: PRT
<213> ORGANISM: Artificial Sequence
<220> FEATURE:
<223> OTHER INFORMATION: a BoNT/D and BoNT/F VAMP1 recognition site

<400> SEQUENCE: 127

Ala Gln Val Glu Glu Val Val Asp Ile Ile Arg Val Asn Val Asp Lys
 1               5                 10                 15

Val Leu Glu Arg Asp Gln Lys Leu Ser Glu Leu Asp Asp Arg Ala Asp
                20                 25                 30

Ala Leu Gln Ala Gly Ala Ser
        35

<210> SEQ ID NO 128
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 membrane targeting domain fragment

<400> SEQUENCE: 128
```

-continued

Cys Gly Leu Cys Val Cys Pro Cys Asn Lys
1               5                   10

<210> SEQ ID NO 129
<211> LENGTH: 10
<212> TYPE: PRT
<213> ORGANISM: Artificial Sequence
<220> FEATURE:
<221> NAME/KEY: PEPTIDE
<222> LOCATION: (1)...(10)
<223> OTHER INFORMATION: SNAP-25 Membrane Targeting Domain fragment

<400> SEQUENCE: 129

Cys Gly Leu Phe Ile Cys Pro Cys Asn Lys
1               5                   10

<210> SEQ ID NO 130
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 Membrane Targeting Domain fragment

<400> SEQUENCE: 130

Cys Gly Leu Cys Ser Cys Pro Cys Asn Lys
1               5                   10

<210> SEQ ID NO 131
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 Membrane Targeting Domain fragment

<400> SEQUENCE: 131

Cys Gly Leu Cys Pro Cys Pro Cys Asn Lys
1               5                   10

<210> SEQ ID NO 132
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 Membrane Targeting Domain fragment

<400> SEQUENCE: 132

Cys Gly Ile Cys Val Cys Pro Trp Lys Lys
1               5                   10

<210> SEQ ID NO 133
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 Membrane Targeting Domain fragment

<400> SEQUENCE: 133

Cys Gly Ile Cys Val Leu Pro Cys Asn Lys
1               5                   10

-continued

```
<210> SEQ ID NO 134
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: SNAP-25 Membrane Targeting Domain fragment

<400> SEQUENCE: 134

Cys Gly Leu Cys Val Leu Pro Trp Asn Lys
 1               5                  10

<210> SEQ ID NO 135
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment
<220> FEATURE:
<221> NAME/KEY: VARIANT
<222> LOCATION: (3)...(3)
<223> OTHER INFORMATION: Xaa=any amino acid

<400> SEQUENCE: 135

Gln Pro Xaa Arg Val
 1               5

<210> SEQ ID NO 136
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment
<220> FEATURE:
<221> NAME/KEY: VARIANT
<222> LOCATION: (3)...(3)
<223> OTHER INFORMATION: Xaa=any amino acid

<400> SEQUENCE: 136

Gln Pro Xaa Arg Ile
 1               5

<210> SEQ ID NO 137
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment

<400> SEQUENCE: 137

Gln Pro Ala Arg Val
 1               5

<210> SEQ ID NO 138
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment

<400> SEQUENCE: 138
```

```
Gln Pro Gln Arg Val
 1               5
```

```
<210> SEQ ID NO 139
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment

<400> SEQUENCE: 139

Gln Pro Gly Arg Val
 1               5
```

```
<210> SEQ ID NO 140
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment

<400> SEQUENCE: 140

Gln Pro Ser Arg Ile
 1               5
```

```
<210> SEQ ID NO 141
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: SNAP-25 Membrane Targeting Domain fragment

<400> SEQUENCE: 141

Gln Pro Met Arg Met
 1               5
```

```
<210> SEQ ID NO 142
<211> LENGTH: 4
<212> TYPE: PRT
<213> ORGANISM: Artificial Sequence
<220> FEATURE:
<221> NAME/KEY: DOMAIN
<222> LOCATION: (1)...(4)
<223> OTHER INFORMATION: SNAP-25 Membrane Targeting Domain fragment

<400> SEQUENCE: 142

Gln Pro Arg Ile
 1
```

```
<210> SEQ ID NO 143
<211> LENGTH: 239
<212> TYPE: PRT
<213> ORGANISM: Aequorea coerulescens

<400> SEQUENCE: 143

Met Val Ser Lys Gly Ala Glu Leu Phe Thr Gly Ile Val Pro Ile Leu
 1               5                  10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45
```

```
Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
                100                 105                 110

Val Lys Phe Glu Gly Asp Thr Leu Val Asn Arg Ile Glu Leu Thr Gly
                115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys
225                 230                 235

<210> SEQ ID NO 144
<211> LENGTH: 231
<212> TYPE: PRT
<213> ORGANISM: Zoanthus sp.

<400> SEQUENCE: 144

Met Ala Gln Ser Lys His Gly Leu Thr Lys Glu Met Thr Met Lys Tyr
1               5                   10                  15

Arg Met Glu Gly Cys Val Asp Gly His Lys Phe Val Ile Thr Gly Glu
                20                  25                  30

Gly Ile Gly Tyr Pro Phe Lys Gly Lys Gln Ala Ile Asn Leu Cys Val
                35                  40                  45

Val Glu Gly Gly Pro Leu Pro Phe Ala Glu Asp Ile Leu Ser Ala Ala
    50                  55                  60

Phe Met Tyr Gly Asn Arg Val Phe Thr Glu Tyr Pro Gln Asp Ile Ala
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
                100                 105                 110

Val Ser Val Glu Glu Asn Cys Met Tyr His Glu Ser Lys Phe Tyr Gly
                115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Leu Lys Asp Gly Gly Arg
                165                 170                 175

Leu Arg Cys Gln Phe Asp Thr Val Tyr Lys Ala Lys Ser Val Pro Arg
```

```
                    180                 185                 190
Lys Met Pro Asp Trp His Phe Ile Gln His Lys Leu Thr Arg Glu Asp
            195                 200                 205

Arg Ser Asp Ala Lys Asn Gln Lys Trp His Leu Thr Glu His Ala Ile
        210                 215                 220

Ala Ser Gly Ser Ala Leu Pro
225                 230

<210> SEQ ID NO 145
<211> LENGTH: 239
<212> TYPE: PRT
<213> ORGANISM: Aequorea victoria

<400> SEQUENCE: 145

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 146
<211> LENGTH: 227
<212> TYPE: PRT
<213> ORGANISM: Montastrea cavernosa

<400> SEQUENCE: 146

Met Gly Val Ile Lys Pro Asp Met Lys Ile Lys Leu Arg Met Glu Gly
 1               5                  10                  15

Ala Val Asn Gly His Lys Phe Val Ile Glu Gly Asp Gly Lys Gly Lys
            20                  25                  30

Pro Phe Glu Gly Lys Gln Thr Met Asp Leu Thr Val Ile Glu Gly Ala
```

-continued

```
                35                  40                  45
Pro Leu Pro Phe Ala Tyr Asp Ile Leu Thr Thr Val Phe Asp Tyr Gly
 50                  55                  60

Asn Arg Val Phe Ala Lys Tyr Pro Lys Asp Ile Pro Asp Tyr Phe Lys
 65                  70                  75                  80

Gln Thr Phe Pro Glu Gly Tyr Ser Trp Glu Arg Ser Met Thr Tyr Glu
                 85                  90                  95

Asp Gln Gly Ile Cys Ile Ala Thr Asn Asp Ile Thr Met Met Lys Gly
                100                 105                 110

Val Asp Asp Cys Phe Val Tyr Lys Ile Arg Phe Asp Gly Val Asn Phe
                115                 120                 125

Pro Ala Asn Gly Pro Val Met Gln Arg Lys Thr Leu Lys Trp Glu Pro
130                 135                 140

Ser Thr Glu Lys Met Tyr Val Arg Asp Gly Val Leu Lys Gly Asp Val
145                 150                 155                 160

Asn Met Ala Leu Leu Leu Glu Gly Gly Gly His Tyr Arg Cys Asp Phe
                165                 170                 175

Lys Thr Thr Tyr Lys Ala Lys Lys Val Val Gln Leu Pro Asp Tyr His
                180                 185                 190

Phe Val Asp His Arg Ile Glu Ile Val Ser His Asp Lys Asp Tyr Asn
                195                 200                 205

Lys Val Lys Leu Tyr Glu His Ala Glu Ala His Ser Gly Leu Pro Arg
210                 215                 220

Gln Ala Gly
225

<210> SEQ ID NO 147
<211> LENGTH: 233
<212> TYPE: PRT
<213> ORGANISM: Renilla reniformis

<400> SEQUENCE: 147

Met Asp Leu Ala Lys Leu Gly Leu Lys Glu Val Met Pro Thr Lys Ile
 1               5                  10                  15

Asn Leu Glu Gly Leu Val Gly Asp His Ala Phe Ser Met Glu Gly Val
                20                  25                  30

Gly Glu Gly Asn Ile Leu Glu Gly Thr Gln Glu Val Lys Ile Ser Val
                35                  40                  45

Thr Lys Gly Ala Pro Leu Pro Phe Ala Phe Asp Ile Val Ser Val Ala
 50                  55                  60

Phe Ser Tyr Gly Asn Arg Ala Tyr Thr Gly Tyr Pro Glu Glu Ile Ser
 65                  70                  75                  80

Asp Tyr Phe Leu Gln Ser Phe Pro Glu Gly Phe Thr Tyr Glu Arg Asn
                 85                  90                  95

Ile Arg Tyr Gln Asp Gly Gly Thr Ala Ile Val Lys Ser Asp Ile Ser
                100                 105                 110

Leu Glu Asp Gly Lys Phe Ile Val Asn Val Asp Phe Lys Ala Lys Asp
                115                 120                 125

Leu Arg Arg Met Gly Pro Val Met Gln Gln Asp Ile Val Gly Met Gln
130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                165                 170                 175
```

```
Met Arg Thr Val Tyr Lys Ser Lys Pro Val Glu Thr Met Pro Leu
            180                 185                 190

Tyr His Phe Ile Gln His Arg Leu Val Lys Thr Asn Val Asp Thr Ala
            195                 200                 205

Ser Gly Tyr Val Val Gln His Glu Thr Ala Ile Ala Ala His Ser Thr
            210                 215                 220

Ile Lys Lys Ile Glu Gly Ser Leu Pro
225                 230

<210> SEQ ID NO 148
<211> LENGTH: 239
<212> TYPE: PRT
<213> ORGANISM: Aequorea victoria

<400> SEQUENCE: 148

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 149
<211> LENGTH: 229
<212> TYPE: PRT
<213> ORGANISM: Anemonia majano

<400> SEQUENCE: 149

Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30
```

-continued

```
Gly Ser Gly Lys Pro Tyr Glu Gly Thr Gln Thr Ser Thr Phe Lys Val
            35                  40                  45

Thr Met Ala Asn Gly Gly Pro Leu Ala Phe Ser Phe Asp Ile Leu Ser
 50                  55                  60

Thr Val Phe Met Tyr Gly Asn Arg Cys Phe Thr Ala Tyr Pro Thr Ser
65                   70                  75                  80

Met Pro Asp Tyr Phe Lys Gln Ala Phe Pro Asp Gly Met Ser Tyr Glu
                 85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Met Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Pro Val Thr Met Pro
            180                 185                 190

Pro Asn His Ala Val Glu His Arg Ile Ala Arg Thr Asp Leu Asp Lys
        195                 200                 205

Gly Gly Asn Ser Val Gln Leu Thr Glu His Ala Val Ala His Ile Thr
    210                 215                 220

Ser Val Val Pro Phe
225

<210> SEQ ID NO 150
<211> LENGTH: 239
<212> TYPE: PRT
<213> ORGANISM: Aequorea victoria

<400> SEQUENCE: 150

Met Val Ser Lys Gly Glu Glu Leu Phe Thr Gly Val Val Pro Ile Leu
 1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr His Gly Val Gln Cys Phe Ser Arg Tyr Pro Asp His Met Lys
65                   70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

-continued

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 151
<211> LENGTH: 239
<212> TYPE: PRT
<213> ORGANISM: Aequorea victoria

<400> SEQUENCE: 151

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 152
<211> LENGTH: 231
<212> TYPE: PRT
<213> ORGANISM: Zoanthus sp.

<400> SEQUENCE: 152

Met Ala His Ser Lys His Gly Leu Lys Glu Glu Met Thr Met Lys Tyr
1               5                   10                  15

His Met Glu Gly Cys Val Asn Gly His Lys Phe Val Ile Thr Gly Glu
            20                  25                  30

```
Gly Ile Gly Tyr Pro Phe Lys Gly Lys Gln Thr Ile Asn Leu Cys Val
            35                  40                  45

Ile Glu Gly Gly Pro Leu Pro Phe Ser Glu Asp Ile Leu Ser Ala Gly
 50                  55                  60

Phe Lys Tyr Gly Asp Arg Ile Phe Thr Glu Tyr Pro Gln Asp Ile Val
65                   70                  75                  80

Asp Tyr Phe Lys Asn Ser Cys Pro Ala Gly Tyr Thr Trp Gly Arg Ser
                 85                  90                  95

Phe Leu Phe Glu Asp Gly Ala Val Cys Ile Cys Asn Val Asp Ile Thr
            100                 105                 110

Val Ser Val Lys Glu Asn Cys Ile Tyr His Lys Ser Ile Phe Asn Gly
        115                 120                 125

Val Asn Phe Pro Ala Asp Gly Pro Val Met Lys Lys Met Thr Thr Asn
    130                 135                 140

Trp Glu Ala Ser Cys Glu Lys Ile Met Pro Val Pro Lys Gln Gly Ile
145                 150                 155                 160

Leu Lys Gly Asp Val Ser Met Tyr Leu Leu Lys Asp Gly Gly Arg
                165                 170                 175

Tyr Arg Cys Gln Phe Asp Thr Val Tyr Lys Ala Lys Ser Val Pro Ser
            180                 185                 190

Lys Met Pro Glu Trp His Phe Ile Gln His Lys Leu Leu Arg Glu Asp
        195                 200                 205

Arg Ser Asp Ala Lys Asn Gln Lys Trp Gln Leu Thr Glu His Ala Ile
    210                 215                 220

Ala Phe Pro Ser Ala Leu Ala
225                 230

<210> SEQ ID NO 153
<211> LENGTH: 225
<212> TYPE: PRT
<213> ORGANISM: Discosoma striata

<400> SEQUENCE: 153

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
65                   70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
```

```
                    165                 170                 175
Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Thr Glu Gly Arg His His Leu Phe
        210                 215                 220

Leu
225

<210> SEQ ID NO 154
<211> LENGTH: 226
<212> TYPE: PRT
<213> ORGANISM: Discosoma striata

<400> SEQUENCE: 154

Met Val Arg Ser Ser Lys Asn Val Ile Lys Glu Phe Met Arg Phe Lys
1               5                   10                  15

Val Arg Met Glu Gly Thr Val Asn Gly His Glu Phe Glu Ile Glu Gly
                20                  25                  30

Glu Gly Glu Gly Arg Pro Tyr Glu Gly His Asn Thr Val Lys Leu Lys
            35                  40                  45

Val Thr Lys Gly Gly Pro Leu Pro Phe Ala Trp Asp Ile Leu Ser Pro
        50                  55                  60

Gln Phe Gln Tyr Gly Ser Lys Val Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
                100                 105                 110

Ser Leu Gln Asp Gly Cys Phe Ile Tyr Lys Val Lys Phe Ile Gly Val
            115                 120                 125

Asn Phe Pro Ser Asp Gly Pro Val Met Gln Lys Lys Thr Met Gly Trp
        130                 135                 140

Glu Ala Ser Thr Glu Arg Leu Tyr Pro Arg Asp Gly Val Leu Lys Gly
145                 150                 155                 160

Glu Ile His Lys Ala Leu Lys Leu Lys Asp Gly Gly His Tyr Leu Val
                165                 170                 175

Glu Phe Lys Ser Ile Tyr Met Ala Lys Lys Pro Val Gln Leu Pro Gly
                180                 185                 190

Tyr Tyr Tyr Val Asp Ser Lys Leu Asp Ile Thr Ser His Asn Glu Asp
            195                 200                 205

Tyr Thr Ile Val Glu Gln Tyr Glu Arg Thr Glu Gly Arg His His Leu
        210                 215                 220

Phe Leu
225

<210> SEQ ID NO 155
<211> LENGTH: 225
<212> TYPE: PRT
<213> ORGANISM: Discosoma striata

<400> SEQUENCE: 155

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
```

-continued

```
                    20                  25                  30
Gly Glu Gly Arg Pro Tyr Glu Gly His Asn Thr Val Lys Leu Lys Val
                35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 156
<211> LENGTH: 244
<212> TYPE: PRT
<213> ORGANISM: Discosoma striata

<400> SEQUENCE: 156

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
                35                  40                  45

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160
```

```
Ile His Lys Ala Leu Lys Leu Lys Asp Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Ala Glu Gly Arg His His Leu Phe
    210                 215                 220

Leu Arg Pro Arg Leu Ile Ile Ile Ser His Thr Thr Phe Val Glu Val
225                 230                 235                 240

Leu Leu Ala Leu

<210> SEQ ID NO 157
<211> LENGTH: 227
<212> TYPE: PRT
<213> ORGANISM: Heteractis crispa

<400> SEQUENCE: 157

Met Ala Gly Leu Leu Lys Glu Ser Met Arg Ile Lys Met Tyr Met Glu
  1               5                  10                  15

Gly Thr Val Asn Gly His Tyr Phe Lys Cys Glu Gly Glu Gly Asp Gly
             20                  25                  30

Asn Pro Phe Thr Gly Thr Gln Ser Met Arg Ile His Val Thr Glu Gly
         35                  40                  45

Ala Pro Leu Pro Phe Ala Phe Asp Ile Leu Ala Pro Cys Cys Glu Tyr
     50                  55                  60

Gly Ser Arg Thr Phe Val His His Thr Ala Glu Ile Pro Asp Phe Phe
 65                  70                  75                  80

Lys Gln Ser Phe Pro Glu Gly Phe Thr Trp Glu Arg Thr Thr Thr Tyr
                 85                  90                  95

Glu Asp Gly Gly Ile Leu Thr Ala His Gln Asp Thr Ser Leu Glu Gly
            100                 105                 110

Asn Cys Leu Ile Tyr Lys Val Lys Val Leu Gly Thr Asn Phe Pro Ala
        115                 120                 125

Asp Gly Pro Val Met Lys Asn Lys Ser Gly Gly Trp Glu Pro Cys Thr
    130                 135                 140

Glu Val Val Tyr Pro Glu Asn Gly Val Leu Cys Gly Arg Asn Val Met
145                 150                 155                 160

Ala Leu Lys Val Gly Asp Arg Arg Leu Ile Cys His Leu Tyr Thr Ser
                165                 170                 175

Tyr Arg Ser Lys Lys Ala Val Arg Ala Leu Thr Met Pro Gly Phe His
            180                 185                 190

Phe Thr Asp Ile Arg Leu Gln Met Pro Arg Lys Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225

<210> SEQ ID NO 158
<211> LENGTH: 232
<212> TYPE: PRT
<213> ORGANISM: Anemonia sulcata

<400> SEQUENCE: 158

Met Ala Ser Leu Leu Lys Lys Thr Met Pro Phe Arg Thr Thr Ile Glu
```

```
                1               5                  10                 15
Gly Thr Val Asn Gly His Tyr Phe Lys Cys Thr Gly Lys Gly Glu Gly
                    20                 25                 30

Asn Pro Leu Glu Gly Thr Gln Glu Met Lys Ile Glu Val Ile Glu Gly
                35                 40                 45

Gly Pro Leu Pro Phe Ala Phe His Ile Leu Ser Thr Ser Cys Met Tyr
            50                 55                 60

Gly Ser Lys Ala Phe Ile Lys Tyr Val Ser Gly Ile Pro Asp Tyr Phe
65                      70                 75                 80

Lys Gln Ser Leu Pro Glu Gly Phe Thr Trp Glu Arg Thr Thr Thr Tyr
                    85                 90                 95

Glu Asp Gly Gly Phe Leu Thr Ala His Gln Asp Thr Ser Leu Asp Gly
                100                105                110

Asp Cys Leu Val Tyr Lys Val Lys Ile Leu Gly Asn Asn Phe Pro Ala
            115                120                125

Asp Gly Pro Val Met Gln Asn Lys Ala Gly Arg Trp Glu Pro Ser Thr
        130                135                140

Glu Ile Val Tyr Glu Val Asp Gly Val Leu Arg Gly Gln Ser Leu Met
145                 150                155                160

Ala Leu Glu Cys Pro Gly Gly Arg His Leu Thr Cys His Leu His Thr
                165                170                175

Thr Tyr Arg Ser Lys Lys Pro Ala Ser Ala Leu Lys Met Pro Gly Phe
            180                185                190

His Phe Glu Asp His Arg Ile Glu Ile Leu Glu Glu Val Glu Lys Gly
                195                200                205

Lys Cys Tyr Lys Gln Tyr Glu Ala Ala Val Gly Arg Tyr Cys Asp Ala
        210                215                220

Ala Pro Ser Lys Leu Gly His Asn
225                 230

<210> SEQ ID NO 159
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: tetracysteine hexapeptide
<220> FEATURE:
<221> NAME/KEY: VARIANT
<222> LOCATION: (3)...(4)
<223> OTHER INFORMATION: Xaa is any amino acid

<400> SEQUENCE: 159

Cys Cys Xaa Xaa Cys Cys
1               5

<210> SEQ ID NO 160
<211> LENGTH: 182
<212> TYPE: PRT
<213> ORGANISM: Homo sapiens

<400> SEQUENCE: 160

Met Asp Lys Asp Cys Glu Met Lys Arg Thr Thr Leu Asp Ser Pro Leu
1               5                  10                 15

Gly Lys Leu Glu Leu Ser Gly Cys Glu Gln Gly Leu His Glu Ile Lys
                20                 25                 30

Leu Leu Gly Lys Gly Thr Ser Ala Ala Asp Ala Val Glu Val Pro Ala
            35                 40                 45
```

-continued

Pro Ala Ala Val Leu Gly Gly Pro Glu Pro Leu Met Gln Ala Thr Ala
        50                  55                  60

Trp Leu Asn Ala Tyr Phe His Gln Pro Glu Ala Ile Glu Glu Phe Pro
 65                  70                  75                  80

Val Pro Ala Leu His His Pro Val Phe Gln Gln Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Ala Ala Thr Ala
            115                 120                 125

Ala Val Lys Thr Ala Leu Ser Gly Asn Pro Val Pro Ile Leu Ile Pro
        130                 135                 140

Cys His Arg Val Val Ser Ser Gly Ala Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 161
<211> LENGTH: 296
<212> TYPE: PRT
<213> ORGANISM: Rhodococcus rhodochrous

<400> SEQUENCE: 161

Met Gly Ser Glu Ile Gly Thr Gly Phe Pro Phe Asp Pro His Tyr Val
 1               5                  10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
 50                  55                  60

Pro Asp Leu Ile Gly Met Gly Lys Ser Asp Lys Pro Asp Leu Asp Tyr
 65                  70                  75                  80

Phe Phe Asp Asp His Val Arg Tyr Leu Asp Ala Phe Ile Glu Ala Leu
                85                  90                  95

Gly Leu Glu Glu Val Val Leu Val Ile His Asp Trp Gly Ser Ala Leu
            100                 105                 110

Gly Phe His Trp Ala Lys Arg Asn Pro Glu Arg Val Lys Gly Ile Ala
        115                 120                 125

Cys Met Glu Phe Ile Arg Pro Ile Pro Thr Trp Asp Glu Trp Pro Glu
    130                 135                 140

Phe Ala Arg Glu Thr Phe Gln Ala Phe Arg Thr Ala Asp Val Gly Arg
145                 150                 155                 160

Glu Leu Ile Ile Asp Gln Asn Ala Phe Ile Glu Gly Ala Leu Pro Met
                165                 170                 175

Gly Val Val Arg Pro Leu Thr Glu Val Glu Met Asp His Tyr Arg Glu
            180                 185                 190

Pro Phe Leu Lys Pro Val Asp Arg Glu Pro Leu Trp Arg Phe Pro Asn
        195                 200                 205

Glu Leu Pro Ile Ala Gly Glu Pro Ala Asn Ile Val Ala Leu Val Glu
    210                 215                 220

Ala Tyr Met Asn Trp Leu His Gln Ser Pro Val Pro Lys Leu Leu Phe

```
                225                 230                 235                 240

Trp Gly Thr Pro Gly Val Leu Ile Pro Pro Ala Glu Ala Arg Leu
                245                 250                 255

Ala Glu Ser Leu Pro Asn Cys Lys Thr Val Asp Ile Gly Pro Gly Leu
                260                 265                 270

Phe Leu Leu Gln Glu Asp Asn Pro Asp Leu Ile Gly Ser Glu Ile Ala
                275                 280                 285

Arg Trp Leu Pro Gly Leu Ala Gly
                290                 295

<210> SEQ ID NO 162
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: flexible spacer

<400> SEQUENCE: 162

Gly Gly Gly Gly Ser
 1               5

<210> SEQ ID NO 163
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: flexible spacer

<400> SEQUENCE: 163

Glu Ala Ala Ala Lys
 1               5

<210> SEQ ID NO 164
<211> LENGTH: 808
<212> TYPE: PRT
<213> ORGANISM: Homo sapiens

<400> SEQUENCE: 164

Met Gly Ala Pro Ala Cys Ala Leu Ala Leu Cys Val Ala Val Ala Ile
 1               5                  10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
    130                 135                 140
```

-continued

```
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
```

-continued

```
                565                 570                 575
Leu Asp Tyr Ser Phe Asp Thr Cys Lys Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 165
<211> LENGTH: 806
<212> TYPE: PRT
<213> ORGANISM: Homo sapiens

<400> SEQUENCE: 165

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125
```

```
Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
```

```
                    545                 550                 555                 560
Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
                690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
                740                 745                 750

Thr Val Thr Ser Thr Asp Glu Tyr Leu Asp Leu Ser Ala Pro Phe Glu
                755                 760                 765

Gln Tyr Ser Pro Gly Gly Gln Asp Thr Pro Ser Ser Ser Ser Ser Gly
                770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 166
<211> LENGTH: 694
<212> TYPE: PRT
<213> ORGANISM: Homo sapiens

<400> SEQUENCE: 166

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110
```

-continued

```
Leu Thr Gln Arg Val Leu Cys His Phe Ser Val Arg Val Thr Asp Ala
            115                 120                 125
Pro Ser Ser Gly Asp Asp Glu Asp Gly Glu Asp Ala Glu Asp Thr
130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Arg Glu Phe Arg Gly Glu His Arg Ile Gly Gly Ile Lys Leu Arg His
                195                 200                 205
Gln Gln Trp Ser Leu Val Met Glu Ser Val Val Pro Ser Asp Arg Gly
            210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
            290                 295                 300
Tyr Val Thr Val Leu Lys Val Ser Leu Glu Ser Asn Ala Ser Met Ser
305                 310                 315                 320
Ser Asn Thr Pro Leu Val Arg Ile Ala Arg Leu Ser Ser Gly Glu Gly
                325                 330                 335
Pro Thr Leu Ala Asn Val Ser Glu Leu Glu Leu Pro Ala Asp Pro Lys
                340                 345                 350
Trp Glu Leu Ser Arg Ala Arg Leu Thr Leu Gly Lys Pro Leu Gly Glu
            355                 360                 365
Gly Cys Phe Gly Gln Val Val Met Ala Glu Ala Ile Gly Ile Asp Lys
            370                 375                 380
Asp Arg Ala Ala Lys Pro Val Thr Val Ala Val Lys Met Leu Lys Asp
385                 390                 395                 400
Asp Ala Thr Asp Lys Asp Leu Ser Asp Leu Val Ser Glu Met Glu Met
                405                 410                 415
Met Lys Met Ile Gly Lys His Lys Asn Ile Ile Asn Leu Leu Gly Ala
                420                 425                 430
Cys Thr Gln Gly Gly Pro Leu Tyr Val Leu Val Glu Tyr Ala Ala Lys
            435                 440                 445
Gly Asn Leu Arg Glu Phe Leu Arg Ala Arg Arg Pro Pro Gly Leu Asp
450                 455                 460
Tyr Ser Phe Asp Thr Cys Lys Pro Pro Glu Glu Gln Leu Thr Phe Lys
465                 470                 475                 480
Asp Leu Val Ser Cys Ala Tyr Gln Val Ala Arg Gly Met Glu Tyr Leu
                485                 490                 495
Ala Ser Gln Lys Cys Ile His Arg Asp Leu Ala Ala Arg Asn Val Leu
                500                 505                 510
Val Thr Glu Asp Asn Val Met Lys Ile Ala Asp Phe Gly Leu Ala Arg
            515                 520                 525
Asp Val His Asn Leu Asp Tyr Tyr Lys Lys Thr Thr Asn Gly Arg Leu
```

-continued

```
                530                 535                 540
Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690

<210> SEQ ID NO 167
<211> LENGTH: 604
<212> TYPE: PRT
<213> ORGANISM: Homo sapiens

<400> SEQUENCE: 167

Ala Gln Arg Arg Lys Glu Arg Glu Glu Leu Ala Gln Gln Tyr Glu Ala
1               5                   10                  15

Ile Leu Arg Glu Cys Gly His Gly Arg Phe Gln Trp Thr Leu Tyr Phe
            20                  25                  30

Val Leu Gly Leu Ala Leu Met Ala Asp Gly Val Glu Val Phe Val Val
        35                  40                  45

Gly Phe Val Leu Pro Ser Ala Glu Lys Asp Met Cys Leu Ser Asp Ser
    50                  55                  60

Asn Lys Gly Met Leu Gly Leu Ile Val Tyr Leu Gly Met Met Val Gly
65                  70                  75                  80

Ala Phe Leu Trp Gly Gly Leu Ala Asp Arg Leu Gly Arg Arg Gln Cys
                85                  90                  95

Leu Leu Ile Ser Leu Ser Val Asn Ser Val Phe Ala Phe Phe Ser Ser
            100                 105                 110

Phe Val Gln Gly Tyr Gly Thr Phe Leu Phe Cys Arg Leu Leu Ser Gly
        115                 120                 125

Val Gly Ile Gly Gly Ser Ile Pro Ile Val Phe Ser Tyr Phe Ser Glu
    130                 135                 140

Phe Leu Ala Gln Glu Lys Arg Gly Glu His Leu Ser Trp Leu Cys Met
145                 150                 155                 160

Phe Trp Met Ile Gly Gly Val Tyr Ala Ala Met Ala Trp Ala Ile
                165                 170                 175

Ile Pro His Tyr Gly Trp Ser Phe Gln Met Gly Ser Ala Tyr Gln Phe
            180                 185                 190

His Ser Trp Arg Val Phe Val Leu Val Cys Ala Phe Pro Ser Val Phe
        195                 200                 205
```

-continued

```
Ala Ile Gly Ala Leu Thr Thr Gln Pro Glu Ser Pro Arg Phe Phe Leu
    210                 215                 220
Glu Asn Gly Lys His Asp Glu Ala Trp Met Val Leu Lys Gln Val His
225                 230                 235                 240
Asp Thr Asn Met Arg Ala Lys Gly His Pro Glu Arg Val Phe Ser Val
                245                 250                 255
Thr His Ile Lys Thr Ile His Gln Glu Asp Glu Leu Ile Glu Ile Gln
            260                 265                 270
Ser Asp Thr Gly Thr Trp Tyr Gln Arg Trp Gly Val Arg Ala Leu Ser
        275                 280                 285
Leu Gly Gly Gln Val Trp Gly Asn Phe Leu Ser Cys Phe Gly Pro Glu
    290                 295                 300
Tyr Arg Arg Ile Thr Leu Met Met Met Gly Val Trp Phe Thr Met Ser
305                 310                 315                 320
Phe Ser Tyr Tyr Gly Leu Thr Val Trp Phe Pro Asp Met Ile Arg His
                325                 330                 335
Leu Gln Ala Val Asp Tyr Ala Ser Arg Thr Lys Val Phe Pro Gly Glu
            340                 345                 350
Arg Val Glu His Val Thr Phe Asn Phe Thr Leu Glu Asn Gln Ile His
        355                 360                 365
Arg Gly Gly Gln Tyr Phe Asn Asp Lys Phe Ile Gly Leu Arg Leu Lys
    370                 375                 380
Ser Val Ser Phe Glu Asp Ser Leu Phe Glu Glu Cys Tyr Phe Glu Asp
385                 390                 395                 400
Val Thr Ser Ser Asn Thr Phe Phe Arg Asn Cys Thr Phe Ile Asn Thr
                405                 410                 415
Val Phe Tyr Asn Thr Asp Leu Phe Glu Tyr Lys Phe Val Asn Ser Arg
            420                 425                 430
Leu Ile Asn Ser Thr Phe Leu His Asn Lys Glu Gly Cys Pro Leu Asp
        435                 440                 445
Val Thr Gly Thr Gly Glu Gly Ala Tyr Met Val Tyr Phe Val Ser Phe
    450                 455                 460
Leu Gly Thr Leu Ala Val Leu Pro Gly Asn Ile Val Ser Ala Leu Leu
465                 470                 475                 480
Met Asp Lys Ile Gly Arg Leu Arg Met Leu Ala Gly Ser Ser Val Met
                485                 490                 495
Ser Cys Val Ser Cys Phe Phe Leu Ser Phe Gly Asn Ser Glu Ser Ala
            500                 505                 510
Met Ile Ala Leu Leu Cys Leu Phe Gly Val Ser Ile Ala Ser Trp
        515                 520                 525
Asn Ala Leu Asp Val Leu Thr Val Glu Leu Tyr Pro Ser Asp Lys Arg
    530                 535                 540
Thr Thr Ala Phe Gly Phe Leu Asn Ala Leu Cys Lys Leu Ala Ala Val
545                 550                 555                 560
Leu Gly Ile Ser Ile Phe Thr Ser Phe Val Gly Ile Thr Lys Ala Ala
                565                 570                 575
Pro Ile Leu Phe Ala Ser Ala Ala Leu Ala Gly Ser Ser Leu Ala
            580                 585                 590
Leu Lys Leu Pro Glu Thr Arg Gly Gln Val Leu Gln
        595                 600

<210> SEQ ID NO 168
<211> LENGTH: 683
<212> TYPE: PRT
```

<213> ORGANISM: Homo sapiens

<400> SEQUENCE: 168

```
Met Asp Asp Tyr Lys Tyr Gln Asp Asn Tyr Gly Gly Tyr Ala Pro Ser
1               5                   10                  15
Asp Gly Tyr Tyr Arg Gly Asn Glu Ser Asn Pro Glu Glu Asp Ala Gln
            20                  25                  30
Ser Asp Val Thr Glu Gly His Asp Glu Asp Glu Ile Tyr Glu Gly
        35                  40                  45
Glu Tyr Gln Gly Ile Pro His Pro Asp Asp Val Lys Ala Lys Gln Ala
    50                  55                  60
Lys Met Ala Pro Ser Arg Met Asp Ser Leu Arg Gly Gln Thr Asp Leu
65                  70                  75                  80
Met Ala Glu Arg Leu Glu Asp Glu Glu Leu Ala His Gln Tyr Glu
                85                  90                  95
Thr Ile Met Asp Glu Cys Gly His Gly Arg Phe Gln Trp Ile Leu Phe
            100                 105                 110
Phe Val Leu Gly Leu Ala Leu Met Ala Asp Gly Val Glu Val Phe Val
        115                 120                 125
Val Ser Phe Ala Leu Pro Ser Ala Glu Lys Asp Met Cys Leu Ser Ser
130                 135                 140
Ser Lys Lys Gly Met Leu Gly Met Ile Val Tyr Leu Gly Met Met Ala
145                 150                 155                 160
Gly Ala Phe Ile Leu Gly Gly Leu Ala Asp Lys Leu Gly Arg Lys Arg
                165                 170                 175
Val Leu Ser Met Ser Leu Ala Val Asn Ala Ser Phe Ala Ser Leu Ser
            180                 185                 190
Ser Phe Val Gln Gly Tyr Gly Ala Phe Leu Phe Cys Arg Leu Ile Ser
        195                 200                 205
Gly Ile Gly Ile Gly Gly Ala Leu Pro Ile Val Phe Ala Tyr Phe Ser
210                 215                 220
Glu Phe Leu Ser Arg Glu Lys Arg Gly Glu His Leu Ser Trp Leu Gly
225                 230                 235                 240
Ile Phe Trp Met Thr Gly Gly Leu Tyr Ala Ser Ala Met Ala Trp Ser
                245                 250                 255
Ile Ile Pro His Tyr Gly Trp Gly Phe Ser Met Gly Thr Asn Tyr His
            260                 265                 270
Phe His Ser Trp Arg Val Phe Val Ile Val Cys Ala Leu Pro Cys Thr
        275                 280                 285
Val Ser Met Val Ala Leu Lys Phe Met Pro Glu Ser Pro Arg Phe Leu
290                 295                 300
Leu Glu Met Gly Lys His Asp Glu Ala Trp Met Ile Leu Lys Gln Val
305                 310                 315                 320
His Asp Thr Asn Met Arg Ala Lys Gly Thr Pro Glu Lys Val Phe Thr
                325                 330                 335
Val Ser Asn Ile Lys Thr Pro Lys Gln Met Asp Glu Phe Ile Glu Ile
            340                 345                 350
Gln Ser Ser Thr Gly Thr Trp Tyr Gln Arg Trp Leu Val Arg Phe Lys
        355                 360                 365
Thr Ile Phe Lys Gln Val Trp Asp Asn Ala Leu Tyr Cys Val Met Gly
370                 375                 380
Pro Tyr Arg Met Asn Thr Leu Ile Leu Ala Val Val Trp Phe Ala Met
385                 390                 395                 400
```

```
Ala Phe Ser Tyr Tyr Gly Leu Thr Val Trp Phe Pro Asp Met Ile Arg
            405                 410                 415

Tyr Phe Gln Asp Glu Glu Tyr Lys Ser Lys Met Lys Val Phe Phe Gly
            420                 425                 430

Glu His Val Tyr Gly Ala Thr Ile Asn Phe Thr Met Glu Asn Gln Ile
            435                 440                 445

His Gln His Gly Lys Leu Val Asn Asp Lys Phe Thr Arg Met Tyr Phe
        450                 455                 460

Lys His Val Leu Phe Glu Asp Thr Phe Phe Asp Gly Cys Tyr Phe Glu
465                 470                 475                 480

Asp Val Thr Ser Thr Asp Thr Tyr Phe Lys Asn Cys Thr Ile Glu Ser
            485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
            515                 520                 525

Asp Leu Glu Gln Asp Asn Asp Phe Leu Ile Tyr Leu Val Ser Phe Leu
        530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
            565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
            595                 600                 605

Ala Leu Asp Val Ile Thr Val Glu Leu Tyr Pro Thr Asn Gln Arg Ala
        610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
            645                 650                 655

Ile Leu Leu Ala Ala Ala Ser Leu Val Gly Gly Gly Leu Ile Ala Leu
            660                 665                 670

Arg Leu Pro Glu Thr Arg Glu Gln Val Leu Ile
            675                 680

<210> SEQ ID NO 169
<211> LENGTH: 727
<212> TYPE: PRT
<213> ORGANISM: Homo sapiens

<400> SEQUENCE: 169

Met Glu Asp Ser Tyr Lys Asp Arg Thr Ser Leu Met Lys Gly Ala Lys
1               5                  10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Tyr Tyr Pro Ala Gly Glu Thr
    50                  55                  60

Tyr Asn Gly Glu Ala Asn Asp Asp Gly Ser Ser Glu Ala Thr Glu
65                  70                  75                  80

Gly His Asp Glu Asp Asp Glu Ile Tyr Glu Gly Glu Tyr Gln Gly Ile
            85                  90                  95
```

-continued

```
Pro Ser Met Asn Gln Ala Lys Asp Ser Ile Val Ser Val Gly Gln Pro
            100                 105                 110
Lys Gly Asp Glu Tyr Lys Asp Arg Arg Glu Leu Glu Ser Glu Arg Arg
        115                 120                 125
Ala Asp Glu Glu Glu Leu Ala Gln Gln Tyr Glu Leu Ile Ile Gln Glu
    130                 135                 140
Cys Gly His Gly Arg Phe Gln Trp Ala Leu Phe Phe Val Leu Gly Met
145                 150                 155                 160
Ala Leu Met Ala Asp Gly Val Glu Val Phe Val Val Gly Phe Val Leu
                165                 170                 175
Pro Ser Ala Glu Thr Asp Leu Cys Ile Pro Asn Ser Gly Ser Gly Trp
            180                 185                 190
Leu Gly Ser Ile Val Tyr Leu Gly Met Met Val Gly Ala Phe Phe Trp
        195                 200                 205
Gly Gly Leu Ala Asp Lys Val Gly Arg Lys Gln Ser Leu Leu Ile Cys
    210                 215                 220
Met Ser Val Asn Gly Phe Phe Ala Phe Leu Ser Ser Phe Val Gln Gly
225                 230                 235                 240
Tyr Gly Phe Phe Leu Phe Cys Arg Leu Leu Ser Gly Phe Gly Ile Gly
                245                 250                 255
Gly Ala Ile Pro Thr Val Phe Ser Tyr Phe Ala Glu Val Leu Ala Arg
            260                 265                 270
Glu Lys Arg Gly Glu His Leu Ser Trp Leu Cys Met Phe Trp Met Ile
        275                 280                 285
Gly Gly Ile Tyr Ala Ser Ala Met Ala Trp Ala Ile Ile Pro His Tyr
    290                 295                 300
Gly Trp Ser Phe Ser Met Gly Ser Ala Tyr Gln Phe His Ser Trp Arg
305                 310                 315                 320
Val Phe Val Ile Val Cys Ala Leu Pro Cys Val Ser Ser Val Val Ala
                325                 330                 335
Leu Thr Phe Met Pro Glu Ser Pro Arg Phe Leu Leu Glu Val Gly Lys
            340                 345                 350
His Asp Glu Ala Trp Met Ile Leu Lys Leu Ile His Asp Thr Asn Met
        355                 360                 365
Arg Ala Arg Gly Gln Pro Glu Lys Val Phe Thr Val Asn Lys Ile Lys
    370                 375                 380
Thr Pro Lys Gln Ile Asp Glu Leu Ile Glu Ile Glu Ser Asp Thr Gly
385                 390                 395                 400
Thr Trp Tyr Arg Arg Cys Phe Val Arg Ile Arg Thr Glu Leu Tyr Gly
                405                 410                 415
Ile Trp Leu Thr Phe Met Arg Cys Phe Asn Tyr Pro Val Arg Asp Asn
            420                 425                 430
Thr Ile Lys Leu Thr Ile Val Trp Phe Thr Leu Ser Phe Gly Tyr Tyr
        435                 440                 445
Gly Leu Ser Val Trp Phe Pro Asp Val Ile Lys Pro Leu Gln Ser Asp
    450                 455                 460
Glu Tyr Ala Leu Leu Thr Arg Asn Val Glu Arg Asp Lys Tyr Ala Asn
465                 470                 475                 480
Phe Thr Ile Asn Phe Thr Met Glu Asn Gln Ile His Thr Gly Met Glu
                485                 490                 495
Tyr Asp Asn Gly Arg Phe Ile Gly Val Lys Phe Lys Ser Val Thr Phe
            500                 505                 510
```

-continued

```
Lys Asp Ser Val Phe Lys Ser Cys Thr Phe Glu Asp Val Thr Ser Val
        515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ser Ile Pro Ile Leu Leu Ala
    690                 695                 700

Ser Thr Val Leu Val Cys Gly Gly Leu Val Gly Leu Cys Leu Pro Asp
705                 710                 715                 720

Thr Arg Thr Gln Val Leu Met
                725

<210> SEQ ID NO 170
<211> LENGTH: 742
<212> TYPE: PRT
<213> ORGANISM: Homo sapiens

<400> SEQUENCE: 170

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Ser Tyr Ser Arg
        35                  40                  45

Phe Glu Glu Asp Asp Asp Asp Phe Pro Ala Pro Ser Asp Gly
    50                  55                  60

Tyr Tyr Arg Gly Glu Gly Thr Gln Asp Glu Glu Gly Gly Ala Ser
65              70                  75                  80

Ser Asp Ala Thr Glu Gly His Asp Glu Asp Glu Ile Tyr Glu Gly
                85                  90                  95

Glu Tyr Gln Asp Ile Pro Arg Ala Glu Ser Gly Gly Lys Gly Glu Arg
            100                 105                 110

Met Ala Asp Gly Ala Pro Leu Ala Gly Val Arg Gly Leu Ser Asp
    115                 120                 125

Gly Glu Gly Pro Pro Gly Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160
```

-continued

```
His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
    290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
        355                 360                 365

Glu Ala Trp Met Val Leu Lys Gln Val His Asp Thr Asn Met Arg Ala
    370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Gly Pro Glu Tyr Arg Arg Ile Thr Leu
        435                 440                 445

Met Met Met Gly Val Trp Phe Thr Met Ser Phe Ser Tyr Tyr Gly Leu
    450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Gly His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575
```

```
Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
            595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
            675                 680                 685

Leu Asn Ala Leu Cys Lys Leu Ala Ala Val Leu Gly Ile Ser Ile Phe
690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 171
<211> LENGTH: 422
<212> TYPE: PRT
<213> ORGANISM: Homo sapiens

<400> SEQUENCE: 171

Met Val Ser Glu Ser His His Glu Ala Leu Ala Ala Pro Pro Val Thr
1               5                   10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys Ile Pro Leu Pro Pro Trp Ala Leu Ile Ala Ile
    50                  55                  60

Ala Ile Val Ala Val Leu Leu Val Leu Thr Cys Cys Phe Cys Ile Cys
65                  70                  75                  80

Lys Lys Cys Leu Phe Lys Lys Lys Asn Lys Lys Gly Lys Glu Lys
                85                  90                  95

Gly Gly Lys Asn Ala Ile Asn Met Lys Asp Val Lys Asp Leu Gly Lys
            100                 105                 110

Thr Met Lys Asp Gln Ala Leu Lys Asp Asp Ala Glu Thr Gly Leu
        115                 120                 125

Thr Asp Gly Glu Glu Lys Glu Glu Pro Lys Glu Glu Lys Leu Gly
    130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Phe Glu Thr Lys Val His Arg Lys Thr Leu Asn Pro Val Phe Asn
        195                 200                 205
```

```
Glu Gln Phe Thr Phe Lys Val Pro Tyr Ser Glu Leu Gly Gly Lys Thr
        210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Gln Glu
            260                 265                 270

Lys Leu Gly Asp Ile Cys Phe Ser Leu Arg Tyr Val Pro Thr Ala Gly
        275                 280                 285

Lys Leu Thr Val Val Ile Leu Glu Ala Lys Asn Leu Lys Lys Met Asp
        290                 295                 300

Val Gly Gly Leu Ser Asp Pro Tyr Val Lys Ile His Leu Met Gln Asn
305                 310                 315                 320

Gly Lys Arg Leu Lys Lys Lys Thr Thr Ile Lys Lys Asn Thr Leu
                325                 330                 335

Asn Pro Tyr Tyr Asn Glu Ser Phe Ser Phe Glu Val Pro Phe Glu Gln
                340                 345                 350

Ile Gln Lys Val Gln Val Val Thr Val Leu Asp Tyr Asp Lys Ile
            355                 360                 365

Gly Lys Asn Asp Ala Ile Gly Lys Val Phe Val Gly Tyr Asn Ser Thr
        370                 375                 380

Gly Ala Glu Leu Arg His Trp Ser Asp Met Leu Ala Asn Pro Arg Arg
385                 390                 395                 400

Pro Ile Ala Gln Trp His Thr Leu Gln Val Glu Glu Val Asp Ala
                405                 410                 415

Met Leu Ala Val Lys Lys
            420

<210> SEQ ID NO 172
<211> LENGTH: 419
<212> TYPE: PRT
<213> ORGANISM: Homo sapiens

<400> SEQUENCE: 172

Met Arg Asn Ile Phe Lys Arg Asn Gln Glu Pro Ile Val Ala Pro Ala
1               5                   10                  15

Thr Thr Thr Ala Thr Met Pro Ile Gly Pro Val Asp Asn Ser Thr Glu
                20                  25                  30

Ser Gly Gly Ala Gly Glu Ser Gln Glu Asp Met Phe Ala Lys Leu Lys
            35                  40                  45

Glu Lys Leu Phe Asn Glu Ile Asn Lys Ile Pro Leu Pro Pro Trp Ala
        50                  55                  60

Leu Ile Ala Ile Ala Val Val Ala Gly Leu Leu Leu Thr Cys Cys
65                  70                  75                  80

Phe Cys Ile Cys Lys Lys Cys Cys Cys Lys Lys Lys Asn Lys Lys
                85                  90                  95

Glu Lys Gly Lys Gly Met Lys Asn Ala Met Asn Met Lys Asp Met Lys
            100                 105                 110

Gly Gly Gln Asp Asp Asp Ala Glu Thr Gly Leu Thr Glu Gly Glu
        115                 120                 125

Gly Glu Gly Glu Glu Glu Lys Glu Pro Glu Asn Leu Gly Lys Leu Gln
            130                 135                 140

Phe Ser Leu Asp Tyr Asp Phe Gln Ala Asn Gln Leu Thr Val Gly Val
```

```
                145                 150                 155                 160
Leu Gln Ala Ala Glu Leu Pro Ala Leu Asp Met Gly Gly Thr Ser Asp
                    165                 170                 175

Pro Tyr Val Lys Val Phe Leu Leu Pro Asp Lys Lys Lys Tyr Glu
                180                 185                 190

Thr Lys Val His Arg Lys Thr Leu Asn Pro Ala Phe Asn Glu Thr Phe
                    195                 200                 205

Thr Phe Lys Val Pro Tyr Gln Glu Leu Gly Gly Lys Thr Leu Val Met
                210                 215                 220

Ala Ile Tyr Asp Phe Asp Arg Phe Ser Lys His Asp Ile Ile Gly Glu
225                 230                 235                 240

Val Lys Val Pro Met Asn Thr Val Asp Leu Gly Gln Pro Ile Glu Glu
                    245                 250                 255

Trp Arg Asp Leu Gln Gly Gly Glu Lys Glu Pro Glu Lys Leu Gly
                260                 265                 270

Asp Ile Cys Thr Ser Leu Arg Tyr Val Pro Thr Ala Gly Lys Leu Thr
                    275                 280                 285

Val Cys Ile Leu Glu Ala Lys Asn Leu Lys Lys Met Asp Val Gly Gly
                    290                 295                 300

Leu Ser Asp Pro Tyr Gly Lys Ile His Leu Met Gln Asn Gly Lys Arg
305                 310                 315                 320

Leu Lys Lys Lys Lys Thr Thr Val Lys Lys Thr Leu Asn Pro Tyr
                    325                 330                 335

Phe Asn Glu Ser Phe Ser Phe Glu Ile Pro Phe Glu Gln Ile Gln Lys
                    340                 345                 350

Val Gln Val Val Val Thr Val Leu Asp Tyr Asp Lys Leu Gly Lys Asn
                    355                 360                 365

Glu Ala Ile Gly Lys Ile Phe Val Gly Ser Asn Ala Thr Gly Thr Glu
                    370                 375                 380

Leu Arg His Trp Ser Asp Met Leu Ala Asn Pro Arg Arg Pro Ile Ala
385                 390                 395                 400

Gln Trp His Ser Leu Lys Pro Glu Glu Glu Val Asp Ala Leu Leu Gly
                    405                 410                 415

Lys Asn Lys

<210> SEQ ID NO 173
<211> LENGTH: 700
<212> TYPE: PRT
<213> ORGANISM: Artificial Sequence
<220> FEATURE:
<221> NAME/KEY: PEPTIDE
<222> LOCATION: (1)...(700)
<223> OTHER INFORMATION: BFP-SNAP25(1-206)-GFP substrate

<400> SEQUENCE: 173

Met Ala Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
         50                  55                  60

Leu Ser His Gly Val Gln Cys Phe Ser Arg Tyr Pro Asp His Met Lys
 65                  70                  75                  80
```

-continued

```
Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ile
225                 230                 235                 240

Asp Gly Gly Gly Gly Met Ala Glu Asp Ala Asp Met Arg Asn Glu
                245                 250                 255

Leu Glu Glu Met Gln Arg Arg Ala Asp Gln Leu Ala Asp Glu Ser Leu
            260                 265                 270

Glu Ser Thr Arg Arg Met Leu Gln Leu Val Glu Glu Ser Lys Asp Ala
        275                 280                 285

Gly Ile Arg Thr Leu Val Met Leu Asp Glu Gln Gly Glu Gln Leu Glu
    290                 295                 300

Arg Ile Glu Glu Gly Met Asp Gln Ile Asn Lys Asp Met Lys Glu Ala
305                 310                 315                 320

Glu Lys Asn Leu Thr Asp Leu Gly Lys Phe Cys Gly Leu Cys Val Cys
                325                 330                 335

Pro Cys Asn Lys Leu Lys Ser Ser Asp Ala Tyr Lys Lys Ala Trp Gly
            340                 345                 350

Asn Asn Gln Asp Gly Val Val Ala Ser Gln Pro Ala Arg Val Val Asp
        355                 360                 365

Glu Arg Glu Gln Met Ala Ile Ser Gly Gly Phe Ile Arg Arg Val Thr
    370                 375                 380

Asn Asp Ala Arg Glu Asn Glu Met Asp Glu Asn Leu Glu Gln Val Ser
385                 390                 395                 400

Gly Ile Ile Gly Asn Leu Arg His Met Ala Leu Asp Met Gly Asn Glu
                405                 410                 415

Ile Asp Thr Gln Asn Arg Gln Ile Asp Arg Ile Met Glu Lys Ala Asp
            420                 425                 430

Ser Asn Lys Thr Arg Ile Asp Glu Ala Asn Gln Arg Ala Thr Lys Met
        435                 440                 445

Leu Gly Ser Gly Gly Asn Ser Gly Gly Gly Gly Ala Ser Lys Gly
    450                 455                 460

Glu Glu Leu Phe Thr Gly Val Val Pro Ile Leu Val Glu Leu Asp Gly
465                 470                 475                 480

Asp Val Asn Gly His Lys Phe Ser Val Ser Gly Glu Gly Glu Gly Asp
                485                 490                 495

Ala Thr Tyr Gly Lys Leu Thr Leu Lys Phe Ile Cys Thr Thr Gly Lys
```

```
                500             505             510
Leu Pro Val Pro Trp Pro Thr Leu Val Thr Thr Leu Cys Tyr Gly Val
            515                 520                 525

Gln Cys Phe Ser Arg Tyr Pro Asp His Met Lys Arg His Asp Phe Phe
        530                 535                 540

Lys Ser Ala Met Pro Glu Gly Tyr Val Gln Glu Arg Thr Ile Phe Phe
545                 550                 555                 560

Lys Asp Asp Gly Asn Tyr Lys Thr Arg Ala Glu Val Lys Phe Glu Gly
                565                 570                 575

Asp Thr Leu Val Asn Arg Ile Glu Leu Lys Gly Ile Asp Phe Lys Glu
            580                 585                 590

Asp Gly Asn Ile Leu Gly His Lys Leu Glu Tyr Asn Tyr Asn Ser His
        595                 600                 605

Asn Val Tyr Ile Met Ala Asp Lys Gln Lys Asn Gly Ile Lys Val Asn
    610                 615                 620

Phe Lys Thr Arg His Asn Ile Glu Asp Gly Ser Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Thr Gln Ser Ala Leu Ser Lys Asp Pro Asn
            660                 665                 670

Glu Lys Arg Asp His Met Val Leu Leu Glu Phe Val Thr Ala Ala Gly
        675                 680                 685

Ile Thr His Gly Met Asp Glu Leu Tyr Asn Ile Asp
    690                 695                 700

<210> SEQ ID NO 174
<211> LENGTH: 627
<212> TYPE: PRT
<213> ORGANISM: Artificial Sequence
<220> FEATURE:
<221> NAME/KEY: PEPTIDE
<222> LOCATION: (1)...(627)
<223> OTHER INFORMATION: BFP-SNAP25(80-206)-GFP substrate

<400> SEQUENCE: 174

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser His Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr His Gly Met Asp Glu Leu Tyr Asn Ile
225                 230                 235                 240

Asp Gly Gly Gly Gly Lys Gly Pro Val Thr Gly Thr Gly Ser Lys
                    245                 250                 255

Phe Cys Gly Leu Cys Val Cys Pro Asn Lys Leu Lys Ser Ser Asp
                260                 265                 270

Ala Tyr Lys Lys Ala Trp Gly Asn Asn Gln Asp Gly Val Val Ala Ser
            275                 280                 285

Gln Pro Ala Arg Val Val Asp Glu Arg Glu Gln Met Ala Ile Ser Gly
            290                 295                 300

Gly Phe Ile Arg Arg Val Thr Asn Asp Ala Arg Glu Asn Glu Met Asp
305                 310                 315                 320

Glu Asn Leu Glu Gln Val Ser Gly Ile Ile Gly Asn Leu Arg His Met
            325                 330                 335

Ala Leu Asp Met Gly Asn Glu Ile Asp Thr Gln Asn Arg Gln Ile Asp
            340                 345                 350

Arg Ile Met Glu Lys Ala Asp Ser Asn Lys Thr Arg Ile Asp Glu Ala
            355                 360                 365

Asn Gln Arg Ala Thr Lys Met Leu Gly Ser Gly Asn Ser Gly Gly
            370                 375                 380

Gly Gly Gly Ala Ser Lys Gly Glu Glu Leu Phe Thr Gly Val Val Pro
385                 390                 395                 400

Ile Leu Val Glu Leu Asp Gly Asp Val Asn Gly His Lys Phe Ser Val
            405                 410                 415

Ser Gly Glu Gly Glu Gly Asp Ala Thr Tyr Gly Lys Leu Thr Leu Lys
            420                 425                 430

Phe Ile Cys Thr Thr Gly Lys Leu Pro Val Pro Trp Pro Thr Leu Val
            435                 440                 445

Thr Thr Leu Cys Tyr Gly Val Gln Cys Phe Ser Arg Tyr Pro Asp His
450                 455                 460

Met Lys Arg His Asp Phe Phe Lys Ser Ala Met Pro Glu Gly Tyr Val
465                 470                 475                 480

Gln Glu Arg Thr Ile Phe Phe Lys Asp Asp Gly Asn Tyr Lys Thr Arg
            485                 490                 495

Ala Glu Val Lys Phe Glu Gly Asp Thr Leu Val Asn Arg Ile Glu Leu
            500                 505                 510

Lys Gly Ile Asp Phe Lys Glu Asp Gly Asn Ile Leu Gly His Lys Leu
            515                 520                 525

Glu Tyr Asn Tyr Asn Ser His Asn Val Tyr Ile Met Ala Asp Lys Gln
            530                 535                 540

Lys Asn Gly Ile Lys Val Asn Phe Lys Thr Arg His Asn Ile Glu Asp
545                 550                 555                 560

Gly Ser Val Gln Leu Ala Asp His Tyr Gln Gln Asn Thr Pro Ile Gly
            565                 570                 575
```

-continued

```
Asp Gly Pro Val Leu Pro Asp Asn His Tyr Leu Ser Thr Gln Ser
            580                 585                 590

Ala Leu Ser Lys Asp Pro Asn Glu Lys Arg Asp His Met Val Leu Leu
            595                 600                 605

Glu Phe Val Thr Ala Ala Gly Ile Thr His Gly Met Asp Glu Leu Tyr
            610                 615                 620

Asn Ile Asp
625

<210> SEQ ID NO 175
<211> LENGTH: 574
<212> TYPE: PRT
<213> ORGANISM: Artificial Sequence
<220> FEATURE:
<221> NAME/KEY: PEPTIDE
<222> LOCATION: (1)...(574)
<223> OTHER INFORMATION: GFP-SNAP25(134-206)-BFP substrate

<400> SEQUENCE: 175

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
```

```
                290                 295                 300
Asn Lys Thr Arg Ile Asp Glu Ala Asn Gln Arg Ala Thr Lys Met Leu
305                 310                 315                 320

Gly Ser Gly Gly Gly Gly Thr Ala Ser Lys Gly Glu Glu Leu Phe
                325                 330                 335

Thr Gly Val Val Pro Ile Leu Val Glu Leu Asp Gly Asp Val Asn Gly
                340                 345                 350

His Lys Phe Ser Val Ser Gly Glu Gly Glu Gly Asp Ala Thr Tyr Gly
                355                 360                 365

Lys Leu Thr Leu Lys Phe Ile Cys Thr Thr Gly Lys Leu Pro Val Pro
370                 375                 380

Trp Pro Thr Leu Val Thr Thr Leu Ser His Gly Val Gln Cys Phe Ser
385                 390                 395                 400

Arg Tyr Pro Asp His Met Lys Arg His Asp Phe Phe Lys Ser Ala Met
                405                 410                 415

Pro Glu Gly Tyr Val Gln Glu Arg Thr Ile Phe Phe Lys Asp Asp Gly
                420                 425                 430

Asn Tyr Lys Thr Arg Ala Glu Val Lys Phe Glu Gly Asp Thr Leu Val
                435                 440                 445

Asn Arg Ile Glu Leu Lys Gly Ile Asp Phe Lys Glu Asp Gly Asn Ile
450                 455                 460

Leu Gly His Lys Leu Glu Tyr Asn Tyr Asn Ser His Asn Val Tyr Ile
465                 470                 475                 480

Met Ala Asp Lys Gln Lys Asn Gly Ile Lys Ala Asn Phe Lys Ile Arg
                485                 490                 495

His Asn Ile Glu Asp Gly Ser Val Gln Leu Ala Asp His Tyr Gln Gln
                500                 505                 510

Asn Thr Pro Ile Gly Asp Gly Pro Val Leu Leu Pro Asp Asn His Tyr
                515                 520                 525

Leu Ser Thr Gln Ser Ala Leu Ser Lys Asp Pro Asn Glu Lys Arg Asp
530                 535                 540

His Met Val Leu Leu Glu Phe Val Thr Ala Ala Gly Ile Thr His Gly
545                 550                 555                 560

Met Asp Glu Leu Tyr Lys Gly Thr His His His His His
                565                 570

<210> SEQ ID NO 176
<211> LENGTH: 334
<212> TYPE: PRT
<213> ORGANISM: Artificial Sequence
<220> FEATURE:
<221> NAME/KEY: PEPTIDE
<222> LOCATION: (1)...(334)
<223> OTHER INFORMATION: GFP-SNAP25(134-206)(Cys) substrate

<400> SEQUENCE: 176

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Cys Tyr Gly Val Gln Cys Phe Ser Arg Tyr Pro Asp His Met Lys
65                  70                  75                  80
```

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Ile Arg Arg Val Thr Asn
                245                 250                 255

Asp Ala Arg Glu Asn Glu Met Asp Glu Asn Leu Glu Gln Val Ser Gly
            260                 265                 270

Ile Ile Gly Asn Leu Arg His Met Ala Leu Asp Met Gly Asn Glu Ile
        275                 280                 285

Asp Thr Gln Asn Arg Gln Ile Asp Arg Ile Met Glu Lys Ala Asp Ser
    290                 295                 300

Asn Lys Thr Arg Ile Asp Glu Ala Asn Gln Arg Ala Thr Lys Met Leu
305                 310                 315                 320

Gly Ser Gly Gly Gly Gly His His His His His Cys
                325                 330

<210> SEQ ID NO 177
<211> LENGTH: 545
<212> TYPE: PRT
<213> ORGANISM: Artificial Sequence
<220> FEATURE:
<221> NAME/KEY: PEPTIDE
<222> LOCATION: (1)...(545)
<223> OTHER INFORMATION: GFP-VAMP1(49-92)-BFP substrate

<400> SEQUENCE: 177

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Arg Val Asn Val Asp Lys
                245                 250                 255

Val Leu Glu Arg Asp Gln Lys Leu Ser Glu Leu Asp Asp Arg Ala Asp
            260                 265                 270

Ala Leu Gln Ala Gly Ala Ser Gln Phe Glu Ser Ser Ala Ala Lys Leu
        275                 280                 285

Lys Arg Lys Tyr Trp Trp Gly Gly Gly Thr Ala Ser Lys Gly Glu
    290                 295                 300

Glu Leu Phe Thr Gly Val Val Pro Ile Leu Val Glu Leu Asp Gly Asp
305                 310                 315                 320

Val Asn Gly His Lys Phe Ser Val Ser Gly Glu Gly Glu Gly Asp Ala
                325                 330                 335

Thr Tyr Gly Lys Leu Thr Leu Lys Phe Ile Cys Thr Thr Gly Lys Leu
            340                 345                 350

Pro Val Pro Trp Pro Thr Leu Val Thr Thr Leu Ser His Gly Val Gln
        355                 360                 365

Cys Phe Ser Arg Tyr Pro Asp His Met Lys Arg His Asp Phe Phe Lys
    370                 375                 380

Ser Ala Met Pro Glu Gly Tyr Val Gln Glu Arg Thr Ile Phe Phe Lys
385                 390                 395                 400

Asp Asp Gly Asn Tyr Lys Thr Arg Ala Glu Val Lys Phe Glu Gly Asp
                405                 410                 415

Thr Leu Val Asn Arg Ile Glu Leu Lys Gly Ile Asp Phe Lys Glu Asp
            420                 425                 430

Gly Asn Ile Leu Gly His Lys Leu Glu Tyr Asn Tyr Asn Ser His Asn
        435                 440                 445

Val Tyr Ile Met Ala Asp Lys Gln Lys Asn Gly Ile Lys Ala Asn Phe
    450                 455                 460

Lys Ile Arg His Asn Ile Glu Asp Gly Ser Val Gln Leu Ala Asp His
465                 470                 475                 480

Tyr Gln Gln Asn Thr Pro Ile Gly Asp Gly Pro Val Leu Leu Pro Asp
                485                 490                 495

Asn His Tyr Leu Ser Thr Gln Ser Ala Leu Ser Lys Asp Pro Asn Glu
            500                 505                 510

Lys Arg Asp His Met Val Leu Leu Glu Phe Val Thr Ala Ala Gly Ile
```

```
                515                 520                 525
Thr His Gly Met Asp Glu Leu Tyr Lys Gly Thr His His His His
    530                 535                 540

His
545
```

<210> SEQ ID NO 178
<211> LENGTH: 563
<212> TYPE: PRT
<213> ORGANISM: Artificial Sequence
<220> FEATURE:
<221> NAME/KEY: PEPTIDE
<222> LOCATION: (1)...(547)
<223> OTHER INFORMATION: GFP-VAMP2(33-94)-BFP substrate

<400> SEQUENCE: 178

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Gln Gln Thr Gln Ala Gln
                245                 250                 255

Val Asp Glu Val Val Asp Ile Met Arg Val Asn Val Asp Lys Val Leu
            260                 265                 270

Glu Arg Asp Gln Lys Leu Ser Glu Leu Asp Asp Arg Ala Asp Ala Leu
        275                 280                 285

Gln Ala Gly Ala Ser Gln Phe Glu Thr Ser Ala Ala Lys Leu Lys Arg
    290                 295                 300

Lys Tyr Trp Trp Lys Asn Leu Lys Gly Gly Gly Thr Ala Ser Lys
305                 310                 315                 320
```

Gly Glu Glu Leu Phe Thr Gly Val Val Pro Ile Leu Val Glu Leu Asp
            325                 330                 335

Gly Asp Val Asn Gly His Lys Phe Ser Val Ser Gly Glu Gly Glu Gly
            340                 345                 350

Asp Ala Thr Tyr Gly Lys Leu Thr Leu Lys Phe Ile Cys Thr Thr Gly
            355                 360                 365

Lys Leu Pro Val Pro Trp Pro Thr Leu Val Thr Thr Leu Ser His Gly
            370                 375                 380

Val Gln Cys Phe Ser Arg Tyr Pro Asp His Met Lys Arg His Asp Phe
385                 390                 395                 400

Phe Lys Ser Ala Met Pro Glu Gly Tyr Val Gln Glu Arg Thr Ile Phe
            405                 410                 415

Phe Lys Asp Asp Gly Asn Tyr Lys Thr Arg Ala Glu Val Lys Phe Glu
            420                 425                 430

Gly Asp Thr Leu Val Asn Arg Ile Glu Leu Lys Gly Ile Asp Phe Lys
            435                 440                 445

Glu Asp Gly Asn Ile Leu Gly His Lys Leu Glu Tyr Asn Tyr Asn Ser
450                 455                 460

His Asn Val Tyr Ile Met Ala Asp Lys Gln Lys Asn Gly Ile Lys Ala
465                 470                 475                 480

Asn Phe Lys Ile Arg His Asn Ile Glu Asp Gly Ser Val Gln Leu Ala
            485                 490                 495

Asp His Tyr Gln Gln Asn Thr Pro Ile Gly Asp Gly Pro Val Leu Leu
            500                 505                 510

Pro Asp Asn His Tyr Leu Ser Thr Gln Ser Ala Leu Ser Lys Asp Pro
            515                 520                 525

Asn Glu Lys Arg Asp His Met Val Leu Leu Glu Phe Val Thr Ala Ala
            530                 535                 540

Gly Ile Thr His Gly Met Asp Glu Leu Tyr Lys Gly Thr His His His
545                 550                 555                 560

His His His

<210> SEQ ID NO 179
<211> LENGTH: 546
<212> TYPE: PRT
<213> ORGANISM: Artificial Sequence
<220> FEATURE:
<221> NAME/KEY: PEPTIDE
<222> LOCATION: (1)...(546)
<223> OTHER INFORMATION: GFP-VAMP3(34-77)-BFP substrate

<400> SEQUENCE: 179

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu

-continued

```
                100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Val Asp Lys Val Leu Glu
                245                 250                 255

Arg Asp Gln Lys Leu Ser Glu Leu Asp Asp Arg Ala Asp Ala Leu Gln
                260                 265                 270

Ala Gly Ala Ser Gln Phe Glu Thr Ser Ala Ala Lys Leu Lys Arg Lys
            275                 280                 285

Tyr Trp Trp Lys Asn Cys Lys Gly Gly Gly Thr Ala Ser Lys Gly
            290                 295                 300

Glu Glu Leu Phe Thr Gly Val Val Pro Ile Leu Val Glu Leu Asp Gly
305                 310                 315                 320

Asp Val Asn Gly His Lys Phe Ser Val Ser Gly Glu Gly Glu Gly Asp
                325                 330                 335

Ala Thr Tyr Gly Lys Leu Thr Leu Lys Phe Ile Cys Thr Thr Gly Lys
                340                 345                 350

Leu Pro Val Pro Trp Pro Thr Leu Val Thr Thr Leu Ser His Gly Val
            355                 360                 365

Gln Cys Phe Ser Arg Tyr Pro Asp His Met Lys Arg His Asp Phe Phe
        370                 375                 380

Lys Ser Ala Met Pro Glu Gly Tyr Val Gln Glu Arg Thr Ile Phe Phe
385                 390                 395                 400

Lys Asp Asp Gly Asn Tyr Lys Thr Arg Ala Glu Val Lys Phe Glu Gly
                405                 410                 415

Asp Thr Leu Val Asn Arg Ile Glu Leu Lys Gly Ile Asp Phe Lys Glu
            420                 425                 430

Asp Gly Asn Ile Leu Gly His Lys Leu Glu Tyr Asn Tyr Asn Ser His
            435                 440                 445

Asn Val Tyr Ile Met Ala Asp Lys Gln Lys Asn Gly Ile Lys Ala Asn
        450                 455                 460

Phe Lys Ile Arg His Asn Ile Glu Asp Gly Ser Val Gln Leu Ala Asp
465                 470                 475                 480

His Tyr Gln Gln Asn Thr Pro Ile Gly Asp Gly Pro Val Leu Leu Pro
                485                 490                 495

Asp Asn His Tyr Leu Ser Thr Gln Ser Ala Leu Ser Lys Asp Pro Asn
            500                 505                 510

Glu Lys Arg Asp His Met Val Leu Leu Glu Phe Val Thr Ala Ala Gly
        515                 520                 525
```

```
Ile Thr His Gly Met Asp Glu Leu Tyr Lys Gly Thr His His His
    530                 535                 540

His His
545

<210> SEQ ID NO 180
<211> LENGTH: 789
<212> TYPE: PRT
<213> ORGANISM: Artificial Sequence
<220> FEATURE:
<221> NAME/KEY: PEPTIDE
<222> LOCATION: (1)...(789)
<223> OTHER INFORMATION: GFP-Syntaxin1(1-288)-BFP substrate

<400> SEQUENCE: 180

Met Ala Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Gly
225                 230                 235                 240

Gly Ala Gly Ser Gly Ala Gly Gly Gly Met Lys Asp Arg Thr Gln
                245                 250                 255

Glu Leu Arg Thr Ala Lys Asp Ser Asp Asp Asp Asp Val Ala Val
            260                 265                 270

Thr Val Asp Arg Asp Arg Phe Met Asp Glu Phe Phe Glu Gln Val Glu
        275                 280                 285

Glu Ile Arg Gly Phe Ile Asp Lys Ile Ala Glu Asn Val Glu Glu Val
    290                 295                 300

Lys Arg Lys His Ser Ala Ile Leu Ala Ser Pro Asn Pro Asp Glu Lys
305                 310                 315                 320
```

```
Thr Lys Glu Glu Leu Glu Leu Met Ser Asp Ile Lys Lys Thr Ala
            325                 330                 335

Asn Lys Val Arg Ser Lys Leu Lys Ser Ile Glu Gln Ser Ile Glu Gln
        340                 345                 350

Glu Glu Gly Leu Asn Arg Ser Ser Ala Asp Leu Arg Ile Arg Lys Thr
            355                 360                 365

Gln His Ser Thr Leu Ser Arg Lys Phe Val Glu Val Met Ser Glu Tyr
    370                 375                 380

Asn Ala Thr Gln Ser Asp Tyr Arg Glu Arg Cys Lys Gly Arg Ile Gln
385                 390                 395                 400

Arg Gln Leu Glu Ile Thr Gly Arg Thr Thr Ser Glu Glu Leu Glu
                405                 410                 415

Asp Met Leu Glu Ser Gly Asn Pro Ala Ile Phe Ala Ser Gly Ile Ile
        420                 425                 430

Met Asp Ser Ser Ile Ser Lys Gln Ala Leu Ser Glu Ile Glu Thr Arg
        435                 440                 445

His Ser Glu Ile Ile Lys Leu Glu Asn Ser Ile Arg Glu Leu His Asp
    450                 455                 460

Met Phe Met Asp Met Ala Met Leu Val Glu Ser Gln Gly Glu Met Ile
465                 470                 475                 480

Asp Arg Ile Glu Tyr Asn Val Glu His Ala Val Asp Tyr Val Glu Arg
                485                 490                 495

Ala Val Ser Asp Thr Lys Lys Ala Val Lys Tyr Gln Ser Lys Ala Arg
            500                 505                 510

Arg Lys Lys Ile Met Ile Ile Ile Cys Cys Val Ile Leu Gly Ile Val
        515                 520                 525

Ile Ala Ser Thr Val Gly Gly Ile Phe Ala Gly Gly Gly Thr Ala
    530                 535                 540

Ser Lys Gly Glu Glu Leu Phe Thr Gly Val Val Pro Ile Leu Val Glu
545                 550                 555                 560

Leu Asp Gly Asp Val Asn Gly His Lys Phe Ser Val Ser Gly Glu Gly
                565                 570                 575

Glu Gly Asp Ala Thr Tyr Gly Lys Leu Thr Leu Lys Phe Ile Cys Thr
            580                 585                 590

Thr Gly Lys Leu Pro Val Pro Trp Pro Thr Leu Val Thr Thr Leu Ser
        595                 600                 605

His Gly Val Gln Cys Phe Ser Arg Tyr Pro Asp His Met Lys Arg His
    610                 615                 620

Asp Phe Phe Lys Ser Ala Met Pro Glu Gly Tyr Val Gln Glu Arg Thr
625                 630                 635                 640

Ile Phe Phe Lys Asp Asp Gly Asn Tyr Lys Thr Arg Ala Glu Val Lys
                645                 650                 655

Phe Glu Gly Asp Thr Leu Val Asn Arg Ile Glu Leu Lys Gly Ile Asp
            660                 665                 670

Phe Lys Glu Asp Gly Asn Ile Leu Gly His Lys Leu Glu Tyr Asn Tyr
        675                 680                 685

Asn Ser His Asn Val Tyr Ile Met Ala Asp Lys Gln Lys Asn Gly Ile
    690                 695                 700

Lys Ala Asn Phe Lys Ile Arg His Asn Ile Glu Asp Gly Ser Val Gln
705                 710                 715                 720

Leu Ala Asp His Tyr Gln Gln Asn Thr Pro Ile Gly Asp Gly Pro Val
                725                 730                 735

Leu Leu Pro Asp Asn His Tyr Leu Ser Thr Gln Ser Ala Leu Ser Lys
```

740                 745                 750
Asp Pro Asn Glu Lys Arg Asp His Met Val Leu Leu Glu Phe Val Thr
            755                 760                 765

Ala Ala Gly Ile Thr His Gly Met Asp Glu Leu Tyr Lys Gly Thr His
    770                 775                 780

His His His His His
785

<210> SEQ ID NO 181
<211> LENGTH: 14
<212> TYPE: PRT
<213> ORGANISM: Artificial Sequence
<220> FEATURE:
<221> NAME/KEY: DOMAIN
<222> LOCATION: (1)...(14)
<223> OTHER INFORMATION: EF hand motif

<400> SEQUENCE: 181

Gly Asp Lys Asn Ala Asp Gly Trp Ile Glu Phe Glu Glu Leu
1               5                   10

<210> SEQ ID NO 182
<211> LENGTH: 14
<212> TYPE: PRT
<213> ORGANISM: Artificial Sequence
<220> FEATURE:
<221> NAME/KEY: DOMAIN
<222> LOCATION: (1)...(14)
<223> OTHER INFORMATION: EF hand motif

<400> SEQUENCE: 182

Gly Asp Lys Asn Ala Asp Gly Phe Ile Cys Phe Glu Glu Leu
1               5                   10

<210> SEQ ID NO 183
<211> LENGTH: 12
<212> TYPE: PRT
<213> ORGANISM: Artificial Sequence
<220> FEATURE:
<221> NAME/KEY: DOMAIN
<222> LOCATION: (1)...(12)
<223> OTHER INFORMATION: EF hand motif

<400> SEQUENCE: 183

Asp Lys Asn Ala Asp Gly Cys Ile Glu Phe Glu Glu
1               5                   10

<210> SEQ ID NO 184
<211> LENGTH: 17
<212> TYPE: PRT
<213> ORGANISM: Artificial Sequence
<220> FEATURE:
<221> NAME/KEY: DOMAIN
<222> LOCATION: (1)...(17)
<223> OTHER INFORMATION: EF hand motif

<400> SEQUENCE: 184

Tyr Ile Asp Thr Asn Asn Asp Gly Trp Tyr Glu Gly Asp Glu Leu Leu
1               5                   10                  15

Ala

<210> SEQ ID NO 185
<211> LENGTH: 32
<212> TYPE: PRT
<213> ORGANISM: Artificial Sequence
<220> FEATURE:

```
<221> NAME/KEY: DOMAIN
<222> LOCATION: (1)...(32)
<223> OTHER INFORMATION: EF hand motif

<400> SEQUENCE: 185
```

Thr Glu Arg Arg Gln Gln Leu Asp Lys Asp Gly Asp Gly Thr Ile Asp
1               5                   10                  15

Glu Arg Glu Ile Lys Ile Trp Phe Gln Asn Lys Arg Ala Lys Ile Lys
            20                  25                  30

```
<210> SEQ ID NO 186
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: CALB9 EF1 hand motif

<400> SEQUENCE: 186
```

Glu Leu Lys Gly Ile Phe Glu Lys Tyr Ala Ala Lys Glu Gly Asp Pro
1               5                   10                  15

Asn Gln Leu Ser Lys Glu Glu Leu Lys Leu Leu Leu Gln Thr Glu
            20                  25                  30

```
<210> SEQ ID NO 187
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALB9 EF2 hand motif

<400> SEQUENCE: 187
```

Thr Leu Asp Glu Leu Phe Glu Glu Leu Asp Lys Asn Gly Asp Gly Glu
1               5                   10                  15

Val Ser Phe Glu Glu Phe Gln Val Leu Val Lys Lys Ile Ser
            20                  25                  30

```
<210> SEQ ID NO 188
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: CALCYC EF1 hand motif

<400> SEQUENCE: 188
```

Leu Leu Ile Gly Ile Phe His Lys Tyr Ser Gly Lys Glu Gly Asp Lys
1               5                   10                  15

His Thr Leu Ser Lys Lys Glu Leu Lys Glu Leu Ile Gln Lys Glu
            20                  25                  30

```
<210> SEQ ID NO 189
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALCYC EF2 hand motif

<400> SEQUENCE: 189
```

Glu Ile Val Lys Leu Met Asp Asp Leu Asp Arg Asn Lys Asp Gln Glu

```
                1               5                   10                  15
Val Asn Phe Gln Glu Tyr Ile Thr Phe Leu Gly Ala Leu Ala
                20                  25                  30

<210> SEQ ID NO 190
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: MRP-8 EF1 hand motif

<400> SEQUENCE: 190

Ser Ile Ile Asp Val Tyr His Lys Tyr Ser Leu Ile Lys Gly Asn Phe
1               5                   10                  15
His Ala Val Tyr Arg Asp Asp Leu Lys Lys Leu Leu Glu Thr Glu
                20                  25                  30

<210> SEQ ID NO 191
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: MRP-8 EF2 hand motif

<400> SEQUENCE: 191

Gly Ala Asp Val Trp Phe Lys Glu Leu Asp Ile Asn Thr Asp Gly Ala
1               5                   10                  15
Val Asn Phe Gln Glu Phe Leu Ile Leu Val Ile Lys Met Gly
                20                  25                  30

<210> SEQ ID NO 192
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: MRP-14 EF1 hand motif

<400> SEQUENCE: 192

Thr Ile Ile Asn Thr Phe His Gln Tyr Ser Val Lys Leu Gly His Pro
1               5                   10                  15
Asp Thr Leu Asn Gln Gly Glu Phe Lys Glu Leu Val Arg Lys Asp
                20                  25                  30

<210> SEQ ID NO 193
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: MRP-14 EF2 hand motif

<400> SEQUENCE: 193

Val Ile Glu His Ile Met Glu Asp Leu Asp Thr Asn Ala Asp Lys Gln
1               5                   10                  15
Leu Ser Phe Glu Glu Phe Ile Met Leu Met Ala Arg Leu Thr
                20                  25                  30

<210> SEQ ID NO 194
```

```
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: CALGRAN-C EF1 hand motif

<400> SEQUENCE: 194

Gly Ile Ile Asn Ile Phe His Gln Tyr Ser Val Arg Leu Gly His Tyr
1               5                   10                  15

Asp Thr Leu Ile Lys Arg Glu Leu Lys Gln Leu Ile Thr Lys Glu
            20                  25                  30

<210> SEQ ID NO 195
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALGRAN-C EF2 hand motif

<400> SEQUENCE: 195

Thr Ile Asp Lys Ile Phe Gln Asn Leu Asp Ala Asn Gln Asp Glu Gln
1               5                   10                  15

Val Ser Phe Lys Glu Phe Val Val Leu Val Thr Asp Val Leu
            20                  25                  30

<210> SEQ ID NO 196
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: p11 EF1 hand motif

<400> SEQUENCE: 196

Thr Met Met Phe Thr Phe His Lys Phe Ala Gly Asp Lys Gly Tyr Leu
1               5                   10                  15

Thr Lys Glu Asp Leu Arg Val Leu Met Glu Lys Glu
            20                  25

<210> SEQ ID NO 197
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: p11 EF2 hand motif

<400> SEQUENCE: 197

Ala Val Asp Lys Ile Met Lys Asp Leu Asp Gln Cys Arg Asp Gly Lys
1               5                   10                  15

Val Gly Phe Gln Ser Phe Phe Ser Leu Ile Ala Gly Leu Thr
            20                  25                  30

<210> SEQ ID NO 198
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100A EF1 hand motif
```

```
<400> SEQUENCE: 198

Thr Leu Ile Asn Val Phe His Ala His Ser Gly Lys Glu Gly Asp Lys
1               5                   10                  15

Tyr Lys Leu Ser Lys Lys Glu Leu Lys Glu Leu Leu Gln Thr Glu
            20                  25                  30

<210> SEQ ID NO 199
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100A EF2 hand motif

<400> SEQUENCE: 199

Ala Val Asp Lys Val Met Lys Glu Leu Asp Glu Asn Gly Asp Gly Glu
1               5                   10                  15

Val Asp Phe Gln Glu Tyr Val Val Leu Val Ala Ala Leu Thr
            20                  25                  30

<210> SEQ ID NO 200
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100B EF1 hand motif

<400> SEQUENCE: 200

Ala Leu Ile Asp Val Phe His Gln Tyr Ser Gly Arg Glu Gly Asp Lys
1               5                   10                  15

His Lys Leu Lys Lys Ser Glu Leu Lys Glu Leu Ile Asn Asn Glu
            20                  25                  30

<210> SEQ ID NO 201
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100B EF2 hand motif

<400> SEQUENCE: 201

Val Val Asp Lys Val Met Glu Thr Leu Asp Ser Asp Gly Asp Gly Glu
1               5                   10                  15

Cys Asp Phe Gln Glu Phe Met Ala Phe Val Ala Met Ile Thr
            20                  25                  30

<210> SEQ ID NO 202
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100C EF1 hand motif

<400> SEQUENCE: 202

Ser Leu Ile Ala Ile Phe Gln Lys His Ala Gly Arg Asp Gly Asn Asn
1               5                   10                  15

Thr Lys Ile Ser Lys Thr Glu Phe Leu Ile Phe Met Asn Thr Glu
            20                  25                  30
```

```
            20                  25                  30
```

<210> SEQ ID NO 203
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100C EF2 hand motif

<400> SEQUENCE: 203

```
Val Leu Asp Arg Met Met Lys Lys Leu Asp Leu Asp Ser Asp Gly Gln
1               5                   10                  15

Leu Asp Phe Gln Glu Phe Leu Asn Leu Ile Gly Gly Leu Ala
            20                  25                  30
```

<210> SEQ ID NO 204
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100D EF1 hand motif

<400> SEQUENCE: 204

```
Thr Met Val Thr Thr Phe His Lys Tyr Ser Gly Arg Glu Gly Ser Lys
1               5                   10                  15

Leu Thr Leu Ser Arg Lys Glu Leu Lys Glu Leu Ile Lys Lys Glu
            20                  25                  30
```

<210> SEQ ID NO 205
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100D EF2 hand motif

<400> SEQUENCE: 205

```
Ser Ile Asp Asp Leu Met Lys Ser Leu Asp Lys Asn Ser Asp Gln Glu
1               5                   10                  15

Ile Asp Phe Lys Glu Tyr Ser Val Phe Leu Thr Met Leu Cys
            20                  25                  30
```

<210> SEQ ID NO 206
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100E EF1 hand motif

<400> SEQUENCE: 206

```
Ala Ile Val Cys Thr Phe Gln Glu Tyr Ala Gly Arg Cys Gly Asp Lys
1               5                   10                  15

Tyr Lys Leu Cys Gln Ala Glu Leu Lys Glu Leu Leu Gln Lys Glu
            20                  25                  30
```

<210> SEQ ID NO 207
<211> LENGTH: 30
<212> TYPE: PRT
<213> ORGANISM: Artificial Sequence

```
<220> FEATURE:
<221> NAME/KEY: DOMAIN
<222> LOCATION: (1)...(30)
<223> OTHER INFORMATION: S100E EF2 hand motif

<400> SEQUENCE: 207

Asp Tyr Asn Lys Phe Met Ser Val Leu Asp Thr Asn Lys Asp Cys Glu
1               5                   10                  15

Val Asp Phe Val Glu Tyr Val Arg Ser Leu Ala Cys Leu Cys
            20                  25                  30

<210> SEQ ID NO 208
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100L EF1 hand motif

<400> SEQUENCE: 208

Val Met Val Ala Thr Phe His Lys Tyr Ser Gly Gln Glu Gly Asp Lys
1               5                   10                  15

Phe Lys Leu Ser Lys Gly Glu Met Lys Glu Leu Leu His Lys Glu
            20                  25                  30

<210> SEQ ID NO 209
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100L EF2 hand motif

<400> SEQUENCE: 209

Gly Leu Lys Lys Leu Met Gly Asp Leu Asp Glu Asn Ser Asp Gln Gln
1               5                   10                  15

Val Asp Phe Gln Glu Tyr Ala Val Phe Leu Ala Leu Ile Thr
            20                  25                  30

<210> SEQ ID NO 210
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: S100P EF1 hand motif

<400> SEQUENCE: 210

Met Ile Ile Asp Val Phe Ser Arg Tyr Ser Gly Ser Glu Gly Ser Thr
1               5                   10                  15

Gln Thr Leu Thr Lys Gly Glu Leu Lys Val Leu Met Glu Lys Glu
            20                  25                  30

<210> SEQ ID NO 211
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: S100P EF2 hand motif

<400> SEQUENCE: 211
```

-continued

```
Ala Val Asp Lys Leu Leu Lys Asp Leu Asp Ala Asn Gly Asp Ala Gln
 1               5                  10                  15

Val Asp Phe Ser Glu Phe Ile Val Phe Val Ala Ala Ile Thr
            20                  25                  30
```

<210> SEQ ID NO 212
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: CAPL EF1 hand motif

<400> SEQUENCE: 212

```
Val Met Val Ser Thr Phe His Lys Tyr Ser Gly Lys Glu Gly Asp Lys
 1               5                  10                  15

Phe Lys Leu Asn Lys Ser Glu Leu Lys Glu Leu Leu Thr Arg Glu
            20                  25                  30
```

<210> SEQ ID NO 213
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CAPL EF2 hand motif

<400> SEQUENCE: 213

```
Ala Phe Gln Lys Leu Met Ser Asn Leu Asp Ser Asn Arg Asp Asn Glu
 1               5                  10                  15

Val Asp Phe Gln Glu Tyr Cys Val Phe Leu Ser Cys Ile Ala
            20                  25                  30
```

<210> SEQ ID NO 214
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALMOD-I EF1 hand motif

<400> SEQUENCE: 214

```
Glu Phe Lys Glu Ala Phe Ser Leu Phe Asp Lys Asp Gly Asp Gly Thr
 1               5                  10                  15

Ile Thr Thr Lys Glu Leu Gly Thr Val Met Arg Ser Leu
            20                  25
```

<210> SEQ ID NO 215
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALMOD-I EF2 hand motif

<400> SEQUENCE: 215

```
Glu Leu Gln Asp Met Ile Asn Glu Val Asp Ala Asp Gly Asn Gly Thr
 1               5                  10                  15

Ile Asp Phe Pro Glu Phe Leu Thr Met Met Ala Arg Lys
            20                  25
```

-continued

<210> SEQ ID NO 216
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALMOD-II EF1 hand motif

<400> SEQUENCE: 216

Glu Ile Arg Glu Ala Phe Arg Val Phe Asp Lys Asp Gly Asn Gly Tyr
1               5                   10                  15

Ile Ser Ala Ala Glu Leu Arg His Val Met Thr Asn Leu
            20                  25

<210> SEQ ID NO 217
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALMOD-II EF2 hand motif

<400> SEQUENCE: 217

Glu Val Asp Glu Met Ile Arg Glu Ala Asp Ile Asp Gly Asp Gly Gln
1               5                   10                  15

Val Asn Tyr Glu Glu Phe Val Gln Met Met Thr Ala Lys
            20                  25

<210> SEQ ID NO 218
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALTRCT-I EF1 hand motif

<400> SEQUENCE: 218

Glu Ile Arg Glu Ala Phe Asp Leu Phe Asp Thr Asp Gly Ser Gly Thr
1               5                   10                  15

Ile Asp Ala Lys Glu Leu Lys Val Ala Met Arg Ala Leu
            20                  25

<210> SEQ ID NO 219
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALTRCT-I EF2 hand motif

<400> SEQUENCE: 219

Glu Ile Lys Lys Met Ile Ser Glu Ile Asp Lys Asp Gly Ser Gly Thr
1               5                   10                  15

Ile Asp Phe Glu Glu Phe Leu Thr Met Met Thr Ala Lys
            20                  25

<210> SEQ ID NO 220
<211> LENGTH: 29
<212> TYPE: PRT
<213> ORGANISM: Artificial Sequence
<220> FEATURE:
<221> NAME/KEY: DOMAIN
<222> LOCATION: (1)...(29)

-continued

<223> OTHER INFORMATION: CALTRCT-II EF1 hand motif

<400> SEQUENCE: 220

Glu Ile Leu Lys Ala Phe Arg Leu Phe Asp Asp Asp Asn Ser Gly Thr
1               5                   10                  15

Ile Thr Ile Lys Asp Leu Arg Arg Val Ala Lys Glu Leu
            20                  25

<210> SEQ ID NO 221
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALTRCT-II EF2 hand motif

<400> SEQUENCE: 221

Glu Leu Gln Glu Met Ile Ala Glu Ala Asp Arg Asn Asp Asp Asn Glu
1               5                   10                  15

Ile Asp Glu Asp Glu Phe Ile Arg Ile Met Lys Lys Thr
            20                  25

<210> SEQ ID NO 222
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: TROPC-I EF1 hand motif

<400> SEQUENCE: 222

Glu Phe Lys Ala Ala Phe Asp Met Phe Asp Ala Asp Gly Gly Gly Asp
1               5                   10                  15

Ile Ser Thr Lys Glu Leu Gly Thr Val Met Arg Met Leu
            20                  25

<210> SEQ ID NO 223
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: TROPC-I EF2 hand motif

<400> SEQUENCE: 223

Glu Leu Asp Ala Ile Ile Glu Glu Val Asp Glu Asp Gly Ser Gly Thr
1               5                   10                  15

Ile Asp Phe Glu Glu Phe Leu Val Met Met Val Arg Gln
            20                  25

<210> SEQ ID NO 224
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: TROPC-II EF1 hand motif

<400> SEQUENCE: 224

Glu Leu Ala Asn Cys Phe Arg Ile Phe Asp Lys Asn Ala Asp Gly Phe
1               5                   10                  15

```
Ile Asp Ile Glu Glu Leu Gly Glu Ile Leu Arg Ala Thr
            20                  25
```

<210> SEQ ID NO 225
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: TROPC-II EF2 hand motif

<400> SEQUENCE: 225

```
Asp Ile Glu Asp Leu Met Lys Asp Ser Asp Lys Asn Asn Asp Gly Arg
 1               5                  10                  15
Ile Asp Phe Asp Glu Phe Leu Lys Met Met Glu Gly Val
            20                  25
```

<210> SEQ ID NO 226
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALL-I EF1 hand motif

<400> SEQUENCE: 226

```
Glu Phe Lys Glu Ala Phe Ser Leu Phe Asp Lys Asp Gly Asp Gly Cys
 1               5                  10                  15
Ile Thr Thr Arg Glu Leu Gly Thr Val Met Arg Ser Leu
            20                  25
```

<210> SEQ ID NO 227
<211> LENGTH: 29
<212> TYPE: PRT
<213> ORGANISM: Artificial Sequence
<220> FEATURE:
<221> NAME/KEY: PEPTIDE
<222> LOCATION: (1)...(29)
<223> OTHER INFORMATION: CALL-I EF2 hand motif

<400> SEQUENCE: 227

```
Glu Leu Arg Asp Met Met Ser Glu Ile Asp Arg Asp Gly Asn Gly Thr
 1               5                  10                  15
Val Asp Phe Pro Glu Phe Leu Gly Met Met Ala Arg Lys
            20                  25
```

<210> SEQ ID NO 228
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALL-II EF1 hand motif

<400> SEQUENCE: 228

```
Glu Ile Arg Glu Ala Phe Arg Val Phe Asp Lys Asp Gly Asn Gly Phe
 1               5                  10                  15
Val Ser Ala Ala Glu Leu Arg His Val Met Thr Arg Leu
            20                  25
```

<210> SEQ ID NO 229
<211> LENGTH: 29
<212> TYPE: PRT

-continued

```
<213> ORGANISM: Artificial Sequence
<220> FEATURE:
<221> NAME/KEY: DOMAIN
<222> LOCATION: (1)...(29)
<223> OTHER INFORMATION: CALL-II EF2 hand motif

<400> SEQUENCE: 229

Glu Val Asp Glu Met Ile Arg Ala Ala Asp Thr Asp Gly Asp Gly Gln
1               5                   10                  15

Val Asn Tyr Glu Glu Phe Val Arg Val Leu Val Ser Lys
            20                  25

<210> SEQ ID NO 230
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CDPK-I EF1 hand motif

<400> SEQUENCE: 230

Gly Leu Lys Glu Leu Phe Lys Met Ile Asp Thr Asp Asn Ser Gly Thr
1               5                   10                  15

Ile Thr Phe Asp Glu Leu Lys Asp Gly Leu Lys Arg Gly
            20                  25

<210> SEQ ID NO 231
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CDPK-I EF2 hand motif

<400> SEQUENCE: 231

Glu Ile Lys Asp Leu Met Asp Ala Ala Asp Ile Asp Lys Ser Gly Thr
1               5                   10                  15

Ile Asp Tyr Gly Glu Phe Ile Ala Ala Thr Val His Leu
            20                  25

<210> SEQ ID NO 232
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CDPK-II EF1 hand motif

<400> SEQUENCE: 232

Asn Leu Val Ser Ala Phe Ser Tyr Phe Asp Lys Asp Gly Ser Gly Tyr
1               5                   10                  15

Ile Thr Leu Asp Glu Ile Gln Gln Ala Cys Lys Asp Phe
            20                  25

<210> SEQ ID NO 233
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CDPK-II EF2 hand motif

<400> SEQUENCE: 233
```

```
His Ile Asp Asp Met Ile Lys Glu Ile Asp Gln Asp Asn Asp Gly Gln
1               5                   10                  15

Ile Asp Tyr Gly Glu Phe Ala Ala Met Met Arg Lys Gly
            20                  25
```

<210> SEQ ID NO 234
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SQUID-I EF1 hand motif

<400> SEQUENCE: 234

```
Glu Ile Lys Asp Ala Phe Asp Met Phe Asp Ile Asp Gly Asp Gly Gln
1               5                   10                  15

Ile Thr Ser Lys Glu Leu Arg Ser Val Met Lys Ser Leu
            20                  25
```

<210> SEQ ID NO 235
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SQUID-I EF2 hand motif

<400> SEQUENCE: 235

```
Glu Leu Glu Glu Met Ile Arg Glu Val Asp Thr Asp Gly Asn Gly Thr
1               5                   10                  15

Ile Glu Tyr Ala Glu Phe Val Glu Met Met Ala Lys Gln
            20                  25
```

<210> SEQ ID NO 236
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SQUID-II EF1 hand motif

<400> SEQUENCE: 236

```
Glu Met Arg Glu Ala Phe Arg Val Phe Asp Lys Asp Gly Asn Gly Leu
1               5                   10                  15

Ile Thr Ala Ala Glu Leu Arg Gln Val Met Ala Asn Phe
            20                  25
```

<210> SEQ ID NO 237
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SQUID-II EF2 hand motif

<400> SEQUENCE: 237

```
Glu Ile Ser Glu Met Ile Arg Glu Ala Asp Ile Asp Gly Asp Gly Met
1               5                   10                  15

Val Asn Tyr Glu Glu Phe Val Lys Met Met Thr Pro Lys
            20                  25
```

<210> SEQ ID NO 238
<211> LENGTH: 31
<212> TYPE: PRT
<213> ORGANISM: Artificial Sequence
<220> FEATURE:
<221> NAME/KEY: DOMAIN
<222> LOCATION: (1)...(31)
<223> OTHER INFORMATION: MYO ELC-I EF1 hand motif

<400> SEQUENCE: 238

Asp Leu Lys Asp Val Phe Glu Leu Phe Asp Phe Trp Asp Gly Arg Asp
1               5                   10                  15

Gly Ala Val Asp Ala Phe Lys Leu Gly Asp Val Cys Arg Cys Leu
            20                  25                  30

<210> SEQ ID NO 239
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: MYO ELC-I EF2 hand motif

<400> SEQUENCE: 239

Glu Asp Val Phe Ala Val Gly Gly Thr His Lys Met Gly Glu Lys Ser
1               5                   10                  15

Leu Pro Phe Glu Glu Phe Leu Pro Ala Tyr Glu Gly Leu
            20                  25

<210> SEQ ID NO 240
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: MYO ELC-II EF1 hand motif

<400> SEQUENCE: 240

Asp Tyr Met Glu Ala Phe Lys Thr Phe Asp Arg Glu Gly Gln Gly Phe
1               5                   10                  15

Ile Ser Gly Ala Glu Leu Arg His Val Leu Thr Ala Leu
            20                  25

<210> SEQ ID NO 241
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: MYO ELC-II EF2 hand motif

<400> SEQUENCE: 241

Asp Glu Ile Ile Lys Leu Thr Asp Leu Gln Glu Asp Leu Glu Gly Asn
1               5                   10                  15

Val Lys Tyr Glu Asp Phe Val Lys Lys Val Met Ala Gly
            20                  25

<210> SEQ ID NO 242
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: MYO RLC-I EF1 hand motif

<400> SEQUENCE: 242

Glu Met Lys Glu Ala Phe Ser Met Ile Asp Val Asp Arg Asp Gly Phe
1               5                   10                  15

Val Ser Lys Glu Asp Ile Lys Ala Ile Ser Glu Gln Leu
            20                  25

<210> SEQ ID NO 243
<211> LENGTH: 25
<212> TYPE: PRT
<213> ORGANISM: Artificial Sequence
<220> FEATURE:
<221> NAME/KEY: DOMAIN
<222> LOCATION: (1)...(25)
<223> OTHER INFORMATION: MYO RLC-I EF2 hand motif

<400> SEQUENCE: 243

Glu Leu Thr Ala Met Leu Lys Glu Ala Pro Gly Pro Leu Asn Phe Thr
1               5                   10                  15

Met Phe Leu Ser Ile Phe Ser Asp Lys
            20                  25

<210> SEQ ID NO 244
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: MYO RLC-II EF1 hand motif

<400> SEQUENCE: 244

Thr Ile Arg Asn Ala Phe Ala Met Phe Asp Glu Gln Glu Thr Lys Lys
1               5                   10                  15

Leu Asn Ile Glu Tyr Ile Lys Asp Leu Leu Glu Asn Met
            20                  25

<210> SEQ ID NO 245
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: MYO RLC-II EF2 hand motif

<400> SEQUENCE: 245

Glu Met Arg Met Thr Phe Lys Glu Ala Pro Val Glu Gly Gly Lys Phe
1               5                   10                  15

Asp Tyr Val Lys Phe Thr Ala Met Ile Lys Gly Ser
            20                  25

<210> SEQ ID NO 246
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: PARV EF1 hand motif

<400> SEQUENCE: 246

Asp Val Lys Lys Val Phe Lys Ala Ile Asp Ala Asp Ala Ser Gly Phe
1               5                   10                  15

```
Ile Glu Glu Glu Glu Leu Lys Phe Val Leu Lys Ser Phe
            20                  25

<210> SEQ ID NO 247
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: PARV EF2 hand motif

<400> SEQUENCE: 247

Glu Thr Lys Ala Phe Leu Lys Ala Ala Asp Lys Asp Gly Asp Gly Lys
 1               5                  10                  15

Ile Gly Ile Asp Glu Phe Glu Thr Leu Val His Glu Ala
            20                  25

<210> SEQ ID NO 248
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SPECTRIN EF1 hand motif

<400> SEQUENCE: 248

Glu Phe Ser Met Met Phe Lys His Phe Asp Lys Asp Lys Ser Gly Arg
 1               5                  10                  15

Leu Asp His Gln Glu Phe Lys Ser Cys Leu Arg Ser Leu
            20                  25

<210> SEQ ID NO 249
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: SPECTRIN EF2 hand motif

<400> SEQUENCE: 249

Glu Phe Glu Ser Ile Leu Asp Thr Val Asp Pro Asn Arg Asp Gly His
 1               5                  10                  15

Val Ser Leu Gln Glu Tyr Met Ala Phe Met Ile Ser Arg
            20                  25

<210> SEQ ID NO 250
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CALCIN-I EF1 hand motif

<400> SEQUENCE: 250

Arg Leu Gly Lys Arg Phe Lys Lys Leu Asp Leu Asp Asn Ser Gly Ser
 1               5                  10                  15

Leu Ser Val Glu Glu Phe Met Ser Leu Pro Glu Leu
            20                  25

<210> SEQ ID NO 251
<211> LENGTH: 29
```

```
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALCIN-I EF2 hand motif

<400> SEQUENCE: 251

Leu Val Gln Arg Val Ile Asp Ile Phe Asp Thr Asp Gly Asn Gly Glu
 1               5                  10                  15

Val Asp Phe Lys Glu Phe Ile Glu Gly Val Ser Gln Phe
            20                  25

<210> SEQ ID NO 252
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALCIN-II EF1 hand motif

<400> SEQUENCE: 252

Lys Leu Arg Phe Ala Phe Arg Ile Tyr Asp Met Asp Lys Asp Gly Tyr
 1               5                  10                  15

Ile Ser Asn Gly Glu Leu Phe Gln Val Leu Lys Met Met
            20                  25

<210> SEQ ID NO 253
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALCIN-II EF2 hand motif

<400> SEQUENCE: 253

Ile Val Asp Lys Thr Ile Ile Asn Ala Asp Lys Asp Gly Asp Gly Arg
 1               5                  10                  15

Ile Ser Phe Glu Glu Phe Cys Ala Val Val Gly Gly Leu
            20                  25

<210> SEQ ID NO 254
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALB28-I EF1 hand motif

<400> SEQUENCE: 254

Gln Phe Phe Glu Ile Trp Leu His Phe Asp Ala Asp Gly Ser Gly Tyr
 1               5                  10                  15

Leu Glu Gly Lys Glu Leu Gln Asn Leu Ile Gln Glu Leu
            20                  25

<210> SEQ ID NO 255
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALB28-I EF2 hand motif
```

-continued

<400> SEQUENCE: 255

Glu Met Lys Thr Phe Val Asp Gln Tyr Gly Gln Arg Asp Asp Gly Lys
1               5                   10                  15

Ile Gly Ile Val Glu Leu Ala His Val Leu Pro Thr Glu Glu
            20                  25                  30

<210> SEQ ID NO 256
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALB28-II EF1 hand motif

<400> SEQUENCE: 256

Glu Phe Met Lys Thr Trp Arg Lys Tyr Asp Thr Asp His Ser Gly Phe
1               5                   10                  15

Ile Glu Thr Glu Glu Leu Lys Asn Phe Leu Lys Asp Leu
            20                  25

<210> SEQ ID NO 257
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALB28-II EF2 hand motif

<400> SEQUENCE: 257

Tyr Thr Asp Leu Met Leu Lys Leu Phe Asp Ser Asn Asn Asp Gly Lys
1               5                   10                  15

Leu Glu Leu Thr Glu Met Ala Arg Leu Leu Pro Val Gln Glu
            20                  25                  30

<210> SEQ ID NO 258
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALB28-III EF1 hand motif

<400> SEQUENCE: 258

Glu Phe Asn Lys Ala Phe Glu Leu Tyr Asp Gln Asp Gly Asn Gly Tyr
1               5                   10                  15

Ile Asp Glu Asn Glu Leu Asp Ala Leu Leu Lys Asp Leu
            20                  25

<210> SEQ ID NO 259
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALB28-III EF2 hand motif

<400> SEQUENCE: 259

Ile Thr Thr Tyr Lys Lys Asn Ile Met Ala Leu Ser Asp Gly Gly Lys
1               5                   10                  15

Leu Tyr Arg Thr Asp Leu Ala Leu Ile Leu Cys Ala Gly Asp
            20                  25                  30

```
<210> SEQ ID NO 260
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALRET-I EF1 hand motif

<400> SEQUENCE: 260

Gln Phe Leu Glu Ile Trp Lys His Phe Asp Ala Asp Gly Asn Gly Tyr
 1               5                  10                  15

Ile Glu Gly Lys Glu Leu Glu Asn Phe Phe Gln Glu Leu
                20                  25

<210> SEQ ID NO 261
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALRET-I EF2 hand motif

<400> SEQUENCE: 261

Lys Met Lys Glu Phe Met Gln Lys Tyr Asp Lys Asn Ser Asp Gly Lys
 1               5                  10                  15

Ile Glu Met Ala Glu Leu Ala Gln Ile Leu Pro Thr Glu Glu
                20                  25                  30

<210> SEQ ID NO 262
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CALRET-II EF1 hand motif

<400> SEQUENCE: 262

Glu Phe Met Glu Ala Trp Arg Lys Tyr Asp Thr Asp Arg Ser Gly Tyr
 1               5                  10                  15

Ile Glu Ala Asn Glu Leu Lys Gly Phe Leu Ser Asp Leu
                20                  25

<210> SEQ ID NO 263
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALRET-II EF2 hand motif

<400> SEQUENCE: 263

Tyr Thr Gln Thr Ile Leu Arg Met Phe Asp Leu Asn Gly Asp Gly Lys
 1               5                  10                  15

Leu Gly Leu Ser Glu Met Ser Arg Leu Leu Pro Val Gln Glu
                20                  25                  30

<210> SEQ ID NO 264
<211> LENGTH: 29
<212> TYPE: PRT
<213> ORGANISM: Artificial Sequence
<220> FEATURE:
```

```
<221> NAME/KEY: DOMAIN
<222> LOCATION: (1)...(29)
<223> OTHER INFORMATION: CALRET-III EF1 hand motif

<400> SEQUENCE: 264

Glu Phe Asn Ala Ile Phe Thr Phe Tyr Asp Lys Asp Arg Ser Gly Tyr
 1               5                  10                  15

Ile Asp Glu His Glu Leu Asp Ala Leu Leu Lys Asp Leu
            20                  25

<210> SEQ ID NO 265
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: CALRET-III EF2 hand motif

<400> SEQUENCE: 265

Asn Tyr Arg Lys Ser Val Met Ser Leu Ala Glu Ala Gly Lys Leu Tyr
 1               5                  10                  15

Arg Lys Asp Leu Glu Ile Val Leu Cys Ser Glu Pro Pro Met
            20                  25                  30

<210> SEQ ID NO 266
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: HIPP-I EF1 hand motif

<400> SEQUENCE: 266

Leu Gln Glu Trp Tyr Lys Gly Phe Leu Lys Asp Cys Pro Thr Gly Ile
 1               5                  10                  15

Leu Asn Val Asp Glu Phe Lys Lys Ile Tyr Ala Asn Phe
            20                  25

<210> SEQ ID NO 267
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: HIPP-I EF2 hand motif

<400> SEQUENCE: 267

Phe Ala Glu His Val Phe Arg Thr Phe Asp Thr Asn Ser Asp Gly Thr
 1               5                  10                  15

Ile Asp Phe Arg Glu Phe Ile Ile Ala Leu Ser Val Thr Ser
            20                  25                  30

<210> SEQ ID NO 268
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: HIPP-II EF1 hand motif

<400> SEQUENCE: 268

Lys Leu Met Trp Ala Phe Ser Met Tyr Asp Leu Asp Gly Asn Gly Tyr
```

```
                  1               5                  10                  15
Ile Ser Arg Glu Glu Met Leu Glu Ile Val Gln Ala Ile
            20                  25
```

<210> SEQ ID NO 269
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: HIPP-II EF2 hand motif

<400> SEQUENCE: 269

```
Arg Thr Glu Lys Ile Phe Arg Gln Met Asp Thr Asn Asn Asp Gly Lys
  1               5                  10                  15

Leu Ser Leu Glu Glu Phe Ile Arg Gly Ala Lys Ser Asp Pro
             20                  25                  30
```

<210> SEQ ID NO 270
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: RECOV-I EF1 hand motif

<400> SEQUENCE: 270

```
Leu Ser Ser Trp Tyr Gln Ser Phe Leu Lys Glu Cys Pro Ser Gly Arg
  1               5                  10                  15

Ile Thr Arg Gln Glu Phe Gln Thr Ile Tyr Ser Lys Phe
             20                  25
```

<210> SEQ ID NO 271
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: RECOV-I EF2 hand motif

<400> SEQUENCE: 271

```
Tyr Ala Gln His Val Phe Arg Ser Phe Asp Ala Asn Ser Asp Gly Thr
  1               5                  10                  15

Leu Asp Phe Lys Glu Tyr Val Ile Ala Leu His Met Thr Ser
             20                  25                  30
```

<210> SEQ ID NO 272
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: RECOV-II EF1 hand motif

<400> SEQUENCE: 272

```
Lys Leu Glu Trp Ala Phe Ser Leu Tyr Asp Val Asp Gly Asn Gly Thr
  1               5                  10                  15

Ile Ser Lys Asn Glu Val Leu Glu Ile Val Thr Ala Ile
             20                  25
```

<210> SEQ ID NO 273

```
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: RECOV-II EF2 hand motif

<400> SEQUENCE: 273

Glu Lys Arg Ala Glu Lys Ile Trp Gly Phe Phe Gly Lys Lys Asp Asp
 1               5                  10                  15

Asp Lys Leu Thr Glu Lys Glu Phe Ile Glu Gly Thr Leu Ala
            20                  25                  30

<210> SEQ ID NO 274
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPI-I EF1 hand motif

<400> SEQUENCE: 274

Glu Asn Phe Lys Ala Leu Phe Arg Gln Leu Ala Gly Glu Asp Met Glu
 1               5                  10                  15

Ile Ser Val Lys Glu Leu Arg Thr Ile Leu Asn Arg Ile
            20                  25

<210> SEQ ID NO 275
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPI-I EF2 hand motif

<400> SEQUENCE: 275

Ser Cys Arg Ser Met Val Asn Leu Met Asp Arg Asp Gly Asn Gly Lys
 1               5                  10                  15

Leu Gly Leu Val Glu Phe Asn Ile Leu Trp Asn Arg
            20                  25

<210> SEQ ID NO 276
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPI-II EF1 hand motif

<400> SEQUENCE: 276

Asn Tyr Leu Ser Ile Phe Arg Lys Phe Asp Leu Asp Lys Ser Gly Ser
 1               5                  10                  15

Met Ser Ala Tyr Glu Met Arg Met Ala Ile Glu Ser Ala
            20                  25

<210> SEQ ID NO 277
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPI-II EF2 hand motif
```

```
<400> SEQUENCE: 277

Lys Leu Tyr Glu Leu Ile Ile Thr Arg Tyr Ser Glu Pro Asp Leu Ala
1               5                   10                  15

Val Asp Phe Asp Asn Phe Val Cys Cys Leu Val Arg
            20                  25

<210> SEQ ID NO 278
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPI-III EF1 hand motif

<400> SEQUENCE: 278

Thr Met Phe Arg Phe Phe Lys Thr Leu Asp Thr Asp Leu Asp Gly Val
1               5                   10                  15

Val Thr Phe Asp Leu Phe Lys Trp Leu Gln Leu Thr Met
            20                  25

<210> SEQ ID NO 279
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPII-I EF1 hand motif

<400> SEQUENCE: 279

Asp Gly Val Arg Arg Leu Phe Ala Gln Leu Ala Gly Glu Asp Ala Glu
1               5                   10                  15

Ile Ser Ala Phe Glu Leu Gln Thr Ile Leu Arg Arg Val
            20                  25

<210> SEQ ID NO 280
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPII-I EF2 hand motif

<400> SEQUENCE: 280

Thr Cys Lys Ile Met Val Asp Met Leu Asp Ser Asp Gly Ser Gly Lys
1               5                   10                  15

Leu Gly Leu Lys Glu Phe Tyr Ile Leu Trp Thr Lys
            20                  25

<210> SEQ ID NO 281
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPII-II EF1 hand motif

<400> SEQUENCE: 281

Lys Tyr Gln Lys Ile Tyr Arg Glu Ile Asp Val Asp Arg Ser Gly Thr
1               5                   10                  15

Met Asn Ser Tyr Glu Met Arg Lys Ala Leu Glu Glu Ala
```

```
            20                  25

<210> SEQ ID NO 282
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPII-II EF2 hand motif

<400> SEQUENCE: 282

Gln Leu His Gln Val Ile Val Ala Arg Phe Ala Asp Asp Gln Leu Ile
1               5                   10                  15

Ile Asp Phe Asp Asn Phe Val Arg Cys Leu Val Arg
            20                  25

<210> SEQ ID NO 283
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPII-III EF1 hand motif

<400> SEQUENCE: 283

Thr Leu Phe Lys Ile Phe Lys Gln Leu Asp Pro Glu Asn Thr Gly Thr
1               5                   10                  15

Ile Glu Leu Asp Leu Ile Ser Trp Leu Cys Phe Ser Val
            20                  25

<210> SEQ ID NO 284
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPIII-I EF1 hand motif

<400> SEQUENCE: 284

Gln Gln Phe Arg Asn Ile Phe Lys Gln Ile Ala Gly Asp Asp Met Glu
1               5                   10                  15

Ile Cys Ala Asp Glu Leu Lys Lys Val Leu Asn Thr Val
            20                  25

<210> SEQ ID NO 285
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPIII-I EF2 hand motif

<400> SEQUENCE: 285

Ser Cys Arg Ser Met Ile Ala Leu Met Asp Thr Asp Gly Ser Gly Lys
1               5                   10                  15

Leu Asn Leu Gln Glu Phe His His Leu Trp Asn Lys
            20                  25

<210> SEQ ID NO 286
<211> LENGTH: 29
<212> TYPE: PRT
<213> ORGANISM: Artificial Sequence
```

```
<220> FEATURE:
<221> NAME/KEY: DOMAIN
<222> LOCATION: (1)...(29)
<223> OTHER INFORMATION: CANPIII-II EF1 hand motif

<400> SEQUENCE: 286

Ala Trp Gln Lys Ile Phe Lys His Tyr Asp Thr Asp Gln Ser Gly Thr
 1               5                  10                  15

Ile Asn Ser Tyr Glu Met Arg Asn Ala Val Asn Asp Ala
             20                  25

<210> SEQ ID NO 287
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: CANPIII-II EF2 hand motif

<400> SEQUENCE: 287

Gln Leu Tyr Asp Ile Ile Thr Met Arg Tyr Ala Asp Lys His Met Asn
 1               5                  10                  15

Ile Asp Phe Asp Ser Phe Ile Cys Cys Phe Val Arg
             20                  25

<210> SEQ ID NO 288
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: CANPIII-III EF1 hand motif

<400> SEQUENCE: 288

Gly Met Phe Arg Ala Phe His Ala Phe Asp Lys Asp Gly Asp Gly Ile
 1               5                  10                  15

Ile Lys Leu Asn Val Leu Glu Trp Leu Gln Leu Thr Met
             20                  25

<210> SEQ ID NO 289
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: smCANP-I EF1 hand motif

<400> SEQUENCE: 289

Arg Gln Phe Arg Arg Leu Phe Ala Gln Leu Ala Gly Asp Asp Met Glu
 1               5                  10                  15

Val Ser Ala Thr Glu Leu Met Asn Ile Leu Asn Lys Val
             20                  25

<210> SEQ ID NO 290
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: smCANP-I EF2 hand motif

<400> SEQUENCE: 290
```

```
Thr Cys Arg Ser Met Val Ala Val Met Asp Ser Asp Thr Thr Gly Lys
 1               5                  10                  15

Leu Gly Phe Glu Glu Phe Lys Tyr Leu Trp Asn Asn
                20                  25
```

<210> SEQ ID NO 291
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: smCANP-II EF1 hand motif

<400> SEQUENCE: 291

```
Arg Trp Gln Ala Ile Tyr Lys Gln Phe Asp Thr Asp Arg Ser Gly Thr
 1               5                  10                  15

Ile Cys Ser Ser Glu Leu Pro Gly Ala Phe Glu Ala Ala
                20                  25
```

<210> SEQ ID NO 292
<211> LENGTH: 28
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: smCANP-II EF2 hand motif

<400> SEQUENCE: 292

```
His Leu Tyr Asn Met Ile Ile Arg Arg Tyr Ser Asp Glu Ser Gly Asn
 1               5                  10                  15

Met Asp Phe Asp Asn Phe Ile Ser Cys Leu Val Arg
                20                  25
```

<210> SEQ ID NO 293
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: smCANP-III EF1 hand motif

<400> SEQUENCE: 293

```
Ala Met Phe Arg Ala Phe Lys Ser Leu Asp Lys Asp Gly Thr Gly Gln
 1               5                  10                  15

Ile Gln Val Asn Ile Gln Glu Trp Leu Gln Leu Thr Met
                20                  25
```

<210> SEQ ID NO 294
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: AMP SARC-I hand motif

<400> SEQUENCE: 294

```
Lys Ile Lys Phe Thr Phe Asp Phe Phe Leu Asp Met Asn His Asp Gly
 1               5                  10                  15

Ser Ile Gln Asp Asn Asp Phe Glu Asp Met Met Thr Arg Tyr
                20                  25                  30
```

```
<210> SEQ ID NO 295
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: AMP SARC-I EF2 hand motif

<400> SEQUENCE: 295

Glu Trp Arg Asp Leu Lys Gly Arg Ala Asp Ile Asn Lys Asp Asp Val
1               5                   10                  15

Val Ser Trp Glu Glu Tyr Leu Ala Met Trp Glu Lys Thr
            20                  25

<210> SEQ ID NO 296
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: AMP SARC-II EF1 hand motif

<400> SEQUENCE: 296

Arg Ile Pro Phe Leu Phe Lys Gly Met Asp Val Ser Gly Asp Gly Ile
1               5                   10                  15

Val Asp Leu Glu Glu Phe Gln Asn Tyr Cys Lys Asn Phe
            20                  25

<210> SEQ ID NO 297
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: AMP SARC-II EF2 hand motif

<400> SEQUENCE: 297

Val Tyr Asn Val Ile Thr Asp Gly Gly Lys Val Thr Phe Asp Leu Asn
1               5                   10                  15

Arg Tyr Lys Glu Leu Tyr Tyr Arg Leu Leu Thr Ser Pro
            20                  25

<210> SEQ ID NO 298
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: NER SARC-I EF1 hand motif

<400> SEQUENCE: 298

Lys Met Lys Thr Tyr Phe Asn Arg Ile Asp Phe Asp Lys Asp Gly Ala
1               5                   10                  15

Ile Thr Arg Met Asp Phe Glu Ser Met Ala Glu Arg Phe
            20                  25

<210> SEQ ID NO 299
<211> LENGTH: 28
```

```
<212> TYPE: PRT
<213> ORGANISM: Artificial Sequence
<220> FEATURE:
<221> NAME/KEY: DOMAIN
<222> LOCATION: (1)...(28)
<223> OTHER INFORMATION: NER SARC-I EF2 hand motif

<400> SEQUENCE: 299

Ser Leu Thr Gly Val Trp Asp Asn Phe Leu Thr Ala Val Ala Gly Gly
 1               5                  10                  15

Lys Gly Ile Asp Glu Thr Thr Phe Ile Asn Ser Met
            20                  25

<210> SEQ ID NO 300
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: NER SARC-II EF1 hand motif

<400> SEQUENCE: 300

Pro Leu Pro Leu Phe Phe Arg Ala Val Asp Thr Asn Glu Asp Asn Asn
 1               5                  10                  15

Ile Ser Arg Asp Glu Tyr Gly Ile Phe Phe Gly Met Leu
            20                  25

<210> SEQ ID NO 301
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: NER SARC-II EF2 hand motif

<400> SEQUENCE: 301

Met Ala Pro Ala Ser Phe Asp Ala Ile Asp Thr Asn Asn Asp Gly Leu
 1               5                  10                  15

Leu Ser Leu Glu Glu Phe Val Ile Ala Gly Ser Asp Phe
            20                  25

<210> SEQ ID NO 302
<211> LENGTH: 30
<212> TYPE: PRT
<213> ORGANISM: Artificial Sequence
<220> FEATURE:
<221> NAME/KEY: DOMAIN
<222> LOCATION: (1)...(30)
<223> OTHER INFORMATION: BM40 EF1 hand motif

<400> SEQUENCE: 302

Pro Val His Trp Gln Phe Gly Gln Leu Asp Gln His Pro Ile Asp Gly
 1               5                  10                  15

Tyr Leu Ser His Thr Glu Leu Ala Pro Leu Arg Ala Pro Leu
            20                  25                  30

<210> SEQ ID NO 303
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: BM40 EF2 hand motif
```

-continued

```
<400> SEQUENCE: 303

Cys Thr Thr Arg Phe Phe Glu Thr Cys Asp Leu Asp Asn Asp Lys Tyr
1               5                   10                  15

Ile Ala Leu Asp Glu Trp Ala Gly Cys Phe Gly Ile Lys
            20                  25
```